US012552800B2

(12) United States Patent
Molette

(10) Patent No.: US 12,552,800 B2
(45) Date of Patent: Feb. 17, 2026

(54) COMPOUNDS FOR DIAGNOSIS

(71) Applicant: AC IMMUNE SA, Lausanne (CH)

(72) Inventor: Jerome Molette, Prevessin-Moens (FR)

(73) Assignee: AC IMMUNE SA, Lausanne (CH)

( * ) Notice: Subject to any disclaimer, the term of this patent is extended or adjusted under 35 U.S.C. 154(b) by 622 days.

(21) Appl. No.: 17/923,771

(22) PCT Filed: May 7, 2021

(86) PCT No.: PCT/EP2021/062215

§ 371 (c)(1),
(2) Date: Nov. 7, 2022

(87) PCT Pub. No.: WO2021/224489

PCT Pub. Date: Nov. 11, 2021

(65) Prior Publication Data

US 2023/0174536 A1 Jun. 8, 2023

(30) Foreign Application Priority Data

May 7, 2020 (EP) .................................... 20173587
Jul. 23, 2020 (EP) .................................... 20187551

(51) Int. Cl.

*C07D 487/04* (2006.01)
*A61K 31/4162* (2006.01)
*A61K 51/00* (2006.01)
*A61K 51/04* (2006.01)
*C07B 59/00* (2006.01)

(52) U.S. Cl.

CPC ........ *C07D 487/04* (2013.01); *A61K 51/0455* (2013.01); *A61K 51/0459* (2013.01); *A61K 51/0463* (2013.01); *C07B 59/002* (2013.01); *C07B 2200/05* (2013.01)

(58) Field of Classification Search

CPC ... C07D 487/04; A61K 31/4162; A61K 51/00
See application file for complete search history.

(56) References Cited

U.S. PATENT DOCUMENTS

| | | | |
|---|---|---|---|
| 8,530,483 | B2 | 9/2013 | Barrow et al. |
| 10,500,207 | B2 | 12/2019 | Kroth et al. |
| 11,059,836 | B2 | 7/2021 | Dominguez et al. |
| 2004/0214856 | A1 | 10/2004 | Carpino et al. |
| 2011/0236307 | A1 | 9/2011 | Jones |
| 2012/0302755 | A1 | 11/2012 | Szardenings et al. |
| 2013/0287700 | A1 | 10/2013 | Schmidt et al. |
| 2014/0142089 | A1 | 5/2014 | Lee et al. |
| 2020/0299305 | A1 | 9/2020 | Molette et al. |
| 2021/0009596 | A1 | 1/2021 | Fan et al. |
| 2021/0252175 | A1 | 8/2021 | Molette |

FOREIGN PATENT DOCUMENTS

WO 2019126431 A1 6/2019

OTHER PUBLICATIONS

Aebi et al. (Pharmaceutica Acta Helvetiae (1963), 38(7-8), 616-622). Abstract.*

International Search report PCT/EP2021/062215 dated Jul. 8, 2021 (pp. 1-5) and written opinion (pp. 1-6).

Xu Ming-Ming et al: "Advances in the development of imaging probes and aggregation inhibitors for alpha-synuclein", Acta Pharmacologica Sinica, Nature Publishing Group, GB, vol. 41, No. 4, Oct. 4, 2019 (Oct. 4, 2019), pp. 483-498, XP037079648, ISSN: 1671-4083, [retrieved on Oct. 4, 2019], DOI: 10.1038/S41401-019-0304-Y.

Kotzbauer Paul T. et al: "Current status of the development of PET radiotracers for imaging alpha synuclein aggregates in Lewy bodies and Lewy neurites", Clinical and Translational Imaging, Jan. 1, 2017 (Jan. 1, 2017), pp. 3-14, XP055816408, Retrieved from the Internet <URL:https://link.springer.com/article/10.1007/s40336-016-0217-4>.

Chu Wenhua et al: "Design, Synthesis, and Characterization of 3-(Benzylidene)indolin-2-one Derivatives as Ligands for [alpha]-Synuclein Fibrils", Journal of Medicinal Chemistry, vol. 58, No. 15, Aug. 13, 2015 (Aug. 13, 2015), pp. 6002-6017, XP055816394, ISSN: 0022-2623, Retrieved from the Internet <URL:https://pubs.acs.org/doi/pdf/10.1021/acs.jmedchem.5b00571> DOI: 10.1021/acs.jmedchem.5b00571.

Watanabe Hiroyuki et al: "Synthesis and biological evaluation of novel radioiodinated benzimidazole derivatives for imaging [alpha]-synuclein aggregates", Bioorganic & Medicinal Chemistry, vol. 25, No. 24, Oct. 14, 2017 (Oct. 14, 2017), pp. 6398-6403, XP085254616, ISSN: 0968-0896, DOI: 10.1016/J.BMC.2017.10.010.

Chen Yan-Fei et al: "Design, synthesis and identification of N, N-dibenzylcinnamamide (DBC) derivatives as novel ligands for [alpha]-synuclein fibrils by SPR evaluation system", Bioorganic & Medicinal Chemistry, Elsevier, Amsterdam, NL, vol. 28, No. 7, Feb. 6, 2020 (Feb. 6, 2020), XP086093753, ISSN: 0968-0896, [retrieved on Feb. 6, 2020], DOI: 10.1016/J.BMC.2020.115358.

(Continued)

*Primary Examiner* — Bruck Kifle
(74) *Attorney, Agent, or Firm* — Csaba Henter; MILLEN, WHITE, ZELANO & BRANIGAN

(57) ABSTRACT

The present invention relates to novel compounds of formula (I), or a detectably labelled compound, stereoisomer, racemic mixture, pharmaceutically acceptable salt, hydrate, or solvate thereof, that can be employed in the imaging of alpha-synuclein aggregates and determining an amount thereof. Furthermore, the compounds can be used for diagnosing a disease, disorder or abnormality associated with an alpha-synuclein aggregates, including, but not limited to, Lewy bodies and/or Lewy neurites (such as Parkinson's disease), determining a predisposition to such a disease, disorder or abnormality, prognosing such a disease, disorder or abnormality, monitoring the evolution of the disease in a patient suffering from such a disease, disorder or abnormality, monitoring the progression of such a disease, disorder or abnormality and predicting responsiveness of a patient suffering from such a disease, disorder or abnormality to a treatment thereof.

21 Claims, 15 Drawing Sheets

(56) References Cited

OTHER PUBLICATIONS

Chinese Office Action dated Nov. 6, 2024, issued in corresponding application CN 202180033627.5 (pp. 1-9).

Von A. Aebi et al. "Uber Synthese und Eigenschaften von acylierten Tetramsauren und deren Ringschlub zu 4-Keto-pyrrolo-[3,4-c]-pyrazolen" Pharmaceutica Acta Helvetiae vol. 38 Dec. 1962, pp. 616-622.

* cited by examiner

A

B

B

COMPOUNDS FOR DIAGNOSIS

FIELD OF THE INVENTION

The present invention relates to novel compounds of formula (I), or a detectably labelled compound, stereoisomer, racemic mixture, pharmaceutically acceptable salt, hydrate, or solvate thereof, that can be employed in the imaging of alpha-synuclein aggregates and determining an amount thereof. Furthermore, the compounds can be used for diagnosing a disease, disorder or abnormality associated with an alpha-synuclein (α-synuclein, A-synuclein, aSynuclein, A-syn, α-syn, aSyn, a-syn) aggregates, including, but not limited to, Lewy bodies and/or Lewy neurites (such as Parkinson's disease), determining a predisposition to such a disease, disorder or abnormality, prognosing such a disease, disorder or abnormality, monitoring the evolution of the disease in a patient suffering from such a disease, disorder or abnormality, monitoring the progression of such a disease, disorder or abnormality and predicting responsiveness of a patient suffering from such a disease, disorder or abnormality to a treatment thereof. The present invention also relates to processes for the preparation of the compounds and their precursors, diagnostic compositions comprising the compounds, methods of using the compounds, kits comprising the compounds and their uses thereof.

BACKGROUND OF THE INVENTION

Many diseases of aging are based on or associated with extracellular or intracellular deposits of amyloid or amyloid-like proteins that contribute to the pathogenesis as well as to the progression of the disease. The best characterized amyloid protein that forms extracellular aggregates is amyloid beta (Abeta or Aβ).

Amyloid-like proteins that form mainly intracellular aggregates include, but are not limited to, Tau, alpha-synuclein, and huntingtin (HTT). Diseases involving alpha-synuclein aggregates are generally listed as synucleinopathies (or α-synucleinopathies) and these include, but are not limited to, Parkinson's disease (PD). Synucleinopathies with primarily neuronal aggregates include, but are not limited to, Parkinson's disease (sporadic, familial with SNCA (the gene encoding for the alpha-synuclein protein) mutations or SNCA gene duplication or triplication, familial with mutations in other genes than SNCA, pure autonomic failure and Lewy body dysphagia), SNCA duplication carrier, Lewy Body dementia (LBD), dementia with Lewy bodies (DLB) ("pure" Lewy body dementia), Parkinson's disease dementia (PDD), diffuse Lewy body disease (DLBD), Alzheimer's disease, sporadic Alzheimer's disease, familial Alzheimer's disease with APP mutations, familial Alzheimer's disease with PS-1, PS-2 or other mutations, familial British dementia, Lewy body variant of Alzheimer's disease and normal aging in Down syndrome. Synucleinopathies with neuronal and glial aggregates of alpha synuclein include but are not limited to multiple system atrophy (MSA) (Shy-Drager syndrome, striatonigral degeneration and olivopontocerebellar atrophy). Other diseases that may have alpha-synuclein-immunoreactive lesions are, but are not limited to, traumatic brain injury, chronic traumatic encephalopathy, dementia puglistica, tauopathies (Pick's disease, frontotemporal dementia, progressive supranuclear palsy, corticobasal degeneration and Niemann-Pick type C1 disease, frontotemporal dementia with Parkinsonism linked to chromosome 17), motor neuron disease, Huntington's disease, amyotrophic lateral sclerosis (sporadic, familial and ALS-dementia complex of Guam), neuroaxonal dystrophy, neurodegeneration with brain iron accumulation type 1 (Hallervorden-Spatz syndrome), prion diseases, Creutzfeldt-Jakob disease, ataxia telangiectatica, Meige's syndrome, subacute sclerosing panencephalitis, Gerstmann-Straussler-Scheinker disease, inclusion-body myositis, Gaucher disease, Krabbe disease as well as other lysosomal storage disorders (including Kufor-Rakeb syndrome and Sanfilippo syndrome) and rapid eye movement (REM) sleep behavior disorder (Jellinger, Mov Disord 2003, 18 Suppl. 6, S2-12; Galvin et al. JAMA Neurology 2001, 58 (2), 186-190; Kovari et al., Acta Neuropathol. 2007, 114(3), 295-8; Saito et al., J Neuropathol Exp Neurol. 2004, 63(4), 323-328; McKee et al., Brain, 2013, 136(Pt 1), 43-64; Puschmann et al., Parkinsonism Relat Disord 2012, 18S1, S24-S27; Usenovic et al., J Neurosci. 2012, 32(12), 4240-4246; Winder-Rhodes et al., Mov Disord. 2012, 27(2), 312-315; Ferman et al., J Int Neuropsychol Soc. 2002, 8(7), 907-914; Smith et al., J Pathol. 2014; 232:509-521, Lippa et al., Ann Neurol. 1999 March; 45(3):353-7; Schmitz et al., Mol Neurobiol. 2018 Aug. 22; Charles et al., Neurosci Lett. 2000 Jul. 28; 289(1): 29-32; Wilhelmsen et al., Arch Neurol. 2004 March; 61(3): 398-406; Yamaguchi et al., J Neuropathol Exp Neurol. 2004, $80^{th}$ annual meeting, vol. 63; Askanas et al., J Neuropathol Exp Neurol. 2000 July; 59(7):592-8).

Alpha-synuclein is a 140 amino acid natively unfolded protein (Iwai et al., Biochemistry 1995, 34(32), 10139-10145). The sequence of alpha-synuclein can be divided into three main domains: 1) the N-terminal region comprising of residues 1-60, which contains the 11-mer amphipatic imperfect repeat residues with highly conserved hexamer (KTKEGV). This region has been implicated in regulating alpha-synuclein binding to membranes and its internalization; 2) the hydrophobic Non Amyloid beta Component (NAC) domain spanning residues 61-95; which is essential for alpha-synuclein fibrillization; and 3) the C-terminal region spanning residues 96-140 which is highly acidic and proline-rich and has no distinct structural propensity. Alpha-synuclein has been shown to undergo several post translational modifications, including truncations, phosphorylation, ubiquitination, oxidation and/or transglutaminase covalent cross linking (Fujiwara et al., Nat Cell Biol 2002, 4(2); 160-164; Hasegawa et al., J Biol Chem 2002, 277(50), 49071-49076; Li et al., Proc Natl Acad Sci USA 2005, 102(6), 2162-2167; Oueslati et al, Prog Brain Res 2010, 183, 115-145; Schmid et al., J Biol Chem 2009, 284(19), 13128-13142). Interestingly, the majority of these modifications involve residues within the C-terminal region.

Several phosphorylation sites have been detected in the carboxyl-terminal region on Tyr-125, -133, and -136, and on Ser-129 (Negro et al., FASEB J 2002, 16(2), 210-212). Tyr-125 residues can be phosphorylated by two Src family protein tyrosine kinases, c-Src and Fyn (Ellis et al., J Biol Chem 2001, 276(6), 3879-3884; Nakamura et al., Biochem Biophys Res Commun 2001, 280(4), 1085-1092). Phosphorylation by Src family kinases does not suppress or enhance the tendency of alpha-synuclein to polymerize. Alpha-synuclein has proved to be an outstanding substrate for protein tyrosine kinase $p72^{syk}$ (Syk) in vitro; once it is extensively Tyr-phosphorylated by Syk or tyrosine kinases with similar specificity, it loses the ability to form oligomers, suggesting a putative anti-neurodegenerative role for these tyrosine kinases (Negro et al., FASEB J 2002, 16(2), 210-212). Alpha-synuclein can be Ser-phosphorylated by protein kinases CKI and CKII (Okochi et al., J Biol Chem 2000, 275(1), 390-397). The residue Ser-129 is also phosphorylated by G-protein-coupled receptor protein kinases (Pronin et al., J Biol Chem 2000, 275(34), 26515-26522). Extensive and selective phosphorylation of alpha-synuclein at Ser-129 is evident in synucleinopathy lesions, including Lewy bodies (Fujiwara et al., Nat Cell Biol 2002, 4(2); 160-164). Other post-translational modifications in the carboxyl-terminal, including glycosylation on Ser-129 (McLean et al., Neurosci Lett 2002, 323(3), 219-223) and nitration on Tyr-125, -133, and -136 (Takahashi et al., Brain Res 2002, 938(1-2), 73-80), may affect aggregation of alpha-synuclein. Truncation of the carboxyl-terminal region by proteolysis has been reported to play a role in alpha-synuclein fibrillogenesis in various neurodegenerative diseases (Rochet et al., Biochemistry 2000, 39(35), 10619-10626). Full-length as well as partially truncated and insoluble aggregates of alpha-synuclein have been detected in highly purified Lewy bodies (Crowther et al., FEBS Lett 1998, 436(3), 309-312).

Abnormal protein aggregation appears to be a common feature in aging brain and in several neurodegenerative diseases (Trojanowski et al., 1998, Cell Death Differ. 1998, 5(10), 832-837, Koo et al., Proc Natl Acad Sci. 1999, 96(18), 9989-9990, Hu et al., Chin. Sci. Bull. 2001, 46, 1-3); although a clear role in the disease process remains to be defined. In in vitro models, alpha-synuclein (or some of its truncated forms) readily assembles into filaments resembling those isolated from the brain of patients with Lewy Body (LB) dementia and familiar PD (Crowther et al., FEBS Lett 1998, 436(3), 309-312). Alpha-synuclein and its mutated forms (A53T and A30P) have a random coil conformation and do not form significant secondary structures in aqueous solution at low concentrations; however, at higher concentrations they are prone to self-aggregate, producing amyloid fibrils (Wood et al., J Biol Chem 1999, 274(28), 19509-19512). Several differences in the aggregation behavior of the PD-linked mutants and the wild-type protein have been documented. Monomeric alpha-synuclein aggregates in vitro form stable fibrils via a metastable oligomeric (i.e., protofibril) state (Volles et al., Biochemistry 2002, 41(14), 4595-4602).

Parkinson's disease (PD) is the most common neurodegenerative motor disorder. PD is mainly an idiopathic disease, although in at least 5% of the PD patients the pathology is linked to mutations in one or several specific genes. Several point mutations have been described in the alpha-synuclein gene (A30P, E46K, H50Q, G51 D, A53T) which cause familial PD with autosomal dominant inheritance. Furthermore, duplications and triplications of the alpha-synuclein gene have been described in patients that developed PD, underlining the role of alpha-synuclein in PD pathogenesis (Lesage et al., Hum. Mol. Genet., 2009, 18, R48-59). The pathogenesis of PD remains elusive. However, growing evidence suggests a role for the pathogenic folding of the alpha-synuclein protein that leads to the formation of amyloid-like fibrils. Indeed, the hallmarks of PD are the presence of intracellular alpha-synuclein aggregate structures called Lewy Bodies and neurites mainly in the nigral neurons, as well as the death of dopaminergic neurons in the substantia nigra and elsewhere. Alpha-synuclein is a natively unfolded presynaptic protein that can misfold and aggregate into larger oligomeric and fibrillar forms which are linked to the pathogenesis of PD. Recent studies have implicated small soluble oligomeric and protofibrillar forms of alpha-synuclein as the most neurotoxic species (Lashuel et al., J. Mol. Biol., 2002, 322, 1089-102). However, the precise role of alpha-synuclein in the neuronal cell toxicity remains to be clarified (review: Cookson, Annu. Rev. Biochem., 2005, 74, 29-52).

Besides Parkinson's disease, the accumulation of aggregated alpha-synuclein into Lewy bodies is a characteristic of all Lewy body diseases, including Parkinson's disease with dementia (PDD), and dementia with Lewy bodies (DLB) (Capouch et al., Neurol Ther. 2018, 7, 249-263). In DLB, Lewy Bodies are diffusely distributed throughout the cortices of the brain and in addition to Lewy Bodies and neurites, more threads and dot-like structures (Lewy dots) were found to be immunopositive for a-syn phosphorylated at Ser-129 (Outeiro et al., Mol Neurodegener. 2019, 14, 5). Alpha-synuclein agggregates are also found in multiple system atrophy (MSA). MSA is a rare and sporadic neurodegenerative disorder that manifests with rapidly progressive autonomic and motor dysfunction, as well as variable cognitive decline. Such disorders include Shy-Drager syndrome, striatonigral degeneration and olivopontocerebellar atrophy. The disease can be clinically sub-classified in parkinsonian (MSA-P) or cerebellar (MSA-C) variant, depending on the predominant motor phenotype (Fanciulli et al., N Engl J Med 2015; 372, 249-63). It is characterized by the aggregation of alpha-synuclein in the cytoplasm of oligodendrocytes, forming glial cytoplasmic inclusions (GCIs). GCIs, consisting primarily of fibrillary forms of a-synuclein, are the neuropathological hallmark of MSA and are found throughout the neocortex, hippocampus, brainstem, spinal cord and dorsal root ganglia (Galvin et al., Arch Neurol. 2001, 58, 186-90). GCIs are considered a central player in the pathogenesis of MSA. A correlation between the GCI load and the degree of neuronal loss has been reported in both the striatonigral and the olivopontocerebellar regions (Stefanova et al., Neuropathol Appl Neurobiol. 2016, 42, 20-32). Furthermore, a causative link between GCIs and the induction of neuronal loss has been shown in transgenic mice overexpressing human alpha-synuclein in oligodendrocytes under various oligodendroglia-specific promoters. A key event in the pathophysiological cascade is considered to be the permissive templating ('prion-like' propagation) of misfolded alpha-synuclein.

The diagnosis of Parkinson's disease is largely clinical and depends on the presence of a specific set of symptoms and signs (the initial core feature being bradykinesia, rigidity, rest tremor and postural instability), the absence of atypical features, a slowly progressive course, and the response to a symptomatic drug therapy, mainly limited to a dopamine replacement therapy. The accurate diagnosis requires sophisticated clinical skills and is open to a degree of subjectivity and error, as several other degenerative and non-degenerative diseases can mimic PD symptoms (multiple system atrophy (MSA), progressive supranuclear palsy (PSP), AD, essential tremor, dystonic tremor), (Guideline No. 113: Diagnosis and pharmacological management of Parkinson's disease, January 2010. SIGN). The final confirmation of the pathology can only be made by post-mortem neuropathological analysis.

Computed tomography (CT) and conventional magnetic resonance imaging (MRI) brain scans of people with PD usually appear normal. These techniques are nevertheless useful to rule out other diseases that can be secondary causes of parkinsonism, such as basal ganglia tumors, vascular pathology and hydrocephalus. A specific technique of MRI, diffusion MRI, has been reported to be useful at discriminating between typical and atypical parkinsonism, although its exact diagnostic value is still under investigation. Dopaminergic function in the basal ganglia can be measured with different PET and SPECT radiotracers. Examples are ioflupane ($^{123}I$) (trade name DaTSCAN) and iometopane (Dopascan) for SPECT or fluorodeoxyglucose ($^{18}F$) ($^{18}F$-

FDG) and dihydrotetrabenazine ($^{11}C$) ($^{11}C$-DTBZ) for PET. A pattern of reduced dopaminergic activity in the basal ganglia can aid in diagnosing PD, particularly in the symptomatic stage (Brooks, J. Nucl. Med., 2010, 51, 596-609; Redmond, Neuroscientist, 2002, 8, 457-88; Wood, Nat. Rev. Neurol., 2014, 10, 305).

Strategies are being developed to apply recent advances in understanding the potential causes of Parkinson's disease to the development of biochemical biomarkers (Schapira Curr Opin Neurol 2013; 26(4):395-400). Such biomarkers that have been investigated in different body fluids (cerebrospinal fluid (CSF), plasma, saliva) include alpha-synuclein levels but also DJ-1, Tau and Abeta, as well as neurofilaments proteins, interleukins, osteopontin and hypocrontin (Schapira Curr Opin Neurol 2013; 26(4):395-400), but so far none of these biomarkers alone or in combination can be used as a determinant diagnostic test. To our knowledge, no approved alpha-synuclein diagnostic agent is currently on the market or available for clinical trials despite a crucial need for Parkinson's disease research and drug development (Eberling et al., J Parkinsons Dis. 2013; 3(4):565-7).

The ability to image alpha-synuclein deposition in the brain would be a huge achievement for alpha-synucleopathies research, including Parkinson's disease research, diagnosis, and drug development. The accumulation of aggregated alpha-synuclein in the brain is considered a key pathological hallmark of PD and can start many years before the appearance of the symptoms. Therefore, alpha-synuclein is a priority target for drug development given not only its likely contribution to neurodegeneration but also because it can offer the possibility to treat the disease while still in the asymptomatic or prodromal stages. In vivo imaging of alpha-synuclein pathology could be useful as a biomarker to (i) detect the presence of the disease potentially in early stages, (ii) to evaluate disease progression and (iii) to be used as a pharmacodynamics tool for drug development. The development of an alpha-synuclein PET imaging agent is considered nowadays key for an accurate diagnosis of synucleinopathies as well as to support the clinical development of therapeutics targeting alpha-synuclein, starting from the optimal selection of the trial population (Eberling, Dave and Frasier, J. Parkinson's Disease, 3, 565-567 (2013)). Despite a huge effort to identify an alpha-synuclein PET ligand, so far only compounds that bind with reasonably high affinity to artificial alpha-synuclein fibrils were identified but none of them were confirmed in human clinical trials. They are not optimal for a number of reasons: low affinity or no binding was observed on pathological aggregates of alpha-synuclein present in the diseased brains, low or no selectivity for alpha-synuclein over other aggregated proteins was reported and inappropriate physicochemical properties for their use as brain-penetrant PET agents (Eberling et al., J Parkinsons Dis. 2013; 3(4):565-7; Neal et al., Mol Imaging Biol. 2013; 15:585-595; Bagchi et al., PLoS One 2013; 8(2):e55031; Yu et al., Bioorganic and Medicinal chemistry 2012; 20:4625-4634; Zhang et al., Appl Sci (Basel) 2014; 4(1):66-78; Chu et al., J Med Chem, 2015, 58 (15):6002-17).

Therefore, there is a clear need to find molecular probes with high alpha-synuclein selectivity which recognize and bind to the pathological alpha-synuclein. In order to reduce background signal interference resulting from non-specific off-target binding and to reduce dosing requirements, alpha-synuclein imaging compounds should bind with high affinity and selectivity to their target. For imaging of alpha-synuclein aggregates associated with neurological diseases such as Parkinson's disease, imaging compounds need to penetrate the blood brain barrier and pass into the relevant regions of the brain. For targeting intracellular amyloid-like inclusions such as alpha-synuclein, cell permeability is a further requirement of imaging compounds. A further prerequisite in order to avoid unnecessary accumulation of the compound which may result in increased risk of unwanted side-effects is a fast compound wash-out from the brain (or other targeting organ).

WO 2011/128455 refers to specific compounds which are suitable for treating disorders associated with amyloid proteins or amyloid-like proteins. US 2012/0302755 relates to certain imaging agents for detecting neurological dysfunction. Further compounds for the diagnosis of neurodegenerative disorders on the olfactory epithelium are discussed in WO 2012/037928.

WO 2010/063701 refers to a certain in vivo imaging agent for use in a method to determine the presence of, or susceptibility to, Parkinson's disease, wherein the in vivo imaging agent comprises an α-synuclein binder labelled with an in vivo imaging moiety, and wherein the in vivo imaging agent binds to α-synuclein with a binding affinity.

US 2014/0142089 relates to a method for preventing or treating a degenerative brain disease, the method comprising administering to a subject in need thereof an effective amount of a pharmaceutical composition comprising a specific compound, a pharmaceutically acceptable salt, an isomer, a solvate, a hydrate, and a combination thereof.

WO 2009/155017 describes aryl or heteroaryl substituted azabenzoxazole derivatives, which are stated to be useful as tracers in positron emission tomography (PET) imaging to study amyloid deposits in the brain in vivo to allow diagnosis of Alzheimer's disease.

WO 2016/033445 refers to a specific compound for imaging huntingtin protein.

WO 2017/153601 and WO 2019/234243 refer to bicyclic compounds for diagnosing a-synuclein aggregates.

It was surprisingly found that a new class of compounds of formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof, is capable of binding to alpha-synuclein. Thus, the compounds qualify as a PET tracer for the imaging of pathological a-syn aggregates in PD and other alpha-synucleinopathies when the inventive compounds are radiolabelled with suitable radioisotopes.

SUMMARY OF THE INVENTION

It is an object of the present invention to provide compounds that can be employed in diagnosing a disease, disorder or abnormality associated with an alpha-synuclein aggregates, including, but not limited to, Lewy bodies and/or Lewy neurites (such as Parkinson's disease), prognosing such a disease, disorder or abnormality, and monitoring the progression of such a disease, disorder or abnormality. In particular, the compounds should be suitable for determining a predisposition to such a disease, disorder or abnormality, monitoring the evolution of the disease, disorder or abnormality, or predicting the responsiveness of a patient who is suffering from such a disease, disorder or abnormality to the treatment with a certain medicament.

Furthermore, there exists a clinical need for compounds which can be used as imaging agents for alpha-synuclein aggregates including, but not limited to, Lewy bodies and/or Lewy neurites. In particular, it was an object of the present invention to provide compounds that are suitable in a diagnostic composition for positron emission tomography imaging of alpha-synucleinopathies, e.g., wherein the compounds are detectably labelled with $^{18}F$ or other labelled moieties.

The present inventors have surprisingly found that these objects can be achieved by the compounds of formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof, as described hereinafter.

The compounds of formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof, display potent binding affinity to alpha-synuclein aggregates in mammalian (e.g., human) tissues. Moreover, the compounds of formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof, display potent selectivity for a-syn over other protein aggregates associated with neurodegeneration enabling the differentiation of PD from other proteinopathies that share common clinical and pathological features. Due to their unique design features, these compounds display properties such as appropriate lipophilicity and molecular weight, brain uptake and pharmacokinetics, cell permeability, solubility, and autofluorescence in order to be successful imaging probes for the detection and quantification of alpha-synuclein aggregates including, but not limited to, Lewy bodies and/or Lewy neurites in vivo, ex vivo and in vitro.

The present invention discloses novel compounds of formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof, or of subformulae thereof, as disclosed herein, having enhanced binding properties to alpha-synuclein aggregates including, but not limited to, Lewy bodies and/or Lewy neurites. The compounds of this invention may be labelled (e.g., radiolabelled), so that they may be used for in vitro, ex vivo and in vivo imaging to detect alpha-synuclein aggregates including, but not limited to, Lewy bodies and/or Lewy neurites. The present invention provides methods for the detection of alpha-synuclein aggregates including, but not limited to, Lewy bodies and/or Lewy neurites, ex vivo using a compound of formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof, or a pharmaceutical composition thereof. The present invention provides compounds of formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof, for use as diagnostic imaging agents, particularly for presymptomatic or prodromal detection of Parkinson's disease and/or other synucleinopathies, e.g., using positron emission tomography (PET). The compounds of the invention can serve as a biomarker for monitoring the topographic and temporal progression of the pathology, leading to improvement of clinical diagnosis study design and outcome. The present invention further provides a diagnostic composition comprising a compound of formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof, and at least one pharmaceutically acceptable excipient, carrier, diluent or adjuvant.

The present invention is summarized in the following items:

The invention is directed to a compound of formula (I):

(I)

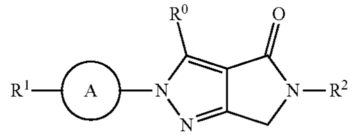

or a detectably labelled compound, stereoisomer, racemic mixture, pharmaceutically acceptable salt, hydrate, or solvate thereof, wherein

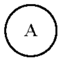

is an aryl or a heteroaryl which is directionally selected from the following:

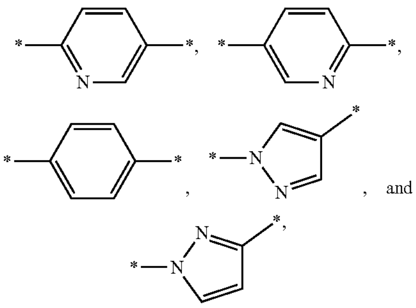

, and $R^0$ is H or $C_1$-$C_4$alkyl;

$R^1$ is —CN; or halo; or $C_1$-$C_4$alkyl; or $C_1$-$C_4$alkoxy; or —N($C_1$-$C_4$alkyl)$_2$; or —NH($C_1$-$C_4$alkyl); or H; or $R^1$ is —NH—$C_3$-$C_6$cycloalkyl, $C_3$-$C_6$cycloalkyl, or heterocyclyl, each of which is optionally substituted with at least one halo;

$R^2$ is aryl, or 5-membered or 6-membered heteroaryl, wherein $R^2$ is selected from the following:

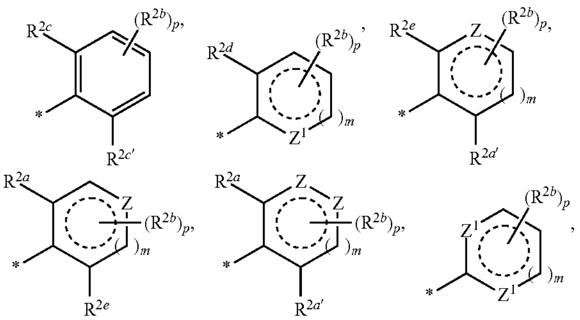

-continued

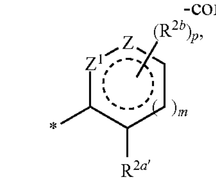,
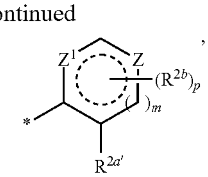,
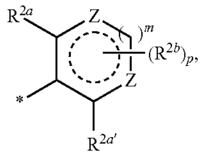 and 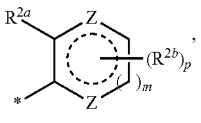, wherein $R^{2a}$, $R^{2a'}$ are independently selected from H, or F;

$R^{2b}$ is independently selected from F, —OH, $C_1$-$C_4$alkyl, halo$C_1$-$C_4$alkyl, —$NH_2$, —CN, or $C_1$-$C_4$alkoxy;

$R^{2c}$, $R^{2c'}$ are independently selected from H, F, OH, $OCH_3$, or $CH_3$;

$R^{2d}$ is selected from H, F, or —OH;

$R^{2e}$ is selected from H, OH, $CH_3$, or F;

Z is independently N, NH, N($C_1$-$C_4$alkyl), N(halo$C_1$-$C_4$alkyl), O, or S;

$Z^1$ is independently N, NH, O, or S;

p is 0, 1 or 2;

m is 0 or 1;

as valency permits,  is a combination of single and double bonds; and

* is the position of bonding.

In another aspect the invention is also directed to a compound having the following formulae (IIa)

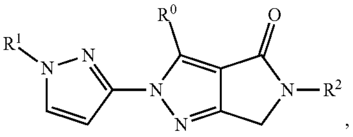, or (IIb)

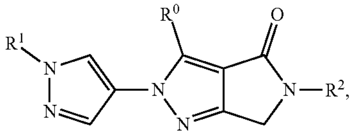, or a detectably labelled compound, stereoisomer, racemic mixture, pharmaceutically acceptable salt, hydrate, or solvate thereof.

In another aspect the invention is also directed to a compound having the following formulae (IIIa)

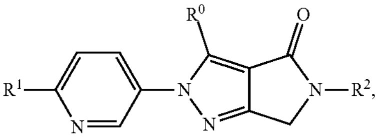, (IIIb)

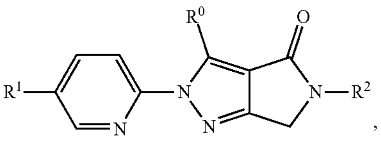, or

-continued (IIIc)

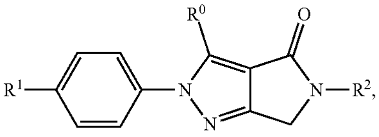, or a detectably labelled compound, stereoisomer, racemic mixture, pharmaceutically acceptable salt, hydrate, or solvate thereof.

In one aspect, the compound of the formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof, is for use in the imaging of alpha-synuclein aggregates including, but not limited to, Lewy bodies and/or Lewy neurites, wherein the compound is preferably for use in positron emission tomography imaging of alpha-synuclein aggregates including, but not limited to, Lewy bodies and/or Lewy neurites.

In a further aspect, the present invention refers to a method of imaging a disease, disorder or abnormality associated with alpha-synuclein aggregates including, but not limited to, Lewy bodies and/or Lewy neurites, in a subject, the method comprising the steps:

(a) Administering a compound of the formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof to the subject;

(b) Allowing the compound to bind to the alpha-synuclein aggregates, including, but not limited to, Lewy bodies and/or Lewy neurites; and (c) Detecting the compound bound to the alpha-synuclein aggregates, including, but not limited to, Lewy bodies and/or Lewy neurites.

In a further aspect, the present invention is directed to a method of imaging a disease, disorder or abnormality associated with alpha-synuclein aggregates including, but not limited to, Lewy bodies and/or Lewy neurites, in a subject, the method comprising the steps:

(a) Administering a compound of the formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof to the subject; and (b) Imaging the brain of the subject.

In a further aspect, the present invention refers to a method of positron emission tomography (PET) imaging of alpha-synuclein aggregates, including but not limited to, Lewy bodies and/or Lewy neurites, in a tissue of a subject, the method comprising the steps:

(a) Administering a compound of the formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof to the subject;

(b) Allowing the compound to penetrate into the tissue of the subject; and (c) Collecting a positron emission tomography (PET) image of the tissue of the subject; wherein the tissue is tissue of the central nervous system (CNS), of the eye or brain tissue, preferably wherein the tissue is brain tissue.

In a further aspect, the present invention is directed a method of detecting a neurological disease, disorder or abnormality associated with alpha-synuclein aggregates, including but not limited to, Lewy bodies and/or Lewy neurites, in a subject, the method comprising the steps:

(a) Administering a compound of the formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof to the subject;

(b) Allowing the compound to bind to the alpha-synuclein aggregates including, but not limited to, Lewy bodies and/or Lewy neurites; and (c) Measuring the radioactive signal of the compound, which is bound to the alpha-synuclein aggregates, including but not limited to, Lewy bodies and/or Lewy neurites.

In a further aspect, the present invention is directed to a method for the detection and/or quantification of alpha-synuclein aggregates, including but not limited to, Lewy bodies and/or Lewy neurites, in a tissue of a subject, the method comprising the steps:

(a) Contacting the tissue with a compound of the formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof to the subject;

(b) Allowing the compound to bind to the alpha-synuclein aggregates, including, but not limited to, Lewy bodies and/or Lewy neurites; and (c) Detecting and/or quantifying the compound bound to the alpha-synuclein aggregates, including but not limited to, Lewy bodies and/or Lewy neurites, using positron emission tomography.

In yet another aspect, the present invention refers to a method of the diagnostic imaging of the brain of a subject, the method comprising the steps:

(a) Administering a compound of the formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof to the subject; and (b) Obtaining an image of the brain of the subject using positron emission tomography.

The present invention is also directed to a method of collecting data for the diagnosis of a disease, disorder or abnormality associated with alpha-synuclein aggregates including, but not limited to, Lewy bodies and/or Lewy neurites, is also disclosed herein, wherein the method comprising the steps:

(a) Bringing a sample or a specific body part or body area suspected to contain alpha-synuclein aggregates including, but not limited to, Lewy bodies and/or Lewy neurites into contact with a compound of the formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof;

(b) Allowing the compound to bind to the alpha-synuclein aggregates including, but not limited to, Lewy bodies and/or Lewy neurites;

(c) Detecting the compound bound to the alpha-synuclein aggregates including, but not limited to, Lewy bodies and/or Lewy neurites; and (d) Optionally correlating the presence or absence of the compound bound to the alpha-synuclein aggregates including, but not limited to, Lewy bodies and/or Lewy neurites with the presence or absence of the alpha-synuclein aggregates including, but not limited to, Lewy bodies and/or Lewy neurites in the sample or specific body part or body area.

The present invention also refers to a method of collecting data for determining a predisposition to a disease, disorder or abnormality associated with alpha-synuclein aggregates including, but not limited to, Lewy bodies and/or Lewy neurites, the method comprising the steps:

(a) Bringing a sample or a specific body part or body area suspected to contain alpha-synuclein aggregates including, but not limited to, Lewy bodies and/or Lewy neurites into contact with a compound of the formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof;

(b) Allowing the compound to bind to the alpha-synuclein aggregates including, but not limited to, Lewy bodies and/or Lewy neurites;

(c) Detecting the compound bound to the alpha-synuclein aggregates including, but not limited to, Lewy bodies and/or Lewy neurites; and (d) Optionally correlating the presence or absence of the compound bound to the alpha-synuclein aggregates including, but not limited to, Lewy bodies and/or Lewy neurites with the presence or absence of the alpha-synuclein aggregates including, but not limited to, Lewy bodies and/or Lewy neurites in the sample or specific body part or body area.

In a further aspect the present invention relates to a method of collecting data for prognosing a disease, disorder or abnormality associated with alpha-synuclein aggregates including, but not limited to, Lewy bodies and/or Lewy neurites, wherein the method comprises the steps:

(a) Bringing a sample, a specific body part or body area suspected to contain alpha-synuclein aggregates including, but not limited to, Lewy bodies and/or Lewy neurites into contact with a compound of the formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof;

(b) Allowing the compound to bind to the alpha-synuclein aggregates including, but not limited to, Lewy bodies and/or Lewy neurites;

(c) Detecting the compound bound to the alpha-synuclein aggregates including, but not limited to, Lewy bodies and/or Lewy neurites;

(d) Optionally correlating the presence or absence of the compound bound to the alpha-synuclein aggregates including, but not limited to, Lewy bodies and/or Lewy neurites with the presence or absence of the alpha-synuclein aggregates including, but not limited to, Lewy bodies and/or Lewy neurites in the sample or specific body part or body area; and (e) Optionally repeating steps (a) to (c) and, if present, optional step (d) at least one time.

In another aspect the present invention is directed to a method of collecting data for monitoring the progression of a disease, disorder or abnormality associated with alpha-synuclein aggregates including, but not limited to, Lewy bodies and/or Lewy neurites in a patient, the method comprising the steps:

(a) Bringing a sample, a specific body part or body area suspected to contain alpha-synuclein aggregates including, but not limited to, Lewy bodies and/or Lewy neurites into contact with the compound of the formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof;
(b) Allowing the compound to bind to the alpha-synuclein aggregates including, but not limited to, Lewy bodies and/or Lewy neurites;
(c) Detecting the compound bound to the alpha-synuclein aggregates including, but not limited to, Lewy bodies and/or Lewy neurites;
(d) Optionally correlating the presence or absence of the compound bound to the alpha-synuclein aggregates including, but not limited to, Lewy bodies and/or Lewy neurites with the presence or absence of the alpha-synuclein aggregates including, but not limited to, Lewy bodies and/or Lewy neurites in the sample or specific body part or body area; and
(e) Optionally repeating steps (a) to (c) and, if present, optional step (d) at least one time.

In a further aspect, the present invention relates to a method of collecting data for predicting responsiveness of a patient suffering from a disease, disorder or abnormality associated with alpha-synuclein aggregates including, but not limited to, Lewy bodies and/or Lewy neurites to a treatment of the disease, disorder or abnormality associated with alpha-synuclein aggregates including, but not limited to, Lewy bodies and/or Lewy neurites, method comprising the steps:

(a) Bringing a sample, a specific body part or body area suspected to contain alpha-synuclein aggregates including, but not limited to, Lewy bodies and/or Lewy neurites into contact with a compound of formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof;
(b) Allowing the compound to bind to the alpha-synuclein aggregates including, but not limited to, Lewy bodies and/or Lewy neurites;
(c) Detecting the compound bound to the alpha-synuclein aggregates including, but not limited to, Lewy bodies and/or Lewy neurites;
(d) Optionally correlating the presence or absence of the compound bound to the alpha-synuclein aggregates including, but not limited to, Lewy bodies and/or Lewy neurites with the presence or absence of the alpha-synuclein aggregates including, but not limited to, Lewy bodies and/or Lewy neurites in the sample or specific body part or body area; and
(e) Optionally repeating steps (a) to (c) and, if present, optional step (d) at least one time.

The invention is further directed to a diagnostic or pharmaceutical composition comprising a compound of formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof, and at least one pharmaceutically acceptable excipient, carrier, diluent or adjuvant.

In another aspect the invention is further directed to a compound of formula (IV-F)

(IV-F)

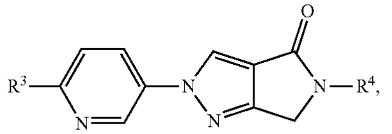

or a detectably labelled compound, stereoisomer, racemic mixture, pharmaceutically acceptable salt, hydrate, or solvate thereof, wherein $R^3$ is selected from

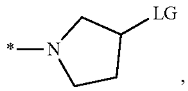
,
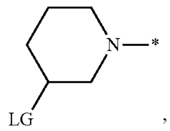
,
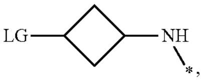
, or
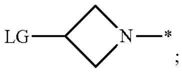
;

$R^4$ is an aryl, or a 5-membered or 6-membered heteroaryl, wherein $R^4$ is selected from

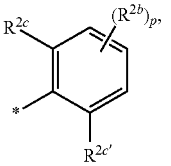
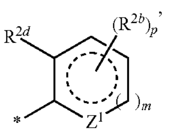
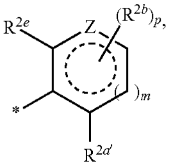
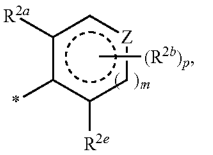
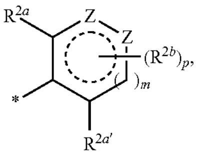
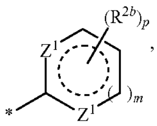
,
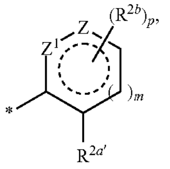
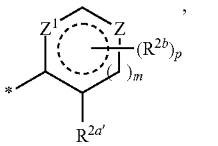
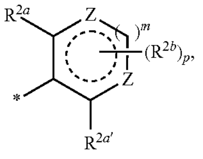
and
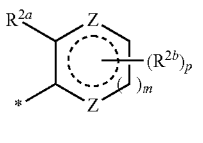

wherein $R^{2a}$, $R^{2a'}$ are independently selected from H, or F;

$R^{2b}$ is independently selected from F, —OH, $C_1$-$C_4$alkyl, halo$C_1$-$C_4$alkyl, —$NH_2$, —CN, or $C_1$-$C_4$alkoxy;

$R^{2c}$, $R^{2c'}$ are independently selected from H, F, OH, $OCH_3$, or $CH_3$;

$R^{2d}$ is selected from H, F, or —OH;

$R^{2e}$ is selected from H, OH, $CH_3$, or F;

Z is independently N, NH, N($C_1$-$C_4$alkyl), N(halo$C_1$-$C_4$alkyl), O, or S;

$Z^1$ is independently N, NH, O, or S;

p is 0, 1 or 2;

m is 0 or 1;

as valency permits,  is a combination of single and double bonds; and

* is the position of bonding.

In another aspect the invention is further directed to compound of formula (IV-H)

(IV-H)

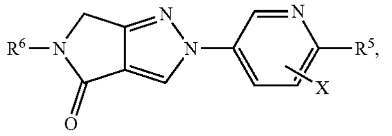

or a detectably labelled compound, stereoisomer, racemic mixture, pharmaceutically acceptable salt, hydrate, or solvate thereof, wherein $R^5$ is selected from

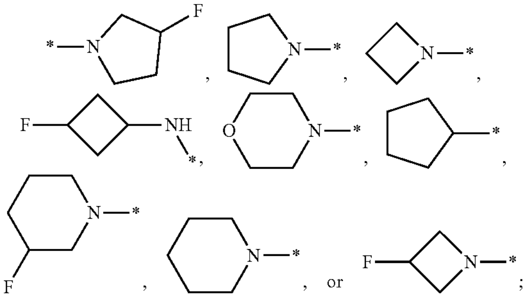

, or ;

$R^6$ is an aryl or a 5-membered or 6-membered heteroaryl, wherein $R^6$ is selected from the following:

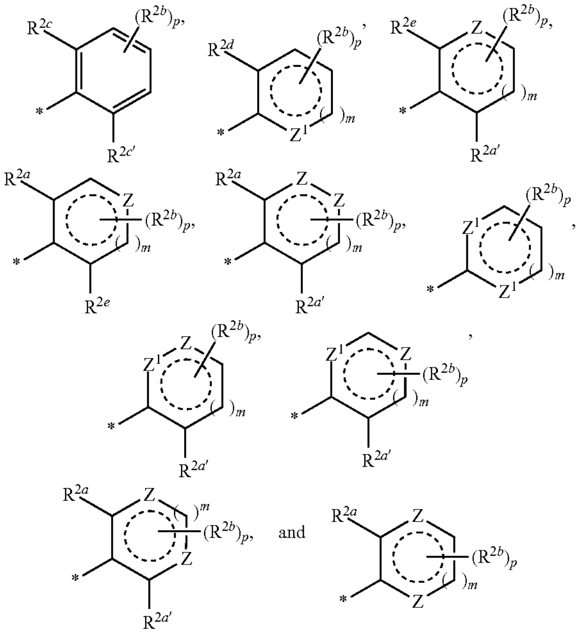

and wherein $R^{2a}$, $R^{2a'}$ are independently selected from H, X or F;

$R^{2b}$ is independently selected from X, F, —OH, $C_1$-$C_4$alkyl, halo$C_1$-$C_4$alkyl, —$NH_2$, —CN, or $C_1$-$C_4$alkoxy, wherein $C_1$-$C_4$alkyl, halo$C_1$-$C_4$alkyl, or $C_1$-$C_4$alkoxy optionally comprise one or more X;

$R^{2c}$, $R^{2c'}$ are independently selected from X, H, F, OH, $OCH_3$, or $CH_3$;

$R^{2d}$ is selected from X, H, F, or —OH;

$R^{2e}$ is selected from X, H, OH, $CH_3$, or F;

Z is independently N, NH, N($C_1$-$C_4$alkyl), N(halo$C_1$-$C_4$alkyl), O, or S;

$Z^1$ is independently N, NH, O, or S;

p is 0, 1 or 2;

m is 0 or 1;

as valency permits,  is a combination of single and double bonds;

* is the position of bonding;

Fluoro is $^{19}F$;

X is Bromo, Chloro, or Iodo; and wherein $R^6$ comprises at least one X.

In another aspect the invention is further directed to a method for preparing the compound of formula (III-F), or a detectably labelled compound, stereoisomer, racemic mixture, pharmaceutically acceptable salt, hydrate, or solvate thereof, comprising reacting the compound of formula (IV-F) with a $^{18}F$-fluorinating agent, so that the Leaving Group (LG) is replaced by $^{18}F$.

The invention is further directed to a method for preparing the compound of formula (III-H), or a detectably labelled compound, stereoisomer, racemic mixture, pharmaceutically acceptable salt, hydrate, or solvate thereof, comprising reacting the compound of formula (IV-H) with a tritating agent, so that X is replaced by $^3H$.

In another aspect the invention is further directed to compound of formula (IV-J), (IV-J)

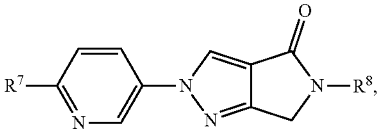

or a stereoisomer, racemic mixture, pharmaceutically acceptable salt, hydrate, or solvate thereof, wherein $R^7$ is selected from,

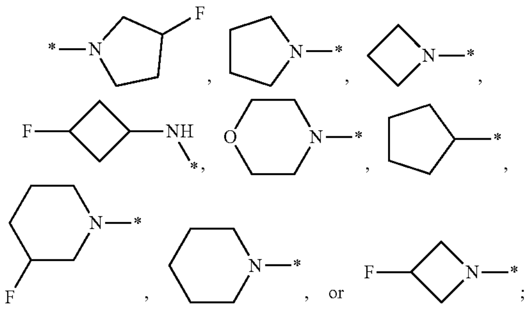

, or ;

$R^8$ is selected from the following:

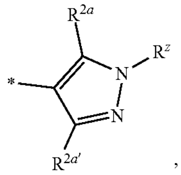
,
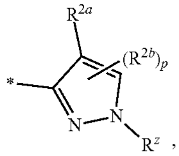
, and
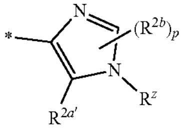

wherein $R^{2a}$, $R^{2a'}$ are independently selected from H, or F;

$R^{2b}$ is independently selected from F, —OH, $C_1$-$C_4$alkyl, halo$C_1$-$C_4$alkyl, —$NH_2$, —CN, or $C_1$-$C_4$alkoxy;

p is 0, 1 or 2;

$R^z$ is selected from H, $C_1$-$C_4$alkyl or halo$C_1$-$C_4$alkyl;

as valency permits,  is a combination of single and double bonds;

Fluoro is $^{19}F$; and

* is the position of bonding.

In another aspect the invention is further directed to a method for preparing the compound of formula (III-H), or a detectably labelled compound, stereoisomer, racemic mixture, pharmaceutically acceptable salt, hydrate, or solvate thereof, comprising reacting the compound of formula (IV-J) with a $^3H$ radiolabeling agent.

The invention is further directed to the use of the compound according to compound of formula (I), or of subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof, as an in vitro analytical reference or an in vitro screening tool.

The invention is further directed to a test kit for detection and/or diagnosis of a disease, disorder or abnormality associated with alpha-synuclein aggregates, wherein the test kit comprises at least one compound of formula (I), or of subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof.

The invention is further directed to a kit for preparing a radiopharmaceutical preparation, wherein the kit comprises a sealed vial containing at least one compound of formula (IV-F) or (IV-H), or (IV-J), or a detectably labelled compound, stereoisomer, racemic mixture, pharmaceutically acceptable salt, hydrate, or solvate thereof.

In the following, the compounds of the formulae (I), or of subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof, are referred to as the compounds of the present invention. The compounds of the formulae (IV-F), (IV-H) and (IV-J) will be referred to as the precursors of the compounds of the present invention.

The present invention is also defined by the following clauses

A1. A compound of formula (I)

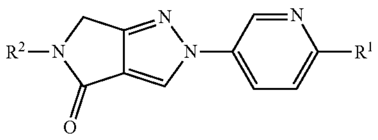
(I)

and all detectably labelled compounds, stereoisomers, racemic mixtures, pharmaceutically acceptable salts, hydrates, or solvates thereof, wherein $R^1$ is a pyrrolidine substituted with fluoro as follows,

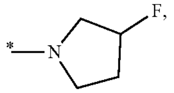

$R^2$ is a 5-membered or 6-membered heteroaryl comprising one or two N atoms, wherein the heteroaryl is optionally substituted with methyl, and

* is the position of bonding.

A2. The compound of formula (I) according to clause A1, wherein $R^1$ is pyrrolidine substituted with $^{18}F$ as follows

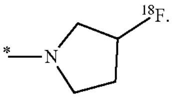

A3. The compound of formula (I) according to clause A1, wherein $R^1$ is pyrrolidine substituted with $^{19}F$ as follows

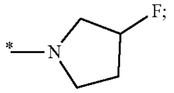

and the compound of formula (I) is detectably labelled at least one available position by $^3H$ (Tritium).

A4. The compound according to any one of clauses A1 to A3 which is

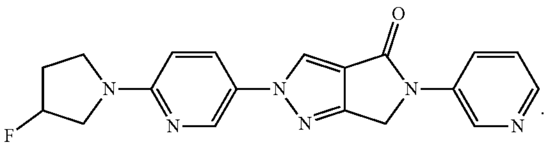 [SMILES: O=C1c2cn(-c3ccc(N4CCC(F)C4)nc3)nc2CN1c1cccnc1]

A5. The compound according to any one of clauses A1 to A4 for use in the imaging of alpha-synuclein aggregates including, but not limited to, Lewy bodies and/or Lewy neurites, wherein the compound is preferably for use in positron emission tomography imaging of alpha-synuclein aggregates including, but not limited to, Lewy bodies and/or Lewy neurites.

A6. The compound according to any one of clauses A1 to A4 for use in the diagnostic of a disease, disorder or abnormality associated with alpha-synuclein aggregates including, but not limited to, Lewy bodies and/or Lewy neurites or a predisposition therefor, wherein the disorder is optionally selected from Parkinson's disease (including sporadic, familial with alpha-synuclein mutations, familial with mutations other than alpha-synuclein, pure autonomic failure or Lewy body dysphagia), Lewy Body dementia (LBD), dementia with Lewy bodies (DLB) (including "pure" Lewy body dementia), Parkinson's disease dementia (PDD), diffuse Lewy body disease (DLBD), sporadic Alzheimer's disease, familial Alzheimer's disease with APP mutations, familial Alzheimer's disease with PS-1, PS-2 or other mutations, familial British dementia, Lewy body variant of Alzheimer's disease, Down syndrome, multiple system atrophy (including Shy-Drager syndrome, striatonigral degeneration or olivopontocerebellar atrophy), traumatic brain injury, chronic traumatic encephalopathy, dementia puglistica, tauopathies (including Pick's disease, frontotemporal dementia, progressive supranuclear palsy, corticobasal degeneration, Niemann-Pick type C1 disease, frontotemporal dementia with Parkinsonism linked to chromosome 17), Creutzfeldt-Jakob disease, Huntington's disease, motor neuron disease, amyotrophic lateral sclerosis (including sporadic, familial or ALS-dementia complex of Guam), neuroaxonal dystrophy, neurodegeneration with brain iron accumulation type 1 (including Hallervorden-Spatz syndrome), prion diseases, ataxia telangiectatica, Meige's syndrome, subacute sclerosing panencephalitis, Gerstmann-Straussler-Scheinker disease, inclusion-body myositis, Gaucher disease, Krabbe disease as well as other lysosomal storage disorders (including Kufor-Rakeb syndrome and Sanfilippo syndrome) and rapid eye movement (REM) sleep behavior disorder, preferably Parkinson's disease.

A7. A method of collecting data for the diagnosis of a disease, disorder or abnormality associated with alpha-synuclein aggregates including, but not limited to, Lewy bodies and/or Lewy neurites in a sample or in a patient, the method comprising:

(a) bringing a sample or a specific body part or body area suspected to contain alpha-synuclein aggregates including, but not limited to, Lewy bodies and/or Lewy neurites into contact with a compound as defined in any one of clauses A1 to A4;

(b) allowing the compound to bind to the alpha-synuclein aggregates including, but not limited to, Lewy bodies and/or Lewy neurites;

(c) detecting the compound bound to the alpha-synuclein aggregates including, but not limited to, Lewy bodies and/or Lewy neurites; and (d) optionally correlating the presence or absence of the compound binding with the alpha-synuclein aggregates including, but not limited to, Lewy bodies and/or Lewy neurites with the presence or absence of alpha-synuclein aggregates including, but not limited to, Lewy bodies and/or Lewy neurites in the sample or specific body part or body area.

A8. A diagnostic composition comprising a compound according to any one of clauses A1 to A4 and a pharmaceutically acceptable excipient, carrier, diluent or adjuvant.

A9. A compound of formula (II-F)

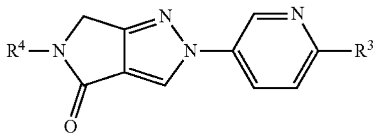

(II-F)

and all detectably labelled compounds, stereoisomers, racemic mixtures, pharmaceutically acceptable salts, hydrates, or solvates thereof, wherein $R^3$ is a pyrrolidine substituted with a Leaving Group (LG) as follows

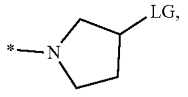

$R^4$ is a 5-membered or 6-membered heteroaryl comprising one or two N atoms, wherein the heteroaryl is optionally substituted with methyl, and is the position of bonding.

A10. The compound of formula (II-F) according to clause A9, wherein LG is selected from halogen, $C_{1-4}$ alkyl sulfonate and $C_{6-10}$ aryl sulfonate.

A11. The compound of formula (II-F) according to clauses A9 or A10 which is

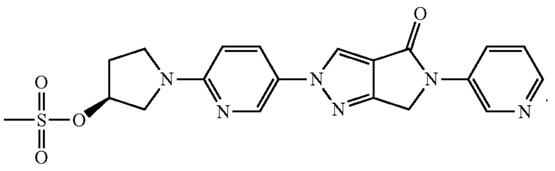 [SMILES: CS(=O)(=O)O[C@H]1CCN(c2ccc(-n3cc4c(n3)CN(c3cccnc3)C4=O)cn2)C1]

A12. A compound of formula (II-H)

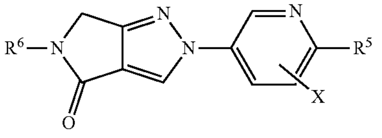

(II-H)

and all detectably labelled compounds, stereoisomers, racemic mixtures, pharmaceutically acceptable salts, hydrates, or solvates thereof, wherein $R^5$ is a pyrrolidine substituted with fluoro as follows

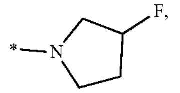 [SMILES: *N1CCC(F)C1]

$R^6$ is a 5-membered or 6-membered heteroaryl comprising one or two N, wherein the heteroaryl is optionally substituted with methyl and/or the heteroaryl is optionally substituted with one or more X, X is halogen or H, with the proviso that at least one X is halogen, and

* is the position of bonding.

A13. The compound of formula (II-H) according to clause A12 which is

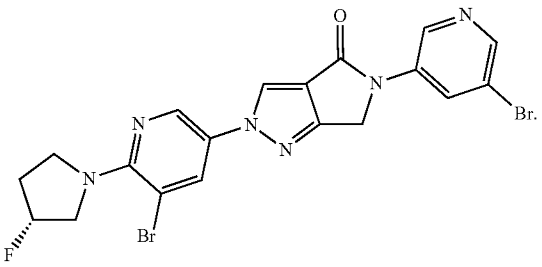 [SMILES: O=C1c2cn(-c3cnc(N4CC[C@@H](F)C4)c(Br)c3)nc2CN1c1cncc(Br)c1]

A14. A method of preparing the compound according to clause A2, comprising reacting the compound according to any one of clauses A9 to A11 with a $^{18}F$-fluorinating agent, so that LG is replaced by $^{18}F$.

A15. The method according to clause 14, wherein the $^{18}F$-fluorinating agent is selected from $K^{18}F$, $H^{18}F$, $Cs^{18}F$, $Na^{18}F$ and tetrabutylammonium [$^{18}F$]fluoride.

A16. Use of the compound according to any one of clauses A1 to A4 as an in vitro analytical reference or an in vitro screening tool.

A17. A test kit for the detection and/or diagnosis of a disorder or abnormality associated with alpha-synuclein aggregates, wherein the test kit comprises at least one compound as defined in any one of clauses A1 to A4.

A18. A kit for preparing a radiopharmaceutical preparation, wherein the kit comprises a sealed vial containing at least one compound as defined in any clauses A9 to A11.

The present invention is also defined by the following clauses

B1. A compound of formula (I)

(I)

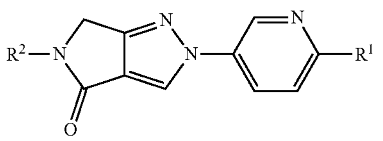

or a detectably labelled compound, stereoisomer, racemic mixture, pharmaceutically acceptable salt, hydrate, or solvate thereof, wherein $R^1$ is a pyrrolidine substituted with fluoro as follows

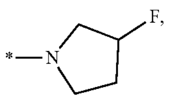 [SMILES: *N1CCC(F)C1]

$R^2$ is a 5-membered or 6-membered heteroaryl comprising one or two N atoms, wherein the heteroaryl is optionally substituted with methyl, and

* is the position of bonding.

B2. The compound of formula (I) according to clause B1, wherein the compound is a detectably labelled compound.

B3. The compound of formula (I) according to clause B2, wherein the detectably labelled compound comprises a detectable label selected from a radioisotope, preferably $^2H$, $^3H$ or $^{18}F$.

B4. The compound of formula (I) according to clause B3, wherein $R^1$ is pyrrolidine substituted with $^{18}F$ as follows

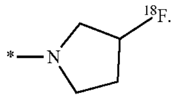

B5. The compound of formula (I) according to clause B3, wherein $R^1$ is pyrrolidine substituted with $^{19}F$ as follows

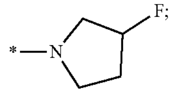 [SMILES: *N1CCC(F)C1]

and the compound of formula (I) is detectably labelled at least at one available position by $^3H$ (Tritium).

B6. The compound according to any one of clauses B1 to B5 which is

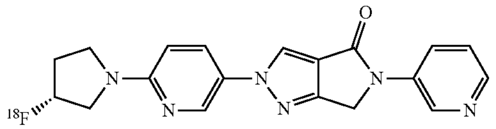

or

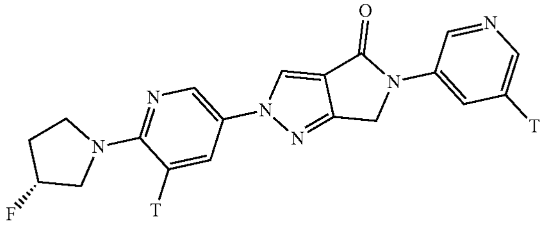

wherein T means $^3H$ (Tritium) and F means $^{19}F$.

B7. The compound according to any one of clauses B1 to B6 for use in the imaging of alpha-synuclein aggregates including, but not limited to, Lewy bodies and/or Lewy neurites, wherein the compound is preferably for use in positron emission tomography imaging of alpha-synuclein aggregates including, but not limited to, Lewy bodies and/or Lewy neurites.

B8. The compound for use according to clause B7, wherein the use is for brain imaging.

B9. The compound for use according to any one of clauses B1 to B6 for use in diagnostics.

B10. The compound for use according to clause B9 for use in the diagnostics of a disease, disorder or abnormality associated with alpha-synuclein aggregates including, but not limited to, Lewy bodies and/or Lewy neurites or a predisposition therefor, wherein the disease, disorder or abnormality is optionally selected from Parkinson's disease (including sporadic, familial with alpha-synuclein mutations, familial with mutations other than alpha-synuclein, pure autonomic failure or Lewy body dysphagia), Lewy Body dementia (LBD), dementia with Lewy bodies (DLB) (including "pure" Lewy body dementia), Parkinson's disease dementia (PDD), diffuse Lewy body disease (DLBD), sporadic Alzheimer's disease, familial Alzheimer's disease with APP mutations, familial Alzheimer's disease with PS-1, PS-2 or other mutations, familial British dementia, Lewy body variant of Alzheimer's disease, Down syndrome, multiple system atrophy (including Shy-Drager syndrome, striatonigral degeneration or olivopontocerebellar atrophy), traumatic brain injury, chronic traumatic encephalopathy, dementia puglistica, tauopathies (including Pick's disease, frontotemporal dementia, progressive supranuclear palsy, corticobasal degeneration, Niemann-Pick type C1 disease, frontotemporal dementia with Parkinsonism linked to chromosome 17), Creutzfeldt-Jakob disease, Huntington's disease, motor neuron disease, amyotrophic lateral sclerosis (including sporadic, familial or ALS-dementia complex of Guam), neuroaxonal dystrophy, neurodegeneration with brain iron accumulation type 1 (including Hallervorden-Spatz syndrome), prion diseases, ataxia telangiectatica, Meige's syndrome, subacute sclerosing panencephalitis, Gerstmann-Straussler-Scheinker disease, inclusion-body myositis, Gaucher disease, Krabbe disease as well as other lysosomal storage disorders (including Kufor-Rakeb syndrome and Sanfilippo syndrome) and rapid eye movement (REM) sleep behavior disorder.

B11. The compound for use according to clauses B10, wherein the disease is Parkinson's disease.

B12. The compound for use according to any one of clauses B7 to B11, wherein the use is in a human.

B13. A method of diagnosing a disease, disorder or abnormality associated with alpha-synuclein aggregates including, but not limited to, Lewy bodies and/or Lewy neurites, or a predisposition therefor in a patient, wherein the method comprises:

a) administering to the patient a diagnostically effective amount of a compound as defined in any one of clauses B1 to B6;

b) allowing the compound to distribute into the tissue of interest; and c) imaging the tissue of interest, wherein an increase in binding of the compound to the tissue of interest compared to a normal control level of binding indicates that the patient is suffering from or is at risk of developing a disease, disorder or abnormality associated with alpha-synuclein aggregates including, but not limited to, Lewy bodies and/or Lewy neurites.

B14. A method of collecting data for the diagnosis of a disease, disorder or abnormality associated with alpha-synuclein aggregates including, but not limited to, Lewy bodies and/or Lewy neurites in a patient, the method comprising:

(a) bringing a sample or a specific body part or body area suspected to contain alpha-synuclein aggregates including, but not limited to, Lewy bodies and/or Lewy neurites into contact with a compound as defined in any one of clauses B1 to B6;

(b) allowing the compound to bind to the alpha-synuclein aggregates including, but not limited to, Lewy bodies and/or Lewy neurites;

(c) detecting the compound bound to the alpha-synuclein aggregates including, but not limited to, Lewy bodies and/or Lewy neurites; and (d) optionally correlating the presence or absence of the compound binding with the alpha-synuclein aggregates including, but not limited to, Lewy bodies and/or Lewy neurites with the presence or absence of alpha-synuclein aggregates including, but not limited to, Lewy bodies and/or Lewy neurites in the sample or specific body part or body area.

B115. A method of collecting data for the diagnosis of a disease, disorder or abnormality associated with alpha-synuclein aggregates in a patient comprising:

(a) bringing a sample or a specific body part or body area suspected to contain alpha-synuclein aggregates into contact with a compound as defined in clauses B1 to B6;

(b) allowing the compound to bind to the alpha-synuclein aggregate;

(c) detecting the compound bound to the alpha-synuclein aggregate; and (d) optionally correlating the presence or absence of compound binding with the alpha-synuclein aggregate with the presence or absence of alpha-synuclein aggregate in the sample or specific body part or body area.

B116. A method of determining the amount of alpha-synuclein aggregate in a tissue and/or a body fluid comprising:

(a) providing a sample representative of the tissue and/or body fluid under investigation;

(b) testing the sample for the presence of alpha-synuclein aggregates with a compound as defined in clauses B1 to B6;

(c) determining the amount of compound bound to the alpha-synuclein aggregates; and (d) calculating the amount of alpha-synuclein aggregates in the tissue and/or body fluid.

B17. A method of collecting data for determining a predisposition to a disease, disorder or abnormality associated with alpha-synuclein aggregates in a patient comprising detecting the specific binding of a compound as defined in clauses B1 to B6 to alpha-synuclein aggregates in a sample or a specific body part or body area which comprises the steps of:

(a) bringing the sample or a specific body part or body area suspected to contain the alpha-synuclein aggregates into contact with the compound as defined in clauses B1 to B6;

(b) allowing the compound to bind to the alpha-synuclein aggregate to form a compound/alpha-synuclein aggregate complex;

(c) detecting the formation of the compound/alpha-synuclein aggregate complex;

(d) optionally correlating the presence or absence of the compound/alpha-synuclein aggregate complex with the presence or absence of alpha-synuclein aggregate in the sample or specific body part or body area; and (e) optionally comparing the amount of the compound/alpha-synuclein aggregate to a normal control value.

B18. A method of collecting data for monitoring residual disease, disorder or abnormality in a patient suffering from a disease, disorder or abnormality associated with alpha-synuclein aggregates who has been treated with a medicament, wherein the method comprises:

(a) bringing a sample or a specific body part or body area suspected to contain alpha-synuclein aggregates into contact with a compound as defined in clauses B1 to B6;

(b) allowing the compound to bind to the alpha-synuclein aggregate to form a compound/alpha-synuclein aggregate complex;
(c) detecting the formation of the compound/alpha-synuclein aggregate complex;
(d) optionally correlating the presence or absence of the compound/alpha-synuclein aggregate complex with the presence or absence of alpha-synuclein aggregates in the sample or specific body part or body area; and
(e) optionally comparing the amount of the compound/alpha-synuclein aggregate to a normal control value.

B19. A method of collecting data for predicting responsiveness of a patient suffering from a disease, disorder or abnormality associated with alpha-synuclein aggregates and being treated with a medicament comprising:
(a) bringing a sample or a specific body part or body area suspected to contain alpha-synuclein aggregates into contact with a compound as defined in clauses B1 to B6;
(b) allowing the compound to bind to the alpha-synuclein aggregate to form a compound/alpha-synuclein aggregate complex;
(c) detecting the formation of the compound/alpha-synuclein aggregate complex;
(d) optionally correlating the presence or absence of the compound/alpha-synuclein aggregate complex with the presence or absence of alpha-synuclein aggregate in the sample or specific body part or body area; and
(e) optionally comparing the amount of the compound/alpha-synuclein aggregate to a normal control value.

B20. A diagnostic composition comprising a compound according to any one of clauses B1 to B6 and a pharmaceutically acceptable excipient, carrier, diluent or adjuvant.

B21. A compound of formula (II-F)

(II-F)

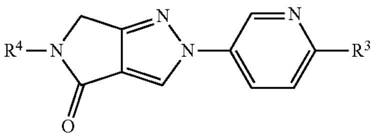

or a stereoisomer, racemic mixture, pharmaceutically acceptable salt, hydrate, or solvate thereof, wherein $R^3$ is a pyrrolidine substituted with a Leaving Group (LG) as follows

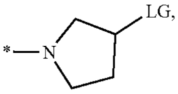

$R^4$ is a 5-membered or 6-membered heteroaryl comprising one or two N atoms, wherein the heteroaryl is optionally substituted with methyl, and

* is the position of bonding.

B22. The compound of formula (II-F) according to clause B21, wherein LG is selected from halogen, $C_{1-4}$ alkyl sulfonate and $C_{6-10}$ aryl sulfonate.

B23. The compound of formula (II-F) according to clause B21 or B22 which is

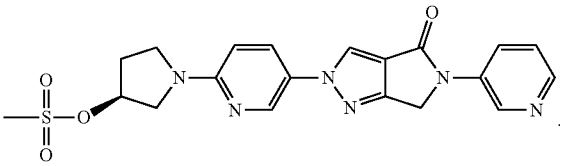 [SMILES: CS(=O)(=O)O[C@H]1CCN(c2ccc(-n3cc4c(n3)CN(c3cccnc3)C4=O)cn2)C1]

B24. A compound of formula (II-H)

(II-H)

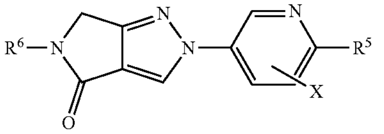

or a stereoisomer, racemic mixture, pharmaceutically acceptable salt, hydrate, or solvate thereof, wherein $R^5$ is a pyrrolidine substituted with fluoro as follows

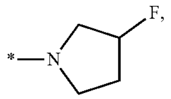

$R^6$ is a 5-membered or 6-membered heteroaryl comprising one or two N, wherein the heteroaryl is optionally substituted with methyl and/or the heteroaryl is optionally substituted with one or more X, X is halogen or H, with the proviso that at least one X is halogen, and

* is the position of bonding.

B25. The compound of formula (II-H) according to clause B24 which is

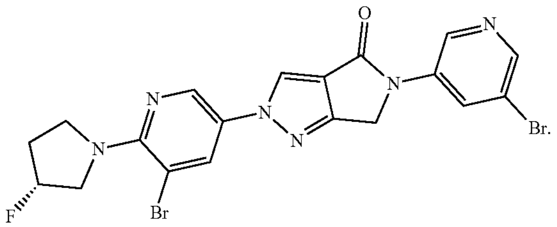 [SMILES: O=C1c2cn(-c3cnc(N4CC[C@@H](F)C4)c(Br)c3)nc2CN1c1cncc(Br)c1]

B26. A method of preparing the compound according to clauses B2, B3 or B4 comprising reacting the compound according to any one of clauses B21 to B23 with a $^{18}F$-fluorinating agent, so that LG is replaced by $^{18}F$.

B27. The method according to clause B26, wherein the $^{18}F$-fluorinating agent is selected from $K^{18}F$, $H^{18}F$, $Cs^{18}F$, $Na^{18}F$ and tetrabutylammonium [$^{18}F$]fluoride.

B28. A method of preparing the compound according to clauses B2, B3 or B5, comprising reacting the compound according to any one of clauses B24 or B25 with a $^{3}H$ radiolabeling agent.

B29. Use of the compound according to any one of clauses B1 to B6 as an in vitro analytical reference or an in vitro screening tool.

B30. A test kit for the detection and/or diagnosis of a disease, disorder or abnormality associated with alpha-synuclein aggregates, wherein the test kit comprises at least one compound as defined in any one of clauses B1 to B6.

B31. A kit for preparing a radiopharmaceutical preparation, wherein the kit comprises a sealed vial containing at least one compound as defined in any clauses B21 to B25.

Within the clauses A and B, "Heterocyclyl" can refer to a carbocyclyl group as defined above in which at least one of the carbon atoms has been replaced by a heteroatom which is, e.g., selected from N, O or S, or heteroatom (e.g., N, O and/or S)-containing moiety. The heterocyclyl group can be unsaturated or saturated. It covers both heteroalkyl groups and heteroaryl groups. The heterocyclyl can also be annelated, connected in a bridged manner or connected in a spiro manner such as 6-membered bicyclic rings, 7-membered bicyclic rings, 8-membered bicyclic rings, 6-membered spirocyclic rings, 7-membered spirocyclic rings or 8-membered spirocyclic rings. Examples include azetidine, pyrrolidine, pyrrole, tetrahydrofuran, furan, thiolane, thiophene, imidazolidine, pyrazolidine, imidazole, pyrazole, oxazolidine, isoxazolidine, oxazole, isoxazole, thiazolidine, isothiazolidine, thiazole, isothiazole, dioxolane, dithiolane, triazole, furazan, oxadiazoles, thiadiazole, dithiazole, tetrazole, piperidine, oxane, thiane, pyridine, pyran, thiopyran, piperazine, diazine (including pyrazine and pyrimidine), morpholine, oxazine, thiomorpholine, thiazine, dioxane, dioxine, dithiane, dithiine, triazine, trioxane, tetrazine, azepane, azepine, oxepane, oxepine, thiepane, thiepine, 3-azabicyclo[3.1.0]hexane, azaspiro[3.3]heptane, diazaspiro[3.3]heptane, azabicyclo[3.2.1]octane and diazabicyclo[3.2.1]octane. Examples of preferred heterocyclyl groups include azetidine, morpholine, piperazine, pyrrolidine, tetrahydrofuran, piperidine, azaspiro[3.3]heptane, etc. Examples of possible heteroaryl groups include pyridine, pyrazole, etc.

With respect to clauses A and B, the following preferred definitions can apply.

Preferably, $R^2$ is

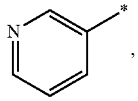
,
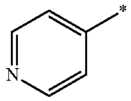
or
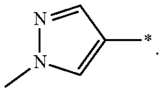

More preferably, $R^2$ is

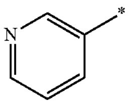
or
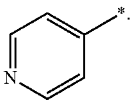

Even more preferably, $R^2$ is

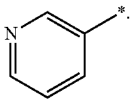

In each of the above embodiments, $R^2$ can be optionally substituted with methyl.

F is preferably $^{19}F$ or $^{18}F$, more preferably $^{18}F$.

In one embodiment of clauses A and B, the compound of formula (I) is a detectably labeled compound (I)

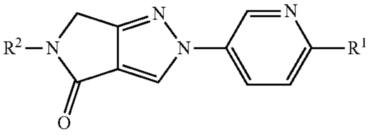

wherein the detectable label is a radioisotope, $R^1$ is a pyrrolidine substituted with fluoro as follows

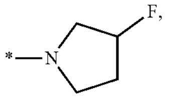

$R^2$ is a 5-membered or 6-membered heteroaryl comprising one or two N atoms, wherein the heteroaryl is optionally substituted with methyl, and

* is the position of bonding.

Preferably, the detectable label is a radioisotope selected from $^{18}F$, $^{2}H$ and $^{3}H$, most preferably $^{18}F$, and $^{3}H$.

In one embodiment of clauses A and B, the compound of formula (I) is a detectably labeled compound of formula (I-F)

(I-F)

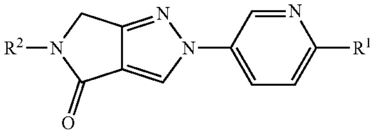

$R^1$ is a pyrrolidine substituted with $^{18}F$ as follows

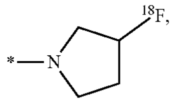

$R^2$ is a 5-membered or 6-membered heteroaryl comprising one or two N atoms, wherein the heteroaryl is optionally substituted with methyl, and

* is the position of bonding.

In one embodiment of clauses A and B, the compound of formula (I) is a detectably labeled compound of formula (I-H)

(I-H)

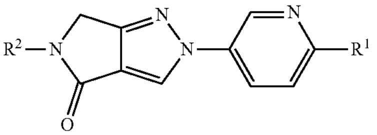

which is detectably labelled at at least one available position by $^{2}H$ or $^{3}H$ (Tritium), preferably $^{3}H$, $R^1$ is a pyrrolidine substituted with fluoro as follows

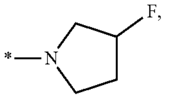 [SMILES: *N1CCC(F)C1]

$R^2$ is a 5-membered or 6-membered heteroaryl comprising one or two N atoms, wherein the heteroaryl is optionally substituted with methyl, Fluoro is $^{19}F$, and

* is the position of bonding.

Preferably, the detectably labeled compound of formula (I-H) is a compound of formula (I-Ha)

(I-Ha)

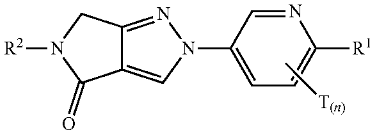

$R^1$ is a pyrrolidine substituted with fluoro as follows

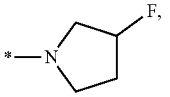 [SMILES: *N1CCC(F)C1]

$R^2$ is a 5-membered or 6-membered heteroaryl comprising one or two N atoms, wherein the heteroaryl is optionally substituted with methyl and/or the heteroaryl is optionally substituted with at least one T, T is $^3H$ (Tritium), n is 0 to 3, with the proviso that the compound of formula (I-Ha) comprises at least one T wherein T is $^3H$ (Tritium), Fluoro is $^{19}F$, and * is the position of bonding.

Preferably, the detectably labeled compound of formula (I-Ha) comprises one or two T.

Preferably, n is 1.

In a further embodiment, the compound of formula (I-H) $R^2$ is a 6-membered heteroaryl comprising one N atom, wherein the heteroaryl is substituted with one or more T. Preferably, $R^2$ is

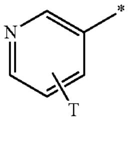 or 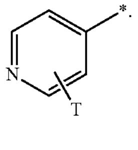

More preferably, $R^6$ is

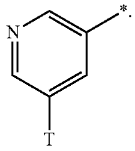

In a preferred embodiment of clauses A and B, the compound of formula (I) is (I)

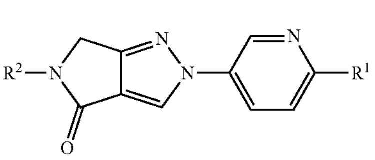

or a detectably labeled compound, stereoisomer, racemic mixture, pharmaceutically acceptable salt, hydrate, or solvate thereof, wherein $R^1$ is a pyrrolidine substituted with fluoro as follows

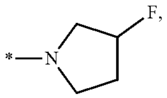

$R^2$ is a 6-membered heteroaryl comprising one or two N atoms, wherein the heteroaryl is optionally substituted with methyl, and

* is the position of bonding.

Preferably, $R^2$ is a 6-membered heteroaryl comprising one N atom. More preferably, $R^2$ is

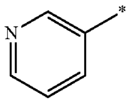 or 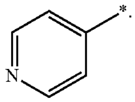

In each of the above embodiments of $R^2$, the 6-membered heteroaryl can be optionally substituted with methyl.

DEFINITIONS

For the purpose of interpreting this specification, the following definitions will apply unless specified otherwise, and when appropriate, terms used in the singular will also include the plural and vice versa.

"Alkyl" refers to a saturated straight or branched organic moiety consisting of carbon and hydrogen atoms. The alkyl group typically does not contain any saturation, and is usually attached to the rest of the molecule by a single bond. Examples of suitable alkyl groups have 1 to 6 carbon atoms, preferably 1 to 4 carbon atoms. The term "$C_1$-$C_4$alkyl" is to be construed accordingly. Examples of "$C_1$-$C_4$alkyl" include, but are not limited to, methyl, ethyl, propyl, isopropyl, 1-methylethyl, n-butyl, t-butyl and isobutyl, such as methyl, ethyl, propyl, isopropyl, n-butyl, t-butyl and isobutyl.

"$C_1$-$C_4$alkoxy" refers to a radical of the formula —ORa where Ra is a $C_1$-$C_4$alkyl radical as generally defined above. Examples of $C_1$-$C_4$alkoxy include, but are not limited to, methoxy, ethoxy, propoxy, isopropoxy, butoxy, and isobutoxy.

"halogen$C_1$-$C_4$alkyl" or "halo$C_1$-$C_4$alkyl" refer to $C_1$-$C_4$alkyl radical, as defined above, substituted by one or more halo radicals, as defined below. Examples of "halo$C_1$-$C_4$alkyl" include, but are not limited to, trifluoromethyl, difluoromethyl, fluoromethyl, trichloromethyl, 2,2,2-trifluoroethyl, 1,3-dibromopropan-2-yl, 3-bromo-2-fluoropropyl and 1,4,4-trifluorobutan-2-yl.

"$C_3$-$C_6$cycloalkyl" refers to a stable monocyclic saturated hydrocarbon radical consisting solely of carbon, and hydrogen atoms, having from three to six carbon atoms. Examples of $C_3$-$C_6$cycloalkyl include, but are not limited to, cyclopropyl, cyclobutyl, cyclopentyl, and cyclohexyl.

"Heterocyclyl" refers to a stable 4- to 6-membered non-aromatic monocyclic ring radical which comprises 1 or 2 heteroatoms which are, e.g., selected from N, O or S. The heterocyclyl group can be unsaturated or saturated. The heterocyclyl radical may be bonded via a carbon atom or heteroatom. Examples include, but are not limited to, azetidinyl, oxetanyl, pyrrolinyl, pyrrolidyl, tetrahydrofuryl, tetrahydrothienyl, piperidyl, piperazinyl, tetrahydropyranyl, morpholinyl or perhydroazepinyl. Examples of preferred heterocyclyl groups include, but are not limited to, azetidinyl, morpholinyl, piperazinyl, pyrrolidinyl, or piperidinyl.

"Aryl" refers to homocyclic aromatic organic moieties (for example containing 1 or 2 rings) consisting of carbon and hydrogen atoms which preferably have 5 to 12 carbon atoms, preferably 6 to 12 carbon atoms, more preferably 6 to 10 carbon atoms, yet more preferably 5 to 10 carbon atoms, even more preferably 5 or 6 carbon atoms. Examples include, but are not limited to, phenyl, biphenyl, and naphthyl.

"Heteroaryl" refers to an aryl group as defined above in which at least one of the carbon atoms has been replaced by a heteroatom which is, e.g., selected from N, O or S, or heteroatom (e.g., N, O and/or S)-containing moiety. Typically the heteroaryl is a 5- to 8-membered ring system, preferably to a 5 to 6 membered ring system, in which at least one of the carbon atoms has been replaced by a heteroatom which is, e.g., selected from N, O or S. Examples of possible heteroaryl groups include, but are not limited to, furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl. Preferred examples thereof include pyridine, pyrazole, etc., more preferably pyridine.

"Hal" or "halogen" or "Halo" refers to F, Cl, Br, and I. With respect to diagnostic and pharmaceutical applications, F (e.g., $^{19}F$ and $^{18}F$) is particularly preferred.

The term "leaving group" (LG) as employed herein is any leaving group and means an atom or group of atoms that can be replaced by another atom or group of atoms. Examples are given e.g. in Synthesis (1982), p. 85-125, table 2, Carey and Sundberg, Organische Synthese, (1995), page 279-281, table 5.8; or Netscher, Recent Res. Dev. Org. Chem., 2003, 7, 71-83, schemes 1, 2, 10 and 15 and others). (Coenen, Fluorine-18 Labeling Methods: Features and Possibilities of Basic Reactions, (2006), in: Schubiger P. A., Friebe M., Lehmann L., (eds), PET-Chemistry—The Driving Force in Molecular Imaging. Springer, Berlin Heidelberg, pp. 15-50, explicitly: scheme 4 pp. 25, scheme 5 pp 28, table 4 pp 30, Figure 7 pp 33). Preferably, the "leaving group" (LG) is selected from halogen, $C_{1-4}$ alkyl sulfonate and $C_{6-10}$ aryl sulfonate, wherein the $C_{6-10}$ aryl can be optionally substituted by $—CH_3$ or $—NO_2$.

Unless specified otherwise, the term "compound of the invention" refers to a compound of formula (I), or subformulae thereof (e.g. (IIa), (IIb), (IIIa), (IIIb), (IIIc), (III-F), (III-H)), or a detectably labelled compounds, stereoisomers (including diastereomeric mixtures and individual diastereomers, enantiomeric mixtures and single enantiomers, mixtures of conformers and single conformers), racemic mixtures, pharmaceutically acceptable salts, hydrates, or solvates thereof. It is understood that every reference to a compound of formula (I), as defined herein, also covers the subformulae thereof (e.g. (IIa), (IIb), (IIIa), (IIIb), (IIIc), (III-F), (III-H)).

Compounds of the present invention and their precursors having one or more optically active carbons can exist as racemates and racemic mixtures, stereoisomers (including diastereomeric mixtures and individual diastereomers, enantiomeric mixtures and single enantiomers, mixtures of conformers and single conformers), tautomers, atropisomers, and rotamers. All isomeric forms are included in the present invention. Compounds described in this specification containing olefinic double bonds include E and Z geometric isomers.

Also included in this invention are all salt forms, polymorphs, hydrates and solvates (such as ethanolates).

"Pharmaceutically acceptable salts" are defined as derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as, but not limited to, hydrochloric, hydrobromic, sulfuric, sulfamic, phosphoric, nitric and the like; and the salts prepared from organic acids such as, but not limited to, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. The pharmaceutically acceptable salts of the compounds of the present invention and their precursors can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Organic solvents include, but are not limited to, nonaqueous media like ethers, ethyl acetate, ethanol, isopropanol, or acetonitrile. Lists of suitable salts can be found in Remington's Pharmaceutical Sciences, $18^{th}$ ed., Mack Publishing Company, Easton, PA, 1990, p. 1445, the disclosure of which is hereby incorporated by reference.

"Pharmaceutically acceptable" is defined as those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The compounds of the present invention can also be provided in the form of a prodrug, namely a compound which is metabolized in vivo to the active metabolite.

The patients or subjects in the present invention are typically animals, particularly mammals, more particularly humans.

Alpha-synuclein aggregates are multimeric beta-sheet rich assemblies of alpha-synuclein monomers that can form either soluble oligomers or soluble/insoluble protofibrils or mature fibrils which coalesce into intracellular deposits detected as a range of Lewy pathologies in Parkinson's disease and other synucleinopathies. Alpha-synuclein aggregates that are composing Lewy pathologies can be detected as having the following morphologies: Lewy bodies, Lewy neurites, premature Lewy bodies or pale bodies, perikaryal deposits with diffuse, granular, punctate or pleomorphic patterns. Moreover, alpha-synuclein aggregates are the major component of intracellular fibrillary inclusions detected in oligodendrocytes (also referred to as glial cytoplasmic inclusions) and in neuronal somata, axons and nuclei (referred to as neuronal cytoplasmic inclusions) that are the histological hallmarks of multiple system atrophy. Alpha-synuclein aggregates in Lewy pathologies often display substantial increase in post-translational modifications such as phosphorylation, ubiquitination, nitration, and truncation.

Lewy bodies are abnormal aggregates of protein that develop inside nerve cells in Parkinson's disease (PD), Lewy body dementia and other synucleinopathies. Lewy bodies appear as spherical masses that displace other cell components. Morphologically, Lewy bodies can be classified as being brainstem or cortical type. Classic brainstem Lewy bodies are eosinophilic cytoplasmic inclusions consisting of a dense core surrounded by a halo of 5-10-nm-wide radiating fibrils, the primary structural component of which is alpha-synuclein; cortical Lewy bodies differ by lacking a halo. The presence of Lewy bodies is a hallmark of Parkinson's disease.

Lewy neurites are abnormal neuronal processes in diseased neurons, containing granular material, abnormal alpha-synuclein (a-syn) filaments similar to those found in Lewy bodies, dot-like, varicose structures and axonal spheroids. Like Lewy bodies, Lewy neurites are a feature of α-synucleinopathies such as dementia with Lewy bodies, Parkinson's disease, and multiple system atrophy.

The terms "disease", "disorder" or "abnormality" are used interchangeably herein.

The compounds of formula (I), or a detectably labelled compound, stereoisomer, racemic mixture, pharmaceutically acceptable salt, hydrate, or solvate thereof, can bind to alpha-synuclein aggregates. The type of bonding between the compounds of formula (I), or a detectably labelled compound, stereoisomer, racemic mixture, pharmaceutically acceptable salt, hydrate, or solvate thereof, has not been elucidated and any type of bonding is covered by the present invention. The wording "compound bound to the alpha-synuclein aggregates", "compound/(alpha-synuclein aggregates including, but not limited to, Lewy bodies and/or Lewy neurites) complex", compound/alpha-synuclein aggregate complex", "compound/protein aggregate complex" and the like are used interchangeably herein and are not considered to be limited to any specific type of bonding.

The preferred definitions given in the "Definition"-section apply to all of the embodiments described below unless stated otherwise. Various embodiments of the invention are described herein, it will be recognized that features specified in each embodiment may be combined with other specified features to provide further embodiments of the present invention.

DETAILED DESCRIPTION OF THE INVENTION

Figure 1:
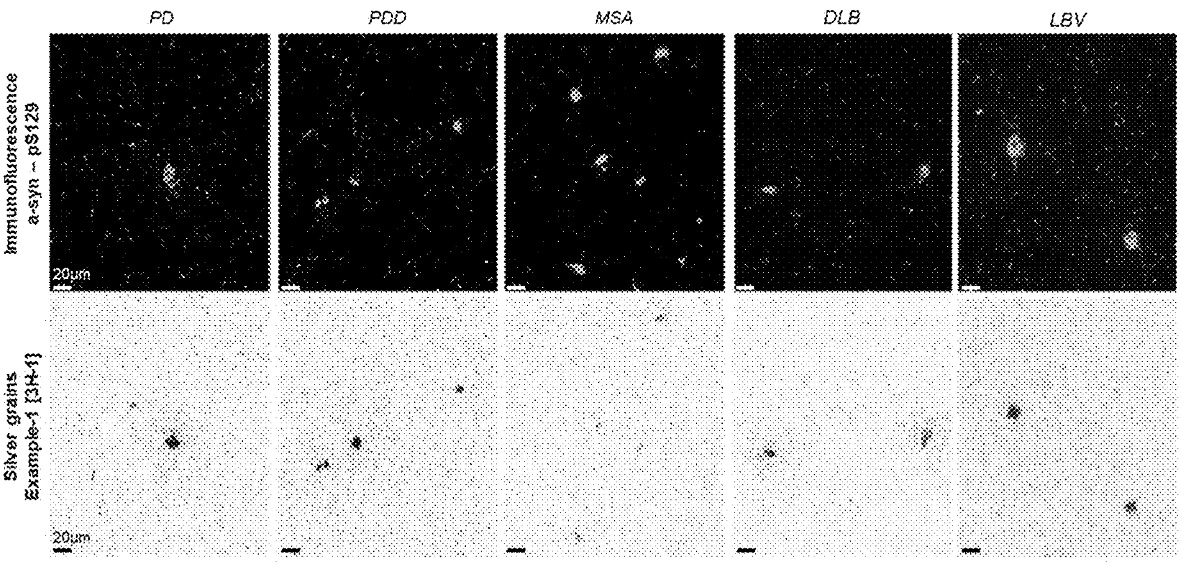
FIG. 1: Target engagement of [3H]-Example-1/Example-1 [$^3$H-1] on tissue from different a-synucleinopathies. Accumulation of silver grains on Lewy bodies and Lewy neurites, as shown in bottom panels. Immunofluorescence staining with a-syn-pS129 antibody was performed on the same sections, shown on top panels, to co-label a-syn aggregates. PD, Parkinson's Disease; PDD, Parkinson's Disease with Dementia; MSA, Multiple System Atrophy; DLB, Dementia with Lewy Bodies; LBV, Lewy Body Variant of Alzheimer's disease. Scale bar, 20 μm.

The compounds of the present invention and their precursors are described in the following. It is to be understood that all possible combinations of the following definitions are also envisaged.

The present invention relates to a compound of formula (I), (I)

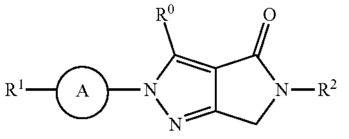

or a detectably labelled compound, stereoisomer, racemic mixture, pharmaceutically acceptable salt, hydrate, or solvate thereof, wherein

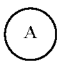

is an aryl or a heteroaryl which is directionally selected from the following:

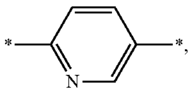, 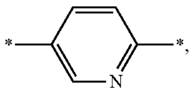,

-continued

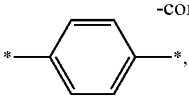, 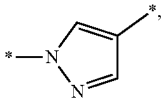, and 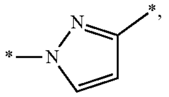, $R^0$ is H or $C_1$-$C_4$alkyl;

$R^1$ is —CN; or halo; or $C_1$-$C_4$alkyl; or $C_1$-$C_4$alkoxy; or —N($C_1$-$C_4$alkyl)$_2$; or —NH($C_1$-$C_4$alkyl); or H, or $R^1$ is —NH—$C_3$-$C_6$cycloalkyl, $C_3$-$C_6$cycloalkyl, or heterocyclyl, each of which is optionally substituted with at least one halo;

$R^2$ is aryl, or 5-membered or 6-membered heteroaryl, wherein $R^2$ is selected from the following:

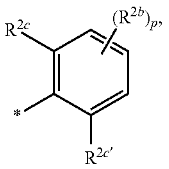

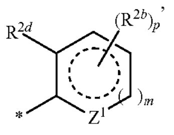

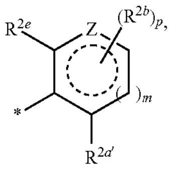

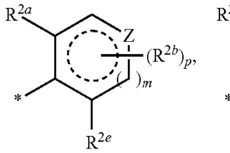

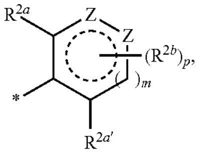

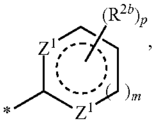

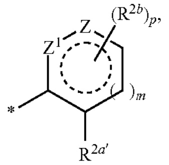

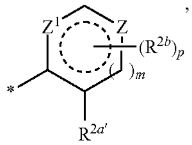

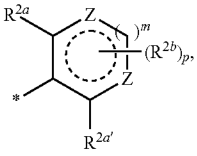

and

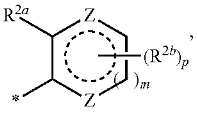

wherein $R^{2a}$, $R^{2a'}$ are independently selected from H, or F;

$R^{2b}$ is independently selected from F, —OH, $C_1$-$C_4$alkyl, halo$C_1$-$C_4$alkyl, —$NH_2$, —CN, or $C_1$-$C_4$alkoxy;

$R^{2c}$, $R^{2c'}$ are independently selected from H, F, OH, $OCH_3$, or $CH_3$;

$R^{2d}$ is selected from H, F, or —OH;

$R^{2e}$ is selected from H, OH, $CH_3$, or F;

Z is independently N, NH, N($C_1$-$C_4$alkyl), N(halo$C_1$-$C_4$alkyl), O, or S;

$Z^1$ is independently N, NH, O, or S;

p is 0, 1 or 2;

m is 0 or 1;

as valency permits, ⸌ is a combination of single and double bonds; and

* is the position of bonding.

In another embodiment, the invention provides a compound of formula (I), having a formula (IIa) or (IIb), (IIa)

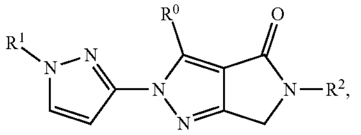

or (IIb)

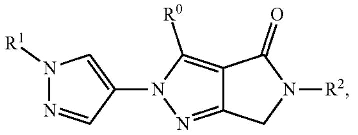

or a detectably labelled compound, stereoisomer, racemic mixture, pharmaceutically acceptable salt, hydrate, or solvate thereof.

In another embodiment, the invention provides a compound of formula (I), having a formula (IIIa), (IIIb), or (IIIc), (IIIa)

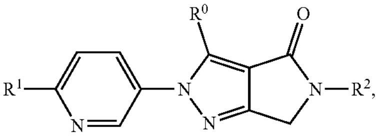

(IIIb)

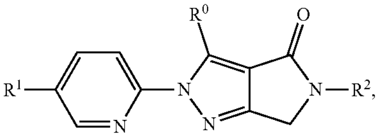

or (IIIc)

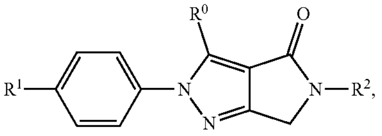

or a detectably labelled compound, stereoisomer, racemic mixture, pharmaceutically acceptable salt, hydrate, or solvate thereof.

$R^0$ is H or $C_1$-$C_4$alkyl. Preferably, $R^0$ is H or $CH_3$, more preferably $R^0$ is H.

In an embodiment, $R^1$ is H, —CN, halo, $C_1$-$C_4$alkyl, $C_1$-$C_4$alkoxy, —N($C_1$-$C_4$alkyl)$_2$, or —NH($C_1$-$C_4$alkyl). Preferably, $R^1$ is —CN, halo, $C_1$-$C_4$alkyl, $C_1$-$C_4$alkoxy, —N($C_1$-$C_4$alkyl)$_2$, or —NH($C_1$-$C_4$alkyl). More preferably, $R^1$ is —CN, F, $C_1$-$C_3$alkyl, $C_1$-$C_3$alkoxy, or —N($C_1$-$C_3$alkyl)$_2$. Even more preferably, $R^1$ is —CN, —$CH(CH_3)_2$, —$OCH_3$, —$OCH(CH_3)_2$, —$N(CH_3)_2$, or —NH—$CH(CH_3)_2$.

In an embodiment, $R^1$ is —NH—$C_3$-$C_6$cycloalkyl, $C_3$-$C_6$cycloalkyl, or heterocyclyl, each of which is optionally substituted with at least one halo. Preferably $R^1$ is selected from the following:

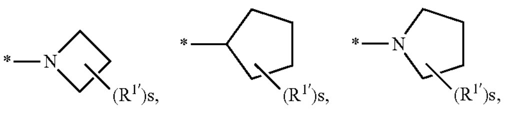

-continued

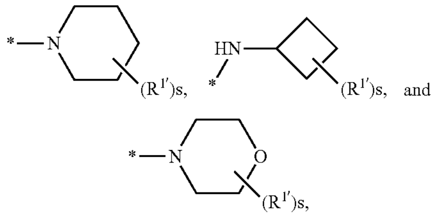

wherein $R^{1'}$ is independently halo; and s=0, 1, 2 or 3.

More preferably, $R^1$ is selected from the following:

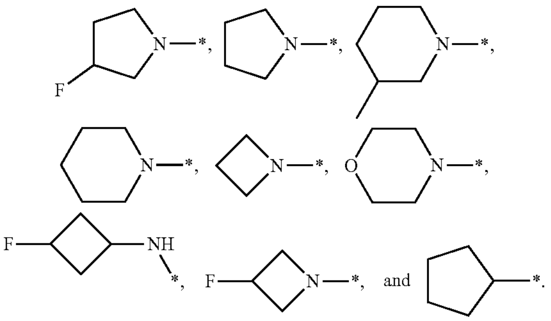

Even more preferably, $R^1$ is selected from

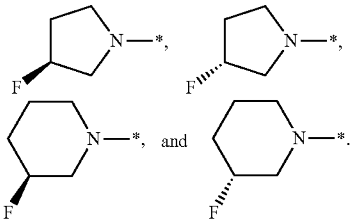

In a preferred embodiment F is preferably $^{19}F$ or $^{18}F$, more preferably $^{18}F$.

In an embodiment $R^2$ is selected from the following:

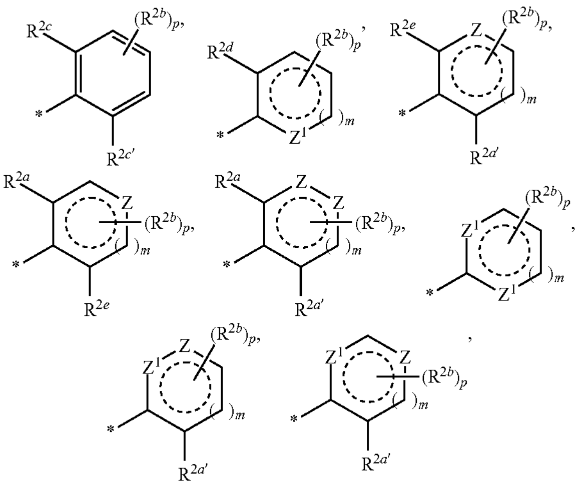

-continued

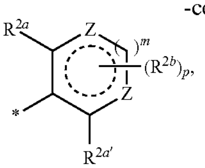

and

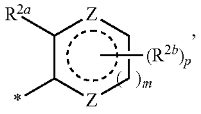

wherein $R^{2a}$, $R^{2a'}$ are independently selected from H, or F;

$R^{2b}$ is independently selected from F, —OH, $C_1$-$C_4$alkyl, halo$C_1$-$C_4$alkyl, —$NH_2$, —CN, or $C_1$-$C_4$alkoxy;

$R^{2c}$, $R^{2c'}$ are independently selected from H, F, OH, $OCH_3$, or $CH_3$;

$R^{2d}$ is selected from H, F, or —OH;

$R^{2e}$ is selected from H, OH, $CH_3$, or F;

Z is independently N, NH, N($C_1$-$C_4$alkyl), N(halo$C_1$-$C_4$alkyl), O, or S;

$Z^1$ is independently N, NH, O, or S;

p is 0, 1 or 2;

m is 0 or 1;

as valency permits,  is a combination of single and double bonds; and

* is the position of bonding.

Preferably, $R^2$ is selected from the following:

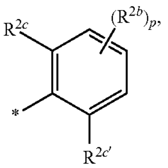

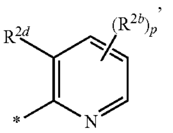

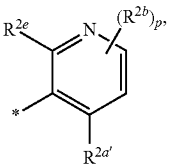

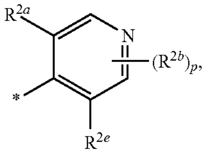

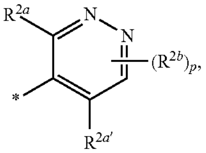

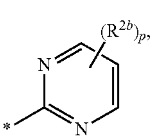

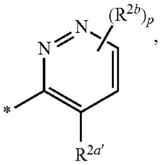

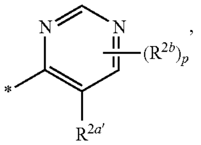

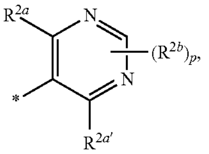

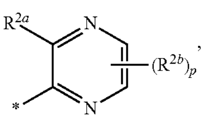

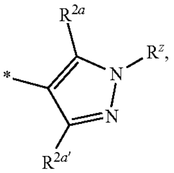

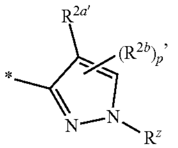

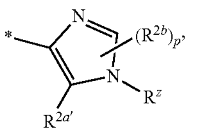

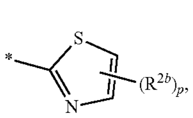

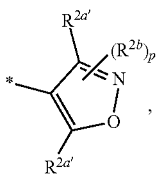

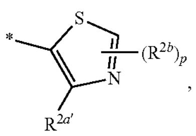

-continued

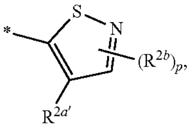

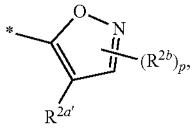

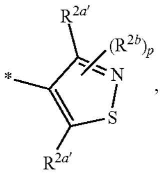

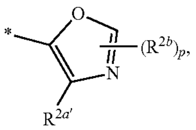

and

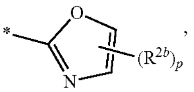

wherein $R^{2a}$, $R^{2a'}$ are independently selected from H, or F;

$R^{2b}$ is independently selected from F, —OH, $C_1$-$C_4$alkyl, halo$C_1$-$C_4$alkyl, —$NH_2$, —CN, or $C_1$-$C_4$alkoxy;

$R^{2c}$, $R^{2c'}$ are independently selected from H, F, OH, $OCH_3$, or $CH_3$;

$R^{2d}$ is selected from H, F, or —OH;

$R^{2e}$ is selected from H, OH, $CH_3$, or F;

$R^z$ is selected from H, $C_1$-$C_4$alkyl or halo$C_1$-$C_4$alkyl;

p is 0, 1 or 2; and

* is the position of bonding.

Preferably, $R^2$ is selected from the following:

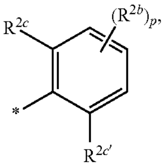

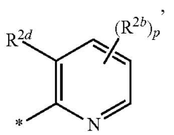

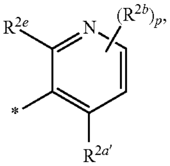

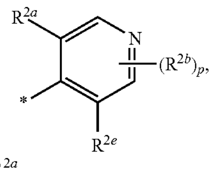

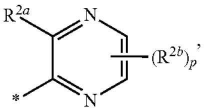

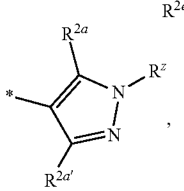

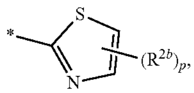

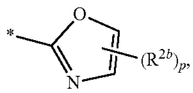

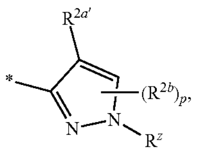

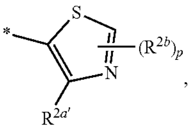

and

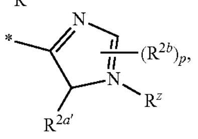

wherein $R^{2a}$, $R^{2a'}$ are independently selected from H, or F;

$R^{2b}$ is independently selected from F, —OH, $C_1$-$C_4$alkyl, halo$C_1$-$C_4$alkyl, —$NH_2$, —CN, or $C_1$-$C_4$alkoxy;

$R^{2c}$, $R^{2c'}$ are independently selected from H, F, OH, $OCH_3$, or $CH_3$;

$R^{2d}$ is selected from H, F, or —OH;

$R^{2e}$ is selected from H, OH, $CH_3$, or F;

$R^z$ is selected from H, $C_1$-$C_4$alkyl or halo$C_1$-$C_4$alkyl;

p is 0, 1 or 2; and

* is the position of bonding.

More preferably, $R^2$ is selected from the following:

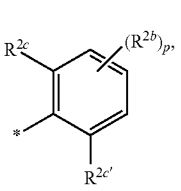
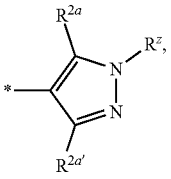
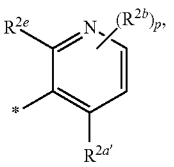
and
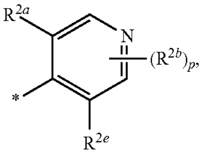

wherein $R^{2a}$, $R^{2a'}$ are independently selected from H, or F;

$R^{2b}$ is independently selected from F, —OH, $C_1$-$C_4$alkyl, halo$C_1$-$C_4$alkyl, —$NH_2$, —CN, or $C_1$-$C_4$alkoxy;

$R^{2c}$, $R^{2c'}$ are independently selected from H, F, OH, $OCH_3$, or $CH_3$;

$R^{2e}$ is selected from H, OH, $CH_3$, or F;

$R^z$ is selected from H, $C_1$-$C_4$alkyl or halo$C_1$-$C_4$alkyl;

p is 0, 1 or 2; and

* is the position of bonding.

Even more preferably, $R^2$ is selected from:

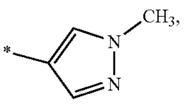
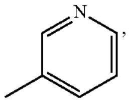
and
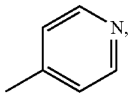

wherein * is the position of bonding.

In another embodiment, the invention provides a compound of any one of subformulae (IIa) or (IIb), (IIa)

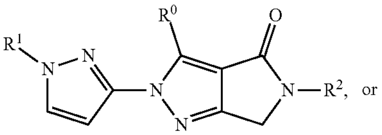
or (IIb)

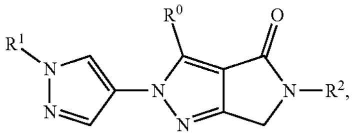

or a detectably labelled compound, stereoisomer, racemic mixture, pharmaceutically acceptable salt, hydrate, or solvate thereof, wherein $R^0$ is methyl or H; $R^1$ is $CH_3$ or H; preferably, $R^1$ is $CH_3$; and $R^2$ comprises at least one fluoro and is preferably selected from the following:

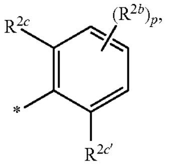
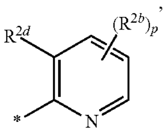
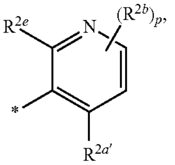
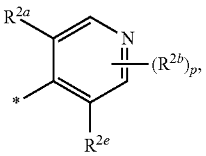
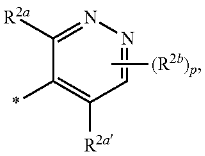
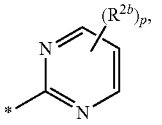
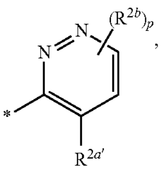
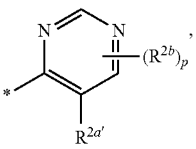
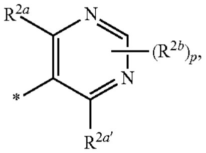
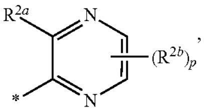
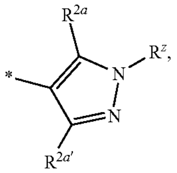
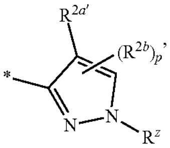
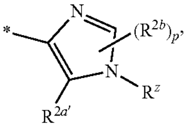
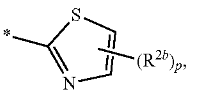
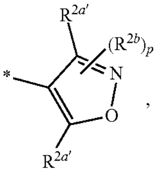
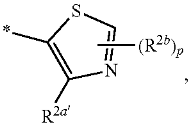
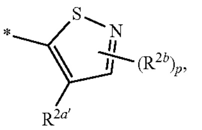
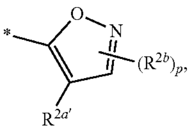
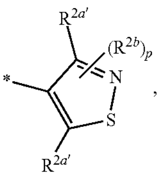
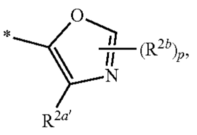
and
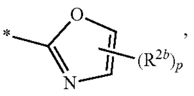

wherein $R^{2a}$, $R^{2a'}$ are independently selected from H, or F;

$R^{2b}$ is independently selected from F, —OH, $C_1$-$C_4$alkyl, halo$C_1$-$C_4$alkyl, —$NH_2$, —CN, or $C_1$-$C_4$alkoxy;

$R^{2c}$, $R^{2c'}$ are independently selected from H, F, OH, $OCH_3$, or $CH_3$;

$R^{2d}$ is selected from H, F, or —OH;

$R^{2e}$ is selected from H, OH, $CH_3$, or F;

$R^z$ is selected from H, $C_1$-$C_4$alkyl or halo$C_1$-$C_4$alkyl;

p is 0, 1 or 2; and

* is the position of bonding.

Most preferably, $R^2$ is selected from

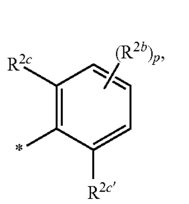
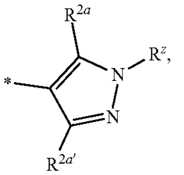
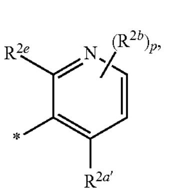
and
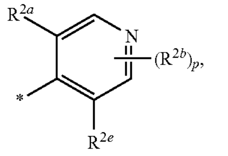

wherein $R^{2a}$, $R^{2a'}$, $R^{2b}$, $R^{2e}$, $R^{2c}$, $R^{2c'}$, $R^z$ and p are as defined herein above; and wherein at least one of $R^{2a}$, $R^{2a'}$, $R^{2b}$, $R^{2c}$, $R^{2c'}$, and $R^{2e}$ is F. F is preferably $^{19}F$ or $^{18}F$, more preferably $^{18}F$.

In another embodiment, the invention provides a compound of any one of subformulae (IIIa) (IIIb), or (IIIc), (IIIa)

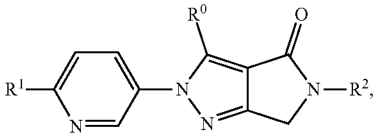

(IIIb)

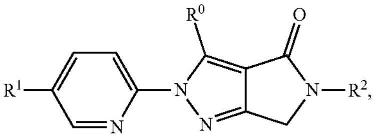

or (IIIc)

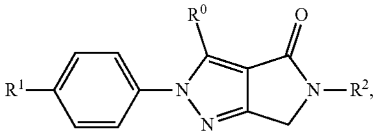

or a detectably labelled compound, stereoisomer, racemic mixture, pharmaceutically acceptable salt, hydrate, or solvate thereof, wherein $R^0$ is methyl or H, preferably $R^0$ is H;

$R^1$ is selected from —CN, halo, $C_1$-$C_4$alkyl; or $C_1$-$C_4$alkoxy, —$N(C_1$-$C_4alkyl)_2$, —$NH(C_1$-$C_4$alkyl), H; or $R^1$ is —NH—$C_3$-$C_6$cycloalkyl, $C_3$-$C_6$cycloalkyl, or heterocyclyl, each of which is optionally substituted with at least one halo;

Preferably, $R^1$ is selected from the following:

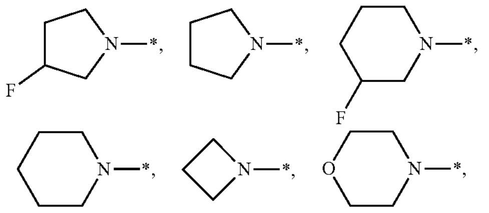

-continued

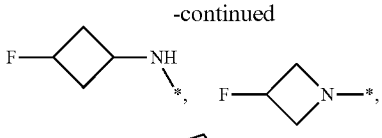

and

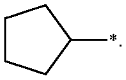

F is preferably $^{19}F$ or $^{18}F$, more preferably $^{18}F$; and $R^2$ is preferably selected from the following:

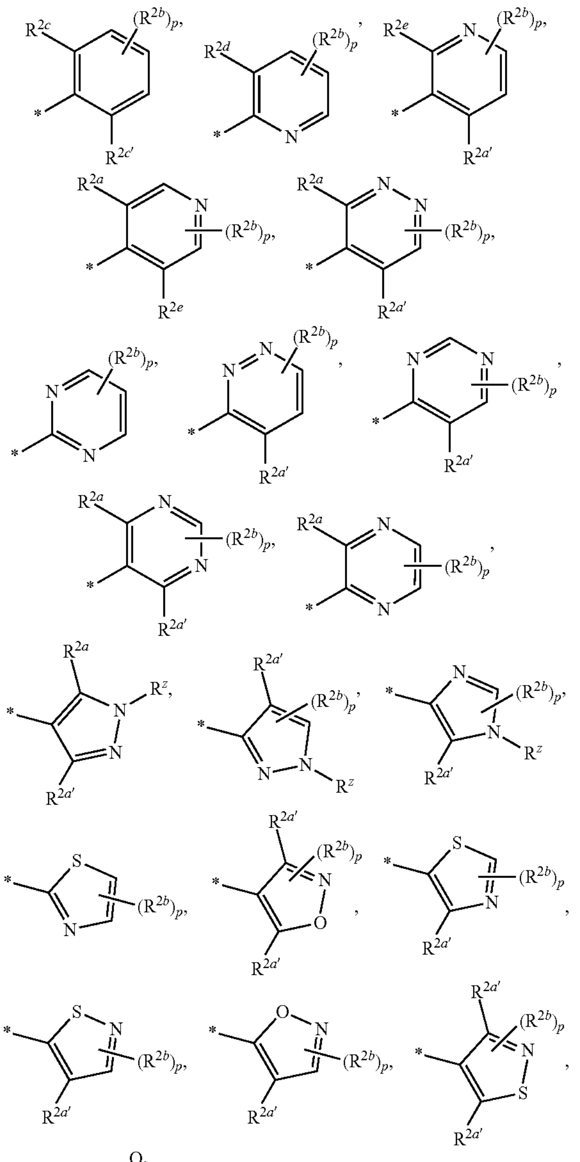
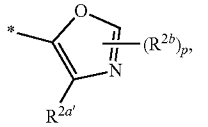
and
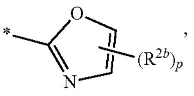

wherein $R^{2a}$, $R^{2a'}$ are independently selected from H, or F;

$R^{2b}$ is independently selected from F, —OH, $C_1$-$C_4$alkyl, halo$C_1$-$C_4$alkyl, —$NH_2$, —CN, or $C_1$-$C_4$alkoxy;

$R^{2c}$, $R^{2c'}$ are independently selected from H, F, OH, $OCH_3$, or $CH_3$;

$R^{2d}$ is selected from H, F, or —OH;

$R^{2e}$ is selected from H, OH, $CH_3$, or F;

$R^z$ is selected from H, $C_1$-$C_4$alkyl or halo$C_1$-$C_4$alkyl;

p is 0, 1 or 2; and

* is the position of bonding.

In another embodiment the present invention relates to a compound of formula (IIIa):

(IIIa)

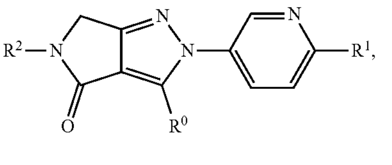

or a detectably labelled compound, stereoisomer, racemic mixture, pharmaceutically acceptable salt, hydrate, or solvate thereof, wherein $R^0$ is methyl or H, preferably $R^0$ is H;

$R^1$ is —NH—$C_3$-$C_6$cycloalkyl, $C_3$-$C_6$cycloalkyl, or heterocyclyl, each of which is optionally substituted with at least one halo, preferably $R^1$ is selected from the following:

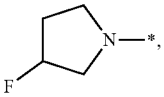
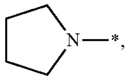
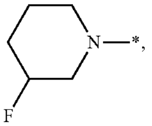
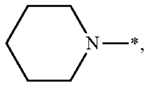
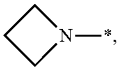
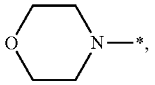
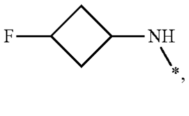
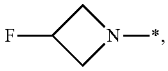
and
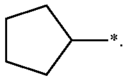

$R^1$ is preferably substituted with fluoro as follows

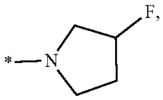
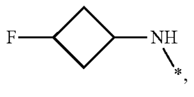
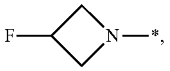
or
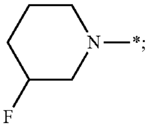

More preferably $R^1$ is

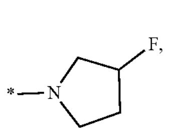
or
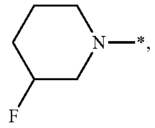

preferably $R^1$ is

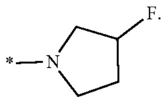

$R^2$ is preferably selected from the following:

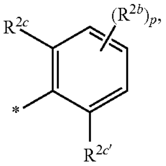
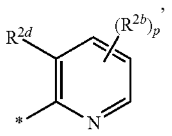
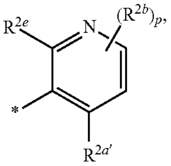
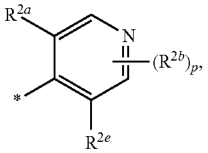
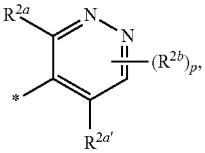
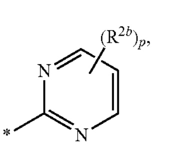
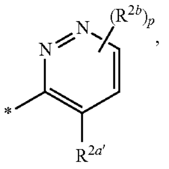
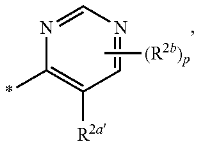
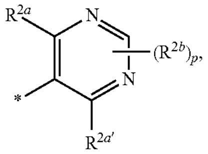
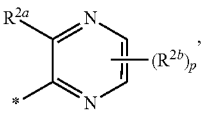
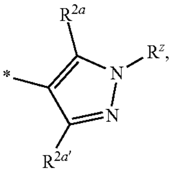
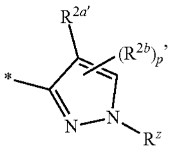
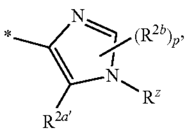
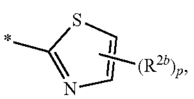
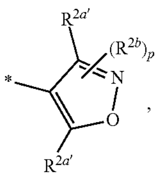
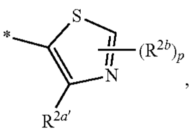
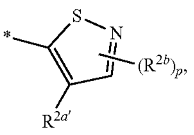
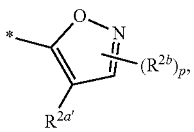
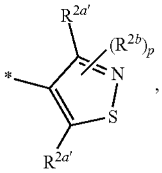

-continued

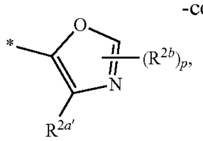 and 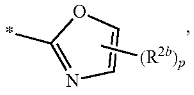 , wherein $R^{2a}$, $R^{2a'}$ are independently selected from H, or F;

$R^{2b}$ is independently selected from F, —OH, $C_1$-$C_4$alkyl, halo$C_1$-$C_4$alkyl, —$NH_2$, —CN, or $C_1$-$C_4$alkoxy;

$R^{2c}$, $R^{2c'}$ are independently selected from H, F, OH, $OCH_3$, or $CH_3$;

$R^{2d}$ is selected from H, F, or —OH;

$R^{2e}$ is selected from H, OH, $CH_3$, or F;

$R^z$ is selected from H, $C_1$-$C_4$alkyl or halo$C_1$-$C_4$alkyl;

p is 0, 1 or 2; and

* is the position of bonding.

Preferably, $R^2$ is selected from the following:

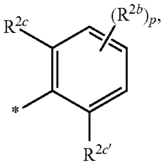

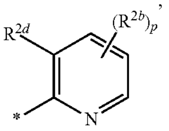

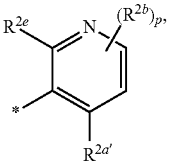

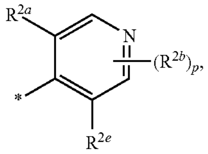

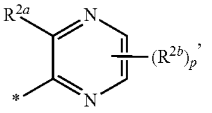

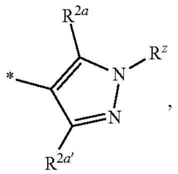 ,

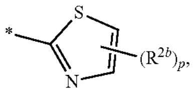

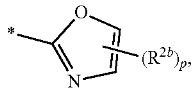

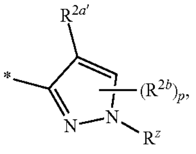

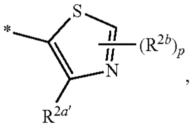 , and

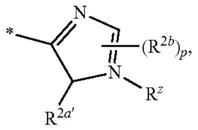

wherein $R^{2a}$, $R^{2a'}$, $R^{2b}$, $R^{2c}$, $R^{2c'}$, $R^{2d}$, $R^{2e}$, $R^z$ and p are as defined hereinabove.

More preferably, $R^2$ is selected from the following:

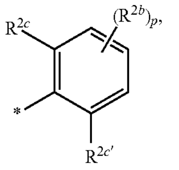

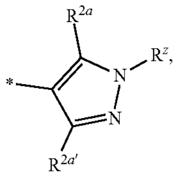

-continued

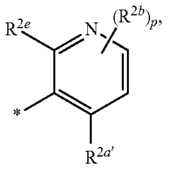 and 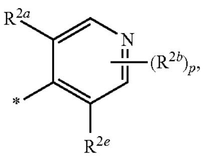

wherein $R^{2a}$, $R^{2a'}$, $R^{2b}$, $R^{2c}$, $R^{2c'}$, $R^{2d}$, $R^{2e}$, $R^z$ and p are as defined hereinabove.

Preferably, $R^2$ is

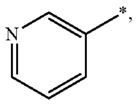 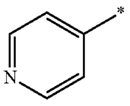 or

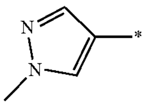

More preferably, $R^2$ is or N

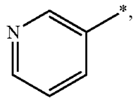 or 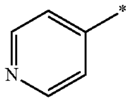

Even more preferably, $R^2$ is

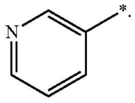

In each of the above embodiments, $R^2$ can be optionally substituted with one or more substituents as disclosed hereinabove. F is preferably $^{19}F$ or $^{18}F$, more preferably $^{18}F$.

In another embodiment the present invention relates to a compound of formula (IIIb):

(IIIb)

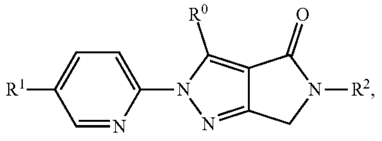

or a detectably labelled compound, stereoisomer, racemic mixture, pharmaceutically acceptable salt, hydrate, or solvate thereof, wherein $R^0$ is methyl or H, preferably $R^0$ is H;

$R^1$ is —NH—$C_3$-$C_6$cycloalkyl, $C_3$-$C_6$cycloalkyl, or heterocyclyl, each of which is optionally substituted with at least one halo, preferably $R^1$ is selected from the following:

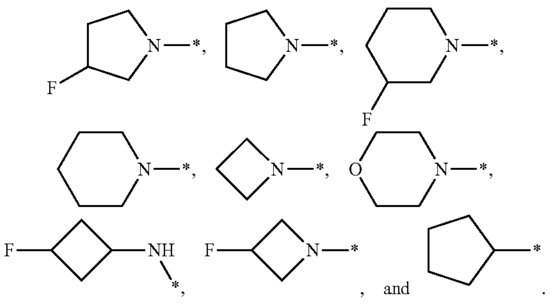

, and .

$R^1$ is preferably substituted with fluoro as follows

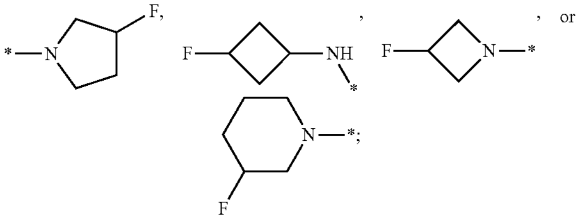

or

More preferably $R^1$ is

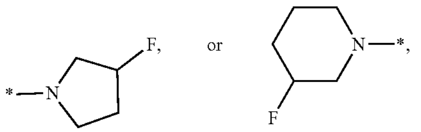

or preferably $R^1$ is

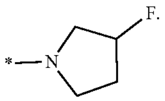 [SMILES: *N1CCC(F)C1]

$R^2$ is preferably selected from the following:

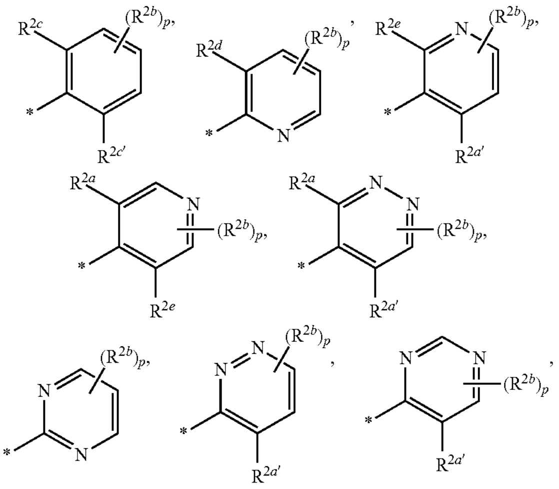

-continued

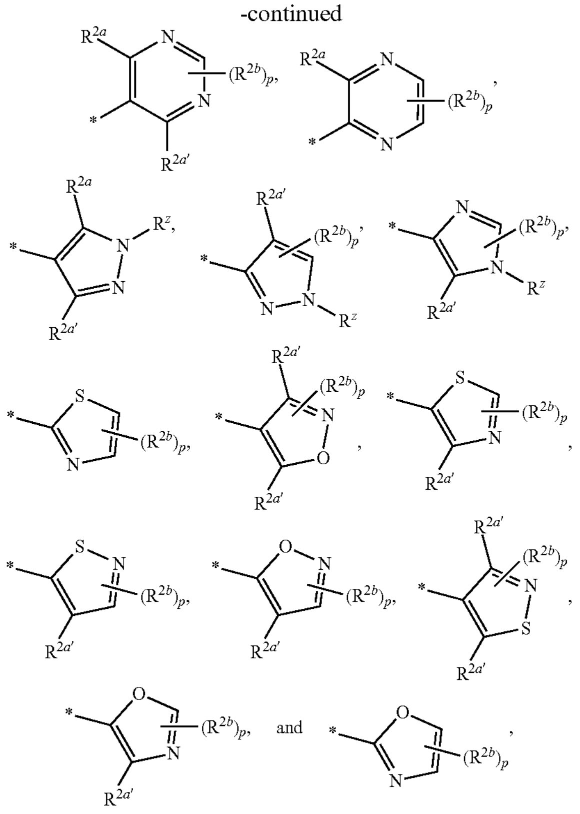

and wherein $R^{2a}$, $R^{2a'}$ are independently selected from H, or F;

$R^{2b}$ is independently selected from F, —OH, $C_1$-$C_4$alkyl, halo$C_1$-$C_4$alkyl, —$NH_2$, —CN, or $C_1$-$C_4$alkoxy;

$R^{2c}$, $R^{2c'}$ are independently selected from H, F, OH, $OCH_3$, or $CH_3$;

$R^{2d}$ is selected from H, F, or —OH;

$R^{2e}$ is selected from H, OH, $CH_3$, or F;

$R^z$ is selected from H, $C_1$-$C_4$alkyl or halo$C_1$-$C_4$alkyl;

p is 0, 1 or 2; and

* is the position of bonding.

Preferably, $R^2$ is selected from the following:

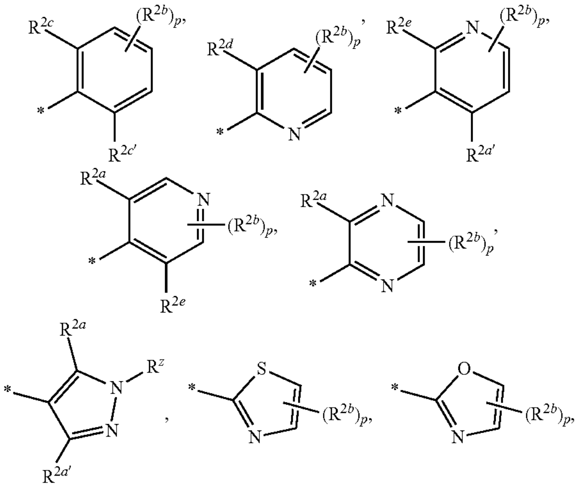

-continued

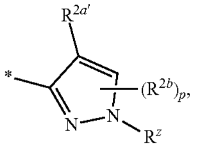

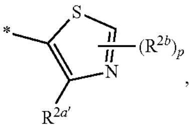

, and

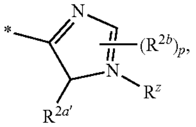

wherein $R^{2a}$, $R^{2a'}$, $R^{2b}$, $R^{2c}$, $R^{2c'}$, $R^{2d}$, $R^{2e}$, $R^z$ and p are as defined hereinabove.

More preferably, $R^2$ is selected from the following:

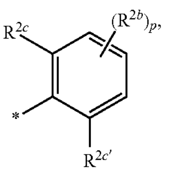

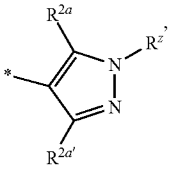

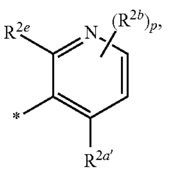

and

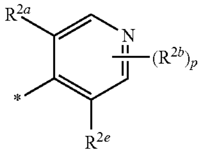

wherein $R^{2a}$, $R^{2a'}$, $R^{2b}$, $R^{2c}$, $R^{2c'}$, $R^{2d}$, $R^{2e}$, $R^z$ and p are as defined hereinabove.

Preferably, $R^2$ is

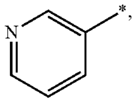

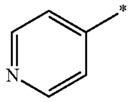

or

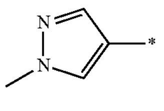

More preferably, $R^2$ is

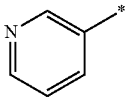

or

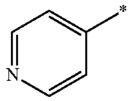

Even more preferably, $R^2$ is.

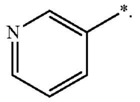

In each of the above embodiments, $R^2$ can be optionally substituted with one or more substituents as disclosed hereinabove. F is preferably $^{19}F$ or $^{18}F$, more preferably $^{18}F$.

In another embodiment the present invention relates to a compound of formula (IIIc):

(IIIc)

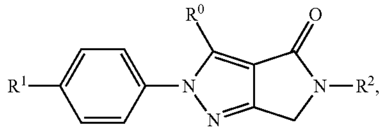

or a detectably labelled compound, stereoisomer, racemic mixture, pharmaceutically acceptable salt, hydrate, or solvate thereof, wherein $R^0$ is methyl or H, preferably $R^0$ is H;

$R^1$ is —NH—$C_3$-$C_6$cycloalkyl, $C_3$-$C_6$cycloalkyl, or heterocyclyl, each of which is optionally substituted with at least one halo, preferably $R^1$ is selected from the following:

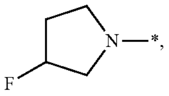

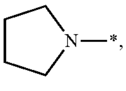

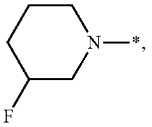

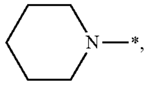

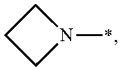

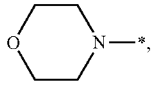

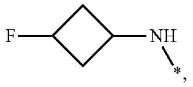

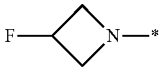

, and

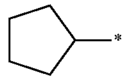

$R^1$ is preferably substituted with fluoro as follows

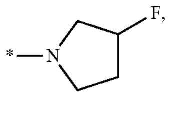

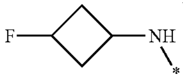

,

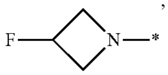

, or

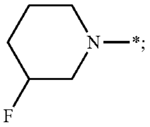

More preferably $R^1$ is

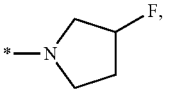

or

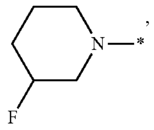

preferably $R^1$ is.

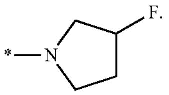

$R^2$ is preferably selected from the following:

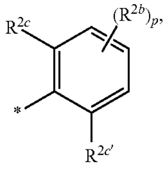
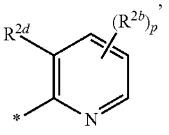
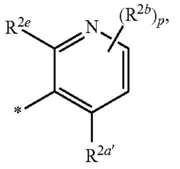
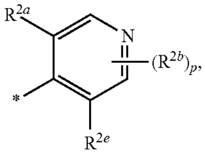
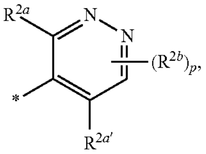
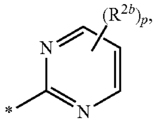
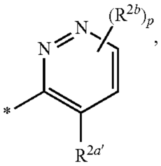
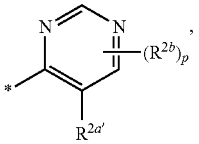
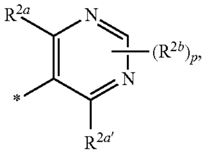
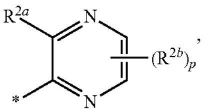
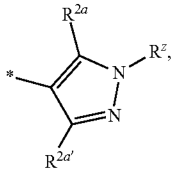
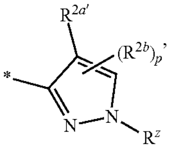
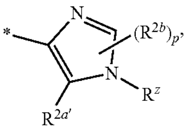
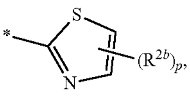
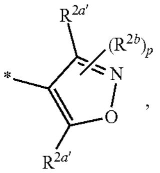
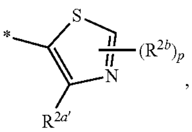
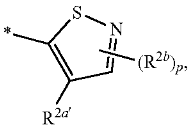
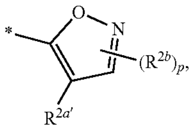
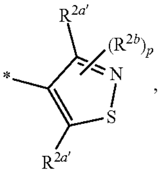
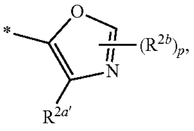
and
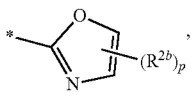

wherein $R^{2a}$, $R^{2a'}$ are independently selected from H, or F;

$R^{2b}$ is independently selected from F, —OH, $C_1$-$C_4$alkyl, halo$C_1$-$C_4$alkyl, —$NH_2$, —CN, or $C_1$-$C_4$alkoxy;

$R^{2c}$, $R^{2c'}$ are independently selected from H, F, OH, $OCH_3$, or $CH_3$;

$R^{2d}$ is selected from H, F, or —OH;

$R^{2e}$ is selected from H, OH, $CH_3$, or F;

$R^z$ is selected from H, $C_1$-$C_4$alkyl or halo$C_1$-$C_4$alkyl;

p is 0, 1 or 2; and

* is the position of bonding.

Preferably, $R^2$ is selected from the following:

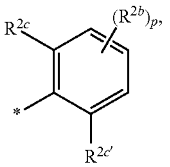
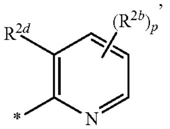
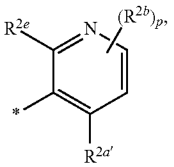
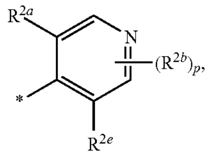
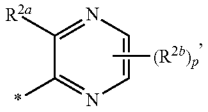
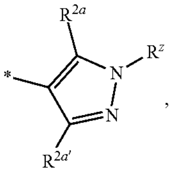
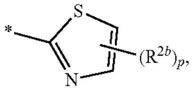
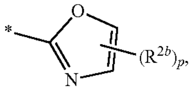
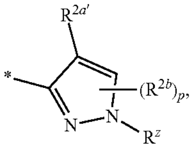
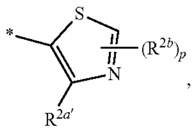
, and
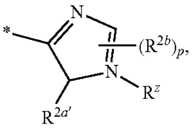

wherein $R^{2a}$, $R^{2a'}$, $R^{2b}$, $R^{2c}$, $R^{2c'}$, $R^{2d}$, $R^{2e}$, $R^z$ and p are as defined hereinabove.

More preferably, $R^2$ is selected from the following:

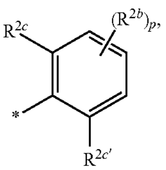
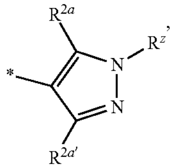
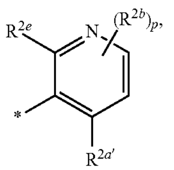
and
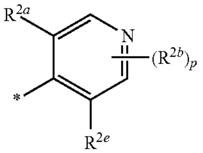

wherein $R^{2a}$, $R^{2a'}$, $R^{2b}$, $R^{2c}$, $R^{2c'}$, $R^{2d}$, $R^{2e}$, $R^z$ and p are as defined hereinabove.

Preferably, $R^2$ is

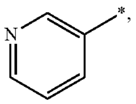
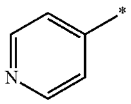
or
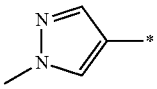

More preferably, $R^2$ is

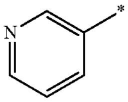

or

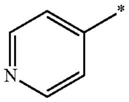

Even more preferably, $R^2$ is

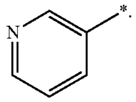

In each of the above embodiments, $R^2$ can be optionally substituted with one or more substituents as disclosed hereinabove. F is preferably $^{19}F$ or $^{18}F$, more preferably $^{18}F$.

In another embodiment, the present invention provides a compound of formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof, wherein the preferred compounds are

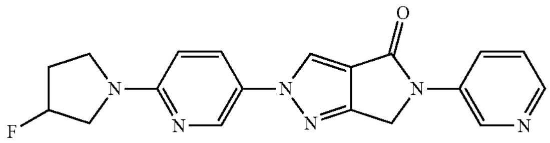

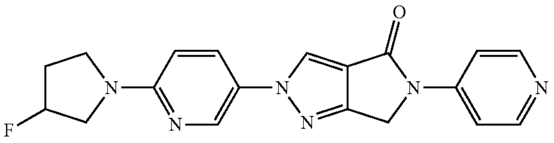

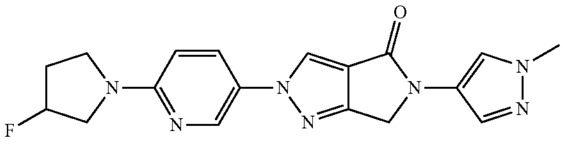

1

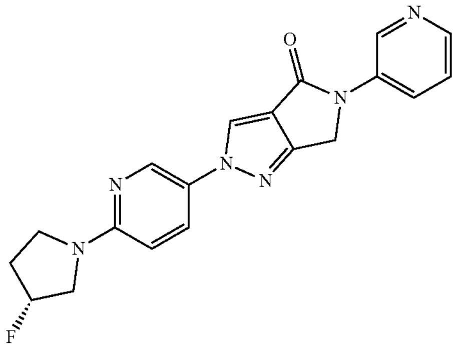

-continued

2

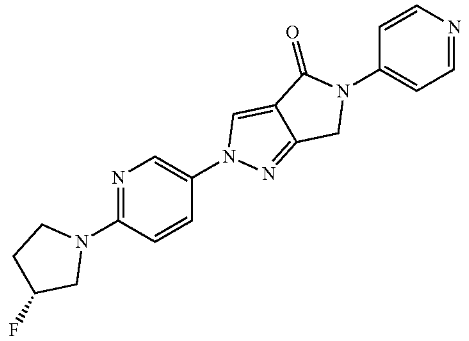

3

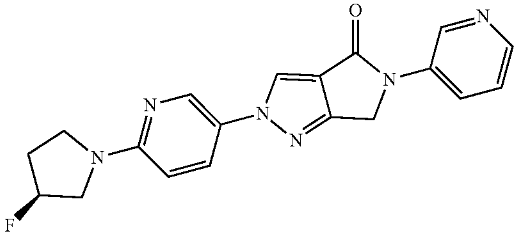

4

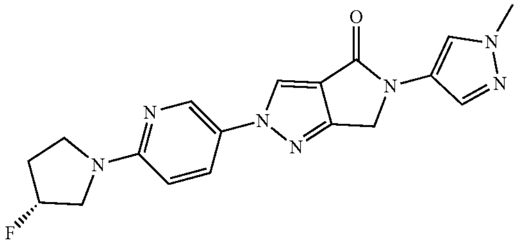

5

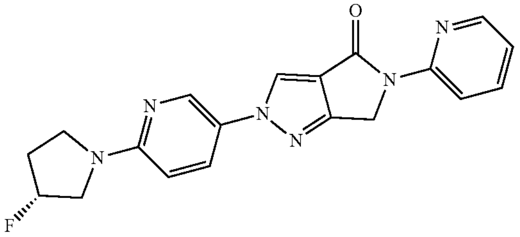

6

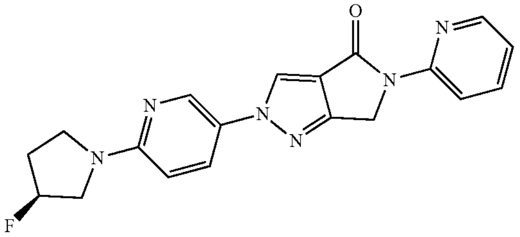

7

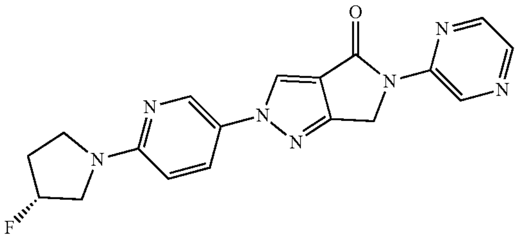

-continued
8
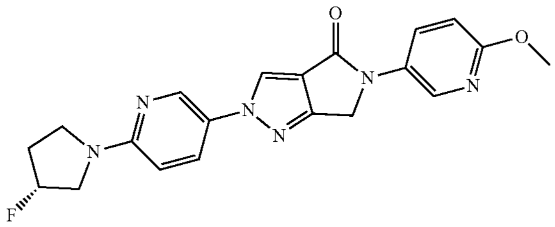
9
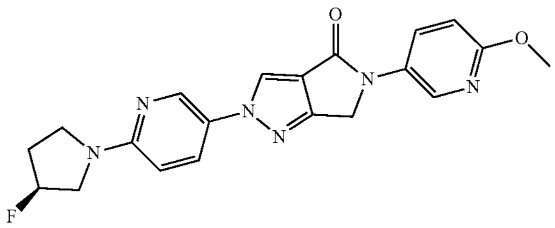
10
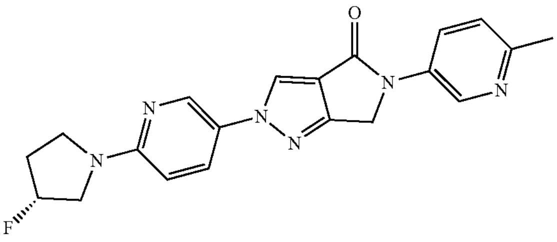
11
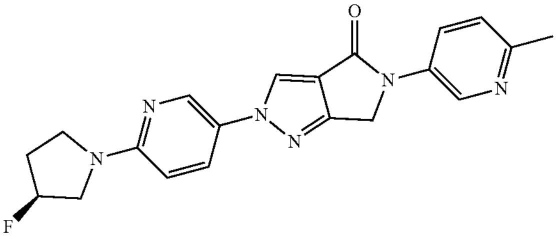
12
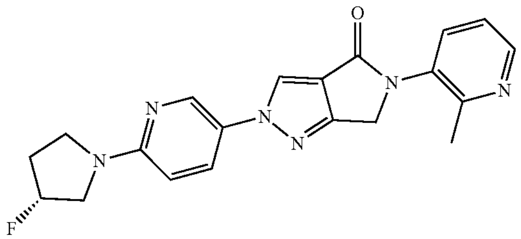
13
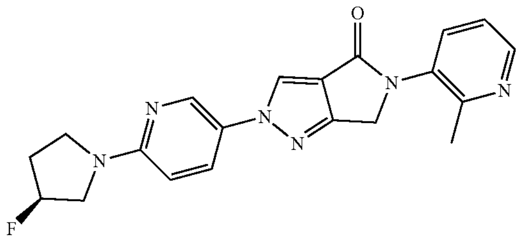
-continued
14
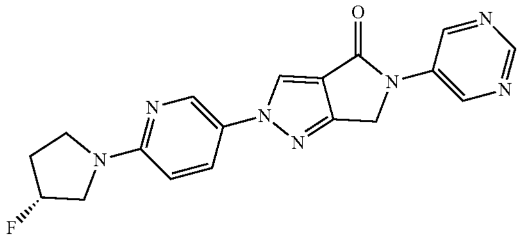
15
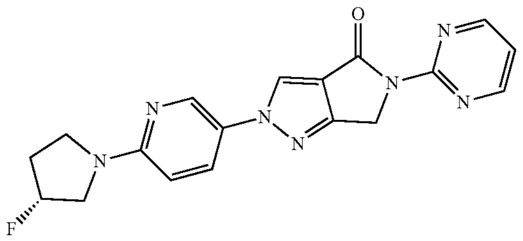
16
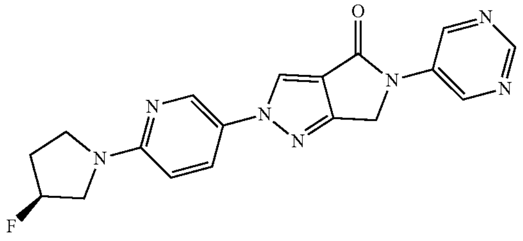
17
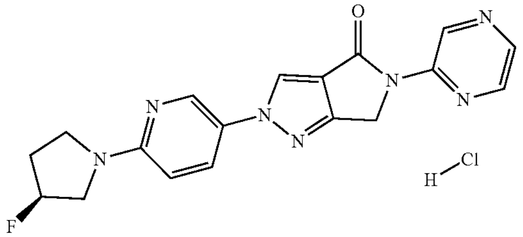
18
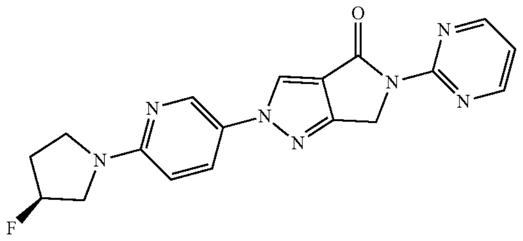
19
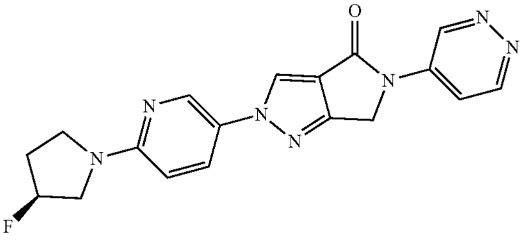

-continued
20
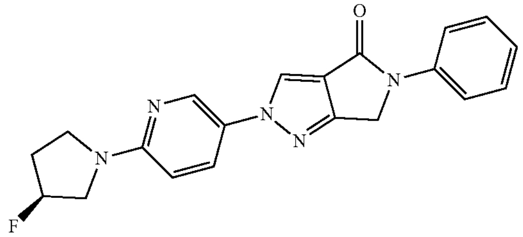
21
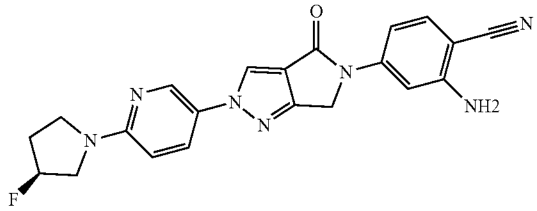
22
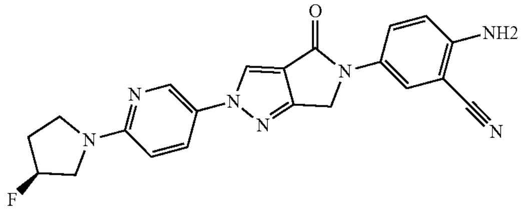
23
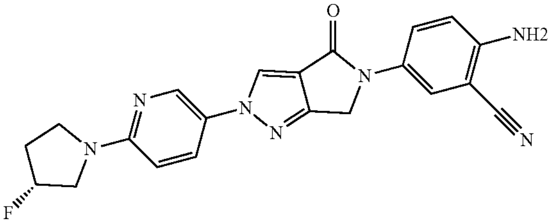
24
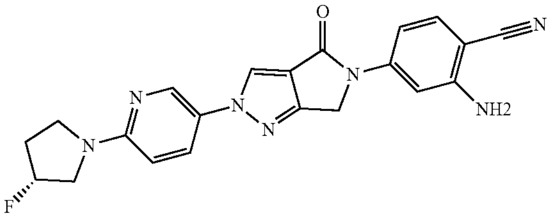
25
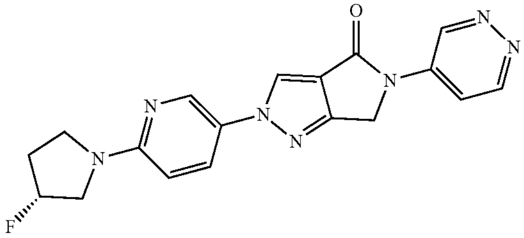
-continued
26
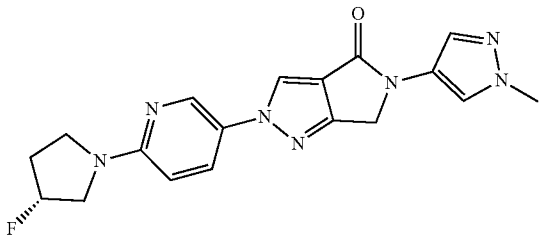
27
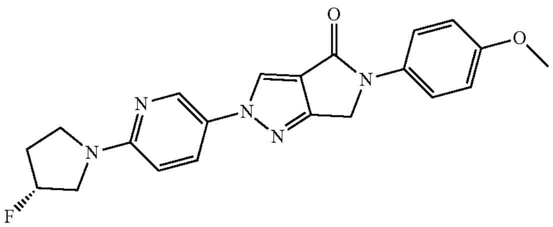
28
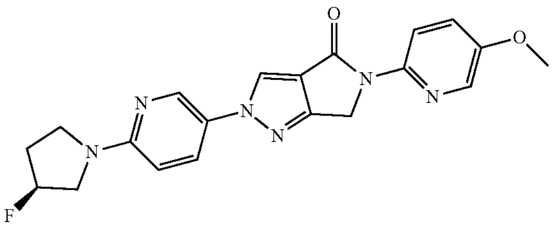
29
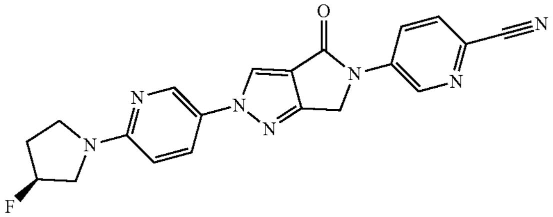
30
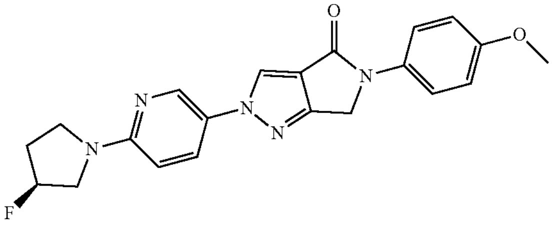
31
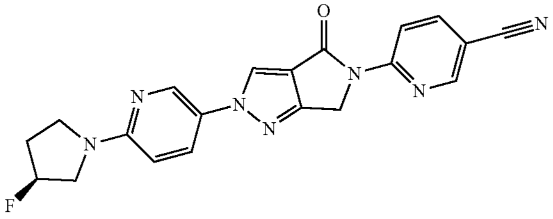

32
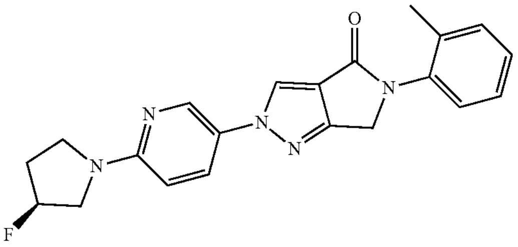
33
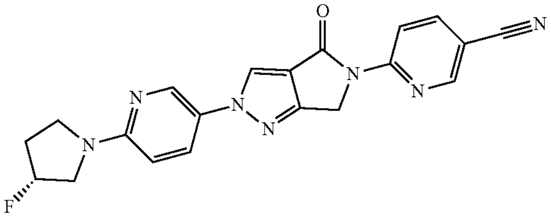
34
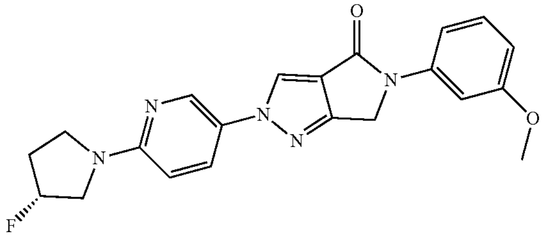
35
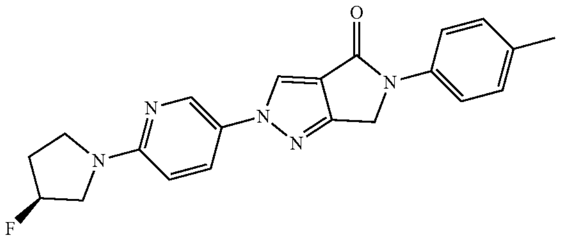
36
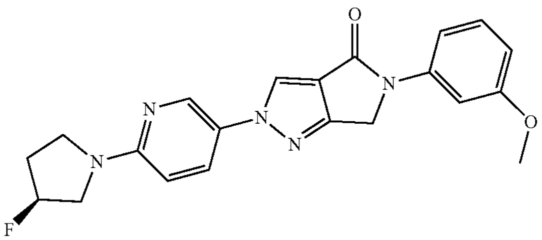
37
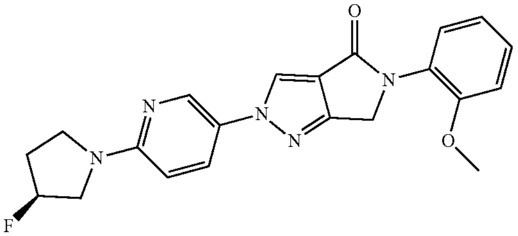
38
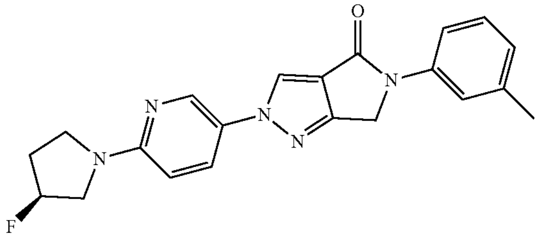
39
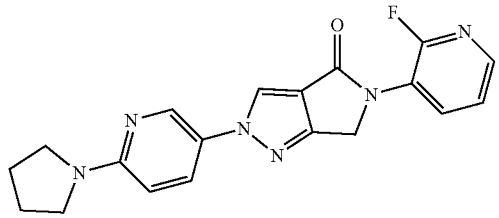
40
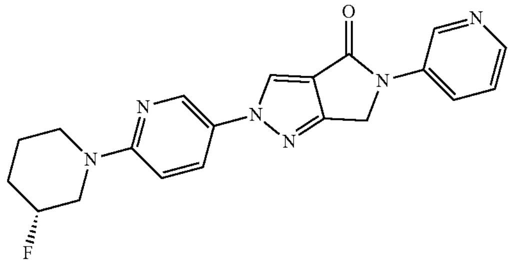
41
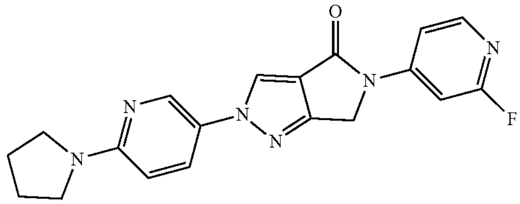
42
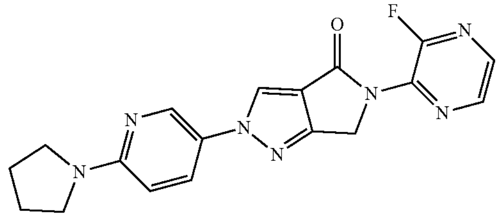
43
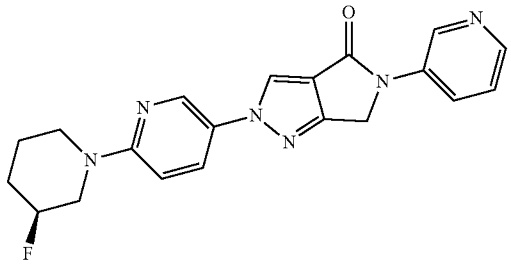

-continued
44
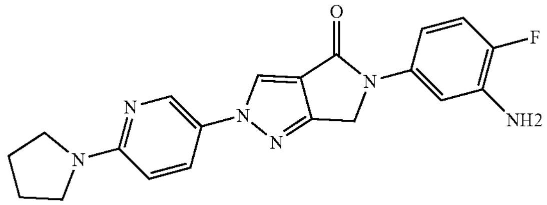
45
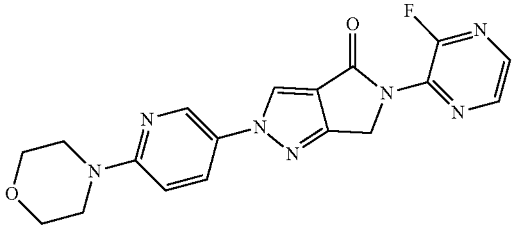
46
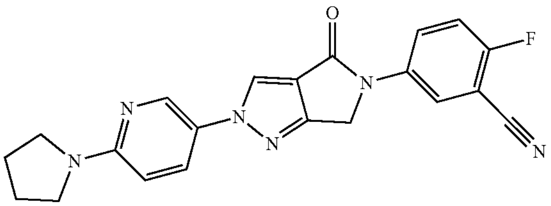
47
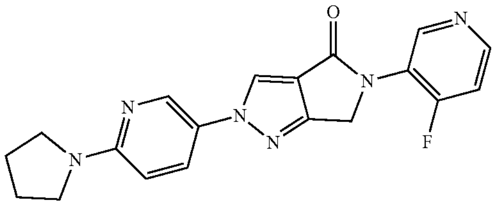
48
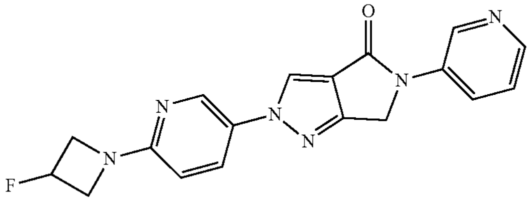
49
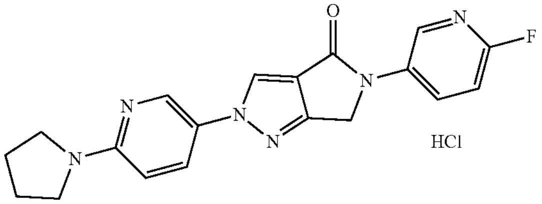
HCl
50
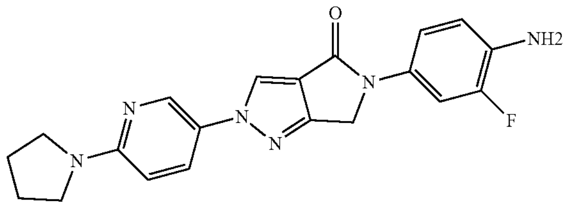
-continued
51
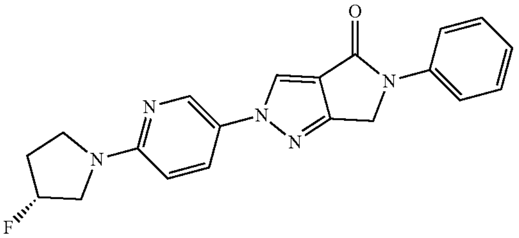
52
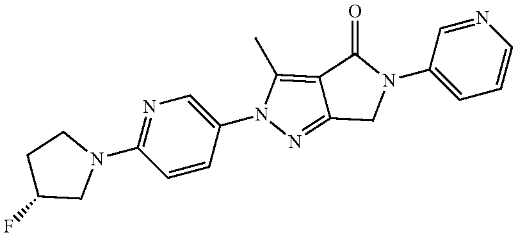
53
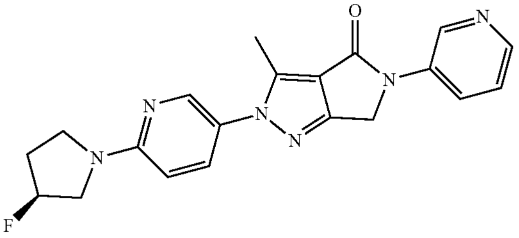
54
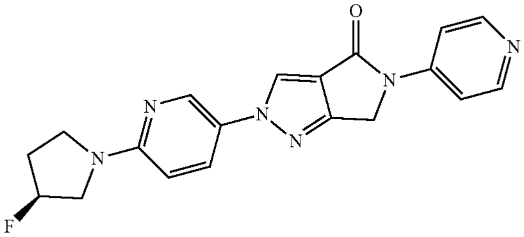
55
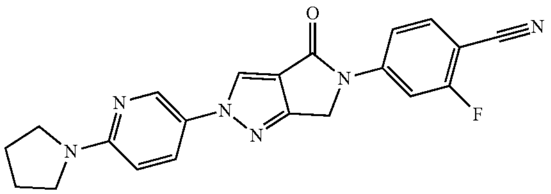
56
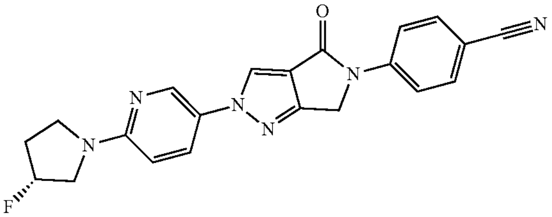

-continued
57
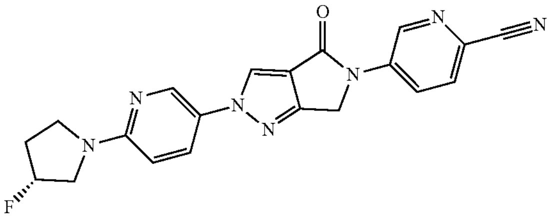
58
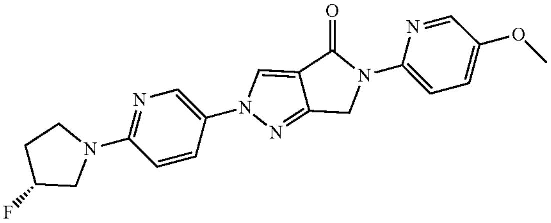
59
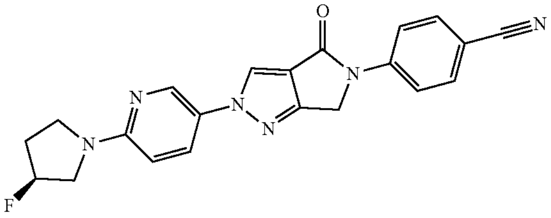
60
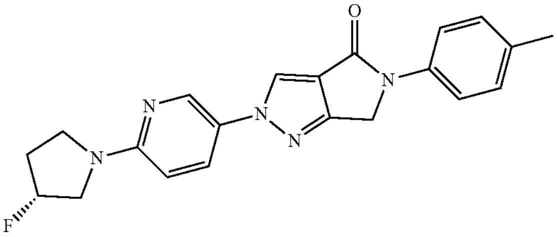
61
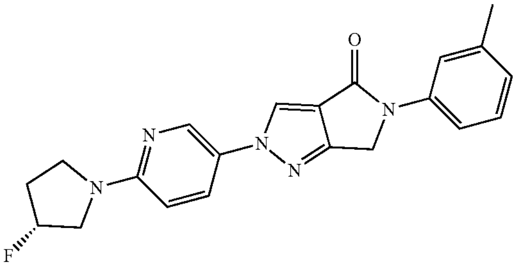
62
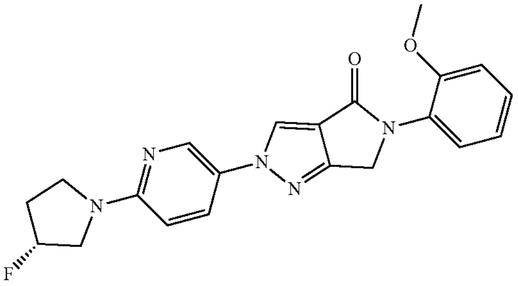
-continued
63
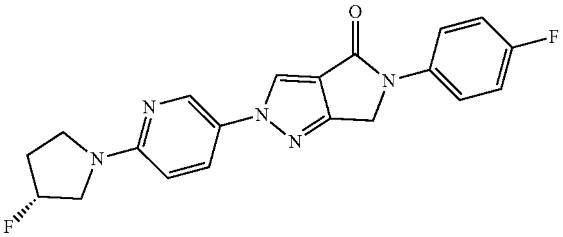
64
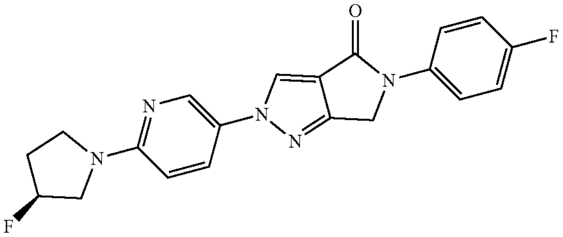
65
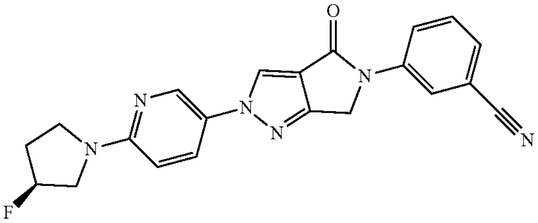
66
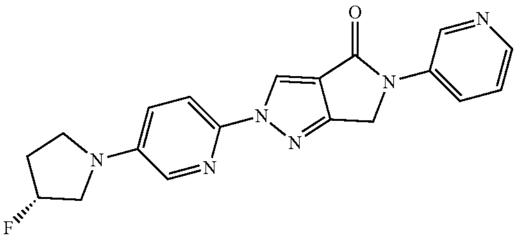
67
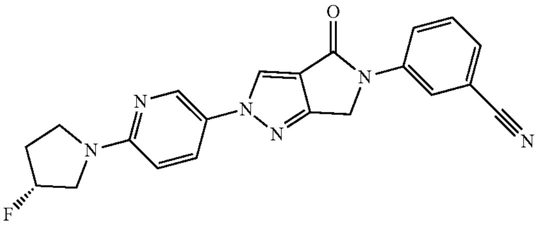
68
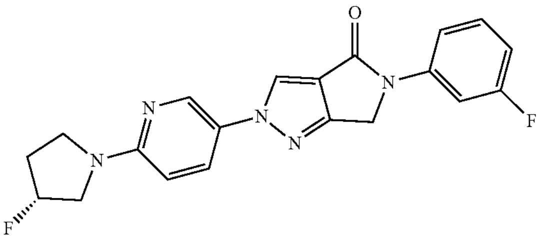

-continued
69
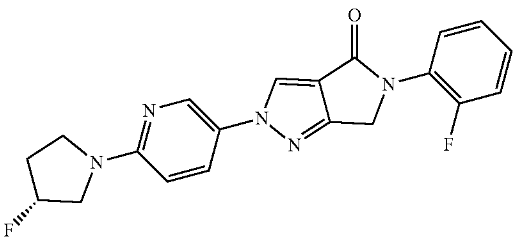
70
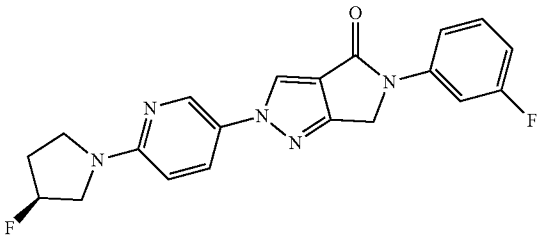
71
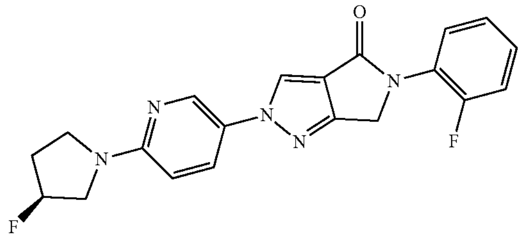
72
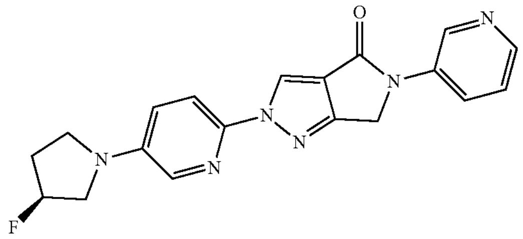
73
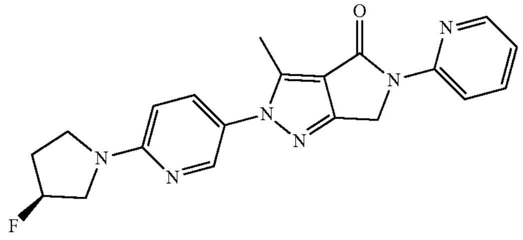
74
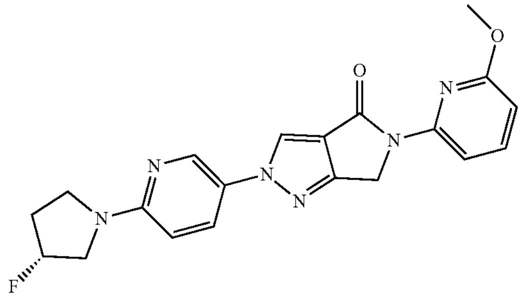
-continued
75
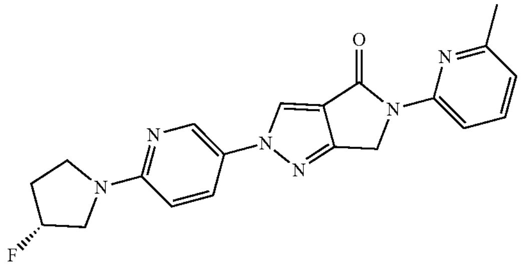
76
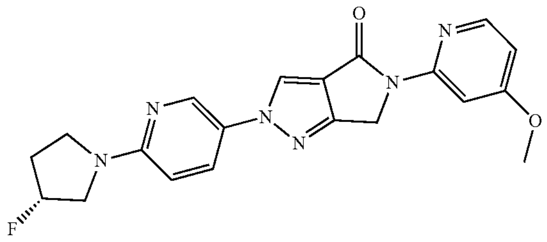
77
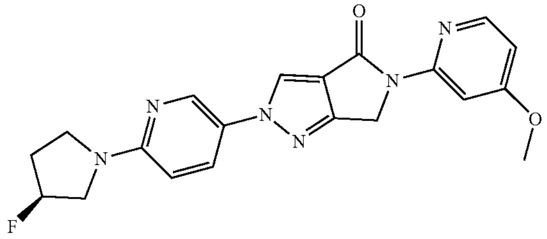
78
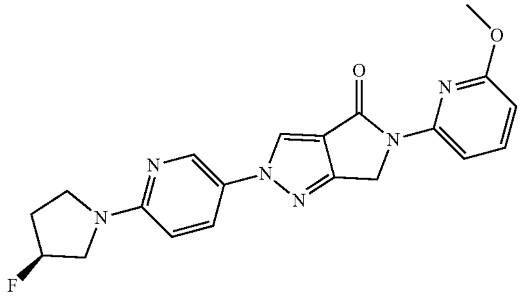
79
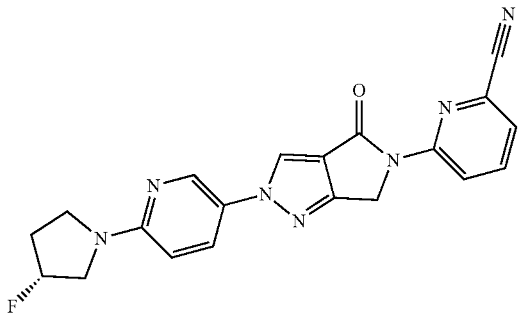

-continued
80
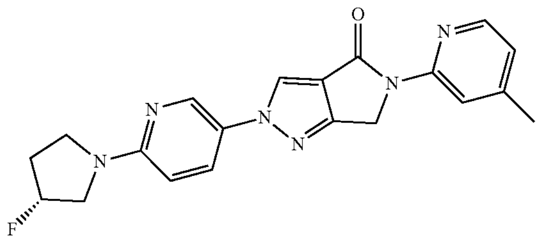
81
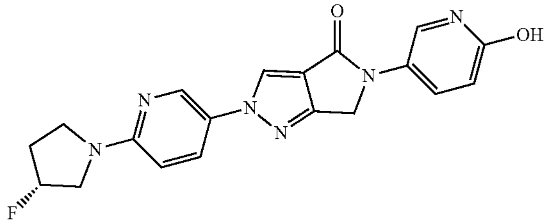
82
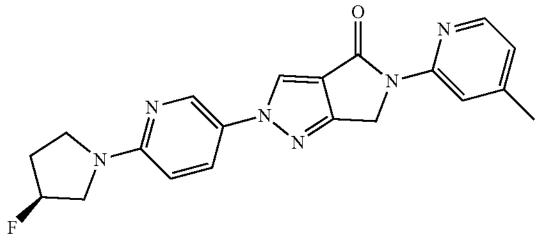
83
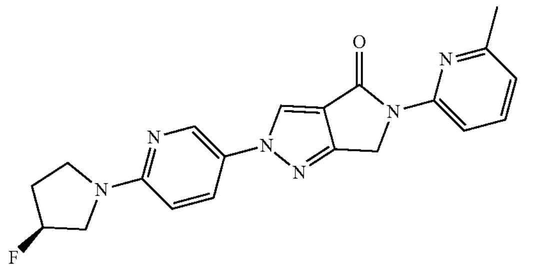
84
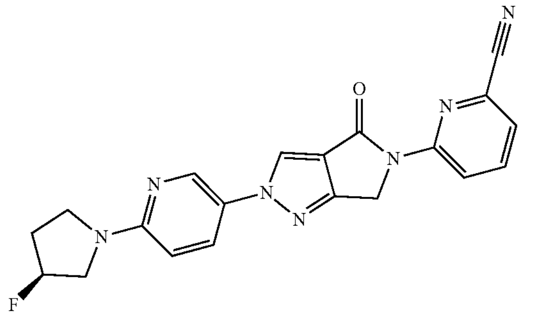
85
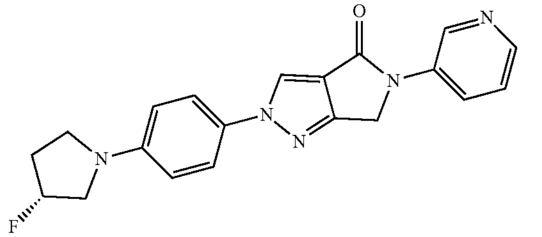
-continued
86
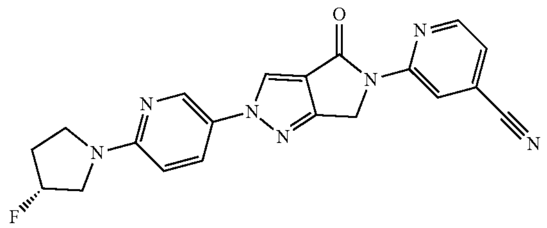
87
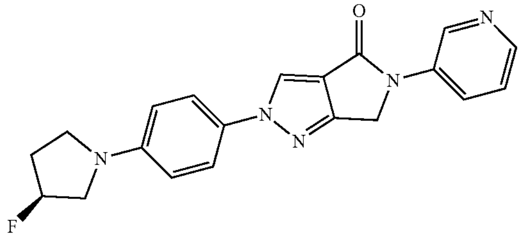
88
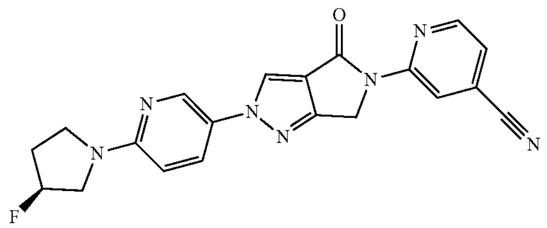
89
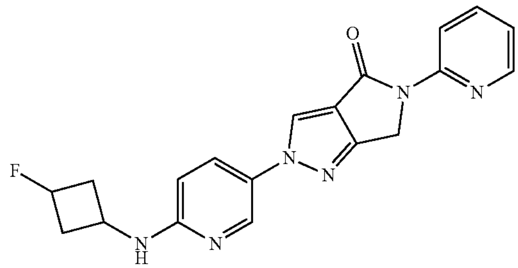
90
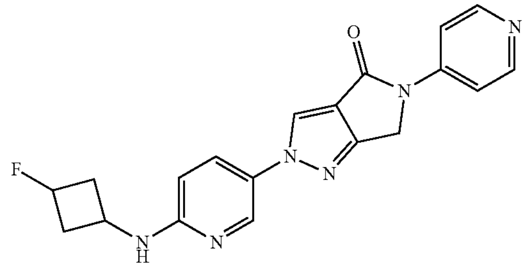
91
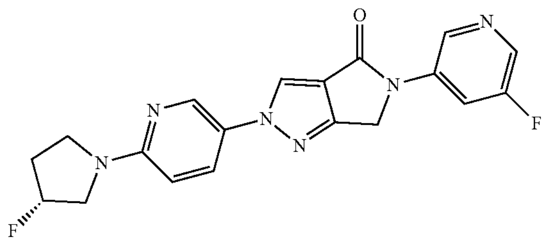

92
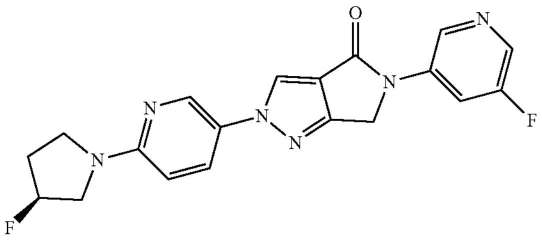
93
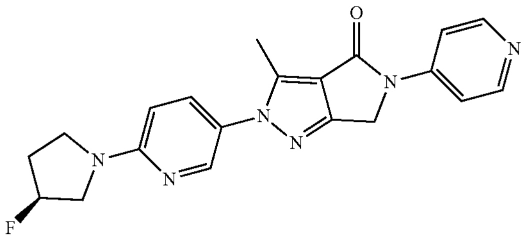
94
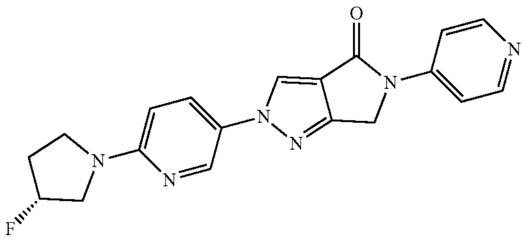
95
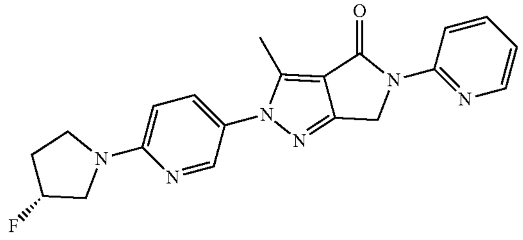
96
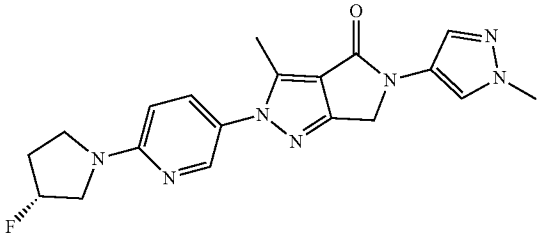
97
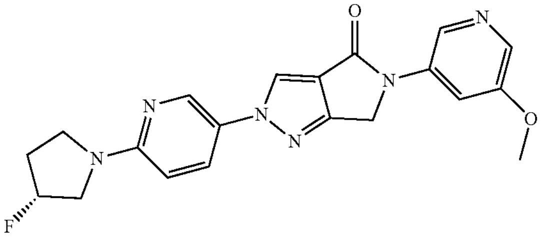
98
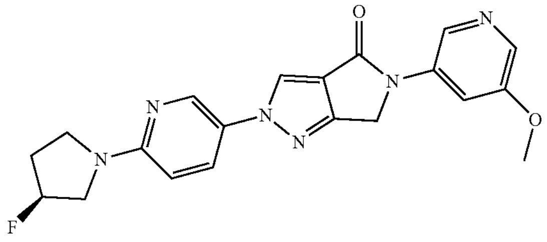
99
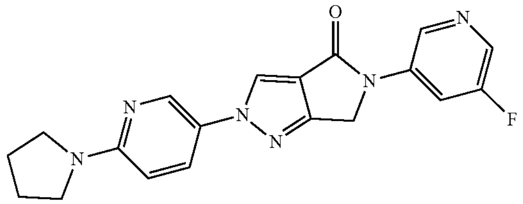
100
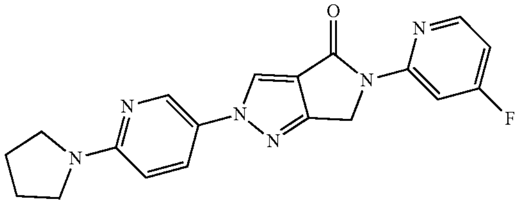
101
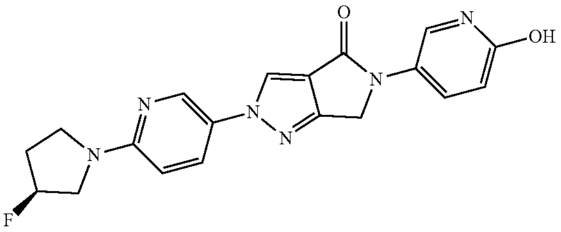
102
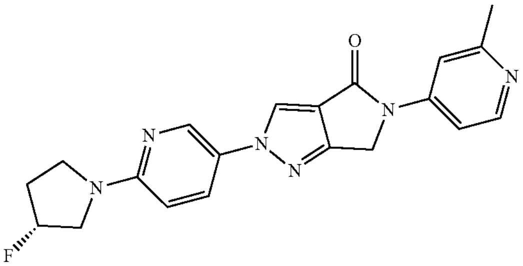
103
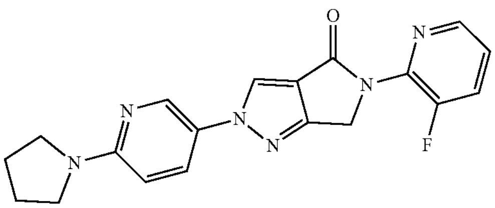

-continued
104
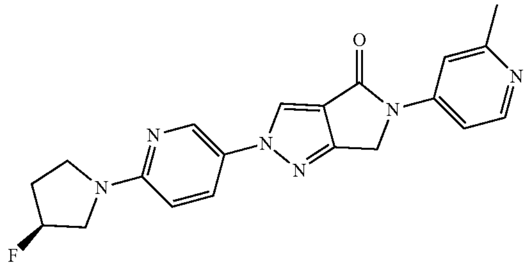
105
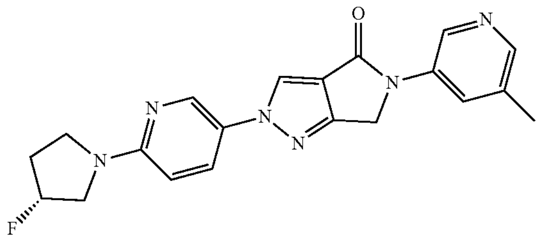
106
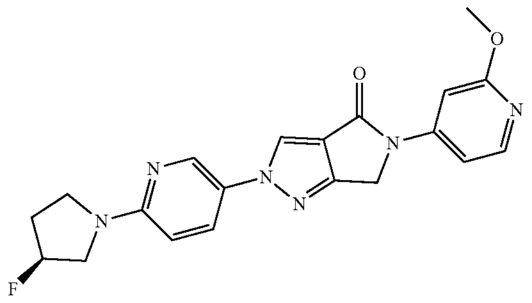
107
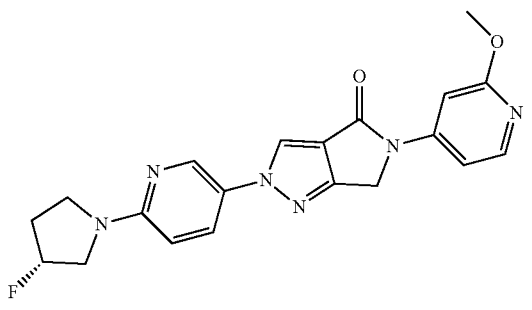
108
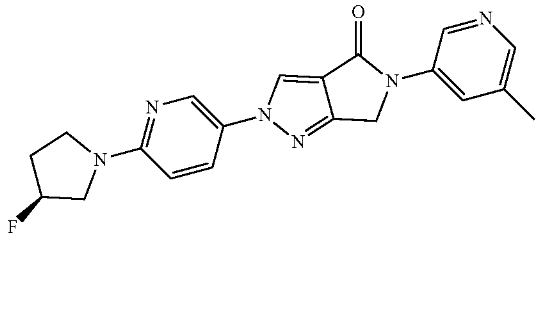
-continued
109
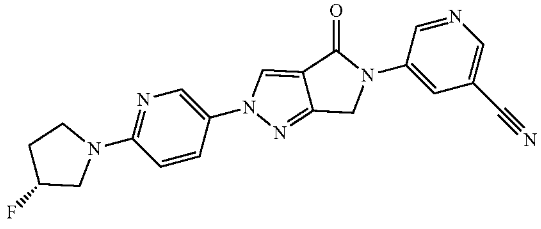
110
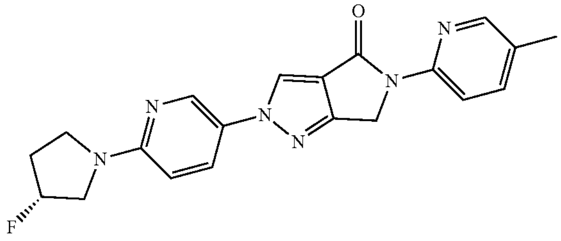
111
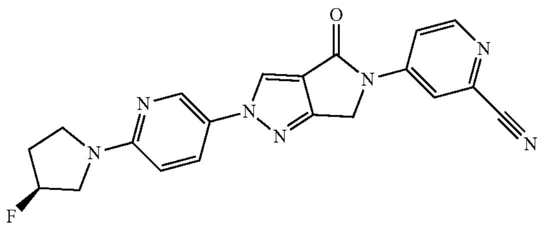
112
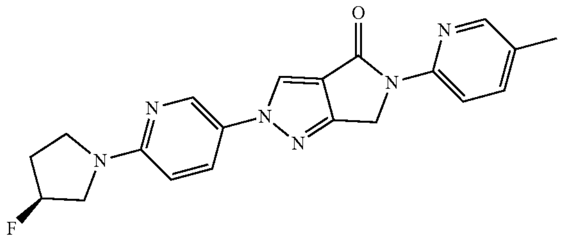
113
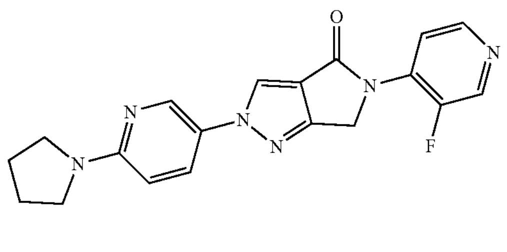
114
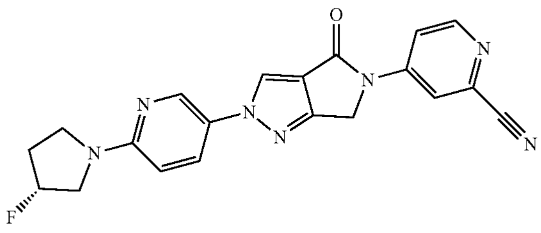

-continued
115
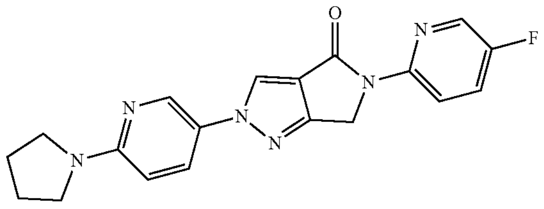
116
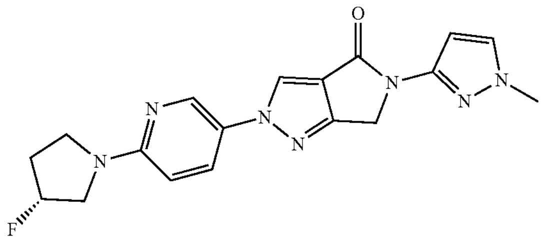
117
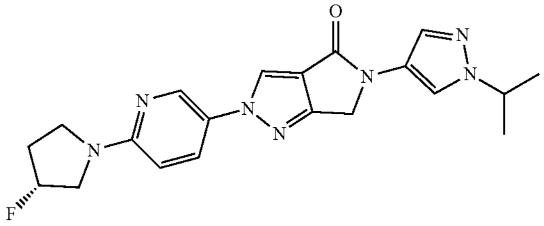
118
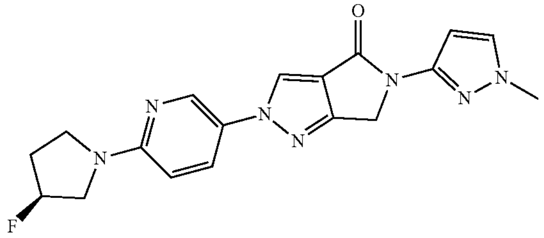
119
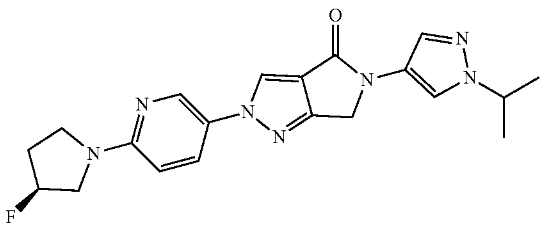
120
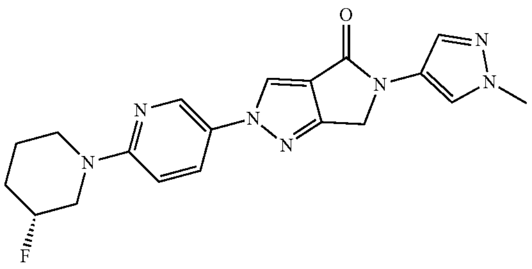
-continued
121
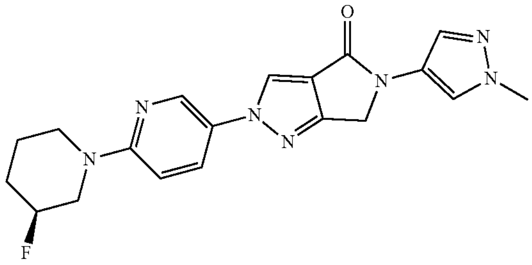
122
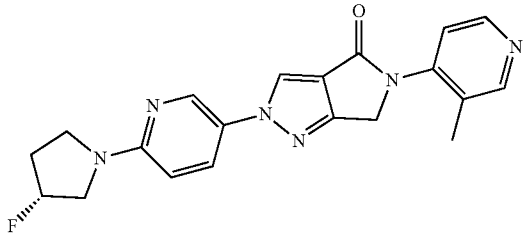
123
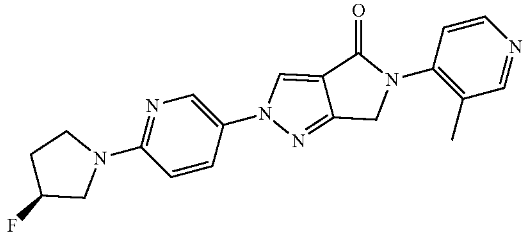
124
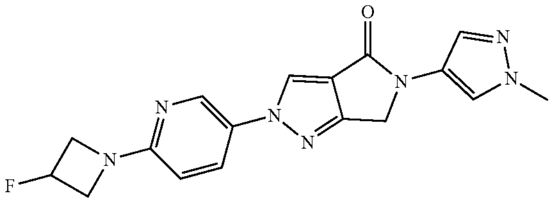
125
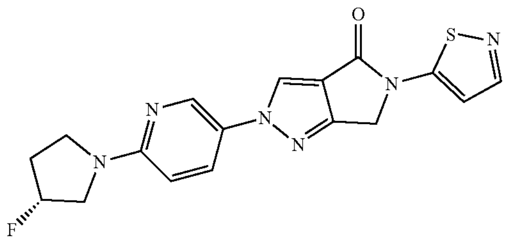
126
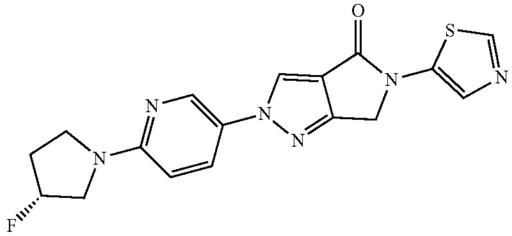

-continued
127
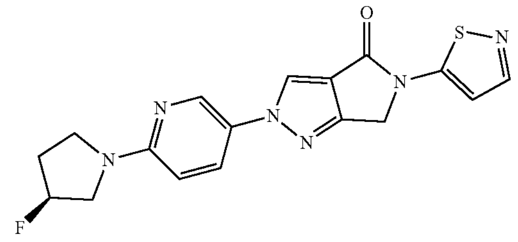
128
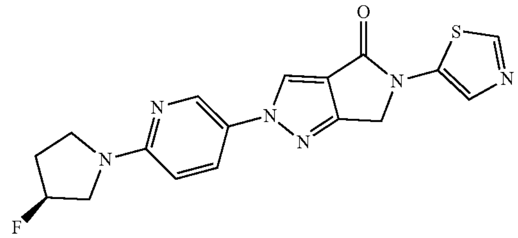
129
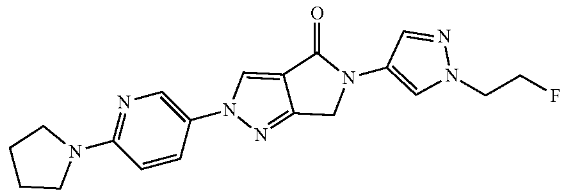
130
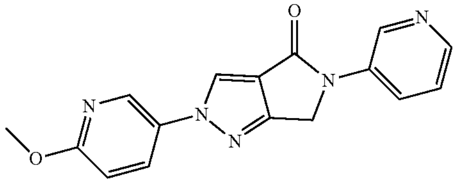
131
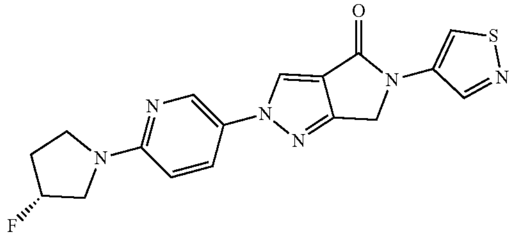
132
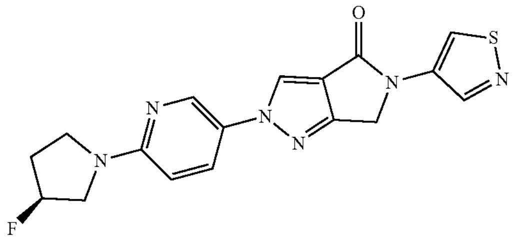
-continued
133
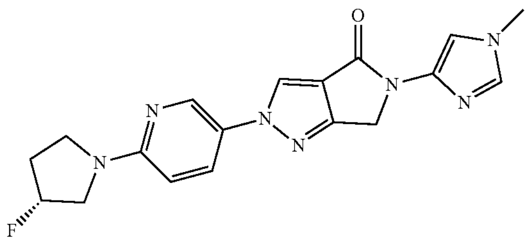
134
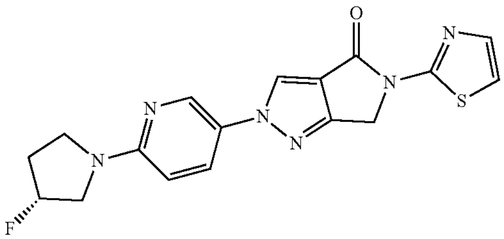
135
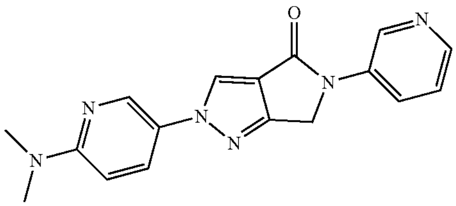
136
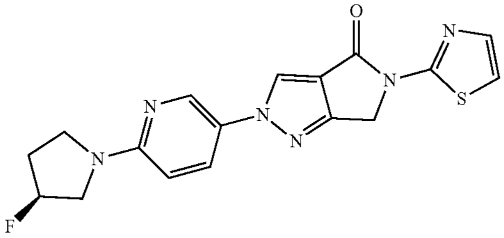
137
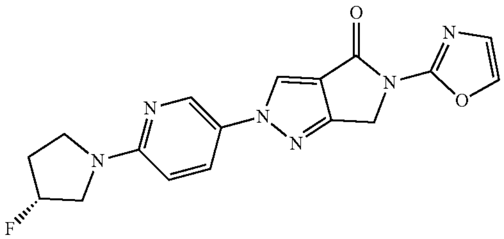
138
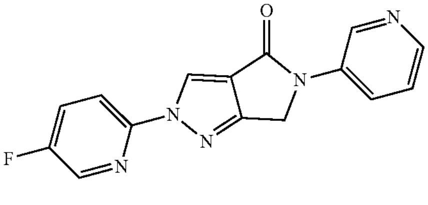

-continued
139
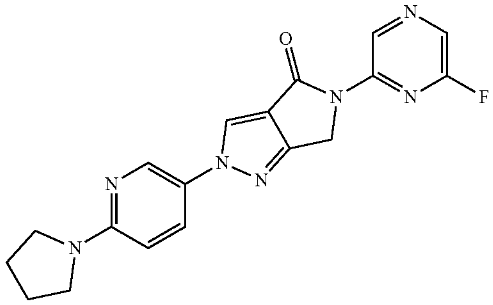
140
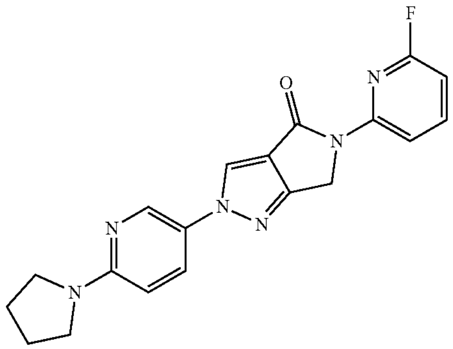
141
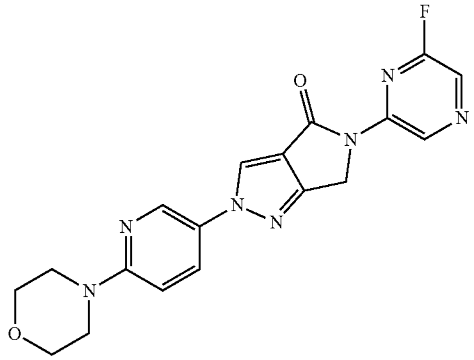
142
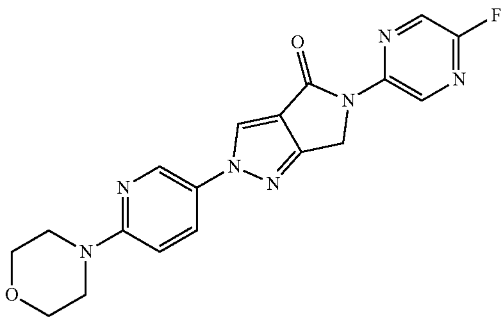
-continued
143
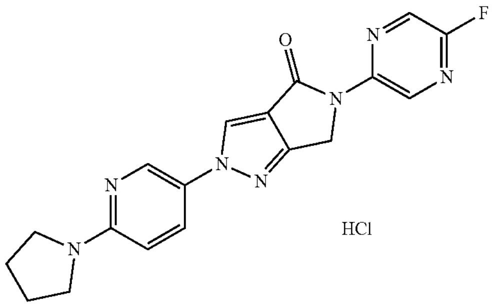
HCl
144
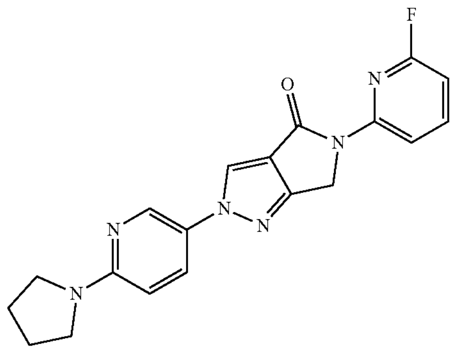
145
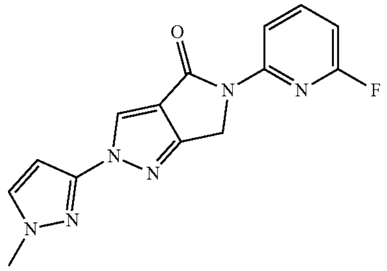
146
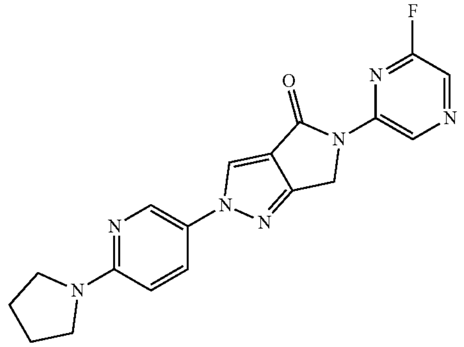

-continued
147
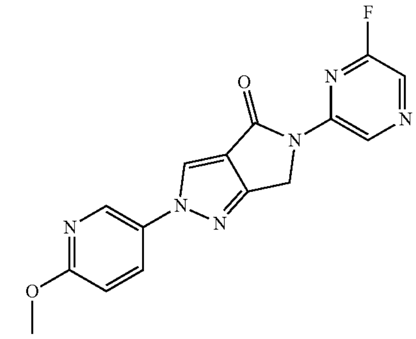
148
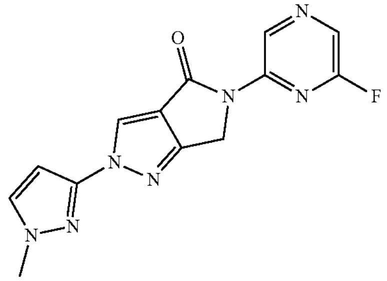
149
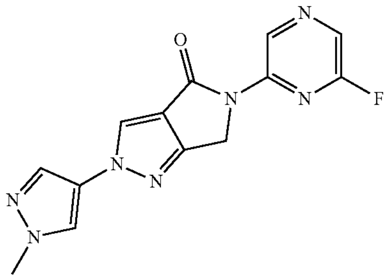
150
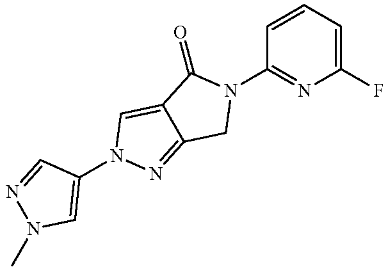
151
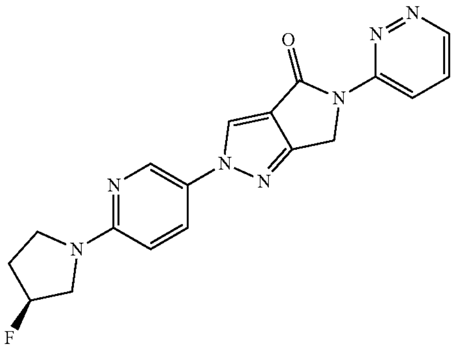
-continued
152
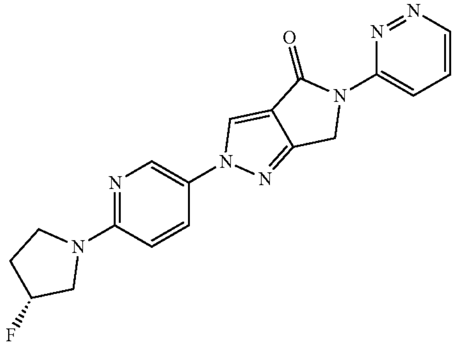
153
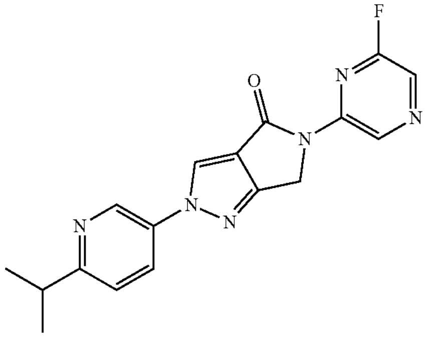
154
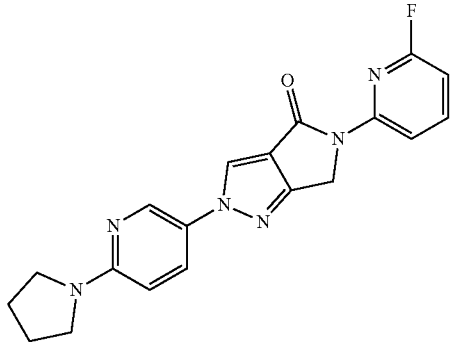
155
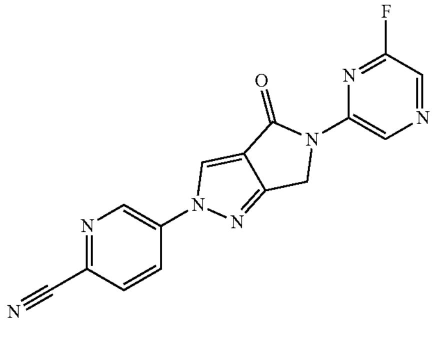

-continued
156
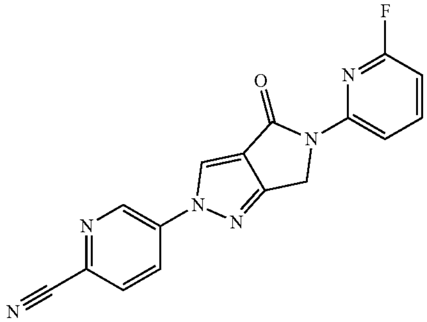
157
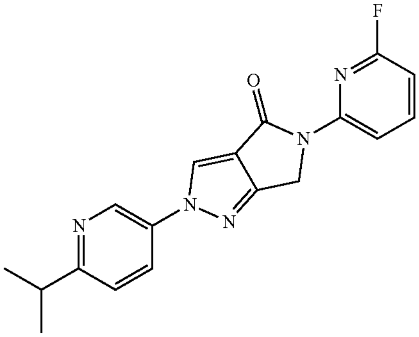
158
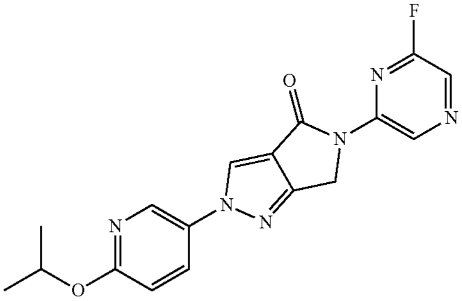
159
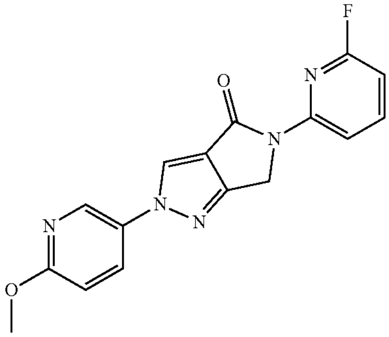
160
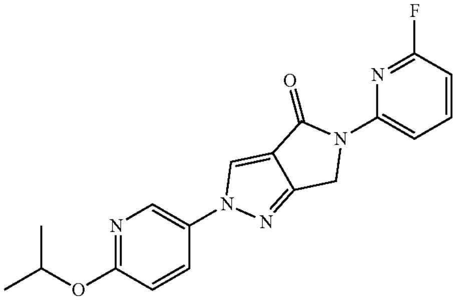
-continued
161
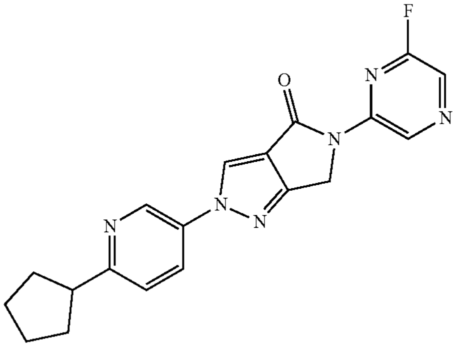
162
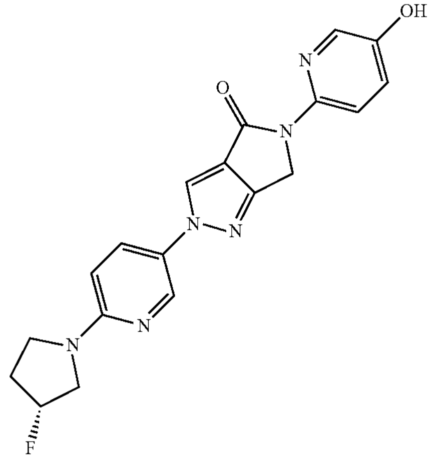
163
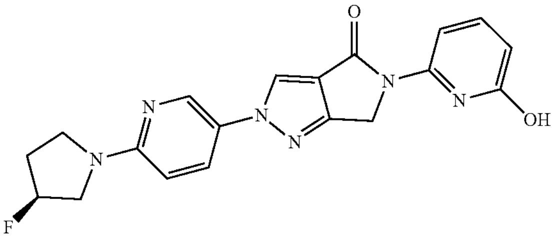
164
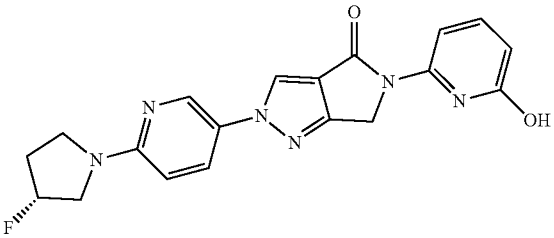
165
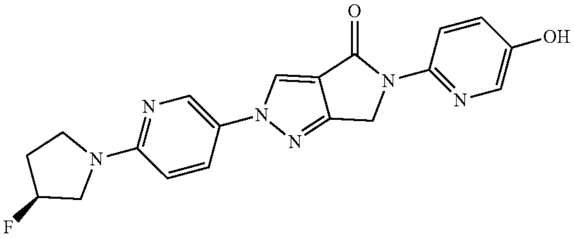

-continued
166
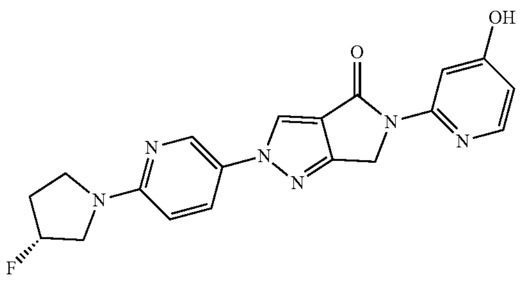
167
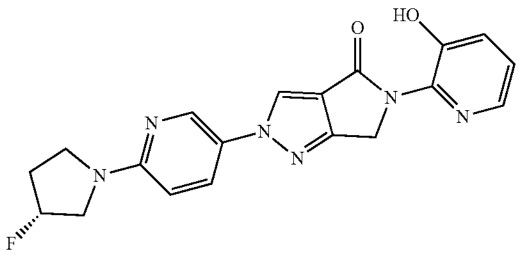
168
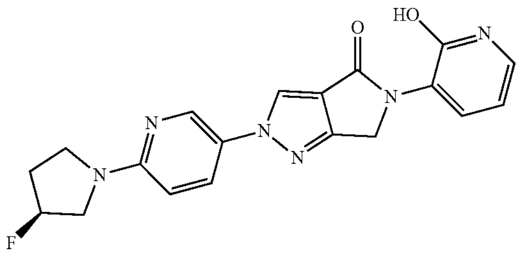
169
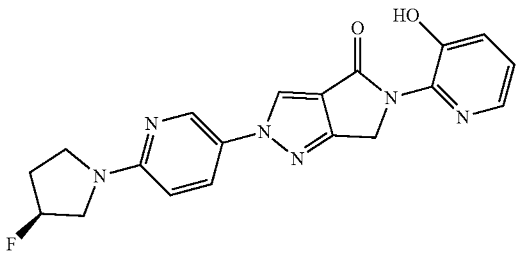
170
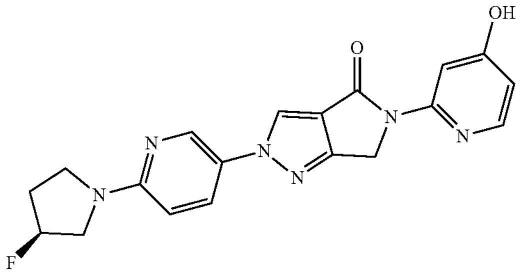
-continued
171
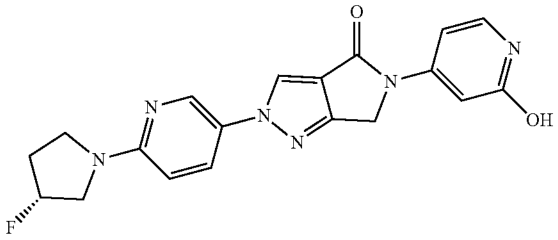
172
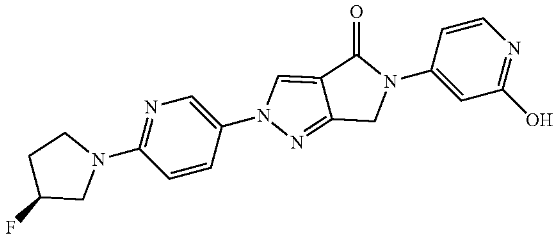
173
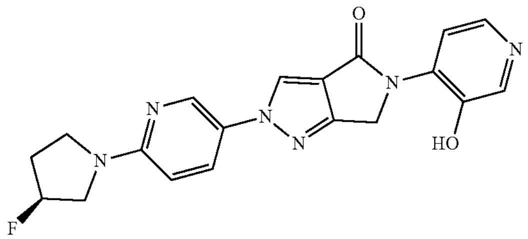
174
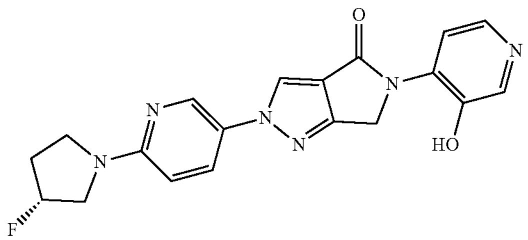
175
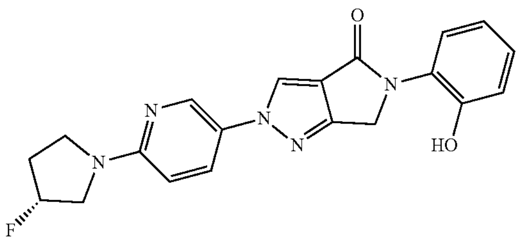
176
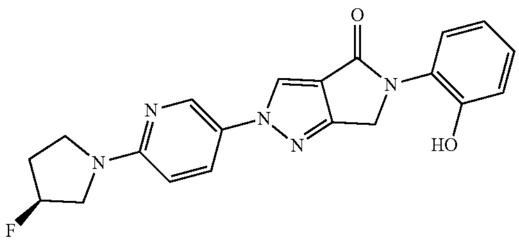

-continued

177

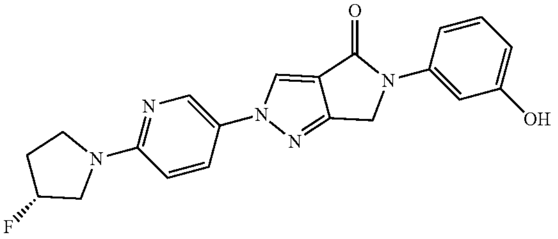

178

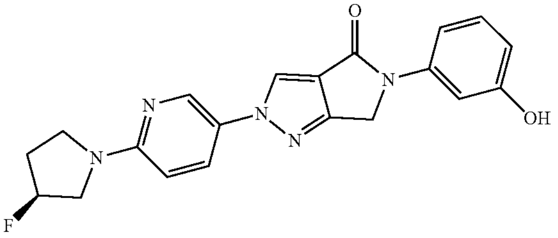

179

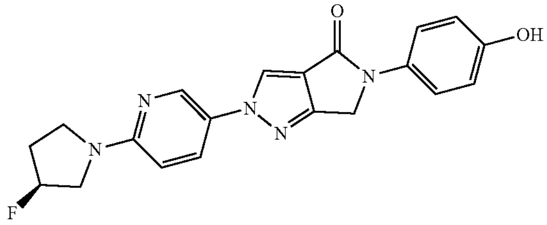

180

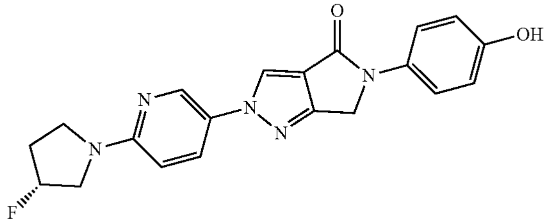

181

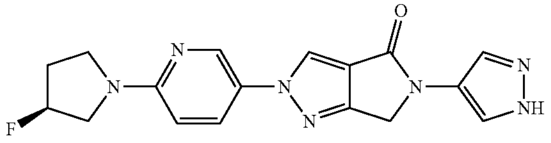

More preferably, stereoisomers of preferred compounds are

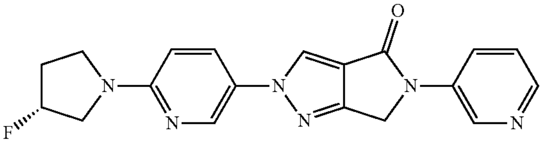
;

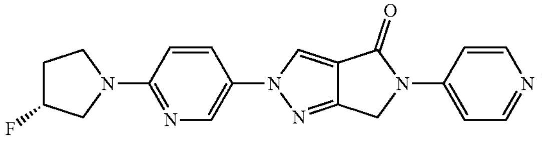
;

-continued

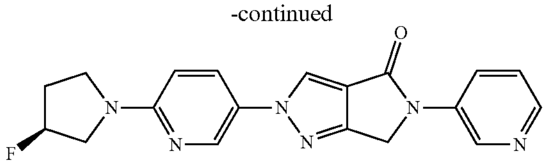
;

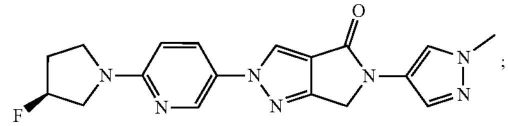
; or

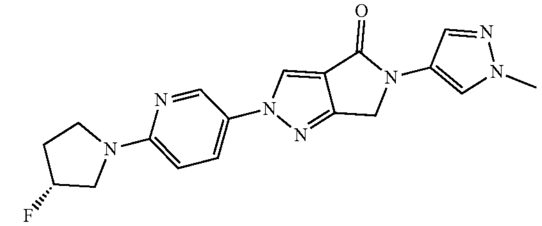

In one embodiment the present invention provides a compound of formula (I), or subformulae thereof (e.g. (IIa), (IIb), (IIIa), (IIIb), (IIIc), (III-F), (III-H)), or a stereoisomer, racemic mixture, pharmaceutically acceptable salt, hydrate, or solvate thereof, wherein the compound of formula (I) is a detectably labelled compound.

One embodiment of the present invention provides a compound of formula (I), or subformulae thereof (e.g. (IIa), (IIb), (IIIa), (IIIb), (IIIc), (III-F), (III-H)), or a stereoisomer, racemic mixture, pharmaceutically acceptable salt, hydrate, or solvate thereof, wherein the compound is a detectably labelled compound, wherein the detectable label is a radioisotope, and wherein the compound of formula (I) comprise at least one radioisotope.

Preferably, the detectable label is a radioisotope selected from $^{18}F$, $^{2}H$ and $^{3}H$, most preferably $^{18}F$ or $^{3}H$.

In one embodiment the present invention provides a compound of formula (I), preferably a compound of subformula (IIIa), or a detectably labelled compound, stereoisomer, racemic mixture, pharmaceutically acceptable salt, hydrate, or solvate thereof, wherein the compound is a detectably labelled compound of formula (III-F)

(III-F)

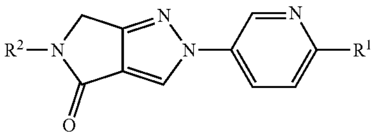
, or a stereoisomer, racemic mixture, pharmaceutically acceptable salt, hydrate, or solvate thereof, wherein $R^1$ is substituted with $^{18}F$ as follows

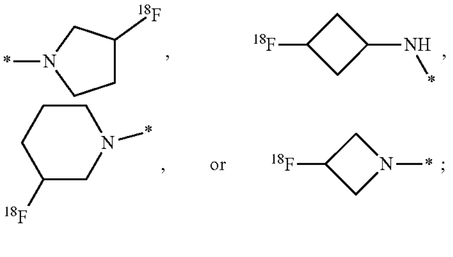

$R^2$ is an aryl, or a 5-membered or 6-membered heteroaryl, wherein $R^2$ is selected from

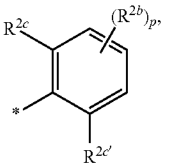 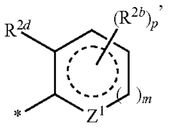 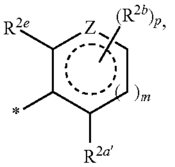

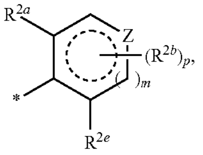 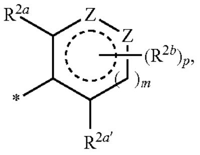 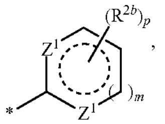

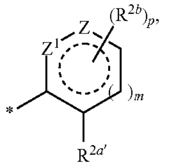 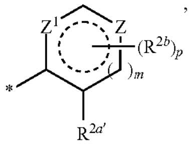

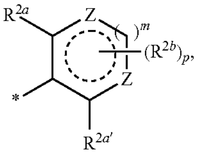 and 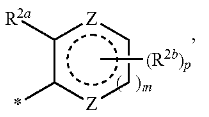

wherein $R^{2a}$, $R^{2a'}$ are independently selected from H, or F;

$R^{2b}$ is independently selected from F, —OH, $C_1$-$C_4$alkyl, halo$C_1$-$C_4$alkyl, —$NH_2$, —CN, or $C_1$-$C_4$alkoxy;

$R^{2c}$, $R^{2c'}$ are independently selected from H, F, OH, $OCH_3$, or $CH_3$;

$R^{2d}$ is selected from H, F, or —OH;

$R^{2e}$ is selected from H, OH, $CH_3$, or F;

Z is independently N, NH, N($C_1$-$C_4$alkyl), N(halo$C_1$-$C_4$alkyl), O, or S;

$Z^1$ is independently N, NH, O, or S;

p is 0, 1 or 2;

m is 0 or 1;

as valency permits,  is a combination of single and double bonds; and

* is the position of bonding.

Preferably $R^2$ is selected from

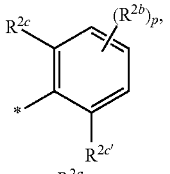 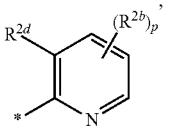 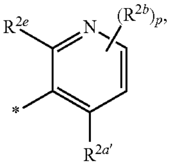

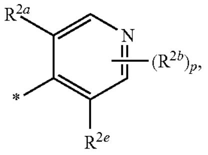 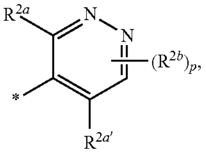

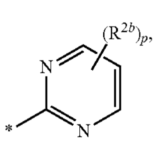 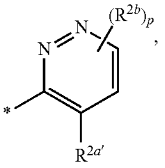 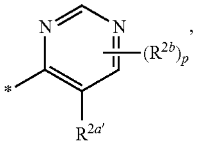

-continued

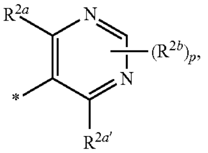 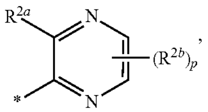

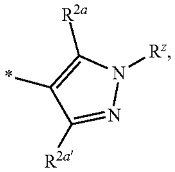 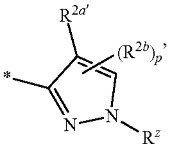 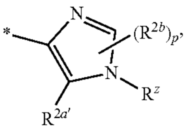

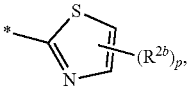 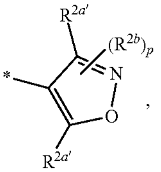 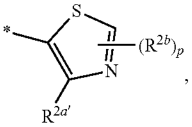

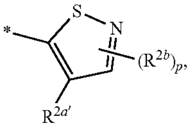 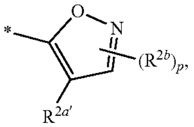 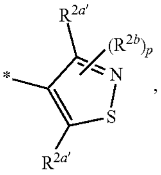

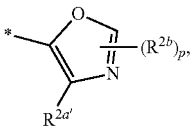 and 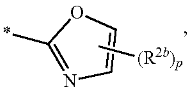

wherein $R^{2a}$, $R^{2a'}$, $R^{2b}$, $R^{2c}$, $R^{2c'}$, $R^{2d}$, $R^{2e}$ and p are as defined hereinabove and $R^z$ is selected from H, $C_1$-$C_4$alkyl or halo$C_1$-$C_4$alkyl.

More preferably, $R^2$ is selected from the following:

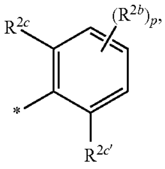 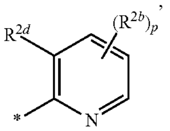 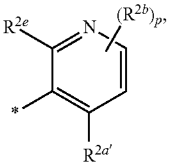

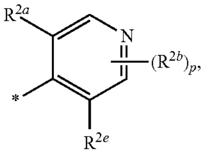 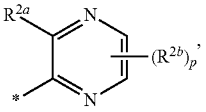

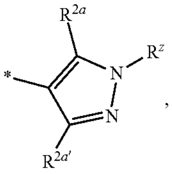 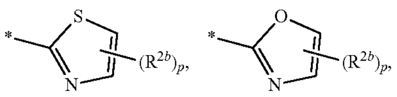

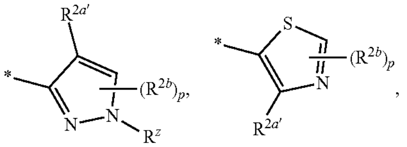 and

-continued

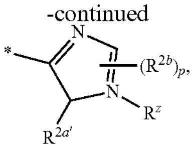

wherein $R^{2a}$, $R^{2a'}$, $R^{2b}$, $R^{2c}$, $R^{2c'}$, $R^{2d}$, $R^{2e}$, $R^z$ and p are as defined hereinabove.

More preferably, $R^2$ is selected from the following:

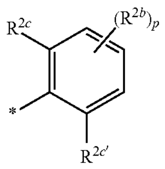,
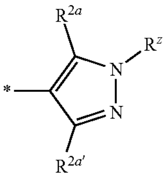,
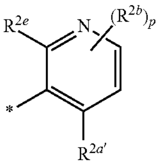, and
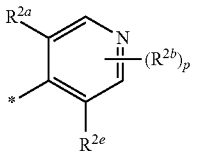

wherein $R^{2a}$, $R^{2a'}$, $R^{2b}$, $R^{2c}$, $R^{2c'}$, $R^{2e}$, $R^z$ and p are as defined hereinabove.

Preferably, the detectably labelled compound of formula (III-F), or a stereoisomer, racemic mixture, pharmaceutically acceptable salt, hydrate, or solvate thereof, comprises at least one $^{18}F$. Preferably, the substituents of $R^2$ (e.g. $R^{2a}$, $R^{2a'}$, $R^{2b}$, $R^{2c}$, $R^{2c'}$, $R^z$, and $R^{2e}$) optionally can be $^{18}F$. More preferably, the detectably labelled compound of formula (III-F), or a stereoisomer, racemic mixture, pharmaceutically acceptable salt, hydrate, or solvate thereof, comprises one or two $^{18}F$. Even more preferably, one $^{18}F$.

Preferred compounds are selected from:

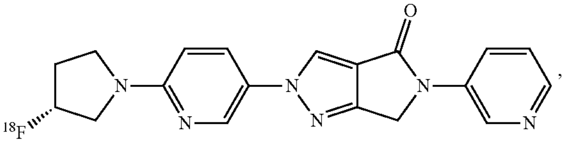,
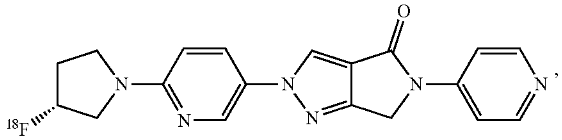,
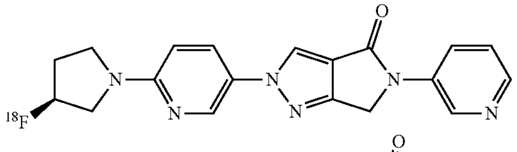, or
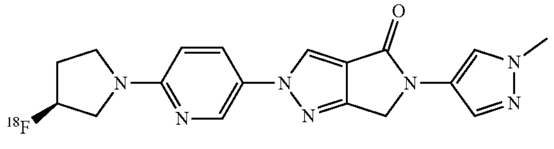, or a pharmaceutically acceptable salt, hydrate, or solvate thereof.

A most preferred compound is

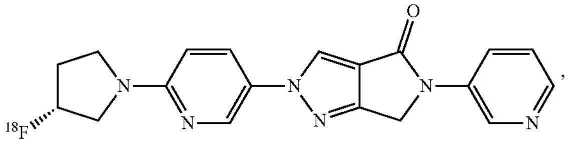 [SMILES: O=C1c2cn(-c3ccc(N4CC[C@@H]([18F])C4)nc3)nc2CN1c1cccnc1], or a pharmaceutically acceptable salt, hydrate, or solvate thereof.

In one embodiment the present invention provides a compound of formula (I), preferably a compound of subformula (IIIa), or a detectably labelled compound, stereoisomer, racemic mixture, pharmaceutically acceptable salt, hydrate, or solvate thereof, wherein the compound is a detectably labelled compound of formula (III-H)

(III-H)

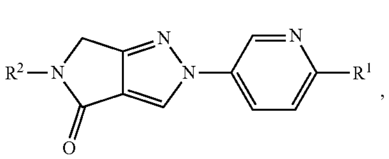, or a stereoisomer, racemic mixture, pharmaceutically acceptable salt, hydrate, or solvate thereof, which is detectably labelled at at least one available position by $^2H$ (deuterium "D") or $^3H$ (Tritium "T"), preferably $^3H$, wherein $R^1$ is —CN; or halo; or $C_1$-$C_4$alkyl; or $C_1$-$C_4$alkoxy; or —N($C_1$-$C_4$alkyl)$_2$; or —NH($C_1$-$C_4$alkyl); or H; or $R^1$ is —NH—$C_3$-$C_6$cycloalkyl, $C_3$-$C_6$cycloalkyl, or heterocyclyl, each of which is optionally substituted with at least one halo; $R^1$ is preferably selected from

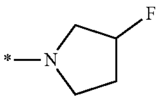,
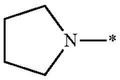,
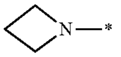,
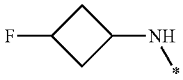,
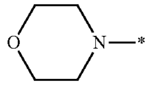,
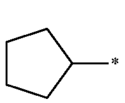,
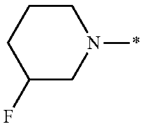,
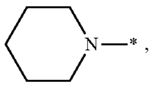, or
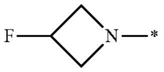;

$R^2$ is an aryl, or a 5-membered or 6-membered heteroaryl, wherein $R^2$ is selected from the following:

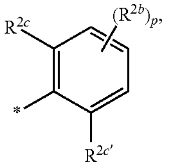,
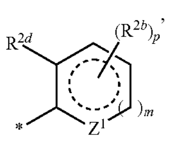,
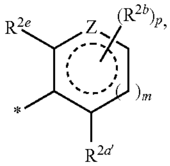,

-continued

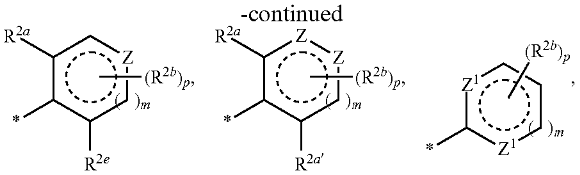

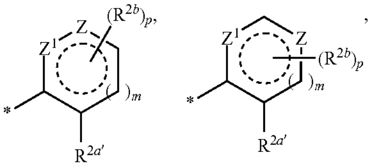

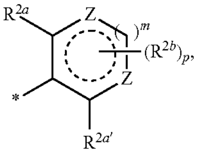

and

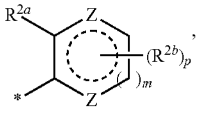

wherein $R^{2a}$, $R^{2a'}$ are independently selected from H, T or F;

$R^{2b}$ is independently selected from T, F, —OH, $C_1$-$C_4$alkyl, halo$C_1$-$C_4$alkyl, —$NH_2$, —CN, $CT_3$, or $C_1$-$C_4$alkoxy;

$R^{2a}$, $R^{2a'}$ are independently selected from T, H, F, OH, $OCH_3$, $CT_3$, or $CH_3$;

$R^{2d}$ is selected from T, H, F, or —OH;

$R^{2e}$ is selected from T, H, OH, $CH_3$, $CT_3$, or F;

Z is independently N, NH, N($C_1$-$C_4$alkyl), N(halo$C_1$-$C_4$alkyl), O, or S;

$Z^1$ is independently N, NH, O, or S;

p is 0, 1 or 2;

m is 0 or 1;

as valency permits, is a combination of single and double bonds;

Fluoro is $^{19}F$;

wherein $C_1$-$C_4$alkyl, halo$C_1$-$C_4$alkyl, or $C_1$-$C_4$alkoxy optionally comprise one or more T, and

* is the position of bonding.

Preferably, the detectably labelled compound of formula (III-H), or a stereoisomer, racemic mixture, pharmaceutically acceptable salt, hydrate, or solvate thereof, comprises one, two or three T. Preferably, the detectably labelled compound of formula (III-Ha), or a stereoisomer, racemic mixture, pharmaceutically acceptable salt, hydrate, or solvate thereof, comprises one T. More preferably, the detectably labelled compound of formula (III-Ha), comprises two T. Even more preferably, the detectably labelled compound of formula (III-Ha), comprises three T.

Preferably, the detectably labelled compound of formula (III-H), or a stereoisomer, racemic mixture, pharmaceutically acceptable salt, hydrate, or solvate thereof, is a compound of formula (III-Ha)

(III-Ha)

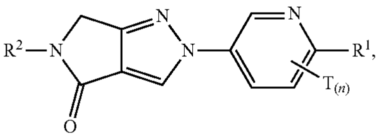

or a stereoisomer, racemic mixture, pharmaceutically acceptable salt, hydrate, or solvate thereof, wherein $R^1$ is —CN; or halo; or $C_1$-$C_4$alkyl; or $C_1$-$C_4$alkoxy; or —N($C_1$-$C_4$alkyl)$_2$; or —NH($C_1$-$C_4$alkyl); or H; or $R^1$ is —NH—$C_3$-$C_6$cycloalkyl, $C_3$-$C_6$cycloalkyl, or heterocyclyl, each of which is optionally substituted with at least one halo;

$R^1$ is preferably selected from

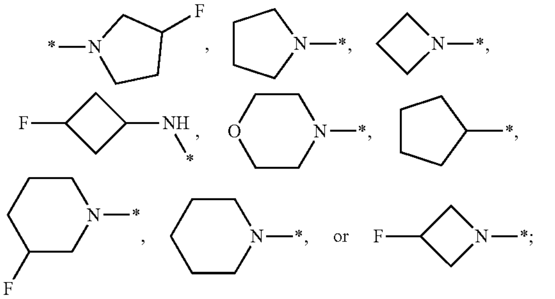

$R^2$ is an aryl, or a 5-membered or 6-membered heteroaryl, wherein $R^2$ is selected from the following and wherein $R^2$ is optionally substituted with at least one T,

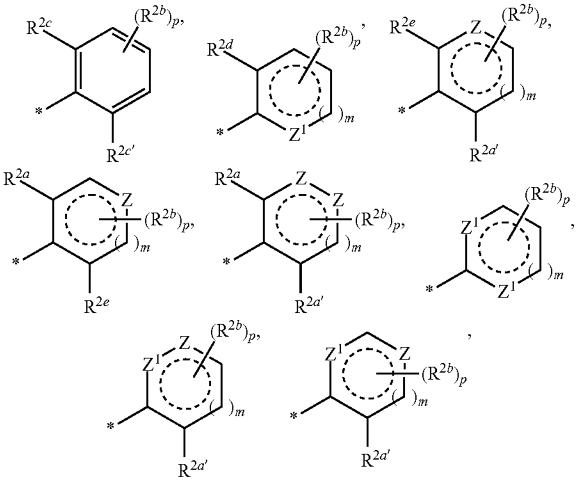

and

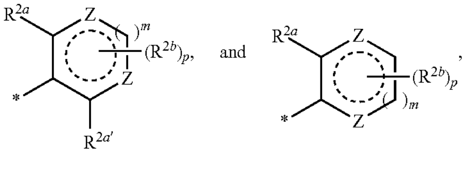

wherein $R^{2a}$, $R^{2a'}$ are independently selected from H, T or F;

$R^{2b}$ is independently selected from T, F, —OH, $C_1$-$C_4$alkyl, halo$C_1$-$C_4$alkyl, —$NH_2$, —CN, $CT_3$, or $C_1$-$C_4$alkoxy, wherein $C_1$-$C_4$alkyl, halo$C_1$-$C_4$alkyl, or $C_1$-$C_4$alkoxy optionally comprise one or more T;

$R^{2c}$, $R^{2c'}$ are independently selected from T, H, F, OH, $OCH_3$, $CT_3$, or $CH_3$;

$R^{2d}$ is selected from T, H, F, or —OH;

$R^{2e}$ is selected from T, H, OH, $CH_3$, $CT_3$, or F;

Z is independently N, NH, N($C_1$-$C_4$alkyl), N(halo$C_1$-$C_4$alkyl), O, or S;

$Z^1$ is independently N, NH, O, or S;

p is 0, 1 or 2;

m is 0 or 1;

as valency permits, is a combination of single and double bonds;

T is $^3$H (Tritium);

n is 0 to 3;

with the proviso that the compound of formula (I-Ha) comprises at least one T;

Fluoro is $^{19}$F; and

* is the position of bonding.

Preferably, the detectably labelled compound of formula (III-Ha), or a stereoisomer, racemic mixture, pharmaceutically acceptable salt, hydrate, or solvate thereof, comprises one, two or three T. Preferably, n is 1.

Preferably, the detectably labelled compound of formula (III-Ha), or a stereoisomer, racemic mixture, pharmaceutically acceptable salt, hydrate, or solvate thereof, comprises one T. More preferably, the detectably labelled compound of formula (III-Ha), or a stereoisomer, racemic mixture, pharmaceutically acceptable salt, hydrate, or solvate thereof, comprises two T. Even more preferably, the detectably labelled compound of formula (III-Ha), or a stereoisomer, racemic mixture, pharmaceutically acceptable salt, hydrate, or solvate thereof, comprises three T.

In a further embodiment, the present invention provides a detectably labelled compound of formulae (III-H) or (III-Ha), or a stereoisomer, racemic mixture, pharmaceutically acceptable salt, hydrate, or solvate thereof, as disclosed hereinabove, wherein $R^2$ is an aryl, or a 5-membered or 6-membered heteroaryl selected from

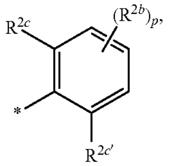 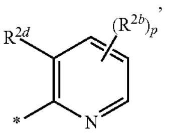, 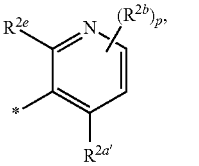

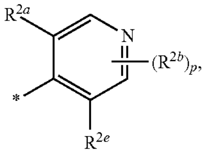 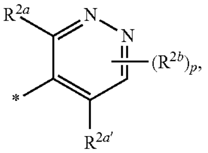

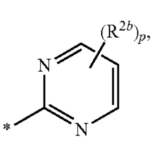 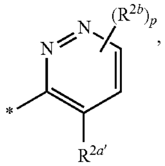, 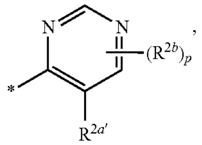,

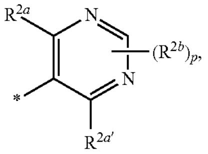 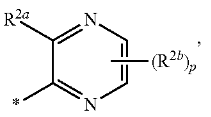,

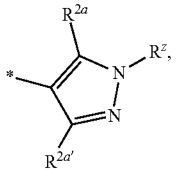 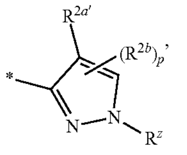 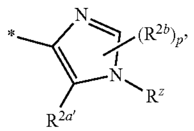

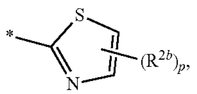 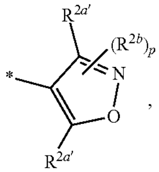, 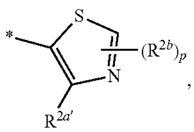,

-continued

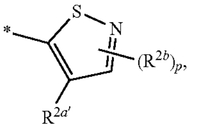 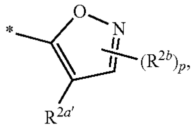 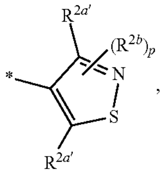,

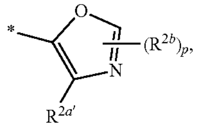 and 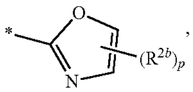, wherein $R^{2a}$, $R^{2a'}$, $R^{2b}$, $R^{2c}$, $R^{2c'}$, $R^{2d}$, $R^{2e}$ and p are as defined hereinabove, $R^z$ is selected from T, H, $C_1$-$C_4$alkyl, $CT_3$, or halo$C_1$-$C_4$alkyl; wherein $C_1$-$C_4$alkyl or halo$C_1$-$C_4$alkyl optionally comprise one or more T.

Preferably, $R^2$ is selected from the following:

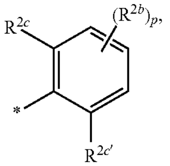 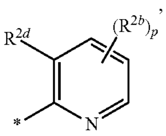 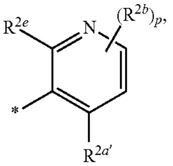

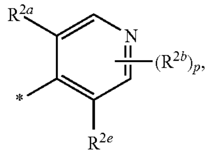 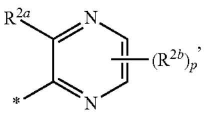

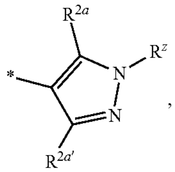, 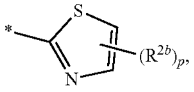 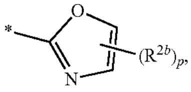

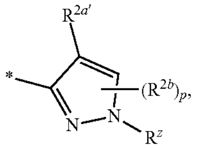 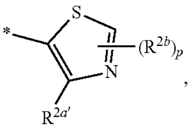, and

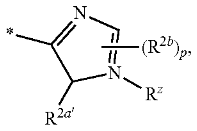

wherein $R^{2a}$, $R^{2a'}$, $R^{2b}$, $R^{2c}$, $R^{2c'}$, $R^{2d}$, $R^{2e}$, $R^z$ and p are as defined hereinabove.

More preferably, $R^2$ is selected from the following:

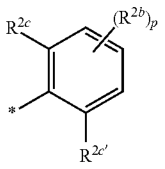, 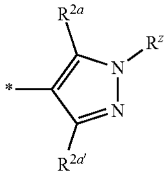,

-continued

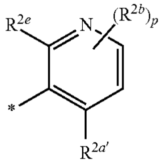

, and

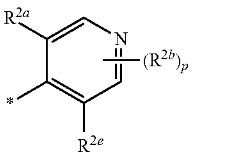

wherein $R^{2a}$, $R^{2a'}$, $R^{2b}$, $R^{2c}$, $R^{2c'}$, $R^{2e}$, $R^{z}$ and p are as defined hereinabove.

Preferably, $R^2$ is

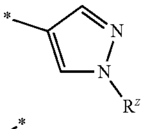

,

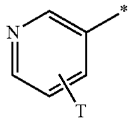

, or

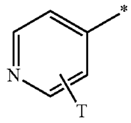

, wherein $R^z$ comprises at least one T.

More preferably, $R^2$ is

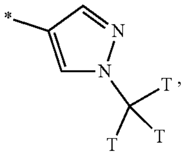

or

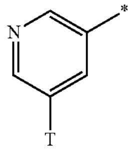

.

A preferred detectably labelled compound of formula (III-H) or (III-Ha), pharmaceutically acceptable salt, hydrate, or solvate thereof is

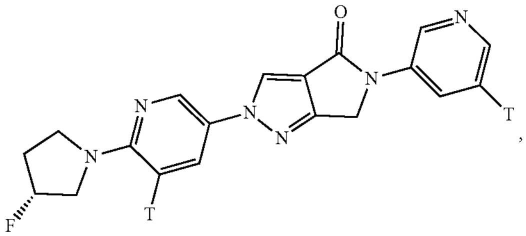

, or

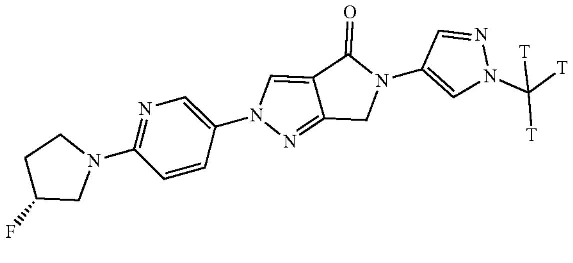

wherein T means $^{3}H$ (Tritium). Preferably, F means $^{19}F$.

In a preferred embodiment, the invention provides a detectably labelled compound of formula (III-H) or (III-Ha), or stereoisomer, racemic mixture, pharmaceutically acceptable salt, hydrate, or solvate thereof, wherein $^{3}H$ Tritium ("T") can be replaced by $^{2}H$ Deuterium ("D").

Preferably, the detectably labelled compounds of formula (I), or of subformulae thereof (e.g. (IIa), (IIb), (IIIa), (IIIb), (IIIc), (III-F), (III-H)), or a stereoisomer, racemic mixture, pharmaceutically acceptable salt, hydrate, or solvate thereof, comprise a detectable label, preferably the detectable label is a radioisotope, in particular selected from $^{18}F$, $^{2}H$ and $^{3}H$.

The compounds of the present invention, or a detectably labelled compound, stereoisomer, racemic mixture, pharmaceutically acceptable salt, hydrate, or solvate thereof, and their precursors can be detectably labelled. The type of the label is not specifically limited and will depend on the detection method chosen. Examples of possible labels include isotopes such as radionuclides, positron emitters, and gamma emitters. With respect to the detectably labelled compounds of the present invention, or stereoisomer, racemic mixture, pharmaceutically acceptable salt, hydrate, or solvate thereof and their precursors which include a radioisotope, a positron emitter, or a gamma emitter, it is to be understood that the radioisotope, positron emitter, or gamma emitter is to be present in an amount which is not identical to the natural amount of the respective radioisotope, positron emitter, or gamma emitter. Furthermore, the employed amount should allow detection thereof by the chosen detection method.

Examples of suitable isotopes such as radionuclides, positron emitters and gamma emitters include $^{2}H$, $^{3}H$, $^{18}F$, $^{11}C$, $^{13}N$, and $^{15}O$, preferably $^{2}H$, $^{3}H$, $^{11}C$, $^{13}N$, $^{15}O$, and $^{18}F$, more preferably $^{2}H$, $^{3}H$ and $^{18}F$, even more preferably $^{3}H$ and $^{18}F$.

$^{18}F$-labelled compounds are particularly suitable for imaging applications such as PET. The corresponding compounds which include fluorine having a natural $^{19}F$ isotope are also of particular interest as they can be used as analytical standards and references during manufacturing, quality control, release and clinical use of their $^{18}F$-analogs.

Further, substitution with isotopes such as deuterium, i.e., $^{2}H$, may afford certain diagnostic and therapeutic advantages resulting from greater metabolic stability by reducing for example defluorination, increased in vivo half-life or reduced dosage requirements, while keeping or improving the original compound efficacy.

Isotopic variations of the compounds of the invention, or a detectably labelled compound, stereoisomer, racemic mixture, pharmaceutically acceptable salt, hydrate, or solvate thereof, and their precursors can generally be prepared by conventional procedures such as by the illustrative methods or by the preparations described in the Examples and Preparative Examples hereafter using appropriate isotopic variations of suitable reagents, which are commercially available or prepared by known synthetic techniques.

Radionuclides, positron emitters and gamma emitters can be included into the compounds of the present invention, or a detectably labelled compound, stereoisomer, racemic mixture, pharmaceutically acceptable salt, hydrate, or solvate thereof, and their precursors by methods which are usual in the field of organic synthesis. Typically, they will be introduced by using a correspondingly labelled starting material when the desired compound of the present invention, or a detectably labelled compound, stereoisomer, racemic mixture, pharmaceutically acceptable salt, hydrate, or solvate thereof, and their precursor is prepared. Illustrative methods of introducing detectable labels are described, for instance, in US 2012/0302755.

The position at which the detectable label is to be attached to the compounds of the present invention and their precursors is not particularly limited.

The radionuclides, positron emitters and gamma emitters, for example, can be attached at any position where the corresponding non-emitting atom can also be attached. For instance, $^{18}F$ can be attached at any position which is suitable for attaching F. The same applies to the other radionuclides, positron emitters and gamma emitters. Due to the ease of synthesis, it is preferred to attach $^{18}F$ at $R^1$. $^3H$ can be attached at any available position. Preferably it is attached to the pyridine ring. If $^2H$ is employed as a detectable label it can be attached at any available position. Preferably it is attached to the pyridine ring.

In another embodiment, the present invention relates further to a compound of formula (IV-F) that is a precursor of the compound of formula (III-F)

(IV - F)

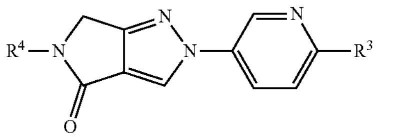

wherein $R^3$ is substituted with a Leaving Group (LG) as follows

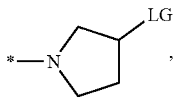,

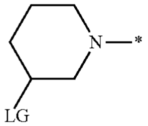,

-continued

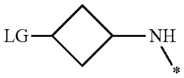, or 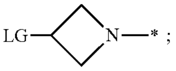;

$R^4$ is an aryl, or a 5-membered or 6-membered heteroaryl, wherein $R^4$ is selected from the same list as $R^2$ of the compound of formula (III-F) as disclosed hereinabove.

Preferably, the Leaving Group (LG) is halogen, $C_{1-4}$ alkyl sulfonate, $C_1$-$C_4$alkyl ammonium, nitro, or $C_{6-10}$ aryl sulfonate, wherein the $C_{6-10}$ aryl can be optionally substituted by —$CH_3$ or —$NO_2$. More preferably, the Leaving Group (LG) is bromo, chloro, iodo, $C_{1-4}$ alkyl sulfonate, or $C_{6-10}$ aryl sulfonate, wherein the $C_{6-10}$ aryl can be optionally substituted by —$CH_3$ or —$NO_2$. Even more preferably, the Leaving Group (LG) is mesylate, tosylate or nosylate. Even more preferably, the Leaving Group (LG) is mesylate, or nosylate. Preferably the Leaving Group (LG) is mesylate.

Preferably, $R^4$ is

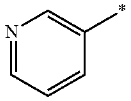, 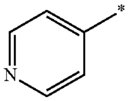 or 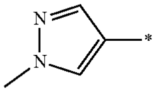.

More preferably, $R^4$ is

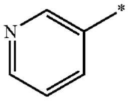 or 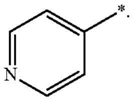.

Even more preferably, $R^4$ is

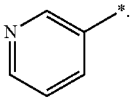.

Preferably, $R^4$ is optionally substituted with a $^{18}F$.

A preferred compound is

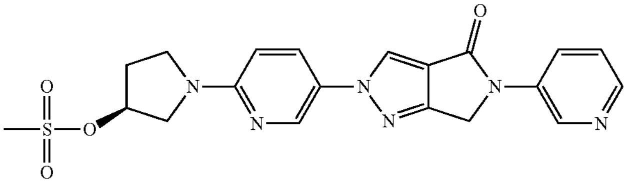; or

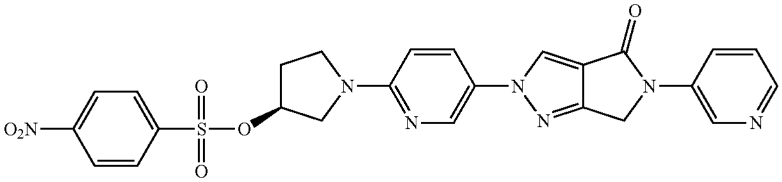.

In another embodiment, the present invention relates further to a compound of formula (IV-H), or a stereoisomer, racemic mixture, pharmaceutically acceptable salt, hydrate, or solvate thereof, that is a precursor of the compound of formula (III-H), or a stereoisomer, racemic mixture, pharmaceutically acceptable salt, hydrate, or solvate thereof (IV-H)

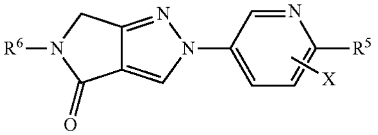

wherein $R^5$ is selected from the same list as $R^1$ of the compound of formula (III-H) as disclosed hereinabove and is preferably selected from

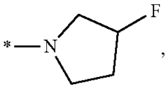, 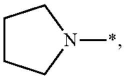, 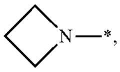,

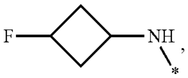, 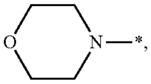, 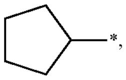,

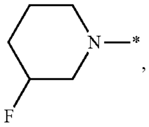, 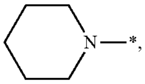, or 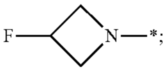;

$R^6$ is an aryl, or a 5-membered or 6-membered heteroaryl, wherein $R^6$ is selected from the following:

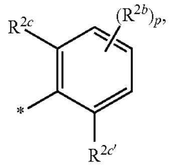 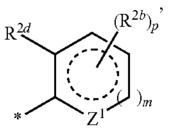, 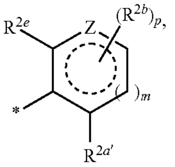,

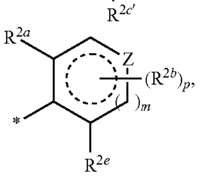 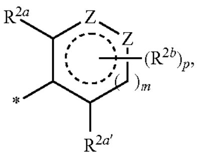 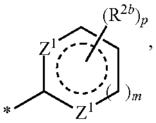,

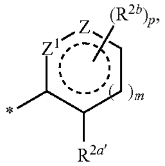 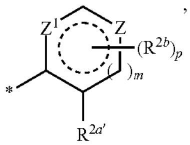,

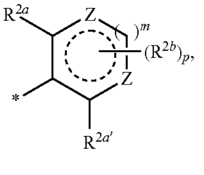 and 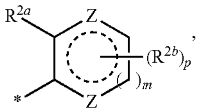, wherein $R^{2a}$, $R^{2a'}$ are independently selected from H, X or F;

$R^{2b}$ is independently selected from X, F, —OH, $C_1$-$C_4$alkyl, halo$C_1$-$C_4$alkyl, —$NH_2$, —CN, or $C_1$-$C_4$alkoxy, wherein $C_1$-$C_4$alkyl, halo$C_1$-$C_4$alkyl, or $C_1$-$C_4$alkoxy optionally comprise one or more X;

$R^{2c}$, $R^{2c'}$ are independently selected from X, H, F, OH, $OCH_3$, or $CH_3$;

$R^{2d}$ is selected from X, H, F, or —OH;

$R^{2e}$ is selected from X, H, OH, $CH_3$, or F;

Z is independently N, NH, N($C_1$-$C_4$alkyl), N(halo$C_1$-$C_4$alkyl), O, or S;

$Z^1$ is independently N, NH, O, or S;

p is 0, 1 or 2;

m is 0 or 1;

as valency permits, ⸌ is a combination of single and double bonds;

* is the position of bonding.

Fluoro is $^{19}F$;

X is Bromo, Chloro or Iodo; and

Wherein $R^6$ comprises at least one X.

In a further embodiment, the compound of formula (IV-H), or a stereoisomer, racemic mixture, pharmaceutically acceptable salt, hydrate, or solvate thereof, $R^6$ is preferably an aryl, or a 6-membered heteroaryl optionally substituted with one or more X, selected from:

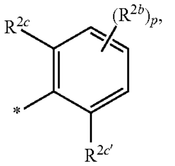, 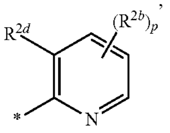, 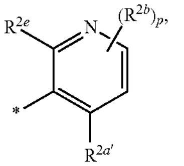,

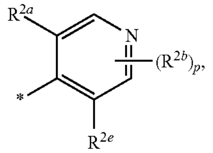, 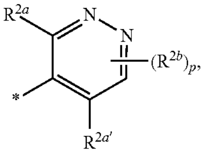,

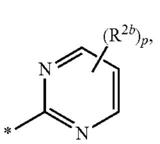, 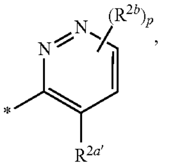, 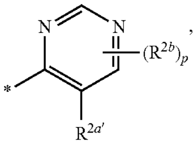,

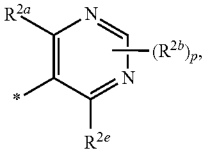, or 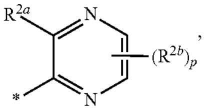, wherein $R^{2a}$, $R^{2a'}$, $R^{2b}$, $R^{2c}$, $R^{2c'}$, $R^{2d}$, $R^{2e}$ and p are as defined hereinabove; as valency permits, ⸌ is a combination of single and double bonds; Fluoro is $^{19}F$; and * is the position of bonding.

Preferably, $R^6$ is

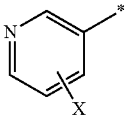 or 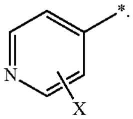.

More preferably, $R^6$ is

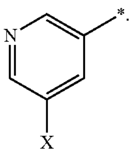.

Even more preferably the compound of formula (IV-H) is

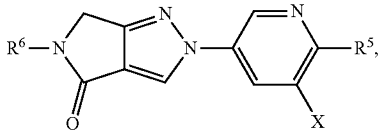, a detectably labelled compound, stereoisomer, racemic mixture, pharmaceutically acceptable salt, hydrate, or solvate thereof, with X being selected from Bromo, Chloro and Iodo.

Preferably, X is bromine.

A preferred compound is

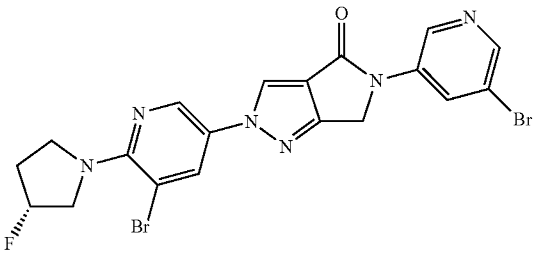 [SMILES: O=C1c2cn(-c3cnc(N4CC[C@@H](F)C4)c(Br)c3)nc2CN1c1cncc(Br)c1]

a detectably labelled compound, pharmaceutically acceptable salt, hydrate, or solvate thereof.

In another embodiment the present invention relates further to a compound of formula (IV-J), or a stereoisomer, racemic mixture, pharmaceutically acceptable salt, hydrate, or solvate thereof, that is a precursor of the compound of formula (III-H), or a stereoisomer, racemic mixture, pharmaceutically acceptable salt, hydrate, or solvate thereof (IV-J)

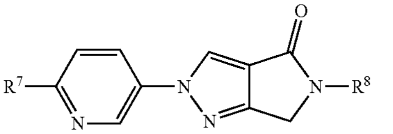

wherein $R^7$ is selected from the same list as $R^1$ of the compound of formula (III-H) as disclosed hereinabove and is preferably selected from

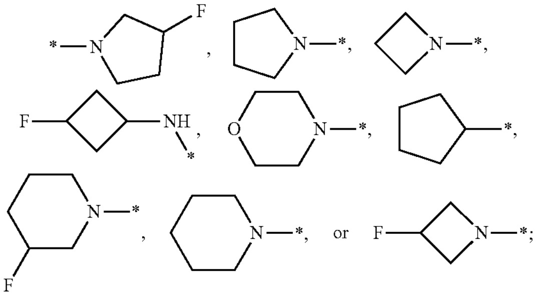

$R^8$ is selected from the following:

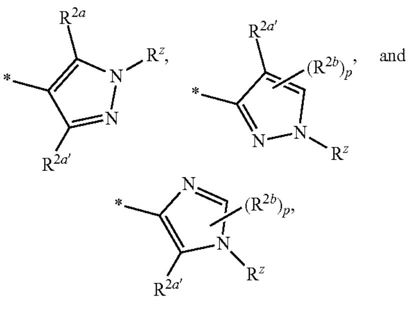

wherein $R^{2a}$, $R^{2a'}$ are independently selected from H, or F;

$R^{2b}$ is independently selected from F, —OH, $C_1$-$C_4$alkyl, halo$C_1$-$C_4$alkyl, —$NH_2$, —CN, or $C_1$-$C_4$alkoxy;

p is 0, 1 or 2;

$R^z$ is selected from H, $C_1$-$C_4$alkyl or halo$C_1$-$C_4$alkyl, as valency permits, is a combination of single and double bonds;

Fluoro is $^{19}F$; and

* is the position of bonding.

Preferably, $R^z$ is H.

In a further embodiment of the compound of formula (IV-J), or a stereoisomer, racemic mixture, pharmaceutically acceptable salt, hydrate, or solvate thereof, $R^8$ is preferably selected from

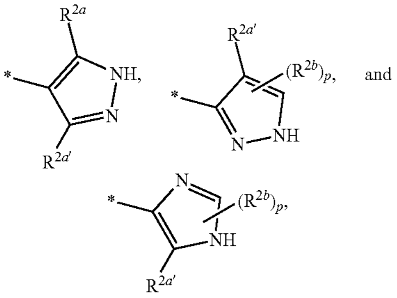

wherein $R^{2a}$, $R^{2a'}$, $R^{2b}$, and p are as defined hereinabove;

More preferably, $R^8$ is selected from:

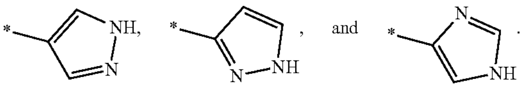

A preferred compound is

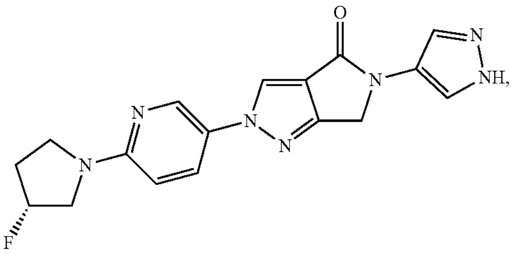 [SMILES: O=C1c2cn(-c3ccc(N4CC[C@@H](F)C4)nc3)nc2CN1c1cn[nH]c1]

or a detectably labelled compound, pharmaceutically acceptable salt, hydrate, or solvate thereof.

Method of Synthesis of Detectably Labelled Compounds

The present invention relates further to a method for preparing a compound of formula (I), or of subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof, and in particular a compound of formula (III-F) or (III-H), or a stereoisomer, racemic mixture, pharmaceutically acceptable salt, hydrate, or solvate thereof comprising a detectable label.

In one embodiment, the present invention relates to a method for preparing a compound of formula (III-F), or a stereoisomer, racemic mixture, pharmaceutically acceptable salt, hydrate, or solvate thereof, by radiolabeling a compound of formula (IV-F) with the radioisotope $^{18}F$

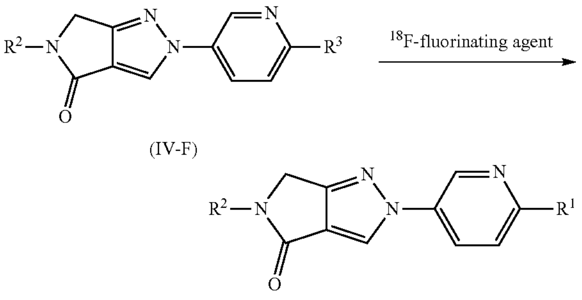

(IV-F)

(III-F)

wherein $R^1$, $R^2$, $R^3$ and $R^4$ are as defined herein.

Suitable solvents for the $^{18}$F-fluorination comprise DMF, DMSO, acetonitrile, DMA, or mixtures thereof, preferably acetonitrile or DMSO.

Suitable agents for the $^{18}$F-fluorination are selected from $K^{18}F$, $Rb^{18}F$, $Cs^{18}F$, $Na^{18}F$, tetra($C_{1-6}$ alkyl) ammonium salt of $^{18}$F, kryptofix[222]$^{18}$F and tetrabutylammonium [$^{18}$F] fluoride.

In one embodiment, the present invention relates to a method of preparing a compound of formula (III-H), or a stereoisomer, racemic mixture, pharmaceutically acceptable salt, hydrate, or solvate thereof, by radiolabeling a compound of formula (IV-H) with the radioisotope $^3$H

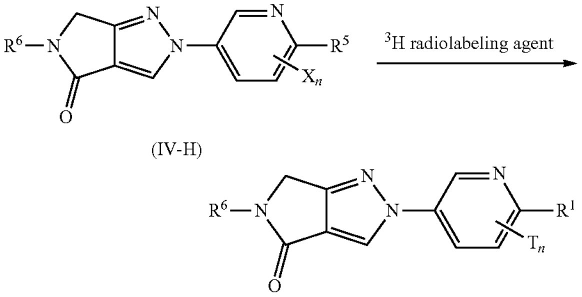

(IV-H)

(III-H)

wherein $R^1$, $R^2$, $R^5$ and $R^6$ are as defined herein, and

T is $^3$H (Tritium), n is 0 to 3, preferably, n is 1 or 2, more preferably, n is 1;

with the proviso that the compound of formula (III-Ha) comprises at least one T, Fluoro is $^{19}$F, X is Bromo, Chloro, Iodo or H, preferably, X is bromine.

The $^3$H radiolabeling agent can be tritium gas. The method can be conducted in the presence of a catalyst such as palladium on carbon (Pd/C), a solvent such as dimethylformamide (DMF) and a base such as N,N-diisopropylethylamine (DIEA).

In a preferred embodiment, F (Fluoro) is $^{19}$F.

In one embodiment, the present invention relates to a method for preparing a compound of formula (III-H), or a stereoisomer, racemic mixture, pharmaceutically acceptable salt, hydrate, or solvate thereof, by radiolabeling a compound of formula (IV-J) with a $CT_3$ radiolabeling agent, wherein T is $^3$H.

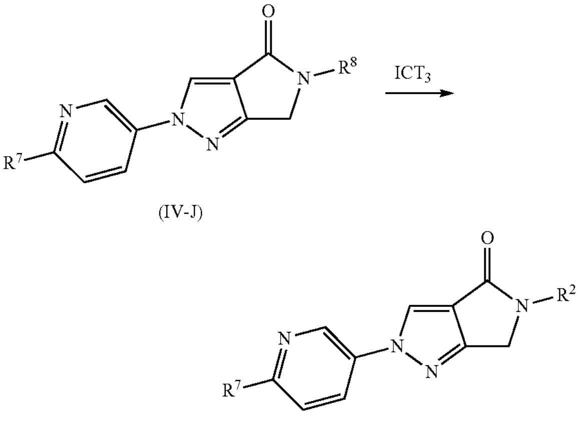

(IV-J)

(III-H)

The $CT_3$ radiolabeling agent can be $ICT_3$ (derivative of iodomethane with $^3$H). The method can be conducted in the presence of a solvent such as dimethylformamide (DMF) and a base such cesium carbonate or sodium hydride.

Diagnostic Compositions

The compounds of the present invention, or a detectably labelled compound, stereoisomer, racemic mixture, pharmaceutically acceptable salt, hydrate, or solvate thereof, are particularly suitable for imaging of alpha-synuclein aggregates including, but not limited to, Lewy bodies and/or Lewy neurites. With respect to alpha-synuclein protein, the compounds are particularly suitable for binding to various types of alpha-synuclein aggregates including, but not limited to, Lewy bodies and/or Lewy neurites. The imaging can be conducted in mammals, preferably in humans. The imaging is preferably in vitro imaging, ex vivo imaging, or in vivo imaging. More preferably the imaging is in vivo imaging: Even more preferably, the imaging is preferably brain imaging. The imaging can also be eye/retinal imaging. The compounds of the present invention, or a detectably labelled compound, stereoisomer, racemic mixture, pharmaceutically acceptable salt, hydrate, or solvate thereof, are particularly suitable for use in diagnostics.

The diagnostics can be conducted for mammals, preferably for humans. The tissue of interest on which the diagnostics is conducted can be brain, tissue of the central nervous system, tissue of the eye (such as retinal tissue) or other tissues, or body fluids such as cerebrospinal fluid (CSF). The tissue is preferably brain tissue.

Due to their design and to the binding characteristics, the compounds of the present invention, or a detectably labelled compound, stereoisomer, racemic mixture, pharmaceutically acceptable salt, hydrate, or solvate thereof, are suitable for use in the diagnosis of diseases, disorders and abnormalities associated with alpha-synuclein aggregates including, but not limited to, Lewy bodies and/or Lewy neurites. The compounds of the present invention, or a detectably labelled compound, stereoisomer, racemic mixture, pharmaceutically acceptable salt, hydrate, or solvate thereof, are particularly suitable for positron emission tomography imaging of alpha-synuclein aggregates including, but not limited to, Lewy bodies and/or Lewy neurites. Diseases involving alpha-synuclein aggregates are generally listed as synucleinopathies (or α-synucleinopathies). The compounds of the present invention, or a detectably labelled compound, stereoisomer, racemic mixture, pharmaceutically acceptable salt, hydrate, or solvate thereof, are suitable for use in the diagnosis of diseases, disorders or abnormalities including, but not limited to, Parkinson's disease (sporadic, familial with alpha-synuclein mutations, familial with mutations other than alpha-synuclein, pure autonomic failure and Lewy body dysphagia), SNCA duplication carrier, dementia with Lewy bodies ("pure" Lewy body dementia), Alzheimer's disease, sporadic Alzheimer's disease, familial Alzheimer's disease with APP mutations, familial Alzheimer's disease with PS-1, PS-2 or other mutations, familial British dementia, Lewy body variant of Alzheimer's disease and normal aging in Down syndrome). Synucleinopathies with neuronal and glial aggregates of alpha synuclein include multiple system atrophy (MSA) (Shy-Drager syndrome, striatonigral degeneration and olivopontocerebellar atrophy). Other diseases that may have alpha-synuclein-immunoreactive lesions include traumatic brain injury, chronic traumatic encephalopathy, tauopathies (Pick's disease, frontotemporal dementia, progressive supranuclear palsy, corticobasal degeneration and Niemann-Pick type C1 disease), motor neuron disease, amyotrophic lateral sclerosis (sporadic, familial and ALS-dementia complex of Guam), neuroaxonal dystrophy, neurodegeneration with brain iron accumulation type 1 (Hallervorden-Spatz syndrome), prion diseases, ataxia telangiectatica, Meige's syndrome, subacute sclerosing panencephalitis, Gaucher disease as well as other lysosomal storage disorders (including Kufor-Rakeb syndrome and Sanfilippo syndrome) and rapid eye movement (REM) sleep behavior disorder (Jellinger, Mov Disord 2003, 18 Suppl. 6, S2-12; Galvin et al. JAMA Neurology 2001, 58 (2), 186-190; Kovari et al., Acta Neuropathol. 2007, 114(3), 295-8; Saito et al., J Neuropathol Exp Neurol. 2004, 63(4), 323-328; McKee et al., Brain, 2013, 136(Pt 1), 43-64; Puschmann et al., Parkinsonism Relat Disord 2012, 18S1, S24-S27; Usenovic et al., J Neurosci. 2012, 32(12), 4240-4246; Winder-Rhodes et al., Mov Disord. 2012, 27(2), 312-315; Ferman et al., J Int Neuropsychol Soc. 2002, 8(7), 907-914). Preferably, the compounds of the present invention are suitable for use in the diagnosis of Parkinson's disease, multiple system atrophy, dementia with Lewy bodies, Parkinson's disease dementia, SNCA duplication carrier, or Alzheimer's disease, more preferably Parkinson's disease (PD).

In the methods of diagnosing a disease, disorder or abnormality associated with alpha-synuclein aggregates including, but not limited to, Lewy bodies and/or Lewy neurites, such as Parkinson's disease, or a predisposition therefor in a subject, the method comprises the steps of:

a) administering to the subject a diagnostically effective amount of a compound of the present invention or a detectably labelled compound, stereoisomer, racemic mixture, pharmaceutically acceptable salt, hydrate, or solvate thereof;
b) allowing the compound of the present invention, or a detectably labelled compound, stereoisomer, racemic mixture, pharmaceutically acceptable salt, hydrate, or solvate thereof, to distribute into the tissue of interest (such as brain or other tissues, or body fluids such as cerebrospinal fluid (CSF)); and
c) imaging the tissue of interest, wherein an increase in binding of the compound of the present invention, or a detectably labelled compound, stereoisomer, racemic mixture, pharmaceutically acceptable salt, hydrate, or solvate thereof, to the tissue of interest compared to a normal control level of binding indicates that the subject is suffering from or is at risk of developing a disease, disorder or abnormality associated with alpha-synuclein aggregates including, but not limited to, Lewy bodies and/or Lewy neurites.

The compounds of the present invention or a detectably labelled compound, stereoisomer, racemic mixture, pharmaceutically acceptable salt, hydrate, or solvate thereof, can be used for imaging of alpha-synuclein aggregates including, but not limited to, Lewy bodies and/or Lewy neurites in any sample or a specific body part or body area of a patient which is suspected to contain alpha-synuclein aggregates including, but not limited to, Lewy bodies and/or Lewy neurites. The compounds are able to pass the blood-brain barrier. Consequently, they are particularly suitable for imaging of alpha-synuclein aggregates including, but not limited to, Lewy bodies and/or Lewy neurites in the brain or peripheral organs such as the gut, as well as in body fluids such as cerebrospinal fluid (CSF).

In diagnostic applications, the compounds of the present invention, or a detectably labelled compound, stereoisomer, racemic mixture, pharmaceutically acceptable salt, hydrate, or solvate thereof, preferably compounds of formula (I), or subformulae thereof (e.g. (IIa), (IIb), (IIIa), (IIIb), (IIIc), (III-F), (III-H)), are preferably administered in the form of a diagnostic composition comprising the compound of the invention or a detectably labelled compound, stereoisomer, racemic mixture, pharmaceutically acceptable salt, hydrate, or solvate thereof. A "diagnostic composition" is defined in the present invention as a composition comprising one or more compounds of the present invention, or a detectably labelled compound, stereoisomer, racemic mixture, pharmaceutically acceptable salt, hydrate, or solvate thereof, in a form suitable for administration to a patient, e.g., a mammal such as a human, and which is suitable for use in the diagnosis of the specific disease, disorder or abnormality at issue. Preferably a diagnostic composition further comprises a physiologically acceptable excipient, carrier, diluent or adjuvant. Administration is preferably carried out as defined below. More preferably by injection of the composition as an aqueous solution. Such a composition may optionally contain further ingredients such as buffers; pharmaceutically acceptable solubilisers (e.g., cyclodextrins or surfactants such as Pluronic, Tween or phospholipids); and pharmaceutically acceptable stabilisers or antioxidants (such as ascorbic acid, gentisic acid or para-aminobenzoic acid). The dose of the compound of the present invention, or a detectably labelled compound, stereoisomer, racemic mixture, pharmaceutically acceptable salt, hydrate, or solvate thereof, will vary depending on the exact compound to be administered, the weight of the patient, and other variables as would be apparent to a physician skilled in the art.

While it is possible for the compounds of the present invention, or a detectably labelled compound, stereoisomer, racemic mixture, pharmaceutically acceptable salt, hydrate, or solvate thereof, to be administered alone, it is preferable to formulate them into a diagnostic composition in accordance with standard pharmaceutical practice. Thus, the invention also provides a diagnostic composition which comprises a diagnostically effective amount of a compound of the present invention, or a detectably labelled compound, stereoisomer, racemic mixture, pharmaceutically acceptable salt, hydrate, or solvate thereof, in admixture with, optionally, at least one pharmaceutically acceptable excipient, carrier, diluent or adjuvant.

Pharmaceutically acceptable excipients are well known in the pharmaceutical art, and are described, for example, in Remington's Pharmaceutical Sciences, $15^{th}$ Ed., Mack Publishing Co., New Jersey (1975). The pharmaceutical excipient can be selected with regard to the intended route of administration and standard pharmaceutical practice. The excipient must be acceptable in the sense of being not deleterious to the recipient thereof.

Pharmaceutically useful excipients, carriers, adjuvants and diluents that may be used in the formulation of the diagnostic composition of the present invention may comprise, for example, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate, binders, adjuvants, solubilizers, thickening agents, stabilizers, disintegrants, glidants, lubricating agents, buffering agents, emulsifiers, wetting agents, suspending agents, sweetening agents, colorants, flavors, coating agents, preservatives, antioxidants, processing agents, drug delivery modifiers and enhancers such as calcium phosphate, magnesium stearate, talc, monosaccharides, disaccharides, starch, gelatin, cellulose, methylcellulose, sodium carboxymethyl cellulose, dextrose, hydroxypropyl-ß-cyclodextrin, polyvinylpyrrolidone, low melting waxes, and ion exchange resins.

The routes for administration (delivery) of the compounds of the invention, preferably compounds of formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof, include, but are not limited to, one or more of: intravenous, gastrointestinal, intraspinal, intraperitoneal, intramuscular, oral (e.g. as a tablet, capsule, or as an ingestible solution), topical, mucosal (e.g. as a nasal spray or aerosol for inhalation), nasal, parenteral (e.g. by an injectable form), intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual. Preferably, the route of administration (delivery) of the compounds of the invention, or a detectably labelled compound, stereoisomer, racemic mixture, pharmaceutically acceptable salt, hydrate, or solvate thereof, is intravenous.

For example, the compounds can be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include starch, a cellulose, milk sugar (lactose) or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

Preferably, in diagnostic applications, the compounds of the present invention, or a detectably labelled compound, stereoisomer, racemic mixture, pharmaceutically acceptable salt, hydrate, or solvate thereof, are administered parenterally. If the compounds of the present invention, or a detectably labelled compound, stereoisomer, racemic mixture, pharmaceutically acceptable salt, hydrate, or solvate thereof, are administered parenterally, then examples of such administration include one or more of: intravenously, intraarterially, intraperitoneally, intrathecally, intraventricularly, intraurethrally, intrasternally, intracranially, intramuscularly or subcutaneously administering the compounds; and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

As indicated, the compounds of the present invention, or a detectably labelled compound, stereoisomer, racemic mixture, pharmaceutically acceptable salt, hydrate, or solvate thereof, can be administered intranasally or by inhalation and are conveniently delivered in the form of a dry powder inhaler or an aerosol spray presentation from a pressurized container, pump, spray or nebulizer with the use of a suitable propellant, e.g. dichlorodifluoromethane, trichlorofluoromethane, dichlorotetrafluoroethane, a hydrofluoroalkane such as 1,1,1,2-tetrafluoroethane (HFA134AT) or 1,1,1,2,3,3,3-heptafluoropropane (HFA 227EA), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of the compound and a suitable powder base such as lactose or starch.

Alternatively, the compounds of the present invention, or a detectably labelled compound, stereoisomer, racemic mixture, pharmaceutically acceptable salt, hydrate, or solvate thereof, can be administered in the form of a suppository or pessary, or it may be applied topically in the form of a gel, hydrogel, lotion, solution, cream, ointment or dusting powder. The compounds of the present invention, or a detectably labelled compound, stereoisomer, racemic mixture, pharmaceutically acceptable salt, hydrate, or solvate thereof, may also be dermally or transdermally administered, for example, by the use of a skin patch.

They may also be administered by the pulmonary or rectal routes. They may also be administered by the ocular route. For ophthalmic use, the compounds can be formulated as micronized suspensions in isotonic, pH was adjusted, sterile saline, or, preferably, as solutions in isotonic, pH was adjusted, sterile saline, optionally in combination with a preservative such as a benzylalkonium chloride. Alternatively, they may be formulated in an ointment such as petrolatum.

For application topically to the skin, the compounds of the present invention, or a detectably labelled compound, stereoisomer, racemic mixture, pharmaceutically acceptable salt, hydrate, or solvate thereof, can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing diagnosis.

The diagnostic compositions of the invention can be produced in a manner known per se to the skilled person as described, for example, in Remington's Pharmaceutical Sciences, $15^{th}$ Ed., Mack Publishing Co., New Jersey (1975).

The compounds of the present invention, or a detectably labelled compound, stereoisomer, racemic mixture, pharmaceutically acceptable salt, hydrate, or solvate thereof, are useful as an in vitro analytical reference or an in vitro screening tool. They are also useful in in vivo diagnostic methods.

The compounds according to the present invention, or a detectably labelled compound, stereoisomer, racemic mixture, pharmaceutically acceptable salt, hydrate, or solvate thereof, can also be provided in the form of a mixture comprising a compound according to the present invention, or a detectably labelled compound, stereoisomer, racemic mixture, pharmaceutically acceptable salt, hydrate, or solvate thereof, and at least one compound selected from an imaging agent different from the compound according to the invention, a pharmaceutically acceptable excipient, carrier, diluent or adjuvant. The imaging agent different from the compound according to the invention is preferably present in a diagnostically effective amount. More preferably the imaging agent different from the compound according to the invention is an Abeta or Tau imaging agent.

Diagnosis of a disease, disorder or abnormality associated with alpha-synuclein aggregates including, but not limited to, Lewy bodies and/or Lewy neurites or of a predisposition to a disease, disorder or abnormality associated with alpha-synuclein aggregates including, but not limited to, Lewy bodies and/or Lewy neurites in a patient may be achieved by detecting the specific binding of a compound according to the invention, or a detectably labelled compound, stereoisomer, racemic mixture, pharmaceutically acceptable salt, hydrate, or solvate thereof, to the alpha-synuclein aggregates including, but not limited to, Lewy bodies and/or Lewy neurites in a sample or a specific body part or body area, which includes the steps of:

(a) bringing the sample or a specific body part or body area suspected to contain the alpha-synuclein aggregates including, but not limited to, Lewy bodies and/or Lewy neurites into contact with a compound of the invention, or a detectably labelled compound, stereoisomer, racemic mixture, pharmaceutically acceptable salt, hydrate, or solvate thereof, which binds the alpha-synuclein aggregates including, but not limited to, Lewy bodies and/or Lewy neurites, (b) allowing the compound of the invention, or a detectably labelled compound, stereoisomer, racemic mixture, pharmaceutically acceptable salt, hydrate, or solvate thereof, to bind to the alpha-synuclein aggregates including, but not limited to, Lewy bodies and/or Lewy neurites to form a compound/(alpha-synuclein aggregates including, but not limited to, Lewy bodies or Lewy neurites) complex (hereinafter "compound/(alpha-synuclein aggregates including, but not limited to, Lewy bodies and/or Lewy neurites) complex" will be abbreviated as "compound/protein aggregate complex"), (c) detecting the formation of the compound/protein aggregate complex, (d) optionally correlating the presence or absence of the compound/protein aggregate complex with the presence or absence of alpha-synuclein aggregates including, but not limited to, Lewy bodies and/or Lewy neurites in the sample or specific body part or area, and (e) optionally comparing the amount of the compound/protein aggregate complex to a normal control value, wherein an increase in the amount of the compound/protein aggregate complex compared to a normal control value may indicate that the patient is suffering from or is at risk of developing a disease, disorder or abnormality associated with alpha-synuclein aggregates including, but not limited to, Lewy bodies and/or Lewy neurites.

The compound of the present invention, or a detectably labelled compound, stereoisomer, racemic mixture, pharmaceutically acceptable salt, hydrate, or solvate thereof, can be brought into contact with the sample or the specific body part or body area suspected to contain the alpha-synuclein aggregates including, but not limited to, Lewy bodies and/or Lewy neurites by a suitable method. In in vitro methods the compound of the present invention, or a detectably labelled compound, stereoisomer, racemic mixture, pharmaceutically acceptable salt, hydrate, or solvate thereof, and a liquid sample can be simply mixed. In in vivo tests the compound of the present invention, or a detectably labelled compound, stereoisomer, racemic mixture, pharmaceutically acceptable salt, hydrate, or solvate thereof, is typically administered to the patient by any suitable means. These routes of administration include, but are not limited to, one or more of: oral (e.g. as a tablet, capsule, or as an ingestible solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual. In some instances, parenteral administration can be preferred.

After the sample or a specific body part or body area has been brought into contact with the compound of the present invention, or a detectably labelled compound, stereoisomer, racemic mixture, pharmaceutically acceptable salt, hydrate, or solvate thereof, the compound is allowed to bind to the alpha-synuclein aggregates including, but not limited to, Lewy bodies and/or Lewy neurites. The amount of time required for binding will depend on the type of test (e.g., in vitro or in vivo) and can be determined by a person skilled in the field by routine experiments.

The compound which has bound to the alpha-synuclein aggregates including, but not limited to, Lewy bodies and/or Lewy neurites, can be subsequently detected by any appropriate method. The specific method chosen will depend on the detectable label which has been chosen. Examples of possible methods include, but are not limited to, a fluorescence imaging technique or a nuclear imaging technique such as positron emission tomography (PET), single photon emission computed tomography (SPECT), magnetic resonance imaging (MRI), and contrast-enhanced magnetic resonance imaging (MRI). These have been described and enable visualization of amyloid biomarkers. The fluorescence imaging technique and/or nuclear imaging technique can be employed for monitoring and/or visualizing the distribution of the detectably labelled compound within the sample or a specific body part or body area.

The presence or absence of the compound/protein aggregate complex is then optionally correlated with the presence or absence of alpha-synuclein aggregates including, but not limited to, Lewy bodies and/or Lewy neurites in the sample or specific body part or area. Finally, the amount of the compound/protein aggregate complex can be compared to a normal control value which has been determined in a sample or a specific body part or body area of a healthy subject, wherein an increase in the amount of the compound/protein aggregate complex compared to a normal control value may indicate that the patient is suffering from or is at risk of developing a disease, disorder or abnormality associated with alpha-synuclein aggregates including, but not limited to, Lewy bodies and/or Lewy neurites.

The present invention also relates to a method of determining the amount of alpha-synuclein aggregates including, but not limited to, Lewy bodies and/or Lewy neurites in a tissue and/or a body fluid. This method comprises the steps of:

(a) providing a sample representative of the tissue and/or body fluid under investigation;
(b) testing the sample for the presence of alpha-synuclein aggregates including, but not limited to, Lewy bodies and/or Lewy neurites with a compound of the present invention;
(c) determining the amount of compound bound to the alpha-synuclein aggregates including, but not limited to, Lewy bodies and/or Lewy neurites; and
(d) calculating the amount of alpha-synuclein aggregates including, but not limited to, Lewy bodies and/or Lewy neurites in the tissue and/or body fluid.

The sample can be tested for the presence of alpha-synuclein aggregates including, but not limited to, Lewy bodies and/or Lewy neurites with a compound of the present invention, or a detectably labelled compound, stereoisomer, racemic mixture, pharmaceutically acceptable salt, hydrate, or solvate thereof, by bringing the sample into contact with a compound of the invention, allowing the compound of the invention to bind to the alpha-synuclein aggregates including, but not limited to, Lewy bodies and/or Lewy neurites to form a compound/protein aggregate complex and detecting the formation of the compound/protein aggregate complex as explained above.

Monitoring minimal residual disease, disorder or abnormality in a patient suffering from a disease, disorder or abnormality associated with alpha-synuclein aggregates including, but not limited to, Lewy bodies and/or Lewy neurites who has been treated with a medicament with a compound according to the invention, or a detectably labelled compound, stereoisomer, racemic mixture, pharmaceutically acceptable salt, hydrate, or solvate thereof, may be achieved by (a) bringing a sample or a specific body part or body area suspected to contain alpha-synuclein aggregates including, but not limited to, Lewy bodies and/or Lewy neurites into contact with a compound of the present invention, or a detectably labelled compound, stereoisomer, racemic mixture, pharmaceutically acceptable salt, hydrate, or solvate thereof;
(b) allowing the compound to bind to the alpha-synuclein aggregates including, but not limited to, Lewy bodies and/or Lewy neurites to form a compound/protein aggregate complex;
(c) detecting the formation of the compound/protein aggregate complex;
(d) optionally correlating the presence or absence of the compound/protein aggregate complex with the presence or absence of alpha-synuclein aggregates including, but not limited to, Lewy bodies and/or Lewy neurites in the sample or specific body part or body area; and
(e) optionally comparing the amount of the compound/protein aggregate complex to a normal control value, wherein an increase in the amount of the aggregate compared to a normal control value may indicate that the patient may still suffer from a minimal residual disease, disorder or abnormality.

How steps (a) to (e) can be conducted has already been explained above.

In the method for monitoring minimal residual disease, disorder or abnormality, the method can further comprises steps (i) to (vi) before step (a):

(i) bringing a sample or specific body part or body area suspected to contain alpha-synuclein aggregates including, but not limited to, Lewy bodies and/or Lewy neurites into contact with the compound of the present invention, or a detectably labelled compound, stereoisomer, racemic mixture, pharmaceutically acceptable salt, hydrate, or solvate thereof, which compound specifically binds to the alpha-synuclein aggregates including, but not limited to, Lewy bodies and/or Lewy neurites;
(ii) allowing the compound to bind to the alpha-synuclein aggregates including, but not limited to, Lewy bodies and/or Lewy neurites to form a compound/(alpha-synuclein aggregates including, but not limited to, Lewy bodies and/or Lewy neurites) complex;
(iii) detecting the formation of the compound/(alpha-synuclein aggregates including, but not limited to, Lewy bodies and/or Lewy neurites) complex;
(iv) correlating the presence or absence of the compound/(alpha-synuclein aggregates including, but not limited to, Lewy bodies and/or Lewy neurites) complex with the presence or absence of alpha-synuclein aggregates including, but not limited to, Lewy bodies and/or Lewy neurites in the sample or specific body part or body area;
(v) optionally comparing the amount of the compound/(alpha-synuclein aggregates including, but not limited to, Lewy bodies and/or Lewy neurites) complex to a normal control value; and
(vi) treating the patient with the medicament.

Optionally the method can further comprise step (A) after step (d) or step (e):

(A) comparing the amount of the compound/(alpha-synuclein aggregates including, but not limited to, Lewy bodies and/or Lewy neurites) complex determined in step (iv) to the amount of the compound/(alpha-synuclein aggregates including, but not limited to, Lewy bodies and/or Lewy neurites) complex determined in step (d).

In order to monitor minimal residual disease, disorder or abnormality over time, steps (a) to (c) and optionally steps (d) and (e) of the method of monitoring minimal residual disease, disorder or abnormality can be repeated one or more times.

In the method for monitoring minimal residual disease, disorder or abnormality the amount of the compound/protein aggregate complex can be optionally compared at various points of time during the treatment, for instance, before and after onset of the treatment or at various points of time after the onset of the treatment. A change, especially a decrease, in the amount of the compound/protein aggregate complex may indicate that the residual disease, disorder or abnormality is decreasing.

Predicting responsiveness of a patient suffering from a disease, disorder or abnormality associated with alpha-synuclein aggregates including, but not limited to, Lewy bodies and/or Lewy neurites and being treated with a medicament can be achieved by (a) bringing a sample or a specific body part or body area suspected to contain alpha-synuclein aggregates including, but not limited to, Lewy bodies and/or Lewy neurites into contact with a compound of the present invention, or a detectably labelled compound, stereoisomer, racemic mixture, pharmaceutically acceptable salt, hydrate, or solvate thereof;

(b) allowing the compound to bind to the alpha-synuclein aggregates including, but not limited to, Lewy bodies and/or Lewy neurites to form a compound/protein aggregate complex;

(c) detecting the formation of the compound/protein aggregate complex;

(d) optionally correlating the presence or absence of the compound/protein aggregate complex with the presence or absence of alpha-synuclein aggregates including, but not limited to, Lewy bodies and/or Lewy neurites in the sample or specific body part or body area; and (e) optionally comparing the amount of the compound/protein aggregate complex to a normal control value.

How steps (a) to (e) can be conducted has already been explained above.

In the method for predicting the responsiveness, the method can further comprises steps (i) to (vi) before step (a):

(i) bringing a sample or specific body part or body area suspected to contain alpha-synuclein aggregates including, but not limited to, Lewy bodies and/or Lewy neurites into contact with the compound of the present invention, or a detectably labelled compound, stereoisomer, racemic mixture, pharmaceutically acceptable salt, hydrate, or solvate thereof, which compound specifically binds to the alpha-synuclein aggregates including, but not limited to, Lewy bodies and/or Lewy neurites;

(ii) allowing the compound to bind to the alpha-synuclein aggregates including, but not limited to, Lewy bodies and/or Lewy neurites to form a compound/(alpha-synuclein aggregates including, but not limited to, Lewy bodies and/or Lewy neurites) complex;

(iii) detecting the formation of the compound/(alpha-synuclein aggregates including, but not limited to, Lewy bodies and/or Lewy neurites) complex;

(iv) correlating the presence or absence of the compound/(alpha-synuclein aggregates including, but not limited to, Lewy bodies and/or Lewy neurites) complex with the presence or absence of alpha-synuclein aggregates including, but not limited to, Lewy bodies and/or Lewy neurites in the sample or specific body part or body area;

(v) optionally comparing the amount of the compound/(alpha-synuclein aggregates including, but not limited to, Lewy bodies and/or Lewy neurites) complex to a normal control value; and (vi) treating the patient with the medicament.

Optionally the method can further comprise step (A) after step (d) or step (e):

(A) comparing the amount of the compound/(alpha-synuclein aggregates including, but not limited to, Lewy bodies and/or Lewy neurites) complex determined in step (iv) to the amount of the compound/(alpha-synuclein aggregates including, but not limited to, Lewy bodies and/or Lewy neurites) complex determined in step (d).

In order to determine the responsiveness over time, steps (a) to (c) and optionally steps (d) and (e) of the method of predicting responsiveness can be repeated one or more times.

In the method for predicting responsiveness the amount of the compound/protein aggregate complex can be optionally compared at various points of time during the treatment, for instance, before and after onset of the treatment or at various points of time after the onset of the treatment. A change, especially a decrease, in the amount of the compound/protein aggregate complex may indicate that the patient has a high potential of being responsive to the respective treatment.

Optionally, the diagnostic composition can be used before, during and after, surgical procedures (e.g. deep brain stimulation (DBS)) and non-invasive brain stimulation (such as repetitive transcranial magnetic stimulation (rTMS)), for visualizing alpha-synuclein aggregates before, during and after such procedures. Surgical techniques, including DBS, improve advanced symptoms of PD on top of the best currently used medical therapy. During the past 2 decades, rTMS has been closely examined as a possible treatment for PD (Ying-hui Chou et al. JAMA Neurol. 2015 Apr. 1; 72(4): 432-440).

In a further embodiment of the invention, the diagnostic composition can be used in a method of collecting data for monitoring residual disease, disorder or abnormality in a patient suffering from a disease, disorder or abnormality associated with alpha-synuclein aggregates including, but not limited to, Lewy bodies and/or Lewy neurites who has been treated with a surgical procedure or non-invasive brain stimulation procedure, wherein the method comprises the steps of:

(a) bringing a sample or specific body part or body area suspected to contain alpha-synuclein aggregates including, but not limited to, Lewy bodies and/or Lewy neurites into contact with a compound of the present invention, or a detectably labelled compound, stereoisomer, racemic mixture, pharmaceutically acceptable salt, hydrate, or solvate thereof, which compound specifically binds to the alpha-synuclein aggregates including, but not limited to, Lewy bodies and/or Lewy neurites;

(b) allowing the compound to bind to the alpha-synuclein aggregates including, but not limited to, Lewy bodies and/or Lewy neurites to form a compound/(alpha-synuclein aggregates including, but not limited to, Lewy bodies and/or Lewy neurites) complex; (c) detecting the formation of the compound/(alpha-synuclein aggregates including, but not limited to, Lewy bodies and/or Lewy neurites) complex;

(d) optionally correlating the presence or absence of the compound/(alpha-synuclein aggregates including, but not limited to, Lewy bodies and/or Lewy neurites) complex with the presence or absence of alpha-synuclein aggregates including, but not limited to, Lewy bodies and/or Lewy neurites in the sample or specific body part or body area; and (e) optionally comparing the amount of the compound/(alpha-synuclein aggregates including, but not limited to, Lewy bodies and/or Lewy neurites) complex to a normal control value.

It is understood that the term "monitoring minimal residual disease" as mentioned herein relates to the monitoring of the evolution of the disease. For example, monitoring of the evolution of the disease, disorder or abnormality in a patient suffering from a disease, disorder or abnormality associated with alpha-synuclein aggregates including, but not limited to, Lewy bodies and/or Lewy neurites.

A compound according to the present invention, or a detectably labelled compound, stereoisomer, racemic mixture, pharmaceutically acceptable salt, hydrate, or solvate thereof, or its precursor can also be incorporated into a test kit for detecting alpha-synuclein protein aggregates including, but not limited to, Lewy bodies and/or Lewy neurites. The test kit typically comprises a container holding one or more compounds according to the present invention, or a detectably labelled compound, stereoisomer, racemic mixture, pharmaceutically acceptable salt, hydrate, or solvate thereof, or its precursor(s) and instructions for using the compound for the purpose of binding to alpha-synuclein aggregates including, but not limited to, Lewy bodies and/or Lewy neurites to form a compound/protein aggregate complex and detecting the formation of the compound/protein aggregate complex such that presence or absence of the compound/protein aggregate complex correlates with the presence or absence of the alpha-synuclein aggregates including, but not limited to, Lewy bodies and/or Lewy neurites.

The term "test kit" refers in general to any diagnostic kit known in the art. More specifically, the latter term refers to a diagnostic kit as described in Zrein et al., Clin. Diagn. Lab. Immunol., 1998, 5, 45-49.

The dose of the detectably labelled compounds of the present invention, or stereoisomer, racemic mixture, pharmaceutically acceptable salt, hydrate, or solvate thereof, preferably compounds of formula (III-F) labelled with $^{18}F$, will vary depending on the exact compound to be administered, the weight of the patient, size and type of the sample, and other variables as would be apparent to a physician skilled in the art. Generally, the dose could preferably lie in the range 0.001 μg/kg to 10 μg/kg, preferably 0.01 μg/kg to 1.0 μg/kg. The radioactive dose can be, e.g., 100 to 600 MBq, more preferably 150 to 450 MBq.

In another embodiment the present invention provides a method of imaging a disease, disorder or abnormality associated with alpha-synuclein aggregates including, but not limited to, Lewy bodies and/or Lewy neurites in a sample or in a specific body part or body area, in particular in a brain or a sample taken from a patient's brain, the method comprising the steps:

(a) Bringing the sample, the specific body part or body area suspected to contain alpha-synuclein aggregates including, but not limited to, Lewy bodies and/or Lewy neurites into contact with a compound of formula (I) or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof;

(b) Allowing the compound to bind to the alpha-synuclein aggregates including, but not limited to, Lewy bodies and/or Lewy neurites; and (c) Imaging the sample, the specific body part or the body area with an imaging system.

In another embodiment the present invention provides a method of determining an amount of alpha-synuclein aggregates including, but not limited to, Lewy bodies and/or Lewy neurites in a sample or a specific body part or body area, the method comprising the steps:

(a) Bringing the sample, the specific body part or body area suspected to contain alpha-synuclein aggregates including, but not limited to, Lewy bodies and/or Lewy neurites into contact with a compound of formula (I) or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof;

(b) Allowing the compound to bind to the alpha-synuclein aggregates including, but not limited to, Lewy bodies and/or Lewy neurites;

(c) Detecting the compound bound to the alpha-synuclein aggregates including, but not limited to, Lewy bodies and/or Lewy neurites;

(d) Determining the amount of the compound bound to the alpha-synuclein aggregates including, but not limited to, Lewy bodies and/or Lewy neurites; and (e) Optionally calculating the amount of the alpha-synuclein aggregates including, but not limited to, Lewy bodies and/or Lewy neurites in the sample, the specific body part or body area.

In another embodiment the present invention provides a method of diagnosing a disease, disorder or abnormality associated with alpha-synuclein aggregates including, but not limited to, Lewy bodies and/or Lewy neurites, the method comprising the steps:

(a) Bringing a sample, a specific body part or body area suspected to contain alpha-synuclein aggregates including, but not limited to, Lewy bodies and/or Lewy neurites into contact with a compound of formula (I) or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof;

(b) Allowing the compound to bind to the alpha-synuclein aggregates including, but not limited to, Lewy bodies and/or Lewy neurites;

(c) Detecting the compound bound to the alpha-synuclein aggregates including, but not limited to, Lewy bodies and/or Lewy neurites; and (d) Correlating the presence or absence of the compound bound to the alpha-synuclein aggregates including, but not limited to, Lewy bodies and/or Lewy neurites with the disease, disorder or abnormality associated with the alpha-synuclein aggregates including, but not limited to, Lewy bodies and/or Lewy neurites.

In another embodiment the present invention provides a method of collecting data for the diagnosis of a disease, disorder or abnormality associated with alpha-synuclein aggregates including, but not limited to, Lewy bodies and/or Lewy neurites, the method comprising the steps:

(a) Bringing a sample or a specific body part or body area suspected to contain alpha-synuclein aggregates including, but not limited to, Lewy bodies and/or Lewy neurites into contact with a compound of formula (I) or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof;

(b) Allowing the compound to bind to the alpha-synuclein aggregates including, but not limited to, Lewy bodies and/or Lewy neurites;

(c) Detecting the compound bound to the alpha-synuclein aggregates including, but not limited to, Lewy bodies and/or Lewy neurites; and (d) Optionally correlating the presence or absence of the compound bound to the alpha-synuclein aggregates including, but not limited to, Lewy bodies and/or Lewy neurites with the presence or absence of the alpha-synuclein aggregates including, but not limited to, Lewy bodies and/or Lewy neurites in the sample or specific body part or body area.

In another embodiment the present invention provides a method of collecting data for determining a predisposition to a disease, disorder or abnormality associated with alpha-synuclein aggregates including, but not limited to, Lewy bodies and/or Lewy neurites, the method comprising the steps:

(a) Bringing a sample or a specific body part or body area suspected to contain alpha-synuclein aggregates including, but not limited to, Lewy bodies and/or Lewy neurites into contact with a compound of formula (I) or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof;

(b) Allowing the compound to bind to the alpha-synuclein aggregates including, but not limited to, Lewy bodies and/or Lewy neurites;

(c) Detecting the compound bound to the alpha-synuclein aggregates including, but not limited to, Lewy bodies and/or Lewy neurites; and (d) Optionally correlating the presence or absence of the compound bound to the alpha-synuclein aggregates including, but not limited to, Lewy bodies and/or Lewy neurites with the presence or absence of the alpha-synuclein aggregates including, but not limited to, Lewy bodies and/or Lewy neurites in the sample or specific body part or body area.

If the amount of the compound bound to the alpha-synuclein aggregates is higher than a normal control value of a healthy/reference subject this indicates that the patient is suffering from or is at risk of developing a disease, disorder or abnormality associated with alpha-synuclein aggregates. In particular, if the amount of the compound bound to the alpha-synuclein aggregates is higher than what expected in a person showing no clinical evidence of neurodegenerative disease, it can be assumed that the patient has a disposition to a disease, disorder or abnormality associated with alpha-synuclein aggregates or a synucleinopathy.

In another embodiment the present invention provides a method of collecting data for prognosing a disease, disorder or abnormality associated with alpha-synuclein aggregates including, but not limited to, Lewy bodies and/or Lewy neurites, wherein the method comprises the steps:

(a) Bringing a sample, a specific body part or body area suspected to contain alpha-synuclein aggregates including, but not limited to, Lewy bodies and/or Lewy neurites into contact with a compound of formula (I) or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof;

(b) Allowing the compound to bind to the alpha-synuclein aggregates including, but not limited to, Lewy bodies and/or Lewy neurites;

(c) Detecting the compound bound to the alpha-synuclein aggregates including, but not limited to, Lewy bodies and/or Lewy neurites;

(d) Optionally correlating the presence or absence of the compound bound to the alpha-synuclein aggregates including, but not limited to, Lewy bodies and/or Lewy neurites with the presence or absence of the alpha-synuclein aggregates including, but not limited to, Lewy bodies and/or Lewy neurites in the sample or specific body part or body area; and (e) Optionally repeating steps (a) to (c) and, if present, optional step (d) at least one time.

The progression of a disease, disorder or abnormality and/or the prospect (e.g., the probability, duration, and/or extent) of recovery can be estimated by a medical practitioner based on the presence or absence of the compound bound to the alpha-synuclein aggregates, the amount of the compound bound to the alpha-synuclein aggregates or the like. If desired, steps (a) to (c) and, if present, optional step (d) can be repeated over time to monitor the progression of the disease, disorder or abnormality and to thus allow a more reliable estimate.

In another embodiment the invention provides a method of collecting data for monitoring the evolution of the disease in a patient suffering from a disease, disorder or abnormality associated with alpha-synuclein aggregates including, but not limited to, Lewy bodies and/or Lewy neurites, the method comprising the steps:

(a) Bringing a sample, a specific body part or body area suspected to contain alpha-synuclein aggregates including, but not limited to, Lewy bodies and/or Lewy neurites into contact with a compound of formula (I) or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof;

(b) Allowing the compound to bind to the alpha-synuclein aggregates including, but not limited to, Lewy bodies and/or Lewy neurites;

(c) Detecting the compound bound to the alpha-synuclein aggregates including, but not limited to, Lewy bodies and/or Lewy neurites;

(d) Optionally correlating the presence or absence of the compound bound to the alpha-synuclein aggregates including, but not limited to, Lewy bodies and/or Lewy neurites with the presence or absence of the alpha-synuclein aggregates including, but not limited to, Lewy bodies and/or Lewy neurites in the sample or specific body part or body area; and (e) Optionally repeating steps (a) to (c) and, if present, optional step (d) at least one time.

Typically the patient is or has been undergoing treatment of the disease, disorder or abnormality associated with alpha-synuclein aggregates or is/has been undergoing treatment of the synucleinopathy. In particular, the treatment can involve administration of a medicament which is suitable for treating the disease, disorder or abnormality associated with alpha-synuclein aggregates.

In another embodiment the present invention provides a method of collecting data for monitoring the progression of a disease, disorder or abnormality associated with alpha-synuclein aggregates including, but not limited to, Lewy bodies and/or Lewy neurites, in a patient, the method comprising the steps:

(a) Bringing a sample, a specific body part or body area suspected to contain alpha-synuclein aggregates including, but not limited to, Lewy bodies and/or Lewy neurites into contact with the compound of formula (I) or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof;

(b) Allowing the compound to bind to the alpha-synuclein aggregates including, but not limited to, Lewy bodies and/or Lewy neurites;

(c) Detecting the compound bound to the alpha-synuclein aggregates including, but not limited to, Lewy bodies and/or Lewy neurites;

(d) Optionally correlating the presence or absence of the compound bound to the alpha-synuclein aggregates including, but not limited to, Lewy bodies and/or Lewy neurites with the presence or absence of the alpha-synuclein aggregates including, but not limited to, Lewy bodies and/or Lewy neurites in the sample or specific body part or body area; and (e) Optionally repeating steps (a) to (c) and, if present, optional step (d) at least one time.

Typically, the patient is or has been undergoing treatment of the disease, disorder or abnormality associated with alpha-synuclein aggregates or is or has been undergoing treatment of the synucleinopathy. In particular, the treatment can involve administration of a medicament which is suitable for treating the disease, disorder or abnormality associated with alpha-synuclein aggregates.

In another embodiment the invention provides a method of collecting data for predicting responsiveness of a patient suffering from a disease, disorder or abnormality associated with alpha-synuclein aggregates including, but not limited to, Lewy bodies and/or Lewy neurites, to a treatment of the disease, disorder or abnormality associated with alpha-synuclein aggregates including, but not limited to, Lewy bodies and/or Lewy neurites, the method comprising the steps:

(a) Bringing a sample, a specific body part or body area suspected to contain alpha-synuclein aggregates including, but not limited to, Lewy bodies and/or Lewy neurites into contact with a compound of formula (I) or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof;

(b) Allowing the compound to bind to the alpha-synuclein aggregates including, but not limited to, Lewy bodies and/or Lewy neurites;

(c) Detecting the compound bound to the alpha-synuclein aggregates including, but not limited to, Lewy bodies and/or Lewy neurites;

(d) Optionally correlating the presence or absence of the compound bound to the alpha-synuclein aggregates including, but not limited to, Lewy bodies and/or Lewy neurites with the presence or absence of the alpha-synuclein aggregates including, but not limited to, Lewy bodies and/or Lewy neurites in the sample or specific body part or body area; and (e) Optionally repeating steps (a) to (c) and, if present, optional step (d) at least one time.

Typically, the patient is or has been undergoing treatment of the disease, disorder or abnormality associated with alpha-synuclein aggregates or is or has been undergoing treatment of the synucleinopathy. In particular, the treatment can involve administration of a medicament which is suitable for treating the disease, disorder or abnormality associated with alpha-synuclein aggregates.

If the amount of the compound bound to the alpha-synuclein aggregates decreases over time, it can be assumed that the patient is responsive to the treatment. If the amount of the compound bound to the alpha-synuclein aggregates is essentially constant or increases over time, it can be assumed that the patient is non-responsive to the treatment.

Alternatively, the responsiveness can be estimated by determining the amount of the compound bound to the alpha-synuclein aggregates. The amount of the compound bound to the alpha-synuclein aggregates can be compared to a control value such as a normal control value, a preclinical control value or a clinical control value. Alternatively, the control value may refer to the control value of subjects known to be responsive to a certain therapy, or the control value may refer to the control value of subjects known to be non-responsive to a certain therapy. The outcome with respect to responsiveness can either be "responsive" to a certain therapy, "non-responsive" to a certain therapy or "response undetermined" to a certain therapy. Response to the therapy may be different for the respective patients.

In yet another embodiment the present invention provides a method, as defined herein, wherein the step of optionally correlating the presence or absence of the compound bound to the alpha-synuclein aggregates including, but not limited to, Lewy bodies and/or Lewy neurites, with the presence or absence of the alpha-synuclein aggregates including, but not limited to, Lewy bodies and/or Lewy neurites in the sample or specific body part or body area comprises determining in which amount of the compound bound to the alpha-synuclein aggregates including, but not limited to, Lewy bodies and/or Lewy;

correlating the amount of the compound bound to the alpha-synuclein aggregates including, but not limited to, Lewy bodies and/or Lewy neurites with the amount of the alpha-synuclein aggregates including, but not limited to, Lewy bodies and/or Lewy neurites in the sample or specific body part or body area; and optionally comparing the amount of the amount of the alpha-synuclein aggregates including, but not limited to, Lewy bodies and/or Lewy neurites in the sample or specific body part or body area to a normal control value in a healthy control subject.

The control value can be, e.g., a normal control value, a preclinical control value and/or a clinical control value.

A "healthy control subject" or "healthy volunteer (HV) subject" is a person showing no clinical evidence of neurodegenerative disease. The person is selected as defined herein, in section 15 "First in human (FIH) study" of the "biological assay description and corresponding results" paragraph.

If in any of the above summarized methods the amount of the compound bound with the alpha-synuclein aggregates is higher than the normal control value, then it can be expected that the patient is suffering from or is likely to from a disease, disorder or abnormality associated with alpha-synuclein aggregates or from a synucleinopathy.

Any of the compounds of the present invention can be used in the above summarized methods. Preferably detectably labeled compounds of the present invention, as disclosed herein, are employed in the above summarized methods.

The specific body part or body area is preferably of a mammal, more preferably of a human, including the full body or partial body area or body part of the patient suspected to contain alpha-synuclein aggregates.

The sample can be selected from tissue or body fluids suspected to contain alpha-synuclein aggregates, the sample being obtained from the patient. Preferably, the tissue is selected from brain tissue. Examples of body fluids include cerebrospinal fluid (CSF) or blood. The sample can be obtained from a mammal, more preferably a human. Preferably, the sample is an in vitro sample from a patient.

In an in vivo method, the specific body part or body area can be brought into contact with a compound of the invention by administering an effective amount of a compound of the invention to the patient. The effective amount of a compound of the invention is an amount which is suitable for allowing the presence or absence of alpha-synuclein aggregates including, but not limited to, Lewy bodies and/or Lewy neurites in the specific body part or body area to be determined using the chosen analytical technique.

The step of allowing the compound to bind to the alpha-synuclein aggregates including, but not limited to, Lewy bodies and/or Lewy neurites includes allowing sufficient time for the compound of the invention to bind to the alpha-synuclein aggregates including, but not limited to, Lewy bodies and/or Lewy neurites. The amount of time required for binding will depend on the type of test (e.g., in vitro or in vivo) and can be determined by a person skilled in the field by routine experiments. In an in vivo method, the amount of time will depend on the time which is required for the compound to reach the specific body part or body area suspected to contain alpha-synuclein aggregates including, but not limited to, Lewy bodies and/or Lewy neurites. The amount of time should not be too extended to avoid washout and/or metabolism of the compound of the invention.

The method of detecting the compound bound to the alpha-synuclein aggregates including, but not limited to, Lewy bodies and/or Lewy neurites is not particularly limited and depends, among others, on the detectable label, the type of sample, specific body part or body area and whether the method is an in vitro or in vivo method. Possible detection methods include, but are not limited to a fluorescence imaging technique or a nuclear imaging technique such as positron emission tomography (PET), single photon emission computed tomography (SPECT), magnetic resonance imaging (MRI), and contrast-enhanced magnetic resonance imaging (MRI). The fluorescence imaging technique and/or nuclear imaging technique can be employed for monitoring and/or visualizing the distribution of the compound of the invention within the sample or the body. The imaging system is such to provide an image of bound detectable label such as radioisotopes, in particular positron emitters or gamma emitters, as present in the tested sample, the tested specific body part or the tested body area. Preferably, the compound bound to the alpha-synuclein aggregates including, but not limited to, Lewy bodies and/or Lewy neurites is detected by an imaging apparatus such as PET or SPECT scanner.

The amount of the compound bound with the alpha-synuclein aggregates including, but not limited to, Lewy bodies and/or Lewy neurites can be determined by the visual or quantitative analysis, for example, using PET scan images.

In any of the above methods, steps (a) to (c) and, if present, optional step (d) can be repeated at least one time. The repetition of the steps is particularly useful in the method of collecting data for prognosing, the method of collecting data for monitoring the evolution of the disease, the method of collecting data for monitoring the progression and the method of collecting data for predicting responsiveness. In these methods, it may be expedient to monitor the patient over time and to repeat the above steps after a certain period of time has elapsed. The time interval before the above mentioned steps are repeated can be determined by a physician depending on the severity of the disease, disorder or abnormality associated with alpha-synuclein aggregates including, but not limited to, Lewy bodies and/or Lewy neurites or the synucleinopathy.

In a further aspect, the present invention refers to a method of imaging a disease, disorder or abnormality associated with alpha-synuclein aggregates including, but not limited to, Lewy bodies and/or Lewy neurites, in a subject, the method comprising the steps:

(a) Administering a compound of the formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof to the subject;
(b) Allowing the compound to bind to the alpha-synuclein aggregates, including, but not limited to, Lewy bodies and/or Lewy neurites; and
(c) Detecting the compound bound to the alpha-synuclein aggregates, including, but not limited to, Lewy bodies and/or Lewy neurites.

In a further aspect, the present invention is directed to a method of imaging a disease, disorder or abnormality associated with alpha-synuclein aggregates including, but not limited to, Lewy bodies and/or Lewy neurites, in a subject, the method comprising the steps:

(a) Administering a compound of the formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof to the subject; and
(b) Imaging the brain of the subject.

The brain of the subject should be imaged when the compound has bound to the alpha-synuclein aggregates, including, but not limited to, Lewy bodies and/or Lewy neurites. The compound bound to the alpha-synuclein aggregates, including, but not limited to, Lewy bodies and/or Lewy neurites, can then be imaged in the subject's brain.

In a further aspect, the present invention refers to a method of positron emission tomography (PET) imaging of alpha-synuclein aggregates, including but not limited to, Lewy bodies and/or Lewy neurites, in a tissue of a subject, the method comprising the steps:

(a) Administering a compound of the formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof to the subject;
(b) Allowing the compound to penetrate into the tissue of the subject; and
(c) Collecting a positron emission tomography (PET) image of the tissue of the subject;

wherein the tissue is tissue of the central nervous system (CNS), of the eye or brain tissue, preferably wherein the tissue is brain tissue.

The PET imaging should be conducted when the compound has penetrate into the tissue and the compound has bound to the alpha-synuclein aggregates, including, but not limited to, Lewy bodies and/or Lewy neurites.

In a further aspect, the present invention is directed a method of detecting a neurological disease, disorder or abnormality associated with alpha-synuclein aggregates, including but not limited to, Lewy bodies and/or Lewy neurites, in a subject, the method comprising the steps:

(a) Administering a compound of the formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof to the subject;

(b) Allowing the compound to bind to the alpha-synuclein aggregates including, but not limited to, Lewy bodies and/or Lewy neurites; and (c) Measuring the radioactive signal of the compound, which is bound to the alpha-synuclein aggregates, including but not limited to, Lewy bodies and/or Lewy neurites.

The radioactive signal, as mentioned herein, is observed when a detectably labelled compound of the invention, which comprises at least one radiolabelled atom (e.g. $^{3}H$, $^{2}H$, or $^{18}F$), is bound to the alpha-synuclein aggregates, including but not limited to, Lewy bodies and/or Lewy neurites.

In a further aspect, the present invention is directed to a method (e.g., an in vivo or in vitro method) for the detection and/or quantification of alpha-synuclein aggregates, including but not limited to, Lewy bodies and/or Lewy neurites, in a tissue of a subject, the method comprising the steps:

(a) Contacting the tissue with a compound of the formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof to the subject;

(b) Allowing the compound to bind to the alpha-synuclein aggregates, including, but not limited to, Lewy bodies and/or Lewy neurites; and (c) Detecting and/or quantifying the compound bound to the alpha-synuclein aggregates, including but not limited to, Lewy bodies and/or Lewy neurites, using positron emission tomography.

In yet another aspect, the present invention refers to a method of the diagnostic imaging of the brain of a subject, the method comprising the steps:

(a) Administering a compound of the formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof to the subject; and (b) Obtaining an image of the brain of the subject using positron emission tomography.

In the methods of the present invention, the compound of the formula (I), or subformulae thereof (e.g. (IIa), (IIb), (IIIa), (IIIb), (IIIc), (III-F), (III-H)), or a detectably labelled compound, stereoisomer, racemic mixture, pharmaceutically acceptable salt, hydrate, or solvate thereof is typically administered in a detectable amount, i.e., an amount which can be detected by the device which is employed in for detecting the compound in the respective method. The amount is not particularly limited and will depend on the compound of the formula (I), the type of detectable label, the sensitivity of the respective analytical method and the respective device. The amount can be chosen appropriately by a skilled person.

Radiopharmaceutical Preparations

The compounds of the present invention, or a detectably labelled compound, stereoisomer, racemic mixture, pharmaceutically acceptable salt, hydrate, or solvate thereof, preferably compounds of formula (I), or of subformulae thereof (e.g. (IIa), (IIb), (IIIa), (IIIb), (IIIc), (III-F), (III-H)), can also be employed in kits for the preparation of radiopharmaceutical preparations. Due to the radioactive decay, the radiopharmaceuticals are usually prepared immediately before use. The kit typically comprises a precursor of the compound of the present invention, or a detectably labelled compound, stereoisomer, racemic mixture, pharmaceutically acceptable salt, hydrate, or solvate thereof, and an agent which reacts with the precursor to introduce a radioactive label into the compound of the present invention, or a detectably labelled compound, stereoisomer, racemic mixture, pharmaceutically acceptable salt, hydrate, or solvate thereof. The precursor of the compound of the present invention, or a detectably labelled compound, stereoisomer, racemic mixture, pharmaceutically acceptable salt, hydrate, or solvate thereof, can, for example, be a compound having the formula (IV-F), (IV-H), or (IV-J). The agent can be an agent which introduces a radioactive label such as $^{18}F$, or $^{3}H$.

Pharmaceutical Compositions

The compounds of the present invention, or a detectably labelled compound, stereoisomer, racemic mixture, pharmaceutically acceptable salt, hydrate, or solvate thereof, can be employed in treating, preventing or alleviating a disease, disorder or abnormality associated with alpha-synuclein aggregates.

The compounds of the present invention, or a detectably labelled compound, stereoisomer, racemic mixture, pharmaceutically acceptable salt, hydrate, or solvate thereof, preferably compounds of formula (I), are suitable for treating, preventing or alleviating a disease, disorder or abnormality associated with alpha-synuclein aggregates including, but not limited to, Lewy bodies and/or Lewy neurites. Diseases involving alpha-synuclein aggregates are generally listed as synucleinopathies (or α-synucleinopathies). The compounds of the present invention, or a detectably labelled compound, stereoisomer, racemic mixture, pharmaceutically acceptable salt, hydrate, or solvate thereof, are suitable for treating, preventing or alleviating diseases, disorders or abnormalities including, but not limited to, Parkinson's disease (sporadic, familial with alpha-synuclein mutations, familial with mutations other than alpha-synuclein, pure autonomic failure and Lewy body dysphagia), SNCA duplication carrier, dementia with Lewy bodies ("pure" Lewy body dementia), Alzheimer's disease, sporadic Alzheimer's disease, familial Alzheimer's disease with APP mutations, familial Alzheimer's disease with PS-1, PS-2 or other mutations, familial British dementia, Lewy body variant of Alzheimer's disease and normal aging in Down syndrome). Synucleinopathies with neuronal and glial aggregates of alpha synuclein include multiple system atrophy (MSA) (Shy-Drager syndrome, striatonigral degeneration and olivopontocerebellar atrophy). Other diseases that may have alpha-synuclein-immunoreactive lesions include traumatic brain injury, chronic traumatic encephalopathy, tauopathies (Pick's disease, frontotemporal dementia, progressive supranuclear palsy, corticobasal degeneration and Niemann-Pick type C1 disease), motor neuron disease, amyotrophic lateral sclerosis (sporadic, familial and ALS-dementia complex of Guam), neuroaxonal dystrophy, neurodegeneration with brain iron accumulation type 1 (Hallervorden-Spatz syndrome), prion diseases, ataxia telangiectatica, Meige's syndrome, subacute sclerosing panencephalitis, Gaucher disease as well as other lysosomal storage disorders (including Kufor-Rakeb syndrome and Sanfilippo syndrome) and rapid eye movement (REM) sleep behavior disorder. (Jellinger, Mov Disord 2003, 18 Suppl. 6, S2-12; Galvin et al. JAMA Neurology 2001, 58 (2), 186-190; Kovari et al., Acta Neuropathol. 2007, 114(3), 295-8; Saito et al., J Neuropathol Exp Neurol. 2004, 63(4), 323-328; McKee et al., Brain, 2013, 136(Pt 1), 43-64; Puschmann et al., Parkinsonism Relat Disord 2012, 18S1, S24-S27; Usenovic et al., J Neurosci. 2012, 32(12), 4240-424 6; Winder-Rhodes et al., Mov Disord. 2012, 27(2), 312-315; Ferman et al., J Int Neuropsychol Soc. 2002, 8(7), 907-914). Preferably, the compounds of the present invention are suitable for treating, preventing or alleviating Parkinson's disease (PD).

In pharmaceutical applications, the compound of the present invention, or a detectably labelled compound, stereoisomer, racemic mixture, pharmaceutically acceptable salt, hydrate, or solvate thereof, is preferably administered in a pharmaceutical composition comprising the compound of the invention. A "pharmaceutical composition" is defined in the present invention as a composition comprising one or more compounds of the present invention, or a detectably labelled compound, stereoisomer, racemic mixture, pharmaceutically acceptable salt, hydrate, or solvate thereof, in a form suitable for administration to a patient, e.g., a mammal such as a human, and which is suitable for treating, alleviating or preventing the specific disease, disorder or abnormality at issue. Preferably a pharmaceutical composition further comprises a physiologically acceptable carrier, diluent, adjuvant or excipient. The dose of the compound of the present invention, or a detectably labelled compound, stereoisomer, racemic mixture, pharmaceutically acceptable salt, hydrate, or solvate thereof, will vary depending on the exact compound to be administered, the weight of the patient, and other variables as would be apparent to a physician skilled in the art.

While it is possible for the compounds of the present invention, or a detectably labelled compound, stereoisomer, racemic mixture, pharmaceutically acceptable salt, hydrate, or solvate thereof, to be administered alone, it is preferable to formulate them into a pharmaceutical composition in accordance with standard pharmaceutical practice. Thus, the invention also provides a pharmaceutical composition which comprises a therapeutically effective amount of a compound of formula (I), or a detectably labelled compound, stereoisomer, racemic mixture, pharmaceutically acceptable salt, hydrate, or solvate thereof, in admixture with, optionally, at least one pharmaceutically acceptable excipient, carrier, diluent or adjuvant.

Pharmaceutically acceptable excipients are well known in the pharmaceutical art, and are described, for example, in Remington's Pharmaceutical Sciences, $15^{th}$ Ed., Mack Publishing Co., New Jersey (1975). The pharmaceutical excipient can be selected with regard to the intended route of administration and standard pharmaceutical practice. The excipient must be acceptable in the sense of being not deleterious to the recipient thereof.

Pharmaceutically useful excipients that may be used in the formulation of the pharmaceutical composition of the present invention, or a detectably labelled compound, stereoisomer, racemic mixture, pharmaceutically acceptable salt, hydrate, or solvate thereof, may comprise, for example, carriers, vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate, binders, adjuvants, solubilizers, thickening agents, stabilizers, disintegrants, glidants, lubricating agents, buffering agents, emulsifiers, wetting agents, suspending agents, sweetening agents, colorants, flavors, coating agents, preservatives, antioxidants, processing agents, drug delivery modifiers and enhancers such as calcium phosphate, magnesium stearate, talc, monosaccharides, disaccharides, starch, gelatin, cellulose, methylcellulose, sodium carboxymethyl cellulose, dextrose, hydroxypropyl-β-cyclodextrin, polyvinylpyrrolidone, low melting waxes, and ion exchange resins.

The compounds of the present invention, or a detectably labelled compound, stereoisomer, racemic mixture, pharmaceutically acceptable salt, hydrate, or solvate thereof, and their precursors can be synthesized by one of the general methods shown in the following schemes. These methods are only given for illustrative purposes and should not to be construed as limiting.

| Abbreviation | Meaning |
|---|---|
| DMFDMA | N,N-dimethylformamide dimethyl acetal |
| SNAr | nucleophilic aromatic substitution |
| CsF | cesium fluoride |
| DMSO | dimethylsulfoxide |
| NBS | N-bromosuccinimide |
| LG | Leaving Group |
| WFI | water for injection |
| HPLC | High Performance Liquid Chromatography |
| SPE | Solid Phase Extraction |

General Synthetic Scheme for the Preparation of Compounds and Precursors of this Invention:

Scheme 1
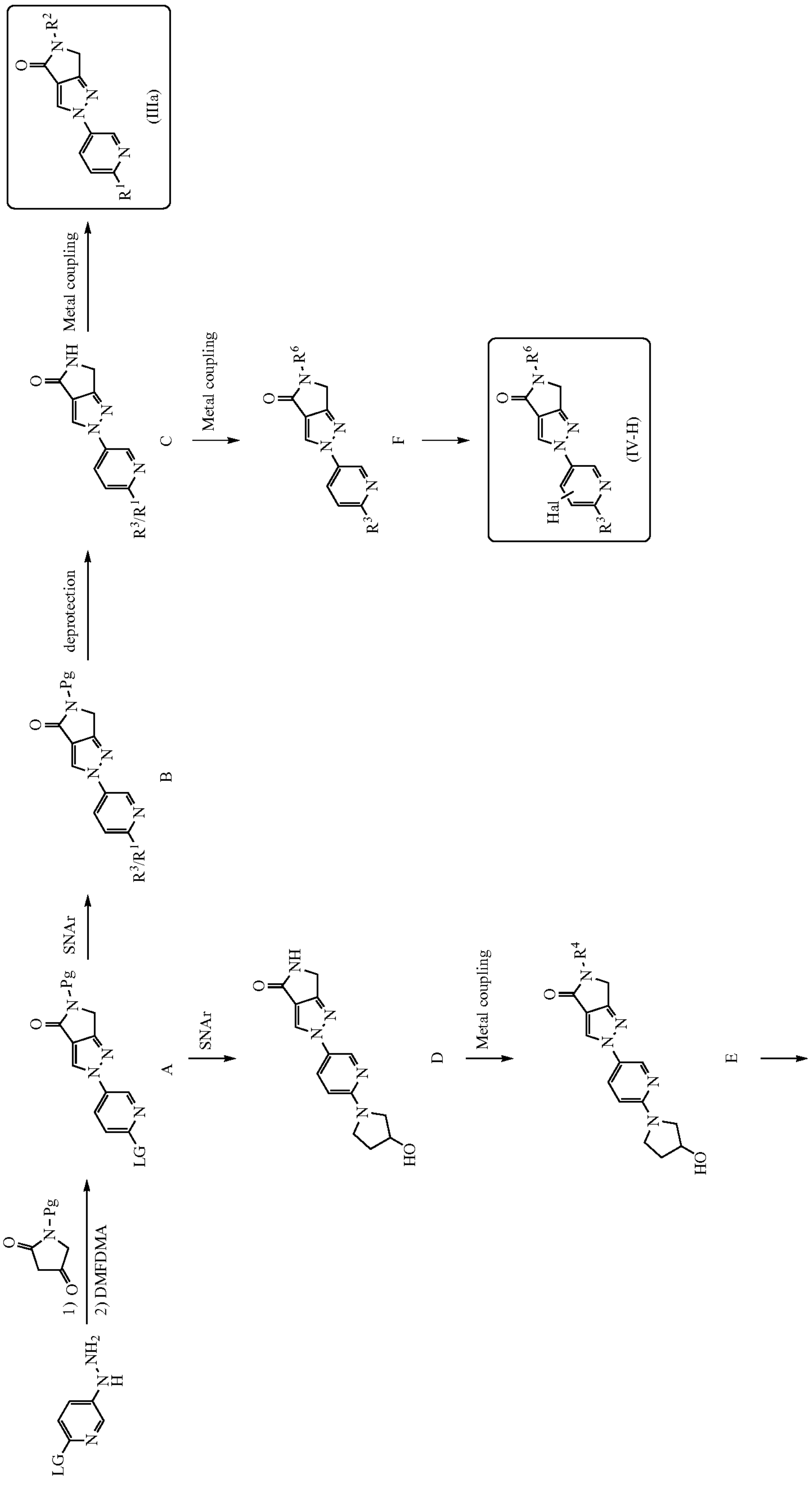

-continued
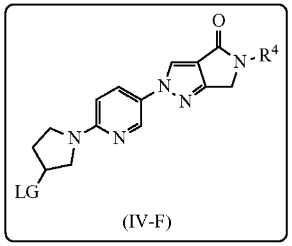
(IV-F)

Commercially available hydrazine can be condensed with the appropriate ketone to afford the corresponding hydrazone. The crude hydrazone can be subjected to ring cyclization using DMF/DMA to give intermediate A. SNAr can be conducted with a suitable nucleophile in a suitable solvent and base to give intermediate B. Alternatively, thermal conditions can be applied without metal catalyst. Deprotection with suitable conditions can afford intermediate C. Finally, intermediate C can be further functionalized using palladium catalyzed amidation or Ullmann reaction to give compounds of formula (I), or of subformulaes thereof (e.g. (IIa), (IIb), (IIIa), (IIIb), (IIIc), (III-F), (III-H)). In this example the starting materials comprise $R^0$ is H. The above general scheme applies to starting material wherein $R^0$ is $C_1$-$C_4$alkyl.

Scheme 1A
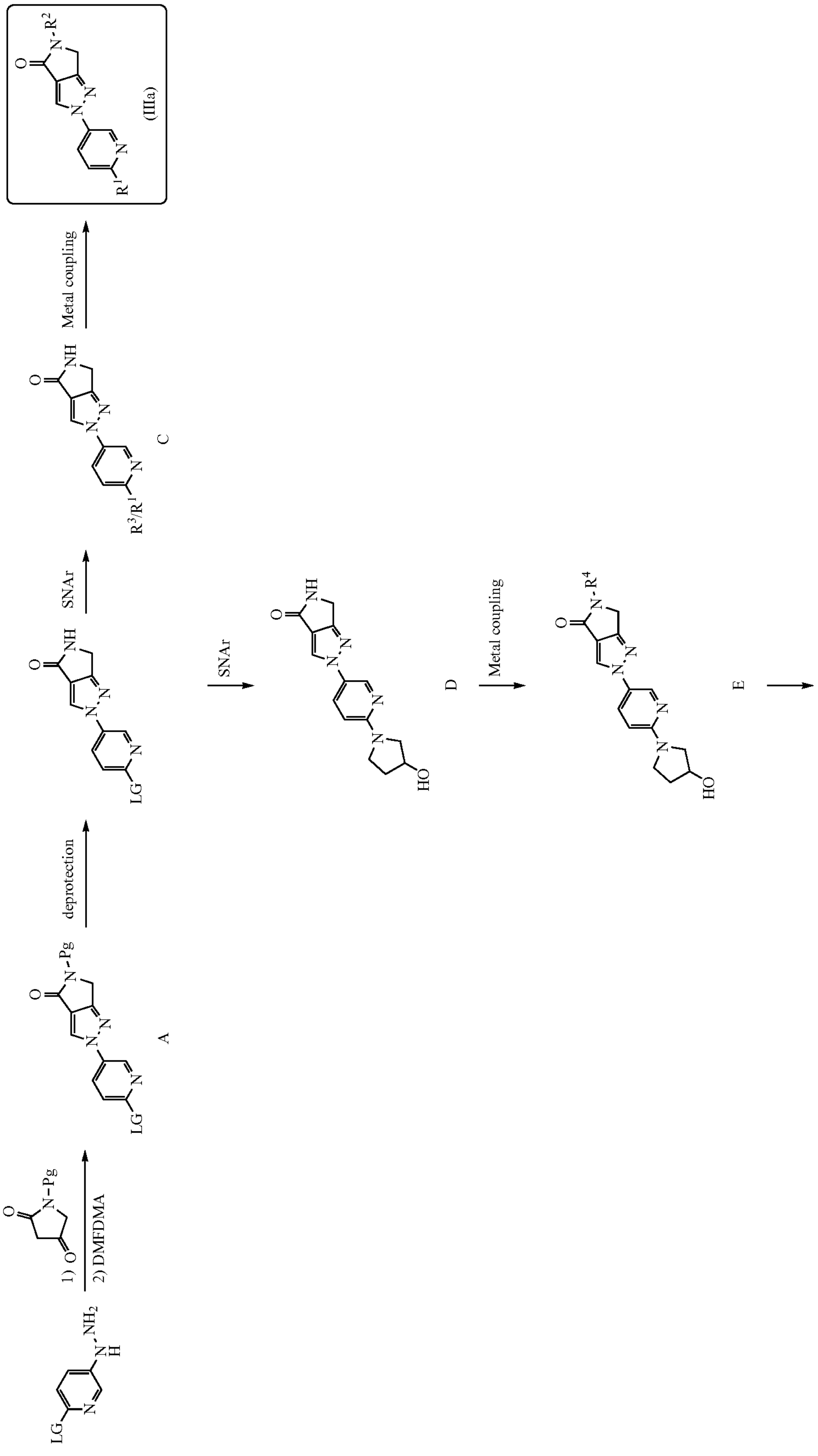
A
C
(IIa)
D
E

-continued
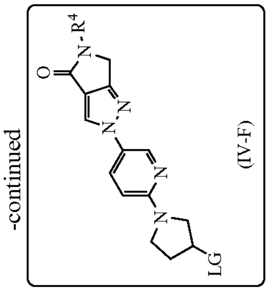
(IV-F)

An alternative approach (Scheme 1A) comprises deprotecting intermediate A, followed by SNAr reaction with a suitable nucleophile which is preferably conducted in the presence of CsF in DMSO. Intermediates C and D can be further functionalized, preferably using copper (I) (Ullmann reaction) in the presence of a base and solvent, to afford formula (IIIa) and intermediate E. Finally, LG can be introduced into intermediate E to give formula (IV-F). In this example the starting materials comprise $R^0$ is H. The above general scheme applies to starting material wherein $R^0$ is $C_1$-$C_4$alkyl.

Scheme 1B
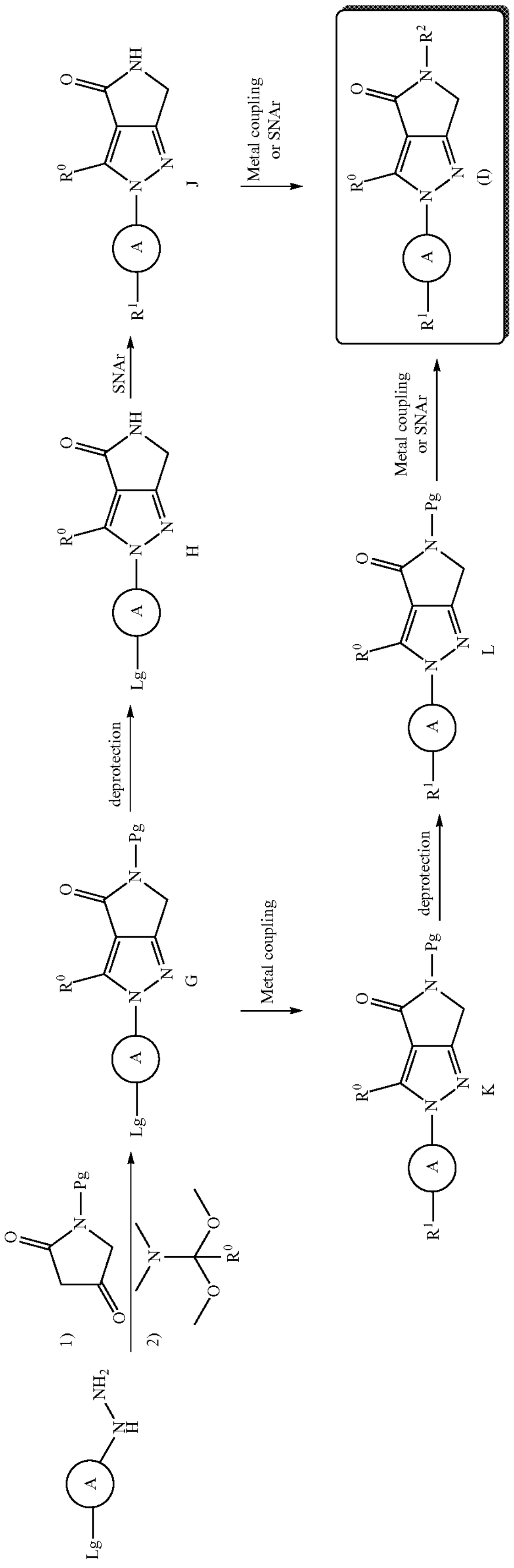

A general approach is depicted in scheme 1B following the same preferred conditions as described in the general scheme 1 or 1A A $^{18}F$-precursor can be obtained by treating intermediate A with hydroxypyrrolidine under heating in a suitable solvent. The $R^4$ group can be introduced by palladium catalyzed amidation or Ullmann reaction. Ultimately, an alcohol intermediate E can be modified into a leaving group using standard conditions to give a compound of formula (IV-F).

The $^{3}H$-precursor can be obtained by introducing an appropriate $R^4$ group by palladium catalyzed amidation or Ullmann reaction into an intermediate C. Finally, halogenation of pyridine using, for example, NBS in a suitable solvent can give a compound of formula (IV-H).

General Synthesis of $^{18}F$-Labelled Compounds of the Present Invention

Compounds having the formula (I) which are labelled by $^{18}F$ can be prepared by reacting a precursor compound, as described below, with an $^{18}F$-fluorinating agent, so that the LG comprised in the precursor compound is replaced by $^{18}F$.

The reagents, solvents and conditions which can be used for the $^{18}F$-fluorination are well-known to a skilled person in the field (L. Cai, S. Lu, V. Pike, Eur. J. Org. Chem 2008, 2853-2873; J. Fluorine Chem., 27 (1985):177-191; Coenen, Fluorine-18 Labeling Methods: Features and Possibilities of Basic Reactions, (2006), in: Schubiger P. A., Friebe M., Lehmann L., (eds), PET-Chemistry—The Driving Force in Molecular Imaging. Springer, Berlin Heidelberg, pp. 15-50). Preferably, the solvents used in the $^{18}F$-fluorination are DMF, DMSO, acetonitrile, DMA, or mixtures thereof, preferably the solvent is acetonitrile or DMSO.

Any suitable $^{18}F$-fluorinating agent can be employed. Typical examples include $H^{18}F$, alkali or alkaline earth $^{18}F$-fluorides (e.g., $K^{18}F$, $Rb^{18}F$, $Cs^{18}F$, and $Na^{18}F$). Optionally, the $^{18}F$-fluorination agent can be used in combination with a chelating agent such as a cryptand (e.g.: 4,7,13,16,21,24-hexaoxa-1,10-diazabicyclo[8.8.8]-hexacosane—Kryptofix®) or a crown ether (e.g.: 18-crown-6). Alternatively, the $^{18}F$-fluorinating agent can be a tetraalkylammonium salt of $^{18}F$ or a tetraalkylphosphonium salt of $^{18}F$; e.g., tetra($C_{1-6}$ alkyl)ammonium salt of $^{18}F$ or a tetra($C_{1-6}$ alkyl)phosphonium salt of $^{18}F$. Preferably, the $^{18}F$-fluorination agent is $K^{18}F$, $H^{18}F$, $Cs^{18}F$, $Na^{18}F$ tetra($C_{1-6}$ alkyl) ammonium salt of $^{18}F$, kryptofix[222]$^{18}F$ or tetrabutylammonium [$^{18}F$]fluoride.

Although the reaction is shown above with respect to $^{18}F$ as a radioactive label, other radioactive labels can be introduced following similar procedures.

The invention is illustrated by the following examples which, however, should not be construed as limiting.

EXAMPLES

All reagents and solvents were obtained from commercial sources and used without further purification. Proton ($^{1}H$) spectra were recorded on a Bruker DRX-400 MHz NMR spectrometer, on a Bruker AV-400 MHz NMR spectrometer or Spinsolve 80 MHz NMR spectrometer in deuterated solvents. Mass spectra (MS) were recorded on an Advion CMS mass spectrometer or an UPLC H-Class Plus with Photodiode Array detector and Qda Mass spectrometer from Waters. Chromatography was performed using silica gel (Fluka: Silica gel 60, 0.063-0.2 mm) and suitable solvents as indicated in the specific examples. Flash purification was conducted with a Biotage Isolera One flash purification system using HP-Sil or KP-NH SNAP cartridges (Biotage) and the solvent gradient indicated in the specific examples. Thin layer chromatography (TLC) was carried out on silica gel plates with UV detection.

Preparative Example 1

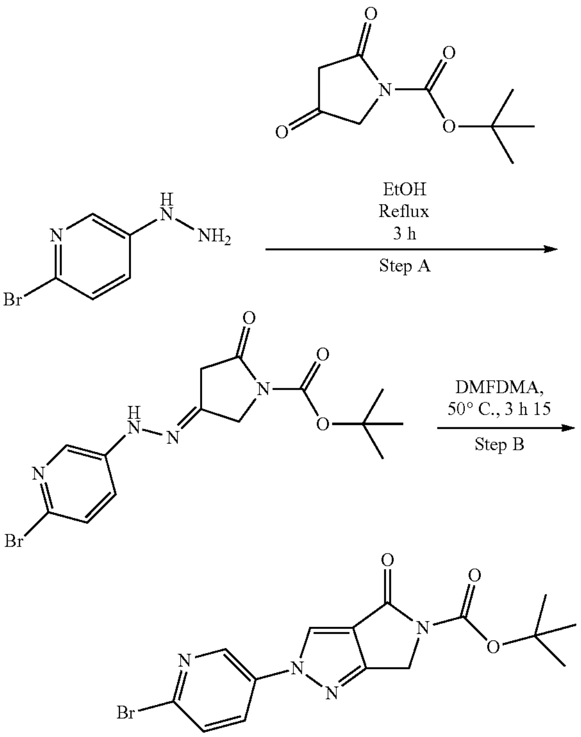

Step A:

A suspension of 2-bromo-5-hydrazinylpyridine (3.21 g, 17.07 mmol) and tert-butyl 2,4-dioxopyrrolidine-1-carboxylate (3.40 g, 17.07 mmol) in ethanol (150 mL) was refluxed for 3 h and monitored by TLC. The crude product was concentrated under reduced pressure and diluted with dichloromethane and water. The layers were separated and the aqueous layer was extracted twice with dichloromethane. The combined organic layers were dried over $Na_2SO_4$, filtered and concentrated under reduced pressure. The crude product was purified by flash chromatography (Silica, 50 g column, 60-80% ethyl acetate in heptane) to afford (E)-tert-butyl 4-(2-(6-bromopyridin-3-yl)hydrazono)-2-oxopyrrolidine-1-carboxylate as a brown solid (4.97 g, 79%). $^{1}H$ NMR (400 MHz, DMSO-d6) δ=9.22 (s, 1H), 8.41 (s, 1H), 7.89 (d, 1H), 7.40 (d, 1H), 7.11 (dd, 1H), 4.57 (s, 1H), 4.30 (s, 2H), 1.45 (s, 9H). MS: 369.06 $[M+H]^+$ Step B:

The compound from step A (3.9 g, 10.56 mmol) was stirred in 1,1-dimethoxy-N,N-dimethylmethanamine (80 mL) at 50° C. for 3 h 15 min. The reaction mixture was concentrated to ~10 mL and ethanol was added. The solid was filtered and washed with small portions of ethanol to afford tert-butyl 2-(6-bromopyridin-3-yl)-4-oxo-4,6-dihydropyrrolo[3,4-c]pyrazole-5(2H)-carboxylate as a light brown powder (2.30 g, 57%). $^{1}H$ NMR (400 MHz, DMSO-d6) δ=9.20 (s, 1H), 9.00 (d, 1H), 8.28 (dd, 1H), 7.89 (d, 1H), 4.84 (s, 2H), 1.53 (s, 9H). MS: 324.83 $[M-tBu^+H]^+$

Preparative Examples 1A to 1H

Following the procedure as described in preparative example 1, using 1,1-dimethoxy-N,N-dimethylmethanamine or N,N-dimethylacetamide dimethyl acetal and the appropriate hydrazone, the following preparative examples were prepared.

| hydrazone | SM | Preparative Example | 1. $^1$H-NMR<br>2. MH$^+$ (ESI) |
|---|---|---|---|
| 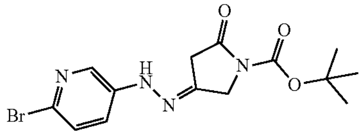 [SMILES: CC(C)(C)OC(=O)N1C/C(=N/Nc2ccc(Br)nc2)CC1=O] | 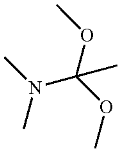 | 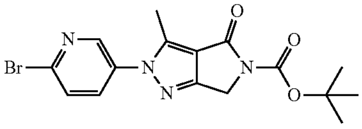 [SMILES: Cc1c2c(nn1-c1ccc(Br)nc1)CN(C(=O)OC(C)(C)C)C2=O]<br>1A | 1. 23%<br>2. $^1$H NMR (400 MHz, DMSO-d6) δ 8.70 (dd, 1H), 8.06 (dd, 1H), 7.90 (dd, 1H), 4.74 (s, 2H), 2.51 (s, 3H), 1.50 (s, 9H).<br>3. 393.0 |
| 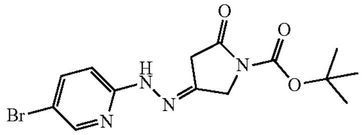 [SMILES: CC(C)(C)OC(=O)N1C/C(=N/Nc2ccc(Br)cn2)CC1=O] | 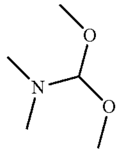 | 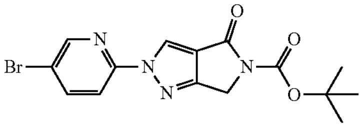 [SMILES: CC(C)(C)OC(=O)N1Cc2nn(-c3ccc(Br)cn3)cc2C1=O]<br>1B | 1. 41%<br>2. $^1$H NMR (500 MHz, DMSO-d6) δ 9.06 (s, 1H), 8.68 (dd, 1H), 8.30 (dd, 1H), 7.93 (dd, 1H), 4.82 (s, 2H), 1.51 (s, 9H).<br>3. 381.2 |
| 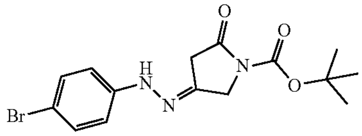 [SMILES: CC(C)(C)OC(=O)N1C/C(=N/Nc2ccc(Br)cc2)CC1=O] | 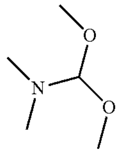 | 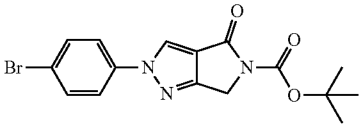 [SMILES: CC(C)(C)OC(=O)N1Cc2nn(-c3ccc(Br)cc3)cc2C1=O]<br>1C | 1. ND<br>2. $^1$H NMR (500 MHz, DMSO-d6) δ 9.13 (s, 1H), 7.92-7.82 (m, 2H), 7.82-7.69 (m, 2H), 4.80 (s, 2H), 1.51 (s, 9H).<br>3. 378.9 |
| 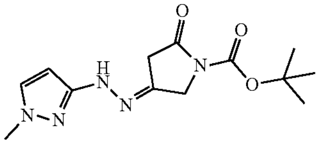 [SMILES: Cn1ccc(N/N=C2\CC(=O)N(C(=O)OC(C)(C)C)C2)n1] | 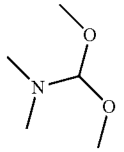 | 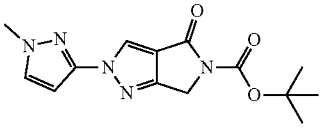 [SMILES: Cn1ccc(-n2cc3c(n2)CN(C(=O)OC(C)(C)C)C3=O)n1]<br>1D | 1. ND<br>2. $^1$H NMR (600 MHz, DMSO-d6) δ 8.68 (s, 1H), 7.82 (d, J = 2.2 Hz, 1H), 6.52 (d, J = 2.2 Hz, 1H), 4.75 (s, 2H), 3.86 (s, 3H), 1.49 (s, 9H).<br>3. 304.0 |
| 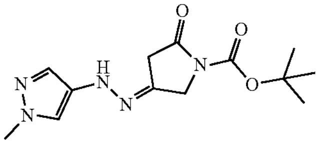 [SMILES: Cn1cc(N/N=C2\CC(=O)N(C(=O)OC(C)(C)C)C2)cn1] | 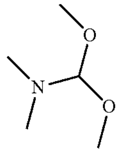 | 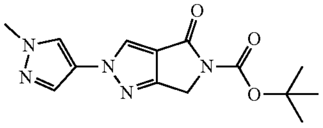 [SMILES: Cn1cc(-n2cc3c(n2)CN(C(=O)OC(C)(C)C)C3=O)cn1]<br>1E | 1. ND<br>2. ND<br>3. 304.0 |
| 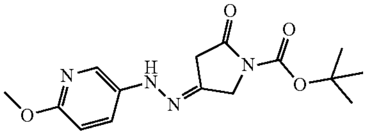 [SMILES: COc1ccc(N/N=C2\CC(=O)N(C(=O)OC(C)(C)C)C2)cn1] | 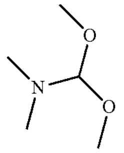 | 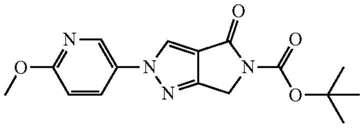 [SMILES: COc1ccc(-n2cc3c(n2)CN(C(=O)OC(C)(C)C)C3=O)cn1]<br>1F | 1. ND<br>2. ND<br>3. 331.2 |
| 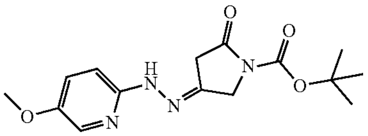 [SMILES: COc1ccc(N/N=C2\CC(=O)N(C(=O)OC(C)(C)C)C2)nc1] | 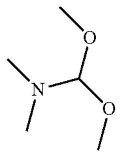 | 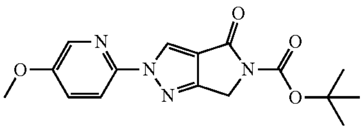 [SMILES: COc1ccc(-n2cc3c(n2)CN(C(=O)OC(C)(C)C)C3=O)nc1]<br>1G | 1. 30%<br>2. $^1$H NMR (500 MHz, DMSO-d6) δ 8.91 (s, 1H), 8.22 (d, 1H), 7.90 (d, 1H), 7.65 (dd, 1H), 4.79 (s, 2H), 3.89 (s, 3H), 1.50 (s, 9H).<br>3. 331.2 |

-continued

| hydrazone | SM | Preparative Example | 1. $^1$H-NMR<br>2. $MH^+$ (ESI) |
|---|---|---|---|
| 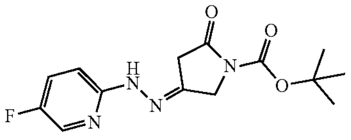 [SMILES: CC(C)(C)OC(=O)N1C/C(=N/Nc2ccc(F)cn2)CC1=O] | 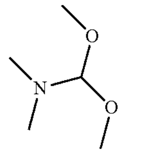 | 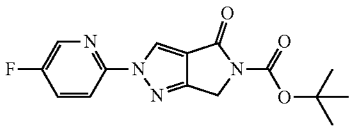 [SMILES: CC(C)(C)OC(=O)N1Cc2nn(-c3ccc(F)cn3)cc2C1=O]<br>1H | 1. 54%<br>2. $^1$H NMR (400 MHz, DMSO-d6) δ 9.03 (s, 1H), 8.57 (s, 1H), 8.02 (m, 2H), 4.82 (s, 2H), 1.51 (s, 9H).<br>3. 319.2 |

Preparative Example A

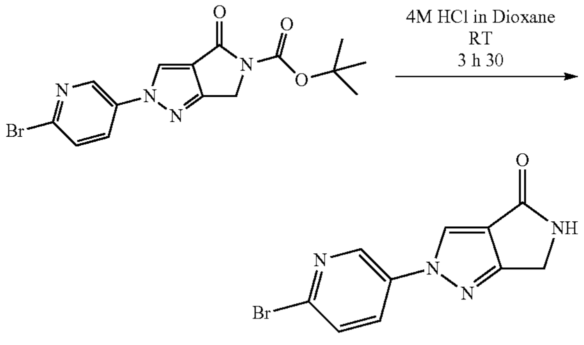

Preparative Example 1 (1000 mg, 2.64 mmol) was stirred in 4 M HCl in dioxane (37 mL) at room temperature for 1 h 45 min. The solvent was evaporated under reduced pressure and the solid dissolved in dichloromethane. A solution of saturated $NaHCO_3$ was added, and the aqueous phase was extracted twice with dichloromethane. The combined organic layers were filtrated to afford 2-(6-bromopyridin-3-yl)-5,6-dihydropyrrolo[3,4-c]pyrazol-4(2H)-one as a beige solid. (682 mg, 93%). $^1$H NMR (80 MHz, DMSO-d6) δ 8.96 (d, 2H), 8.37-8.14 (m, 2H), 7.83 (d, 1H), 4.39 (s, 2H). MS: 280.95 $[M+H]^+$

Preparative Examples A1 to A6

Following the procedure as described in preparative example A, the following preparative examples were prepared.

| SM | Preparative Example | 1. $^1$H-NMR<br>2. $MH^+$ (ESI) |
|---|---|---|
| 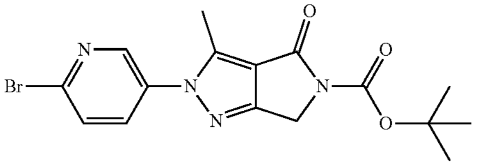 | 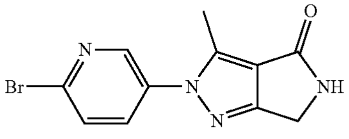 [SMILES: Cc1c2c(nn1-c1ccc(Br)nc1)CNC2=O]<br>A1 | 1. 91%<br>2. $^1$H NMR (500 MHz, DMSO-d6) δ 8.68 (d, 1H), 8.06 (s, 1H), 8.03 (dd, 1H), 7.87 (d, 1H), 4.30 (d, 2H), 2.47 (s, 3H).<br>3. 295.11 |
| 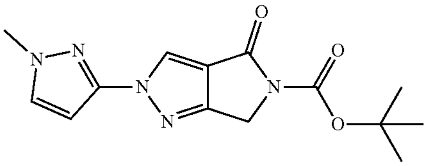 | 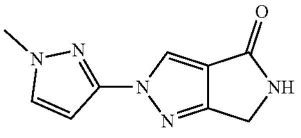<br>A2 | 1. quantitative<br>2. ND.<br>3. 204.0 |
| 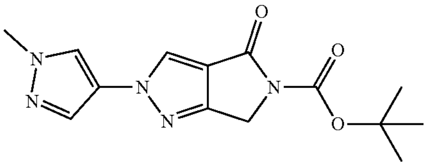 | 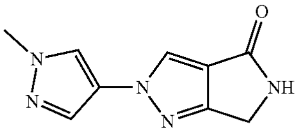<br>A3 | 1. quantitative<br>2. ND.<br>3. 204.2 |

-continued

| SM | Preparative Example | 1. $^1$H-NMR<br>2. MH$^+$ (ESI) |
|---|---|---|
| 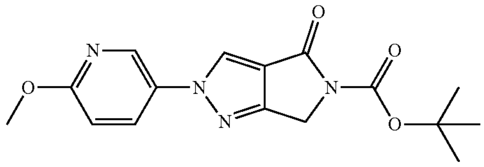 | 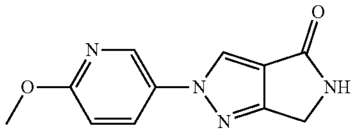 [SMILES: COc1ccc(-n2cc3c(n2)CNC3=O)cn1]<br>A4 | 1. quantitative<br>2. ND.<br>3. 231.0 |
| 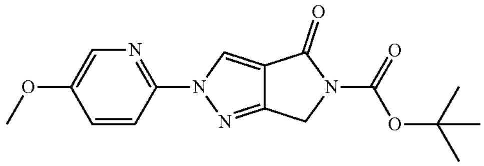 | 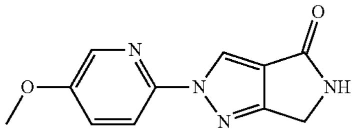 [SMILES: COc1ccc(-n2cc3c(n2)CNC3=O)nc1]<br>A5 | 1. quantitative<br>2. $^1$H NMR (400 MHz, DMSO-d6) δ 8.69 (s, 1H), 8.26-8.10 (m, 2H), 7.88 (d, 1H), 7.63 (dd, 1H), 4.37 (s, 2H), 3.88 (s, 3H).<br>3. 231.0 |
| 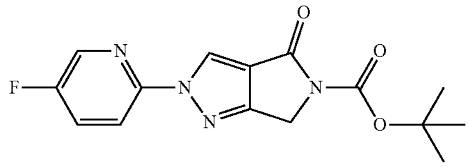 | 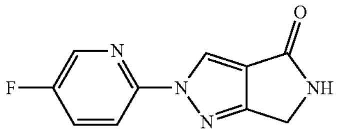 [SMILES: O=C1NCc2nn(-c3ccc(F)cn3)cc21]<br>A6 | 1. 98%<br>2. 1H NMR (400 MHz, DMSO-d6) δ 8.69 (s, 1H), 8.26-8.10 (m, 2H), 7.88 (d, 1H), 7.63 (dd, 1H), 4.37 (s, 2H), 3.88 (s, 3H).<br>3. 219.0 |

Preparative Example 2

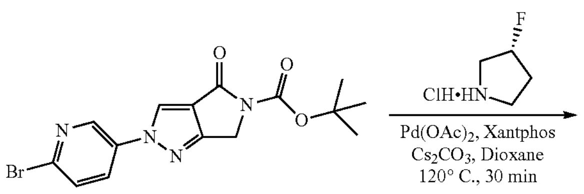

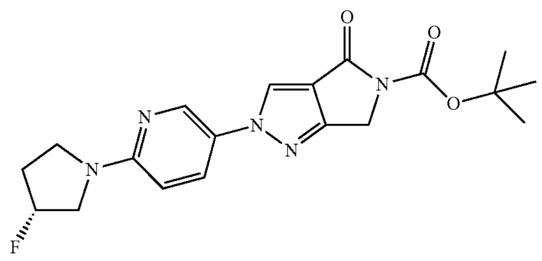

In a flask under argon, palladium (II) acetate (41.4 mg, 0.185 mmol) and xantphos (320 mg, 0.554 mmol) were mixed in 1,4-dioxane (18 mL) and heated at 100° C. for a few seconds on a pre-heated block to form the pd-xantphos complex. (R)-3-Fluoropyrrolidine hydrochloride (348 mg, 2.77 mmol), cesium carbonate (1804 mg, 5.54 mmol) and preparative example 1 (700 mg, 1.846 mmol) were added. The flask was degassed and filled with argon three times and the reaction mixture was heated at 120° C. for 30 min. The reaction mixture was cooled at room temperature and the residue was taken up with ethyl acetate and water. The phases were separated and the aqueous phase was extracted twice. The organic layers were combined, dried over $Na_2SO_4$ and evaporated. The product was purified by flash chromatography (Silica, Silica 25 g column, 0-60% ethyl acetate in dichloromethane) to afford (R)-tert-butyl 2-(6-(3-fluoropyrrolidin-1-yl)pyridin-3-yl)-4-oxo-4,6-dihydropyrrolo[3,4-c]pyrazole-5(2H)-carboxylate as a white solid (200.5 mg, 28%). $^1$H NMR (400 MHz, DMSO-d6) δ=8.92 (s, 1H), 8.60 (d, 1H), 8.01 (dd, 1H), 6.67 (d, 1H), 5.46 (d, 1H), 4.80 (s, 2H), 3.86-3.57 (m, 2H), 3.54-3.44 (m, 2H), 2.36-2.12 (m, 2H), 1.53 (s, 9H). MS: 388.15 [M+H]$^+$ Preparative Examples 3 to 3D Following the Pd-coupling procedure as described in preparative example 2, using the halogenated starting material and the appropriate amine indicated in Table 1a below, the following preparative example was prepared.

TABLE 1a

| Halogenated starting material | Amine | Preparative Example | 1. Yield<br>2. $^1$H-NMR<br>3. MH$^+$ (ESI) |
|---|---|---|---|
| 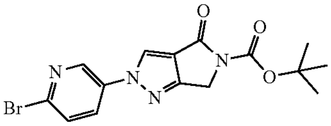 [SMILES: CC(C)(C)OC(=O)N1Cc2nn(-c3ccc(Br)nc3)cc2C1=O] | 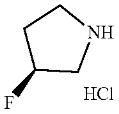 | 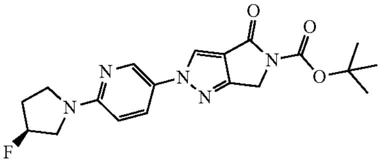 [SMILES: CC(C)(C)OC(=O)N1Cc2nn(-c3ccc(N4CC[C@H](F)C4)nc3)cc2C1=O]<br>3 | 1. 23%<br>2. $^1$H NMR (80 MHz, DMSO-d6) δ = 8.90 (s, 1H), 8.58 (d, 1H), 8.00 (dd, 1H), 6.66 (d, 1H), 5.47 (d, 1H), 4.78 (s, 2H), 4.04-3.39 (m, 4H), 2.46-1.88 (m, 2H), 1.52 (s, 9H).<br>3. 388.16 |
| 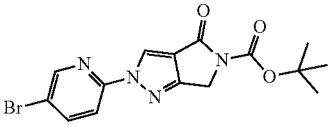 [SMILES: CC(C)(C)OC(=O)N1Cc2nn(-c3ccc(Br)cn3)cc2C1=O] | 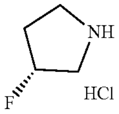 | 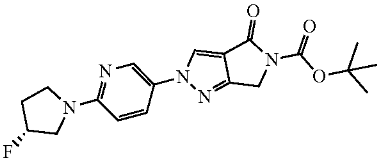 [SMILES: CC(C)(C)OC(=O)N1Cc2nn(-c3ccc(N4CC[C@@H](F)C4)nc3)cc2C1=O]<br>3A | 1. 24%<br>2. $^1$H NMR (500 MHz, DMSO-d6) δ 8.87 (s, 1H), 7.86 (d, 1H), 7.79 (d, 1H), 7.22 (dd, 1H), 5.62-5.39 (m, 1H), 4.79 (s, 2H), 3.77-3.47 (m, 3H), 3.43 (td, 1H), 2.44-2.06 (m, 2H), 1.51 (s, 9H).<br>3. 388.2 |
| 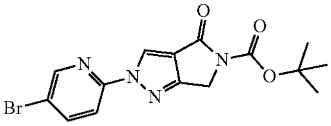 [SMILES: CC(C)(C)OC(=O)N1Cc2nn(-c3ccc(Br)cn3)cc2C1=O] | 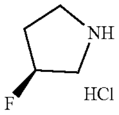 | 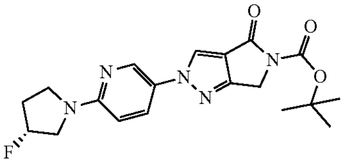 [SMILES: CC(C)(C)OC(=O)N1Cc2nn(-c3ccc(N4CC[C@@H](F)C4)nc3)cc2C1=O]<br>3B | 1. 33%<br>2. $^1$H NMR (500 MHz, DMSO-d6) δ 8.86 (s, 1H), 7.86 (d, 1H), 7.79 (d, 1H), 7.22 (dd, 1H), 5.63-5.36 (m, 1H), 4.79 (s, 2H), 3.75-3.47 (m, 3H), 3.47-3.38 (m, 1H), 2.39-2.10 (m, 2H), 1.51 (s, 9H).<br>3. [-tBu] 332.5 |
| 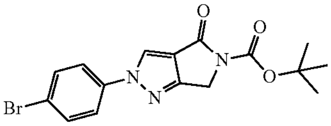 [SMILES: CC(C)(C)OC(=O)N1Cc2nn(-c3ccc(Br)cc3)cc2C1=O] | 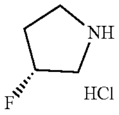 | 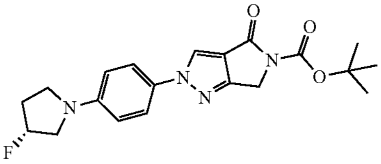 [SMILES: CC(C)(C)OC(=O)N1Cc2nn(-c3ccc(N4CC[C@@H](F)C4)cc3)cc2C1=O]<br>3C | 1. 31%<br>2. $^1$H NMR (500 MHz, DMSO-d6) δ 8.88 (s, 1H), 7.78-7.61 (m, 2H), 6.79-6.54 (m, 2H), 5.64-5.35 (m, 1H), 4.77 (s, 2H), 3.70-3.37 (m, 4H), 2.34-2.10 (m, 2H), 1.51 (s, 9H).<br>3. 387.2 |
| 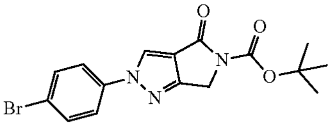 [SMILES: CC(C)(C)OC(=O)N1Cc2nn(-c3ccc(Br)cc3)cc2C1=O] | 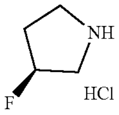 | 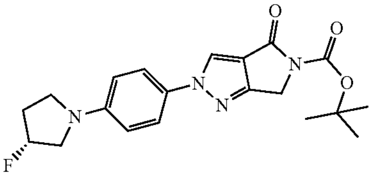 [SMILES: CC(C)(C)OC(=O)N1Cc2nn(-c3ccc(N4CC[C@@H](F)C4)cc3)cc2C1=O]<br>3D | 1. 42%<br>2. $^1$H NMR (500 MHz, $CDCl_3$) δ 8.07 (s, 1H), 7.51 (d, 2H), 6.62 (d, 2H), 5.50-5.31 (m, 1H), 4.76 (s, 2H), 3.71-3.45 (m, 4H), 2.49-2.36 (m, 1H), 2.30-2.09 (m, 1H), 1.59 (s, 9H).<br>3. 387.3 |

Preparative Example 4

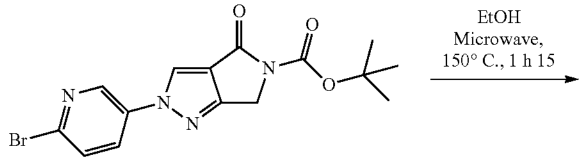

-continued

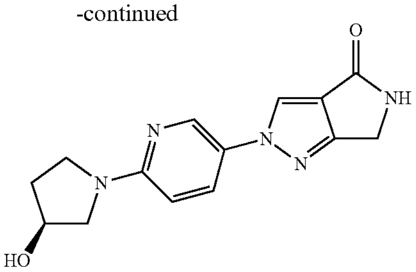

In a microwave vial, preparative example 1 (250 mg, 0.659 mmol) and (S)-pyrrolidin-3-ol (172 mg, 1.978 mmol) were mixed in ethanol (10 mL). The vial was irradiated at 150° C. for 30 minutes in the microwave. (S)-Pyrrolidin-3-ol (172 mg, 1.978 mmol) was again added and the reaction mixture was irradiated once again at 150° C. for 45 minutes. The reaction mixture was filtered and washed with ethanol to afford (S)-2-(6-(3-hydroxypyrrolidin-1-yl)pyridin-3-yl)-5,6-dihydropyrrolo[3,4-c]pyrazol-4(2H)-one as a white solid (83.5 mg, 44.4%). $^1$H NMR (80 MHz, DMSO-d6) δ=8.60 (s, 1H), 8.51 (d, 1H), 8.07 (s, 1H), 7.92 (dd, 1H), 6.56 (d, 1H), 4.97 (d, 1H), 4.34 (s, 3H), 3.69-3.37 (m, 4H), 2.24-1.80 (m, 2H). MS: 286.05 [M+H]$^+$ Preparative Example 5

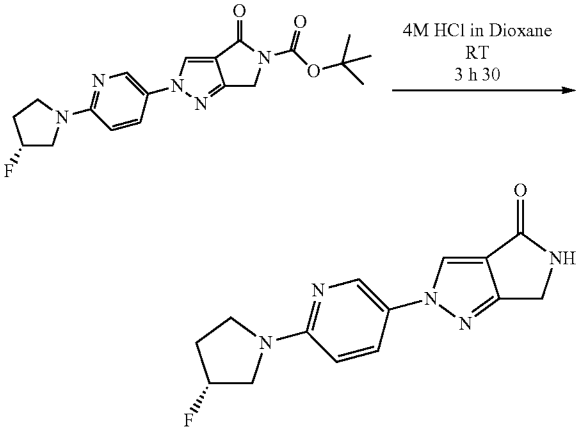

Preparative example 2 (160 mg, 0.413 mmol) was stirred in 4 M HCl in dioxane (10 mL) at RT for 3 h30. The solvent was evaporated under reduced pressure and the solid was dissolved in dichloromethane. A solution of saturated $NaHCO_3$ was added, and the aqueous phase extracted twice with dichloromethane. The combined organic layers were dried over $Na_2SO_4$, filtered and concentrated to dryness to afford (R)-2-(6-(3-fluoropyrrolidin-1-yl)pyridin-3-yl)-5,6-dihydropyrrolo[3,4-c]pyrazol-4(2H)-one as a white solid (101.5 mg, 86%). $^1$H NMR (80 MHz, DMSO-d6) δ=8.62 (s, 1H), 8.55 (d, 1H), 7.96 (dd, 1H), 6.63 (d, 1H), 5.75 (s, 1H), 4.34 (s, 2H), 3.92-3.37 (m, 4H), 2.45-1.78 (m, 2H). MS: 287.80 [M+H]+

Alternative Preparative Example 5

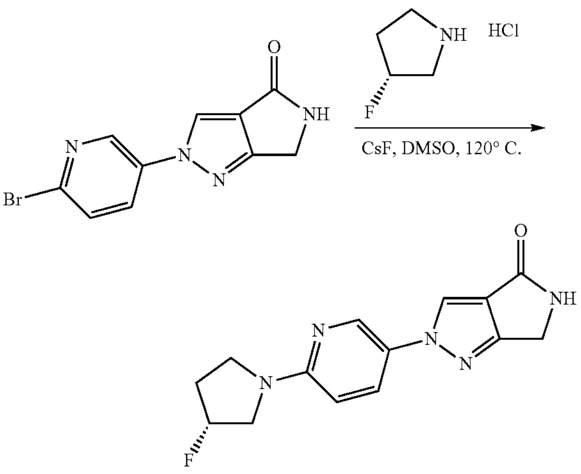

In a vial under argon, Preparative Example A (400 mg, 0.1.433 mmol), (R)-3-fluoropyrrolidine hydrochloride (720 mg, 5.73 mmol), and cesium fluoride (1306 mg, 8.60 mmol) were mixed in dry DMSO (4 mL). The reaction mixture was flushed with argon and stirred at 120° C. for 6 h 30 min. The reaction mixture was cooled down and poured into cold water (pre-cooled in an ice bath). The resulting solution was filtered, and the solid was rinsed with water. 1 mL of isopropanol was used to triturate the solid directly in the fritte, and the solid was dried to afford the product as a beige solid (287 mg, 0.998 mmol, 70%). $^1$H NMR (80 MHz, DMSO-d6) 8.63 (s, 1H), 8.55 (d, 1H), 8.15-7.79 (m, 2H), 6.64 (d, 1H), 5.46 (d, 1H), 4.34 (s, 2H), 3.96-3.40 (m, 4H), 2.28-1.56 (m, 2H). MS: 288.11 [M+H]$^+$ Alternative Preparative Examples 4 to 4K Following the SNAr procedure as described in alternative preparative example 5, using the appropriate amine indicated in Table 1 b below, the following preparative examples were prepared.

TABLE 1b

| Halogenated starting material | Amine | Preparative Example | 1. Yield<br>2. $^1$H-NMR<br>3. MH$^+$ (ESI) |
|---|---|---|---|
| 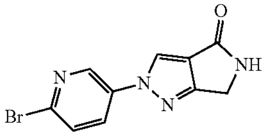 [SMILES: O=C1NCc2nn(-c3ccc(Br)nc3)cc21] | 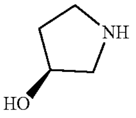 | 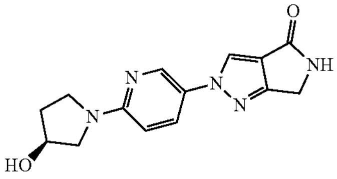 [SMILES: O=C1NCc2nn(-c3ccc(N4CC[C@H](O)C4)nc3)cc21]<br>4 | 1. 89%<br>2. $^1$H NMR (80 MHz, DMSO-d6) δ 8.56 (s, 1H), 8.47 (d, 1H), 8.04 (s, 1H), 7.87 (dd, 1H), 6.51 (d, 1H), 4.97 (s, 1H), 4.30 (s, 3H), 3.66-3.35 (m, 4H), 2.13-1.77 (m, 2H).<br>3. 286.08 |
| 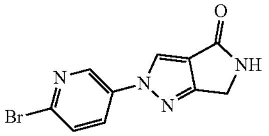 [SMILES: O=C1NCc2nn(-c3ccc(Br)nc3)cc21] | 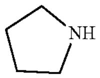 | 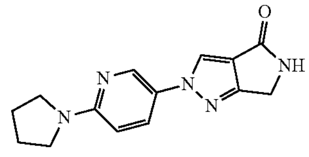 [SMILES: O=C1NCc2nn(-c3ccc(N4CCCC4)nc3)cc21]<br>4A | 1. 69%<br>2. $^1$H NMR (400 MHz, DMSO-d6) δ 8.60 (s, 1H), 8.51 (d, 1H), 8.08 (s, 1H), 7.91 (dd, 1H), 6.56 (d, 1H), 4.34 (d, 2H), 3.49-3.39 (m, 4H), 2.04-1.91 (m, 4H).<br>3. 270.19 |

TABLE 1b-continued

| Halogenated starting material | Amine | Preparative Example | 1. Yield<br>2. $^1$H-NMR<br>3. MH$^+$ (ESI) |
|---|---|---|---|
| 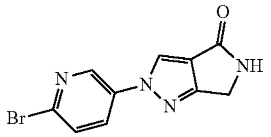 [SMILES: O=C1NCc2nn(-c3ccc(Br)nc3)cc21] | 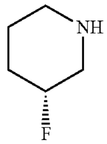 | 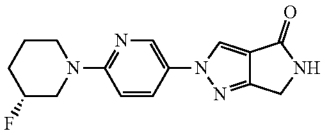 [SMILES: O=C1NCc2nn(-c3ccc(N4CCC[C@@H](F)C4)nc3)cc21]<br>4B | 1. 47%<br>2. $^1$H NMR (500 MHz, DMSO-d6) δ 8.65 (s, 1 H), 8.55 (d, 1H), 8.10 (s, 1H), 7.95 (dd, 1H), 7.01 (d, 1H), 4.92-4.66 (m, 1H), 4.34 (d, 2H), 3.90 (ddd, 1H), 3.82-3.65 (m, 2H), 3.44-3.37 (m, 1H), 2.02-1.72 (m, 3H), 1.61-1.47 (m, 1H).<br>3. 302.2 |
| 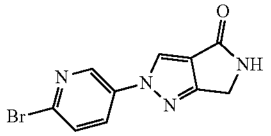 [SMILES: O=C1NCc2nn(-c3ccc(Br)nc3)cc21] | 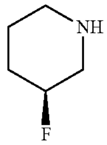 | 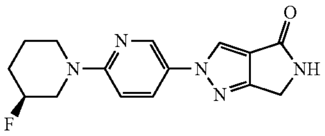 [SMILES: O=C1NCc2nn(-c3ccc(N4CCC[C@H](F)C4)nc3)cc21]<br>4C | 1. 74%<br>2. $^1$H NMR (400 MHz, DMSO-d6) δ 8.65 (s, 1H), 8.55 (dd, 1H), 8.10 (s, 1H), 7.95 (dd, 1H), 7.11-6.94 (m, 1H), 4.93-4.64 (m, 1H), 4.34 (s, 2H), 3.90 (ddd, 1H), 3.84-3.63 (m, 2H), 3.50-3.35 (m, 1H), 2.06-1.68 (m, 3H), 1.63-1.44 (m, 1H).<br>3. 302.2 |
| 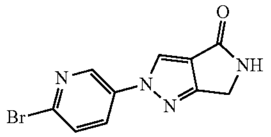 [SMILES: O=C1NCc2nn(-c3ccc(Br)nc3)cc21] | 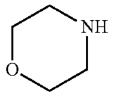 | 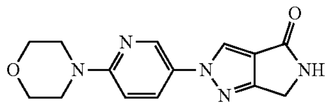 [SMILES: O=C1NCc2nn(-c3ccc(N4CCOCC4)nc3)cc21]<br>4D | 1. 58%<br>2. $^1$H NMR (500 MHz, DMSO-d6) δ 8.68 (s, 1H), 8.60 (d, 1H), 8.12 (s, 1H), 8.01 (dd, 1H), 6.99 (d, 1H), 4.35 (s, 2H), 3.71 (t, 4H), 3.50 (t, 4H).<br>3. 286.2 |
| 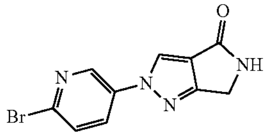 [SMILES: O=C1NCc2nn(-c3ccc(Br)nc3)cc21] | 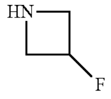 | 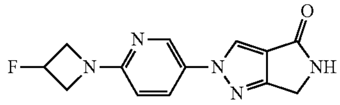 [SMILES: O=C1NCc2nn(-c3ccc(N4CC(F)C4)nc3)cc21]<br>4E | 1. 52%<br>2. $^1$H NMR (500 MHz, DMSO-d6) δ 8.63 (s, 1H), 8.53 (d, 1H), 8.08 (s, 1H), 7.96 (dd, 1H), 6.57 (d, 1H), 5.64-5.33 (m, 1H), 4.49-4.17 (m, 5H), 4.14-3.91 (m, 2H).<br>3. 274.3 |
| 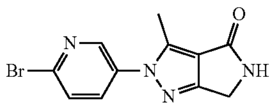 [SMILES: Cc1c2c(nn1-c1ccc(Br)nc1)CNC2=O] | 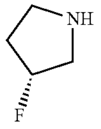 | 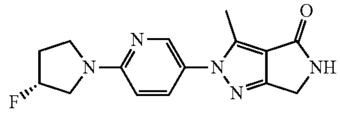<br>4F | 1. 76%<br>2. $^1$H NMR (400 MHz, DMSO-d6) δ 8.24 (d, 1H), 7.94 (s, 1H), 7.69 (dd, 1H), 6.63 (d, 1H), 5.61-5.35 (m, 1H), 4.25 (s, 2H), 3.88-3.57 (m, 3H), 3.47 (td, 1H), 2.41-2.10 (m, 5H).<br>3. 302.3 |
| 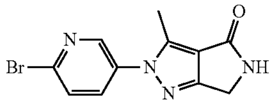 | 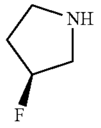 | 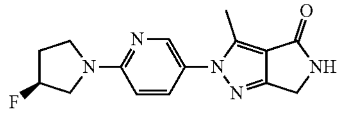 [SMILES: Cc1c2c(nn1-c1ccc(N3CC[C@H](F)C3)nc1)CNC2=O]<br>4G | 1. 60%<br>2. $^1$H NMR (500 MHz, DMSO-d6) δ 8.20 (dd, 1H), 7.89 (s, 1H), 7.65 (dd, 1H), 6.59 (dd, 1H), 5.56-5.31 (m, 1H), 4.22 (d, 2H), 3.84-3.53 (m, 3H), 3.44 (td, 1H), 2.37-2.03 (m, 5H).<br>3. 302.2 |
| 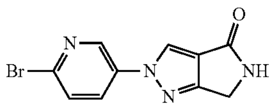 [SMILES: O=C1NCc2nn(-c3ccc(Br)nc3)cc21] | 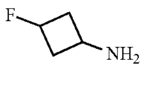 | 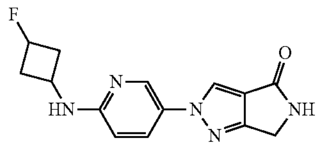 [SMILES: O=C1NCc2nn(-c3ccc(NC4CC(F)C4)nc3)cc21]<br>4H | 1. 23%<br>2. $^1$H NMR (500 MHz, DMSO-d6) δ 8.57 (s, 1H), 8.43 (d, 1H), 8.08 (s, 1H), 7.83 (dd, 1H), 7.22 (d, 1H), 6.55 (dd, 1H), 5.36-5.12 (m, 1H), 4.47-4.36 (m, 1H), 4.33 (s, 2H), 2.63-2.51 (m, 2H), 2.40-2.22 (m, 2H).<br>3. 288.4 |

TABLE 1b-continued

| Halogenated starting material | Amine | Preparative Example | 1. Yield<br>2. $^1$H-NMR<br>3. $MH^+$ (ESI) |
|---|---|---|---|
| 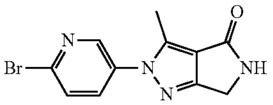 | 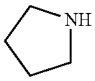 | 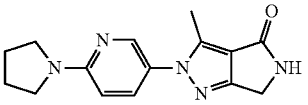 [SMILES: Cc1c2c(nn1-c1ccc(N3CCCC3)nc1)CNC2=O]<br>4I | 1. 91%<br>2. ND.<br>3. 284.2 |
| 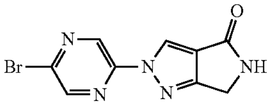 | 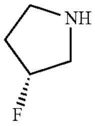 | 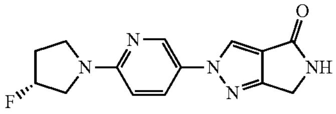 [SMILES: O=C1NCc2nn(-c3ccc(N4CC[C@@H](F)C4)nc3)cc21]<br>4J | 1. 49%<br>2. $^1$H NMR (400 MHz, DMSO-d6) δ 8.65 (d, 1H), 8.61 (s, 1H), 8.17 (s, 1H), 7.93 (d, 1H), 5.64-5.38 (m, 1H), 4.38 (s, 2H), 3.90-3.60 (m, 3H), 3.53 (td, 1H), 2.40-2.10 (m, 2H).<br>3. 289.2 |
| 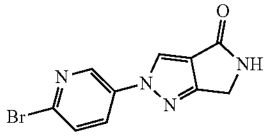 [SMILES: O=C1NCc2nn(-c3ccc(Br)nc3)cc21] | 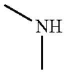 | 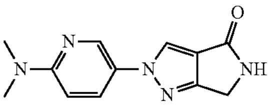 [SMILES: CN(C)c1ccc(-n2cc3c(n2)CNC3=O)cn1]<br>4K | 1. 91%<br>2. $^1$H NMR (400 MHz, DMSO-d6) δ 8.62 (s, 1H), 8.56-8.51 (m, 1H), 8.08 (s, 1H), 7.93 (dd, 1H), 6.77 (d, 1H), 4.34 (d, 2H), 3.07 (s, 6H).<br>3. 244.3 |

Preparative Examples 6 to 6D

Following the deprotection procedure of preparative example 5, the following preparative examples were prepared.

TABLE 2

| Starting material | Preparative Example | 1. Yield<br>2. $^1$H-NMR<br>3. $MH^+$ (ESI) |
|---|---|---|
| 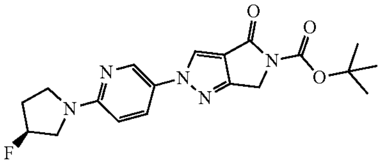 [SMILES: CC(C)(C)OC(=O)N1Cc2nn(-c3ccc(N4CC[C@H](F)C4)nc3)cc2C1=O] | 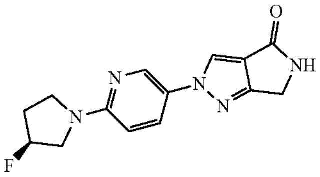 [SMILES: O=C1NCc2nn(-c3ccc(N4CC[C@H](F)C4)nc3)cc21]<br>6 | 1. 96%<br>2. $^1$H NMR (80 MHz, DMSO-d6) δ = 8.63 (s, 1H), 8.56 (d, 1H), 8.14-7.82 (m, 1H), 7.34 (s, 1H), 6.64 (d, 1H), 5.45 (d, 1H), 4.35 (s, 2H), 3.99-3.39 (m, 4H), 2.21-1.39 (m, 2H).<br>3. 287.79 |
| 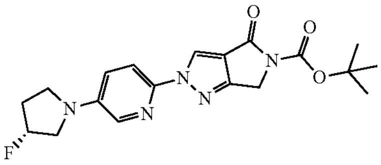 [SMILES: CC(C)(C)OC(=O)N1Cc2nn(-c3ccc(N4CC[C@@H](F)C4)cn3)cc2C1=O] | 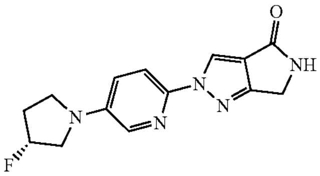 [SMILES: O=C1NCc2nn(-c3ccc(N4CC[C@@H](F)C4)cn3)cc21]<br>6A | 1. 84%<br>2. $^1$H NMR (500 MHz, DMSO-D6) δ 8.63 (s, 1H), 8.14 (s, 1H), 7.85 (d, 1H), 7.76 (d, 1H), 7.21 (dd, 1H), 5.58-5.41 (m, 1H), 4.36 (d, 2H), 3.68-3.46 (m, 3H), 3.46-3.37 (m, 1H), 2.34-2.07 (m, 2H).<br>3. 288.2 |
| 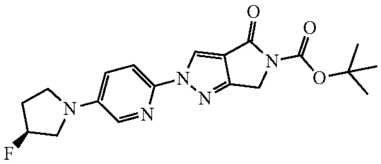 [SMILES: CC(C)(C)OC(=O)N1Cc2nn(-c3ccc(N4CC[C@H](F)C4)cn3)cc2C1=O] | 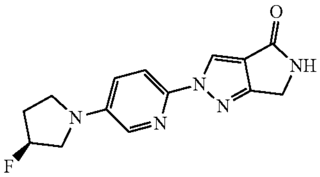 [SMILES: O=C1NCc2nn(-c3ccc(N4CC[C@H](F)C4)cn3)cc21]<br>6B | 1. 72%<br>2. $^1$H NMR (500 MHz, DMSO-d6) δ 8.63 (s, 1H), 8.13 (s, 1H), 7.85 (d, 1H), 7.76 (d, 1H), 7.21 (dd, 1H), 5.62-5.39 (m, 1H), 4.36 (s, 2H), 3.76-3.39 (m, 4H), 2.35-2.06 (m, 2H).<br>3. 288.2 |

TABLE 2-continued

| Starting material | Preparative Example | 1. Yield<br>2. $^1$H-NMR<br>3. MH$^+$ (ESI) |
|---|---|---|
| 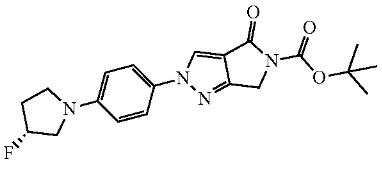 [SMILES: CC(C)(C)OC(=O)N1Cc2nn(-c3ccc(N4CC[C@@H](F)C4)cc3)cc2C1=O] | 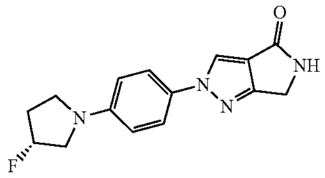 [SMILES: O=C1NCc2nn(-c3ccc(N4CC[C@@H](F)C4)cc3)cc21]<br>6C | 1. 90%<br>2. $^1$H NMR (500 MHz, CF3COOD) δ 8.71 (d, 1H), 8.20 (dd, 2H), 8.12 (dd, 2H), 6.03-5.78 (m, 1H), 5.08 (d, 2H), 4.80-4.52 (m, 2H), 4.52-4.32 (m, 2H), 3.13-2.76 (m, 2H).<br>3. 287.2 |
| 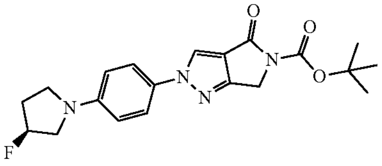 [SMILES: CC(C)(C)OC(=O)N1Cc2nn(-c3ccc(N4CC[C@H](F)C4)cc3)cc2C1=O] | 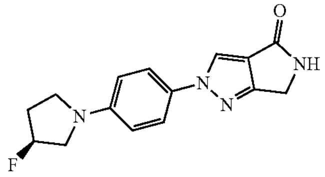 [SMILES: O=C1NCc2nn(-c3ccc(N4CC[C@H](F)C4)cc3)cc21]<br>6D | 1. 94%<br>2. $^1$H NMR (400 MHz, DMSO-d6) δ 8.61 (s, 1 H), 8.06 (s, 1 H), 7.73-7.58 (m, 2H), 6.76-6.54 (m, 2H), 5.60-5.34 (m, 1H), 4.33 (d, 2H), 3.67-3.34 (m, 4H), 2.39-2.03 (m, 2H).<br>3. 287.2 |

Preparative Example 7

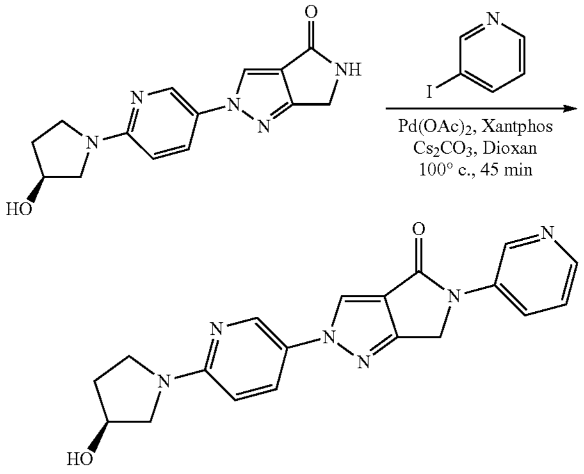

In a vial under argon, palladium (II) acetate (13.14 mg, 0.059 mmol) and xantphos (50.8 mg, 0.088 mmol) were mixed in 1,4-dioxane (3 mL), degassed with argon and heated at 100° C. for a few seconds on a pre-heated block to form the pd-xantphos complex. Then, preparative example 4 (83.5 mg, 0.293 mmol), 3-iodopyridine (66.0 mg, 0.322 mmol) and cesium carbonate (286 mg, 0.878 mmol) were added, the mixture was degassed with argon and heated at 100° C. for 45 min. The reaction mixture was filtered and washed with ethyl acetate. The filtrate was recovered, and evaporated to obtain the product as a yellow gum-solid (134.5 mg, 0.371 mmol, quantitative). $^1$H NMR (80 MHz, DMSO-d6) δ=9.04 (d, 1H), 8.83 (s, 1H), 8.57 (d, 1H), 8.43-8.13 (m, 2H), 7.96 (dd, 1H), 7.44 (dd, 1H), 6.58 (d, 1H), 5.08 (s, 2H), 4.99 (d, 1H), 4.42 (d, 1H), 3.64-3.40 (m, 4H), 2.17-1.75 (m, 2H). MS: 363.08 [M+H]$^+$

Preparative Example 8

Following the Pd-coupling procedure as described in preparative example 7, using the amide starting material and the appropriate halogenated heteroaryl indicated in Table 3 below, the following preparative example was prepared.

TABLE 3

| Amide | halogenated heteroaryl | Preparative Example | 1. Yield<br>2. $^1$H-NMR<br>3. MH$^+$ (ESI) |
|---|---|---|---|
| 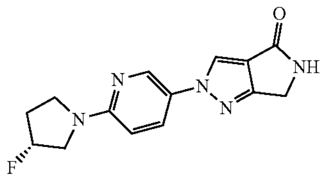 [SMILES: O=C1NCc2nn(-c3ccc(N4CC[C@@H](F)C4)nc3)cc21] | 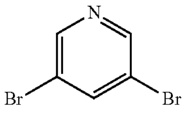 | 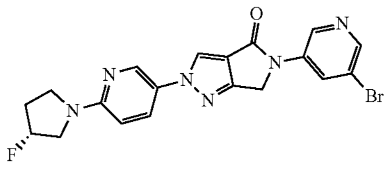 [SMILES: O=C1c2cn(-c3ccc(N4CC[C@@H](F)C4)nc3)nc2CN1c1cncc(Br)c1]<br>8 | 1. 63%<br>2. $^1$H NMR (80 MHz, $CDCl_3$) δ = 8.78 (d, 1H), 8.60 (t, 1H), 8.51 (d, 1H), 8.43 (d, 1H), 8.20 (s, 1H), 7.95 (dd, 1H), 6.62 (d, 1H), 5.35 (d, 1H), 4.88 (s, 2H), 4.07 (s, 1H), 3.97-3.56 (m, 3H),<br>2.67-2.28 (m, 2H).<br>3. 444.01 |

Preparative Example 9

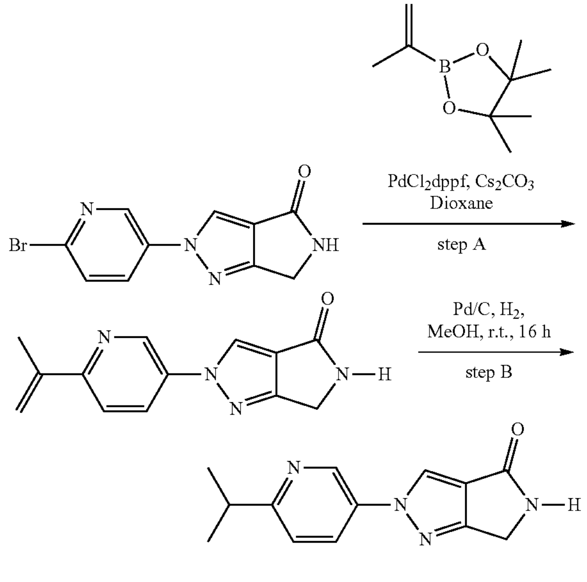

Step A

Under argon atmosphere to a solution of 2-(6-bromopyridin-3-yl)-5,6-dihydropyrrolo[3,4-c]pyrazol-4(2H)-one (0.5 g, 1.79 mol) in dioxane (20 ml) was added 4,4,5,5-tetramethyl-2-(prop-1-en-2-yl)-1,3,2-dioxaborolane (0.451 g, 2.7 mmol), [(dppf)PdCl2] (146 mg, 0.179 mmol) and $Cs_2CO_3$ (1.16 g, 3.58 mmol) in $H_2O$ (0.2 ml). The mixture was heated at 80° C. for 2 h. The mixture was cooled, the solvent was evaporated under a high vacuum. The residue was dissolved in ethyl acetate and solid filtered. The filter residue was washed with water, and dried to obtain product 0.450 g. MS: 241.1 $[M+H]^+$ Step B To a solution of 2-(6-(prop-1-en-2-yl)pyridin-3-yl)-5,6-dihydropyrrolo[3,4-c]pyrazol-4(2H)-one (1 g, 4.16 mmol) in MeOH (75 mL) was added Pd/C (100 mg, 5%). The mixture was stirred at room temperature for 12 hours under $H_2$ (15 psi). Upon completion, the reaction slurry was filtered and the filtrate was concentrated to give 2-(6-(propan-2-yl)pyridin-3-yl)-5,6-dihydropyrrolo[3,4-c]pyrazol-4(2H)-one (0.85 g). MS: 243.2 $[M+H]^+$ Preparative Example 10

Following the procedure as described in alternative preparative example 9, using the appropriate boronic ester indicated in Table 3b below, the following preparative example was prepared.

TABLE 3b

| Halogenated starting material | Boronic ester | Preparative Example | $MH^+$ (ESI) |
|---|---|---|---|
| 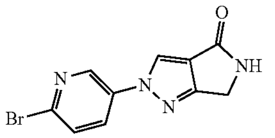 [SMILES: O=C1NCc2nn(-c3ccc(Br)nc3)cc21] | 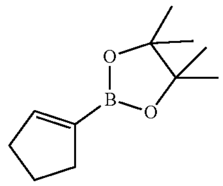 | 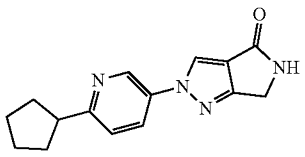 [SMILES: O=C1NCc2nn(-c3ccc(C4CCCC4)nc3)cc21]<br>1B | 269.2 |

Preparative Example 11

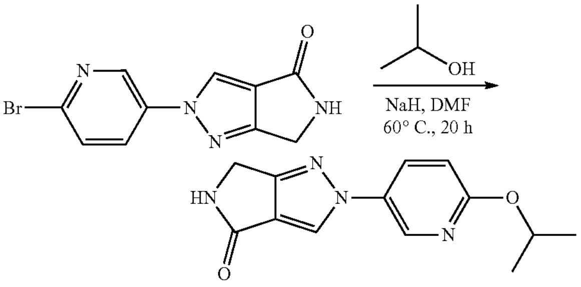

2-Propanol (50 μL, 0.7176 mmol) in 0.4 mL DMF was added to a suspension of sodium hydride (36 mg/60% in mineral oil, 0.9 mmol) in 2 mL DMF at RT. The mixture was stirred for 30 minutes, then added to a stirred solution of 2-(6-bromopyridin-3-yl)-5,6-dihydropyrrolo[3,4-c]pyrazol-4(2H)-one (100 mg, 0.358 mmol) in 2 mL DMF at 60° C. The reaction mixture was heated at 60° C. for 20 hours. After cooling to RT, water and ethyl acetate were added and the layers were separated. The aqueous layer was extracted with ethyl acetate and the organics were combined, dried over $MgSO_4$, filtered, and concentrated under reduced pressure to provide 2-(6-isopropoxypyridin-3-yl)-5,6-dihydropyrrolo[3,4-c]pyrazol-4(2H)-one (0.16 g, 35%): MS: 259.2 $[M+H]^+$ Preparative Example 12

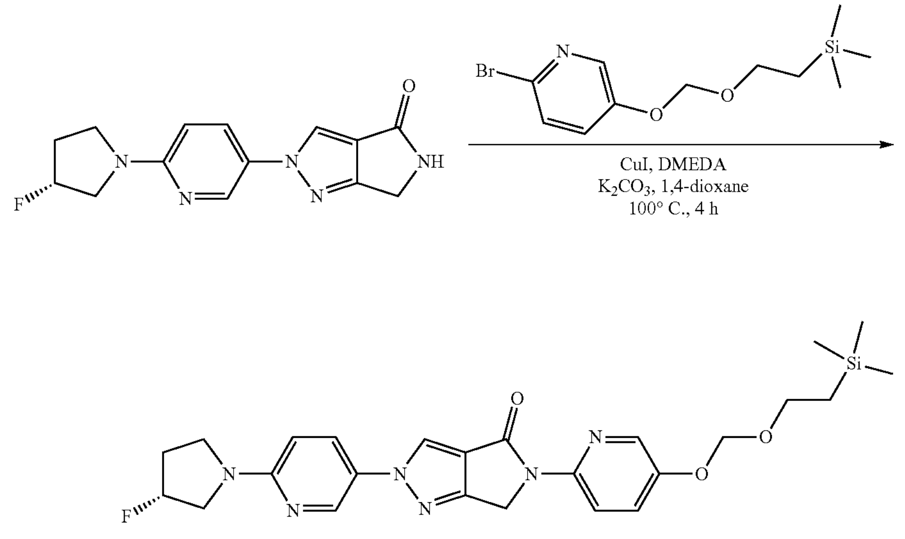

In a seal tube under nitrogen, (R)-2-(6-(3-fluoropyrrolidin-1-yl)pyridin-3-yl)-5,6-dihydropyrrolo[3,4-c]pyrazol-4(2H)-one (120 mg, 0.417 mmol), 2-bromo-5-((2-(trimethylsilyl)ethoxy)methoxy)pyridine (253 mg, 0.835 mmol), copper(I)-iodide (16 mg, 0.0835 mmol) and potassium carbonate (115 mg, 0.835 mmol) were charged and the system was flushed with nitrogen. 1,4-Dioxane (6 mL) and N,N'-dimethylethylenediamine (0.017 mL, 0.167 mmol) were added and the mixture was stirred at 100° C. for 4 h. The reaction mixture was concentrated under reduced pressure and the residue was dissolved in 10 ml of water, and extracted with DCM/MeOH (9:1, 50 ml×2). The combined organic layers were dried over $NaSO_4$ (5 g), filtered, and concentrated to obtain 80 mg of a pale yellow solid crude. The crude was purified by column chromatography on basic silica gel (100-200 mesh) using a dichloromethane/methanol gradient (100/0→98/2) to afford the desired product as a pale yellow solid (50 mg, 23% yield). $^1H$ NMR (400 MHz, DMSO-d6) δ 8.86 (s, 1H), 8.60 (d, 1H), 8.42-8.33 (m, 1H), 8.18 (dd, 1H), 8.01 (dd, 1H), 7.58 (dd, 1H), 6.66 (d, 1H), 5.54 (s, 1H), 5.28 (s, 2H), 5.05 (s, 2H), 3.85-3.54 (m, 5H), 3.54-3.42 (m, 1H), 2.39-2.08 (m, 2H), 0.90 (dd, 2H), −0.01 (s, 9H). MS: 511.3 $[M+H]^+$ Preparative Examples 13 to 31

Following the Cu-coupling procedure as described in preparative example 12, using the amide starting material and the appropriate halogenated heteroaryl indicated in Table 3c below, the following preparative examples were prepared.

TABLE 3c

| Amide | halogenated heteroaryl | Preparative Example | 1. Yield<br>2. $^1H$-NMR<br>3. $MH^+$ (ESI) |
|---|---|---|---|
| 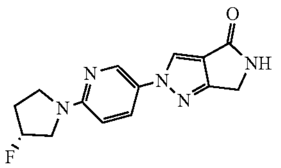 [SMILES: O=C1NCc2nn(-c3ccc(N4CC[C@@H](F)C4)nc3)cc21] | 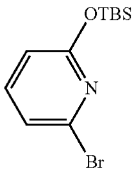 [SMILES: CC(C)(C)[Si](C)(C)Oc1cccc(Br)n1] | 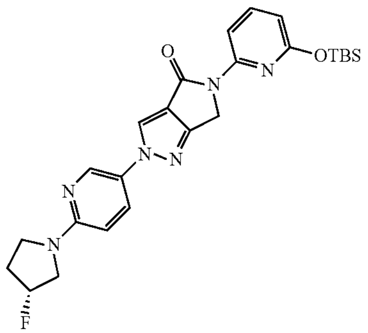 [SMILES: CC(C)(C)[Si](C)(C)Oc1cccc(N2Cc3nn(-c4ccc(N5CC[C@@H](F)C5)nc4)cc3C2=O)n1] | 1. crude<br>2. ND<br>3. ND |

TABLE 3c-continued
| Amide | halogenated heteroaryl | Preparative Example | 1. Yield<br>2. $^{1}$H-NMR<br>3. $MH^{+}$ (ESI) |
|---|---|---|---|
| 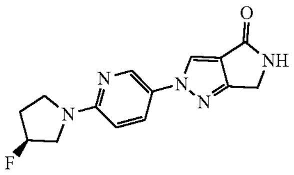 [SMILES: O=C1NCc2nn(-c3ccc(N4CC[C@H](F)C4)nc3)cc21] | 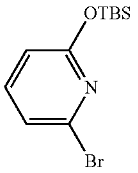 [SMILES: CC(C)(C)[Si](C)(C)Oc1cccc(Br)n1] | 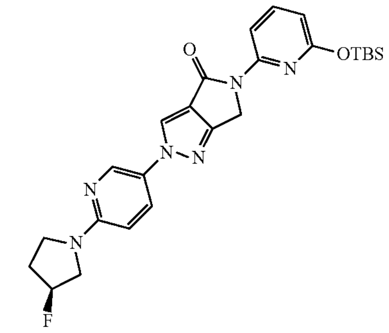 [SMILES: CC(C)(C)[Si](C)(C)Oc1cccc(N2Cc3nn(-c4ccc(N5CC[C@H](F)C5)nc4)cc3C2=O)n1]<br>14 | 1. crude<br>2. ND<br>3. ND |
| 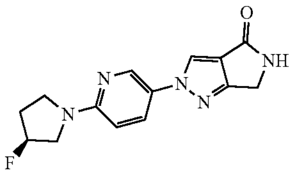 [SMILES: O=C1NCc2nn(-c3ccc(N4CC[C@H](F)C4)nc3)cc21] | 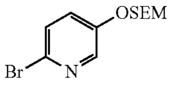 | 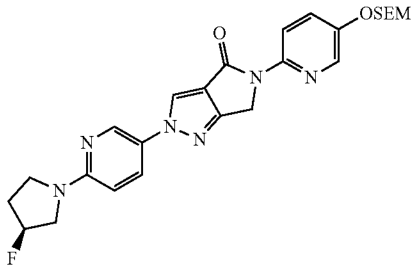<br>15 | 1. 31%<br>2. $^{1}$H-NMR (500 MHz, DMSO-d6) δ 8.85 (s, 1H), 8.57 (d, 1H), 8.21 (d, 1H), 8.09 (d, 1H), 7.98 (dd, 1H), 6.79 (dd, 1H), 6.63 (d, 1H), 5.56-5.34 (m, 1H), 5.31 (s, 2H), 5.03 (s, 2H), 3.86-3.52 (m, 5H), 3.52-3.36 (m, 1H), 2.31-2.02 (m, 2H), 0.87 (t, 2H), −0.06 (s, 9H).<br>3. 511.4 |
| 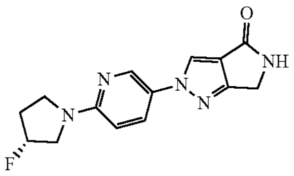 [SMILES: O=C1NCc2nn(-c3ccc(N4CC[C@@H](F)C4)nc3)cc21] | 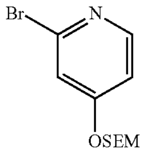 | 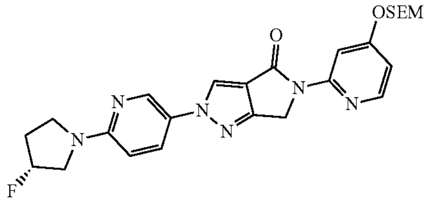<br>16 | 1. 35%<br>2. $^{1}$H-NMR (500 MHz, DMSO-d6) δ 8.81 (s, 1H), 8.61-8.56 (m, 1H), 8.16 (dd, 1H), 7.99 (dd, 1H), 7.87 (dd, 1H), 7.15 (dd, 1H), 6.67 (d, 1H), 5.57 (s, 2H), 5.55-5.39 (m, 1H), 4.86 (s, 2H), 3.88-3.58 (m, 5H), 3.48 (td, 1H), 2.36-2.10 (m, 2H), 0.97-0.75 (m, 2H), −0.09 (s, 9H).<br>3. 511.2 |
| 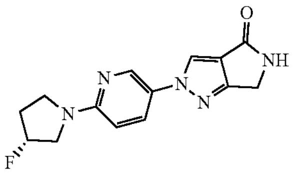 [SMILES: O=C1NCc2nn(-c3ccc(N4CC[C@@H](F)C4)nc3)cc21] | 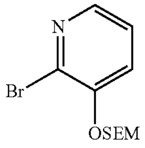 | 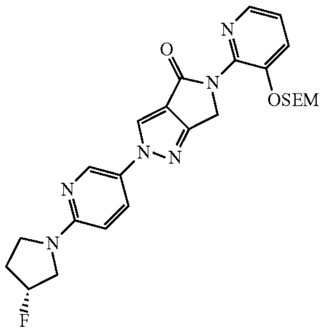<br>17 | 1. 32%<br>2. $^{1}$H-NMR (500 MHz, DMSO-d6) δ 8.80 (s, 1H), 8.59 (d, 1H), 8.16 (dd, 1H), 8.00 (dd, 1H), 7.68 (dd, 1H), 7.39 (dd, 1H), 6.67 (d, 1H), 5.56-5.38 (m, 1H), 5.29 (s, 2H), 4.92 (s, 2H), 3.86-3.58 (m, 5H), 3.48 (td, 1H), 2.35-2.08 (m, 2H), 0.95-0.79 (m, 2H), −0.07 (s, 9H).<br>3. 511.4 |

TABLE 3c-continued

| Amide | halogenated heteroaryl | Preparative Example | 1. Yield<br>2. $^1$H-NMR<br>3. $MH^+$ (ESI) |
|---|---|---|---|
| 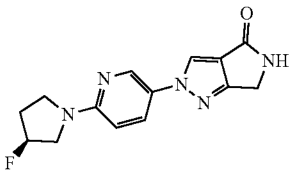 [SMILES: O=C1NCc2nn(-c3ccc(N4CC[C@H](F)C4)nc3)cc21] | 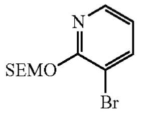 | 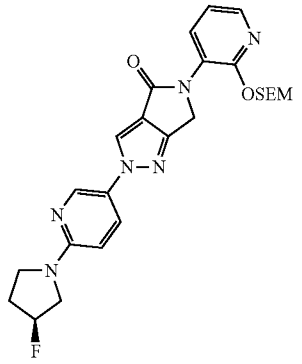<br>18 | 1. 37%<br>2. $^1$H-NMR (400 MHz, DMSO-d6) δ 8.82 (s, 1H), 8.58 (d, 1H), 8.16 (dd, 1H), 7.99 (dd, 1H), 7.87 (dd, 1H), 7.15 (dd, 1H), 6.67 (d, 1H), 5.57 (s, 2H), 5.56-5.33 (m, 1H), 4.86 (s, 2H), 3.86-3.54 (m, 5H), 3.48 (td, 1H), 2.36-2.11 (m, 2H), 0.91-0.75 (m, 2H), −0.10 (s, 9H).<br>3. 511.1 |
| 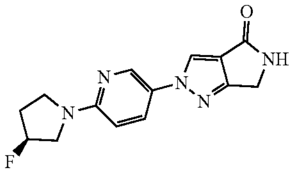 [SMILES: O=C1NCc2nn(-c3ccc(N4CC[C@H](F)C4)nc3)cc21] | 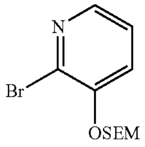 | 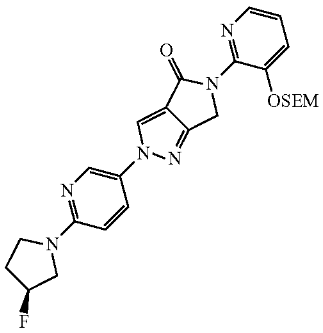<br>19 | 1. 37%<br>2. $^1$H-NMR (500 MHz, DMSO-d6) δ 7.98 (s, 1H), 7.77 (dd, 1H), 7.34 (dd, 1H), 7.19 (dd, 1H), 6.87 (dd, 1H), 6.57 (dd, 1H), 5.85 (d, 1H), 4.75-4.56 (m, 1H), 4.47 (s, 2H), 4.10 (s, 2H), 3.06-2.76 (m, 5H), 2.66 (td, 1H), 1.53-1.30 (m, 2H), 0.09--0.04 (m, 2H), −0.89 (s, 9H).<br>3. 511.4 |
| 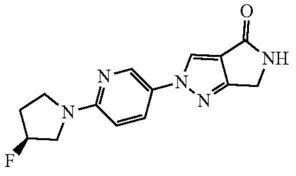 [SMILES: O=C1NCc2nn(-c3ccc(N4CC[C@H](F)C4)nc3)cc21] | 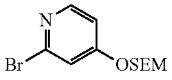 | 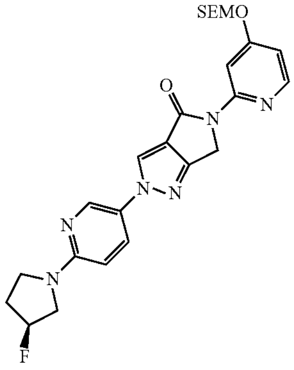<br>20 | 1. 56%<br>2. $^1$H-NMR (500 MHz, DMSO-d6) δ 8.88 (s, 1H), 8.60 (d, 1H), 8.24 (d, 1H), 8.13 (d, 1H), 8.02 (dd, 1H), 6.83 (dd, 1H), 6.67 (d, 1H), 5.57-5.41 (m, 1H), 5.35 (s, 2H), 5.06 (s, 2H), 3.87-3.57 (m, 5H), 3.57-3.42 (m, 1H), 2.36-2.09 (m, 2H), 0.91 (t, 2H), −0.02 (s, 9H).<br>3. 511.4 |
| 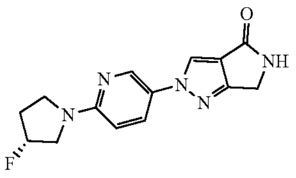 [SMILES: O=C1NCc2nn(-c3ccc(N4CC[C@@H](F)C4)nc3)cc21] | 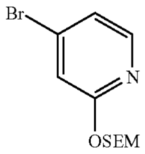 | 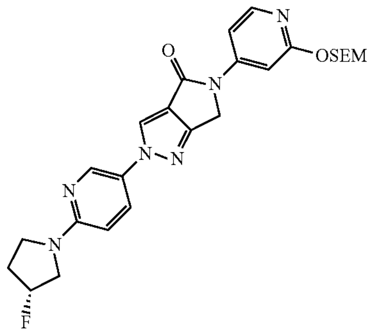<br>21 | 1. 37%<br>2. $^1$H-NMR (500 MHz, DMSO-d6) δ 8.86 (s, 1H), 8.56 (d, 1H), 7.97 (dd, 1H), 7.64 (d, 1H), 7.18 (dd, 1H), 6.63 (d, 1H), 6.48 (d, 1H), 5.53-5.32 (m, 1H), 5.19 (s, 2H), 4.93 (s, 2H), 3.84-3.49 (m, 5H), 3.49-3.34 (m, 1H), 2.30-2.04 (m, 2H), 0.87-0.80 (m, 2H), −0.06 (s, 9H).<br>3. 511.3 |

TABLE 3c-continued
| Amide | halogenated heteroaryl | Preparative Example | 1. Yield<br>2. $^{1}$H-NMR<br>3. $MH^{+}$ (ESI) |
| --- | --- | --- | --- |
| 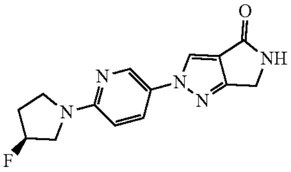 [SMILES: O=C1NCc2nn(-c3ccc(N4CC[C@H](F)C4)nc3)cc21] | 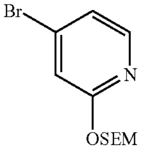 | 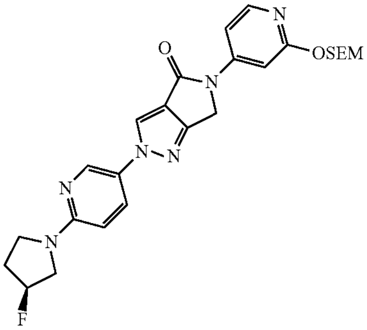<br>22 | 1. 25%<br>2. $^{1}$H-NMR (500 MHz, DMSO-d6) δ 8.86 (s, 1H), 8.56 (d, 1H), 7.97 (dd, 1H), 7.64 (d, 1H), 7.18 (dd, 1H), 6.63 (d, 1H), 6.48 (d, 1H), 5.50-5.34 (m, 1H), 5.19 (s, 2H), 4.93 (s, 2H), 3.75-3.50 (m, 5H), 3.48-3.39 (m, 1H), 2.31-2.04 (m, 2H), 0.89-0.81 (m, 2H), −0.06 (s, 9H).<br>3. 511.4 |
| 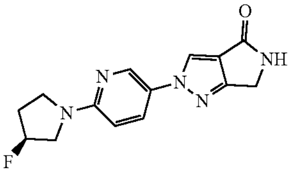 [SMILES: O=C1NCc2nn(-c3ccc(N4CC[C@H](F)C4)nc3)cc21] | 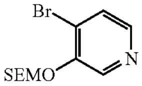 | 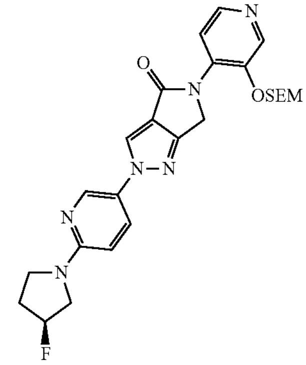<br>23 | 1. 39%<br>2. ND<br>3. 511.4 |
| 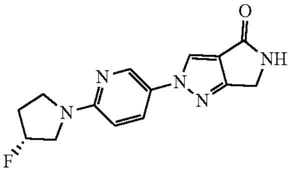 [SMILES: O=C1NCc2nn(-c3ccc(N4CC[C@@H](F)C4)nc3)cc21] | 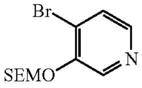 | 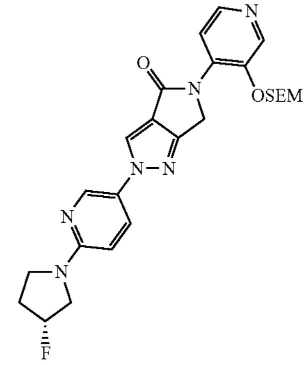<br>24 | 1. 28%<br>2. ND<br>3. 511.4 |
| 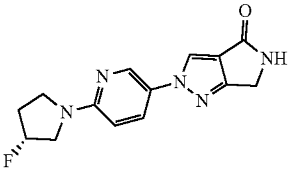 [SMILES: O=C1NCc2nn(-c3ccc(N4CC[C@@H](F)C4)nc3)cc21] | 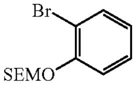 | 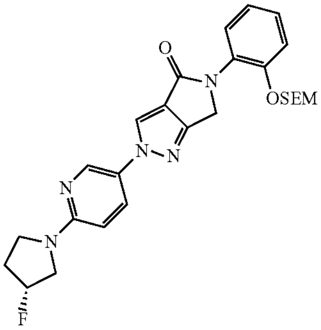 | 1. 28%<br>2. $^{1}$H-NMR (400 MHz, DMSO-d6) δ 8.78 (s, 1H), 8.58 (dd, 1H), 7.99 (dd, 1H), 7.40 (dd, 1H), 7.33 (ddd, 1H), 7.24 (dd, 1H), 7.07 (td, 1H),6.68 (s, 1H), 5.58-5.37 (m, 1H), 5.25 (s, 2H), 4.81 (s, 2H), 3.85-3.57 (m, 5H), 3.48 (td, 1H), 2.37-2.04 (m, 2H), 0.90-0.77 (m, 2H), −0.08 (s, 9H).<br>3. 510.4 |

TABLE 3c-continued
| Amide | halogenated heteroaryl | Preparative Example | 1. Yield<br>2. $^1$H-NMR<br>3. $MH^+$ (ESI) |
|---|---|---|---|
| | | 25 | |
| 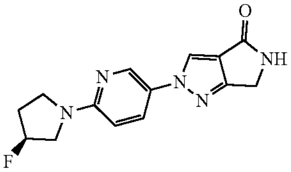 [SMILES: O=C1NCc2nn(-c3ccc(N4CC[C@H](F)C4)nc3)cc21] | 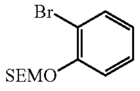 | 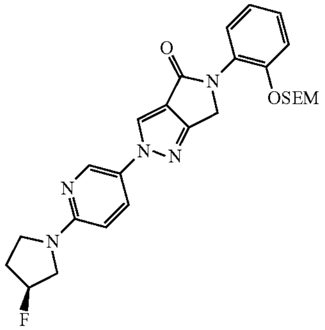<br>26 | 1. 46%<br>2. $^1$H-NMR (400 MHz, DMSO-d6) δ 8.78 (s, 1H), 8.58 (dd, 1H), 7.99 (dd, 1H), 7.40 (dd, 1H), 7.33 (ddd, 1H), 7.24 (dd, 1H), 7.07 (td, 1H), 6.74-6.61 (m, 1H), 5.60-5.34 (m, 1H), 5.25 (s, 2H), 4.81 (s, 2H), 3.86-3.55 (m, 5H), 3.48 (td, 1H), 2.38-2.08 (m, 2H), 0.90-0.79 (m, 2H), −0.08 (s, 9H).<br>3. 510.3 |
| 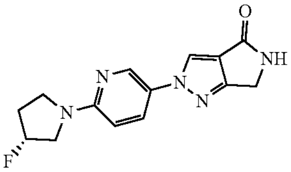 [SMILES: O=C1NCc2nn(-c3ccc(N4CC[C@@H](F)C4)nc3)cc21] | 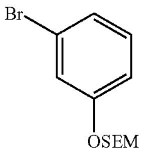 | 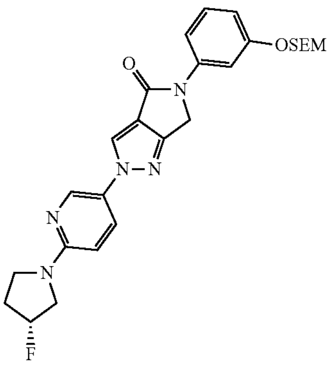<br>27 | 1. 28%<br>2. $^1$H-NMR (500 MHz, DMSO-d6) δ 8.82 (s, 1H), 8.60 (d, 1H), 8.04-7.94 (m, 1H), 7.58 (s, 1H), 7.46-7.35 (m, 1H), 7.31 (t, 1H), 6.90-6.73 (m, 1H), 6.67 (d, 1H), 5.57-5.32 (m, 1H), 5.25 (s, 2H), 5.00 (s, 2H), 3.87-3.54 (m, 5H), 3.54-3.42 (m, 1H), 2.37-2.08 (m, 2H), 0.91 (t, 2H), −0.01 (d, 10H).<br>3. 510.3 |
| 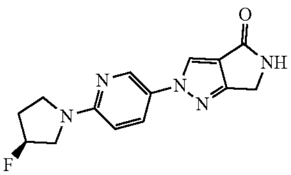 [SMILES: O=C1NCc2nn(-c3ccc(N4CC[C@H](F)C4)nc3)cc21] | 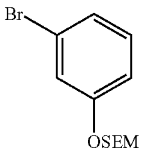 | 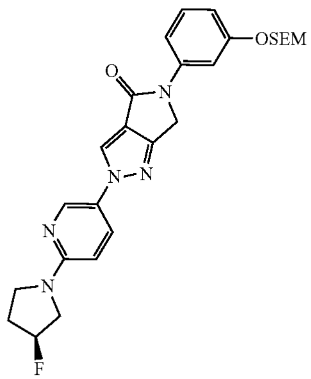<br>28 | 1. 46%<br>2. $^1$H-NMR (500 MHz, DMSO-d6) δ 8.82 (s, 1H), 8.60 (dd, 1H), 8.01 (dd, 1H), 7.58 (t, 1H), 7.40 (ddd, 1H), 7.31 (t, 1H), 6.82 (ddd, 1H), 6.67 (dd, 1H), 5.59-5.37 (m, 1H), 5.25 (s, 2H), 5.00 (s, 2H), 3.86-3.57 (m, 5H), 3.47 (td, 1H), 2.36-2.11 (m, 2H), 0.96-0.86 (m, 2H), −0.01 (s, 9H).<br>3. 510.3 |

TABLE 3c-continued
| Amide | halogenated heteroaryl | Preparative Example | 1. Yield<br>2. $^1$H-NMR<br>3. $MH^+$ (ESI) |
|---|---|---|---|
| 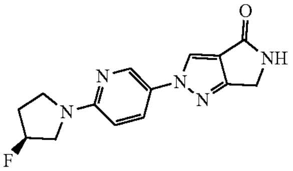 [SMILES: O=C1NCc2nn(-c3ccc(N4CC[C@H](F)C4)nc3)cc21] | 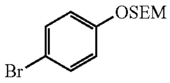 | 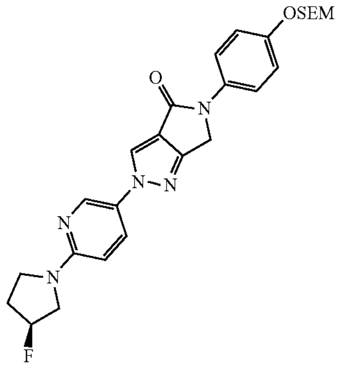<br>29 | 1. 47%<br>2. $^1$H-NMR (400 MHz, DMSO-d6) δ 8.79 (s, 1H), 8.63-8.57 (m, 1H), 8.00 (dd, 1H), 7.70 (d, 2H), 7.06 (d, 2H), 6.66 (d, 1H), 5.57-5.34 (m, 1H), 5.23 (s, 2H), 4.98 (s, 2H), 3.85-3.54 (m, 5H), 3.47 (td, 1H), 2.37-2.05 (m, 2H), 0.96-0.86 (m, 2H), −0.01 (s, 9H).<br>3. 510.5 |
| 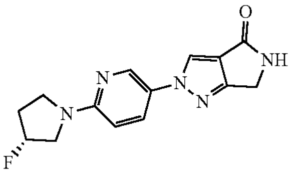 [SMILES: O=C1NCc2nn(-c3ccc(N4CC[C@@H](F)C4)nc3)cc21] | 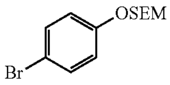 | 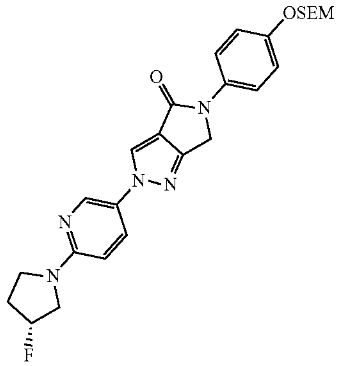<br>30 | 1. 18%<br>2. $^1$H-NMR (500 MHz, DMSO-d6) δ 8.79 (s, 1H), 8.59 (dd, 1H), 8.00 (dd, 1H), 7.70 (d, 2H), 7.06 (d, 2H), 6.67 (d, 1H), 5.59-5.31 (m, 1H), 5.23 (s, 2H), 4.98 (s, 2H), 3.86-3.56 (m, 5H), 3.48 (td, 1H), 2.34-2.10 (m, 2H), 0.95-0.86 (m, 2H), −0.01 (s, 9H).<br>3. 510.3 |
| 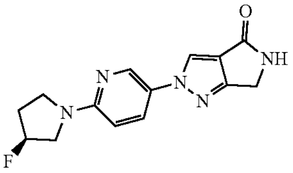 [SMILES: O=C1NCc2nn(-c3ccc(N4CC[C@H](F)C4)nc3)cc21] | 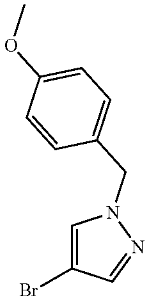 | 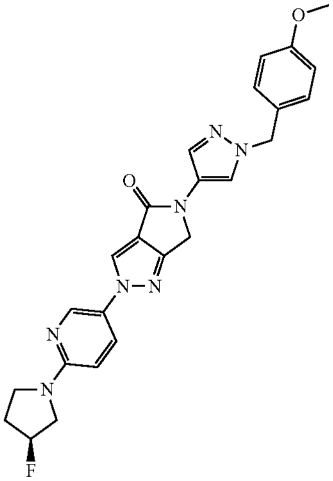 [SMILES: COc1ccc(Cn2cc(N3Cc4nn(-c5ccc(N6CC[C@H](F)C6)nc5)cc4C3=O)cn2)cc1]<br>31 | 1. 53%<br>2. $^1$H-NMR (80 MHz, DMSO-d6) δ 8.75 (s, 1H), 8.57 (d, 1H), 8.13 (s, 1H), 7.97 (dd, 1H), 7.70 (s, 1H), 7.25 (d, 2H), 6.90 (d, 2H), 6.65 (d, 1H), 5.89-5.02 (m, 3H), 4.82 (s, 2H), 3.96-3.48 (m, 7H), 2.26-1.55 (m, 2H).<br>3. 474.2 |

Examples 1 to 4

Following the Pd-coupling procedure as described in preparative example 7, using the amide starting material and the appropriate halogenated heteroaryl indicated in the Table 4 below, the following compounds were prepared.

TABLE 4

| Amide | halogenated heteroaryl | Compound of example | 1. Yield<br>2. $^1$H-NMR<br>3. $MH^+$ (ESI) |
|---|---|---|---|
| 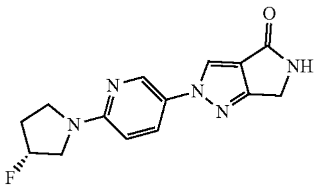 | 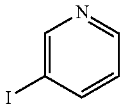 | 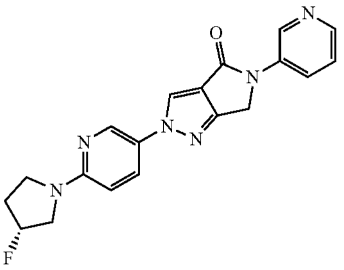 [SMILES: O=C1c2cn(-c3ccc(N4CC[C@@H](F)C4)nc3)nc2CN1c1cccnc1]<br>1 | 1. 26%<br>2. $^1$H NMR (80 MHz, DMSO-d6) δ = 9.03 (d, 1H), 8.86 (s, 1H), 8.60 (d, 1H), 8.43-8.16 (m, 2H), 8.02 (dd, 1H), 7.45 (dd, 1H), 6.67 (d, 1H), 5.80 (s, 1H), 5.09 (s, 2H), 3.85-3.39 (m, 4H), 2.28-1.85 (m, 2H).<br>3. 365.06 |
| 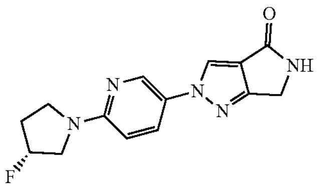 | 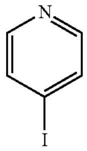 | 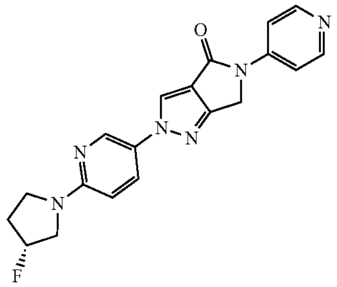 [SMILES: O=C1c2cn(-c3ccc(N4CC[C@@H](F)C4)nc3)nc2CN1c1ccncc1]<br>2 | 1. 52%<br>2. $^1$H NMR (400 MHz, DMSO-d6) δ = 8.91 (s, 1H), 8.61 (d, 1H), 8.52 (dd, 2H), 8.02 (dd, 1H), 7.85 (dd, 2H), 6.68 (d, 1H), 5.48 (d, 1H), 5.05 (s, 2H), 3.85-3.41 (m, 4H), 2.35-2.14 (m, 2H).<br>3. 365.12 |
| 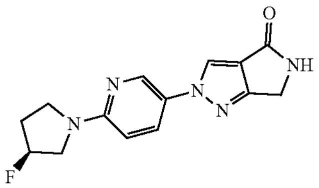 | 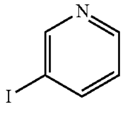 | 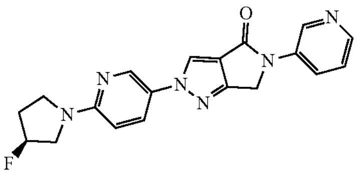 [SMILES: O=C1c2cn(-c3ccc(N4CC[C@H](F)C4)nc3)nc2CN1c1cccnc1]<br>3 | 1. 17%<br>2. $^1$H NMR (80 MHz, DMSO-d6) δ = 9.04 (d, 1H), 8.86 (s, 1H), 8.60 (d, 1H), 8.42-8.17 (m, 2H), 8.02 (dd, 1H), 7.45 (q, 1H), 6.67 (d, 1H), 5.09 (d, 3H), 3.99-3.37 (m, 4H), 2.38-1.57 (m, 2H).<br>3. 365.13 |
| 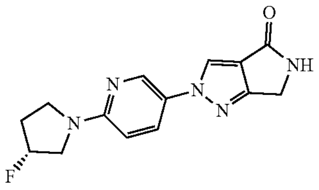 | 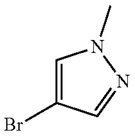 | 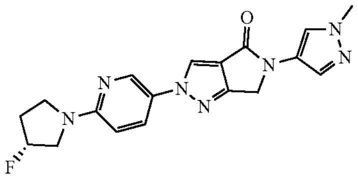 [SMILES: Cn1cc(N2Cc3nn(-c4ccc(N5CC[C@@H](F)C5)nc4)cc3C2=O)cn1]<br>4 | 1. 18%<br>2. $^1$H NMR (80 MHz, DMSO-d6) δ = 8.76 (s, 1H), 8.58 (d, 1H), 8.06 (s, 1H), 7.93 (d, 1H), 7.68 (s, 1H), 6.65 (d, 1H), 5.46 (d, 1H), 4.82 (s, 2H), 3.99-3.40 (m, 7H), 2.29-1.62 (m, 2H).<br>3. 367.80 |

Alternative Example 1

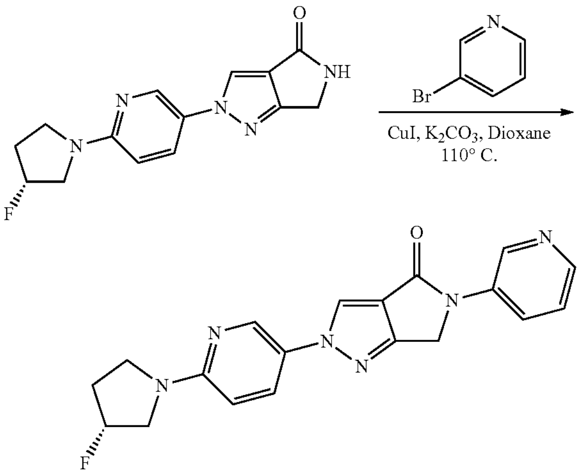

In a flask under argon, Preparative Example 5 (285 mg, 0.992 mmol), 3-bromopyridine (0.191 mL, 1.984 mmol), potassium carbonate (274 mg, 1.984 mmol) and copper(I) iodide (37.8 mg, 0.198 mmol) were mixed and the system was flushed with argon. Dioxane (12 mL) and N1,N2-dimethylethane-1,2-diamine (0.042 mL, 0.397 mmol) were added and the mixture was stirred at 110° C. for 4 h. The crude was concentrated under reduced pressure and dissolved in 20 mL of water. Aqueous ammonia (16.30 mL, 114 mmol) was added until the solution was basic (pH 12). The aqueous layer was extracted twice with a solution of DCM/MeOH (9:1). The combined organic layers were dried over $Na_2SO_4$, filtered and concentrated to dryness. The solid was suspended in DCM and stirred at 40° C. for 15 minutes. The mixture was cooled down and filtered to afford the product as a white solid (234.3 mg, 65%). $^1H$ NMR (80 MHz, DMSO-d6) δ 9.03 (d, 1H), 8.86 (s, 1H), 8.60 (d, 1H), 8.42-8.15 (m, 2H), 8.01 (dd, 1H), 7.45 (dd, 1H), 6.67 (d, 1H), 5.41 (d, 1H), 5.09 (s, 2H), 4.00-3.37 (m, 4H), 2.28-1.48 (m, 2H). MS: 365.12 $[M+H]^+$

Examples 5 to 138

Following the procedures as described in preparative example 7, Alternative Example 1 or using the amide starting material and the appropriate halogenated heteroaryl indicated in the Table 4a below, the following Examples were prepared. Alternatively, $Pd_2(dba)_3$, BINAP and $Cs_2CO_3$ conditions could be applied.

TABLE 4a

| Amide | halogenated heteroaryl | Compound of example | 1. Yield<br>2. $^1H$-NMR<br>3. $MH^+$ (ESI) |
|---|---|---|---|
| 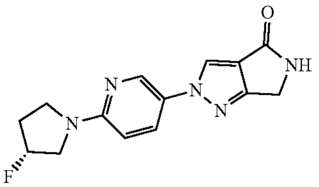 | 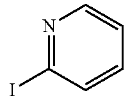 | 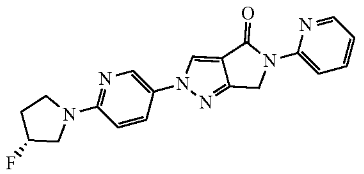 [SMILES: O=C1c2cn(-c3ccc(N4CC[C@@H](F)C4)nc3)nc2CN1c1ccccn1]<br>5 | 1. 26%<br>2. $^1H$ NMR (500 MHz, DMSO-d6) δ 8.89 (s, 1H), 8.61 (d, 1H), 8.43 (dd, 2H), 8.02 (dd, 1H), 7.85 (t, 1H), 7.25-7.06 (m, 1H), 6.67 (d, 1H), 5.47 (d, 1H), 5.09 (s, 2H), 3.86-3.53 (m, 3H), 3.53-3.41 (m, 1H), 2.35-2.12 (m, 2H).<br>3. 365.2 |
| 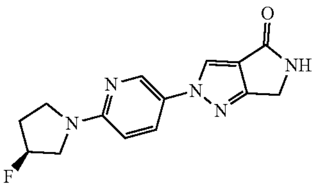 | 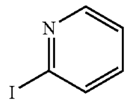 | 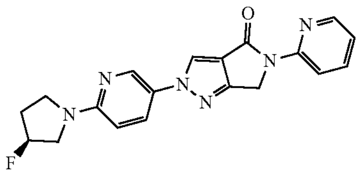 [SMILES: O=C1c2cn(-c3ccc(N4CC[C@H](F)C4)nc3)nc2CN1c1ccccn1]<br>6 | 1. 14%<br>2. $^1H$ NMR (500 MHz, DMSO-d6) δ 8.89 (s, 1H), 8.61 (d, 1H), 8.47-8.39 (m, 2H), 8.02 (dd, 1H), 7.88-7.81 (m, 1H), 7.15 (ddd, 1H), 6.67 (d, 1H), 5.47 (d, 1H), 5.09 (s, 2H), 3.83-3.56 (m, 3H), 3.52-3.42 (m, 1H), 2.31-2.23 (m, 2H).<br>3. 365.2 |
| 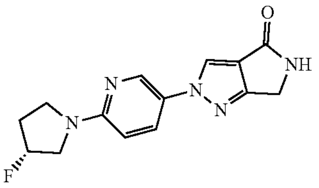 | 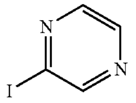 | 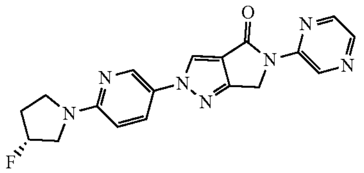 [SMILES: O=C1c2cn(-c3ccc(N4CC[C@@H](F)C4)nc3)nc2CN1c1cnccn1]<br>7 | 1. 19%<br>2. $^1H$ NMR (500 MHz, DMSO-d6) δ 9.69 (d, 1 H), 8.95 (s, 1H), 8.61 (dd, 1H), 8.49 (dd, 1H), 8.39 (d, 1H), 8.03 (dd, 1H), 6.68 (d, 1H), 5.55-5.38 (m, 1H), 5.08 (s, 2H), 3.83-3.58 (m, 3H), 3.53-3.46 (m, 1H), 2.32-2.10 (m, 2H).<br>3. 366.2 |

TABLE 4a-continued

| Amide | halogenated heteroaryl | Compound of example | 1. Yield<br>2. $^{1}$H-NMR<br>3. $MH^+$ (ESI) |
|---|---|---|---|
| 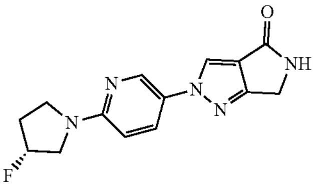 [SMILES: O=C1NCc2nn(-c3ccc(N4CC[C@@H](F)C4)nc3)cc21] | 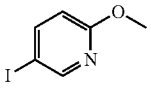 | 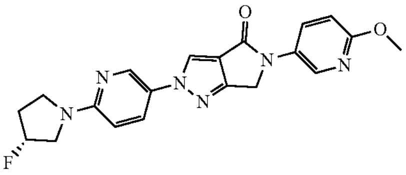 [SMILES: COc1ccc(N2Cc3nn(-c4ccc(N5CC[C@@H](F)C5)nc4)cc3C2=O)cn1]<br>8 | 1. 51%<br>2. $^{1}$H NMR (500 MHz, DMSO-d6) δ 8.82 (s, 1H), 8.61-8.57 (m, 1H), 8.50 (dd, 1H), 8.18 (dd, 1H), 8.01 (dd, 1H), 6.90 (dd, 1H), 6.67 (d, 1H), 5.54-5.40 (m, 1H), 5.01 (s, 2H), 3.86 (s, 3H), 3.83-3.55 (m, 3H), 3.48 (td, 1H), 2.35-2.09 (m, 2H)<br>3. 395.2 |
| 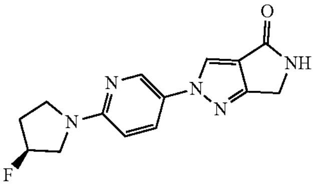 [SMILES: O=C1NCc2nn(-c3ccc(N4CC[C@H](F)C4)nc3)cc21] | 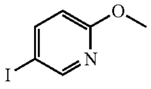 | 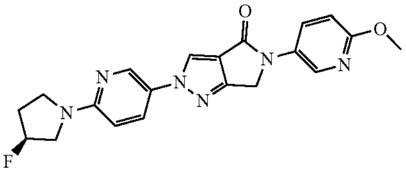 [SMILES: COc1ccc(N2Cc3nn(-c4ccc(N5CC[C@H](F)C5)nc4)cc3C2=O)cn1]<br>9 | 1. 36%<br>2. $^{1}$H NMR (500 MHz, DMSO-d6) δ 8.82 (s, 1H), 8.59 (d, 1H), 8.50 (d, 1H), 8.18 (dd, 1H), 8.01 (dd, 1H), 6.90 (d, 1H), 6.67 (d, 1H), 5.54-5.36 (m, 1H), 5.01 (s, 2H), 3.86 (s, 3H), 3.83-3.57 (m, 3H), 3.48 (td, 1H), 2.32-2.12 (m, 2H)<br>3. 395.3 |
| 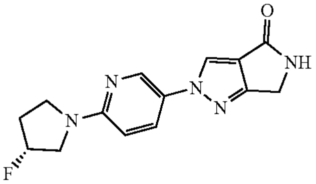 [SMILES: O=C1NCc2nn(-c3ccc(N4CC[C@@H](F)C4)nc3)cc21] | 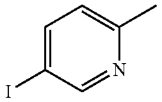 | 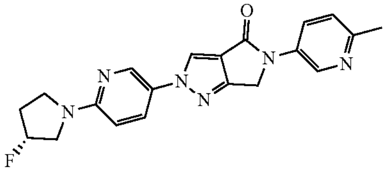 [SMILES: Cc1ccc(N2Cc3nn(-c4ccc(N5CC[C@@H](F)C5)nc4)cc3C2=O)cn1]<br>10 | 1. 16%<br>2. $^{1}$H NMR (500 MHz, DMSO-d6) δ 8.89 (s, 1H), 8.84 (s, 1H), 8.59 (d, 1H), 8.13 (dd, 1H), 8.01 (dd, 1H), 7.31 (d, 1H), 6.66 (d, 1H), 5.55-5.38 (m, 1H), 5.04 (s, 2H), 3.82-3.57 (m, 3H), 3.47 (td, 1H), 2.46 (s, 3H), 2.37-2.11 (m, 2H).<br>3. 379.2 |
| 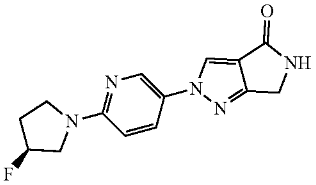 [SMILES: O=C1NCc2nn(-c3ccc(N4CC[C@H](F)C4)nc3)cc21] | 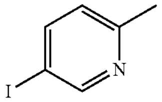 | 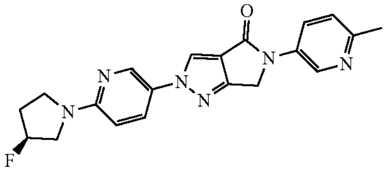 [SMILES: Cc1ccc(N2Cc3nn(-c4ccc(N5CC[C@H](F)C5)nc4)cc3C2=O)cn1]<br>11 | 1. 47%<br>2. $^{1}$H NMR (500 MHz, DMSO-d6) δ 8.89 (s, 1H), 8.84 (s, 1H), 8.62-8.58 (m, 1H), 8.13 (dd, 1H), 8.01 (dd, 1H), 7.31 (d, 1H), 6.67 (d, 1H), 5.54-5.38 (m, 1H), 5.05 (s, 2H), 3.87-3.58 (m, 3H), 3.47 (td, 1H), 2.46 (s, 3H), 2.38-2.11 (m, 2H).<br>3. 379.2 |
| 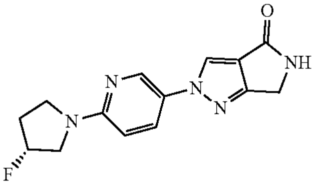 [SMILES: O=C1NCc2nn(-c3ccc(N4CC[C@@H](F)C4)nc3)cc21] | 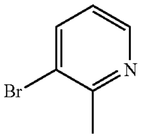 | 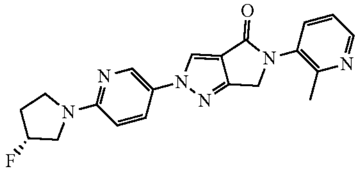 [SMILES: Cc1ncccc1N1Cc2nn(-c3ccc(N4CC[C@@H](F)C4)nc3)cc2C1=O]<br>12 | 1. 21%<br>2. $^{1}$H NMR (400 MHz, DMSO-d6) δ 8.81 (s, 1H), 8.59 (d, 1H), 8.46 (s, 1H), 8.00 (dd, 1H), 7.85 (dd, 1H), 7.36 (dd, 1H), 6.67 (d, 1H), 5.56-5.36 (m, 1H), 4.91 (s, 2H), 3.85-3.56 (m, 3H), 3.48 (td, 1H), 2.40 (s, 3H), 2.35-2.09 (m, 2H).<br>3. 379.2 |
| 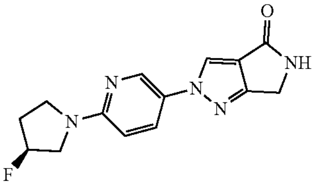 [SMILES: O=C1NCc2nn(-c3ccc(N4CC[C@H](F)C4)nc3)cc21] | 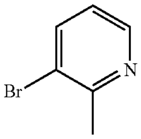 | 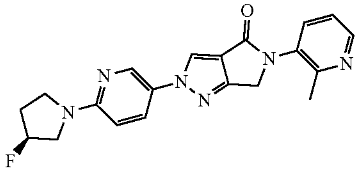 [SMILES: Cc1ncccc1N1Cc2nn(-c3ccc(N4CC[C@H](F)C4)nc3)cc2C1=O]<br>13 | 1. 19%<br>2. $^{1}$H NMR (400 MHz, DMSO-d6) δ 8.80 (s, 1H), 8.59 (d, 1H), 8.47 (s, 1H), 8.00 (dd, 1H),7.85 (d, 1H), 7.45-7.25 (m, 1H), 6.67 (d, 1H), 5.60-5.34 (m, 1H), 4.90 (s, 2H), 4.03-3.56 (m,3H), 3.56-3.40 (m, 1H), 2.40 (s, 3H), 2.35-2.13 (m, 2H).<br>3. 379.2 |

TABLE 4a-continued

| Amide | halogenated heteroaryl | Compound of example | 1. Yield<br>2. $^1$H-NMR<br>3. MH$^+$ (ESI) |
|---|---|---|---|
| 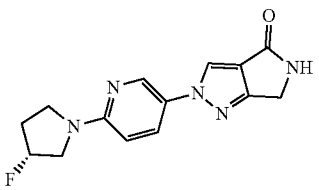 [SMILES: O=C1NCc2nn(-c3ccc(N4CC[C@@H](F)C4)nc3)cc21] | 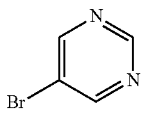 | 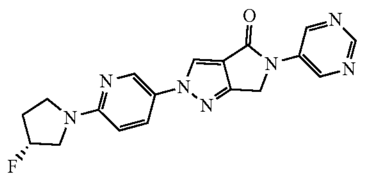 [SMILES: O=C1c2cn(-c3ccc(N4CC[C@@H](F)C4)nc3)nc2CN1c1cncnc1]<br>14 | 1. 39%<br>2. $^1$H NMR (400 MHz, DMSO-d6) δ 9.30 (s, 2H), 8.96 (s, 1H), 8.91 (s, 1H), 8.61 (dd, 1H), 8.02 (dd, 1H), 6.67 (d, 1H), 5.65-5.36 (m, 1H), 5.12 (s, 2H), 3.92-3.57 (m, 3H), 3.48 (td, 1H), 2.38-2.10 (m, 2H).<br>3. 366.2 |
| 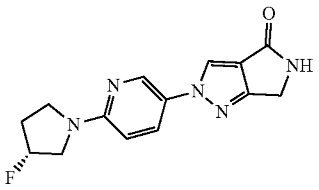 [SMILES: O=C1NCc2nn(-c3ccc(N4CC[C@@H](F)C4)nc3)cc21] | 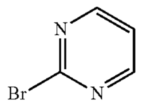 | 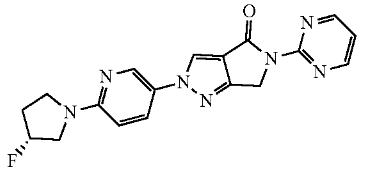 [SMILES: O=C1c2cn(-c3ccc(N4CC[C@@H](F)C4)nc3)nc2CN1c1ncccn1]<br>15 | 1. 26%<br>2. $^1$H NMR (500 MHz, DMSO-d6) δ 8.90 (s, 1H), 8.75 (d, 2H), 8.60 (d, 1H), 8.02 (dd, 1H), 7.24 (t, 1H), 6.67 (d, 1H), 5.60-5.32 (m, 1H), 5.09 (s, 2H), 3.88-3.54 (m, 3H), 3.54-3.38 (m, 1H), 2.39-2.05 (m, 2H).<br>3. 366.2 |
| 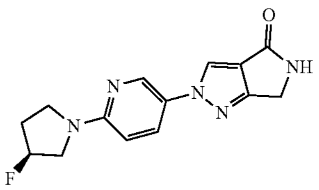 | 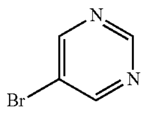 | 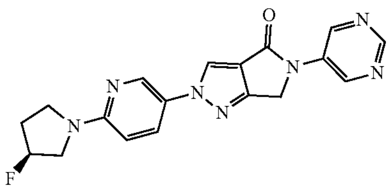 [SMILES: O=C1c2cn(-c3ccc(N4CC[C@H](F)C4)nc3)nc2CN1c1cncnc1]<br>16 | 1. 9%<br>2. $^1$H NMR (400 MHz, DMSO-d6) δ 9.30 (s, 2H), 8.96 (s, 1H), 8.91 (s, 1H), 8.61 (d, 1H), 8.02 (dd, 1H), 6.67 (d, 1H), 5.65-5.36 (m, 1H), 5.12 (s, 2H), 3.88-3.57 (m, 3H), 3.48 (td, 1H), 2.40-2.08 (m, 2H).<br>3. 366.2 |
| 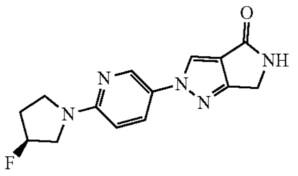 [SMILES: O=C1NCc2nn(-c3ccc(N4CC[C@H](F)C4)nc3)cc21] | 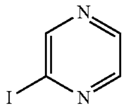 | 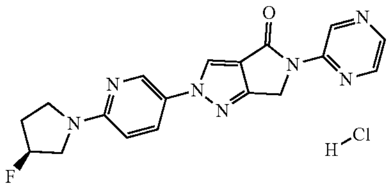 [SMILES: O=C1c2cn(-c3ccc(N4CC[C@H](F)C4)nc3)nc2CN1c1cnccn1 ; Cl]<br>17 | 1. 29%<br>2. $^1$H (80 MHz, DMSO-d6) δ 9.69 (d, 1H), 8.96 (s, 1H), 8.61 (d, 1H), 8.48 (d, 1H), 8.38 (d, 1H), 8.18-7.91 (m, 1H), 6.71 (d, 1H), 5.90-5.03 (m, 3H), 3.98-3.55 (m, 4H), 2.22-1.76<br>3. 366.1 |
| 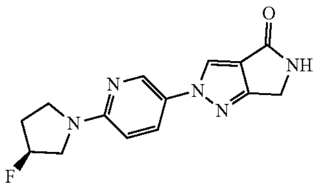 [SMILES: O=C1NCc2nn(-c3ccc(N4CC[C@H](F)C4)nc3)cc21] | 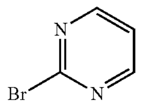 | 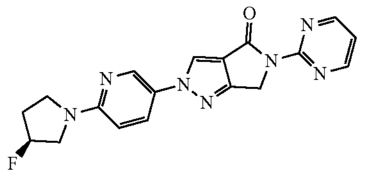 [SMILES: O=C1c2cn(-c3ccc(N4CC[C@H](F)C4)nc3)nc2CN1c1ncccn1]<br>18 | 1. 26%<br>2. $^1$H NMR (500 MHz, DMSO-d6) δ 8.90 (s, 1H), 8.75 (d, 2H), 8.60 (d, 1H), 8.02 (dd, 1H), 7.24 (t, 1H), 6.67 (d, 1H), 5.60-5.36 (m, 1H), 5.09 (s, 2H), 3.88-3.55 (m, 3H), 3.48 (td, 1H), 2.35-2.10 (m, 2H).<br>3. 366.2 |
| 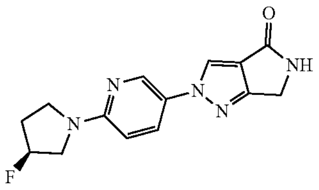 | 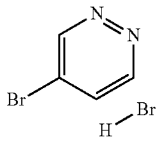 | 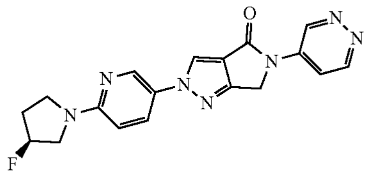 [SMILES: O=C1c2cn(-c3ccc(N4CC[C@H](F)C4)nc3)nc2CN1c1ccnnc1]<br>19 | 1. 10%<br>2. $^1$H NMR (500 MHz, DMSO-d6) δ 9.76 (dd, 1H), 9.10 (dd, 1H), 8.95 (s, 1H), 8.61 (d, 1H), 8.03 (ddd, 2H), 6.67 (d, 1H), 5.61-5.37 (m, 1H), 5.11 (s, 2H), 3.94-3.56 (m, 3H), 3.48 (td, 1H), 2.39-2.05 (m, 2H).<br>3. 366.2 |

TABLE 4a-continued

| Amide | halogenated heteroaryl | Compound of example | 1. Yield<br>2. $^1$H-NMR<br>3. $MH^+$ (ESI) |
|---|---|---|---|
| 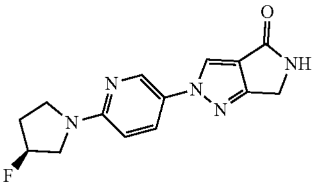 [SMILES: O=C1NCc2nn(-c3ccc(N4CC[C@H](F)C4)nc3)cc21] | 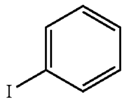 | 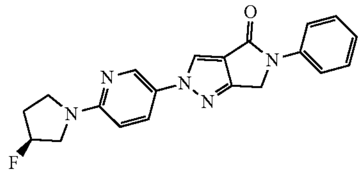<br>20 | 1. 29%<br>2. $^1$H NMR (500 MHz, DMSO-d6) δ 8.82 (s, 1H), 8.60 (d, 1H), 8.01 (dd, 1H), 7.91-7.77 (m, 2H), 7.51-7.34 (m, 2H), 7.25-7.09 (m, 1H), 6.67 (d, 1H), 5.60-5.37 (m, 1H), 5.03 (s, 2H), 3.88-3.55 (m, 3H), 3.48 (td, 1H), 2.39-2.10 (m, 2H).<br>3. 364.2 |
| 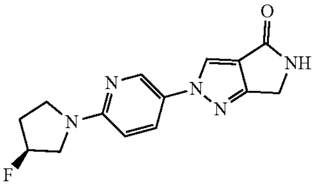 | 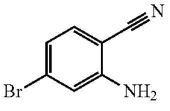 | 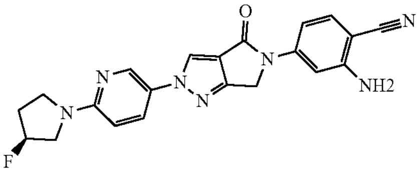 [SMILES: N#Cc1ccc(N2Cc3nn(-c4ccc(N5CC[C@H](F)C5)nc4)cc3C2=O)cc1N]<br>21 | 1. 28%<br>2. $^1$H NMR (400 MHz, DMSO-d6) δ 8.04 (s, 1H), 7.77 (d, 1H), 7.18 (dd, 1H), 6.67-6.54 (m, 2H), 6.24 (dd, 1H), 5.84 (d, 1H), 5.24 (s, 2H), 4.78-4.53 (m, 1H), 4.15 (s, 2H), 3.06-2.72 (m, 3H), 2.72-2.59 (m, 1H), 1.56-1.25 (m, 2H).<br>3. 404.2 |
| 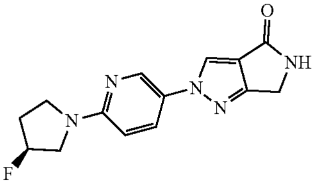 | 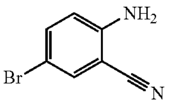 | 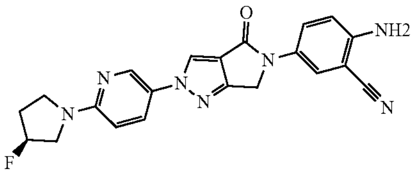 [SMILES: N#Cc1cc(N2Cc3nn(-c4ccc(N5CC[C@H](F)C5)nc4)cc3C2=O)ccc1N]<br>22 | 1. 17%<br>2. $^1$H NMR (400 MHz, DMSO-d6) δ 8.79 (s, 1H), 8.58 (d, 1H), 8.00 (dd, 1H), 7.75 (d, 2H), 6.99-6.79 (m, 1H), 6.66 (d, 1H), 6.16-5.93 (m, 2H), 5.61-5.31 (m, 1H), 4.93 (s, 2H), 3.87-3.55 (m, 3H), 3.47 (td, 1H), 2.38-2.09 (m, 2H).<br>3. 404.3 |
| 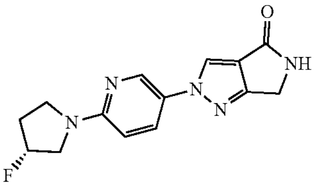 [SMILES: O=C1NCc2nn(-c3ccc(N4CC[C@@H](F)C4)nc3)cc21] | 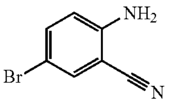 | 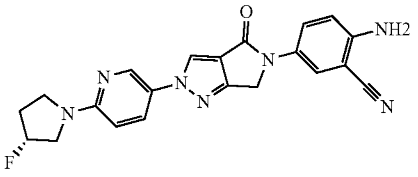 [SMILES: N#Cc1cc(N2Cc3nn(-c4ccc(N5CC[C@@H](F)C5)nc4)cc3C2=O)ccc1N]<br>23 | 1. 17%<br>2. $^1$H NMR (500 MHz, DMSO-d6) δ 8.78 (s, 1H), 8.58 (d, 1H), 8.00 (dd, 1H), 7.75 (d, 2H), 6.85 (d, 1H), 6.66 (d, 1H), 6.01 (s, 2H), 5.64-5.35 (m, 1H), 4.92 (s, 2H), 3.88-3.55 (m, 3H), 3.47 (q, 1H), 2.39-2.07 (m, 2H).<br>3. 404.3 |
| 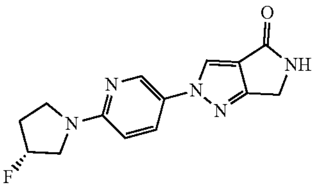 [SMILES: O=C1NCc2nn(-c3ccc(N4CC[C@@H](F)C4)nc3)cc21] | 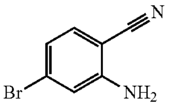 | 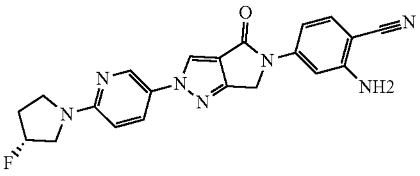 [SMILES: N#Cc1ccc(N2Cc3nn(-c4ccc(N5CC[C@@H](F)C5)nc4)cc3C2=O)cc1N]<br>24 | 1. 17%<br>2. $^1$H NMR (500 MHz, DMSO-d6) δ 8.86 (s, 1H), 8.59 (d, 1H), 8.01 (dd, 1H), 7.53-7.33 (m, 2H), 7.06 (dd, 1H), 6.67 (d, 1H), 6.07 (s, 2H), 5.61-5.35 (m, 1H), 4.97 (s, 2H), 3.83-3.54 (m, 3H), 3.53-3.45 (m, 1H), 2.38-2.07 (m, 2H).<br>3. 404.3 |
| 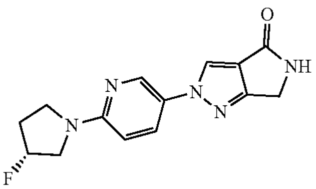 [SMILES: O=C1NCc2nn(-c3ccc(N4CC[C@@H](F)C4)nc3)cc21] | 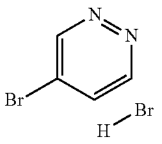 | 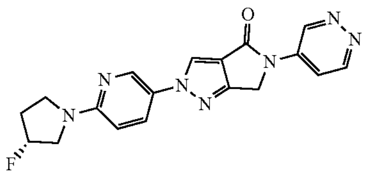 [SMILES: O=C1c2cn(-c3ccc(N4CC[C@@H](F)C4)nc3)nc2CN1c1ccnnc1]<br>25 | 1. 15%<br>2. $^1$H NMR (400 MHz, DMSO-d6) δ 9.76 (dd, 1H), 9.11 (dd, 1H), 8.96 (s, 1H), 8.61 (d, 1H), 8.18-7.92 (m, 2H), 6.68 (d, 1H), 5.62-5.34 (m, 1H), 5.11 (s, 2H), 3.90-3.55 (m, 3H), 3.55-3.40 (m, 1H), 2.37-2.07 (m, 2H).<br>3. 366.2 |

TABLE 4a-continued

| Amide | halogenated heteroaryl | Compound of example | 1. Yield<br>2. $^1$H-NMR<br>3. MH$^+$ (ESI) |
|---|---|---|---|
| 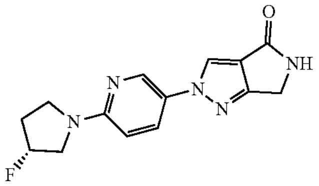 [SMILES: O=C1NCc2nn(-c3ccc(N4CC[C@@H](F)C4)nc3)cc21] | 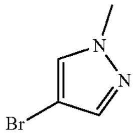 | 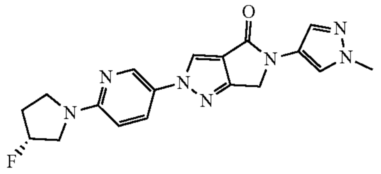 [SMILES: Cn1cc(N2Cc3nn(-c4ccc(N5CC[C@@H](F)C5)nc4)cc3C2=O)cn1]<br>26 | 1. 58%<br>2. $^1$H NMR (80 MHz, DMSO-d6) δ 8.76 (s, 1H), 8.58 (d, 1H), 8.11-7.88 (m, 2H), 7.68 (s, 1H), 6.66 (d, 1H), 5.47 (d, 1H), 4.83 (s, 2H), 3.71 (m, 7H), 2.20-1.94 (m, 2H).<br>3. 368.1 |
| 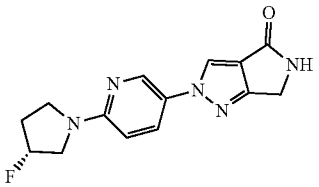 [SMILES: O=C1NCc2nn(-c3ccc(N4CC[C@@H](F)C4)nc3)cc21] | 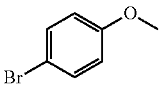 | 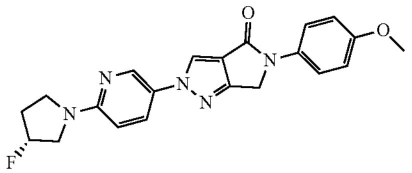 [SMILES: COc1ccc(N2Cc3nn(-c4ccc(N5CC[C@@H](F)C5)nc4)cc3C2=O)cc1]<br>27 | 1. 36%<br>2. $^1$H NMR (500 MHz, DMSO-d6) δ 8.78 (s, 1H), 8.65-8.51 (m, 1H), 8.00 (dd, 1H), 7.77-7.62 (m, 2H), 7.13-6.91 (m, 2H), 6.66 (d, 1H), 5.60-5.36 (m, 1H), 4.97 (s, 2H), 3.84-3.58 (m, 6H), 3.47 (td, 1H), 2.35-2.12 (m, 2H).<br>3. 394.2 |
| 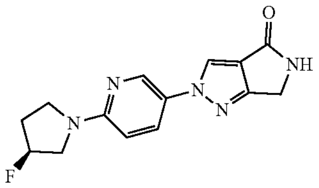 [SMILES: O=C1NCc2nn(-c3ccc(N4CC[C@H](F)C4)nc3)cc21] | 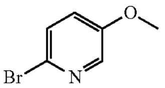 | 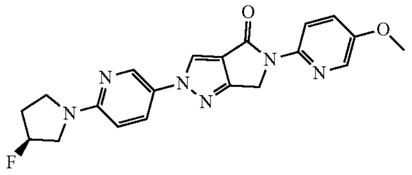 [SMILES: COc1ccc(N2Cc3nn(-c4ccc(N5CC[C@H](F)C5)nc4)cc3C2=O)nc1]<br>28 | 1. 9%<br>2. $^1$H NMR (500 MHz, DMSO-d6) δ 8.85 (s, 1H), 8.60 (d, 1H), 8.36 (d, 1H), 8.14 (d, 1H), 8.01 (dd, 1H), 7.52 (dd, 1H), 6.67 (d, 1H), 5.56-5.38 (m, 1H), 5.05 (s, 2H), 3.83 (s, 3H), 3.82-3.56 (m, 3H), 3.47 (td, 1H), 2.35-2.11 (m, 2H).<br>3. 395.5 |
| 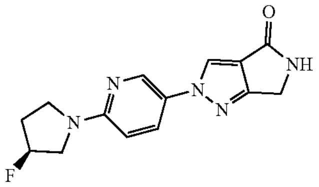 [SMILES: O=C1NCc2nn(-c3ccc(N4CC[C@H](F)C4)nc3)cc21] | 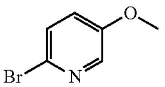 | 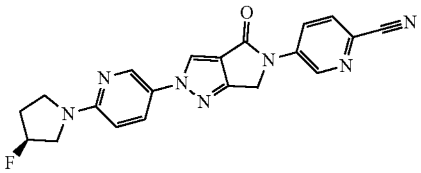 [SMILES: N#Cc1ccc(N2Cc3nn(-c4ccc(N5CC[C@H](F)C5)nc4)cc3C2=O)cn1]<br>29 | 1. 18%<br>2. $^1$H NMR (500 MHz, DMSO-d6) δ 8.41 (d, 1H), 8.11 (s, 1H), 7.79 (d, 1H), 7.66 (dd, 1H), 7.27 (d, 1H), 7.20 (dd, 1H), 5.85 (d, 1H), 4.75-4.54 (m, 1H), 4.32 (s, 2H), 3.07-2.75 (m, 3H), 2.66 (td, 1H), 1.54-1.30 (m, 2H).<br>3. 390.2 |
| 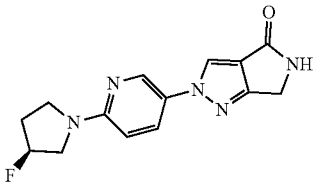 [SMILES: O=C1NCc2nn(-c3ccc(N4CC[C@H](F)C4)nc3)cc21] | 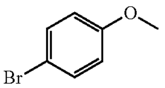 | 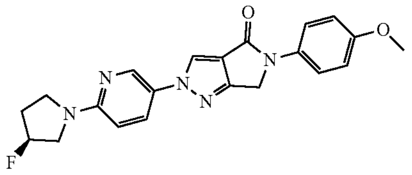 [SMILES: COc1ccc(N2Cc3nn(-c4ccc(N5CC[C@H](F)C5)nc4)cc3C2=O)cc1]<br>30 | 1. 13%<br>2. $^1$H NMR (400 MHz, DMSO-d6) δ 8.79 (s, 1H), 8.59 (d, 1H), 8.00 (dd, 1H), 7.69 (d, 2H), 6.99 (d, 2H), 6.67 (d, 1H), 5.65-5.33 (m, 1H), 4.97 (s, 2H), 3.85-3.56 (m, 6H), 3.47 (td, 1H), 2.39-2.09 (m, 2H).<br>3. 394.2 |
| 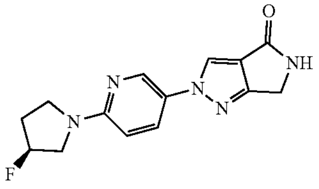 [SMILES: O=C1NCc2nn(-c3ccc(N4CC[C@H](F)C4)nc3)cc21] | 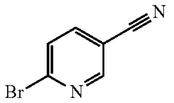 | 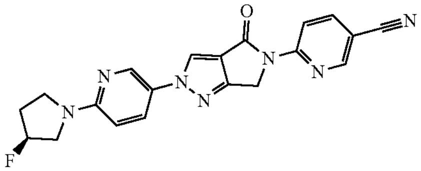 [SMILES: N#Cc1ccc(N2Cc3nn(-c4ccc(N5CC[C@H](F)C5)nc4)cc3C2=O)nc1]<br>31 | 1. 9%<br>2. $^1$H NMR (500 MHz, $CF_3COOD$) δ 9.31 (s, 1H), 9.10-8.89 (m, 2H), 8.85 (s, 1H), 8.68 (d, 1H), 8.24 (d, 1H), 7.56 (s, 1H), 5.98-5.76 (m, 1H), 5.72 (s, 2H), 4.48-4.09 (m, 4H), 3.10-2.60 (m, 2H).<br>3. 390.1 |

TABLE 4a-continued

| Amide | halogenated heteroaryl | Compound of example | 1. Yield<br>2. $^1$H-NMR<br>3. $MH^+$ (ESI) |
| --- | --- | --- | --- |
| 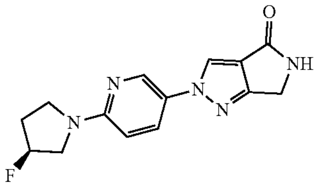 [SMILES: O=C1NCc2nn(-c3ccc(N4CC[C@H](F)C4)nc3)cc21] | 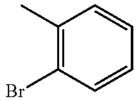 | 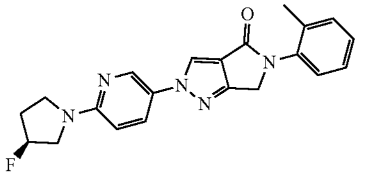 [SMILES: Cc1ccccc1N1Cc2nn(-c3ccc(N4CC[C@H](F)C4)nc3)cc2C1=O]<br>32 | 1. 19%<br>2. $^1$H NMR (500 MHz, DMSO-d6) δ 8.77 (s, 1H), 8.59 (d, 1H), 8.00 (dd, 1H), 7.46-7.37 (m, 1H), 7.37-7.32 (m, 1H), 7.32-7.25 (m, 2H), 6.67 (d, 1H), 5.62-5.37 (m, 1H), 4.85 (s, 2H), 3.86-3.57 (m, 3H), 3.48 (td, 1H), 2.35-2.13 (m, 5H).<br>3. 378.2 |
| 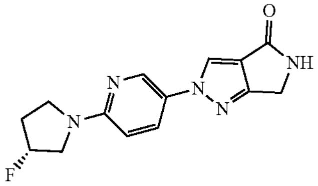 [SMILES: O=C1NCc2nn(-c3ccc(N4CC[C@@H](F)C4)nc3)cc21] | 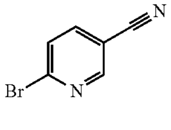 | 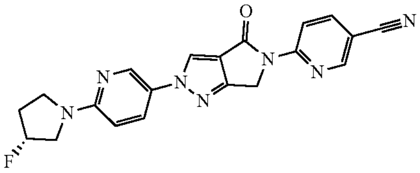 [SMILES: N#Cc1ccc(N2Cc3nn(-c4ccc(N5CC[C@@H](F)C5)nc4)cc3C2=O)nc1]<br>33 | 1. 18%<br>2. $^1$H NMR (500 MHz, $CF_3COOD$) δ 9.21-9.05 (m, 1H), 8.87-8.75 (m, 2H), 8.66 (d, 1H), 8.50 (td, 1H), 8.14-7.99 (m, 1H), 7.36 (s, 1H), 5.76-5.55 (m, 1H), 5.55-5.46 (m, 2H), 4.29-3.90 (m, 4H), 2.77 (s, 1H), 2.65-2.32 (m, 1H).<br>3. 390.2 |
| 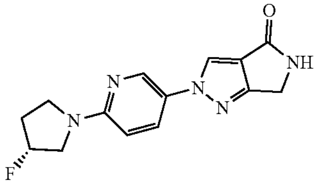 [SMILES: O=C1NCc2nn(-c3ccc(N4CC[C@@H](F)C4)nc3)cc21] | 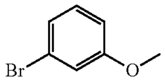 | 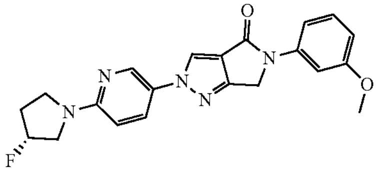 [SMILES: COc1cccc(N2Cc3nn(-c4ccc(N5CC[C@@H](F)C5)nc4)cc3C2=O)c1]<br>34 | 1. 18%<br>2. $^1$H NMR (400 MHz, DMSO-d6) δ 8.82 (s, 1H), 8.60 (d, 1H), 8.01 (dd, 1H), 7.50 (t, 1H), 7.43-7.25 (m, 2H), 6.74 (dd, 1H), 6.67 (d, 1H), 5.61-5.36 (m, 1H), 5.02 (s, 2H), 3.91-3.45 (m, 7H), 2.41-2.10 (m, 2H).<br>3. 394.2 |
| 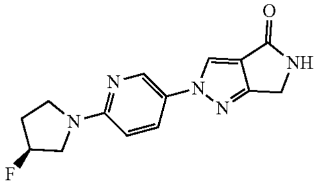 [SMILES: O=C1NCc2nn(-c3ccc(N4CC[C@H](F)C4)nc3)cc21] | 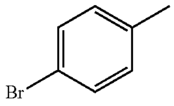 | 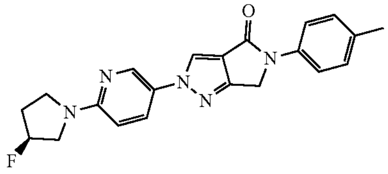 [SMILES: Cc1ccc(N2Cc3nn(-c4ccc(N5CC[C@H](F)C5)nc4)cc3C2=O)cc1]<br>35 | 1. 19%<br>2. $^1$H NMR (400 MHz, DMSO-d6) δ 8.80 (s, 1H), 8.59 (d, 1H), 8.01 (dd, 1H), 7.79-7.62 (m, 2H), 7.22 (d, 2H), 6.67 (d, 1H), 5.63-5.34 (m, 1H), 4.99 (s, 2H), 3.89-3.55 (m, 3H), 3.55-3.42 (m, 1H), 2.38-2.10 (m, 5H).<br>3. 378.2 |
| 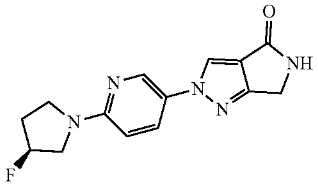 [SMILES: O=C1NCc2nn(-c3ccc(N4CC[C@H](F)C4)nc3)cc21] | 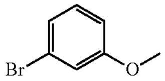 | 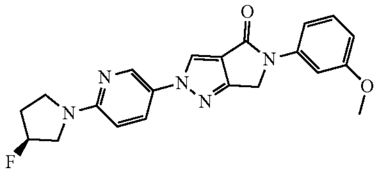 [SMILES: COc1cccc(N2Cc3nn(-c4ccc(N5CC[C@H](F)C5)nc4)cc3C2=O)c1]<br>36 | 1. 18%<br>2. $^1$H NMR (400 MHz, DMSO-d6) δ 8.82 (s, 1H), 8.60 (d, 1H), 8.01 (dd, 1H), 7.50 (t, 1H), 7.43-7.21 (m, 2H), 6.74 (ddd, 1H), 6.67 (d, 1H), 5.61-5.35 (m, 1H), 5.02 (s, 2H), 3.87-3.54 (m, 6H), 3.47 (td, 1H), 2.37-2.08 (m, 2H).<br>3. 394.2 |
| 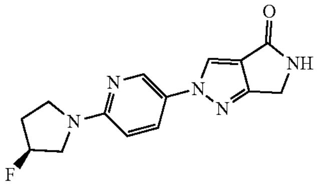 [SMILES: O=C1NCc2nn(-c3ccc(N4CC[C@H](F)C4)nc3)cc21] | 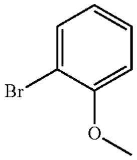 | 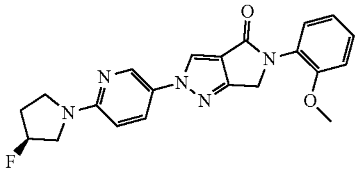 [SMILES: COc1ccccc1N1Cc2nn(-c3ccc(N4CC[C@H](F)C4)nc3)cc2C1=O]<br>37 | 1. 18%<br>2. $^1$H NMR (400 MHz, DMSO-d6) δ 8.76 (s, 1H), 8.58 (d, 1H), 8.00 (dd, 1H), 7.43-7.30 (m, 2H), 7.16 (dd, 1H), 7.02 (td, 1H), 6.67 (d, 1H), 5.64-5.34 (m, 1H), 4.78 (s, 2H), 3.85-3.54 (m, 6H), 3.48 (td, 1H), 2.36-2.10 (m, 2H).<br>3. 394.2 |

TABLE 4a-continued

| Amide | halogenated heteroaryl | Compound of example | 1. Yield<br>2. $^{1}$H-NMR<br>3. $MH^{+}$ (ESI) |
|---|---|---|---|
| 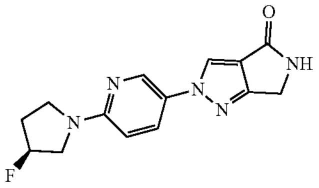 [SMILES: O=C1NCc2nn(-c3ccc(N4CC[C@H](F)C4)nc3)cc21] | 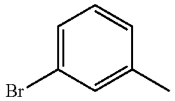 | 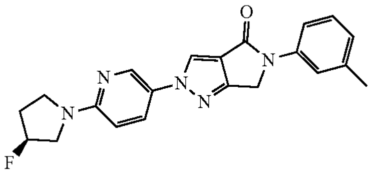 [SMILES: Cc1cccc(N2Cc3nn(-c4ccc(N5CC[C@H](F)C5)nc4)cc3C2=O)c1]<br>38 | 1. 23%<br>2. $^{1}$H NMR (400 MHz, DMSO-d6) δ 8.82 (s, 1H), 8.60 (d, 1H), 8.01 (dd, 1H), 7.71-7.58 (m, 2H), 7.29 (t, 1H), 7.03-6.91 (m, 1H), 6.67 (d, 1H), 5.60-5.35 (m, 1H), 5.01 (s, 2H), 3.88-3.55 (m, 3H), 3.53-3.42 (m, 1H), 2.39-2.06 (m, 5H).<br>3. 378.2 |
| 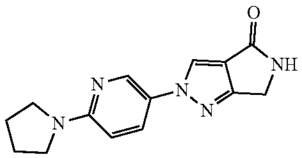 [SMILES: O=C1NCc2nn(-c3ccc(N4CCCC4)nc3)cc21] | 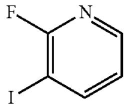 | 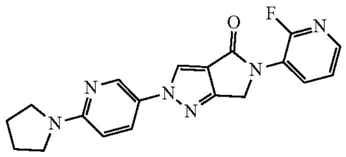 [SMILES: O=C1c2cn(-c3ccc(N4CCCC4)nc3)nc2CN1c1cccnc1F]<br>39 | 1. 23%<br>2. $^{1}$H NMR (500 MHz, DMSO-d6) δ 8.84 (s, 1H), 8.61-8.53 (m, 1H), 8.25-8.17 (m, 2H), 7.95 (dd, 1H), 7.49 (ddd, 1H), 6.60 (d, 1H), 4.98 (s, 2H), 3.46-3.42 (m, 4H), 1.99-1.95 (m, 4H).<br>3. 365.3 |
| 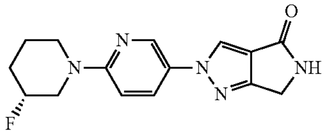 [SMILES: O=C1NCc2nn(-c3ccc(N4CCC[C@@H](F)C4)nc3)cc21] | 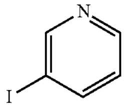 | 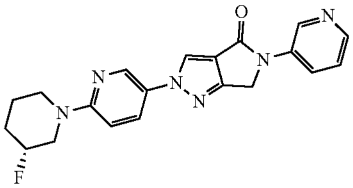 [SMILES: O=C1c2cn(-c3ccc(N4CCC[C@@H](F)C4)nc3)nc2CN1c1cccnc1]<br>40 | 1. 20%<br>2. $^{1}$H NMR (500 MHz, DMSO-d6) δ 9.09 (s, 1H), 8.88 (s, 1H), 8.60 (d, 1H), 8.41 (s, 1H), 8.27 (d, 1H), 7.99 (dd, 1H), 7.48 (s, 1H), 7.04 (d, 1H), 5.09 (s, 2H), 4.92-4.61 (m, 1H), 4.10-3.66 (m, 3H), 3.42 (t, 1H), 2.06-1.33 (m, 4H).<br>3. 379.2 |
| 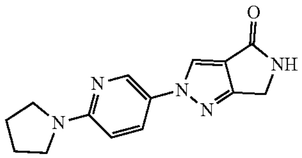 [SMILES: O=C1NCc2nn(-c3ccc(N4CCCC4)nc3)cc21] | 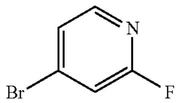 | 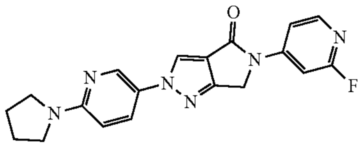 [SMILES: O=C1c2cn(-c3ccc(N4CCCC4)nc3)nc2CN1c1ccnc(F)c1]<br>41 | 1. 15%<br>2. $^{1}$H NMR (400 MHz, $CF_3COOD$) δ 8.87 (s, 1H), 8.75-8.59 (m, 3H), 8.59-8.43 (m, 2H), 7.42 (d, 1H), 5.54 (s, 2H), 3.97 (s, 4H), 2.52 (s, 4H).<br>3. 365.2 |
| 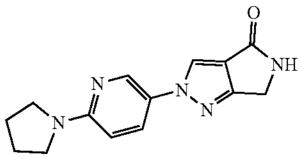 [SMILES: O=C1NCc2nn(-c3ccc(N4CCCC4)nc3)cc21] | 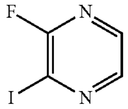 | 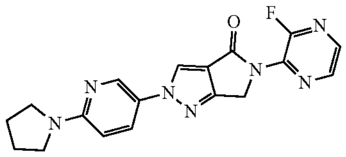 [SMILES: O=C1c2cn(-c3ccc(N4CCCC4)nc3)nc2CN1c1nccnc1F]<br>42 | 1. 37%<br>2. $^{1}$H NMR (400 MHz, DMSO-d6) δ 8.90 (s, 1H), 8.57 (dd, 2H), 8.28 (dd, 1H), 7.97 (dd, 1H), 6.60 (d, 1H), 5.15 (s, 2H), 3.49-3.40 (m, 4H), 2.02-1.92 (m, 4H).<br>3. 366.2 |
| 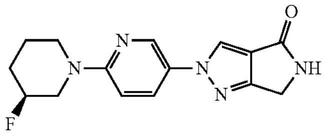 [SMILES: O=C1NCc2nn(-c3ccc(N4CCC[C@H](F)C4)nc3)cc21] | 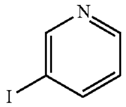 | 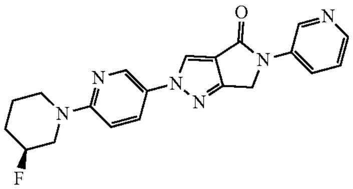 [SMILES: O=C1c2cn(-c3ccc(N4CCC[C@H](F)C4)nc3)nc2CN1c1cccnc1]<br>43 | 1. 25%<br>2. $^{1}$H NMR (400 MHz, DMSO-d6) δ 9.02 (s, 1H), 8.84 (s, 1H), 8.56 (d, 1H), 8.34 (s, 1H), 8.27-8.19 (m, 1H), 7.96 (dd, 1H), 7.56-7.27 (m, 1H), 7.00 (d, 1H), 5.05 (s, 2H), 4.92-4.61 (m, 1H), 4.05-3.57 (m, 3H), 3.39 (dd, 1H), 2.05-1.41 (m, 4H).<br>3. 379.2 |

TABLE 4a-continued

| Amide | halogenated heteroaryl | Compound of example | 1. Yield 2. $^{1}$H-NMR 3. $MH^{+}$ (ESI) |
|---|---|---|---|
| 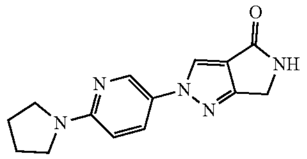 [SMILES: O=C1NCc2nn(-c3ccc(N4CCCC4)nc3)cc21] | 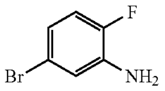 | 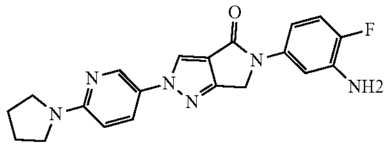 [SMILES: Nc1cc(N2Cc3nn(-c4ccc(N5CCCC5)nc4)cc3C2=O)ccc1F] 44 | 1. 51% 2. $^{1}$H NMR (500 MHz, DMSO-d6) δ 8.77 (s, 1H), 8.55 (d, 1H), 7.95 (dd, 1H), 7.36 (dd, 1H), 7.00 (dd, 1H), 6.82 (ddd, 1H), 6.59 (d, 1H), 5.24 (s, 2H), 4.91 (s, 2H), 3.47-3.40 (m, 4H), 2.01-1.92 (m, 4H). 3. 379.3 |
| 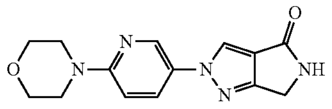 [SMILES: O=C1NCc2nn(-c3ccc(N4CCOCC4)nc3)cc21] | 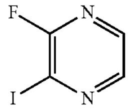 | 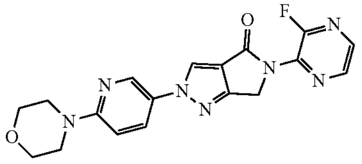 [SMILES: O=C1c2cn(-c3ccc(N4CCOCC4)nc3)nc2CN1c1nccnc1F] 45 | 1. 22% 2. $^{1}$H NMR (500 MHz, DMSO-d6) δ 8.97 (s, 1H), 8.66 (d, 1H), 8.57 (dd, 1H), 8.31-8.26 (m, 1H), 8.06 (dd, 1H), 7.03 (d, 1H), 5.16 (s, 2H), 3.75-3.69 (m, 4H), 3.55-3.50 (m, 4H). 3. 382.2 |
| 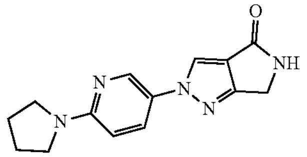 [SMILES: O=C1NCc2nn(-c3ccc(N4CCCC4)nc3)cc21] | 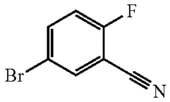 | 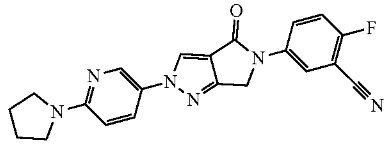 [SMILES: N#Cc1cc(N2Cc3nn(-c4ccc(N5CCCC5)nc4)cc3C2=O)ccc1F] 46 | 1. 37% 2. $^{1}$H NMR (500 MHz, $CF_3COOD$) δ 9.34-9.18 (m, 1H), 9.12 (dd, 1H), 9.02 (ddd, 1H), 8.90 (dt, 1H), 8.80 (ddd, 1H), 8.18 (td, 1H), 8.08-7.89 (m, 1H), 6.14-5.74 (m, 2H), 4.50 (s, 4H), 3.06 (s, 4H). 3. 389.1 |
| 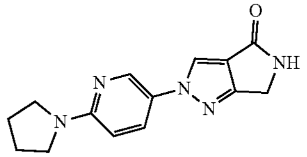 [SMILES: O=C1NCc2nn(-c3ccc(N4CCCC4)nc3)cc21] | 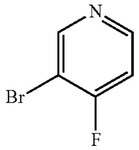 | 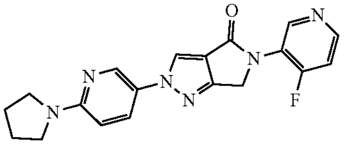 [SMILES: O=C1c2cn(-c3ccc(N4CCCC4)nc3)nc2CN1c1cnccc1F] 47 | 1. 7% 2. $^{1}$H NMR (400 MHz, $CF_3COOD$) δ 9.67 (dd, 1H), 9.00-8.85 (m, 1H), 8.61 (s, 1H), 8.44 (d, 1H), 8.29 (dd, 1H), 8.01 (dd, 1H), 7.22 (d, 1H), 5.36 (s, 2H), 3.78 (s, 4H), 2.32 (s, 4H). 3. 365.1 |
| 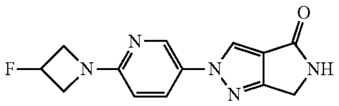 [SMILES: O=C1NCc2nn(-c3ccc(N4CC(F)C4)nc3)cc21] | 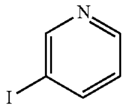 | 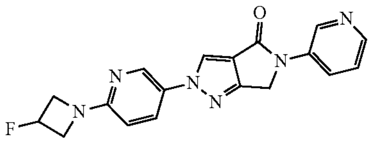 [SMILES: O=C1c2cn(-c3ccc(N4CC(F)C4)nc3)nc2CN1c1cccnc1] 48 | 1. 28% 2. $^{1}$H NMR (500 MHz, $CF_3COOD$) δ 9.97 (s, 1H), 8.92 (d, 1H), 8.74-8.58 (m, 2H), 8.50 (s, 1H), 8.35 (d, 1H), 8.22 (dd, 1H), 7.03 (d, 1H), 5.72-5.49 (m, 1H), 5.36 (s, 2H), 4.84 (td, 2H), 4.72-4.58 (m, 2H). 3. 351.2 |
| 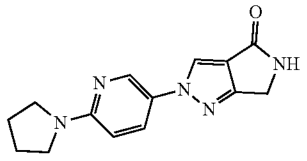 [SMILES: O=C1NCc2nn(-c3ccc(N4CCCC4)nc3)cc21] | 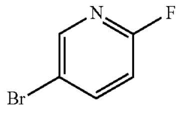 | 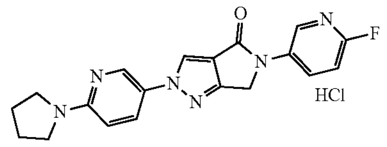 [SMILES: O=C1c2cn(-c3ccc(N4CCCC4)nc3)nc2CN1c1ccc(F)nc1 ; Cl] 49 | 1. 10% 2. $^{1}$H NMR (80 MHz, DMSO-d6) δ 8.89 (s, 1H), 8.70-8.34 (m, 3H), 8.09 (dd, 1H), 7.30 (dd, 1H), 6.74 (d, 1H), 5.08 (s, 2H), 3.51-3.26 (m, 4H), 2.12-1.86 (m, 4H). 3. 365.2 |

TABLE 4a-continued

| Amide | halogenated heteroaryl | Compound of example | 1. Yield<br>2. $^1$H-NMR<br>3. $MH^+$ (ESI) |
|---|---|---|---|
| 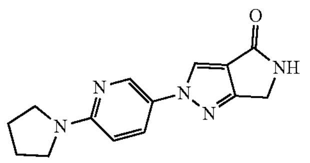 [SMILES: O=C1NCc2nn(-c3ccc(N4CCCC4)nc3)cc21] | 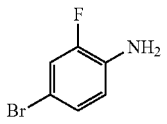 | 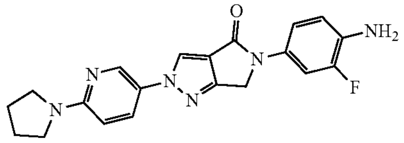 [SMILES: Nc1ccc(N2Cc3nn(-c4ccc(N5CCCC5)nc4)cc3C2=O)cc1F]<br>50 | 1. 47%<br>2. $^1$H NMR (500 MHz, DMSO-d6) δ 8.74 (d, 1 H), 8.54 (d, 1H), 7.95 (dd, 1H), 7.57 (dd, 1H), 7.23 (dd, 1H), 6.79 (dd, 1H), 6.59 (d, 1H), 5.07 (s, 2H), 4.90 (s, 2H), 3.56-3.39 (m, 4H), 2.09-1.87 (m, 4H).<br>3. 379.2 |
| 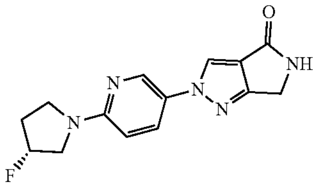 [SMILES: O=C1NCc2nn(-c3ccc(N4CC[C@@H](F)C4)nc3)cc21] | 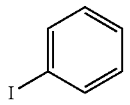 | 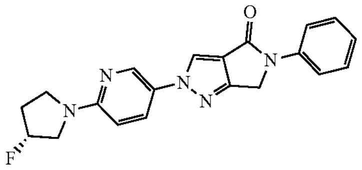 [SMILES: O=C1c2cn(-c3ccc(N4CC[C@@H](F)C4)nc3)nc2CN1c1ccccc1]<br>51 | 1. 39%<br>2. $^1$H NMR (400 MHz, DMSO-d6) δ 8.83 (s, 1H), 8.60 (d, 1H), 8.01 (dd, 1H), 7.91-7.76 (m, 2H), 7.50-7.34 (m, 2H), 7.15 (tt, 1H), 6.67 (d, 1H), 5.65-5.35 (m, 1H), 5.03 (s, 2H), 3.92-3.55 (m, 3H), 3.47 (td, 1H), 2.38-2.09 (m, 2H).<br>3. 364.2 |
| 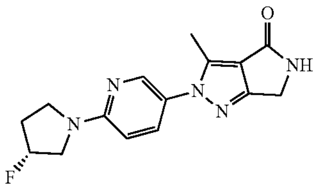 | 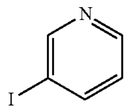 | 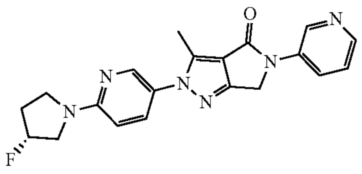 [SMILES: Cc1c2c(nn1-c1ccc(N3CC[C@@H](F)C3)nc1)CN(c1cccnc1)C2=O]<br>52 | 1. 24%<br>2. $^1$H NMR (500 MHz, $CF_3COOD$) δ 10.43 (d, 1H), 9.26 (ddd, 1H), 9.04 (d, 1H), 8.79 (s, 1H), 8.69-8.47 (m, 2H), 7.84-7.60 (m, 1H), 6.13-5.83 (m, 1H), 5.71 (s, 2H), 4.69-4.29 (m, 4H), 3.06 (s, 5H).<br>3. 379.2 |
| 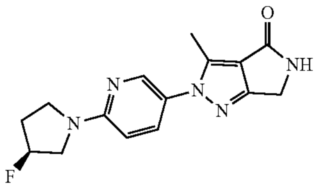 | 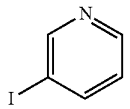 | 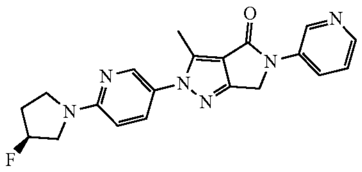 [SMILES: Cc1c2c(nn1-c1ccc(N3CC[C@H](F)C3)nc1)CN(c1cccnc1)C2=O]<br>53 | 1. 20%<br>2. $^1$H NMR (400 MHz, $CF_3COOD$) δ 9.99 (d, 1H), 8.84 (ddd, 1H), 8.61 (dt, 1H), 8.36 (s, 1H), 8.15 (ddd, 2H), 7.27 (q, 1H), 5.70-5.41 (m, 1H), 5.28 (s, 2H), 4.21-3.85 (m, 4H), 2.89-2.25 (m, 5H).<br>3. 379.2 |
| 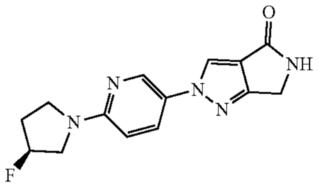 [SMILES: O=C1NCc2nn(-c3ccc(N4CC[C@H](F)C4)nc3)cc21] | 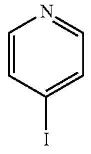 | 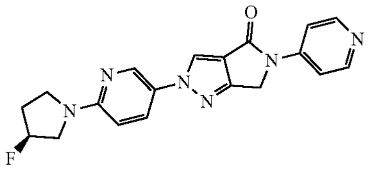 [SMILES: O=C1c2cn(-c3ccc(N4CC[C@H](F)C4)nc3)nc2CN1c1ccncc1]<br>54 | 1. 17%<br>2. $^1$H NMR (80 MHz, DMSO-d6) δ 8.90 (s, 1H), 8.66-8.41 (m, 3H), 8.12-7.74 (m, 3H), 6.67 (d, 1H), 5.90-4.96 (m, 3H), 3.98-3.36 (m, 4H), 2.38-1.52 (m, 2H)<br>3. 365.1 |
| 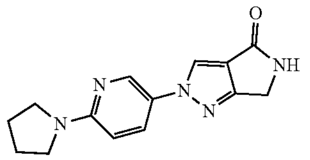 [SMILES: O=C1NCc2nn(-c3ccc(N4CCCC4)nc3)cc21] | 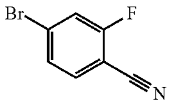 | 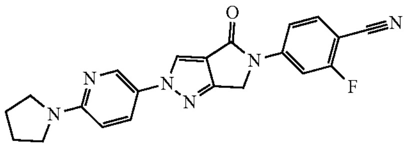 [SMILES: N#Cc1ccc(N2Cc3nn(-c4ccc(N5CCCC5)nc4)cc3C2=O)cc1F]<br>55 | 1. 48%<br>2. $^1$H NMR (400 MHz, DMSO-d6) δ 8.91 (s, 1H), 8.57 (d, 1H), 8.08 (d, 1H), 8.02-7.91 (m, 2H), 7.86 (d, 1H), 6.60 (d, 1H), 5.09 (s, 2H), 3.51-3.41 (m, 4H), 2.06-1.91 (m, 4H).<br>3. 389.4 |

TABLE 4a-continued

| Amide | halogenated heteroaryl | Compound of example | 1. Yield<br>2. $^1$H-NMR<br>3. $MH^+$ (ESI) |
|---|---|---|---|
| 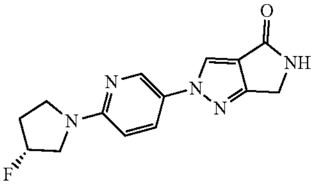 [SMILES: O=C1NCc2nn(-c3ccc(N4CC[C@@H](F)C4)nc3)cc21] | 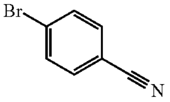 | 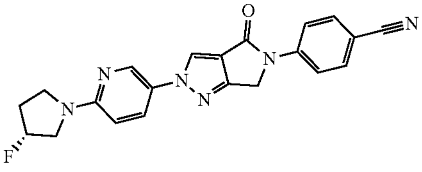 [SMILES: N#Cc1ccc(N2Cc3nn(-c4ccc(N5CC[C@@H](F)C5)nc4)cc3C2=O)cc1]<br>56 | 1. 9%<br>2. $^1$H NMR (400 MHz, DMSO-d6) δ 8.90 (s, 1H), 8.60 (d, 1H), 8.04 (dd, 3H), 7.88 (d, 2H), 6.67 (d, 1H), 5.64-5.33 (m, 1H), 5.09 (s, 2H), 3.70 (d, 3H), 3.49 (t, 1H), 2.39-2.03 (m, 2H).<br>3. 389.3 |
| 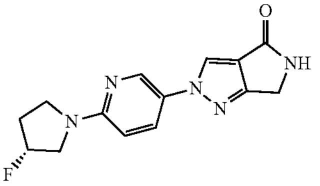 [SMILES: O=C1NCc2nn(-c3ccc(N4CC[C@@H](F)C4)nc3)cc21] | 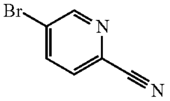 | 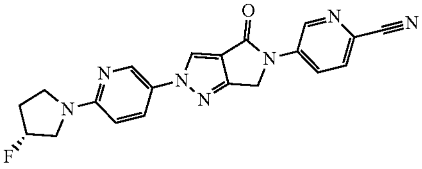 [SMILES: N#Cc1ccc(N2Cc3nn(-c4ccc(N5CC[C@@H](F)C5)nc4)cc3C2=O)cn1]<br>57 | 1. 13%<br>2. $^1$H NMR (400 MHz, DMSO-d6) δ 9.23 (d, 1H), 8.94 (s, 1H), 8.60 (d, 1H), 8.48 (dd, 1H), 8.09 (d, 1H), 8.02 (dd, 1H), 6.67 (d, 1H), 5.58-5.35 (m, 1H), 5.14 (s, 2H), 3.86-3.55 (m, 3H), 3.48 (td, 1H), 2.38-2.09 (m, 2H).<br>3. 390.4 |
| 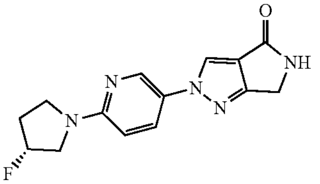 [SMILES: O=C1NCc2nn(-c3ccc(N4CC[C@@H](F)C4)nc3)cc21] | 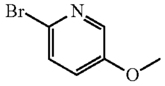 | 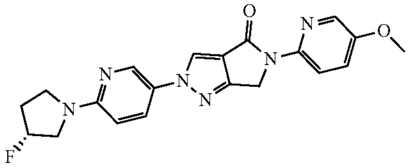 [SMILES: COc1ccc(N2Cc3nn(-c4ccc(N5CC[C@@H](F)C5)nc4)cc3C2=O)nc1]<br>58 | 1. 27%<br>2. $^1$H NMR (500 MHz, DMSO-d6) δ 8.85 (s, 1H), 8.60 (d, 1H), 8.36 (d, 1H), 8.14 (d, 1H), 8.01 (dd, 1H), 7.52 (dd, 1H), 6.67 (d, 1H), 5.60-5.33 (m, 1H), 5.05 (s, 2H), 3.83 (s, 3H), 3.82-3.55 (m, 3H), 3.56-3.42 (m, 1H), 2.38-2.08 (m, 2H).<br>3. 395.3 |
| 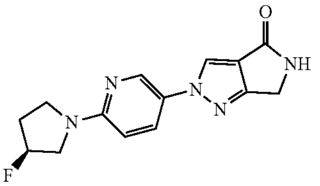 [SMILES: O=C1NCc2nn(-c3ccc(N4CC[C@H](F)C4)nc3)cc21] | 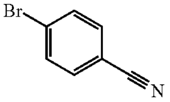 | 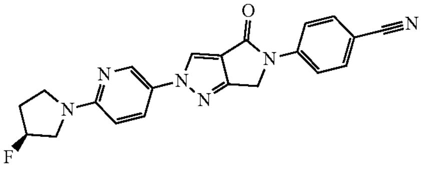 [SMILES: N#Cc1ccc(N2Cc3nn(-c4ccc(N5CC[C@H](F)C5)nc4)cc3C2=O)cc1]<br>59 | 1. 14%<br>2. $^1$H NMR (400 MHz, DMSO-d6) δ 8.90 (s, 1H), 8.60 (d, 1H), 8.16-7.95 (m, 3H), 7.95-7.80 (m, 2H), 6.67 (d, 1H), 5.65-5.31 (m, 1H), 5.09 (s, 2H), 3.88-3.54 (m, 3H), 3.54-3.38 (m, 1H), 2.39-2.06 (m, 2H).<br>3. 389.6 |
| 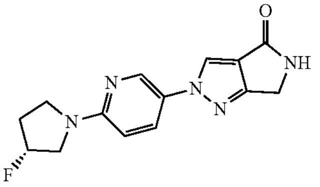 [SMILES: O=C1NCc2nn(-c3ccc(N4CC[C@@H](F)C4)nc3)cc21] | 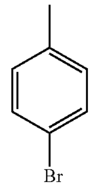 | 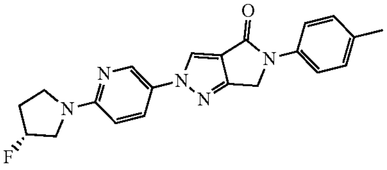 [SMILES: Cc1ccc(N2Cc3nn(-c4ccc(N5CC[C@@H](F)C5)nc4)cc3C2=O)cc1]<br>60 | 1. 19%<br>2. $^1$H NMR (500 MHz, DMSO-d6) δ 7.99 (s, 1H), 7.83-7.72 (m, 1H), 7.19 (dd, 1H), 6.96-6.82 (m, 2H), 6.40 (d, 2H), 5.85 (d, 1H), 4.80-4.56 (m, 1H), 4.17 (s, 2H), 3.06-2.76 (m, 3H), 2.73-2.60 (m, 1H), 1.58-1.26 (m, 5H).<br>3. 378.3 |
| 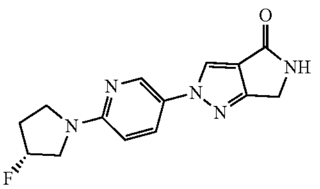 [SMILES: O=C1NCc2nn(-c3ccc(N4CC[C@@H](F)C4)nc3)cc21] | 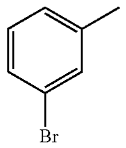 | 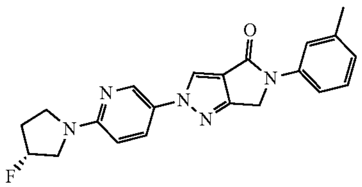 [SMILES: Cc1cccc(N2Cc3nn(-c4ccc(N5CC[C@@H](F)C5)nc4)cc3C2=O)c1]<br>61 | 1. 23%<br>2. $^1$H NMR (500 MHz, DMSO-d6) δ 8.82 (s, 1H), 8.64-8.55 (m, 1H), 8.01 (dd, 1H), 7.67-7.64 (m, 1H), 7.62 (dd, 1H), 7.29 (t, 1H), 6.97 (d, 1H), 6.67 (d, 1H), 5.58-5.37 (m, 1H), 5.01 (s, 2H), 3.90-3.57 (m, 3H), 3.48 (td, 1H), 2.35 (s, 3H), 2.32-2.07 (m, 2H).<br>3. 378.2 |

TABLE 4a-continued

| Amide | halogenated heteroaryl | Compound of example | 1. Yield<br>2. $^1$H-NMR<br>3. $MH^+$ (ESI) |
| --- | --- | --- | --- |
| 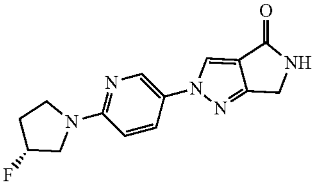 [SMILES: O=C1NCc2nn(-c3ccc(N4CC[C@@H](F)C4)nc3)cc21] | 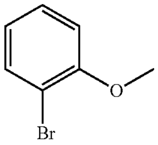 | 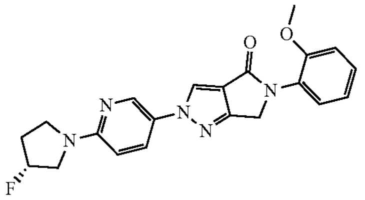 [SMILES: COc1ccccc1N1Cc2nn(-c3ccc(N4CC[C@@H](F)C4)nc3)cc2C1=O]<br>62 | 1. 12%<br>2. $^1$H NMR (500 MHz, DMSO-d6) δ 7.94 (s, 1H), 7.77 (d, 1H), 7.18 (dd, 1H), 6.67-6.48 (m, 2H), 6.34 (dd, 1H), 6.21 (td, 1H), 5.85 (d, 1H), 4.79-4.54 (m, 1H), 3.96 (s, 2H), 3.02-2.76 (m, 6H), 2.66 (td, 1H), 1.52-1.26 (m, 2H).<br>3. 394.2 |
| 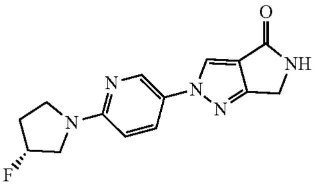 [SMILES: O=C1NCc2nn(-c3ccc(N4CC[C@@H](F)C4)nc3)cc21] | 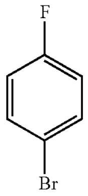 | 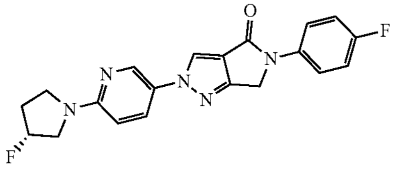 [SMILES: O=C1c2cn(-c3ccc(N4CC[C@@H](F)C4)nc3)nc2CN1c1ccc(F)cc1]<br>63 | 1. 18%<br>2. $^1$H NMR (400 MHz, DMSO-d6) δ 8.00 (s, 1H), 7.77 (d, 1H), 7.19 (dd, 1H), 7.10-6.93 (m, 2H), 6.57-6.36 (m, 2H), 5.85 (d, 1H), 4.79-4.52 (m, 1H), 4.20 (s, 2H), 3.09-2.74 (m, 3H), 2.72-2.60 (m, 1H), 1.57-1.21 (m, 2H).<br>3. 382.2 |
| 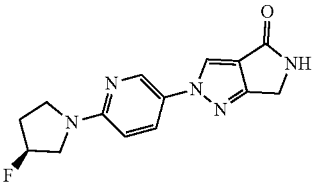 [SMILES: O=C1NCc2nn(-c3ccc(N4CC[C@H](F)C4)nc3)cc21] | 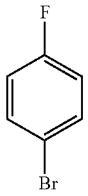 | 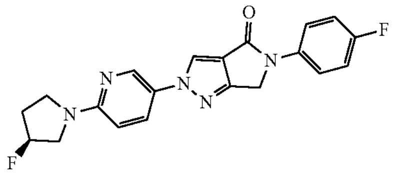 [SMILES: O=C1c2cn(-c3ccc(N4CC[C@H](F)C4)nc3)nc2CN1c1ccc(F)cc1]<br>64 | 1. 14%<br>2. $^1$H NMR (400 MHz, DMSO-d6) δ 8.83 (s, 1H), 8.59 (d, 1H), 8.01 (dd, 1H), 7.92-7.75 (m, 2H), 7.38-7.17 (m, 2H), 6.67 (d, 1H), 5.60-5.36 (m, 1H), 5.02 (s, 2H), 3.89-3.55 (m, 3H), 3.47 (td, 1H), 2.37-2.10 (m, 2H).<br>3. 382.2 |
| 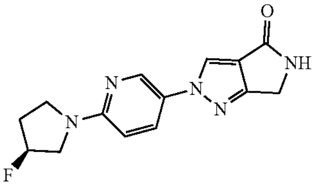 [SMILES: O=C1NCc2nn(-c3ccc(N4CC[C@H](F)C4)nc3)cc21] | 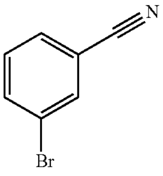 | 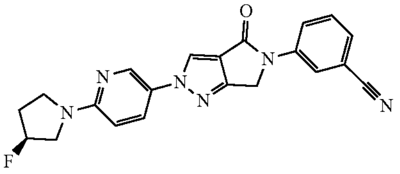 [SMILES: N#Cc1cccc(N2Cc3nn(-c4ccc(N5CC[C@H](F)C5)nc4)cc3C2=O)c1]<br>65 | 1. 13%<br>2. $^1$H NMR (500 MHz, CF3COOD) δ 8.62 (s, 1H), 8.58 (d, 1H), 8.46 (dd, 1H), 8.30 (t, 1H), 8.20-8.04 (m, 1H), 7.92-7.69 (m, 2H), 7.36 (d, 1H), 5.81-5.55 (m, 1H), 5.30 (s, 2H), 4.28-3.97 (m, 4H), 2.88-2.69 (m, 1H), 2.66-2.38 (m, 1H).<br>3. 389.2 |
| 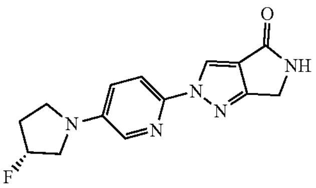 [SMILES: O=C1NCc2nn(-c3ccc(N4CC[C@@H](F)C4)cn3)cc21] | 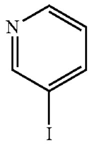 | 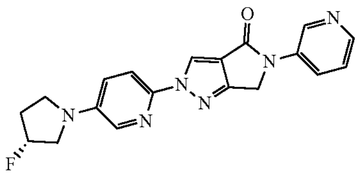 [SMILES: O=C1c2cn(-c3ccc(N4CC[C@@H](F)C4)cn3)nc2CN1c1cccnc1]<br>66 | 1. 23%<br>2. $^1$H NMR (400 MHz, CF3COOD) δ 10.14 (d, 1H), 9.23-9.00 (m, 2H), 8.87 (d, 1H), 8.56-8.31 (m, 2H), 8.16 (d, 1H), 8.02 (dd, 1H), 5.97-5.61 (m, 1H), 5.52 (s, 2H), 4.11-3.78 (m, 4H), 2.82 (t, 1H), 2.71-2.42 (m, 1H).<br>3. 365.2 |
| 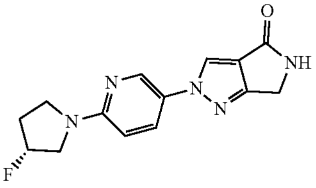 [SMILES: O=C1NCc2nn(-c3ccc(N4CC[C@@H](F)C4)nc3)cc21] | 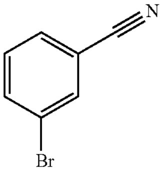 | 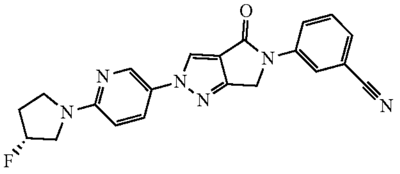 [SMILES: N#Cc1cccc(N2Cc3nn(-c4ccc(N5CC[C@@H](F)C5)nc4)cc3C2=O)c1]<br>67 | 1. 26%<br>2. $^1$H NMR (500 MHz, CF3COOD) δ 8.50 (s, 1H), 8.47 (d, 1H), 8.35 (dd, 1H), 8.19 (t, 1H), 8.03 (ddd, 1H), 7.80-7.64 (m, 2H), 7.24 (d, 1H), 5.71-5.44 (m, 1H), 5.19 (s, 2H), 4.14-3.87 (m, 4H), 2.83-2.58 (m, 1H), 2.54-2.27 (m, 1H).<br>3. 389.2 |

TABLE 4a-continued

| Amide | halogenated heteroaryl | Compound of example | 1. Yield<br>2. $^{1}$H-NMR<br>3. $MH^+$ (ESI) |
|---|---|---|---|
| 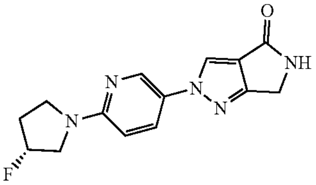 [SMILES: O=C1NCc2nn(-c3ccc(N4CC[C@@H](F)C4)nc3)cc21] | 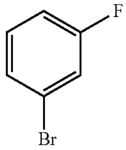 | 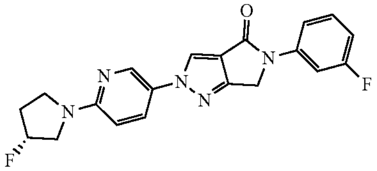 [SMILES: O=C1c2cn(-c3ccc(N4CC[C@@H](F)C4)nc3)nc2CN1c1cccc(F)c1]<br>68 | 1. 32%<br>2. $^{1}$H NMR (400 MHz, DMSO-d6) δ 8.86 (s, 1H), 8.60 (d, 1H), 8.01 (dd, 1H), 7.82 (dt, 1H), 7.63 (ddd, 1H), 7.45 (td, 1H), 7.05-6.91 (m, 1H), 6.67 (d, 1H), 5.60-5.34 (m, 1H), 5.04 (s, 2H), 3.90-3.55 (m, 3H), 3.48 (td, 1H), 2.39-2.03 (m, 1H).<br>3. 382.2 |
| 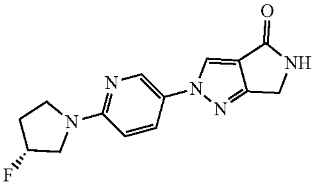 [SMILES: O=C1NCc2nn(-c3ccc(N4CC[C@@H](F)C4)nc3)cc21] | 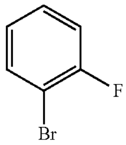 | 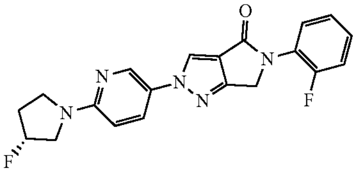 [SMILES: O=C1c2cn(-c3ccc(N4CC[C@@H](F)C4)nc3)nc2CN1c1ccccc1F]<br>69 | 1. 32%<br>2. $^{1}$H NMR (500 MHz, DMSO-d6) δ 8.83 (s, 1H), 8.59 (dd, 1H), 8.01 (dd, 1H), 7.62 (td, 1H), 7.48-7.24 (m, 3H), 6.79-6.61 (m, 1H), 5.65-5.36 (m, 1H), 4.93 (s, 2H), 3.92-3.57 (m, 3H), 3.48 (td, 1H), 2.41-2.11 (m, 2H).<br>3. 382.2 |
| 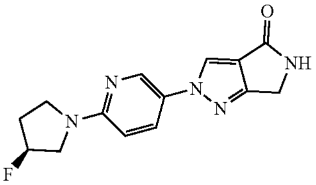 [SMILES: O=C1NCc2nn(-c3ccc(N4CC[C@H](F)C4)nc3)cc21] | 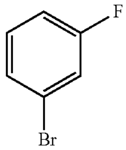 | 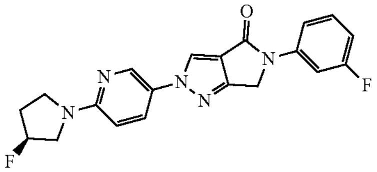 [SMILES: O=C1c2cn(-c3ccc(N4CC[C@H](F)C4)nc3)nc2CN1c1cccc(F)c1]<br>70 | 1. 12%<br>2. $^{1}$H NMR (500 MHz, DMSO-d6) δ 8.86 (s, 1H), 8.60 (dd, 1H), 8.01 (dd, 1H), 7.82 (dt, 1H), 7.63 (ddd, 1H), 7.45 (td, 1H), 6.98 (tdd, 1H), 6.67 (dd, 1H), 5.57-5.34 (m, 1H), 5.04 (s, 2H), 3.92-3.55 (m, 3H), 3.47 (td, 1H), 2.40-2.08 (m, 2H).<br>3. 382.2 |
| 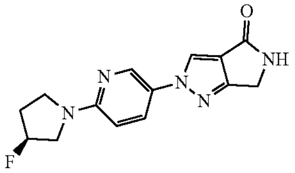 [SMILES: O=C1NCc2nn(-c3ccc(N4CC[C@H](F)C4)nc3)cc21] | 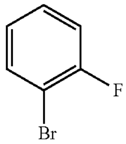 | 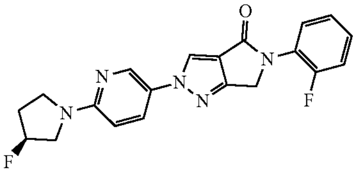 [SMILES: O=C1c2cn(-c3ccc(N4CC[C@H](F)C4)nc3)nc2CN1c1ccccc1F]<br>71 | 1. 16%<br>2. $^{1}$H NMR (400 MHz, DMSO-d6) δ 8.83 (s, 1H), 8.59 (d, 1H), 8.00 (dd, 1H), 7.62 (td, 1H), 7.49-7.23 (m, 3H), 6.67 (d, 1H), 5.60-5.35 (m, 1H), 4.93 (s, 2H), 3.98-3.55 (m, 3H), 3.48 (td, 1H), 2.41-2.03 (m, 2H).<br>3. 382.2 |
| 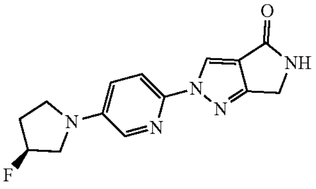 [SMILES: O=C1NCc2nn(-c3ccc(N4CC[C@H](F)C4)cn3)cc21] | 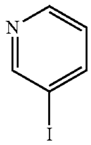 | 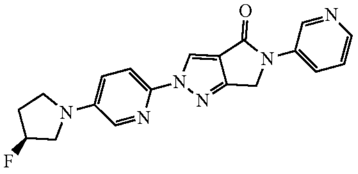 [SMILES: O=C1c2cn(-c3ccc(N4CC[C@H](F)C4)cn3)nc2CN1c1cccnc1]<br>72 | 1. 22%<br>2. $^{1}$H NMR (500 MHz, CF3COOD) δ 9.89 (d, 1H), 8.94-8.77 (m, 2H), 8.63 (d, 1H), 8.27-8.11 (m, 2H), 7.92 (d, 1H), 7.77 (dd, 1H), 5.70-5.36 (m, 1H), 5.27 (s, 2H), 3.87-3.63 (m, 4H), 2.57 (t, 1H), 2.47-2.18 (m, 1H).<br>3. 365.2 |
| 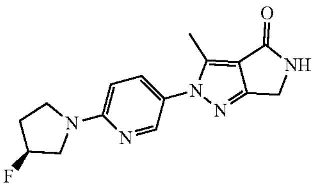 [SMILES: Cc1c2c(nn1-c1ccc(N3CC[C@H](F)C3)nc1)CNC2=O] | 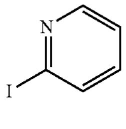 | 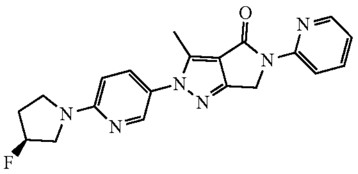 [SMILES: Cc1c2c(nn1-c1ccc(N3CC[C@H](F)C3)nc1)CN(c1ccccn1)C2=O]<br>73 | 1. ND<br>2. $^{1}$H NMR (500 MHz, CF3COOD) δ 9.89 (d, 1H), 8.94-8.77 (m, 2H), 8.63 (d, 1H), 8.27-8.11 (m, 2H), 7.92 (d, 1H), 7.77 (dd, 1H), 5.70-5.36 (m, 1H), 5.27 (s, 2H), 3.87-3.63 (m, 4H), 2.57 (t, 1H), 2.47-2.18 (m, 1H).<br>3. 365.2 |

TABLE 4a-continued

| Amide | halogenated heteroaryl | Compound of example | 1. Yield<br>2. $^1$H-NMR<br>3. MH$^+$ (ESI) |
|---|---|---|---|
| 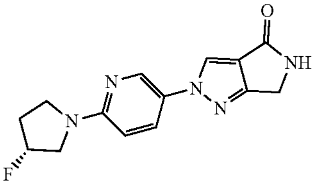 [SMILES: O=C1NCc2nn(-c3ccc(N4CC[C@@H](F)C4)nc3)cc21] | 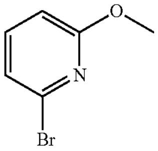 | 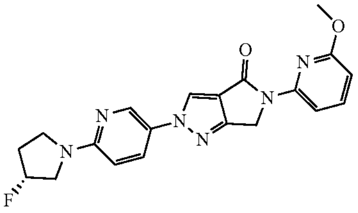 [SMILES: COc1cccc(N2Cc3nn(-c4ccc(N5CC[C@@H](F)C5)nc4)cc3C2=O)n1]<br>74 | 1. 36%<br>2. $^1$H NMR (400 MHz, DMSO-d6) δ 8.87 (s, 1H), 8.60 (d, 1H), 8.10-7.93 (m, 2H), 7.74 (t, 1H), 6.67 (d, 1H), 6.55 (d, 1H), 5.62-5.34 (m, 1H), 5.12 (s, 2H), 3.90 (s, 3H), 3.86-3.55 (m, 3H), 3.47 (td, 1H), 2.39-2.08 (m, 2H).<br>3. 395.2 |
| 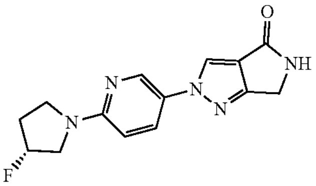 [SMILES: O=C1NCc2nn(-c3ccc(N4CC[C@@H](F)C4)nc3)cc21] | 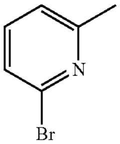 | 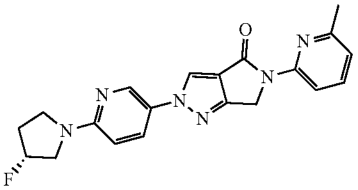 [SMILES: Cc1cccc(N2Cc3nn(-c4ccc(N5CC[C@@H](F)C5)nc4)cc3C2=O)n1]<br>75 | 1. 28%<br>2. $^1$H NMR (500 MHz, DMSO-d6) δ 8.87 (s, 1H), 8.60 (dd, 1H), 8.32-8.18 (m, 1H), 8.02 (dd, 1H), 7.72 (dd, 1H), 7.01 (d, 1H), 6.67 (dd, 1H), 5.64-5.31 (m, 1H), 5.07 (s, 2H), 3.88-3.58 (m, 3H), 3.48 (td, 1H), 2.47 (s, 3H), 2.38-2.10 (m, 2H).<br>3. 379.2 |
| 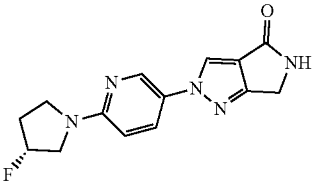 [SMILES: O=C1NCc2nn(-c3ccc(N4CC[C@@H](F)C4)nc3)cc21] | 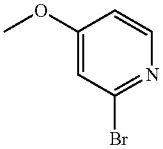 | 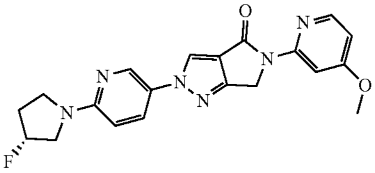 [SMILES: COc1ccnc(N2Cc3nn(-c4ccc(N5CC[C@@H](F)C5)nc4)cc3C2=O)c1]<br>76 | 1. 24%<br>2. $^1$H NMR (500 MHz, DMSO-d6) δ 8.89 (s, 1H), 8.61 (dd, 1H), 8.23 (d, 1H), 8.06 (d, 1H), 8.02 (dd, 1H), 6.79 (dd, 1H), 6.67 (dd, 1H), 5.62-5.38 (m, 1H), 5.07 (s, 2H), 3.86 (s, 3H), 3.83-3.58 (m, 3H), 3.47 (td, 1H), 2.35-2.10 (m, 2H).<br>3. 395.5 |
| 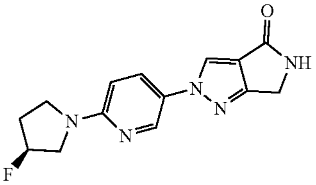 [SMILES: O=C1NCc2nn(-c3ccc(N4CC[C@H](F)C4)nc3)cc21] | 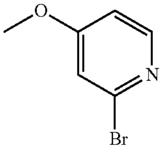 | 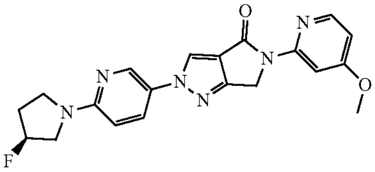 [SMILES: COc1ccnc(N2Cc3nn(-c4ccc(N5CC[C@H](F)C5)nc4)cc3C2=O)c1]<br>77 | 1. 13%<br>2. $^1$H NMR (500 MHz, DMSO-d6) δ 8.89 (s, 1H), 8.71-8.55 (m, 1H), 8.24 (s, 1H), 8.07 (d, 1H), 8.02 (dd, 1H), 6.79 (dd, 1H), 6.67 (d, 1H), 5.64-5.34 (m, 1H), 5.07 (s, 2H), 3.86 (s, 3H), 3.79-3.59 (m, 3H), 3.51-3.45 (m, 1H), 2.38-2.07 (m, 2H).<br>3. 395.2 |
| 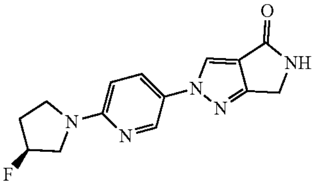 [SMILES: O=C1NCc2nn(-c3ccc(N4CC[C@H](F)C4)nc3)cc21] | 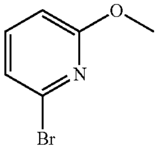 | 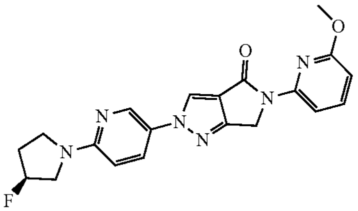 [SMILES: COc1cccc(N2Cc3nn(-c4ccc(N5CC[C@H](F)C5)nc4)cc3C2=O)n1]<br>78 | 1. 15%<br>2. $^1$H NMR (500 MHz, DMSO-d6) δ 8.88 (s, 1H), 8.60 (dd, 1H), 8.01 (dd, 1H), 7.98 (dd, 1H), 7.74 (t, 1H), 6.67 (dd, 1H), 6.55 (dd, 1H), 5.60-5.36 (m, 1H), 5.13 (s, 2H), 3.91 (s, 3H), 3.83-3.56 (m, 3H), 3.49 (dd, 1H), 2.34-2.12 (m, 2H).<br>3. 395.4 |

TABLE 4a-continued

| Amide | halogenated heteroaryl | Compound of example | 1. Yield<br>2. $^{1}$H-NMR<br>3. $MH^{+}$ (ESI) |
|---|---|---|---|
| 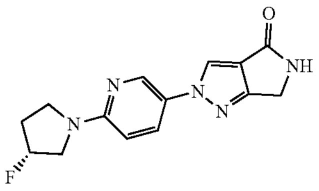 [SMILES: O=C1NCc2nn(-c3ccc(N4CC[C@@H](F)C4)nc3)cc21] | 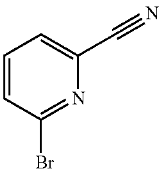 | 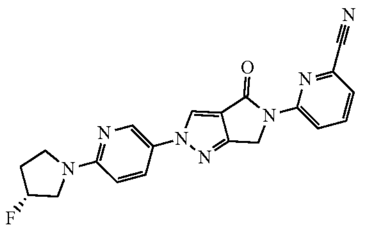 [SMILES: N#Cc1cccc(N2Cc3nn(-c4ccc(N5CC[C@@H](F)C5)nc4)cc3C2=O)n1]<br>79 | 1. 10%<br>2. $^{1}$H NMR (400 MHz, DMSO-d6) δ 8.12 (s, 1H), 7.93 (dd, 1H), 7.78 (d, 1H), 7.39-7.11 (m, 2H), 6.96 (dd, 1H), 5.84 (d, 1H), 4.76-4.53 (m, 1H), 4.27 (s, 2H), 3.17-2.73 (m, 3H), 2.65 (td, 1H), 1.56-1.24 (m, 2H).<br>3. 390.1 |
| 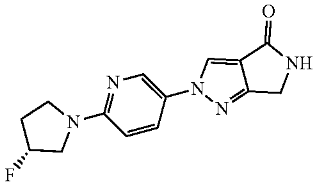 [SMILES: O=C1NCc2nn(-c3ccc(N4CC[C@@H](F)C4)nc3)cc21] | 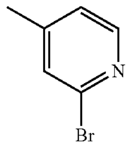 | 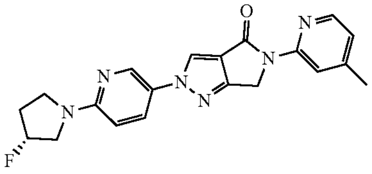 [SMILES: Cc1ccnc(N2Cc3nn(-c4ccc(N5CC[C@@H](F)C5)nc4)cc3C2=O)c1]<br>80 | 1. 18%<br>2. $^{1}$H NMR (500 MHz, CF3COOD) δ 8.68 (s, 1H), 8.52 (s, 1H), 8.34 (dd, 2H), 7.61 (s, 1H), 7.51 (d, 1H), 7.23 (s, 1H), 5.66-5.39 (m, 1H), 5.32 (s, 2H), 4.27-3.79 (m, 4H), 2.72 (d, 4H), 2.54-2.23 (m, 1H).<br>3. 379.2 |
| 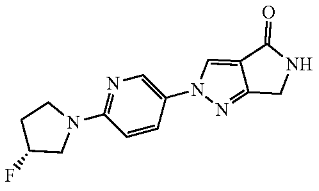 [SMILES: O=C1NCc2nn(-c3ccc(N4CC[C@@H](F)C4)nc3)cc21] | 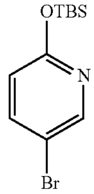 | 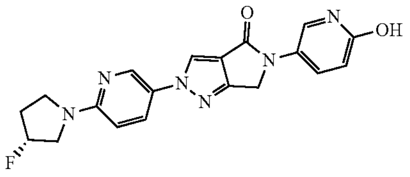 [SMILES: O=C1c2cn(-c3ccc(N4CC[C@@H](F)C4)nc3)nc2CN1c1ccc(O)nc1]<br>81 | 1. 3%<br>2. $^{1}$H NMR (500 MHz, CF3COOD) δ 8.96 (d, 1H), 8.69 (dd, 1H), 8.57 (s, 1H), 8.50 (d, 1H), 8.37 (dd, 1H), 7.49 (d, 1H), 7.27 (s, 1H), 5.69-5.45 (m, 1H), 5.24 (s, 2H), 4.24-3.83 (m, 4H), 2.69 (s, 1H), 2.56-2.30 (m, 1H).<br>3. 381.2 |
| 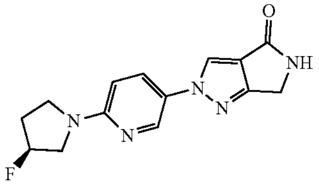 [SMILES: O=C1NCc2nn(-c3ccc(N4CC[C@H](F)C4)nc3)cc21] | 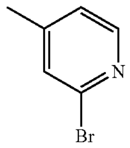 | 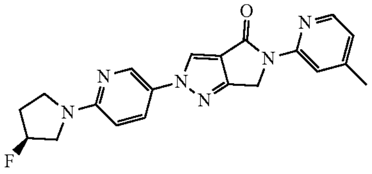<br>82 | 1. 9%<br>2. $^{1}$H NMR (400 MHz, DMSO-d6) δ 8.89 (s, 1H), 8.60 (d, 1H), 8.42-8.23 (m, 2H), 8.02 (dd, 1H), 7.07-6.95 (m, 1H), 6.67 (d, 1H), 5.60-5.35 (m, 1H), 5.07 (s, 2H), 3.93-3.55 (m, 3H), 3.54-3.42 (m, 1H), 2.45-2.06 (m, 5H).<br>3. 379.2 |
| 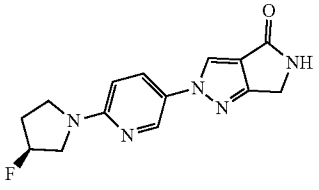 [SMILES: O=C1NCc2nn(-c3ccc(N4CC[C@H](F)C4)nc3)cc21] | 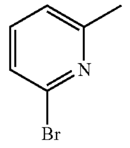 | 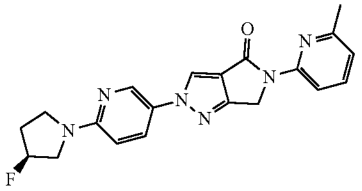<br>83 | 1. 9%<br>2. $^{1}$H NMR (500 MHz, CF3COOD) δ 8.82-8.61 (m, 1H), 8.53 (s, 1H), 8.50-8.33 (m, 2H), 7.53 (t, 2H), 7.25 (s, 1H), 5.70-5.41 (m, 1H), 5.32 (d, 2H), 4.23-3.80 (m, 4H), 2.94-2.79 (m, 3H), 2.66 (s, 1H), 2.56-2.28 (m, 1H).<br>3. 379.2 |
| 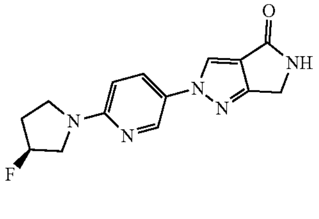 | 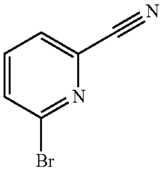 | 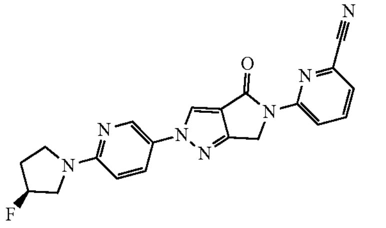 [SMILES: N#Cc1cccc(N2Cc3nn(-c4ccc(N5CC[C@H](F)C5)nc4)cc3C2=O)n1]<br>84 | 1. 12%<br>2. $^{1}$H NMR (500 MHz, DMSO-d6) δ 8.94 (s, 1H), 8.76 (dd, 1H), 8.61 (dd, 1H), 8.19-7.97 (m, 2H), 7.79 (dd, 1H), 6.67 (dd, 1H), 5.63-5.39 (m, 1H), 5.10 (s, 2H), 3.99-3.60 (m, 3H), 3.53-3.42 (m, 1H), 2.36-2.09 (m, 2H).<br>3. 390.2 |

TABLE 4a-continued

| Amide | halogenated heteroaryl | Compound of example | 1. Yield<br>2. $^1$H-NMR<br>3. $MH^+$ (ESI) |
|---|---|---|---|
| 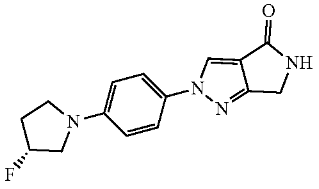 | 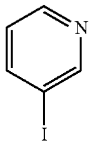 | 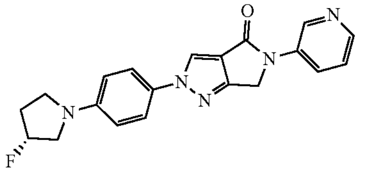<br>85 | 1. 19%<br>2. $^1$H NMR (500 MHz, CF3COOD) δ 9.90 (d, 1H), 8.87 (d, 1H), 8.71-8.54 (m, 2H), 8.14 (dd, 1H), 7.95 (d, 2H), 7.87 (d, 2H), 5.81-5.54 (m, 1H), 5.35 (s, 2H), 4.62-4.26 (m, 2H), 4.26-4.04 (m, 2H), 2.89-2.46 (m, 2H).<br>3. 364.1 |
| 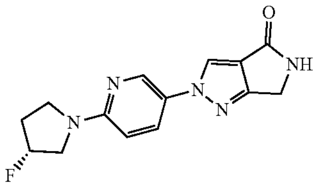 [SMILES: O=C1NCc2nn(-c3ccc(N4CC[C@@H](F)C4)nc3)cc21] | 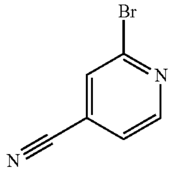 | 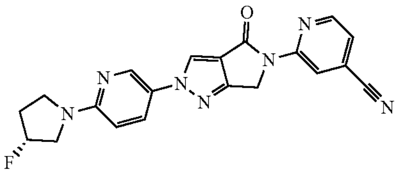 [SMILES: N#Cc1ccnc(N2Cc3nn(-c4ccc(N5CC[C@@H](F)C5)nc4)cc3C2=O)c1]<br>86 | 1. 42%<br>2. $^1$H NMR (500 MHz, CF3COOD) δ 8.79 (dd, 1H), 8.74 (s, 1H), 8.58 (s, 1H), 8.42 (dd, 1H), 8.31 (dd, 1H),7.94 (dd, 1H), 7.30 (s, 1H), 5.74-5.49 (m, 1H), 5.47 (s, 2H), 4.31-3.85 (m, 4H), 2.70 (s, 1H), 2.59-2.29 (m, 1H).<br>3. 390.2 |
| 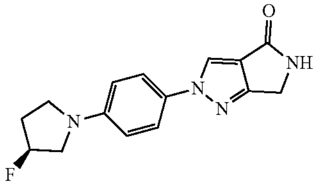 | 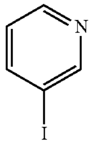 | 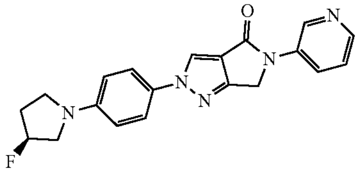<br>87 | 1. 22%<br>2. $^1$H NMR (500 MHz, DMSO-d6) δ 9.16-8.97 (m, 1H), 8.84 (s, 1H), 8.37 (s, 1H), 8.27 (ddd, 1H), 7.78-7.61 (m, 2H), 7.59-7.38 (m, 1H), 6.70 (d, 2H), 5.59-5.40 (m, 1H), 5.07 (s, 2H), 3.76-3.39 (m, 4H), 2.33-2.04 (m, 2H).<br>3. 364.1 |
| 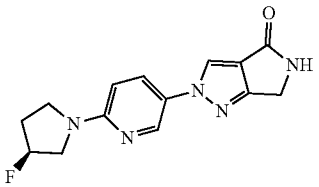 | 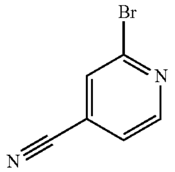 | 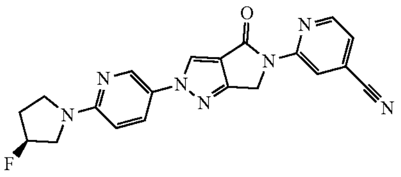 [SMILES: N#Cc1ccnc(N2Cc3nn(-c4ccc(N5CC[C@H](F)C5)nc4)cc3C2=O)c1]<br>88 | 1. 10%<br>2. $^1$H NMR (500 MHz, CF3COOD) δ 8.93 (d, 1H), 8.88 (s, 1H), 8.72 (d, 1H), 8.55 (dd, 1H), 8.44 (d, 1H), 8.08 (dd, 1H), 7.43 (s, 1H), 5.84-5.62 (m, 1H), 5.60 (s, 2H), 4.37-3.93 (m, 4H), 2.84 (s, 1H), 2.74-2.48 (m, 1H).<br>3. 390.2 |
| 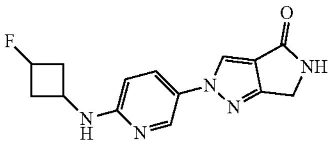 [SMILES: O=C1NCc2nn(-c3ccc(NC4CC(F)C4)nc3)cc21] | 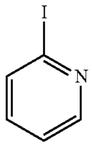 | 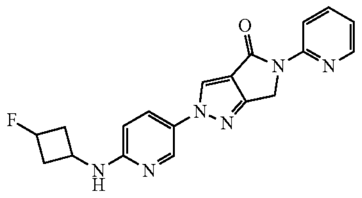 [SMILES: O=C1c2cn(-c3ccc(NC4CC(F)C4)nc3)nc2CN1c1ccccn1]<br>89 | 1. 9%<br>2. $^1$H NMR (500 MHz, CF3COOD) δ 8.63 (d, 1H), 8.59-8.45 (m, 4H), 8.33 (d, 1H), 7.75 (d, 1H), 7.70 (td, 1H), 7.19 (d, 1H), 5.33 (s, 3H), 4.60-4.36 (m, 1H), 2.98-2.77 (m, 2H), 2.70-2.44 (m, 2H).<br>3. 365.2 |
| 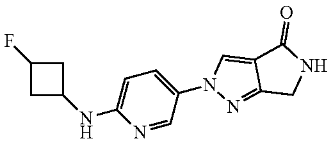 [SMILES: O=C1NCc2nn(-c3ccc(NC4CC(F)C4)nc3)cc21] | 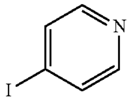 | 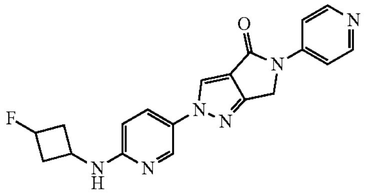 [SMILES: O=C1c2cn(-c3ccc(NC4CC(F)C4)nc3)nc2CN1c1ccncc1]<br>90 | 1. 15%<br>2. $^1$H NMR (400 MHz, CF3COOD) δ 8.77-8.57 (m, 3H), 8.57-8.41 (m, 3H), 8.29 (d, 1H), 7.16 (d, 1H), 5.44-5.14 (m, 3H), 4.50 (dt, 1H), 2.94-2.70 (m, 2H), 2.68-2.42 (m, 2H).<br>3. 365.2 |

TABLE 4a-continued

| Amide | halogenated heteroaryl | Compound of example | 1. Yield<br>2. $^{1}$H-NMR<br>3. MH$^{+}$ (ESI) |
|---|---|---|---|
| 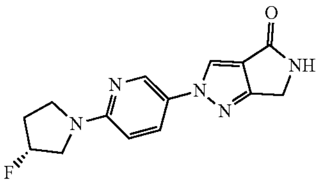 [SMILES: O=C1NCc2nn(-c3ccc(N4CC[C@@H](F)C4)nc3)cc21] | 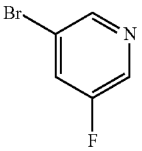 | 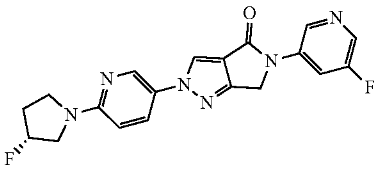 [SMILES: O=C1c2cn(-c3ccc(N4CC[C@@H](F)C4)nc3)nc2CN1c1cncc(F)c1]<br>91 | 1. 16%<br>2. $^{1}$H NMR (500 MHz, CF3COOD) δ 9.69 (d, 1H), 8.77 (dt, 1H), 8.68-8.50 (m, 2H), 8.44 (d, 1H), 8.29 (dd, 1H), 7.18 (s, 1H), 5.60-5.35 (m, 1H), 5.26 (s, 2H), 4.26-3.72 (m, 4H), 2.60 (s, 1H), 2.50-2.20 (m, 1H).<br>3. 383.0 |
| 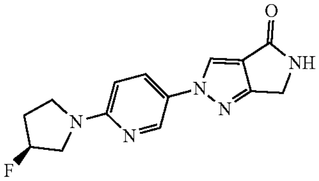 [SMILES: O=C1NCc2nn(-c3ccc(N4CC[C@H](F)C4)nc3)cc21] | 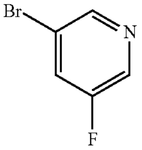 | 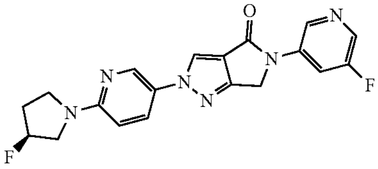 [SMILES: O=C1c2cn(-c3ccc(N4CC[C@H](F)C4)nc3)nc2CN1c1cncc(F)c1]<br>92 | 1. 7%<br>2. $^{1}$H NMR (500 MHz, CF3COOD) δ 9.69 (d, 1H), 8.78 (dt, 1H), 8.57 (s, 1H), 8.53 (t, 1H), 8.44 (d, 1H), 8.29 (dd, 1H), 7.18 (s, 1H), 5.74-5.37 (m, 1H), 5.27 (s, 2H), 4.26-3.65 (m, 4H), 2.60 (s, 1H), 2.52-2.21 (m, 1H).<br>3. 383.0 |
| 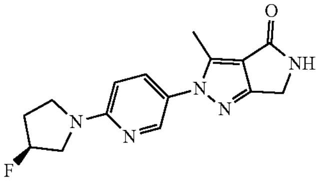 | 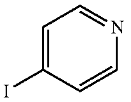 | 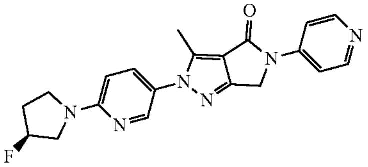 [SMILES: Cc1c2c(nn1-c1ccc(N3CC[C@H](F)C3)nc1)CN(c1ccncc1)C2=O]<br>93 | 1. ND<br>2. $^{1}$H NMR (600 MHz, DMSO-d6) δ 7.85 (s, 2H), 8.54 (s, 2H), 8.29 (s, 1H), 7.74 (d, 1H), 6.66 (d, 1H), 5.66-5.37 (m, 1 H), 4.96 (s, 2H), 3.95-3.61 (m, 3H), 3.49 (q, 1H), 2.43 (s, 3H), 2.35-2.07 (m, 2H).<br>3. 379.2 |
| 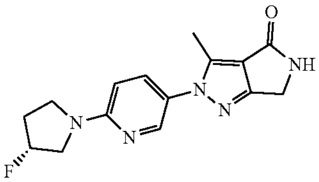 [SMILES: Cc1c2c(nn1-c1ccc(N3CC[C@@H](F)C3)nc1)CNC2=O] | 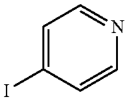 | 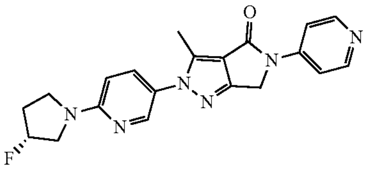 [SMILES: Cc1c2c(nn1-c1ccc(N3CC[C@@H](F)C3)nc1)CN(c1ccncc1)C2=O]<br>94 | 1. ND<br>2. $^{1}$H NMR (600 MHz, DMSO-d6) δ 8.50 (s, 2H), 8.29 (d, 1H), 7.82 (d, 2H), 7.78-7.72 (m, 1H), 6.66 (d, 1H), 5.65-5.40 (m, 1H), 4.96 (s, 2H), 3.93-3.60 (m, 3H), 3.53-3.45 (m, 1H), 2.43 (s, 3H), 2.36-2.08 (m, 2H).<br>3. 379.2 |
| 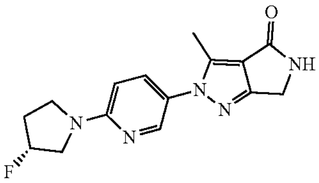 [SMILES: Cc1c2c(nn1-c1ccc(N3CC[C@@H](F)C3)nc1)CNC2=O] | 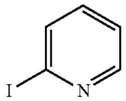 | 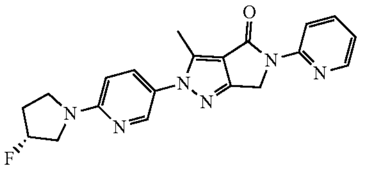 [SMILES: Cc1c2c(nn1-c1ccc(N3CC[C@@H](F)C3)nc1)CN(c1ccccn1)C2=O]<br>95 | 1. ND<br>2. $^{1}$H NMR (600 MHz, DMSO-d6) δ 8.46-8.38 (m, 2H), 8.29 (d, 1H), 7.84 (t, 1H), 7.74 (dd, 1H), 7.16-7.11 (m, 1H), 6.65 (d, 1H), 5.65-5.33 (m, 1H), 5.00 (s, 2H), 3.94-3.59 (m, 3H), 3.49 (q, 1H), 2.43 (s, 3H), 2.37-1.99 (m, 2H).<br>3. 379.2 |
| 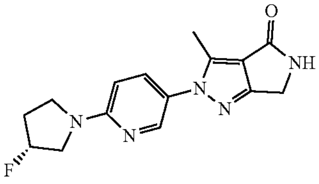 [SMILES: Cc1c2c(nn1-c1ccc(N3CC[C@@H](F)C3)nc1)CNC2=O] | 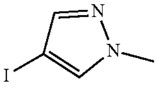 | 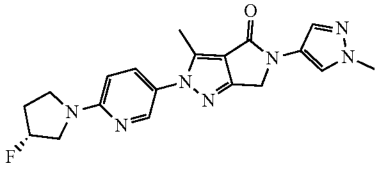 [SMILES: Cc1c2c(nn1-c1ccc(N3CC[C@@H](F)C3)nc1)CN(c1cnn(C)c1)C2=O]<br>96 | 1. ND<br>2. $^{1}$H NMR (600 MHz, DMSO-d6) δ 8.27 (d, 1H), 8.01 (s, 1H), 7.72 (dd, 1H), 7.67 (s, 1H), 6.64 (d, 1H), 5.61-5.38 (m, 1H), 4.73 (s, 2H), 3.84 (s, 3H), 3.81-3.59 (m, 3H), 3.52-3.45 (m, 1H), 2.38 (s, 3H), 2.34-2.09 (m, 2H).<br>3. 382.2 |

TABLE 4a-continued

| Amide | halogenated heteroaryl | Compound of example | 1. Yield<br>2. $^{1}$H-NMR<br>3. $MH^{+}$ (ESI) |
|---|---|---|---|
| 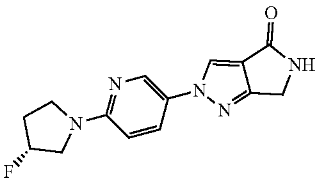 [SMILES: O=C1NCc2nn(-c3ccc(N4CC[C@@H](F)C4)nc3)cc21] | 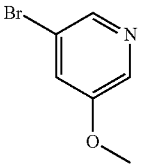 | 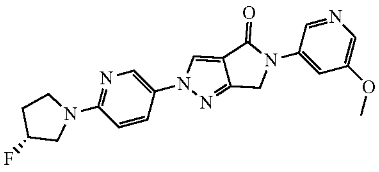 [SMILES: COc1cncc(N2Cc3nn(-c4ccc(N5CC[C@@H](F)C5)nc4)cc3C2=O)c1]<br>97 | 1. 10%<br>2. $^{1}$H NMR (500 MHz, DMSO-d6) δ 8.88 (s, 1H), 8.70 (s, 1H), 8.61 (dd, 1H), 8.16 (s, 1H), 8.02 (dd, 1H), 7.94 (s, 1H), 6.67 (d, 1H), 5.63-5.33 (m, 1H), 5.09 (s, 2H), 3.88 (s, 3H), 3.84-3.56 (m, 3H), 3.48 (td, 1H), 2.41-2.07 (m, 2H).<br>3. 395.2 |
| 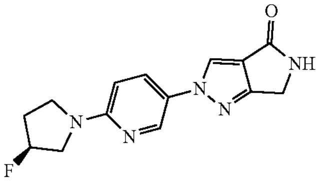 [SMILES: O=C1NCc2nn(-c3ccc(N4CC[C@H](F)C4)nc3)cc21] | 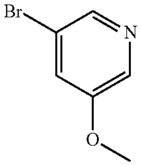 | 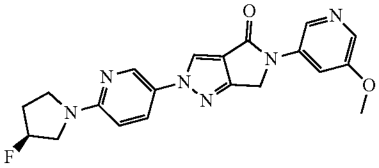 [SMILES: COc1cncc(N2Cc3nn(-c4ccc(N5CC[C@H](F)C5)nc4)cc3C2=O)c1]<br>98 | 1. 10%<br>2. $^{1}$H NMR (500 MHz, DMSO-d6) δ 8.87 (s, 1H), 8.67 (s, 1H), 8.60 (dd, 1H), 8.13 (s, 1H), 8.02 (dd, 1H), 7.93 (d, 1H), 6.67 (d, 1H), 5.60-5.37 (m, 1H), 5.09 (s, 2H), 3.87 (s, 3H), 3.83-3.58 (m, 3H), 3.48 (td, 1H), 2.39-2.07 (m, 2H).<br>3. 395.3 |
| 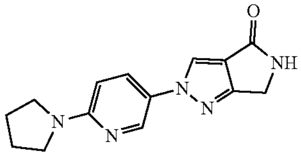 [SMILES: O=C1NCc2nn(-c3ccc(N4CCCC4)nc3)cc21] | 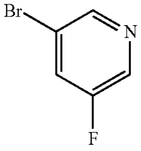 | 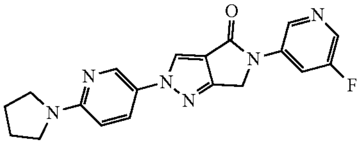 [SMILES: O=C1c2cn(-c3ccc(N4CCCC4)nc3)nc2CN1c1cncc(F)c1]<br>99 | 1. 27%<br>2. $^{1}$H NMR (500 MHz, DMSO-d6) δ 8.93 (t, 1H), 8.88 (s, 1H), 8.57 (dd, 1H), 8.37 (d, 1H), 8.28 (dt, 1H), 7.97 (dd, 1H), 6.60 (d, 1H), 5.10 (s, 2H), 3.51-3.40 (m, 4H), 2.08-1.92 (m, 4H).<br>3. 365.3 |
| 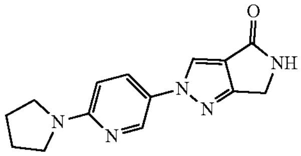 [SMILES: O=C1NCc2nn(-c3ccc(N4CCCC4)nc3)cc21] | 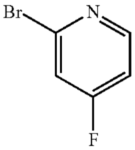 | 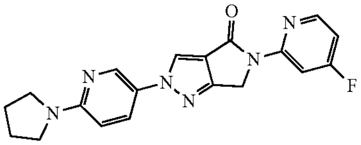 [SMILES: O=C1c2cn(-c3ccc(N4CCCC4)nc3)nc2CN1c1cc(F)ccn1]<br>100 | 1. 64%<br>2. $^{1}$H NMR (500 MHz, CF3COOD) δ 8.71-8.62 (m, 2H), 8.48 (d, 1H), 8.32 (dd, 1H), 7.55 (dd, 1H), 7.46 (td, 1H), 7.24 (d, 1H), 5.36 (s, 2H), 3.89-3.60 (m, 4H), 2.33 (s, 4H).<br>3. 365.3 |
| 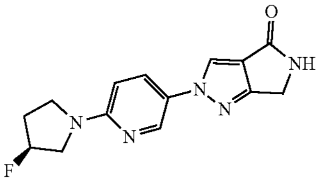 [SMILES: O=C1NCc2nn(-c3ccc(N4CC[C@H](F)C4)nc3)cc21] | 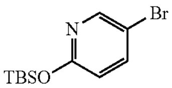 | 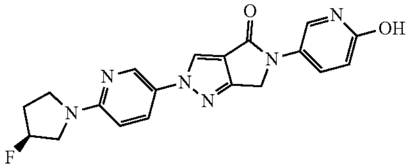 [SMILES: O=C1c2cn(-c3ccc(N4CC[C@H](F)C4)nc3)nc2CN1c1ccc(O)nc1]<br>101 | 1. ND<br>2. $^{1}$H NMR (400 MHz, CF3COOD) δ 8.97 (d, 1H), 8.86-8.24 (m, 4H), 7.50 (d, 1H), 7.29 (s, 1H), 5.81-5.41 (m, 1H), 5.25 (s, 2H), 4.38-3.80 (m, 4H), 2.71 (s, 1H), 2.59-2.17 (m, 1H).<br>3. 381.3 |
| 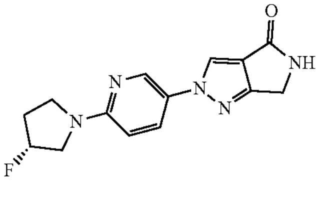 [SMILES: O=C1NCc2nn(-c3ccc(N4CC[C@@H](F)C4)nc3)cc21] | 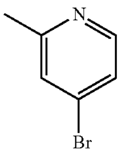 | 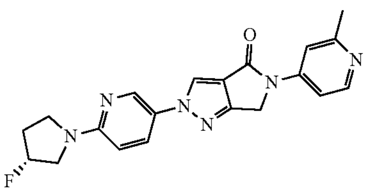 [SMILES: Cc1cc(N2Cc3nn(-c4ccc(N5CC[C@@H](F)C5)nc4)cc3C2=O)ccn1]<br>102 | 1. 14%<br>2. $^{1}$H NMR (400 MHz, DMSO-d6) δ 8.90 (s, 1H), 8.60 (d, 1H), 8.37 (d, 1H), 8.01 (dd, 1H), 7.69 (d, 2H), 6.67 (d, 1H), 5.69-5.34 (m, 1H), 5.02 (s, 2H), 3.92-3.56 (m, 3H), 3.56-3.42 (m, 1H), 2.47 (s, 3H), 2.40-2.07 (m, 2H).<br>3. 379.5 |

TABLE 4a-continued

| Amide | halogenated heteroaryl | Compound of example | 1. Yield<br>2. $^1$H-NMR<br>3. $MH^+$ (ESI) |
|---|---|---|---|
| 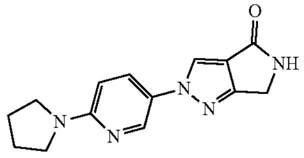 [SMILES: O=C1NCc2nn(-c3ccc(N4CCCC4)nc3)cc21] | 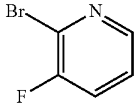 | 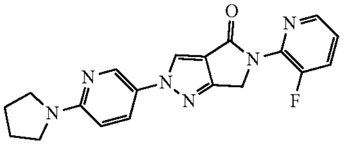 [SMILES: O=C1c2cn(-c3ccc(N4CCCC4)nc3)nc2CN1c1ncccc1F]<br>103 | 1. 54%<br>2. $^1$H NMR (400 MHz, DMSO-d6) δ 8.85 (s, 1H), 8.57 (d, 1H), 8.38 (dt, 1H), 7.96 (dd, 1H), 7.89 (ddd, 1H), 7.46 (ddd, 1H), 6.60 (d, 1H), 5.09 (s, 2H), 3.49-3.40 (m, 4H), 2.02-1.91 (m, 4H).<br>3. 365.0 |
| 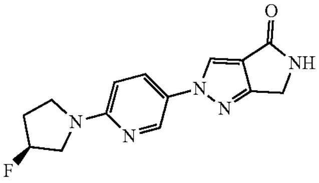 [SMILES: O=C1NCc2nn(-c3ccc(N4CC[C@H](F)C4)nc3)cc21] | 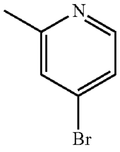 | 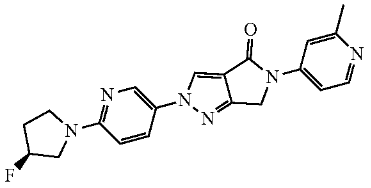 [SMILES: Cc1cc(N2Cc3nn(-c4ccc(N5CC[C@H](F)C5)nc4)cc3C2=O)ccn1]<br>104 | 1. 9%<br>2. $^1$H NMR (400 MHz, DMSO-d6) δ 8.86 (s, 1H), 8.56 (dd, 1H), 8.33 (d, 1H), 7.97 (dd, 1H), 7.66 (dt, 2H), 6.63 (d, 1H), 5.57-5.25 (m, 1H), 4.98 (s, 2H), 3.87-3.52 (m, 3H), 3.44 (td, 1H), 2.45 (s, 3H), 2.35-2.04 (m, 2H).<br>3. 379.1 |
| 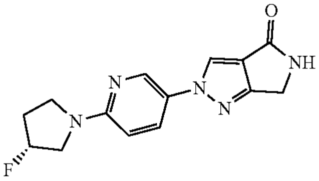 [SMILES: O=C1NCc2nn(-c3ccc(N4CC[C@@H](F)C4)nc3)cc21] | 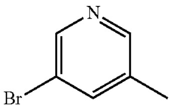 | 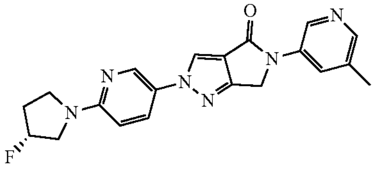 [SMILES: Cc1cncc(N2Cc3nn(-c4ccc(N5CC[C@@H](F)C5)nc4)cc3C2=O)c1]<br>105 | 1. 14%<br>2. $^1$H NMR (400 MHz, DMSO-d6) δ 8.99-8.79 (m, 2H), 8.60 (d, 1H), 8.23 (s, 1H), 8.10 (s, 1H), 8.01 (dd, 1H), 6.67 (d, 1H), 5.62-5.33 (m, 1H), 5.11-5.01 (m, 2H), 3.90-3.54 (m, 3H), 3.48 (td, 1H), 2.35 (s, 5H).<br>3. 379.1 |
| 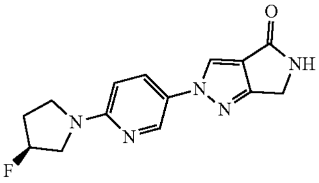 [SMILES: O=C1NCc2nn(-c3ccc(N4CC[C@H](F)C4)nc3)cc21] | 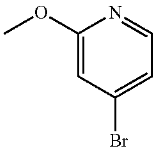 | 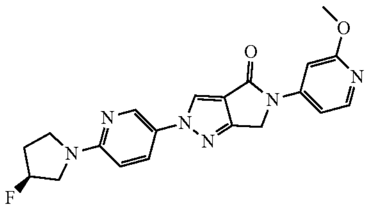 [SMILES: COc1cc(N2Cc3nn(-c4ccc(N5CC[C@H](F)C5)nc4)cc3C2=O)ccn1]<br>106 | 1. 31%<br>2. $^1$H NMR (400 MHz, DMSO-d6) δ 8.90 (s, 1H), 8.60 (d, 1H), 8.11 (d, 1H), 8.01 (dd, 1H), 7.56 (dd, 1H), 7.21 (d, 1H), 6.67 (d, 1H), 5.56-5.35 (m, 1H), 5.02 (s, 2H), 3.86 (s, 3H), 3.84-3.55 (m, 3H), 3.48 (td, 1H), 2.33-2.06 (m, 2H).<br>3. 395.1 |
| 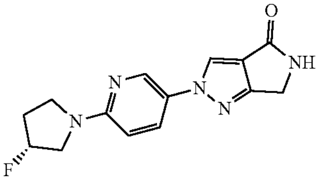 [SMILES: O=C1NCc2nn(-c3ccc(N4CC[C@@H](F)C4)nc3)cc21] | 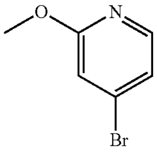 | 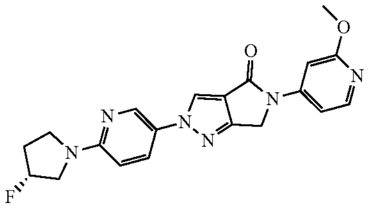 [SMILES: COc1cc(N2Cc3nn(-c4ccc(N5CC[C@@H](F)C5)nc4)cc3C2=O)ccn1]<br>107 | 1. 18%<br>2. $^1$H NMR (400 MHz, DMSO-d6) δ 8.89 (s, 1H), 8.60 (d, 1H), 8.11 (d, 1H), 8.01 (dd, 1H), 7.55 (dd, 1H), 7.21 (d, 1H), 6.67 (d, 1H), 5.62-5.33 (m, 1H), 5.02 (s, 2H), 3.86 (s, 3H), 3.84-3.56 (m, 3H), 3.47 (td, 1H), 2.39-2.06 (m, 2H).<br>3. 395.1 |
| 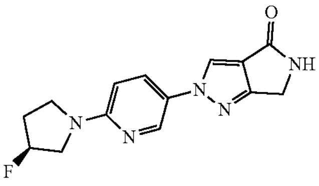 [SMILES: O=C1NCc2nn(-c3ccc(N4CC[C@H](F)C4)nc3)cc21] | 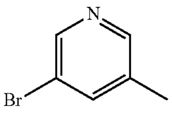 | 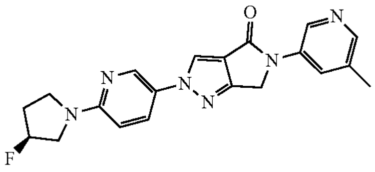 [SMILES: Cc1cncc(N2Cc3nn(-c4ccc(N5CC[C@H](F)C5)nc4)cc3C2=O)c1]<br>108 | 1. 7%<br>2. $^1$H NMR (400 MHz, DMSO-d6) δ 9.06-8.73 (m, 1H), 8.60 (d, 1H), 8.21 (s, 1H), 8.10 (s, 1H), 8.01 (dd, 1H), 6.67 (d, 1H), 5.64-5.37 (m, 1H), 5.06 (s, 2H), 4.00-3.55 (m, 3H), 3.48 (td, 1H), 2.42-2.08 (m, 5H).<br>3. 379.1 |

TABLE 4a-continued

| Amide | halogenated heteroaryl | Compound of example | 1. Yield<br>2. $^{1}$H-NMR<br>3. $MH^{+}$ (ESI) |
|---|---|---|---|
| 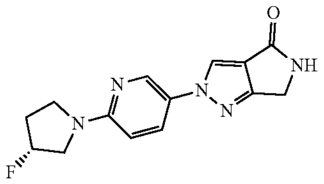 [SMILES: O=C1NCc2nn(-c3ccc(N4CC[C@@H](F)C4)nc3)cc21] | 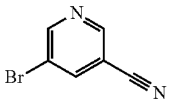 | 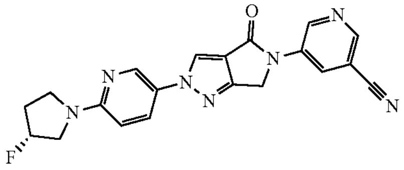 [SMILES: N#Cc1cncc(N2Cc3nn(-c4ccc(N5CC[C@@H](F)C5)nc4)cc3C2=O)c1]<br>109 | 1. 13%<br>2. $^{1}$H NMR (500 MHz, CF3COOD) δ 10.43 (dt, 1H), 9.77-9.46 (m, 1H), 9.40-9.24 (m, 1H), 8.88 (dd, 1H), 8.73 (d, 1H), 8.59 (ddd, 1H), 7.49 (s, 1H), 5.95-5.66 (m, 1H), 5.61 (s, 2H), 4.53-4.05 (m, 4H), 2.90 (s, 1H), 2.78-2.48 (m, 1H).<br>3. 390.2 |
| 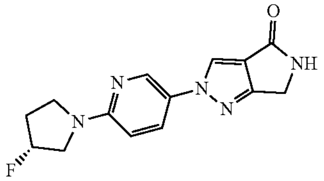 [SMILES: O=C1NCc2nn(-c3ccc(N4CC[C@@H](F)C4)nc3)cc21] | 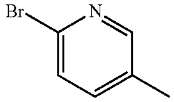 | 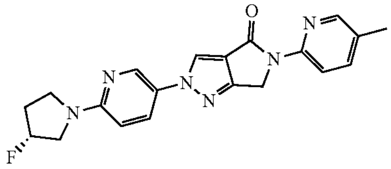 [SMILES: Cc1ccc(N2Cc3nn(-c4ccc(N5CC[C@@H](F)C5)nc4)cc3C2=O)nc1]<br>110 | 1. 28%<br>2. $^{1}$H NMR (400 MHz, CF3COOD) δ 8.66 (s, 1H), 8.53 (s, 1H), 8.48-8.29 (m, 3H), 7.69 (d, 1H), 7.25 (s, 1H), 5.75-5.42 (m, 1H), 5.34 (s, 2H), 4.32-3.78 (m, 4H), 2.57 (s, 5H).<br>3. 379.3 |
| 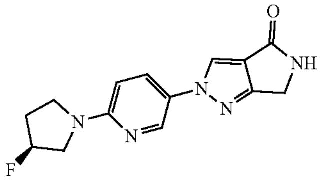 [SMILES: O=C1NCc2nn(-c3ccc(N4CC[C@H](F)C4)nc3)cc21] | 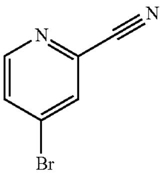 | 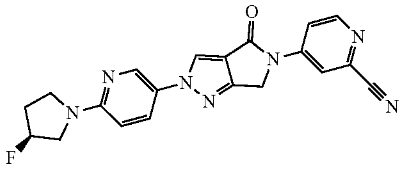 [SMILES: N#Cc1cc(N2Cc3nn(-c4ccc(N5CC[C@H](F)C5)nc4)cc3C2=O)ccn1]<br>111 | 1. 23%<br>2. $^{1}$H NMR (400 MHz, CF3COOD) δ 9.18 (d, 1H), 8.84 (d, 1H), 8.68 (s, 1H), 8.62 (dd, 1H), 8.52 (d, 1H), 8.36 (dd, 1H), 7.24 (d, 1H), 5.72-5.43 (m, 1H), 5.35 (s, 2H), 4.19-3.80 (m, 4H), 2.99-2.55 (m, 1H), 2.55-2.20 (m, 1H).<br>3. 390.3 |
| 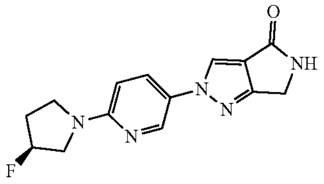 [SMILES: O=C1NCc2nn(-c3ccc(N4CC[C@H](F)C4)nc3)cc21] | 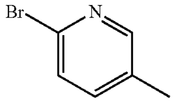 | 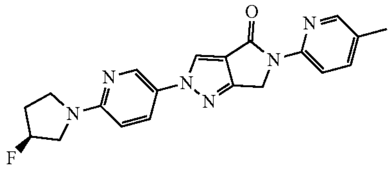 [SMILES: Cc1ccc(N2Cc3nn(-c4ccc(N5CC[C@H](F)C5)nc4)cc3C2=O)nc1]<br>112 | 1. 28%<br>2. $^{1}$H (500 MHz, CF3COOD) δ 8.63 (s, 1H), 8.56-8.45 (m, 1H), 8.45-8.25 (m, 3H), 7.66 (d, 1H), 7.22 (s, 1H), 5.70-5.37 (m, 1H), 5.31 (s, 2H), 4.18-3.75 (m, 4H), 2.76-2.21 (m, 5H).<br>3. 379.1 |
| 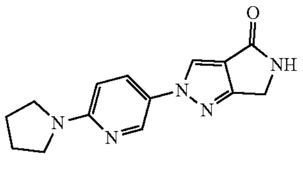 [SMILES: O=C1NCc2nn(-c3ccc(N4CCCC4)nc3)cc21] | 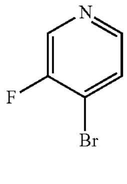 | 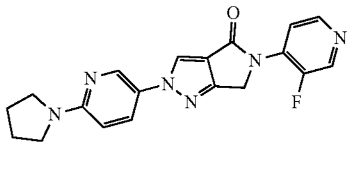 [SMILES: O=C1c2cn(-c3ccc(N4CCCC4)nc3)nc2CN1c1ccncc1F]<br>113 | 1. 13%<br>2. $^{1}$H NMR (500 MHz, DMSO-d6) δ 8.89 (s, 1H), 8.66 (d, 1H), 8.57 (d, 1H), 8.45 (d, 1H), 7.96 (dd, 1H), 7.91 (dd, 1H), 6.60 (d, 1H), 5.11 (d, 2H), 3.53-3.38 (m, 4H), 2.09-1.90 (m, 4H).<br>3. 365.1 |
| 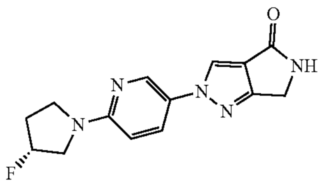 [SMILES: O=C1NCc2nn(-c3ccc(N4CC[C@@H](F)C4)nc3)cc21] | 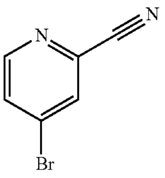 | 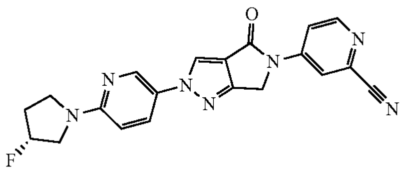 [SMILES: N#Cc1cc(N2Cc3nn(-c4ccc(N5CC[C@@H](F)C5)nc4)cc3C2=O)ccn1]<br>114 | 1. 18%<br>2. $^{1}$H NMR (500 MHz, CF3COOD) δ 9.33 (s, 1H), 8.99 (dt, 1H), 8.84 (d, 1H), 8.81-8.71 (m, 1H), 8.67 (s, 1H), 8.51 (d, 1H), 7.40 (s, 1H), 5.82-5.57 (m, 1H), 5.50 (d, 2H), 4.35-3.96 (m, 4H), 2.81 (s, 1H), 2.68-2.43 (m, 1 H)<br>3. 390.3 |

TABLE 4a-continued

| Amide | halogenated heteroaryl | Compound of example | 1. Yield<br>2. ¹H-NMR<br>3. MH⁺ (ESI) |
|---|---|---|---|
| 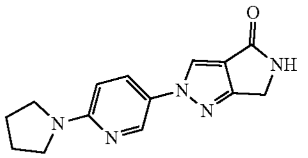 [SMILES: O=C1NCc2nn(-c3ccc(N4CCCC4)nc3)cc21] | 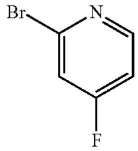 | 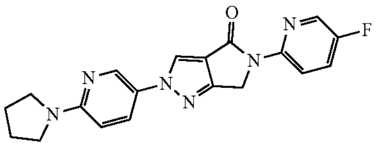 [SMILES: O=C1c2cn(-c3ccc(N4CCCC4)nc3)nc2CN1c1ccc(F)cn1]<br>115 | 1. 63%<br>2. ¹H NMR (400 MHz, DMSO-d6) δ 8.87 (s, 1H), 8.57 (dd, 1H), 8.53-8.45 (m, 1H), 8.43 (d, 1H), 7.97 (dd, 1H), 7.83 (ddd, 1H), 6.59 (d, 1H), 5.08 (s, 2H), 3.49-3.34 (m, 4H), 2.01-1.91 (m, 4H).<br>3. 365.1 |
| 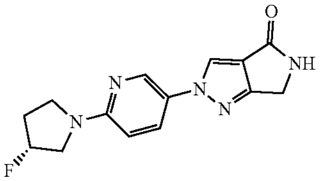 [SMILES: O=C1NCc2nn(-c3ccc(N4CC[C@@H](F)C4)nc3)cc21] | 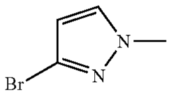 | 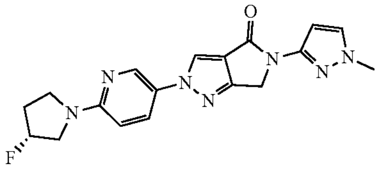 [SMILES: Cn1ccc(N2Cc3nn(-c4ccc(N5CC[C@@H](F)C5)nc4)cc3C2=O)n1]<br>116 | 1. 29%<br>2. ¹H NMR (500 MHz, DMSO-d6) δ 8.81 (s, 1H), 8.59 (d, 1H), 8.00 (dd, 1H), 7.66 (d, 1H), 6.75-6.59 (m, 2H), 5.59-5.35 (m, 1H), 4.89 (s, 2H), 3.93-3.56 (m, 5H), 3.47 (td, 1H), 2.34-2.12 (m, 1H).<br>3. 368.1 |
| 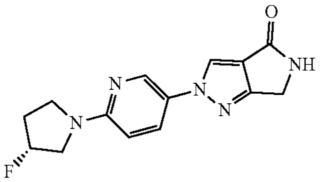 [SMILES: O=C1NCc2nn(-c3ccc(N4CC[C@@H](F)C4)nc3)cc21] | 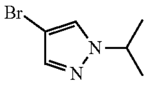 | 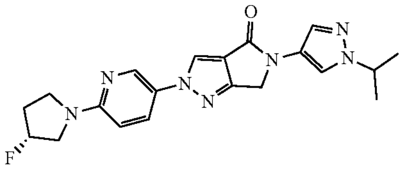 [SMILES: CC(C)n1cc(N2Cc3nn(-c4ccc(N5CC[C@@H](F)C5)nc4)cc3C2=O)cn1]<br>117 | 1. 22%<br>2. ¹H NMR (500 MHz, DMSO-d6) δ 8.77 (s, 1H), 8.58 (d, 1H), 8.09 (s, 1H), 7.99 (dd, 1H), 7.71 (s, 1H), 6.66 (d, 1H), 5.59-5.38 (m, 1H), 4.83 (s, 2H), 4.51 (hept, 1H), 3.88-3.57 (m, 3H), 3.47 (td, 1H), 2.38-2.11 (m, 2H), 1.42 (d, 6H).<br>3. 396.1 |
| 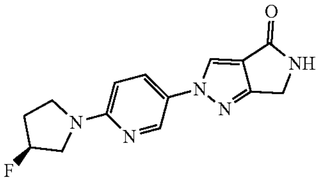 [SMILES: O=C1NCc2nn(-c3ccc(N4CC[C@H](F)C4)nc3)cc21] | 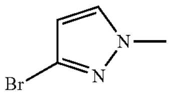 | 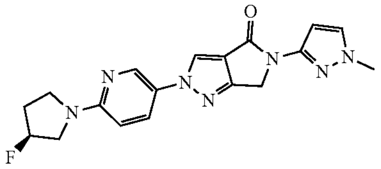 [SMILES: Cn1ccc(N2Cc3nn(-c4ccc(N5CC[C@H](F)C5)nc4)cc3C2=O)n1]<br>118 | 1. 49%<br>2. ¹H NMR (500 MHz, DMSO-d6) δ 7.99 (s, 1H), 7.77 (d, 1H), 7.18 (dd, 1H), 6.84 (d, 1H), 5.93-5.79 (m, 2H), 4.74-4.53 (m, 1H), 4.07 (s, 2H), 3.05-2.75 (m, 6H), 2.74-2.61 (m, 1H), 1.52-1.27 (m, 2H).<br>3. 368.3 |
| 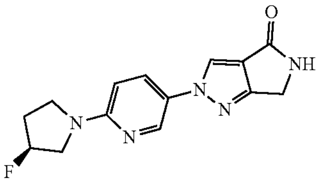 [SMILES: O=C1NCc2nn(-c3ccc(N4CC[C@H](F)C4)nc3)cc21] | 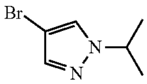 | 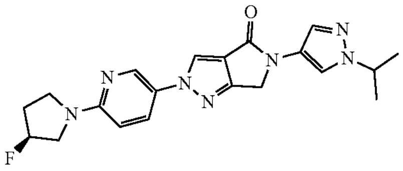 [SMILES: CC(C)n1cc(N2Cc3nn(-c4ccc(N5CC[C@H](F)C5)nc4)cc3C2=O)cn1]<br>119 | 1. 63%<br>2. ¹H NMR (500 MHz, DMSO-d6) δ 8.77 (s, 1H), 8.58 (d, 1H), 8.09 (d, 1H), 7.99 (dd, 1H), 7.71 (d, 1H), 6.66 (d, 1H), 5.58-5.33 (m, 1H), 4.83 (s, 2H), 4.51 (hept, 1H), 3.90-3.54 (m, 3H), 3.47 (td, 1H), 2.36-2.05 (m, 2H), 1.42 (d, 6H).<br>3. 396.2 |
| 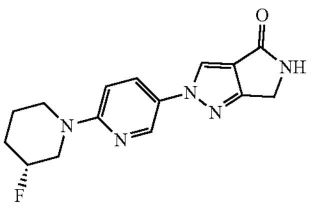 [SMILES: O=C1NCc2nn(-c3ccc(N4CCC[C@@H](F)C4)nc3)cc21] | 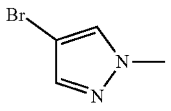 | 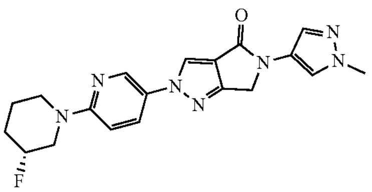 [SMILES: Cn1cc(N2Cc3nn(-c4ccc(N5CCC[C@@H](F)C5)nc4)cc3C2=O)cn1]<br>120 | 1. 24%<br>2. ¹H NMR (500 MHz, DMSO-d6) δ 8.78 (s, 1H), 8.57 (d, 1H), 8.06 (d, 1H), 7.97 (dd, 1H), 7.67 (d, 1H), 7.03 (d, 1H), 4.83 (s, 3H), 4.06-3.62 (m, 7H), 3.42 (t, 1H), 2.07-1.48 (m, 3H).<br>3. 382.3 |

TABLE 4a-continued

| Amide | halogenated heteroaryl | Compound of example | 1. Yield<br>2. $^1$H-NMR<br>3. MH$^+$ (ESI) |
|---|---|---|---|
| 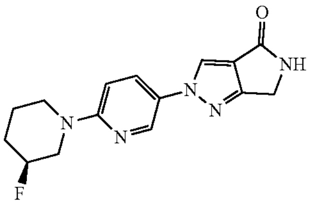 [SMILES: O=C1NCc2nn(-c3ccc(N4CCC[C@H](F)C4)nc3)cc21] | 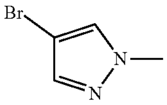 | 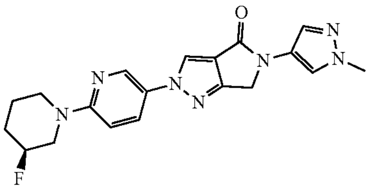 [SMILES: Cn1cc(N2Cc3nn(-c4ccc(N5CCC[C@H](F)C5)nc4)cc3C2=O)cn1]<br>121 | 1. 14%<br>2. $^1$H NMR (400 MHz, DMSO-d6) δ 8.75 (s, 1H), 8.54 (d, 1H), 8.02 (d, 1H), 7.93 (dd, 1H), 7.64 (d, 1H), 6.99 (d, 1H), 4.95-4.62 (m, 3H), 3.98-3.60 (m, 6H), 3.48-3.32 (m, 1H), 2.10-1.44 (m, 4H).<br>3. 382.3 |
| 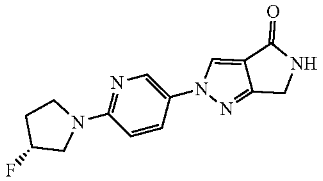 [SMILES: O=C1NCc2nn(-c3ccc(N4CC[C@@H](F)C4)nc3)cc21] | 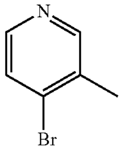 | 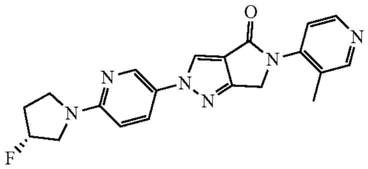 [SMILES: Cc1cnccc1N1Cc2nn(-c3ccc(N4CC[C@@H](F)C4)nc3)cc2C1=O]<br>122 | 1. 19%<br>2. $^1$H NMR (500 MHz, DMSO-d6) δ 8.01 (s, 1H), 7.89-7.70 (m, 2H), 7.66 (d, 1H), 7.18 (dd, 1H), 6.67 (d, 1H), 5.86 (d, 1H), 4.81-4.54 (m, 1H), 4.16 (s, 2H), 3.23-2.73 (m, 3H), 2.66 (td, 1H), 1.57-1.25 (m, 5H).<br>3. 379.3 |
| 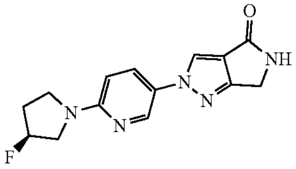 | 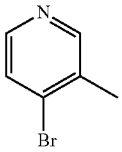 | 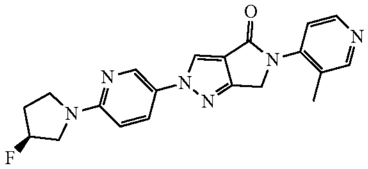 [SMILES: Cc1cnccc1N1Cc2nn(-c3ccc(N4CC[C@H](F)C4)nc3)cc2C1=O]<br>123 | 1. 38%<br>2. $^1$H NMR (400 MHz, DMSO-d6) δ 8.83 (s, 1H), 8.59 (dd, 1H), 8.54 (s, 1H), 8.48 (d, 1H), 8.00 (dd, 1H), 7.49 (d, 1H), 6.78-6.58 (m, 1H), 5.62-5.30 (m, 1H), 4.98 (s, 2H), 3.88-3.55 (m, 3H), 3.48 (td, 1H), 2.39-2.09 (m, 5H).<br>3. 379.3 |
| 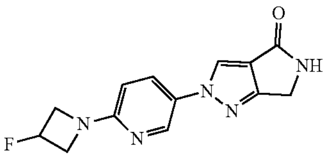 [SMILES: O=C1NCc2nn(-c3ccc(N4CC(F)C4)nc3)cc21] | 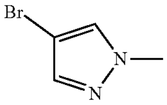 | 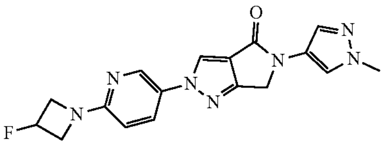 [SMILES: Cn1cc(N2Cc3nn(-c4ccc(N5CC(F)C5)nc4)cc3C2=O)cn1]<br>124 | 1. 31%<br>2. $^1$H NMR (500 MHz, DMSO-d6) δ 8.79 (s, 1H), 8.59 (d, 1H), 8.06 (s, 1H), 8.03 (dd, 1H), 7.67 (d, 1H), 6.62 (d, 1H), 5.67-5.43 (m, 1H), 4.83 (s, 2H), 4.46-4.23 (m, 2H), 4.14-4.01 (m, 2H), 3.85 (s, 3H).<br>3. 354.3 |
| 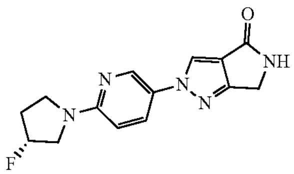 | 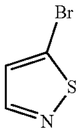 | 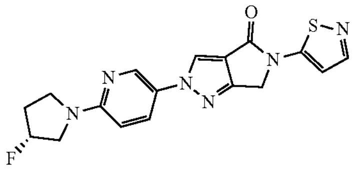 [SMILES: O=C1c2cn(-c3ccc(N4CC[C@@H](F)C4)nc3)nc2CN1c1ccns1]<br>125 | 1. 39%<br>2. $^1$H NMR (500 MHz, DMSO-d6) δ 8.99 (s, 1H), 8.72-8.53 (m, 1H), 8.34 (d, 1H), 8.02 (dd, 1H), 7.08 (d, 1H), 6.68 (d, 1H), 5.57-5.40 (m, 1H), 5.11 (s, 2H), 3.92-3.55 (m, 3H), 3.48 (td, 1H), 2.38-2.02 (m, 2H).<br>3. 371.2 |
| 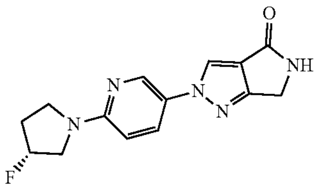 [SMILES: O=C1NCc2nn(-c3ccc(N4CC[C@@H](F)C4)nc3)cc21] | 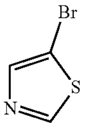 | 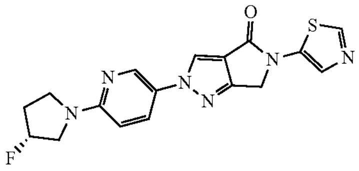 [SMILES: O=C1c2cn(-c3ccc(N4CC[C@@H](F)C4)nc3)nc2CN1c1cncs1]<br>126 | 1. 14%<br>2. $^1$H NMR (500 MHz, DMSO-d6) δ 8.91 (s, 1H), 8.69 (d, 1H), 8.60 (dd, 1H), 8.01 (dd, 1H), 7.73 (d, 1H), 6.67 (d, 1H), 5.60-5.34 (m, 1H), 5.08 (s, 2H), 3.96-3.56 (m, 3H), 3.56-3.39 (m, 1H), 2.36-1.97 (m, 2H).<br>3. 371.2 |

TABLE 4a-continued

| Amide | halogenated heteroaryl | Compound of example | 1. Yield<br>2. $^{1}$H-NMR<br>3. $MH^{+}$ (ESI) |
|---|---|---|---|
| 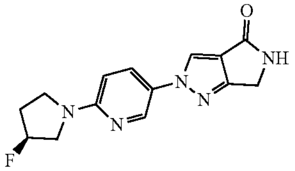 | 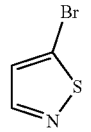 | 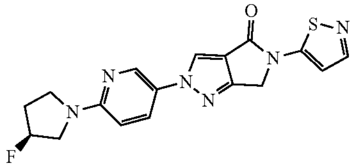 [SMILES: O=C1c2cn(-c3ccc(N4CC[C@H](F)C4)nc3)nc2CN1c1ccns1]<br>127 | 1. 62%<br>2. $^{1}$H NMR (400 MHz, DMSO-d6) δ 8.17 (s, 1H), 7.78 (d, 1H), 7.51 (d, 1H), 7.20 (dd, 1H), 6.25 (d, 1H), 5.85 (d, 1H), 4.79-4.49 (m, 1H), 4.29 (s, 2H), 3.04-2.73 (m, 3H), 2.65 (td, 1H), 1.56-1.22 (m, 2H).<br>3. 371.1 |
| 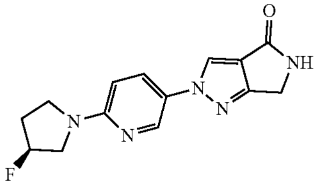 [SMILES: O=C1NCc2nn(-c3ccc(N4CC[C@H](F)C4)nc3)cc21] | 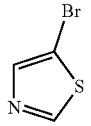 | 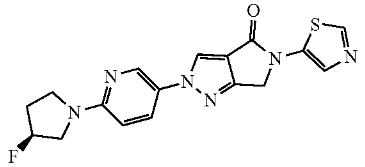 [SMILES: O=C1c2cn(-c3ccc(N4CC[C@H](F)C4)nc3)nc2CN1c1cncs1]<br>128 | 1. 29%<br>2. $^{1}$H NMR (500 MHz, DMSO-d6) δ 8.91 (s, 1H), 8.70 (s, 1H), 8.60 (d, 1H), 8.01 (dd, 1H), 7.74 (s, 1H), 6.67 (d, 1H), 5.62-5.31 (m, 1H), 5.08 (s, 2H), 3.88-3.57 (m, 3H), 3.48 (td, 1H), 2.37-1.93 (m, 2H).<br>3. 371.1 |
| 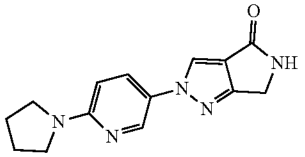 [SMILES: O=C1NCc2nn(-c3ccc(N4CCCC4)nc3)cc21] | 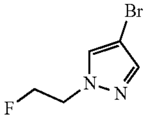 | 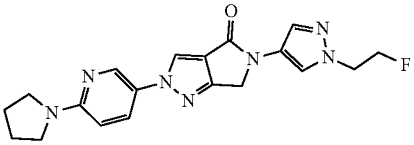 [SMILES: O=C1c2cn(-c3ccc(N4CCCC4)nc3)nc2CN1c1cnn(CCF)c1]<br>129 | 1. 13%<br>2. $^{1}$H NMR (400 MHz, DMSO-d6) δ 8.77 (s, 1H), 8.53 (d, 1H), 8.16 (s, 1H), 7.99 (d, 1H), 7.75 (d, 1H), 6.64 (d, 1H), 4.95-4.65 (m, 4H), 4.60-4.33 (m, 2H), 3.45 (d, 4H), 2.05-1.90 (m, 4H).<br>3. 382.3 |
| 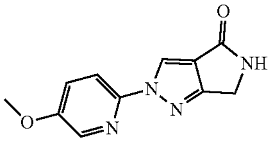 [SMILES: COc1ccc(-n2cc3c(n2)CNC3=O)nc1] | 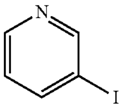 | 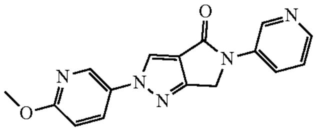 [SMILES: COc1ccc(-n2cc3c(n2)CN(c2cccnc2)C3=O)cn1]<br>130 | 1. ND<br>2. $^{1}$H NMR (600 MHz, DMSO-d6) δ 9.05 (s, 1H), 8.92 (s, 1H), 8.37 (s, 1H), 8.25 (s, 2H), 7.94 (s, 1H), 7.68 (s, 1H), 7.47 (s, 1H), 5.11 (s, 2H), 3.90 (s, 3H).<br>3. 308.2 |
| 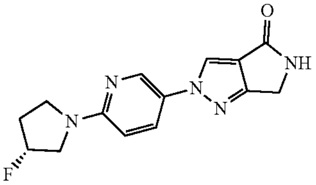 [SMILES: O=C1NCc2nn(-c3ccc(N4CC[C@@H](F)C4)nc3)cc21] | 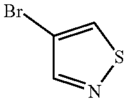 | 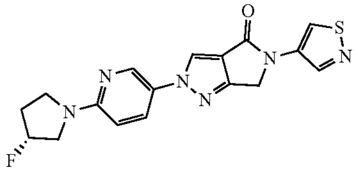 [SMILES: O=C1c2cn(-c3ccc(N4CC[C@@H](F)C4)nc3)nc2CN1c1cnsc1]<br>131 | 1. 23%<br>2. $^{1}$H NMR (500 MHz, DMSO-d6) δ 9.03 (s, 1H), 8.99 (s, 1H), 8.87 (s, 1H), 8.60 (d, 1H), 8.01 (dd, 1H), 6.67 (d, 1H), 5.63-5.35 (m, 1H), 5.06 (s, 2H), 3.92-3.56 (m, 3H), 3.47 (td, 1H), 2.38-2.01 (m, 2H).<br>3. 371.3 |
| 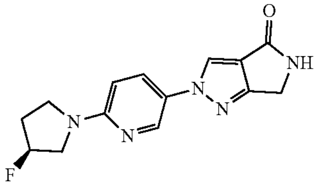 [SMILES: O=C1NCc2nn(-c3ccc(N4CC[C@H](F)C4)nc3)cc21] | 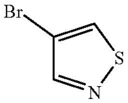 | 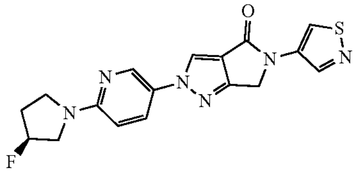 [SMILES: O=C1c2cn(-c3ccc(N4CC[C@H](F)C4)nc3)nc2CN1c1cnsc1]<br>132 | 1. 38%<br>2. $^{1}$H NMR (400 MHz, DMSO-d6) δ 9.03 (s, 1H), 8.99 (s, 1H), 8.87 (s, 1H), 8.60 (dd, 1H), 8.01 (dd, 1H), 6.67 (d, 1H), 5.69-5.30 (m, 1H), 5.06 (s, 2H), 3.96-3.54 (m, 3H), 3.48 (td, 1H), 2.38-2.07 (m, 2H).<br>3. 371.3 |

TABLE 4a-continued

| Amide | halogenated heteroaryl | Compound of example | 1. Yield<br>2. $^1$H-NMR<br>3. $MH^+$ (ESI) |
|---|---|---|---|
| 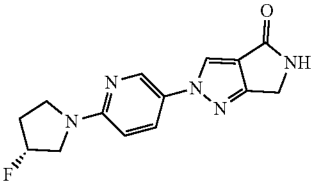 [SMILES: O=C1NCc2nn(-c3ccc(N4CC[C@@H](F)C4)nc3)cc21] | 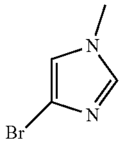 | 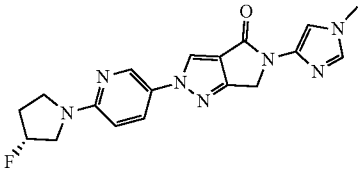 [SMILES: Cn1cnc(N2Cc3nn(-c4ccc(N5CC[C@@H](F)C5)nc4)cc3C2=O)c1]<br>133 | 1. 14%<br>2. $^1$H NMR (500 MHz, CF3COOD) δ 8.61 (s, 1H), 8.58-8.51 (m, 1H), 8.50 (d, 1H), 8.38 (dd, 1H), 7.52 (d, 1H), 7.28 (s, 1H), 5.86-5.45 (m, 1H), 5.21 (s, 2H), 4.31-3.87 (m, 6H), 2.71 (s, 1H), 2.61-2.30 (m, 1H).<br>3. 368.3 |
| 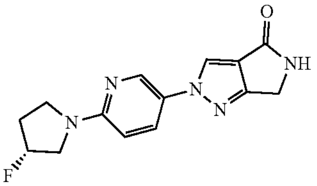 [SMILES: O=C1NCc2nn(-c3ccc(N4CC[C@@H](F)C4)nc3)cc21] | 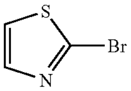 | 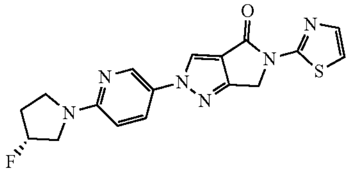 [SMILES: O=C1c2cn(-c3ccc(N4CC[C@@H](F)C4)nc3)nc2CN1c1nccs1]<br>134 | 1. 24%<br>2. $^1$H NMR (500 MHz, DMSO-d6) δ 8.98 (s, 1H), 8.61 (d, 1H), 8.02 (dd, 1H), 7.54 (d, 1H), 7.33 (d, 1H), 6.68 (d, 1H), 5.60-5.38 (m, 1H), 5.16 (s, 2H), 3.85-3.57 (m, 3H), 3.57-3.38 (m, 1H), 2.39-2.08 (m, 2H).<br>3. 371.1 |
| 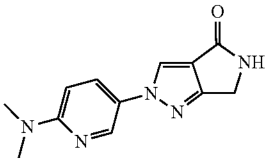 [SMILES: CN(C)c1ccc(-n2cc3c(n2)CNC3=O)cn1] | 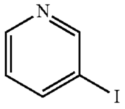 | 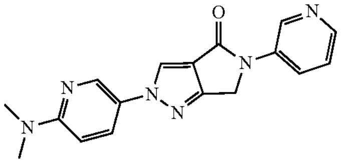 [SMILES: CN(C)c1ccc(-n2cc3c(n2)CN(c2cccnc2)C3=O)cn1]<br>135 | 1. 16%<br>2. $^1$H NMR (500 MHz, DMSO-d6) δ 9.03 (d, 1H), 8.86 (s, 1H), 8.59 (d, 1H), 8.35 (dd, 1H), 8.27 (ddd, 1H), 7.98 (dd, 1H), 7.45 (dd, 1H), 6.79 (d, 1H), 5.08 (s, 2H), 3.09 (s, 6H).<br>3. 321.3 |
| 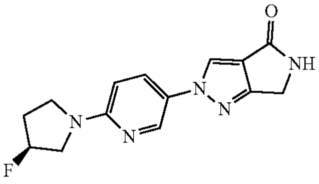 [SMILES: O=C1NCc2nn(-c3ccc(N4CC[C@H](F)C4)nc3)cc21] | 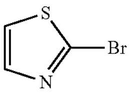 | 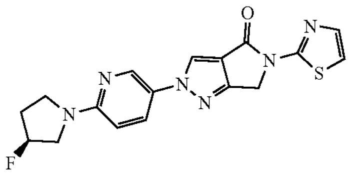 [SMILES: O=C1c2cn(-c3ccc(N4CC[C@H](F)C4)nc3)nc2CN1c1nccs1]<br>136 | 1. 48%<br>2. $^1$H NMR (500 MHz, DMSO-d6) δ 8.98 (s, 1H), 8.61 (d, 1H), 8.02 (dd, 1H), 7.54 (d, 1H), 7.33 (d, 1H), 6.68 (d, 1H), 5.64-5.37 (m, 1H), 5.17 (s, 2H), 3.88-3.58 (m, 3H), 3.54-3.39 (m, 1H), 2.35-2.11 (m, 2H).<br>3. 371.1 |
| 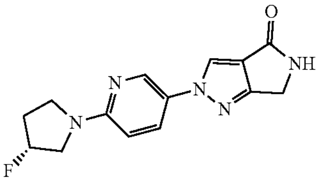 [SMILES: O=C1NCc2nn(-c3ccc(N4CC[C@@H](F)C4)nc3)cc21] | 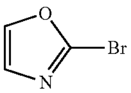 | 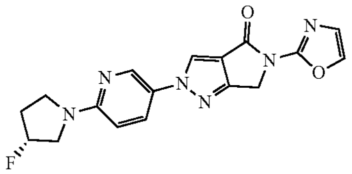<br>137 | 1. 16%<br>2. $^1$H NMR (500 MHz, DMSO-d6) δ 8.94 (s, 1H), 8.59 (d, 1H), 8.00 (dd, 1H), 7.96 (d, 1H), 7.17 (d, 1H), 6.67 (d, 1H), 5.58-5.34 (m, 1H), 5.04 (s, 2H), 3.87-3.54 (m, 3H), 3.47 (td, 1H), 2.45-2.07 (m, 2H).<br>3. 355.3 |
| 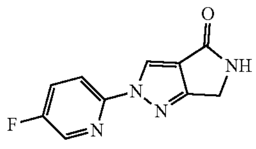 [SMILES: O=C1NCc2nn(-c3ccc(F)cn3)cc21] | 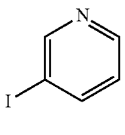 | 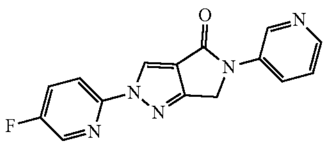 [SMILES: O=C1c2cn(-c3ccc(F)cn3)nc2CN1c1cccnc1]<br>138 | 1. ND<br>2. $^1$H NMR (400 MHz, DMSO-d6) δ 9.05 (s, 1H), 9.02 (s, 1H), 8.61-8.57 (m, 1H), 8.38 (d, 1H), 8.28 (d, 1H), 8.10-8.01 (m, 2H), 7.47 (dd, 1H), 5.15 (s, 2H).<br>3. 296.2 |

Example 139

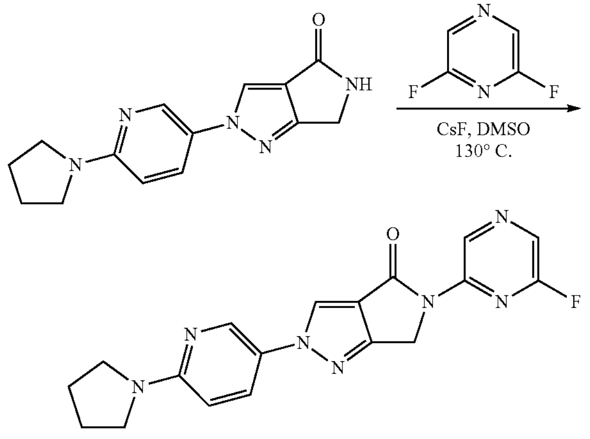

A suspension of 2-(6-(pyrrolidin-1-yl)pyridin-3-yl)-5,6-dihydropyrrolo[3,4-c]pyrazol-4(2H)-one (0.08 g, 0.286 mmol), 2,6-difluoropyrazine (0.199 g, 1.72 mmol) and CsF (0.348 g, 2.293 mmol) in DMSO (4 mL) was heated at 130° C. for 30 minutes under microwave irradiation. Then, the reaction mixture was cooled down and poured into ice cold water (3 mL). The resulting slurry was filtered and the solid was rinsed with water (5 mL). The residue was purified by silica-gel (100-200 mesh) column chromatography using 2 to 5% MeOH in DCM to give the desired product (32 mg, 29%). $^1$H-NMR (400 MHz, DMSO-d6) δ 9.65-9.59 (m, 1H), 8.96 (s, 1H), 8.60-8.55 (m, 1H), 8.38 (dd, 1H), 7.97 (dd, 1H), 6.59 (d, 1H), 5.03 (s, 2H), 3.46-3.41 (m, 4H), 2.01-1.93 (m, 4H). MS: 366.1 [M+H]$^+$ Examples 140 to 161

Following the procedures as described in Example 54, using the amide starting material and the appropriate amide and fluoro-heteroaryl indicated in the Table 4b below, the following Examples were prepared.

TABLE 4b

| Amide | halogenated heteroaryl | Compound of example | 1. Yield<br>2. $^1$H-NMR<br>3. MH$^+$ (ESI) |
|---|---|---|---|
| 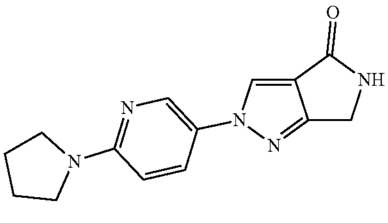 [SMILES: O=C1NCc2nn(-c3ccc(N4CCCC4)nc3)cc21] | 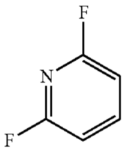 | 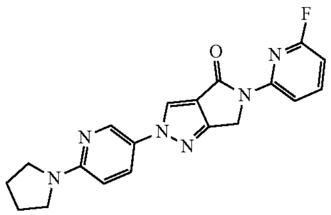<br>140 | 1. 29%<br>2. $^1$H NMR (500 MHz, DMSO-d6) δ 8.89 (s, 1H), 8.56 (d, 1H), 8.35 (dd, 1H), 8.06-7.94 (m, 2H), 6.89 (dd, 1H), 6.59 (d, 1H), 5.03 (s, 2H), 3.44 (t, 4H), 2.03-1.91 (m, 4H).<br>3. 365.2 |
| 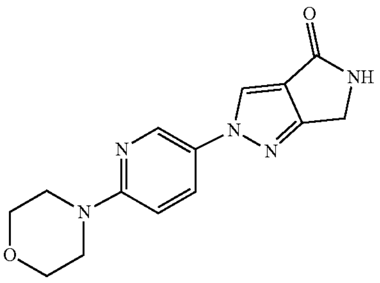 [SMILES: O=C1NCc2nn(-c3ccc(N4CCOCC4)nc3)cc21] | 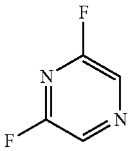 | 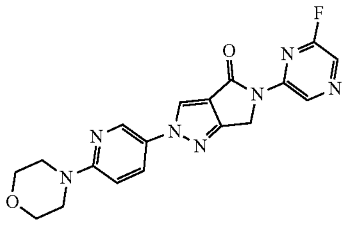<br>141 | 1. 12%<br>2. $^1$H NMR (400 MHz, DMSO-d6) δ 9.62 (d, 1H), 9.03 (s, 1H), 8.66 (d, 1H), 8.39 (d, 1H), 8.07 (dd, 1H), 7.02 (d, 1H), 5.04 (s, 2H), 3.72 (t, 4H), 3.53 (t, 4H).<br>3. 382.5 |
| 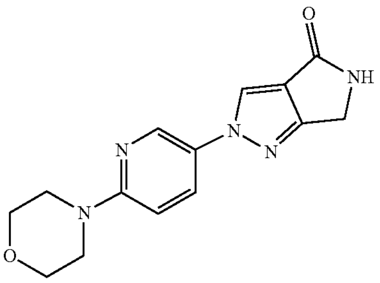 [SMILES: O=C1NCc2nn(-c3ccc(N4CCOCC4)nc3)cc21] | 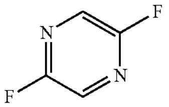 | 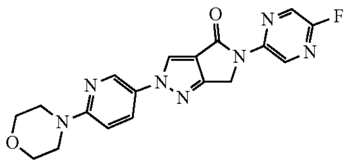<br>142 | 1. 13%<br>2. $^1$H NMR (400 MHz, DMSO-d6) δ 9.28 (t, 1H), 9.00 (s, 1H), 8.66 (d, 1H), 8.57 (dd, 1H), 8.07 (dd, 1H), 7.02 (d, 1H), 5.09 (s, 2H), 3.75-3.68 (m, 4H), 3.56-3.45 (m, 4H).<br>3. 382.3 |

TABLE 4b-continued

| Amide | halogenated heteroaryl | Compound of example | 1. Yield<br>2. $^{1}$H-NMR<br>3. $MH^{+}$ (ESI) |
|---|---|---|---|
| 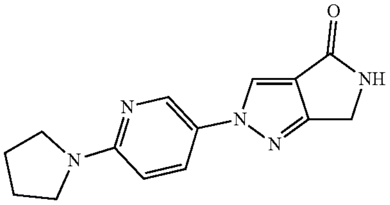 [SMILES: O=C1NCc2nn(-c3ccc(N4CCCC4)nc3)cc21] | 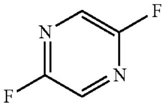 | 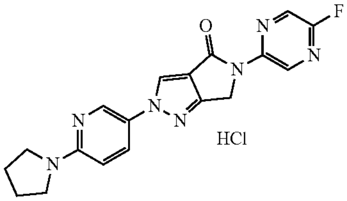<br>143 | 1. 9%<br>2. $^{1}$H NMR (80 MHz, DMSO-d6) δ 9.28 (s, 1H), 8.97 (s, 1H), 8.67-8.47 (m, 1H), 8.24 (s, 1H), 8.11 (dd, 1H), 6.75 (d, 1H), 5.09 (s, 2H), 3.79-3.57 (m, 4H), 2.11-1.80 (m, 4H)<br>3. 366.2 |
| 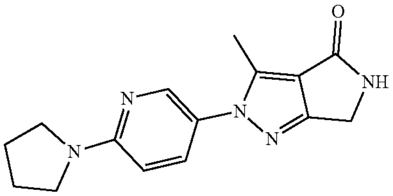 [SMILES: Cc1c2c(nn1-c1ccc(N3CCCC3)nc1)CNC2=O] | 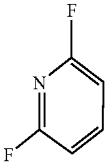 | 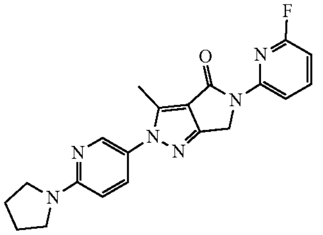<br>144 | 1. ND<br>2. $^{1}$H NMR (400 MHz, DMSO-d6) δ 8.34 (d, 1H), 8.25 (d, 1H),8.01 (q, 1H), 7.69 (dd, 1H), 6.87 (d, 1H), 6.57 (d, 1H), 4.95 (d, 2H), 3.58-3.40 (m, 4H), 2.42 (s, 3H), 2.01 - 1.93 (m, 4H).<br>3. 379.2 |
| 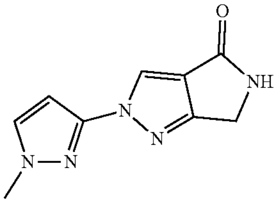 | 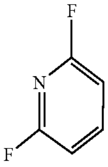 | 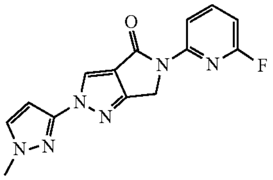<br>145 | 1. 8%<br>2. $^{1}$H NMR (400 MHz, $CDCl_3$) δ 8.43 (d, 1H), 8.36 (s, 1H), 7.81 (q, 1H), 7.40 (d, 1H), 6.65 (dd, 1H), 6.53 (d, 1H), 5.06 (s, 2H), 3.94 (s, 3H).<br>3. 299.2 |
| 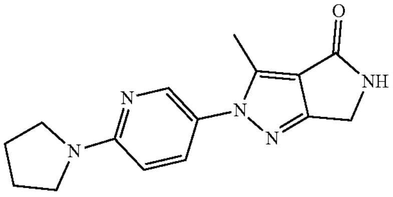 [SMILES: Cc1c2c(nn1-c1ccc(N3CCCC3)nc1)CNC2=O] | 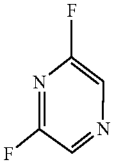 | 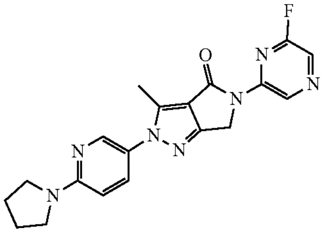<br>146 | 1. ND<br>2. $^{1}$H NMR (400 MHz, $CDCl_3$) δ 9.77 (d, 1H), 8.22 (s, 1H), 8.13 (d, 1H), 7.54 (s, 1H), 6.47 (d, 1H), 4.94 (s, 2H), 3.54 (s, 4H), 2.51 (s, 3H), 2.07 (s, 4H).<br>3. 380.2 |
| 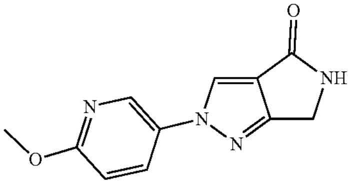 [SMILES: COc1ccc(-n2cc3c(n2)CNC3=O)cn1] | 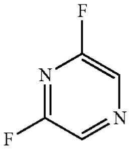 | 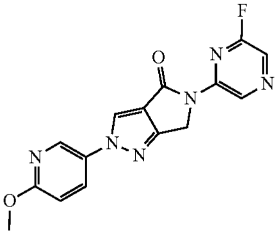<br>147 | 1. 2%<br>2. $^{1}$H NMR (500 MHz, DMSO-d6) δ 9.62 (d, 1H), 9.11 (s, 1H), 8.73 (d, 1H), 8.40 (d, 1H), 8.24 (dd, 1H), 7.05 (d, 1H), 5.06 (s, 2H), 3.93 (d, 3H).<br>3. 327.2 |
| 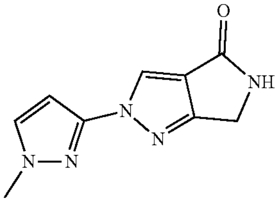 | 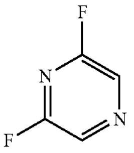 | 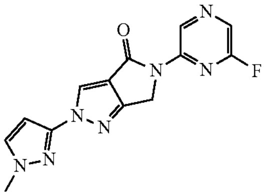<br>148 | 1. 8%<br>2. $^{1}$H NMR (400 MHz, $CDCl_3$) δ 9.78 (d, 1H), 8.40 (s, 1H), 8.15(d, 1H), 7.41 (s, 1H), 6.54 (d, 1H), 5.01 (s, 2H), 3.94 (s, 3H).<br>3. 300.2 |

TABLE 4b-continued

| Amide | halogenated heteroaryl | Compound of example | 1. Yield<br>2. $^1$H-NMR<br>3. $MH^+$ (ESI) |
|---|---|---|---|
| 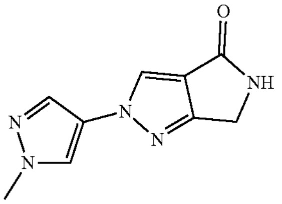 | 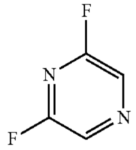 | 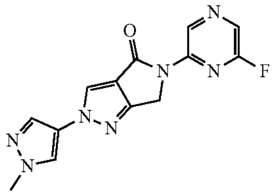<br>149 | 1. 5%<br>2. $^1$H NMR (500 MHz, DMSO-d6) δ 9.61 (d, 1H), 8.83 (dd, 1H), 8.38 (dd, 1H), 8.28 (dd, 1H), 7.93 (dd, 1H), 5.28-4.50 (m, 2H), 3.95-3.86 (m, 3H).<br>3. 300.0 |
| 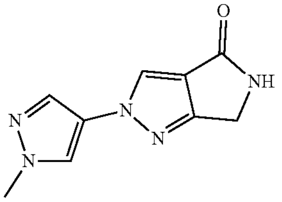 | 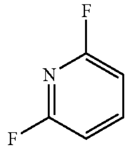 | 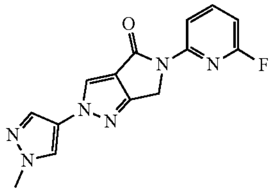<br>150 | 1. 9%<br>2. $^1$H NMR (500 MHz, DMSO-d6) δ 9.61 (d, 1H), 8.83 (dd, 1H), 8.38 (dd, 1H), 8.28 (dd, 1H), 7.93 (dd, 1H), 5.28-4.50 (m, 2H), 3.95-3.86 (m, 3H).<br>3. 299.2 |
| 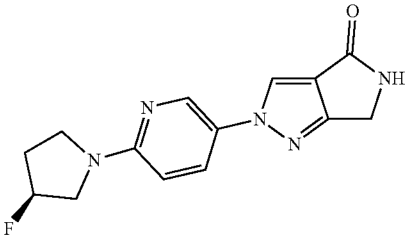 [SMILES: O=C1NCc2nn(-c3ccc(N4CC[C@H](F)C4)nc3)cc21] | 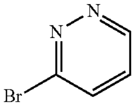 | 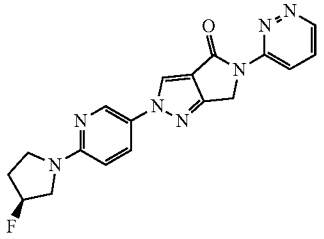<br>151 | 1 .4%<br>2. $^1$H NMR (500 MHz, $CF_3COOD$) δ 9.71 (d, 1H), 9.30 (d, 1H), 8.62 (s, 1H), 8.49 (dd, 2H), 8.34 (d, 1H), 7.20 (s, 1H), 5.63 -5.40 (m, 1H), 5.33 (s, 2H), 4.17-3.80 (m, 4H), 2.62 (s, 1H), 2.52-2.22 (m, 1H).<br>3. 366.2 |
| 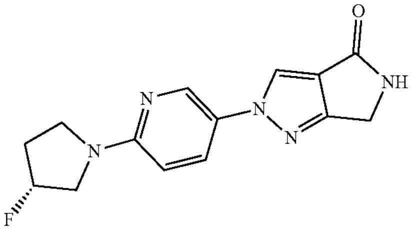 [SMILES: O=C1NCc2nn(-c3ccc(N4CC[C@@H](F)C4)nc3)cc21] | 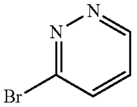 | 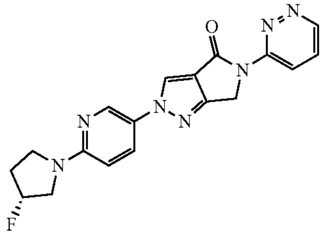<br>152 | 1. 4%<br>2. $^1$H NMR (500 MHz, $CF_3COOD$) δ 9.73 (d, 1H), 9.32 (dd, 1H), 8.64 (s, 1H), 8.61 -8.47 (m, 2H), 8.36 (dd, 1H), 7.22 (d, 1H), 5.84-5.40 (m, 1H), 5.35 (s, 2H), 4.17-3.75 (m, 4H), 2.78-2.24 (m, 2H).<br>3. 366.2 |
| 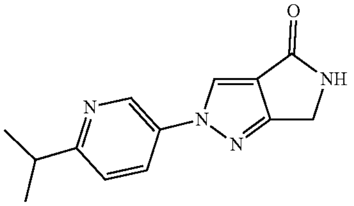 [SMILES: CC(C)c1ccc(-n2cc3c(n2)CNC3=O)cn1] | 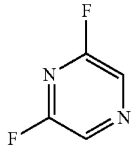 | 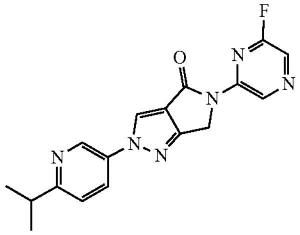<br>153 | 1. ND<br>2. $^1$H NMR (400 MHz, DMSO-d6) δ 9.63 (d, 1H), 9.21 (s, 1H), 9.06 (s, 1H), 8.41 (d, 1H), 8.24 (d, 1H), 7.51 (d, 1H),5.08 (s, 2H), 3.18-3.02 (m, OH), 1.27 (d, 6H).<br>3. 339.2 |

TABLE 4b-continued

| Amide | halogenated heteroaryl | Compound of example | 1. Yield<br>2. $^1$H-NMR<br>3. MH$^+$ (ESI) |
|---|---|---|---|
| 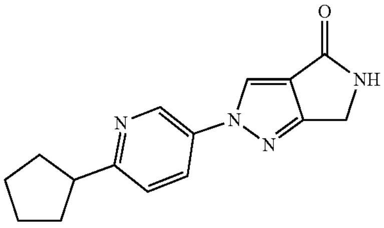 [SMILES: O=C1NCc2nn(-c3ccc(C4CCCC4)nc3)cc21] | 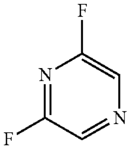 | 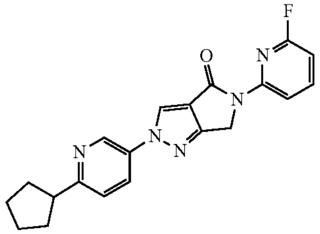<br>154 | 1. ND<br>2. $^1$H NMR (400 MHz, DMSO-d6) δ 9.14 (s, 1H), 9.05 (d, 1H),8.36 (d, 1H), 8.24-8.15 (m, 1H), 8.10 -7.98 (m, 1H), 7.49 (d, 1H), 7.00-6.84 (m, 1H), 5.08 (s, 2H), 3.24 (d, 1H), 2.02 (s, 2H), 1.83-1.61 (m, 6H).<br>3. 364.0 |
| 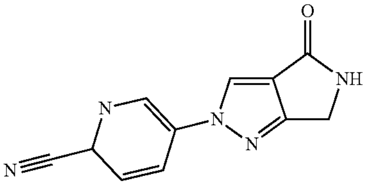 | 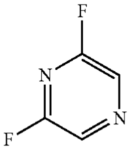 | 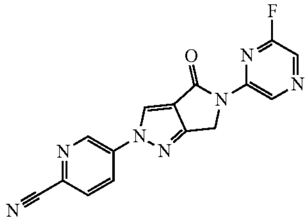<br>155 | 1. ND<br>2. $^1$H NMR (400 MHz, DMSO-d6) δ 9.62 (d, 1H), 9.43-9.36 (m, 2H), 8.59 (dd, 1H), 8.43 (d, 1H), 8.30 (d, 1H), 5.11 (s, 2H).<br>3. 322.2 |
| 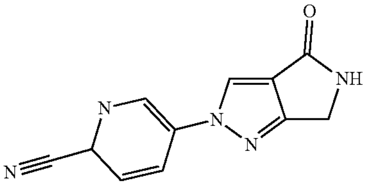 | 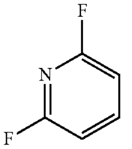 | 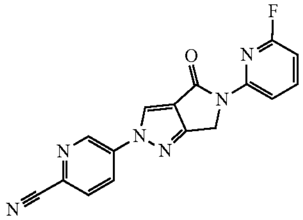<br>156 | 1. ND<br>2. $^1$H NMR (400 MHz, DMSO-d6) δ 9.39 (s, 1H), 9.35 (s, 1H), 8.65-8.52 (m, 1H), 8.36 (d, 1H), 8.32-8.25 (m, 1H), 8.06 (d, 1H), 7.06-6.80 (m, 1H), 5.12 (s, 2H).<br>3. 321.0 |
| 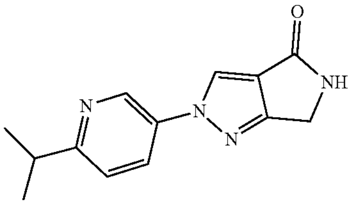 [SMILES: CC(C)c1ccc(-n2cc3c(n2)CNC3=O)cn1] | 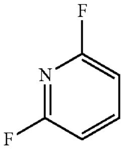 | 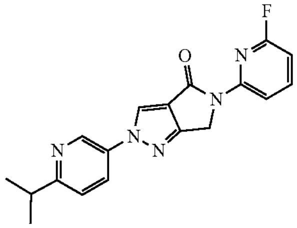<br>157 | 1. ND<br>2. $^1$H NMR (400 MHz, cdcl3) δ 8.93 (s, 1H), 8.43 (d, 1H),8.24 (s, 1H), 8.13 -8.00 (m, 1H), 7.93 - 7.73 (m, 1H), 7.39 (d, 1H), 6.67 (d, 1H), 5.10(s, 2H), 3.33-3.08 (m, 1H), 1.37 (d, 6H).<br>3. 338.2 |
| 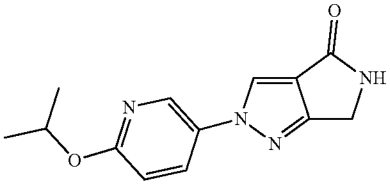 [SMILES: CC(C)Oc1ccc(-n2cc3c(n2)CNC3=O)cn1] | 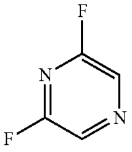 | 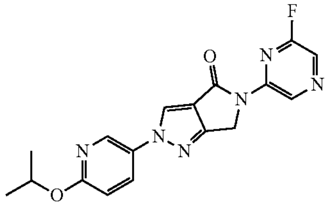<br>158 | 1. ND<br>2. $^1$H NMR (400 MHz, DMSO-d6) δ 9.62 (d, 1H), 9.09 (s, 1H), 8.70 (d, 1H), 8.41 (d, 1H), 8.21 (dd, 1H), 6.96 (d, 1H), 5.33-5.26 (m, 1H), 5.06 (s, 2H), 1.33 (d, 6H).<br>3. 355.2 |

TABLE 4b-continued

| Amide | halogenated heteroaryl | Compound of example | 1. Yield<br>2.$^1$H-NMR<br>3. MH+ (ESI) |
| --- | --- | --- | --- |
| 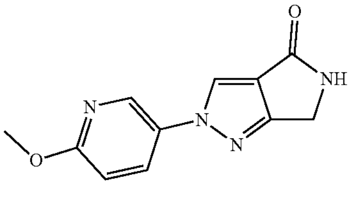 [SMILES: COc1ccc(-n2cc3c(n2)CNC3=O)cn1] | 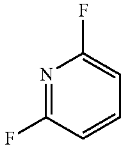 | 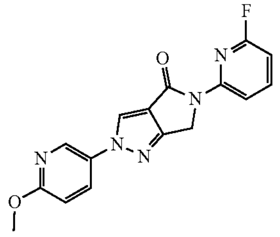<br>159 | 1. 23%<br>2. $^{1}$H NMR (400 MHz, DMSO) δ 8.99 (s, 1H), 8.71 (s, 1H), 8.34 (d, 1H), 8.22 (d, 1H), 8.02 (d, 1H), 7.02 (d, 1H),6.88 (d, 1H), 5.06 (s, 2H), 3.93 (d, 3H).<br>3. 326.2 |
| 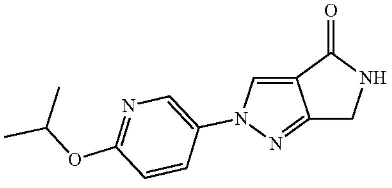 [SMILES: CC(C)Oc1ccc(-n2cc3c(n2)CNC3=O)cn1] | 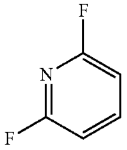 | 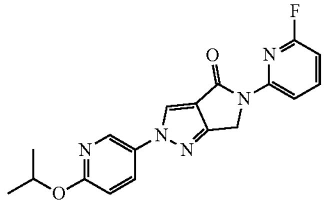<br>160 | 1. ND<br>2. $^{1}$H NMR (600 MHz, DMSO-d6) δ 9.02 (d, 1H), 8.69 (t, 1H), 8.35 (dd, 1H), 8.19 (dt, 1H), 8.03 (q, 1H),6.94 (d, 1H), 6.90 (dd, 1H), 5.29 (td, 1H), 5.06 (d, 2H), 1.33 (dd, 6H).<br>3. 354.2 |
| 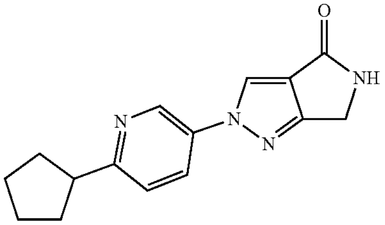 [SMILES: O=C1NCc2nn(-c3ccc(C4CCCC4)nc3)cc21] | 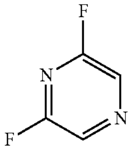 | 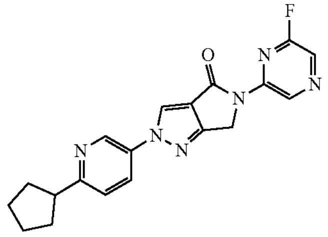<br>161 | 1. ND<br>2. $^{1}$H NMR (400 MHz, DMSO-d6) δ 9.62 (d, 1H), 9.20 (s, 1H), 9.05 (d, 1H), 8.40 (d, 1H), 8.30-8.16 (m, 1H), 7.49 (d, 1H), 5.07 (s, 2H), 3.28-3.11 (m, 1H), 2.13-1.92 (m, 2H), 1.88-1.48 (m, 6H).<br>3. 365.2 |

Example 162

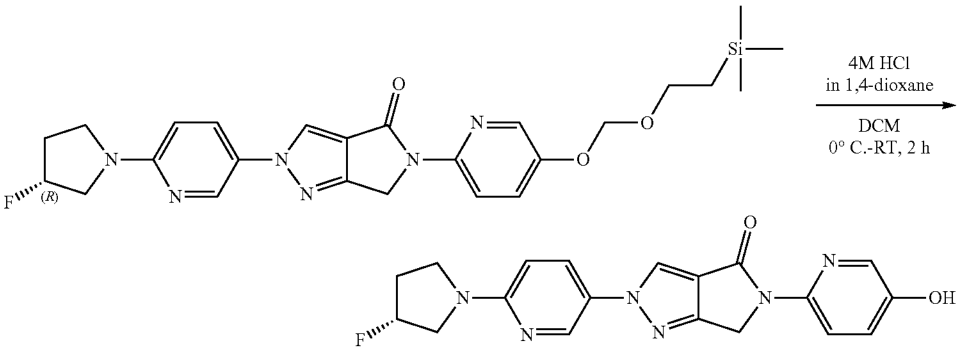

(R)-2-(6-(3-Fluoropyrrolidin-1-yl)pyridin-3-yl)-5-(5-((2-(trimethylsilyl)ethoxy)methoxy)pyridin-2-yl)-5,6-dihydro-pyrrolo[3,4-c]pyrazol-4(2H)-one (50 mg, 0.098 mmol) was dissolved in DCM (1.5 mL) and cooled to 0° C. in an ice-bath with stirring. 4M HCl in 1,4-dioxane (0.2 mL) was added to the solution and stirring was continued at RT for 4 h. After completion of the reaction, the solvent was removed under reduced pressure. The residue obtained was dissolved in ice cold water and basified with aq. sat. sodium bicarbonate solution to pH 8-9. The compound was precipitated, and the solids were removed by filtration. The solid was washed with pentane (3 mL) and further dried on high vacuum for 30 mins to afford the desired compound as pale yellow solid (10 mg, 27%). $^{1}$H NMR (500 MHz, CF3COOD) δ 8.85 (s, 1H), 8.72 (d, 1H), 8.57 (dd, 1H), 8.52-8.32 (m, 2H), 7.90 (d, 1H), 7.46 (s, 1H), 5.86-5.62 (m, 1H), 5.53 (s, 2H), 4.52-4.01 (m, 4H), 2.87 (s, 1H), 2.75-2.44 (m, 1H). MS: 381.1 $[M+H]^+$ Examples 163 to 181

Following the deprotection procedure as described example 162, using the O-protected starting material indicated in the Table 4c below, the following examples were prepared.

TABLE 4c

| Preparative Example | Compound of example | 1.Yield<br>2. $^1$H-NMR<br>3. MH$^+$ (ESI) |
|---|---|---|
| 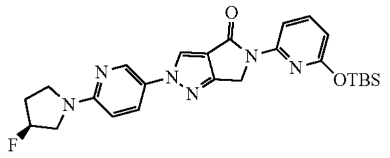 [SMILES: CC(C)(C)[Si](C)(C)Oc1cccc(N2Cc3nn(-c4ccc(N5CC[C@H](F)C5)nc4)cc3C2=O)n1] | 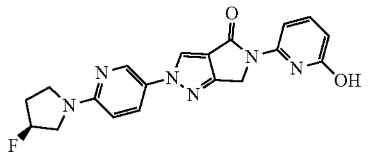 [SMILES: O=C1c2cn(-c3ccc(N4CC[C@H](F)C4)nc3)nc2CN1c1cccc(O)n1]<br>163 | 1. ND<br>2. $^1$H NMR (500 MHz, CF3COOD) δ 8.62 (s, 1H), 8.48 (d, 1H), 8.41-8.19 (m, 2H), 7.22 (s, 1H), 7.05 (dd, 2H), 5.72-5.39 (m, 1 H), 5.22 (s, 2H), 4.23-3.77 (m, 5H), 2.63 (s, 1H), 2.53-2.23 (m, 1H).<br>3. 381.3 |
| 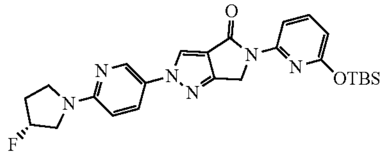 [SMILES: CC(C)(C)[Si](C)(C)Oc1cccc(N2Cc3nn(-c4ccc(N5CC[C@@H](F)C5)nc4)cc3C2=O)n1] | 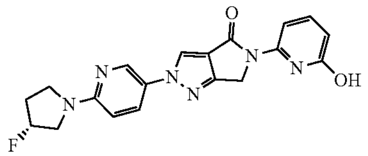 [SMILES: O=C1c2cn(-c3ccc(N4CC[C@@H](F)C4)nc3)nc2CN1c1cccc(O)n1]<br>164 | 1. ND<br>2. $^1$H NMR (400 MHz, CF3COOD) δ 8.73 (s, 1H), 8.60 (d, 1 H), 8.55-8.27 (m, 2H), 7.33 (d, 1H), 7.16 (dd, 2H), 5.77-5.48 (m, 1 H), 5.33 (s, 2H), 4.40-3.85 (m, 4H), 2.73 (d, 1H), 2.65-2.33 (m, 1H).<br>3. 381.3 |
| 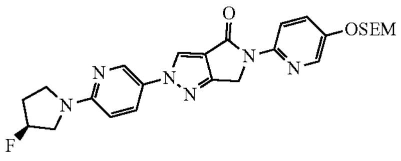 | 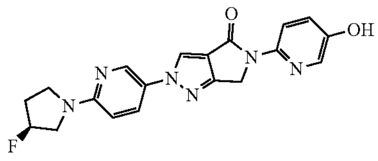 [SMILES: O=C1c2cn(-c3ccc(N4CC[C@H](F)C4)nc3)nc2CN1c1ccc(O)cn1]<br>165 | 1. 55%<br>2. $^1$H NMR (500 MHz, CF3COOD) δ 8.62 (s, 1H), 8.49 (s, 1H), 8.42-8.29 (m, 1 H), 8.29-8.07 (m, 2H), 7.67 (d, 1H), 7.22 (s, 1H), 5.63-5.40 (m, 1H), 5.29 (s, 2H), 4.17-3.83 (m, 4H), 2.63 (s, 1 H), 2.52-2.24 (m, 1H).<br>3. 381.1 |
| 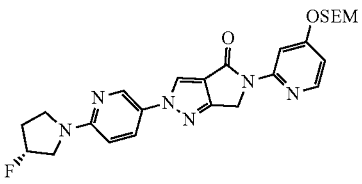 | 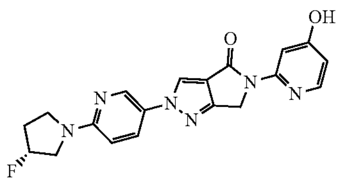 [SMILES: O=C1c2cn(-c3ccc(N4CC[C@@H](F)C4)nc3)nc2CN1c1cc(O)ccn1]<br>166 | 1. 67%<br>2. $^1$H NMR (500 MHz, CF3COOD) δ 8.60 (s, 1H), 8.47 (s, 1H), 8.33 (dd, 1H), 8.22 (d, 1H), 7.21 (s, 1H), 7.11 (dd, 1H), 7.01 (d, 1 H), 5.72-5.39 (m, 1 H), 5.20 (s, 2H), 4.23-3.65 (m, 4H), 2.62 (s, 1 H), 2.51-2.22 (m, 1H).<br>3. 381.3 |
| 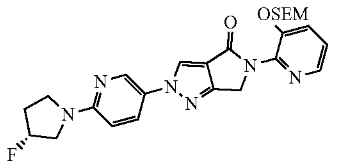 | 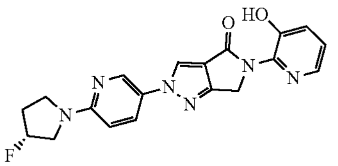 [SMILES: O=C1c2cn(-c3ccc(N4CC[C@@H](F)C4)nc3)nc2CN1c1ncccc1O]<br>167 | 1. 48%<br>2. $^1$H NMR (500 MHz, CF3COOD) δ 8.62 (s, 1H), 8.49 (s, 1H), 8.33 (d, 1H), 8.25-8.00 (m, 2H), 7.58 (dd, 1H),7.19 (s, 1H), 5.68 (s, 2H), 5.58-5.34 (m, 1 H), 4.17-3.69 (m, 4H), 2.61 (s, 1 H), 2.48-2.19 (m, 1H).<br>3. 381.4 |
| 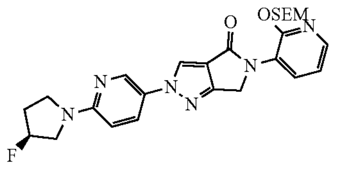 | 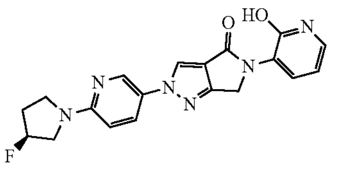 [SMILES: O=C1c2cn(-c3ccc(N4CC[C@H](F)C4)nc3)nc2CN1c1cccnc1O]<br>168 | 1. 38%<br>2. $^1$H NMR (500 MHz, CF3COOD) δ 8.66-8.38 (m, 2H), 8.28 (dd, 2H), 8.10-7.85 (m, 1 H), 7.36-6.99 (m, 2H), 5.61-5.36 (m, 1H), 5.16 (s, 2H), 4.14-3.75 (m, 4H), 2.61 (s, 1H), 2.49-2.19 (m, 1H).<br>3. 381.1 |

TABLE 4c-continued

| Preparative Example | Compound of example | 1.Yield<br>2. ¹H-NMR<br>3. MH⁺ (ESI) |
|---|---|---|
| 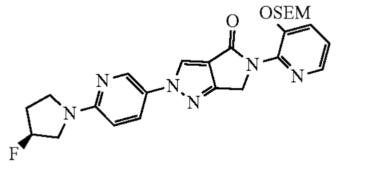 | 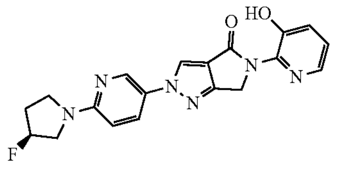 [SMILES: O=C1c2cn(-c3ccc(N4CC[C@H](F)C4)nc3)nc2CN1c1ncccc1O]<br>169 | 1. 42%<br>2. ¹H NMR (500 MHz, CF3COOD) δ 8.69 (s, 1H), 8.56 (s, 1H), 8.50-8.37 (m, 1H), 8.31-8.13 (m, 2H), 7.67 (dd, 1H), 7.28 (s, 1H), 5.77 (s, 2H), 5.70-5.36 (m, 1 H), 4.31-3.80 (m, 4H), 2.69 (s, 1 H), 2.59-2.29 (m, 1H).<br>3. 381.4 |
| 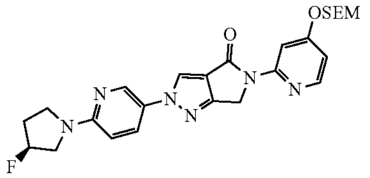 | 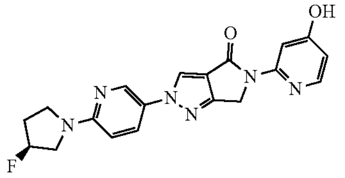 [SMILES: O=C1c2cn(-c3ccc(N4CC[C@H](F)C4)nc3)nc2CN1c1cc(O)ccn1]<br>170 | 1. 50%<br>2. ¹H NMR (400 MHz, CF3COOD) δ 9.01-8.84 (m, 1 H), 8.77 (s, 1H), 8.70-8.58 (m, 1 H), 8.52 (d, 1H), 7.52 (s, 1H), 7.46-7.35 (m, 1H), 7.35-7.23 (m, 1H), 6.10-5.62 (m, 1 H), 5.50 (s, 2H), 4.42-4.08 (m, 4H), 2.92 (s, 1 H), 2.81-2.47 (m, 1H).<br>3. 381.3 |
| 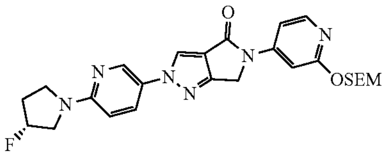 | 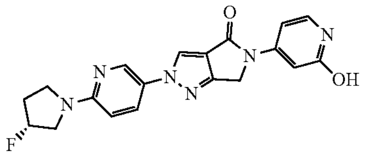 [SMILES: O=C1c2cn(-c3ccc(N4CC[C@@H](F)C4)nc3)nc2CN1c1ccnc(O)c1]<br>171 | 1. 33%<br>2. ¹H NMR (500 MHz, CF3COOD) δ 8.63 (s, 1H), 8.50 (s, 1H), 8.34 (d, 1H), 8.08 (d, 1H), 8.01 (d, 1H), 7.89 (dd, 1H), 7.22 (s, 1H), 5.78-5.39 (m, 1H), 5.22 (s, 2H), 4.18-3.78 (m, 4H), 2.82-2.20 (m, 2H).<br>3. 381.2 |
| 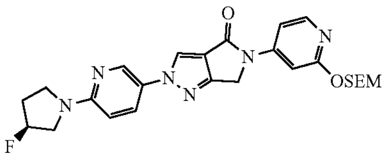 | 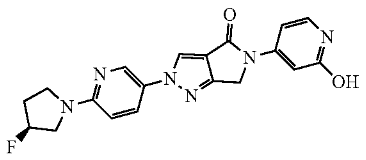 [SMILES: O=C1c2cn(-c3ccc(N4CC[C@H](F)C4)nc3)nc2CN1c1ccnc(O)c1]<br>172 | 1. 22%<br>2. ¹H NMR (400 MHz, CF3COOD) δ 8.73 (s, 1H), 8.61 (s, 1H), 8.46 (d, 1H), 8.35-8.09 (m, 2H), 8.01 (dd, 1H), 7.34 (d, 1H), 5.81-5.47 (m, 1 H), 5.35 (s, 2H), 4.37-3.84 (m, 4H), 2.94-2.34 (m, 2H).<br>3. 381.3 |
| 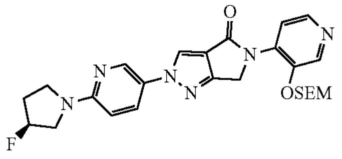 | 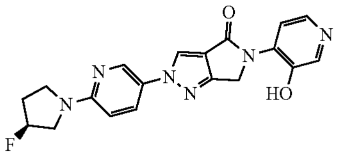 [SMILES: O=C1c2cn(-c3ccc(N4CC[C@H](F)C4)nc3)nc2CN1c1ccncc1O]<br>173 | 1. 38%<br>2. ¹H NMR (500 MHz, CF3COOD) δ 9.32-8.07 (m, 5H), 7.31 (s, 2H), 5.81-5.35 (m, 3H), 4.28-3.83 (m, 4H), 2.62-2.32 (m, 2H).<br>3. 381.0 |
| 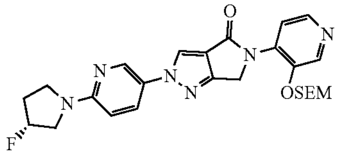 | 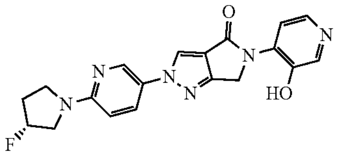 [SMILES: O=C1c2cn(-c3ccc(N4CC[C@@H](F)C4)nc3)nc2CN1c1ccncc1O]<br>174 | 1. 40%<br>2. ¹H NMR (400 MHz, CF3COOD) δ 8.75 (s, 1H), 8.70-8.55 (m, 2H), 8.55-8.35 (m, 3H), 7.34 (s, 1 H), 5.58 (s, 3H), 4.24-3.90 (m, 4H), 2.76 (s, 1 H), 2.64-2.34 (m, 1H).<br>3. 381.3 |
| 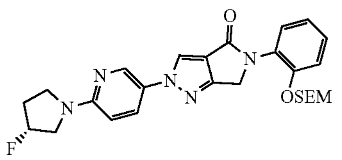 | 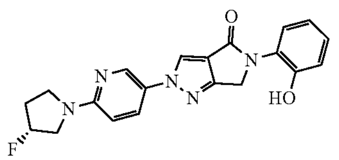 [SMILES: O=C1c2cn(-c3ccc(N4CC[C@@H](F)C4)nc3)nc2CN1c1ccccc1O]<br>175 | 1. 56%<br>2. ¹H NMR (400 MHz, CF3COOD) δ 9.08-8.53 (m, 3H), 8.00-7.24 (m, 5H), 6.05-5.71 (m, 1H), 5.46 (d, 2H), 4.33 (s, 4H), 3.01 (s, 1H), 2.90-2.58 (m, 1H).<br>3. 380.6 |

TABLE 4c-continued

| Preparative Example | Compound of example | 1.Yield<br>2. $^{1}$H-NMR<br>3. $MH^{+}$ (ESI) |
|---|---|---|
| 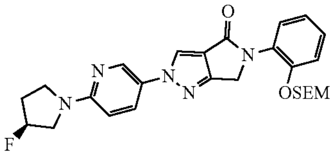 | 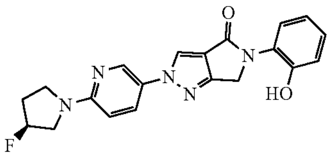 [SMILES: O=C1c2cn(-c3ccc(N4CC[C@H](F)C4)nc3)nc2CN1c1ccccc1O]<br>176 | 1. 67%<br>2. $^{1}$H NMR (500 MHz, CF3COOD) δ 8.47 (s, 1H), 8.42 (s, 1H), 8.31 (d, 1H), 7.59-7.28 (m, 2H), 7.22 (s, 1 H), 7.15-7.07 (m, 2H), 5.64-5.38 (m, 1H), 5.09 (s, 2H), 4.18-3.81 (m, 4H), 2.63 (s, 1 H), 2.51-2.24 (m, 1H).<br>3. 380.2 |
| 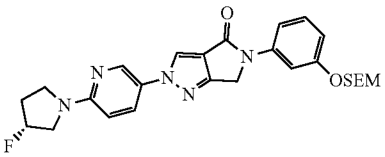 | 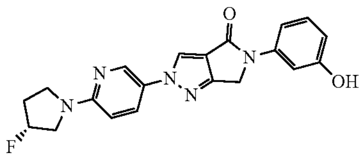 [SMILES: O=C1c2cn(-c3ccc(N4CC[C@@H](F)C4)nc3)nc2CN1c1cccc(O)c1]<br>177 | 1. 54%<br>2. $^{1}$H NMR (500 MHz, CF3COOD) δ 8.54 (d, 2H), 8.42 (dd, 1H), 7.51 (dt, 1H), 7.39 (d, 1H), 7.32 (d, 1H), 7.25 (dd, 1H), 7.11 (dd, 1H), 5.76-5.49 (m, 1H), 5.20 (s, 2H), 4.27-3.89 (m, 4H), 2.74 (s, 1 H), 2.63-2.34 (m, 1H).<br>3. 380.2 |
| 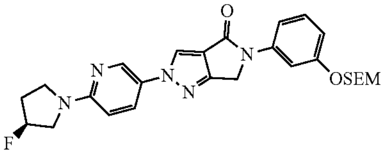 | 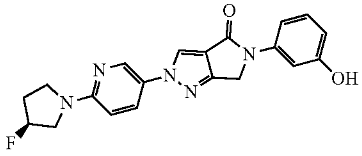 [SMILES: O=C1c2cn(-c3ccc(N4CC[C@H](F)C4)nc3)nc2CN1c1cccc(O)c1]<br>178 | 1. 54%<br>2. $^{1}$H NMR (500 MHz, CF3COOD) δ 8.59 (d, 2H), 8.46 (dd, 1H), 7.56 (dt, 1H), 7.44 (d, 1H), 7.37 (s, 1H), 7.30 (d, 1H), 7.15 (dd, 1H), 5.94-5.55 (m, 1H), 5.25 (s, 2H), 4.46-3.93 (m, 4H), 2.79 (s, 1 H), 2.68-2.33 (m, 1H).<br>3. 380.2 |
| 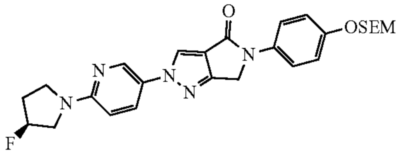 | 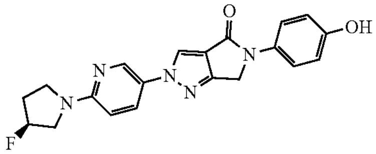 [SMILES: O=C1c2cn(-c3ccc(N4CC[C@H](F)C4)nc3)nc2CN1c1ccc(O)cc1]<br>179 | 1. 51%<br>2. $^{1}$H NMR (500 MHz, CF3COOD) δ 8.42 (d, 1H), 8.29 (d, 1H), 7.39 (d, 1H), 7.19 (s, 1H), 7.06 (d, 1H), 5.77-5.27 (m, 1H), 5.04 (s, 1H), 4.17-3.65 (m, 2H), 2.61 (s, 1H), 2.51-2.08 (m, 1H).<br>3. 380.3 |
| 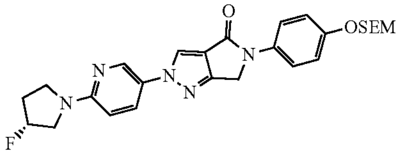 | 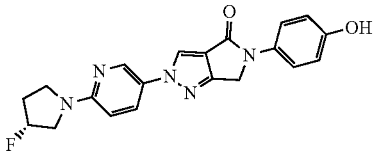 [SMILES: O=C1c2cn(-c3ccc(N4CC[C@@H](F)C4)nc3)nc2CN1c1ccc(O)cc1]<br>180 | 1. 81%<br>2. $^{1}$H NMR (500 MHz, CF3COOD) δ 8.50 (d, 2H), 8.40-8.34 (m, 1H), 7.47 (d, 2H), 7.27 (s, 1H), 7.14 (d, 2H), 5.78-5.44 (m, 1H), 5.12 (s, 2H), 4.29-3.73 (m, 4H), 2.69 (s, 1H), 2.61-2.28 (m, 1H).<br>3. 380.3 |
| 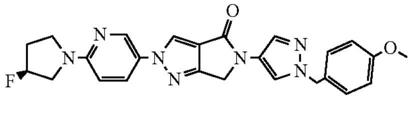 [SMILES: COc1ccc(Cn2cc(N3Cc4nn(-c5ccc(N6CC[C@H](F)C6)nc5)cc4C3=O)cn2)cc1]<br>Reaction performed at 150° C. | 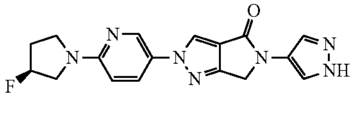 [SMILES: O=C1c2cn(-c3ccc(N4CC[C@H](F)C4)nc3)nc2CN1c1cn[nH]c1]<br>181 | 1. 40%<br>2. $^{1}$H NMR (80 MHz, DMSO-d6) δ 8.75 (s, 1H), 8.58 (d, 1H), 8.09-7.89 (m, 3H), 6.65 (d, 1H), 5.46 (d, 1H), 4.84 (s, 2H), 3.98-3.65 (m, 4H), 2.25-1.89 (m, 2H).<br>3. 354.1 |

Precursor 1

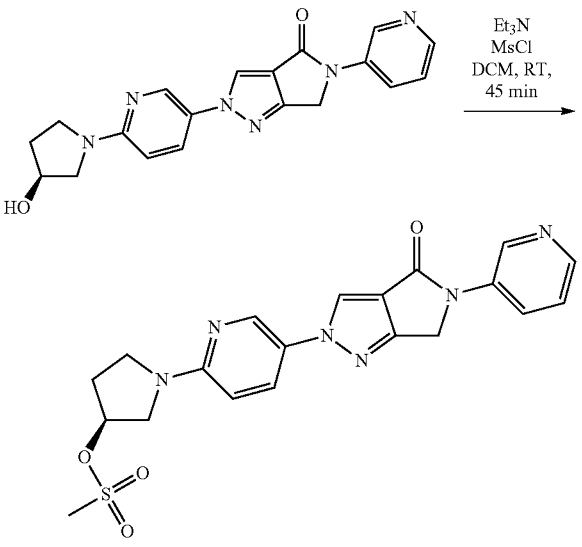

In a flask under argon, preparative example 7 (135 mg, 0.373 mmol) was dissolved in dichloromethane. Triethylamine (1.038 ml, 7.45 mmol) was added and the reaction mixture was stirred for 5 minutes. Then methanesulfonyl chloride (0.290 ml, 3.73 mmol) was added dropwise to the reaction mixture. The mixture was stirred at room temperature for 20 min. Methanesulfonyl chloride (0.290 ml, 3.73 mmol) was added and the reaction mixture was stirred for 25 min. The reaction mixture was quenched with a 1N aqueous solution of NaOH and then extracted three times with dichloromethane. The combined organic layers were dried over $Na_2SO_4$, filtered and concentrated to dryness. The product was purified by flash chromatography (Silica, Silica 12 g column; 0-10% methanol in dichloromethane) to afford (S)-1-(5-(4-oxo-5-(pyridin-3-yl)-5,6-dihydropyrrolo[3,4-c]pyrazol-2(4H)-yl)pyridin-2-yl)pyrrolidin-3-yl methanesulfonate as a white solid (17.4 mg, 11%). $^1$H NMR (80 MHz, DMSO-d6) δ=9.03 (d, 1H), 8.87 (s, 1H), 8.61 (d, 1H), 8.44-8.15 (m, 2H), 8.03 (dd, 1H), 7.45 (q, 1H), 6.68 (d, 1H), 5.45 (s, 1H), 5.09 (s, 2H), 3.67 (d, 4H), 3.27 (s, 3H), 2.41-2.08 (m, 2H). MS: 441.08 $[M+H]^+$ Alternative Procedure In a vial under argon and cooled to 0° C., (S)-2-(6-(3-hydroxypyrrolidin-1-yl)pyridin-3-yl)-5-(pyridin-3-yl)-5,6-dihydropyrrolo[3,4-c]pyrazol-4(2H)-one (100 mg, 0.276 mmol), and 4-dimethylaminopyridine (337 mg, 2.76 mmol) were mixed in pyridine (17 mL). Mesyl-Cl (0.108 mL, 1.380 mmol) was added and the mixture was flushed with argon. The reaction mixture was allowed to warm up to RT and was stirred for 2 h, after this time 4-dimethylaminopyridine (169 mg, 1.380 mmol) and Mesyl-Cl (0.054 mL, 0.690 mmol) were added at 0° C. After 40 min, 0.1 N NaOH in water (20 mL) was added to the mixture to basify it. The solution was poured into cold water and filtered. It was washed with water until the pH of the water was 7. The solid was dried under high vacuum for 30 min to afford the compound as an orange solid (86 mg, 71%). $^1$H NMR (400 MHz, DMSO-d6) δ 9.03 (d, 1H), 8.87 (s, 1H), 8.61 (d, 1H), 8.35 (d, 1H), 8.26 (d, 1H), 8.02 (dd, 1H), 7.45 (dd, 1H), 6.68 (d, 1H), 5.44 (s, 1H), 5.08 (s, 2H), 3.86-3.42 (m, 4H), 3.27 (s, 3H), 2.40-2.24 (m, 2H). MS: 441.1 $[M+H]^+$ Precursor 2

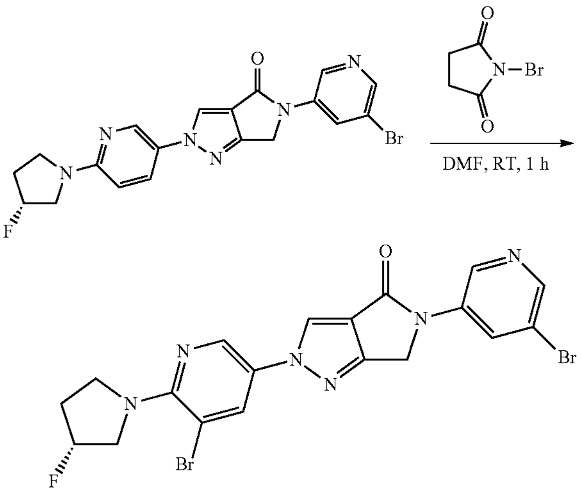

N-Bromosuccinimide (22 mg, 0.126 mmol) was added to a solution of preparative example 8 (43 mg, 0.097 mmol) in dimethylformamide (3 mL). After stirring for 1 h at room temperature, the reaction mixture was then diluted with water and ethyl acetate. The layers were separated and the aqueous layer was extracted twice with ethyl acetate. The combined organic layers were dried over sodium sulfate, filtered and concentrated under reduced pressure. The residue was triturated in acetonitrile and the solid was collected by filtration. The crude solid was then purified by flash chromatography (Silica, Silica 12 g column; 2-5% methanol in dichloromethane). The fractions were concentrated under reduced pressure and the residue was triturated in acetonitrile. The solid was collected by filtration to afford (R)-2-(5-bromo-6-(3-fluoropyrrolidin-1-yl)pyridin-3-yl)-5-(5-bromopyridin-3-yl)-5,6-dihydropyrrolo[3,4-c]pyrazol-4(2H)-one as a beige solid (16 mg, 32%). $^1$H-NMR δ 8.88 (d, 1H), 8.83-8.70 (m, 1H), 8.51-8.32 (m, 2H), 8.22-7.83 (m, 2H), 5.75-4.77 (m, 3H), 4.32-3.72 (m, 4H), 0.98-0.67 (m, 2H). MS: 523.10 $[M+H]^+$ Precursor 3

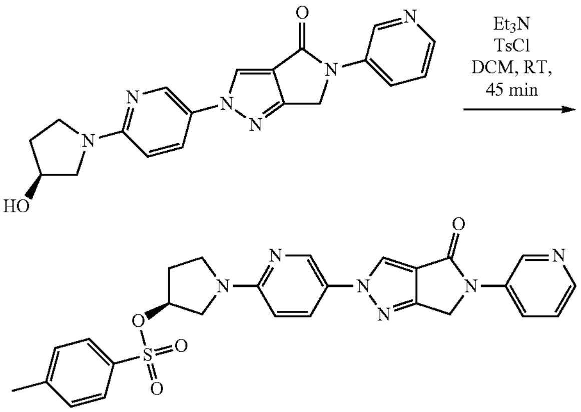

To a solution of preparative example 7 (70 mg, 0.193 mmol) in DCM (3.5 mL) at RT was added triethylamine (0.08 mL, 0.5797 mmol) under $N_2$ atm. The reaction mixture was cooled to 0° C. then p-toluenesulfonyl chloride (73 mg, 0.3865 mmol) was added portionwise over a period of 10 mins, followed by DMAP (23 mg, 0.193 mmol). Then, the reaction mixture was warmed to RT and allowed to stir for 12 h, progress of the reaction was monitored by TLC. After completion of the reaction, the mixture was diluted with sat aq. $NaHCO_3$ (5 ml) at RT and extracted with 5% MeOH in DCM twice (2×20 ml). The combined organic layers were dried over with $Na_2SO_4$. Solvent was distilled off under reduced pressure to get a pale yellow coloured solid. The crude compound was purified by column chromatography on basic silica gel (100-200 mesh) by eluting with a DCM/MeOH gradient (100/0→98/2) to afford the desired compound as an off white solid (20 mg, 20%). $^1$H NMR (400 MHz, DMSO-D6) δ 9.03 (d, 1H), 8.86 (d, 1H), 8.58 (dd, 1H), 8.35 (dd, 1H), 8.32-8.18 (m, 1H), 7.99 (ddd, 1H), 7.69-7.54 (m, 2H), 7.44 (td, 3H), 6.62 (dd, 1H), 5.25-5.01 (m, 3H), 3.76-3.39 (m, 4H), 2.39 (d, 3H), 2.36-2.01 (m, 2H). MS: [M+H]+ 517.3

Precursor 4

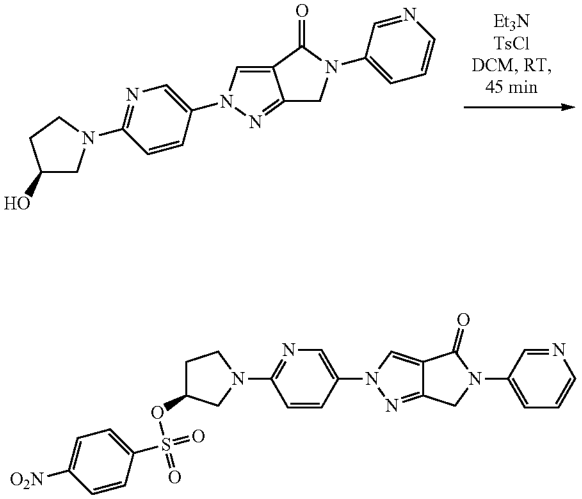

In a flask under argon, preparative example 7 (700 mg, 1.93 mmol) and 4-DMAP (236 mg, 1.93 mmol) were suspended in 9.4 ml pyridine and cooled to 0° C. 4-Nitrobenzolsulfonyl chloride (2.14 g, 9.66 mmol) was added and the suspension was stirred at room temperature for 4 h. 4-DMAP (118 mg, 0.97 mmol) and 4-nitrobenzolsulfonyl chloride (1.07 g, 4.83 mmol) were added at 0° C. The reaction mixture was stirred overnight. Further 4-DMAP (118 mg, 0.97 mmol) and 4-nitrobenzolsulfonyl chloride (1.07 g, 4.83 mmol) were added at 0° C. and the reaction mixture was stirred for 1 day at room temperature. 40 ml 1M NaOH was added and the resulting mixture was centrifuged for 5 min at 6000 ppm. The centrifugation vial was decanted and the remaining solid was washed 4 times with 40 mL water. Water was removed by centrifugation/decantation after each washing step. The remaining solid was suspended in water, transferred to a flask and evaporated to yield the desired product as a brownish solid (871 mg, 83%). $^1$H NMR (400 MHz, DMSO-d6) δ=9.04 (s, 1H), 8.85 (s, 1H), 8.68-7.90 (m, 8H), 7.46 (bs, 1H), 6.63 (d, 1H), 5.42 (s, 1H), 5.09 (s, 2H), 3.86-3.39 (m, 4H), 2.36-2.05 (m, 2H). MS: $[M+H]^+$ 547.97

Radioligand Synthesis

Example-1 [$^3$H-1]

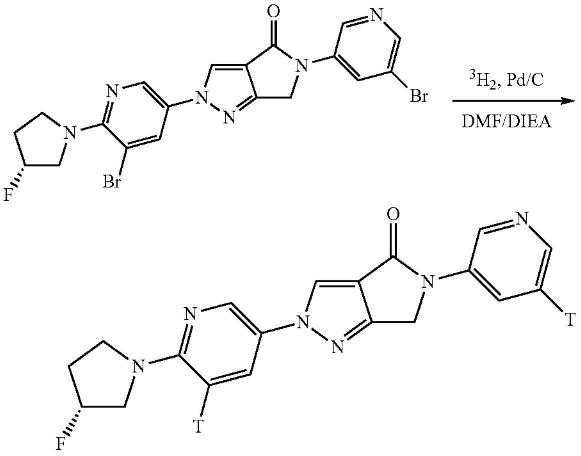

Precursor 2 (0.5 mg) was dissolved in dimethylformamide (DMF) (0.3 mL) and N,N-diisopropylethylamine (DIEA) (5 μL) in a tritium reaction vessel. 10% Pd/C (0.5 mg) was added and the vessel was pressurized to 0.5 atm with tritium gas at −200° C. The solution was stirred for 1 h at room temperature, cooled to −200° C. and excess gas was removed. The reaction flask was rinsed with 4×1 mL $CH_3OH$, passing each of the $CH_3OH$ washes through a celite pad. The combined methanol was removed under vacuum. The material was purified by HPLC. The mobile phase was removed and the product was redissolved in absolute ethanol. (5 mCi with a radiochemical purity of >99% and a specific activity of 43.6 Ci/mmol). T means Tritium ($^3$H). MS (ESI): m/z=369 (100%) $[M+H]^+$ Example 1-[$^{18}$F-1]

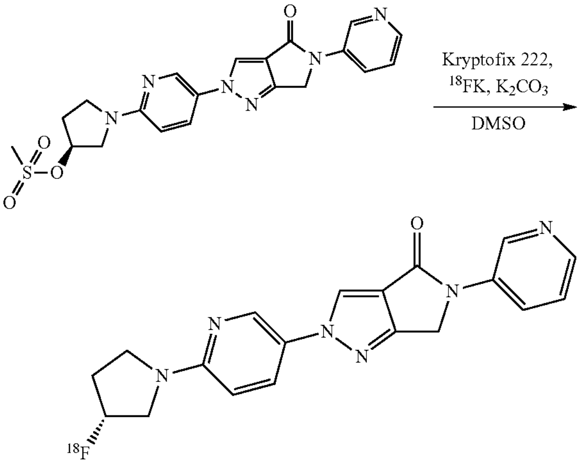

Drying step: In a typical procedure, [$^{18}$F]fluoride in a shipping vial (target water obtained from a commercial cyclotron facility) was transferred onto and trapped on an ion exchange cartridge. It was then eluted with a solution of potassium carbonate and Kryptofix 222 into the reaction vessel (RV1) of the TRACERlab® module. The solution was first evaporated by heating at 95° C. for 4 min under vacuum and helium flow. Acetonitrile (1 mL) was added to RV1 and the evaporation was continued under the same conditions for 2 min under vacuum and helium flow. After a second addition of acetonitrile (1 mL), final evaporation was carried out at 95° C. for 2 min under vacuum and helium flow. The reactor was then cooled to 60° C.

Radiolabeling: A solution of Precursor 1 (1 mg) in anhydrous dimethylsulfoxide (0.7 mL) was added to the reaction vessel and the reaction mixture was heated at 100° C. for 10 min. The reactor was cooled to 40° C., diluted with HPLC mobile phase (1.8 mL) and the contents were transferred into the loop-loading vial (RV2). The reactor was rinsed with water for injection (2.5 mL) and the rinse was transferred into RV2. The contents of RV2 were transferred into the HPLC injector loop for purification.

HPLC purification: Purification was performed by HPLC using a semi-preparative Phenomenex Synergi C18 column (5 μm, 250×10 mm) and eluted with a mixture of acetonitrile/ammonium acetate solution (20 mM) (35/65, v/v) at a flow rate of 4 mL/min. The product fraction was collected in Flask1, containing 20 mL of sodium ascorbate (5 mg/mL) in WFI. The diluted product mixture was passed through a C18 solid-phase extraction cartridge and the cartridge was rinsed with 10 mL of sodium ascorbate (5 mg/mL) in WFI. The radiolabelled product was eluted from the SPE cartridge with 1.0 mL of 200-proof USP grade ethanol into the formulation flask, pre-loaded with 10 mL of formulation base (sodium ascorbate (4.67 mg/mL) in saline). The cartridge was rinsed with 4.0 mL of formulation base and the rinse was mixed with the contents of the formulation flask. The resulting solution was passed through a sterilizing 0.2 μm membrane filter into a sterile, filter-vented vial (final product vial, FPV), pre-filled with 15 mL of normal saline (27% decay corrected yield).

Example-4 [$^3$H-4]

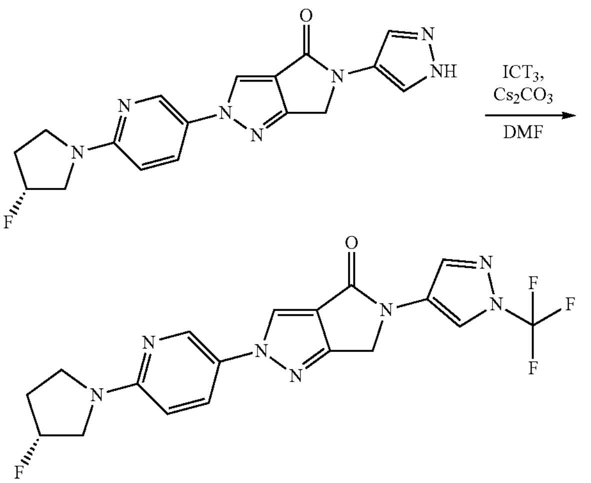

Example 4 (1.0 mg) was added to a tritium reaction vessel, followed by cesium carbonate (1.0 mg), then DMF (0.1 mL), and finally iodomethane, [3H] (100 mCi). The vessel was sealed and the solution was stirred for 18 h at room temperature. The reaction mixture was transferred to a larger flask and the reaction vessel was rinsed with 4×2 mL methanol. The combined methanol was removed under vacuum. Crude yield: 38 mCi. The material was purified by silica gel column. Mobile phase was removed under vacuum and the product was re-dissolved in 0.05% TFA in water/acetonitrile. The material was further purified by semi-preparative reverse phase HPLC. Mobile phase was removed under vacuum and the product was re-dissolved in absolute ethanol. (4.8 mCi, purity >99%). The specific activity was determined to be 79.98 Ci/mmol by MS.

MS (ESI): m/z=374 (100%) $[M+H]^+$

Biological Assay Description and Corresponding Results

1. Preparation of Human Parkinson's Disease (PD) Brain-Derived Alpha-Synuclein (a-Syn) Aggregates The procedure was adapted from the protocol described in Spillantini et al., 1998. Frozen tissue blocks from PD donors were thawed on ice and homogenized using a glass dounce homogenizer. The homogenate was then centrifuged at 11,000×g (12,700 RPM) in an ultracentrifuge (Beckman, XL100K) for 20 minutes at 4° C. using a pre-cooled 70.1 rotor (Beckman, 342184). Pellets were resuspended in extraction buffer [10 mM Tris-HCl pH 7.4, 10% sucrose, 0.85 mM NaCl, 1% protease inhibitor (Calbiochem 539131), 1 mM EGTA, 1% phosphatase inhibitor (Sigma P5726 and P0044)] and centrifuged at 15,000×g (14,800 RPM, a 70.1 Ti rotor) for 20 minutes at 4° C. Pellets were discarded and sarkosyl (20% stock solution, Sigma L7414) was added to the supernatants to a final concentration of 1% at room temperature for one hour. This solution was then centrifuged at 100,000×g (38,000 RPM, 70.1 Ti rotor) for one hour at 4° C. Pellets containing enriched a-syn aggregates were resuspended in PBS and stored at −80° C. until use.

2. Micro-Radiobinding Competition Assay for the Determination of Binding Affinity PD brain-derived a-syn aggregates were spotted onto microarray slides. The slides were incubated with the tritiated reference ligand, [$^3$H]-a-syn-Ref (as described in WO2017/153601) at 20 nM and the example compounds of this invention (non-radiolabelled) either at 1 μM or at increasing concentrations in the range of 50 pM to 2 μM. After incubation, slides were washed and exposed to a phosphor storage screen (GE healthcare, BAS-IP TR 2025). Following exposure, phosphor storage screens were scanned with a laser imaging system (Typhoon FLA 7000) to readout the signal from the radiobinding experiments described above. Quantification of the signal was performed using the ImageJ software package. Non-specific signal was determined with an excess of non-radiolabelled reference ligand (1 μM) and specific binding was calculated by subtracting the non-specific signal from the total signal. Competition was calculated as percent, where 0% was defined as the specific binding in the presence of vehicle and 100% as the values obtained in the presence of excess of the non-radiolabelled reference ligand. All measurements were performed with at least two technical replicates. $K_i$ values were calculated in GraphPad Prism7 by applying a nonlinear regression curve fit using a one site, specific binding model.

Example compounds were assessed for their potency to compete with the binding of [3H] radiolabelled reference ligand to PD patient brain-derived a-syn aggregates. Results of the micro-radiobinding competition assay for the example compounds tested are shown in Table 5 as: % competition at 1 μM and $K_i$ value. All measurements were performed on the same PD brain-derived a-syn aggregates. The $K_i$ value of compound 1 reported here is the average of two independent experiments.

TABLE 5

| | Micro-radiobinding competition assay | |
|---|---|---|
| Example Compound no. | Competition at 1 μM (%) | Ki (nM) |
| 1 | 94 | 30 |
| 2 | 68 | Not determined |

Table 5: Assessment of binding affinity by micro-radiobinding competition assay on human PD brain-derived a-syn aggregates. Left, percent (%) competition over the tritiated reference ligand in the presence of 1 μM of example compounds 1 and 2. Right, the Ki value for example compound 1 is shown. As shown in Table 5, example compounds 1 and 2 of the present invention show good binding to PD brain-derived a-syn aggregates.

3. Assessment of Target Engagement of Example-1 [$^3$H-1] in a-Synucleinopathies and AD Tissues 3A: By High Resolution Micro-Autoradiography The protocol was adapted from Marquie et al., 2015. Sections were incubated with tritiated example compound 1 (Example-1 [3H-1]) or a reference Tau ligand ([3H]-Tau-Ref at 60 nM for one hour at room temperature (RT). Sections were then washed as follows: One time in ice-cold 50 mM Tris-HCl pH 7.4 buffer for one minute, two times in 70% ice-cold ethanol for one minute, one time in ice-cold 50 mM Tris-HCl pH 7.4 buffer for one minute and finally rinsed briefly in ice-cold distilled water. Sections were subsequently dried and then exposed to Ilford Nuclear Emulsion Type K5 (Agar Scientific, AGP9281) in a light-proof slide storage box. After five days, the sections were developed by immersing them successively in the following solutions: 1.) Ilford Phenisol Developer (1:5 dilution in $H_2O$, Agar Scientific, AGP9106), 2.) Ilfostop solution (1:20 dilution in $H_2O$, Agar Scientific, AGP9104), 3.) Ilford Hypam Fixer (1:5 dilution in $H_2O$, Agar Scientific, AGP9183) and finally rinsed with $H_2O$.

When indicated, immunostaining was also performed on the same section. For image acquisition, sections were mounted using ProLong Gold Antifade reagent (Invitrogen P36930) and imaged on a Panoramic150 Slide Scanner (3DHistech) with a 20× objective capturing separately brightfield and fluorescent images.

3B. By Staining of Sections Using Antibodies

Brain sections were immunostained using a commercially available antibody, specific for phosphorylated serine at amino acid 129 a-synuclein (a-syn-pS129, rabbit monoclonal, Abcam 51253) or a mouse conformation-dependent anti-Tau antibody (MC1, kindly provided by Peter Davies, Northwell, US) or a commercially available antibody specific for TDP-43 phosphorylated serine at amino acid 409/410 (anti-pTDP-43 pS409/410, Biolegend 829901). Sections were fixed for 15 minutes at 4° C. with 4% formaldehyde (Sigma, 252549) and washed three times for five minutes with 1×PBS (Dulbecco's phosphate buffered saline, Sigma D1408) at RT. Next, sections were saturated and permeabilized in blocking buffer (PBS, 10% NGS, 0.25% Triton X-100) for one hour at RT and incubated overnight at 4° C. with the primary antibody corresponding to a-syn-pS129 or MC1 (in PBS, 5% NGS, 0.25% Triton X-100). The following day, sections were washed three times for five minutes with 1×PBS before incubation with a secondary, AlexaFluor647-labelled goat-anti-rabbit (Abcam, ab150079) or goat-anti-mouse (115-605-166, Jackson ImmunoResearch) antibody for 45 minutes at RT. Following incubation with secondary antibodies the sections were washed three times in PBS before being processed further. For image acquisition, sections were mounted using ProLong Gold Antifade reagent (Invitrogen P36930) and imaged with a Panoramic150 Slide Scanner (3DHistech; Hungary).

Results: High-resolution micro-autoradiography with Example-1 [$^3$H-1] was performed on frozen human brain sections from different a-synucleinopathy cases. Strong autoradiography signal from Example-1 [$^3$H-1] was detected in the form of accumulating silver grains (FIG. 1 bottom) and co-localized with immunofluorescence signal from a-syn-pS129 antibody (FIG. 1 top) suggesting strong target engagement on Lewy bodies and Lewy neurites, as well as a-syn aggregates of very small size, in PD and other a-synucleinopathies, including Multiple System Atrophy (MSA), Dementia with Lewy bodies (DLB), Lewy Body Variant of Alzheimer's disease (LBV) and PDD.

4. Assessment of Specific Binding of Example-1 [$^3$H-1] in Brain Sections from PD, PDD and Non-Demented Control (NDC) Donors by Autoradiography Frozen human brain sections from one familial PD case (a-synuclein [SNCA] gene G51 D missense mutation), labelled as SNCA (G51 D), one PDD case and two non-demented control (NDC) cases were first briefly fixed for 15 minutes at 4° C. with 4% paraformaldehyde (Sigma, 252549) and washed three times for five minutes with PBS (Dulbecco's phosphate buffered saline, Sigma) at RT. All slides were then equilibrated for 20 minutes in 50 mM Tris-HCl pH 7.4 buffer prior to use in the experiment. Each brain section was incubated with a fixed concentration (10 nM) of tritiated example compound 1 (Example-1 [$^3$H-1]) or a reference a-syn ligand ([3H]-a-syn-Ref), or increasing concentrations of Example-1 [$^3$H-1] in the range of 1.25 nM to 80 nM of tritiated compound in Tris-HCl buffer for two hours at RT (Total binding, '–'). To determine non-specific (NS) binding Example-1 [$^3$H-1] or [3H]-a-syn-Ref was mixed with 1 μM of non-radiolabelled compound (Example 1 or a-syn-Ref respectively, self-block, '+'). The slides were washed and placed under Phosphor imaging screens (GE healthcare, BAS-IP TR 2025) in imaging cassettes. Imaging screens were scanned using a laser imaging system (Typhoon, FLA 7000) and resulting images were analyzed using the ImageJ software package. Specific binding was determined by subtracting the non-specific signal from the total signal. $K_d$ values were calculated in GraphPad Prism7 by applying a nonlinear regression curve fit using a one site specific binding model.

Figure 2A:
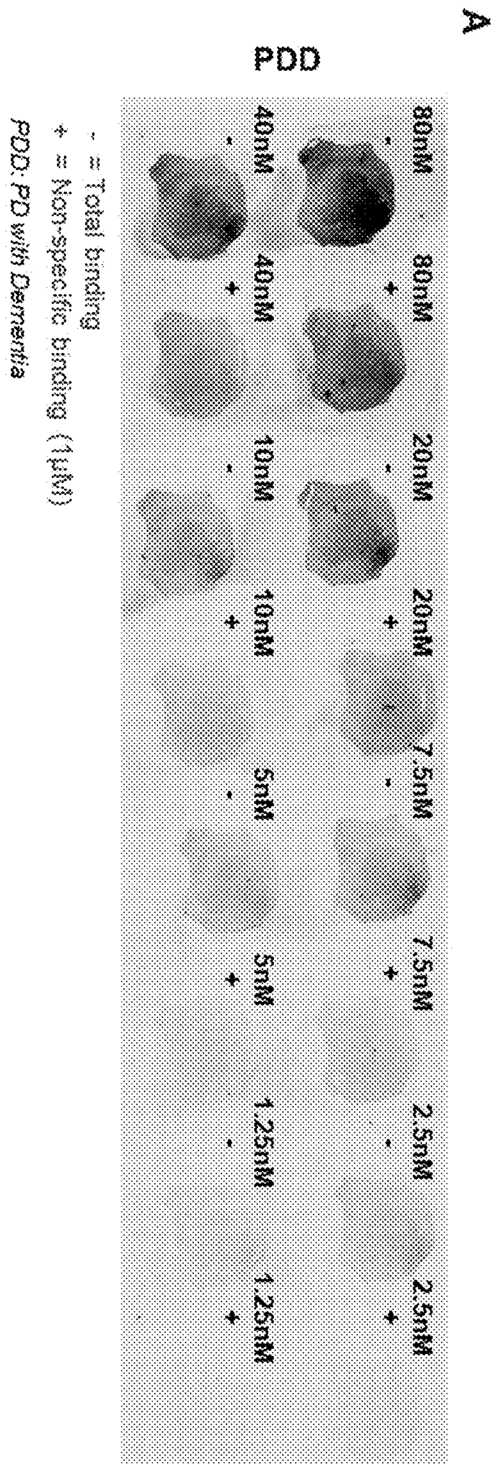
FIG. 2: Assessment of binding affinity of Example-1 [$^3$H-1] on human PDD brain tissue by autoradiography. A) Autoradiography images, B) Immunofluorescence staining with an a-syn-pS129 antibody, C) Specific binding of Example-1 [$^3$H-1], (R.U.: relative units). Scale bar, 2 mm. '−', total binding; '+', self-block, non-specific binding.
Figure 2B:
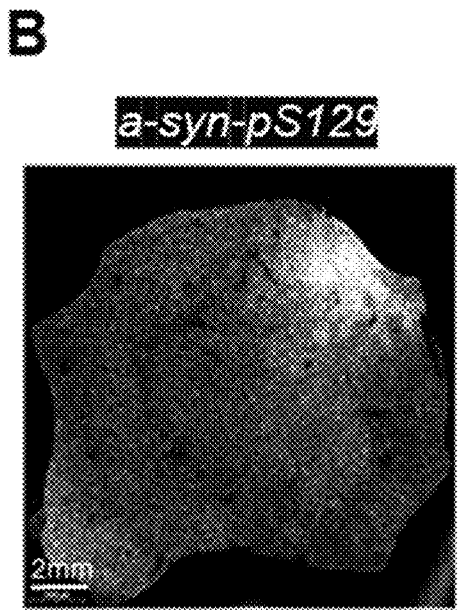
Figure 2C:
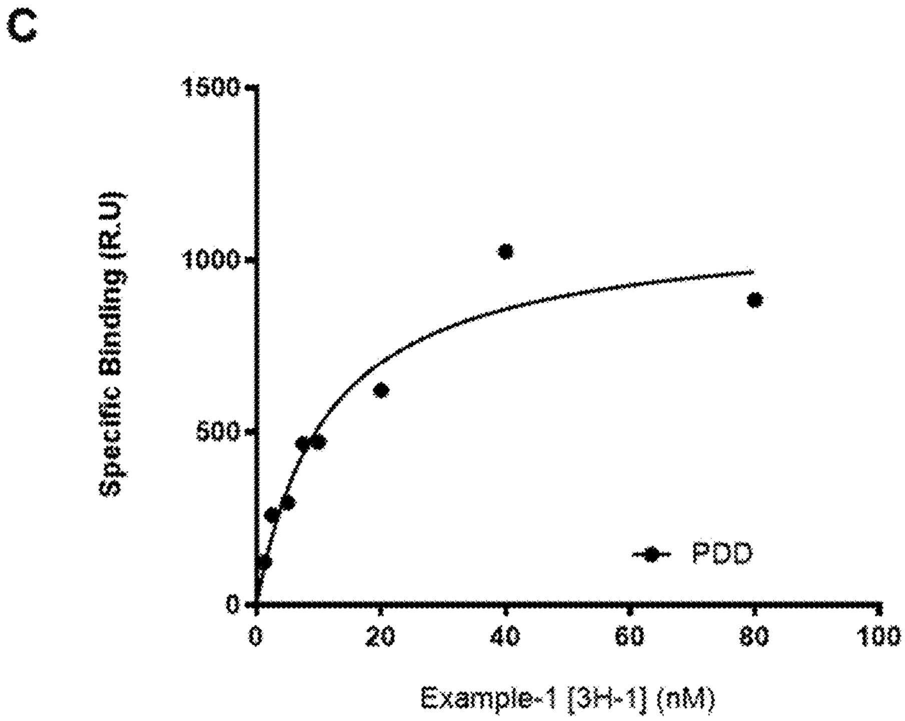
Figure 3A:
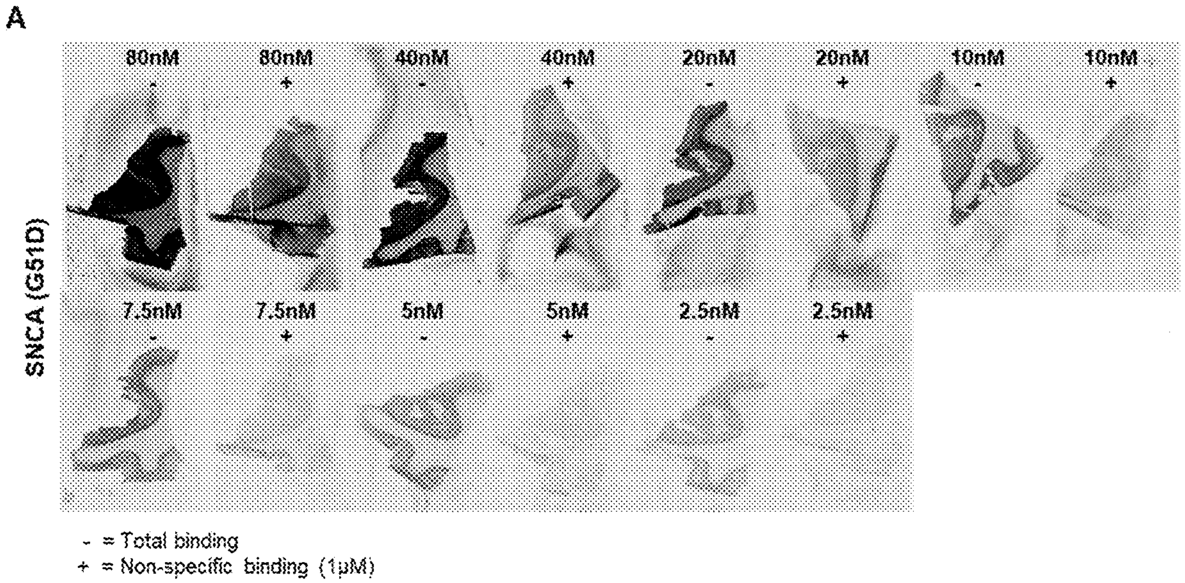
FIG. 3: Assessment of binding affinity of Example-1 [$^3$H-1] on human brain tissue from a familial PD case (G51 D missense mutation) by autoradiography. A) Autoradiography images, B) Immunofluorescence staining with an a-syn-pS129 antibody, C) Specific binding of Example-1 [$^3$H-1], (R.U.: relative units). Scale bar, 5 mm. '−', total binding; '+', self-block, non-specific binding.
Figure 3B:
Figure 3C:
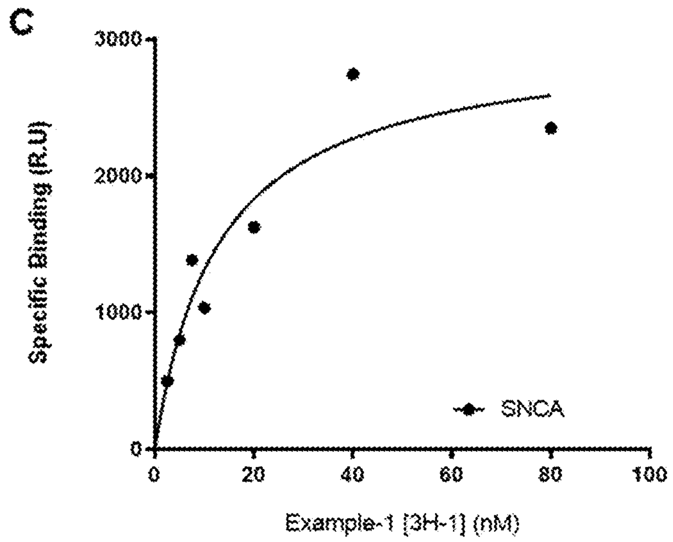

Results: Example-1 [$^3$H-1] displayed a dose-dependent autoradiography signal in different a-synucleinopathy tissues, including a PDD (FIG. 2A) and a genetic PD case (FIG. 3A). The displaceable signal, in both cases, correlated well with the localization of a-syn pathology, as determined by staining with a-syn-pS129 antibody, indicating specific binding of the compound to PDD and PD tissue (FIGS. 2B and 3B). By quantifying the specific signal, the dissociation constant ($K_d$) was calculated at 11-13 nM (FIG. 2C/Table 6 and FIG. 3C/Table 6), suggesting good binding affinity to pathological a-synuclein aggregates.

TABLE 6

| Example-1 [$^3$H-1] | PDD | Genetic PD (SNCA (G51D)) |
|---|---|---|
| B max | 1104 | 3004 |
| Kd | 11 nM | 13 nM |
| $R^2$ | 0.93 | 0.88 |

Table 6: Assessment of binding affinity of Example-1 [$^3$H-1] on human brain tissue from an idiopathic PD case (PDD) and a familial PD case (G51 D missense mutation) by autoradiography. The dissociation constant ($K_d$) and binding site occupancy ($B_{max}$) were calculated by applying a non-linear regression curve fit using a one site, specific binding model in GraphPad Prism7. $R^2$ is the coefficient of determination.

Figure 4A:
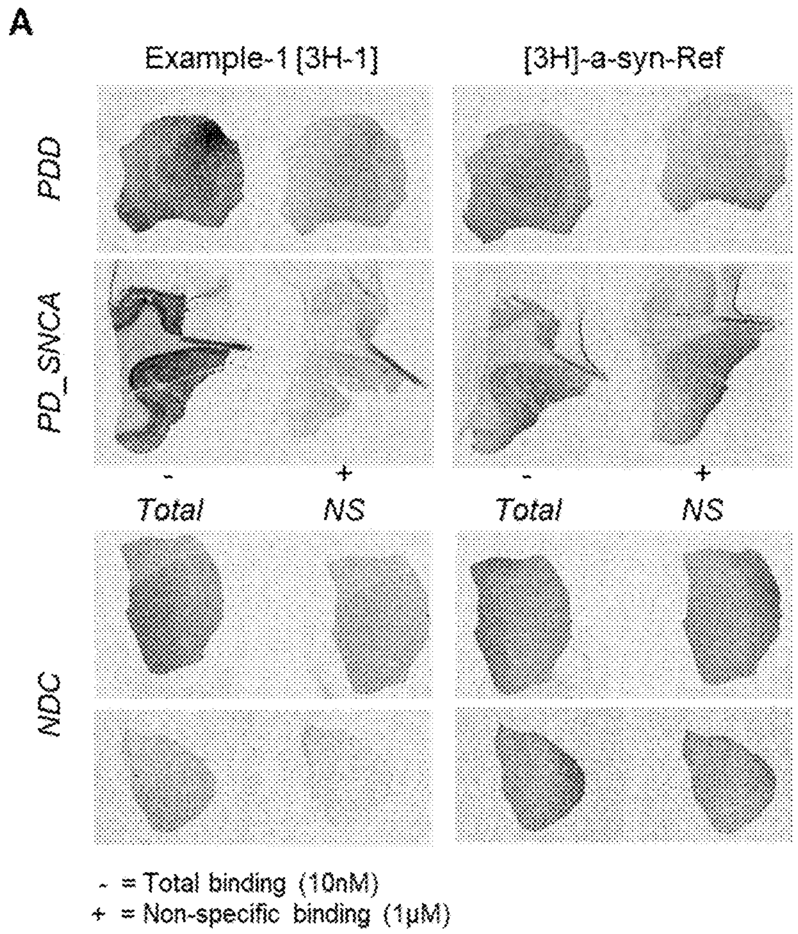
FIG. 4: Assessment of binding specificity of Example-1 [$^3$H-1] and head-to-head comparison to a reference a-syn binder ([3H]-a-syn-Ref) by autoradiography. A) Autoradiography images, B) Immunofluorescence staining with an a-syn-pS129 antibody. Scale bar, 2 mm. PDD, Parkinson's Disease with Dementia; PD_SNCA, a-synuclein [SNCA] gene G51 D missense mutation; NDC, Non-Demented Control. '−', total binding; '+', self-block, non-specific (NS) binding.
Figure 4B:

Additionally, when compared to a reference a-syn ligand, Example-1 [$^3$H-1] displayed improved total and excellent specific binding on tissues from different a-synucleinopathy cases, as well as very weak binding in non-diseased tissue (NDC), (FIG. 4A and FIG. 4B).

5. Saturation Binding Studies on PD Brain-Derived a-Syn Aggregates by Micro-Radiobinding PD brain-derived a-syn aggregates were spotted onto microarray slides. The slides were incubated with Example-1 [$^3$H-1] or [3H]-a-syn-Ref at increasing concentrations in the range of 300 pM to 150 nM. After incubation, slides were washed and exposed to a phosphor storage screen (GE healthcare, BAS-IP TR 2025). Following exposure, phosphor storage screens were scanned with a laser imaging system (Typhoon FLA 7000) to readout the signal from the radiobinding experiments described above. Quantification of the signal was performed using the ImageJ software package. Non-specific signal was determined with an excess of non-radiolabelled reference ligand (Example-1 or a-syn-Ref, respectively, at 2 μM) and specific binding was calculated by subtracting the non-specific signal from the total signal. $K_d$ values were calculated in GraphPad Prism7 by applying a nonlinear regression curve fit using a one site specific binding model.

Figure 5:
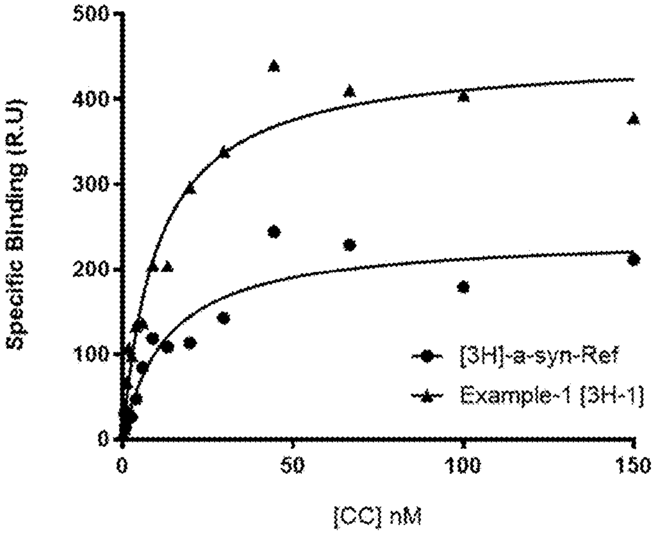
FIG. 5: Saturation binding with [3H]-Example 1 on PD brain-derived a-syn aggregates and head-to-head comparison with [3H]-a-syn-Ref by micro-radiobinding. The plot displays specific binding, (R.U.: relative units).

Results: Example-1 [$^3$H-1] was assessed in saturation binding studies on PD tissue homogenates by micro-radiobinding and compared head-to-head with a reference a-syn binder. As shown in FIG. 5, Example-1 [$^3$H-1] displayed high and improved binding site occupancy on PD brain-derived a-syn aggregates.

6. Assessment of Displacement of Example-1 [$^3$H-1] with a-Syn-Ref on PD Brain-Derived a-Syn Aggregates by Micro-Radiobinding PD brain-derived a-syn aggregates were spotted onto microarray slides. The slides were incubated with Example-1 [$^3$H-1] at 20 nM and either a-syn-Ref or compound of Example 1 (non-radiolabelled) at increasing concentrations in the range of 50 pM to 2 μM. After incubation, slides were washed and exposed to a phosphor storage screen (GE healthcare, BAS-IP TR 2025). Following exposure, phosphor storage screens were scanned with a laser imaging system (Typhoon FLA 7000) to readout the signal from the radiobinding experiments described above. Quantification of the signal was performed using the ImageJ software package. Non-specific signal was determined with an excess of non-radiolabelled example compound 1 (2 μM) and specific binding was calculated by subtracting the non-specific signal from the total signal. Competition was calculated as percent, where 0% was defined as the specific binding in the presence of vehicle and 100% as the values obtained in the presence of excess of the non-radiolabelled reference ligand. All measurements were performed with at least two technical replicates.

Figure 6:
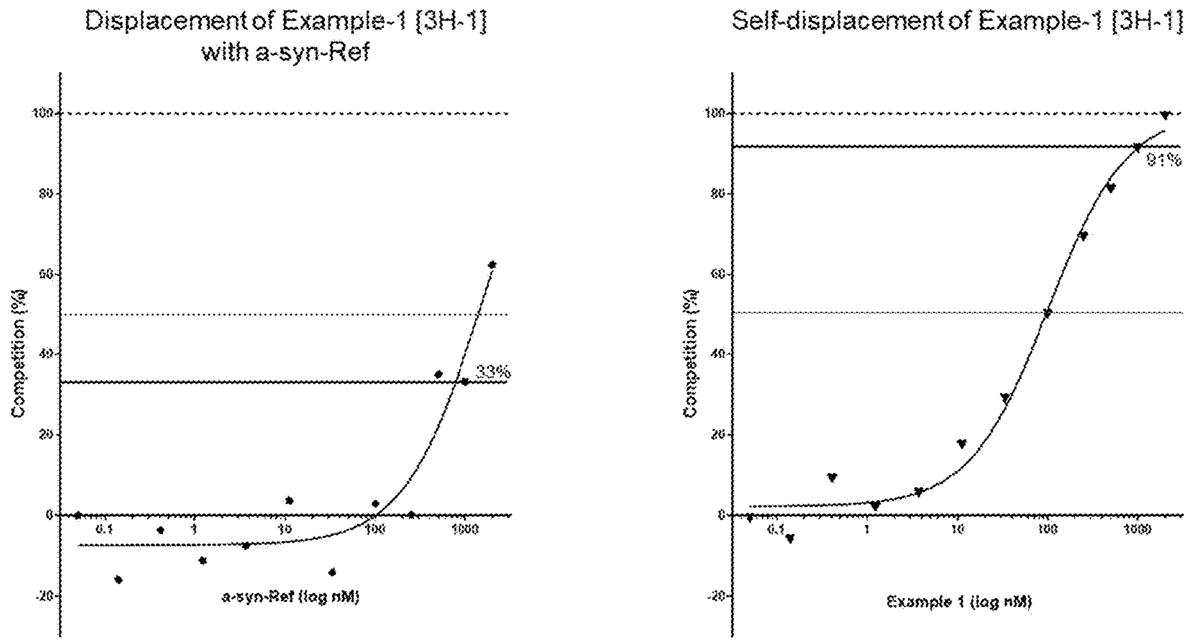
FIG. 6: Competition binding of Example-1 [$^3$H-1] with a-syn-Ref on idiopathic PD brain-derived a-syn aggregates. Percent competition values of Example-1 [$^3$H-1] are plotted against increasing concentrations of non-radiolabelled a-syn-Ref (left) or Example 1 (right) compound. Mean values of two technical replicates are shown.

Results: It was evaluated whether Example-1 [$^3$H-1] can be displaced by non-radiolabelled a-syn-Ref compound. The a-syn-Ref compound only partially competed with Example-1 [$^3$H-1] on brain-derived a-syn aggregates from idiopathic PD cases (FIG. 6), suggesting that the example compound 1 binds a different or partially overlapping binding pocket of the pathological a-syn aggregates compared to a-syn-Ref compound.

7. Radiobinding Competition Assay for Determination of Inhibitor Constant ($K_i$) of Example Compound 1 on AD Brain Homogenates Preparation of Human Alzheimer's Disease (AD) Brain Homogenates:

The procedure was adapted from the protocol described in Bagchi et al., 2013. Frozen tissue blocks from AD donors were thawed on ice and homogenized in high salt buffer (50 mM Tris-HCl pH 7.5, 0.75M NaCl, 5 mM EDTA) supplemented with protease inhibitors (Complete; Roche 11697498001) at 4° C. using a glass Dounce homogenizer. The homogenate was centrifuged at 100,000×g (38,000 RPM) in an ultracentrifuge (Beckman, XL100K) for one hour at 4° C. using a pre-cooled 70.1 rotor (Beckman, 342184). Pellets were resuspended in high salt buffer supplemented with 1% Triton X-100 and homogenized at 4° C. using a glass Dounce homogenizer. The homogenates were centrifuged again at 100,000×g (38,000 RPM, 70.1 rotor) for one hour at 4° C. Pellets were resuspended in high salt buffer supplemented with 1% Triton X-100 and 1 M sucrose and homogenized at 4° C. using a glass Dounce homogenizer. The homogenates were centrifuged at 100,000×g (38,000 RPM, 70.1 rotor) for one hour at 4° C. The resulting pellets containing the insoluble fraction were resuspended in PBS, aliquoted and stored at −80° C. until use.

A fixed concentration of AD insoluble fraction was incubated with a tritiated reference Abeta ligand ([$^3$H]-Abeta-Ref) at 10 nM and increasing concentrations of non-radiolabelled example compound 1 in the range of 400 μM to 2 μM for two hours at RT. The samples were then filtered under vacuum in GF/C filter plates (PerkinElmer) to trap the aggregates with the bound radioligand and washed five times with 50 mM Tris pH 7.5. The GF/C filters were then dried and scintillation liquid (UltimateGold, PerkinElmer) was added in each well. The filters were analyzed on a Microbeta2 scintillation counter (PerkinElmer). Non-specific signal was determined with an excess of non-radiolabelled reference ligand (2 μM) and specific binding was calculated by subtracting the non-specific signal from the total signal. Competition was calculated as percent, where 0% was defined as the specific binding in the presence of vehicle and 100% as the values obtained in the presence of excess of the non-radiolabelled reference ligand. $K_i$ values were calculated in GraphPad Prism7 by applying a nonlinear regression curve fit using a one site, specific binding model. Measurements were performed with at least two replicates.

Figure 7:
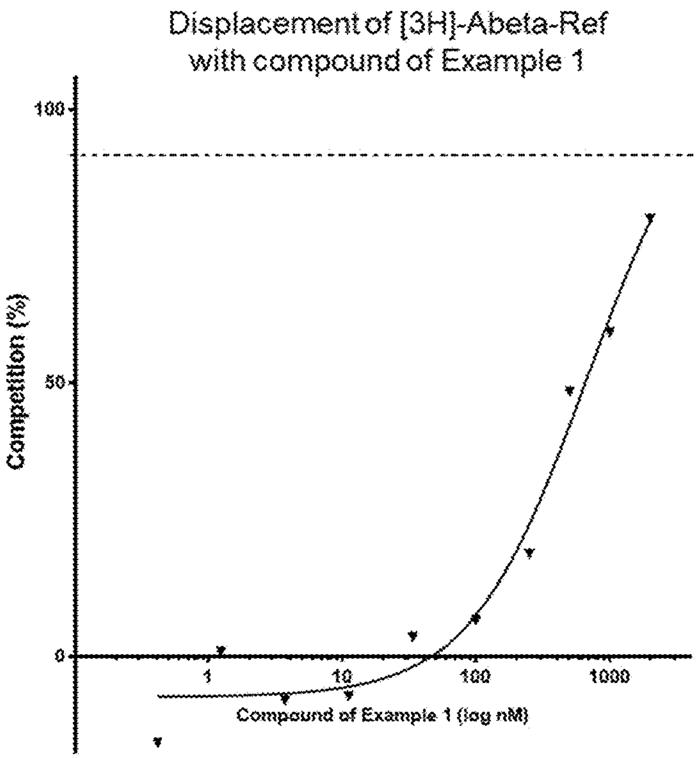
FIG. 7: Assessment of $K_i$ value of the compound of Example 1 for the displacement of reference Abeta compound ([3H]-Abeta-Ref) with non-radiolabelled compound of Example 1 on AD brain-derived homogenates. Percent competition values of [$^3$H]-Abeta-Ref binding are plotted against increasing concentrations of non-radiolabelled compound of Example 1. Mean values of two technical replicates are shown.
Figure 8A:
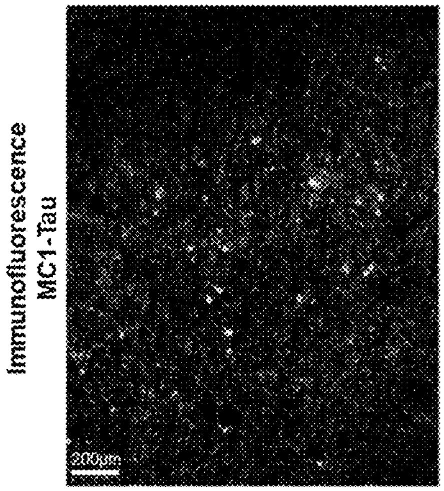
FIG. 8: Assessment of target engagement of Example-1 [$^3$H-1] on AD tissue containing pathological Tau aggregates. A) Immunofluorescence staining with MC1 antibody on the same tissue labelling Tau aggregates, B) No accumulation of silver grains on Tau tangles with Example-1 [$^3$H-1], as compared to a reference Tau ligand ([3H]-Tau-Ref).
Figure 8B:
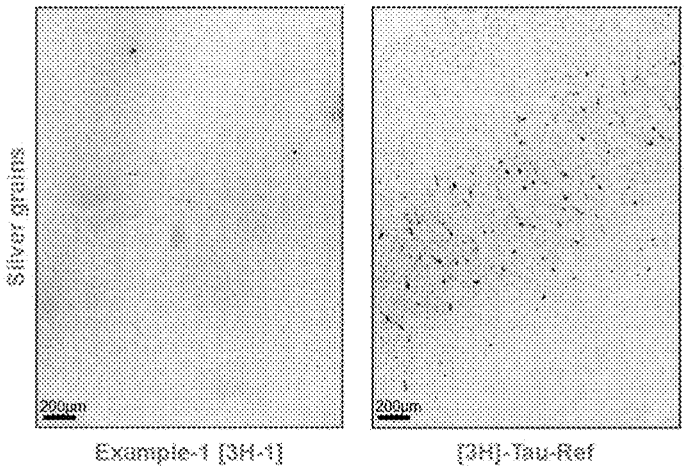
Figure 8B:
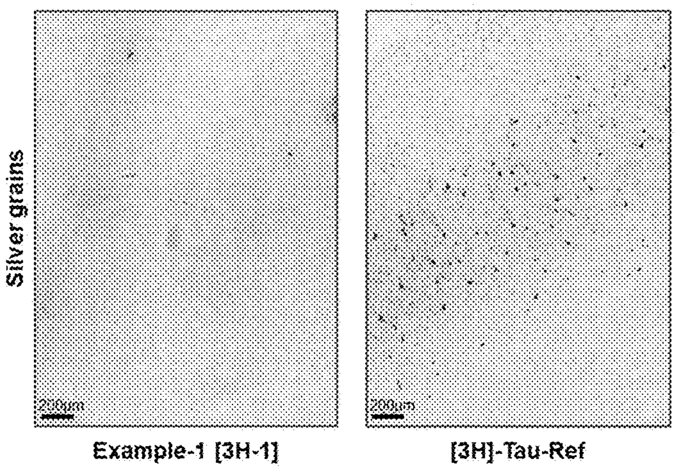
Figure 9:
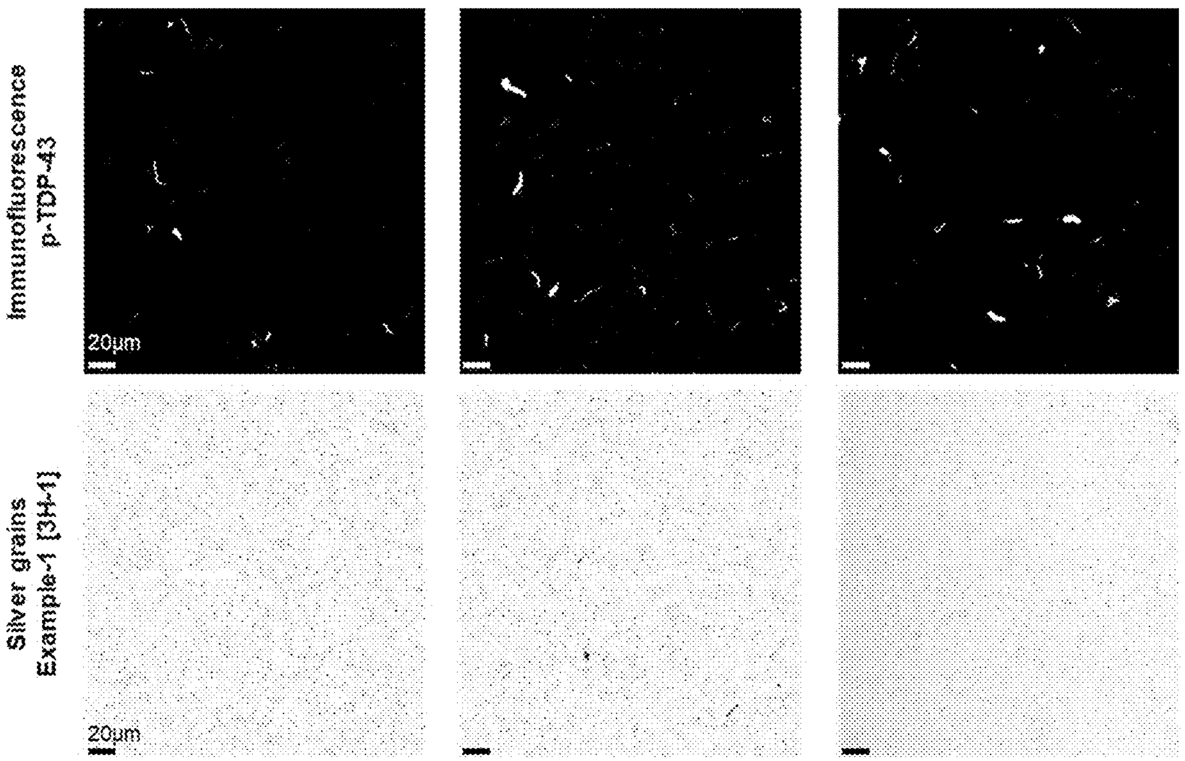
FIG. 9: Assessment of target engagement of Example-1 [$^3$H-1] on Frontotemporal Lobar Degeneration (FTLD) TDP type C tissue containing pathological TDP-43 aggregates. Immunofluorescence staining with phospho-TDP-43 antibody on the same tissue labelling TDP-43 aggregates (top panels). No accumulation of silver grains on TDP-43 aggregates with Example-1 [$^3$H-1] (bottom panels). Scale bar, 20 μm.

Results: As shown in FIG. 7 and Table 7, the $K_i$ value of example compound 1 in AD brain-derived homogenates was determined at 330 nM. Based on the binding affinity of Example-1 [$^3$H-1] on PD brain tissue by autoradiography and in PD brain homogenates by micro-radiobinding, example compound 1 showed good selectivity for a-syn over Abeta pathological aggregates present in the human AD brain homogenates. Additionally, Example-1 [$^3$H-1] did not display specific target engagement on Tau aggregates in AD brain tissue, as compared to a reference Tau binder used as a positive control (FIG. 8), suggesting good selectivity over Tau pathological aggregates. Adding to this, Example-1 [$^3$H-1] displayed very weak to no binding to TAR DNA-binding protein 43 (TDP-43) aggregates, present in Frontotemporal Lobar Degeneration TDP (FTLD-TDP) Type C brain tissue (FIG. 9), indicating good selectivity over TDP-43 pathological aggregates. Overall, these data indicate the selectivity of example compound 1.

TABLE 7

| Example compound 1 | |
|---|---|
| Ki | 330 nM |
| $R^2$ | 0.97 |

Table 7: Ki value determination of example compound 1 for the displacement of [3H]-Abeta-Ref with non-radiolabelled example compound 1 on AD brain-derived homogenates. $K_i$, and $R^2$ values were calculated by applying a nonlinear regression curve fit using a one site, specific binding model in GraphPad Prism7.

8. PK Studies in a Healthy Monkey

Figure 10:
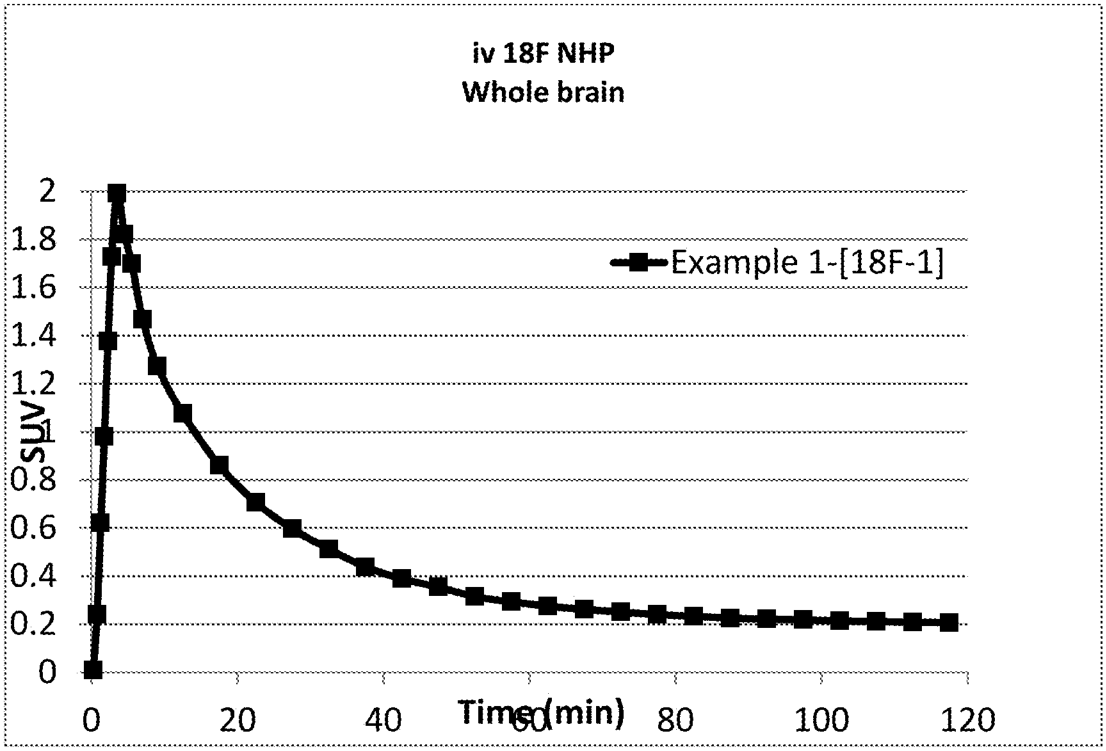
FIG. 10: iv NHP PK in whole monkey brain using Example 1-[$^{18}$F-1].

Non-Human Primate (NHP) was injected intravenously (iv) with the $^{18}$F-labelled Example-1 [$^{18}$F-1] (6.5 mCi) using 1 mL ethanol and 14 mL ascorbate/saline (ascorbate solution was prepared at a concentration of 9.3 mg/mL). Monkey PET scans were performed using a Siemens Focus 220. PET acquisition started immediately before the radioactive dose was injected. Images were generated as dynamic scans for 120 minutes with head focused. Example-1 [$^{18}$F-1] had a quick uptake (3.5 min post injection) with 2.0 SUVmax whole brain. In addition, Example-1 [$^{18}$F-1] had a quick washout with peak to half peak of 14 min (FIG. 10). This data proves a PK profile of Example-1 [$^{18}$F-1] in non-human primates suitable for its use as brain PET agent in humans.

9. Assessment of Specific Binding of Example-1 [$^3$H-1] in Brain Sections from PD, PDD, MSA, LBV and Non-Demented Control (NDC) Donors by Autoradiography Frozen human brain sections from one PD case, two PDD cases, two MSA cases, one LBV case and three non-demented control (NDC) cases were first briefly fixed for 15 minutes at 4° C. with 4% paraformaldehyde (Sigma, 252549) and washed three times for five minutes with PBS (Dulbecco's phosphate buffered saline, Sigma) at RT. All slides were then equilibrated for 20 minutes in 50 mM Tris-HCl pH 7.4 buffer prior to use in the experiment. Each brain section was incubated with a fixed concentration (10 nM) of tritiated example compound 1 (Example-1 [$^3$H-1]) in Tris-HCl buffer for two hours at RT (Total binding, 'Total'). To determine non-specific binding (NSB) Example-1 [$^3$H-1] was mixed with 5 μM of non-radiolabelled compound Example 1. The slides were washed and then exposed and scanned in a real-time autoradiography system (BeaQuant instrument, ai4R).

Figure 11A:
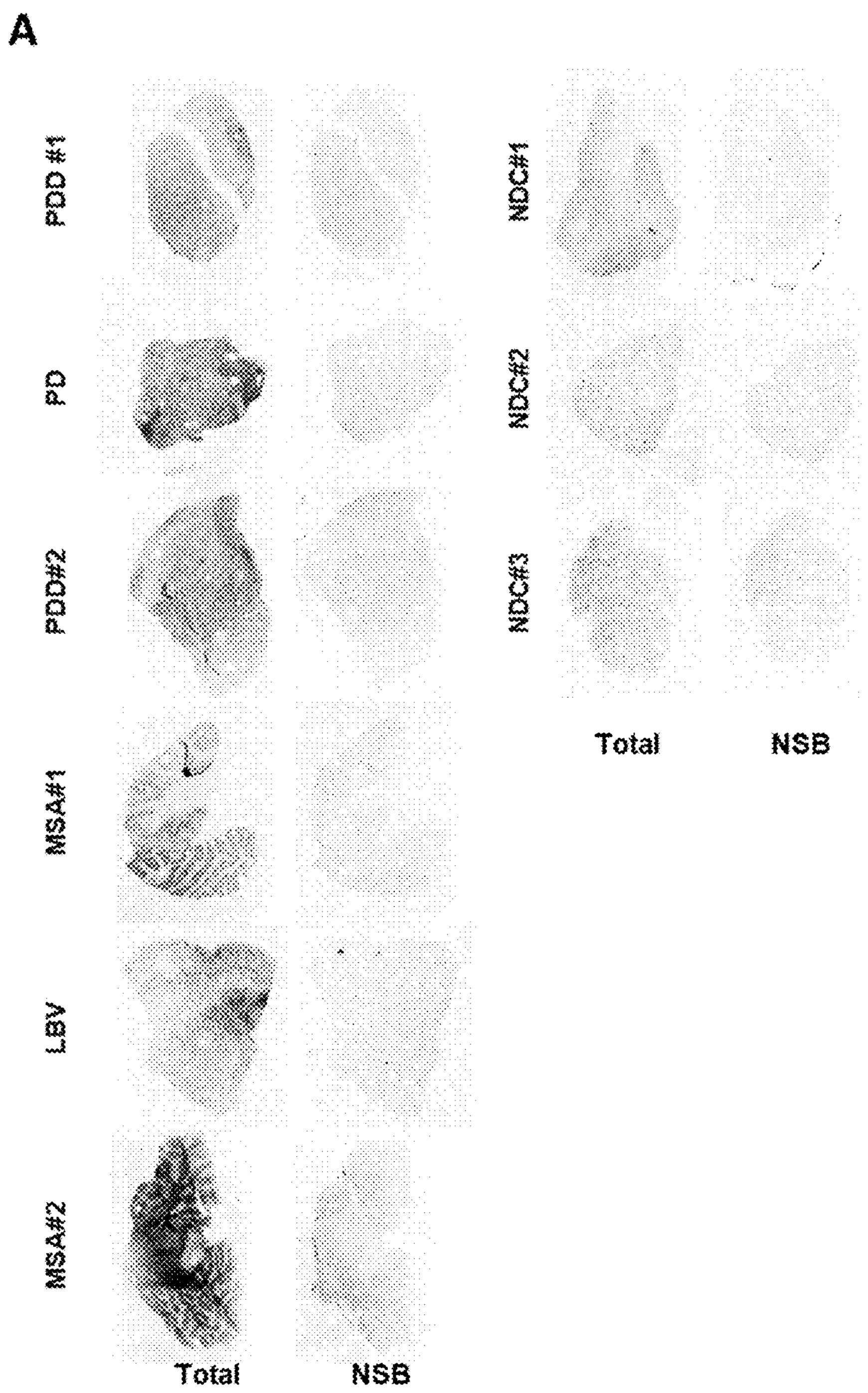
FIG. 11: Assessment of binding specificity of Example-1 [$^3$H-1] to diverse a-synucleinopathies and non-demented control (NDC) cases by autoradiography. A) Autoradiography images; B) immunofluorescence staining with an a-syn-pS129 antibody for the diseased donors. Scale bar, 5 mm. PDD, Parkinson's Disease with Dementia; MSA, Multiple System Atrophy; LBV, Lewy Body Variant of Alzheimer's disease, NDC, Non-Demented Control. 'Total', total binding; 'NSB', non-specific binding.
Figure 11B:
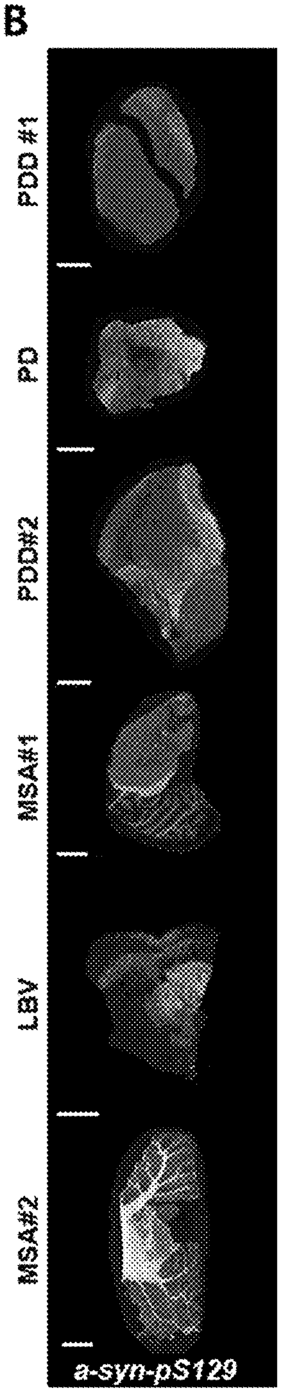

Results: Example-1 [$^3$H-1] displayed target engagement in various a-synucleinopathy tissues, including two MSA, one LBV and two PDD cases (FIG. 11A). The displaceable signal correlated well with the localization and load of a-syn pathology, as determined by staining with a-syn-pS129 antibody (FIG. 11B), indicating specific binding of the compound. Furthermore, the autoradiographic signal appeared greater in diseased donors compared to multiple non-demented control cases, for which signal was weak.

10. Micro-Radiobinding Competition Assay for the Determination of Binding Affinity PD brain-derived a-syn aggregates were spotted onto microarray slides. The slides were incubated with the Example-1 [$^3$H-1] at 6 nM or 20 nM and the example compounds (non-radiolabelled) at 1 μM and 100 nM. In some cases, the non-radiolabelled example compounds were further assessed for a range of different concentrations, varying from 0.05 nM to 2 μM. After incubation, slides were washed and scanned by a real-time autoradiography system (BeaQuant, ai4R). Quantification of the signal was performed by using the Beamage image analysis software (ai4R). Non-specific signal was determined with an excess of non-radiolabelled Example-1 (2 μM) and specific binding was calculated by subtracting the non-specific signal from the total signal. Competition was calculated as percent, where 0% was defined as the specific binding in the presence of vehicle and 100% as the values obtained in the presence of excess of the non-radiolabelled Example-1. $K_1$ values were calculated in GraphPad Prism7 by applying a nonlinear regression curve fit using a one site, specific binding model. All measurements were performed with at least two technical replicates. For compounds tested in more than one experiment, the mean of the replicates or K; values in independent experiments is reported.

Results: Example compounds were assessed for their potency to compete with the binding of Example-1 [$^3$H-1] ligand to PD patient brain-derived a-syn aggregates. Results of the micro-radiobinding competition assay for the example compounds tested are shown in Table 8 as: % competition at 1 μM and 100 nM. The Table 8 also shows $K_i$ values.

TABLE 8

Assessment of binding affinity by micro-radiobinding competition assay on human PD brain-derived a-syn aggregates. Percent (%) competition over the tritiated Example-1 [$^3$H-1] ligand in the presence of 1 μM and 100 nM of example compounds 2-181.

| | Micro-radiobinding competition assay | | |
|---|---|---|---|
| Example Compound no. | Competition at 1 μM (%) | Competition at 100 nM (%) | Ki (nM) |
| 2 | 98 | 72 | 7 |
| 3 | 89 | 45 | 57 |
| 4 | 92 | 58 | 50* |
| 5 | 98 | 68 | 26 |
| 6 | 98 | 87 | 19 |
| 7 | 101 | 87 | 5 |
| 8 | 91 | 67 | |
| 9 | 90 | 69 | |
| 10 | 90 | 58 | 61** |
| 11 | 98 | 50 | |
| 12 | 25 | | |
| 13 | 31 | 4 | |
| 14 | 77 | 42 | |
| 15 | 91 | 61 | |
| 16 | 70 | 32 | |
| 17 | 100 | 68 | 21 |
| 18 | 86 | 23 | 111 |
| 19 | 83 | 23 | 74 |
| 20 | 90 | 48 | |
| 21 | 84 | | |
| 22 | 72 | | |
| 23 | 81 | | |
| 24 | 97 | | |
| 25 | 94 | 64 | 68 |
| 26 | 108 | 87 | 20 |
| 27 | 99 | 87 | 13 |
| 28 | 99 | 89 | |
| 29 | | 91 | |
| 30 | 95 | 80 | |

TABLE 8-continued

Assessment of binding affinity by micro-radiobinding competition assay on human PD brain-derived a-syn aggregates. Percent (%) competition over the tritiated Example-1 [$^3$H-1] ligand in the presence of 1 μM and 100 nM of example compounds 2-181.

| | | Micro-radiobinding competition assay | |
|---|---|---|---|
| Example Compound no. | Competition at 1 μM (%) | Competition at 100 nM (%) | Ki (nM) |
| 31 | | 86 | |
| 32 | 25 | 16 | |
| 33 | | 75 | |
| 34 | 89 | 80 | |
| 35 | | 73 | |
| 36 | 91 | 74 | |
| 37 | | 37 | |
| 38 | | 70 | |
| 39 | 66 | 43 | |
| 40 | 77 | 50 | 49 |
| 41 | 93 | 61 | |
| 42 | 89 | 57 | |
| 43 | 88 | 47 | |
| 44 | | 90 | |
| 45 | 92 | 78 | 52** |
| 46 | | 61 | |
| 47 | | 39 | |
| 48 | 77 | 42 | 132 |
| 49 | 84 | 48 | |
| 50 | 103 | 94 | 8 |
| 51 | 100 | 80 | |
| 52 | 29 | 26 | |
| 53 | 54 | 27 | |
| 54 | 88 | 71 | 19 |
| 55 | 38 | 11 | |
| 56 | | 93 | |
| 57 | | 88 | |
| 58 | 98 | 85 | |
| 59 | | 86 | |
| 60 | 71 | 70 | |
| 61 | 80 | 53 | |
| 62 | 27 | 8 | |
| 63 | 96 | 79 | |
| 64 | 95 | 54 | 2 |
| 65 | | 64 | |
| 66 | 92 | 72 | |
| 67 | | 71 | |
| 68 | | 63 | |
| 69 | 48 | 16 | |
| 70 | | 65 | |
| 71 | 51 | 18 | |
| 72 | 79 | 45 | |
| 73 | 66 | 33 | |
| 74 | 39 | 22 | |
| 75 | 73 | 58 | |
| 76 | 93 | 69 | |
| 77 | 94 | 95 | |
| 78 | | 60 | |
| 79 | | 74 | |
| 80 | 83 | 51 | 56 |
| 81 | 90 | 56 | 118 |
| 82 | | 84 | |
| 83 | | 47 | |
| 84 | 38 | 14 | |
| 85 | 99 | 72 | |
| 86 | | 64 | |
| 87 | 92 | 67 | 15** |
| 88 | | 75 | |
| 89 | 75 | 29 | |
| 90 | 51 | 18 | |
| 91 | 84 | 44 | 42 |
| 92 | 73 | 32 | |
| 93 | 47 | 12 | |
| 94 | 70 | 18 | |
| 95 | 68 | 34 | 54 |
| 96 | 39 | 24 | |
| 97 | 84 | 33 | 84 |

TABLE 8-continued

Assessment of binding affinity by micro-radiobinding competition assay on human PD brain-derived a-syn aggregates. Percent (%) competition over the tritiated Example-1 [$^3$H-1] ligand in the presence of 1 μM and 100 nM of example compounds 2-181.

| | | Micro-radiobinding competition assay | |
|---|---|---|---|
| Example Compound no. | Competition at 1 μM (%) | Competition at 100 nM (%) | Ki (nM) |
| 98 | 76 | 38 | 89 |
| 99 | 92 | 56 | 82 |
| 100 | | 78 | |
| 101 | 75 | | 311 |
| 102 | 68 | 59 | |
| 103 | 70 | 41 | |
| 104 | 98 | 86 | |
| 105 | 83 | 57 | 149 |
| 106 | 100 | 95 | |
| 107 | 100 | 92 | |
| 108 | 81 | 54 | 182 |
| 109 | | 67 | |
| 110 | 105 | 75 | |
| 111 | 97 | 82 | |
| 112 | 105 | 85 | |
| 113 | 91 | 75 | 40 |
| 114 | 99 | 92 | |
| 115 | 98 | 92 | |
| 116 | 97 | 71 | |
| 117 | 67 | 17 | |
| 118 | 94 | 61 | |
| 119 | 51 | 12 | |
| 120 | 83 | 45 | |
| 121 | 84 | 40 | |
| 122 | 61 | 34 | |
| 123 | 58 | 32 | |
| 124 | 98 | 61 | |
| 125 | 99 | 80 | |
| 126 | 83 | 75 | |
| 127 | 86 | 71 | |
| 128 | 85 | 55 | |
| 129 | 74 | 25 | |
| 130 | 85 | 74 | |
| 131 | 98 | 72 | |
| 132 | 93 | 63 | |
| 133 | | 59 | |
| 134 | | 74 | |
| 135 | 96 | 67 | |
| 136 | | 75 | |
| 137 | 84 | 35 | |
| 138 | 57 | 32 | |
| 139 | 77 | 58 | 7 |
| 140 | | 67 | |
| 141 | 66 | 51 | |
| 142 | 99 | 92 | 6 |
| 143 | 91 | 80 | 8 |
| 144 | 68 | 49 | |
| 145 | 76 | 46 | |
| 146 | 53 | 32 | |
| 147 | 86 | 72 | |
| 148 | 91 | 77 | 40 |
| 149 | 53 | | |
| 150 | 46 | 37 | |
| 151 | 81 | 51 | 226 |
| 152 | 86 | 39 | |
| 153 | 57 | 31 | |
| 154 | 99 | 81 | |
| 155 | 94 | 51 | |
| 156 | 85 | 80 | |
| 157 | 43 | 21 | |
| 158 | 54 | 19 | |
| 159 | 67 | 46 | |
| 160 | 73 | 51 | |
| 161 | 65 | 42 | |
| 162 | 110 | 92 | |
| 163 | 99 | 49 | 67 |
| 164 | 87 | 44 | |

TABLE 8-continued

Assessment of binding affinity by micro-radiobinding competition assay on human PD brain-derived a-syn aggregates. Percent (%) competition over the tritiated Example-1 [$^3$H-1] ligand in the presence of 1 μM and 100 nM of example compounds 2-181.

| Example Compound no. | Competition at 1 μM (%) | Micro-radiobinding competition assay Competition at 100 nM (%) | Ki (nM) |
|---|---|---|---|
| 165 | 107 | 88 | |
| 166 | 96 | 72 | 55 |
| 167 | 93 | 68 | 56 |
| 168 | 36 | 30 | |
| 169 | 96 | 73 | 45 |
| 170 | 102 | 65 | |
| 171 | | 48 | |
| 172 | 85 | 44 | |
| 173 | 54 | 12 | |
| 174 | 64 | 46 | |
| 175 | 65 | 32 | |
| 176 | 54 | 13 | |
| 177 | 100 | 76 | |
| 178 | 103 | 77 | |
| 179 | 95 | 80 | |
| 180 | 96 | 77 | |
| 181 | 75 | 67 | 136 |

$K_i$ values are also shown for selected example compounds.
*mean of Ki values in independent experiments using PD brain-derived homogenates from three different donors.
**mean of Ki values in independent experiments using PD brain-derived homogenates from two different donors. As shown in Table 8, example compounds 2-181 of the present invention show potent binding to PD brain-derived a-syn aggregates.

11. Assessment of Target Engagement of Example-4 [$^3$H-4] in a-Synucleinopathies 11A: By High Resolution Micro-Autoradiography The protocol was adapted from Marquie et al., 2015. Sections were incubated with tritiated example compound 4 (Example-4 [$^3$H-4]) or a reference Tau ligand ([$^3$H]-Tau-Ref at 20 nM for one hour at RT. Sections were then washed as follows: One time in ice-cold 50 mM Tris-HCl pH 7.4 buffer for one minute, two times in 70% ice-cold ethanol for one minute, one time in ice-cold 50 mM Tris-HCl pH 7.4 buffer for one minute and finally rinsed briefly in ice-cold distilled water. Sections were subsequently dried and then exposed to Ilford Nuclear Emulsion Type K5 (Agar Scientific, AGP9281) in a light-proof slide storage box. After five days, the sections were developed by immersing them successively in the following solutions: 1.) Ilford Phenisol Developer (1:5 dilution in $H_2O$, Agar Scientific, AGP9106), 2.) Ilfostop solution (1:20 dilution in $H_2O$, Agar Scientific, AGP9104), 3.) Ilford Hypam Fixer (1:5 dilution in $H_2O$, Agar Scientific, AGP9183) and finally rinsed with $H_2O$.

When indicated, immunostaining was also performed on the same section. For image acquisition, sections were mounted using ProLong Gold Antifade reagent (Invitrogen P36930) and imaged on a Panoramic150 Slide Scanner (3DHistech) with a 20× objective capturing separately brightfield and fluorescent images.

11B. By Staining of Sections Using Antibodies

Brain sections were immunostained using a commercially available antibody, specific for phosphorylated serine at amino acid 129 a-synuclein (a-syn-pS129, rabbit monoclonal, Abcam 51253). Sections were fixed for 15 minutes at 4° C. with 4% formaldehyde (Sigma, 252549) and washed three times for five minutes with 1×PBS (Dulbecco's phosphate buffered saline, Sigma D1408) at RT. Next, sections were saturated and permeabilized in blocking buffer (PBS, 10% NGS, 0.25% Triton X-100) for one hour at RT and incubated overnight at 4° C. with the primary antibody corresponding to a-syn-pS129. The following day, sections were washed three times for five minutes with 1×PBS before incubation with a secondary, AlexaFluor647-labelled goat-anti-rabbit (Abcam, ab150079) antibody for 45 minutes at RT. Following incubation with secondary antibodies the sections were washed three times in PBS before being processed further. For image acquisition, sections were mounted using ProLong Gold Antifade reagent (Invitrogen P36930) and imaged with a Panoramic150 Slide Scanner (3DHistech; Hungary).

Figure 12:
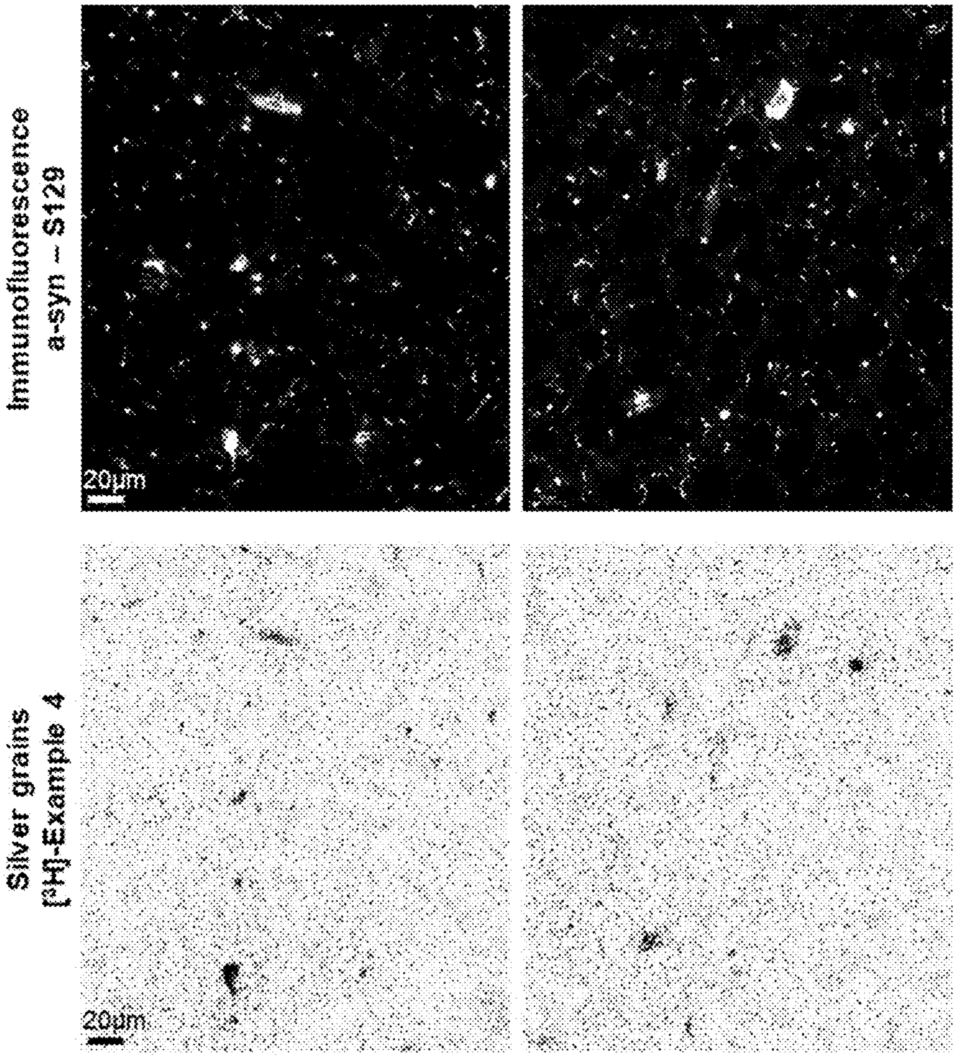
FIG. 12: Target engagement of [$^3$H]-Example-4/Example-4 [$^3$H-4] on a PD tissue. Accumulation of silver grains on Lewy bodies and Lewy neurites, as shown in bottom panels. Immunofluorescence staining with a-syn-pS129 antibody was performed on the same sections, shown on top panels, to co-label a-syn aggregates. Scale bar, 20 μm.

Results: High-resolution micro-autoradiography with Example-4 [$^3$H-4] was performed on frozen human brain sections from a PD donor. Strong autoradiography signal from Example-4 [$^3$H-4] was detected in the form of accumulating silver grains (FIG. 12 bottom) and co-localized with immunofluorescence signal from a-syn-pS129 antibody (FIG. 12 top) suggesting strong target engagement on Lewy bodies and Lewy neurites, as well as a-syn aggregates of very small size, in the PD tissue.

12. Assessment of Specific Binding of Example-4 [$^3$H-4] in Brain Sections from PD, MSA and Non-Demented Control (NDC) Donors by Autoradiography Frozen human brain sections from one familial PD case (a-synuclein [SNCA] gene G51 D missense mutation), labelled as SNCA, one idiopathic PD case, one MSA case and two non-demented control (NDC) cases were first briefly fixed for 15 minutes at 4° C. with 4% paraformaldehyde (Sigma, 252549) and washed three times for five minutes with PBS (Dulbecco's phosphate buffered saline, Sigma) at RT. All slides were then equilibrated for 20 minutes in 50 mM Tris-HCl pH 7.4 buffer prior to use in the experiment. Each brain section was incubated with a fixed concentration (10 nM) of tritiated example compound 4 (Example-4 [$^3$H-4]) in Tris-HCl buffer for two hours at RT (Total binding, 'Total'). To determine non-specific binding Example-4 [$^3$H-4] was mixed with 5 μM of non-radiolabelled compound (Example 4, 'NSB'). The slides were washed and then exposed and scanned in a real-time autoradiography system (BeaQuant instrument, ai4R).

Figure 13A:
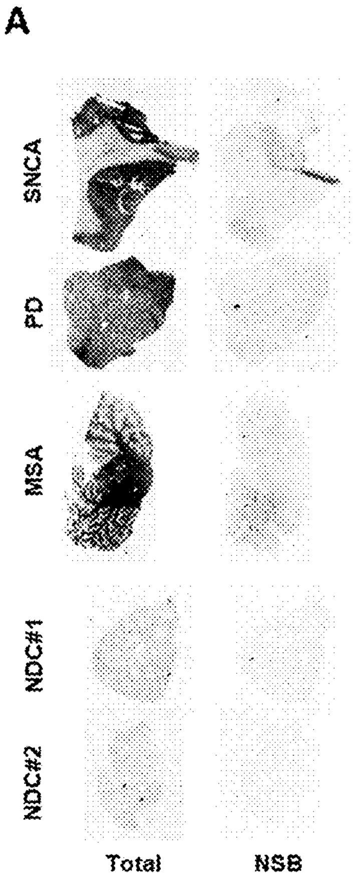
FIG. 13: Assessment of binding specificity of Example-4 [$^3$H-4] to diverse a-synucleinopathies and non-demented control cases by autoradiography. A) Autoradiography images; B) Immunofluorescence staining with an a-syn-pS129 antibody for the diseased donors. Scale bar, 2 mm. SNCA, a-synuclein [SNCA] gene G51 D missense mutation; PD, Parkinson's Disease; MSA, Multiple System Atrophy; NDC, Non-Demented Control. 'Total', total binding; 'NSB', non-specific binding.
Figure 13B:
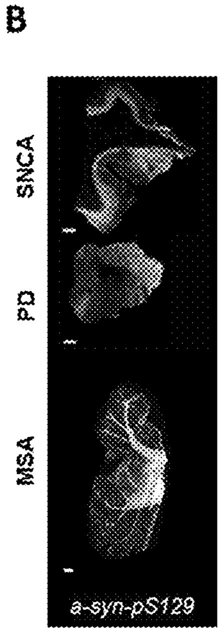

Results: Example-4 [$^3$H-4] displayed specific binding in various a-synucleinopathy tissues, including a MSA case, a familial PD case and an idiopathic PD case (FIG. 13A). The autoradiographic signal appeared greater in diseased donors compared to non-demented controls confirming target engagement and correlated nicely with the distribution of pathological a-synuclein load (FIG. 13B). Additionally, Example-4 [$^3$H-4] displayed displaceable signal in the various a-synucleinopathies cases examined and a very weak signal in the multiple non-diseased control cases.

13. Saturation Binding Studies on PD Brain-Derived a-Syn Aggregates by Micro-Radiobinding PD brain-derived a-syn aggregates were spotted onto microarray slides. The slides were incubated with Example-4 [$^3$H-4] at increasing concentrations in the range of 1.56 nM to 80 nM. After incubation, slides were scanned by a real-time autoradiography system (BeaQuant instrument, ai4R). Quantification of the signal was performed by using the Beamage image analysis software (ai4R). Non-specific signal was determined with an excess of non-radiolabelled reference ligand (Example-4 at 2 μM) and specific binding was calculated by subtracting the non-specific signal from the total signal. $K_d$ values were calculated in GraphPad Prism7 by applying a nonlinear regression curve fit using a one site specific binding model.

Figure 14:
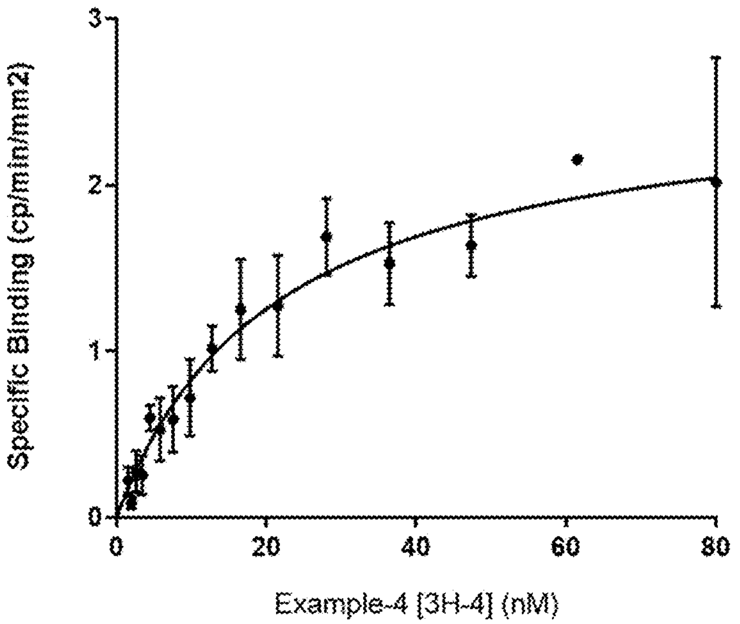
FIG. 14: Saturation binding with [$^3$H]-Example 4 on PD brain-derived a-syn aggregates by micro-radiobinding. The plot displays specific binding, (counts per minute per mm$^2$). Mean values of four independent experiments are shown (Mean±SD).

Results: Example-4 [$^3$H-4] was assessed in saturation binding studies on PD tissue homogenates by micro-radiobinding (FIG. 14). The dissociation constant ($K_d$) was calculated at 21 nM (FIG. 14/Table 9), suggesting good binding affinity to pathological a-synuclein aggregates.

TABLE 9

| Example-4 [$^3$H-4] | PD homogenates |
|---|---|
| Kd | 21 nM |
| $R^2$ | 0.86 |

Table 9: Assessment of binding affinity of Example-4 [$^3$H-4] on human PD brain tissue homegenates by micro-radiobinding. The dissociation constant ($K_d$) and binding site occupancy ($B_{max}$) were calculated by applying a non-linear regression curve fit using a one site, specific binding model in GraphPad Prism7. $R^2$ is the coefficient of determination.

14. Radiobinding Competition Assay for Determination of Inhibitor Constant ($K_i$) of Example Compound 4 on AD Brain Homogenates Human Alzheimer's disease (AD) brain homogenates were prepared according to the procedure disclosed in Example 7 (see above).

A fixed concentration of AD insoluble fraction was incubated with a tritiated reference Abeta ligand ([$^3$H]-Abeta-Ref) at 10 nM and increasing concentrations of non-radiolabelled example compound 1 in the range of 400 pM to 2 μM for two hours at RT. The samples were then filtered under vacuum in GF/C filter plates (PerkinElmer) to trap the aggregates with the bound radioligand and washed five times with 50 mM Tris pH 7.5. The GF/C filters were then dried and scintillation liquid (UltimateGold, PerkinElmer) was added in each well. The filters were analyzed on a Microbeta2 scintillation counter (PerkinElmer). Non-specific signal was determined with an excess of non-radiolabelled reference ligand (2 μM) and specific binding was calculated by subtracting the non-specific signal from the total signal. Competition was calculated as percent, where 0% was defined as the specific binding in the presence of vehicle and 100% as the values obtained in the presence of excess of the non-radiolabelled reference ligand. $K_i$ values were calculated in GraphPad Prism7 by applying a nonlinear regression curve fit using a one site, specific binding model. Measurements were performed in two independent experiments with two technical replicates.

Figure 15:
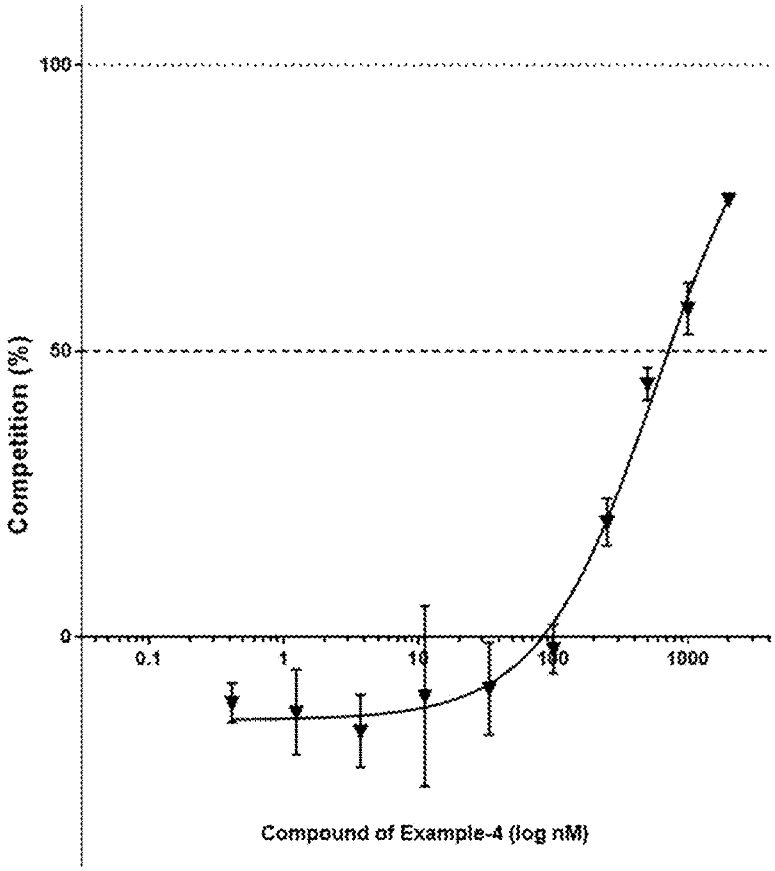
FIG. 15: Assessment of $K_i$ value of the compound of Example 4 for the displacement of a reference Abeta compound ([$^3$H]-Abeta-Ref) with non-radiolabelled compound of Example 4 on AD brain-derived homogenates. Percent competition values of [$^3$H]-Abeta-Ref binding are plotted against increasing concentrations of non-radiolabelled compound of Example 4. Mean values of two independent experiments with two technical replicates are shown (Mean±SD).
Figure 16:
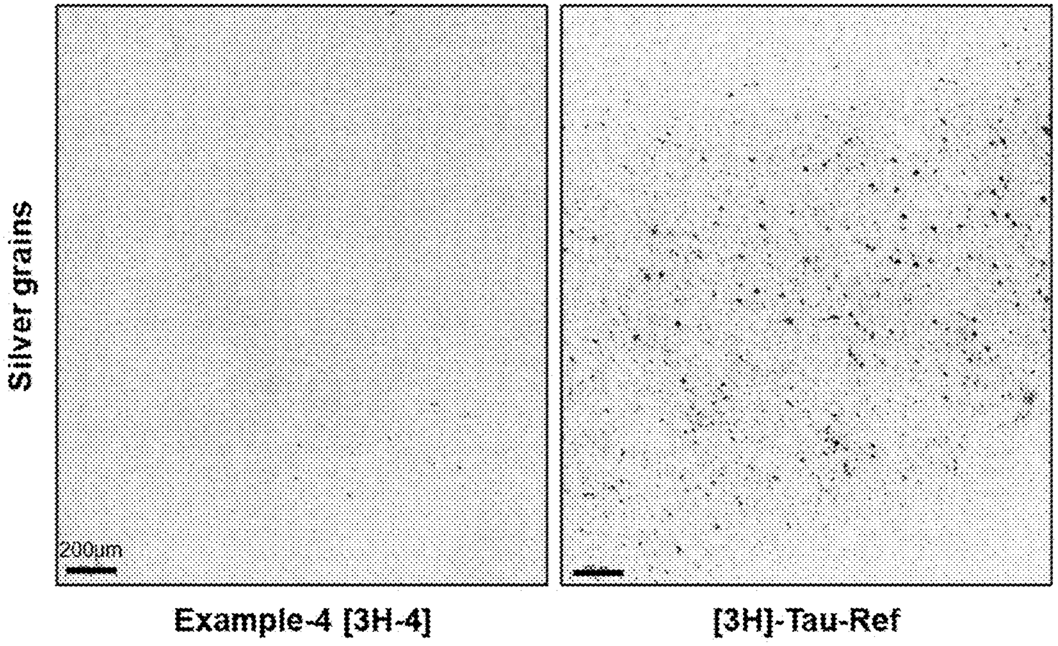
FIG. 16: Assessment of target engagement of Example-4 [$^3$H-4] on AD tissue containing pathological Tau aggregates by micro-autoradiography. No accumulation of silver grains is observed on Tau tangles with Example-4 [$^3$H-1], as compared to a reference Tau ligand ([$^3$H]-Tau-Ref).

Results: As shown in FIG. 15 and Table 10, the Ki value of example compound 4 in AD brain-derived homogenates was determined at 297 nM. Based on the binding affinity of Example-4 [$^3$H-4] in PD brain homogenates by micro-radiobinding, as reported in the Example 13 (above) with the value of 21 nM, and the specific binding in a-synucleinopathies brain tissue by autoradiography, example compound 4 showed good selectivity for a-syn over Abeta pathological aggregates present in the human AD brain homogenates. Additionally, Example-4 [$^3$H-4] did not display specific target engagement on Tau aggregates in an AD brain tissue, as compared to a reference Tau binder used as a positive control (FIG. 16), suggesting good selectivity over Tau pathological aggregates. Overall, these data indicate the desired selectivity for a-syn aggregates of example compound 4.

TABLE 10

| Example compound 4 | |
|---|---|
| Ki | 297 nM |
| $R^2$ | 0.97 |

Table 10: Ki value determination of example compound 4 for the displacement of [$^3$H]-Abeta-Ref with non-radiolabelled example compound 4 on AD brain-derived homogenates. $K_i$, and $R^2$ values were calculated by applying a nonlinear regression curve fit using a one site, specific binding model in GraphPad Prism7.

15. First in Human (FIH) Study

A Phase 1 study to evaluate $^{18}$F-Example 1 as a potential PET radioligand for imaging a-synuclein deposits in the brain of patients with suspected a-synuclein pathology compared to healthy volunteers (HVs) is ongoing. The study objectives are to characterize safety as well as imaging and pharmacokinetics properties of $^{18}$F-Example 1, in individuals with suspected idiopathic Parkinson's Disease (PD) and healthy volunteer (HV) subjects. A total of up to 10 subjects may be enrolled (target of up to 5 HV subjects and up to 5 subjects with idiopathic PD).

Inclusion Criteria for all Subjects:

- Subject is able to provide written informed consent, which must be obtained before any assessment is performed.
- Female subjects must not be of childbearing potential, or if they are of childbearing potential to agree to use contraception and not donate eggs. At the discretion of the Investigator, subjects without documentation of non-childbearing potential may receive pregnancy testing.
- Male subjects with their partners of childbearing potential must commit to the use of 2 methods of contraception, 1 of which is a barrier method for male subjects for the study duration and 90 days after study completion.
- Male subjects must not donate sperm for the study duration and for 90 days after study completion.
- For subjects receiving arterial cannulation, adequate circulation to the hand for safe placement of arterial line (as determined by Allen's test) and blood clotting (Prothrombin Time [PT] and Partial Thromboplastin Time [PTT]).
- If subject takes bupropion, subject must agree to hold this medication for at least 12 hours prior to DaTscan imaging (if performed).

Additional Inclusion Criteria for HV Subjects:

- Males and females aged ≤21 years.
- Healthy with no clinically relevant finding on physical examination at Screening and upon reporting to the clinic for the tracer Imaging Visit.
- No family history of α-synucleinopathy, including PD, or other early-onset neurological disease associated with dementia.
- No personal history of clinically significant neurologic and/or psychiatric disorders.
- No evidence of dopamine transporter deficit on Dopamine active transporter (DaT) scan performed either as part of Screening or on previously acquired DaTscan (within 6 months prior to signing consent).
- Have a Montreal Cognitive Assessment (MoCA) score 26.
- No cognitive impairment as judged by the person in charge (PI).

Additional Inclusion Criteria for Subjects with α-Synucleinopathy:

- Males and females aged ≤40 years.
- Subjects diagnosed with any of the following:
  - Idiopathic PD
  - PD with genetic risk factor (except leucine-rich repeat kinase 2 [LRRK2] mutation)
- A brain magnetic resonance imaging (MRI) consistent with a diagnosis of α-synucleinopathy, with no evidence of focal disease to account for the subject's neurological symptoms.
- Evidence of dopamine transporter deficit on DaTscan performed either as part of Screening or on previously acquired DaTscan.
- Medications taken for symptomatic treatment of α-synucleinopathy must be maintained on a stable dosage regimen for at least 30 days before Screening Visit.
- Ability to tolerate lying in the scanner for up to ~180 minutes without excessive head or jaw tremor or dyskinesia sufficient to cause significant motion artifact on the PET scans.

After enrollment, subjects will receive 1 intravenous injection of $^{18}$F-Example 1 of no more than 10 mCi. $^{18}$F-Example 1 brain uptake and pharmacokinetics in human subjects will be visually and quantitatively assessed and safety data acquired. $^{18}$F-Example 1 PET signal in suspected idiopathic PD cases will be compared cross-sectionally to HV.

16: Formulation $^{18}$F trapping and elution: [$^{18}$F]-fluoride was transferred onto and trapped on an ion exchange cartridge. It was then eluted with an aqueous acetonitrile solution of potassium carbonate (1.6 mg) and Kryptofix 222 (10 mg) into the reaction vessel (RV1). The solution was first evaporated by heating at 95° C. for 4 min under vacuum and helium flow. Acetonitrile (1 mL) was then added to RV1 and the evaporation was continued under the same conditions for 2 min under vacuum and helium flow. After a second addition of acetonitrile (1 mL), a final evaporation was carried out at 95° C. for 2 min under vacuum and helium flow. Finally, the reactor was cooled to 60° C.

Radiolabeling reaction: A solution of the precursor (1.0 mg) in anhydrous dimethylsulfoxide was added to the reaction vessel and the reaction mixture was heated at 100° C. for 10 min. The reactor is cooled to 40° C., diluted with HPLC mobile phase (1.8 mL) and the contents are transferred into the loop-loading vial (RV2). The reactor was rinsed with water for injection (2.5 mL) and the rinse was transferred into RV2. The contents of RV2 were transferred into the HPLC injector loop for purification.

Purification and drug product formulation: Purification was performed by HPLC using a semi-preparative Agilent Eclipse XDB C18 column (5 μm, 250×9.4 mm) and eluted with a mixture of methanol/ammonium acetate solution (20 mM, 50/50, v/v) at a flow rate of 4 mL/min. The product fraction was collected in a flask, containing 20 mL of sodium ascorbate (5 mg/mL) in water for injection (WFI). The diluted product mixture was passed through a C18 solid-phase extraction cartridge and the cartridge was rinsed with 10 mL of sodium ascorbate (5 mg/mL) in WFI. The radiolabeled product was eluted from the SPE cartridge with 1.0 mL of 200-proof USP grade ethanol into the formulation flask, pre-loaded with 10 mL of sodium ascorbate (10 mg/mL) in saline. The cartridge was rinsed with 4.0 mL of sodium ascorbate in saline (10 mg/mL) and the rinse was mixed with the contents of the formulation flask. The resulting solution was passed through a sterilizing 0.2 μm membrane filter into a sterile, filter-vented vial (final product vial, FPV), pre-filled with 15 mL of normal saline.

The stability of the radiolabelled product over time was studied and validated to remain within specifications for 8 hours after the end of synthesis.

The batch formula quantities are presented in Table 11:

| Precursor | 1 mg [a] |
|---|---|
| [18F] Fluoride | <4 Ci |
| Normal saline | 50 mL |
| Ethanol | 1 mL |
| Sodium ascorbate | 500 mg |

[a] Removed during processing

The final formulation of the radiolabelled product developed for this study has a volume of 30 mL, with the intent to achieve the following content based on an injected volume of 10 ml in the final dosage form is shown in Table 12:

| Radioactive amount | Carrier | Normal saline | Sodium Ascorbate | Ethanol |
|---|---|---|---|---|
| ≤10 mCi | ≤10 μg | ≤9.67 ml | ≤46.7 mg | ≤0.33 ml |

The invention claimed is:

1. A compound of formula (I)

(I)

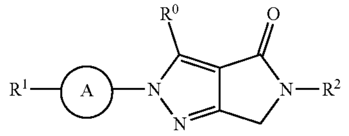

or a detectably labelled compound, stereoisomer, racemic mixture, pharmaceutically acceptable salt, hydrate, or solvate thereof, wherein

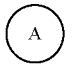

is an aryl or a heteroaryl which is directionally selected from the group consisting of:

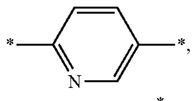, 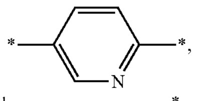, 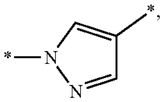, and 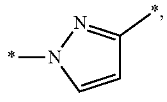, $R^0$ is H or $C_1$-$C_4$alkyl;

$R^1$ is —CN; or halo; or $C_1$-$C_4$alkyl; or $C_1$-$C_4$alkoxy; or —N($C_1$-$C_4$alkyl)$_2$; or —NH($C_1$-$C_4$alkyl); or H;

or $R^1$ is —NH—$C_3$-$C_6$cycloalkyl, $C_3$-$C_6$cycloalkyl, or heterocyclyl, wherein the heterocyclyl is a 4- to 6-membered non-aromatic monocyclic ring radical containing 1 or 2 heteroatoms, each of which is optionally substituted with at least one halo;

$R^2$ is selected from the group consisting of:

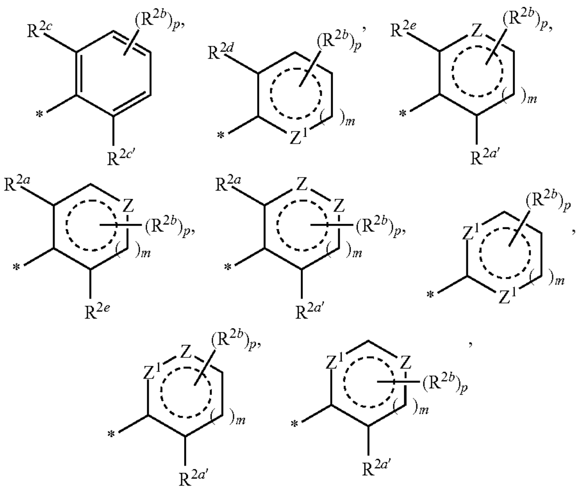

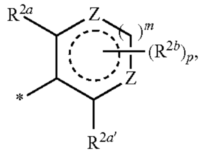

and

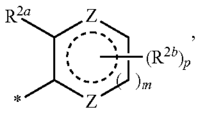

wherein $R^{2a}$, $R^{2a'}$ are independently H, or F;

$R^{2b}$ is independently F, OH, $C_1$-$C_4$alkyl, halo$C_1$-$C_4$alkyl, $NH_2$, CN, or $C_1$-$C_4$alkoxy;

$R^{2c}$, $R^{2c'}$ are independently H, F, OH, $OCH_3$, or $CH_3$;

$R^{2d}$ is H, F, or OH;

$R^{2e}$ is H, OH, $CH_3$, or F;

Z is independently N, NH, N($C_1$-$C_4$alkyl), N(halo$C_1$-$C_4$alkyl), O, or S;

$Z^1$ is independently N, NH, O, or S;

p is 0, 1 or 2;

m is 0 or 1;

as valency permits, ⸤ is a combination of single and double bonds; and

* is the position of bonding.

2. The compound according to claim 1, having a formula (IIa), (IIb), (IIIa), (IIIb), or (IIIc)

(IIa)

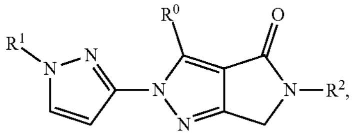

(IIb)

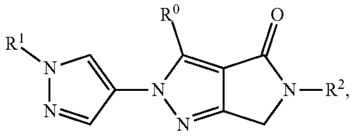

-continued (IIIa)

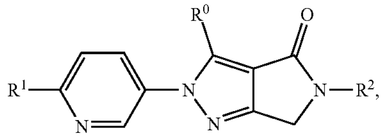

(IIIb)

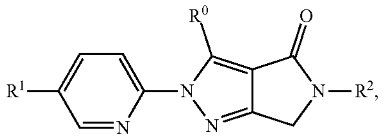

or (IIIc)

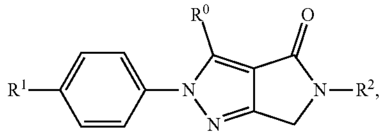

or a detectably labelled compound, stereoisomer, racemic mixture, pharmaceutically acceptable salt, hydrate, or solvate thereof.

3. The compound according to claim 1, wherein $R^1$ is —NH—$C_3$-$C_6$cycloalkyl, $C_3$-$C_6$cycloalkyl, or heterocyclyl, each of which is optionally substituted with at least one halo, wherein the heterocyclyl is a 4- to 6-membered non-aromatic monocyclic ring radical containing 1 or 2 heteroatoms.

4. A compound, which is one of the following compounds:

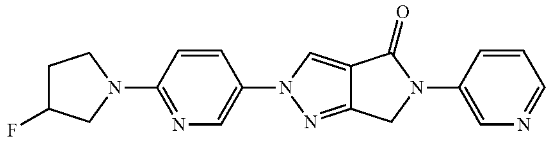

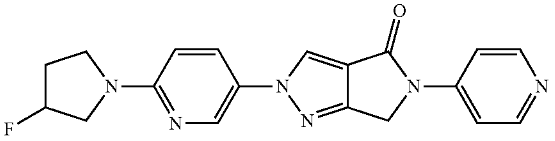

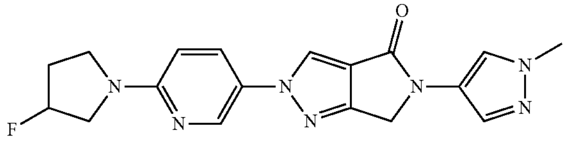

1

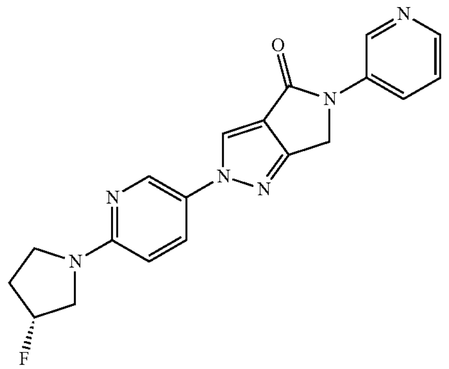

-continued
2
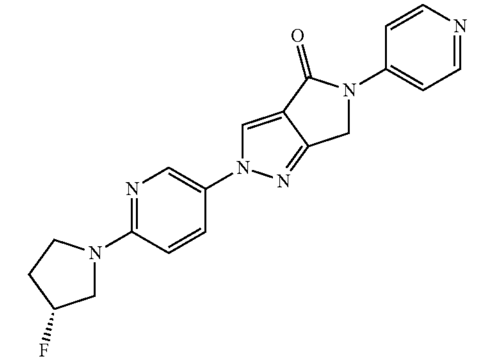
3
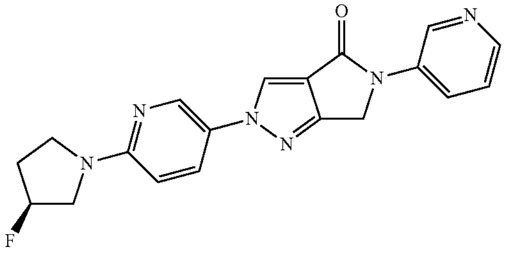
4
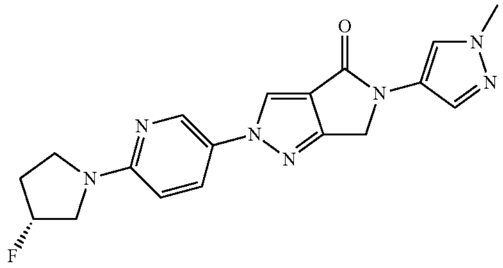
5
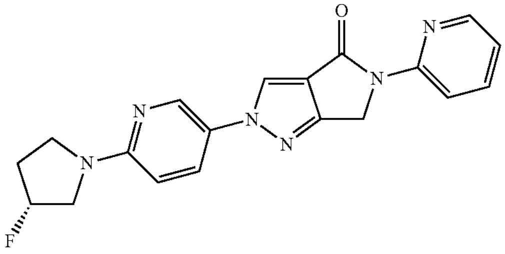
6
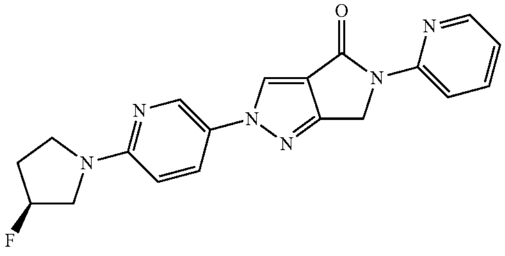
-continued
7
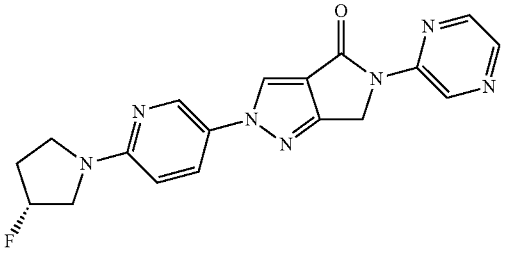
8
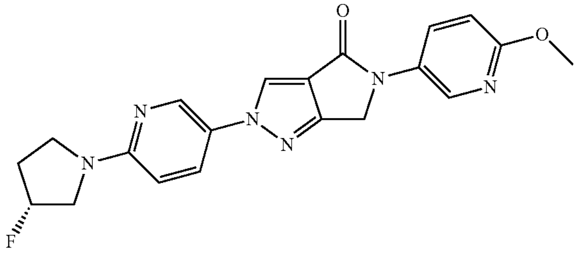
9
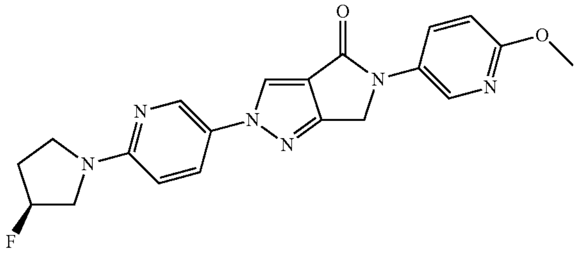
10
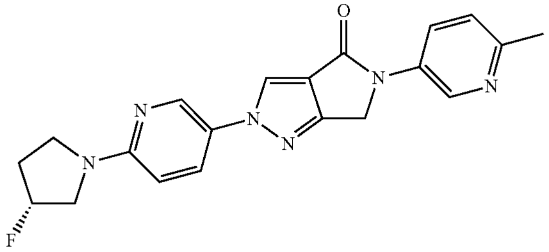
11
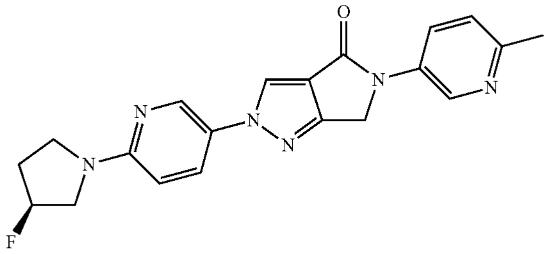
12
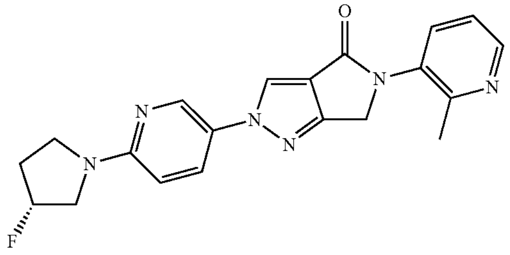

-continued
13
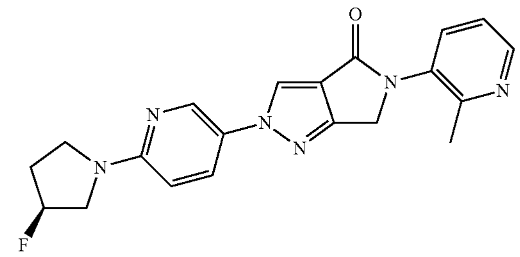
14
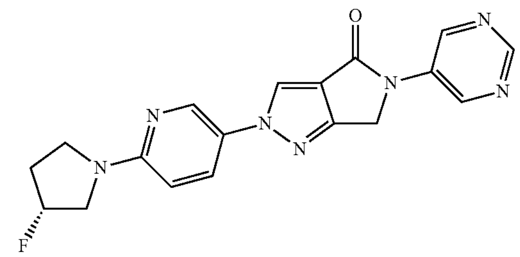
15
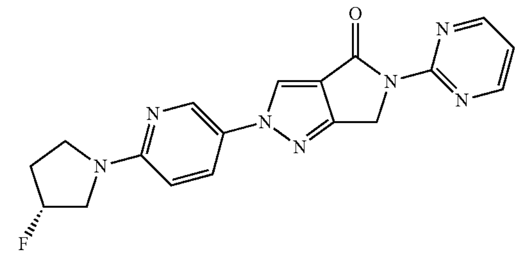
16
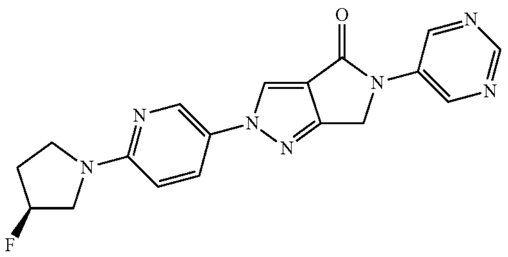
17
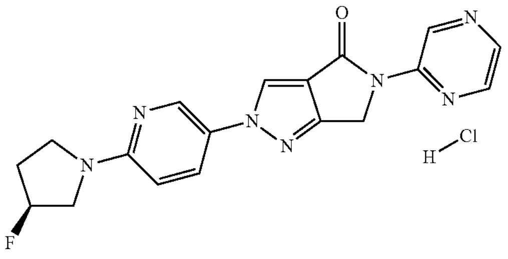
18
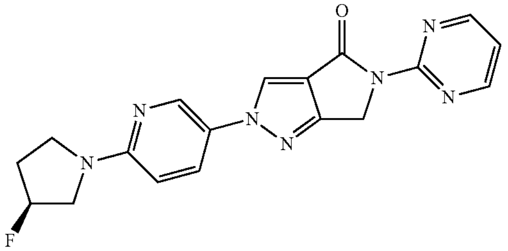
-continued
19
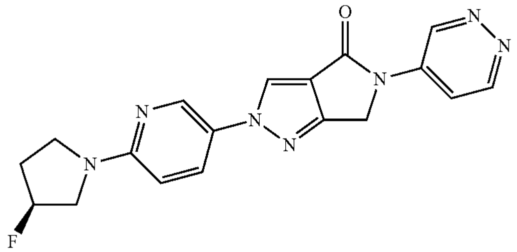
20
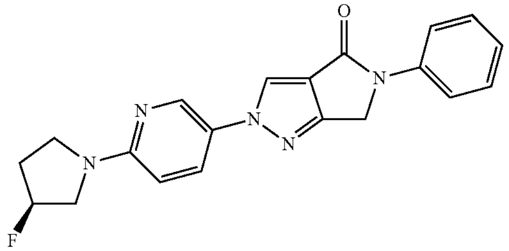
21
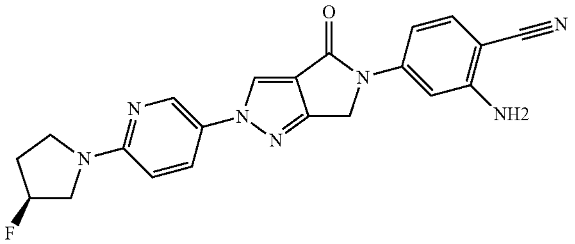
22
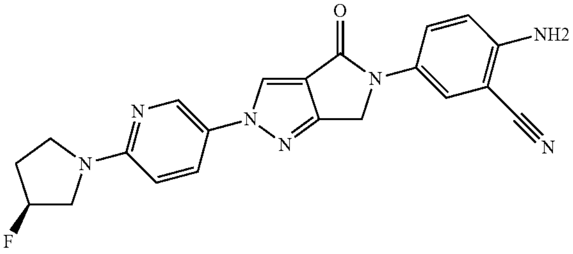
23
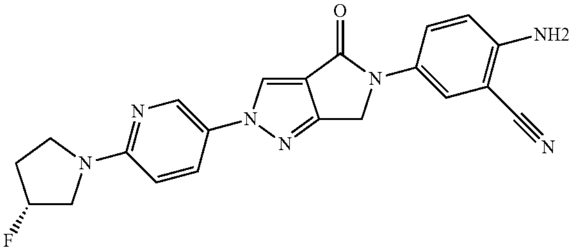
24
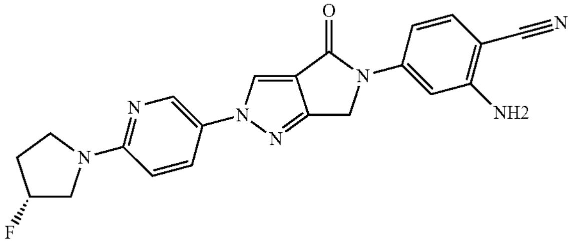

-continued
25
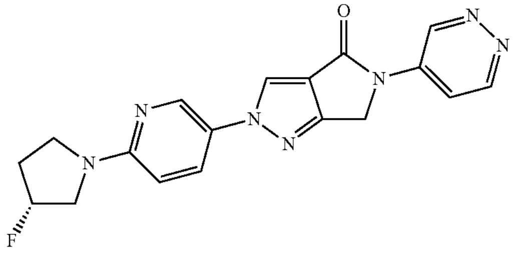
26
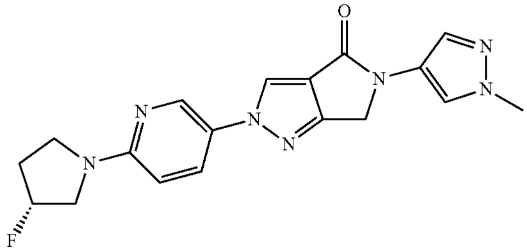
27
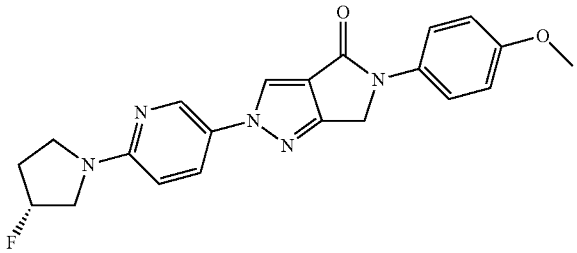
28
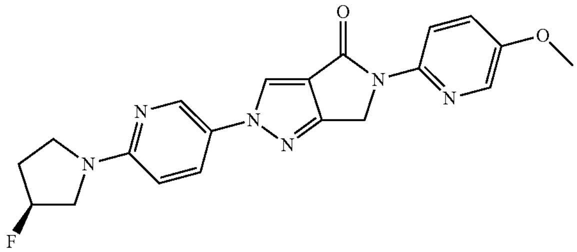
29
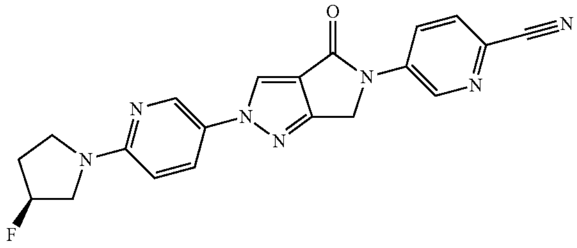
30
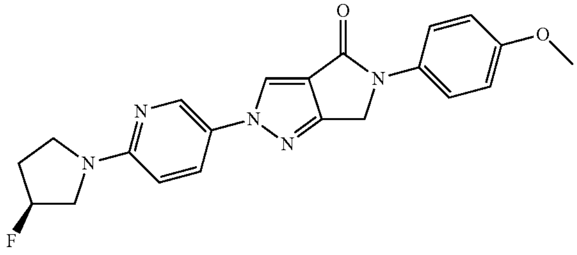
-continued
31
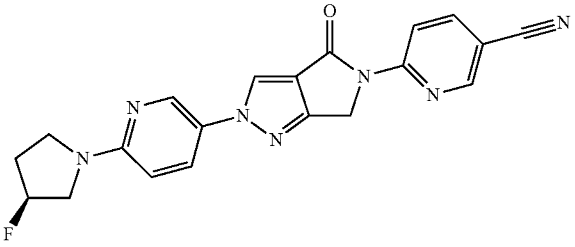
32
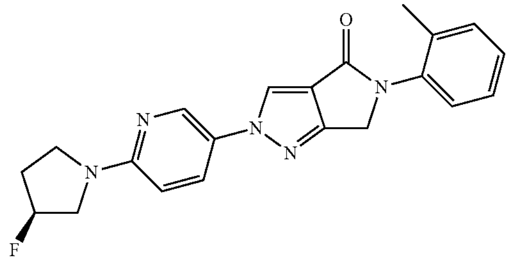
33
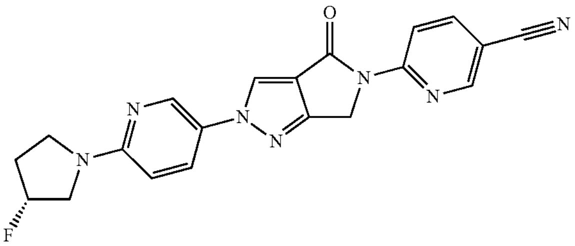
34
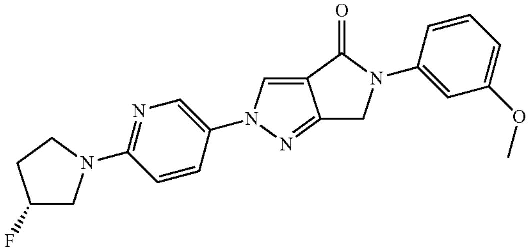
35
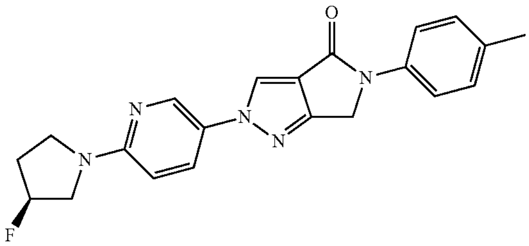
36
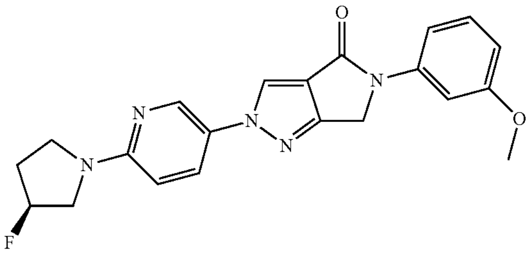

-continued
37
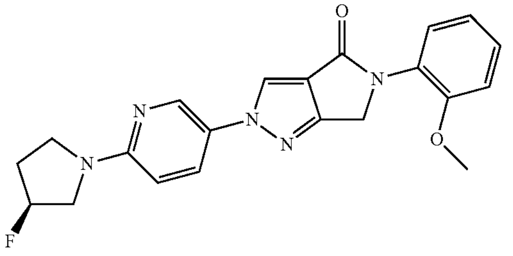
38
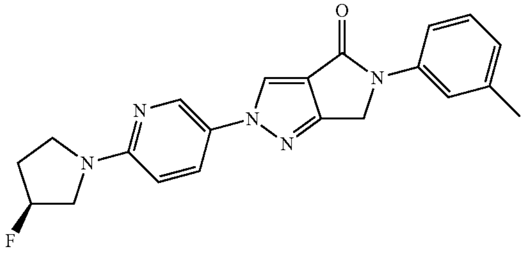
39
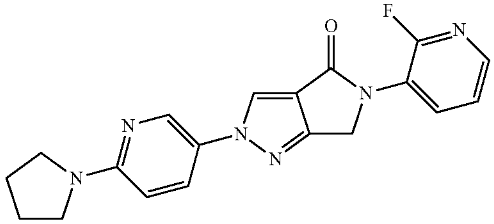
40
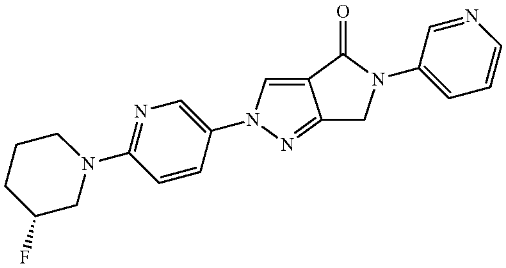
41
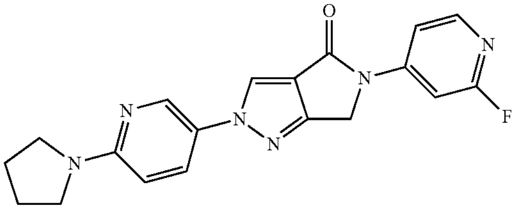
42
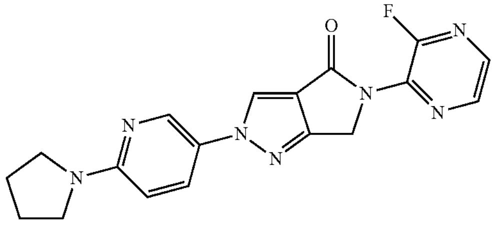
-continued
43
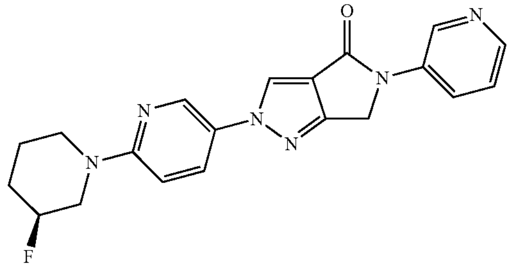
44
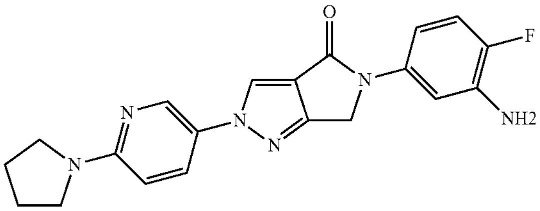
45
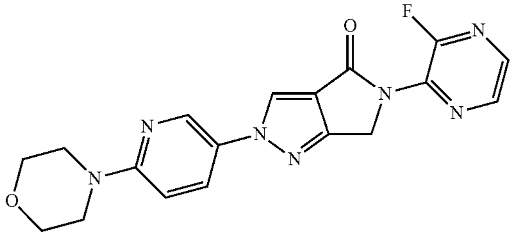
46
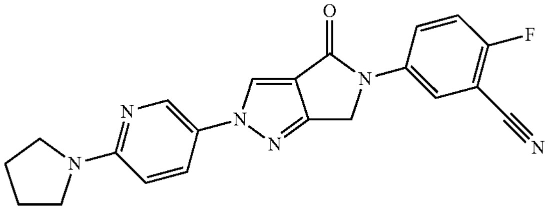
47
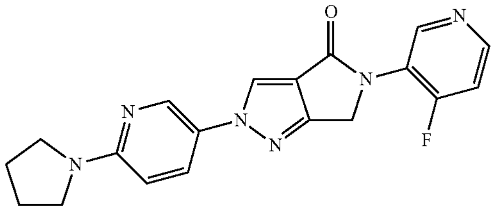
48
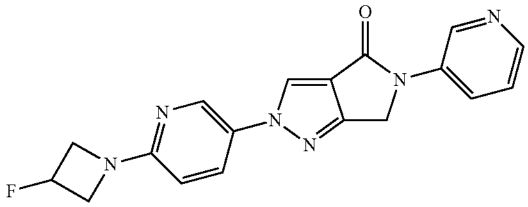

-continued
49
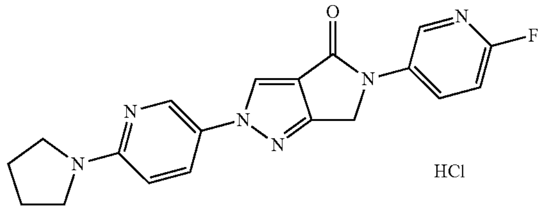
50
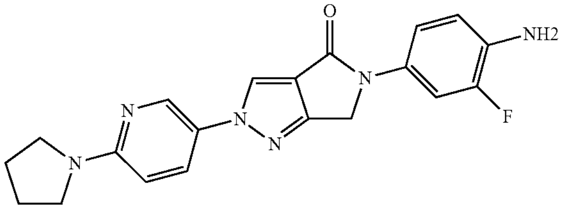
51
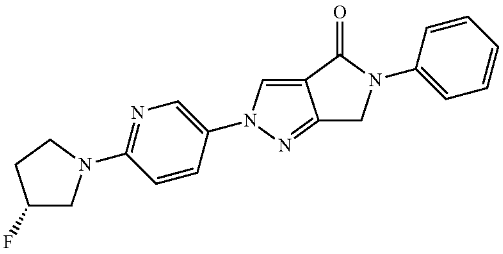
52
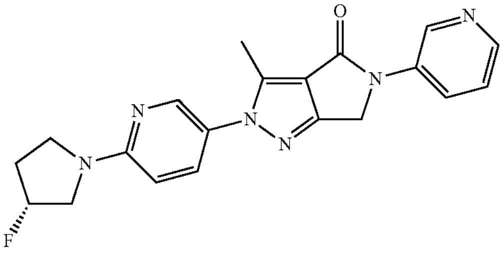
53
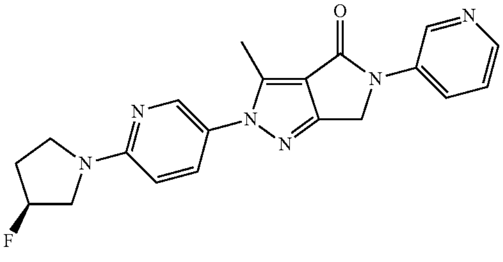
54
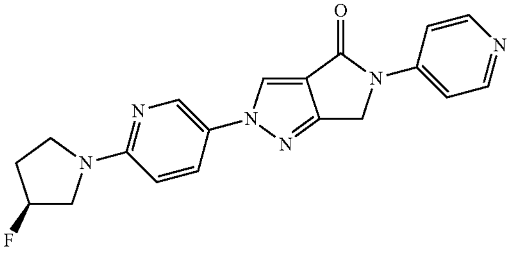
-continued
55
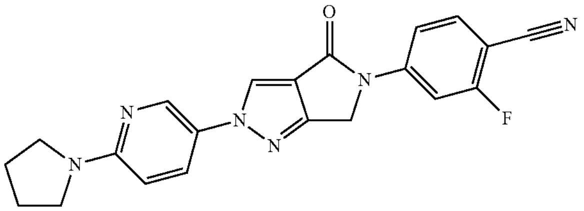
56
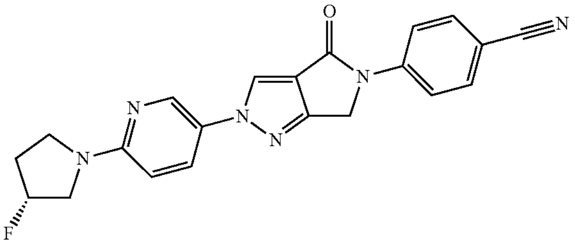
57
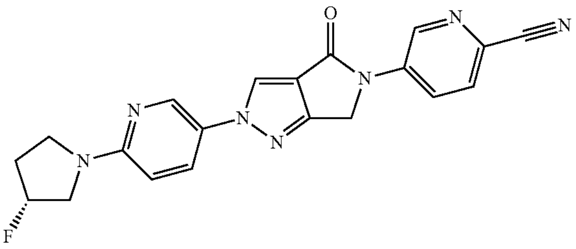
58
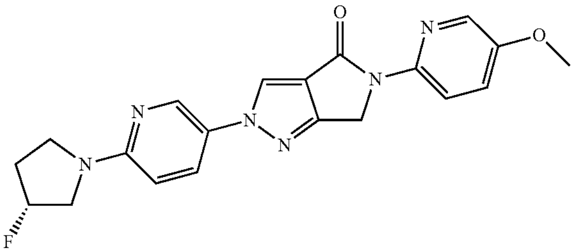
59
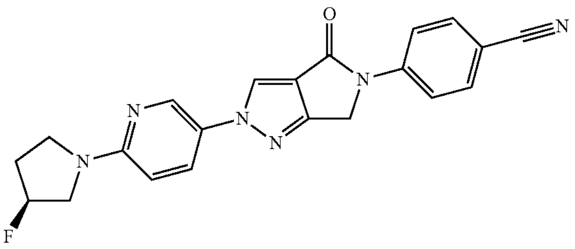
60
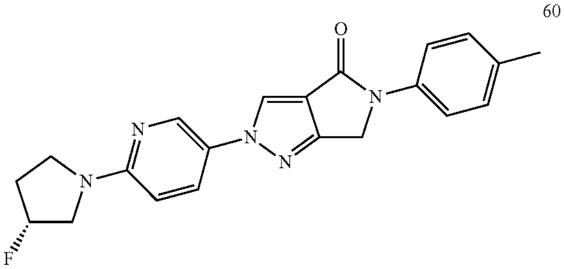

-continued
61
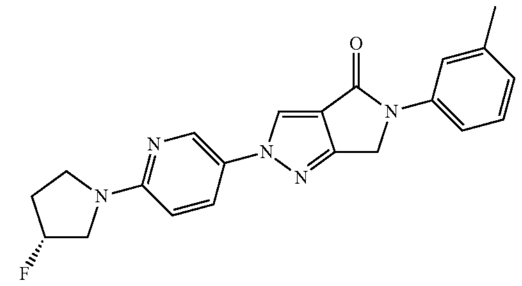
62
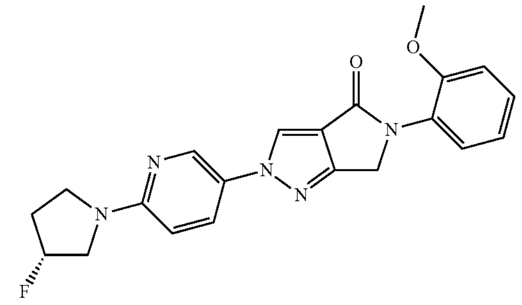
63
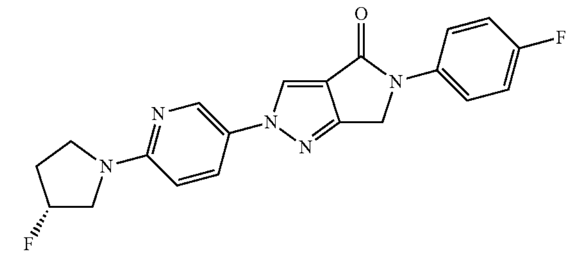
64
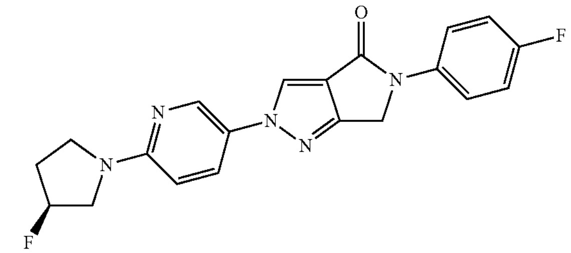
65
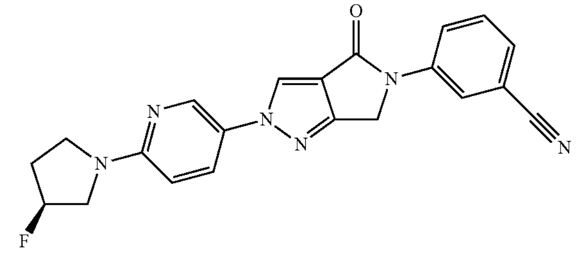
-continued
66
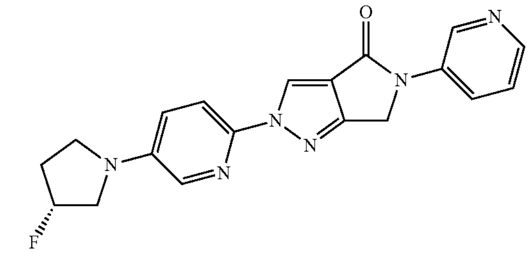
67
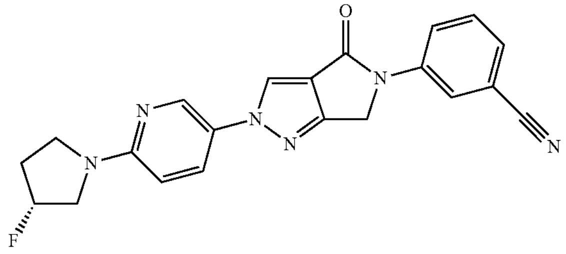
68
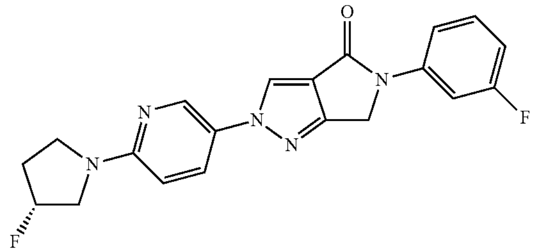
69
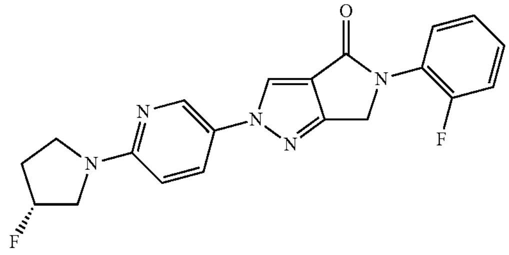
70
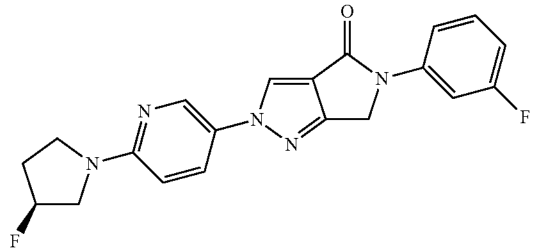
71
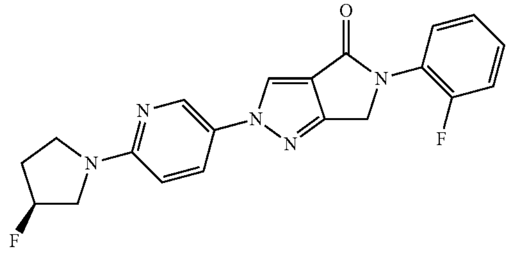

-continued
72
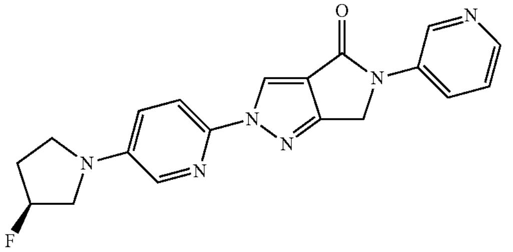
73
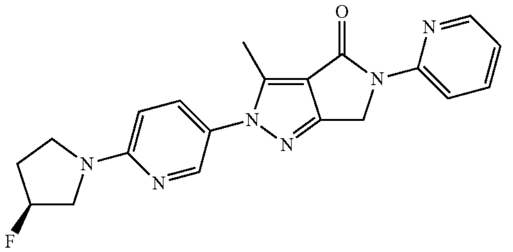
74
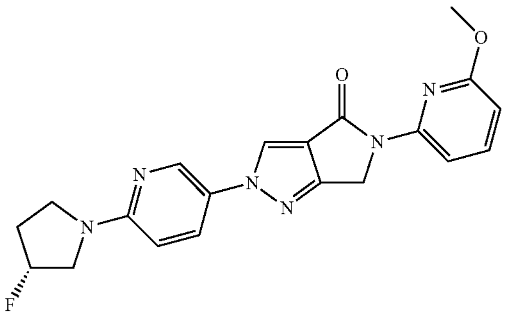
75
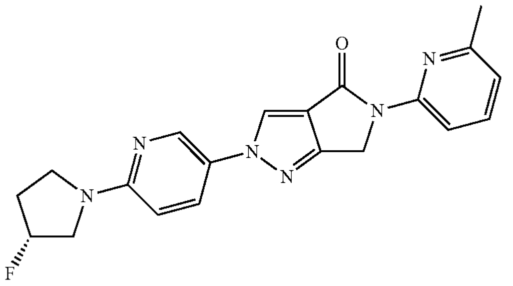
76
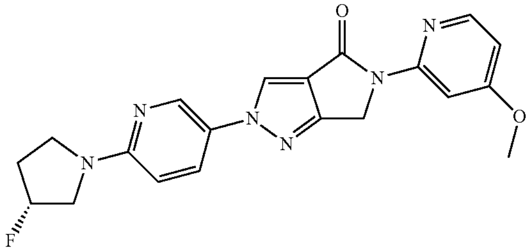
77
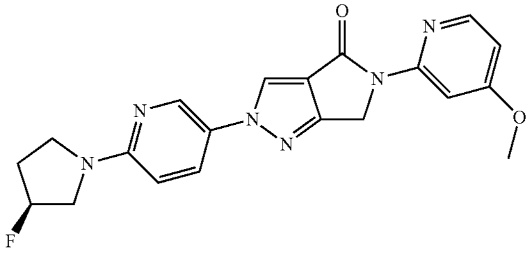
-continued
78
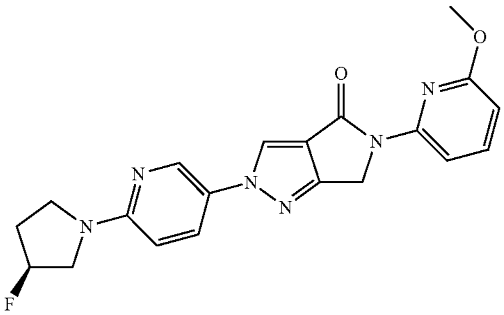
79
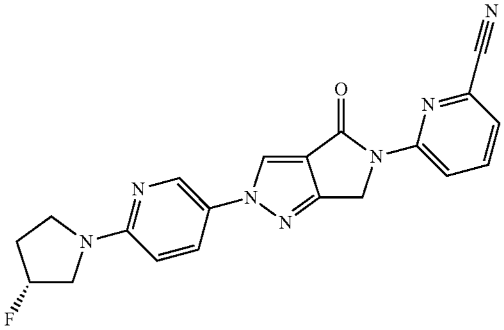
80
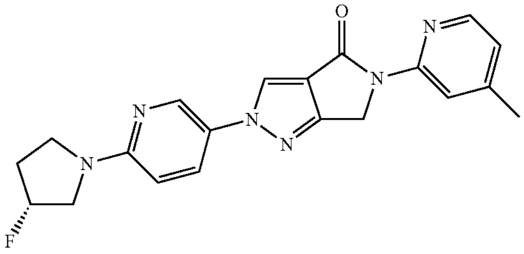
81
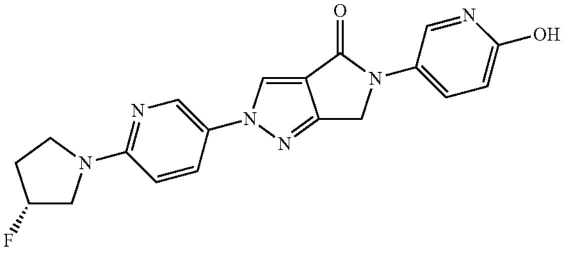
82
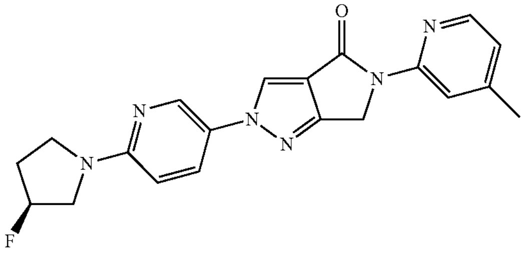

-continued
83
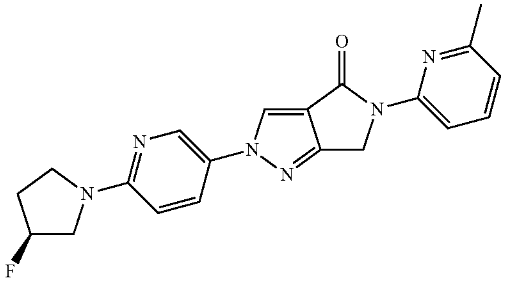
84
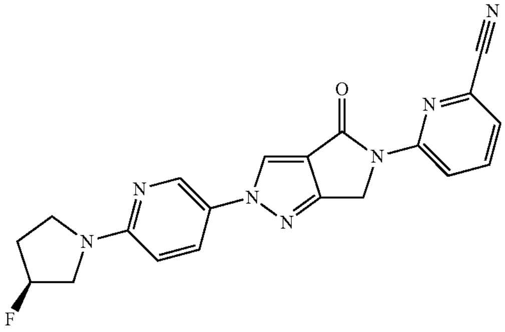
85
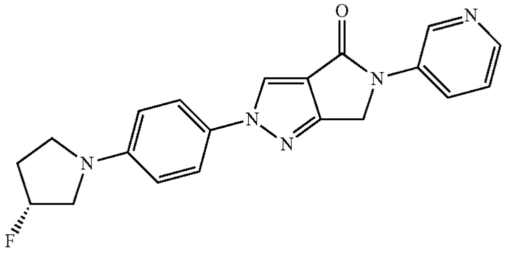
86
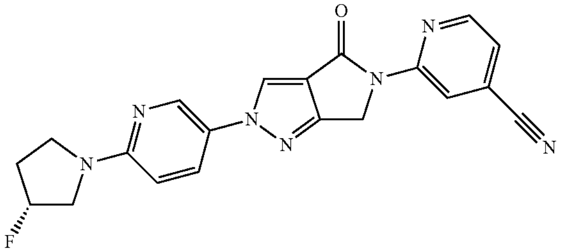
87
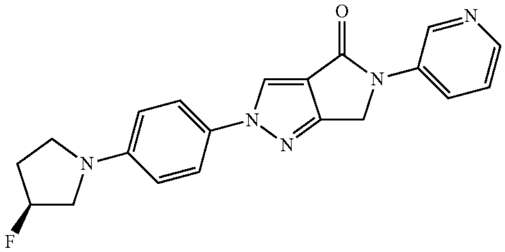
-continued
88
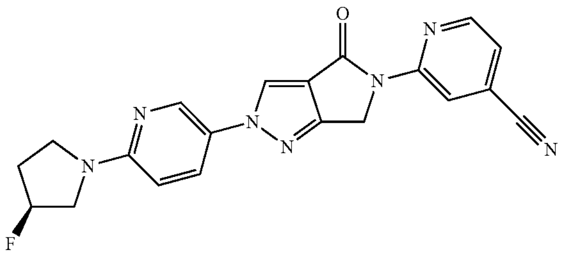
89
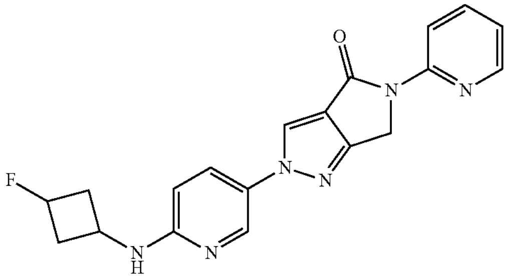
90
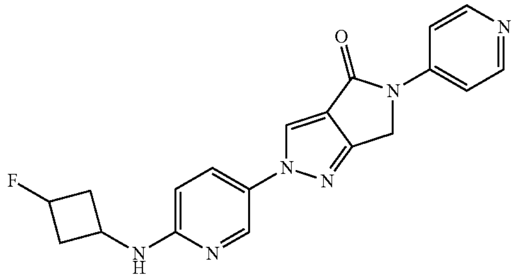
91
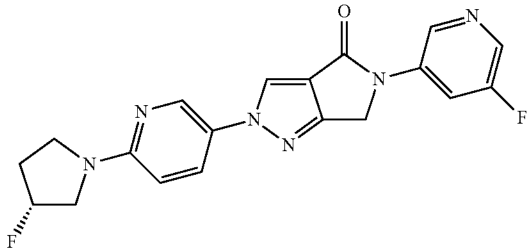
92
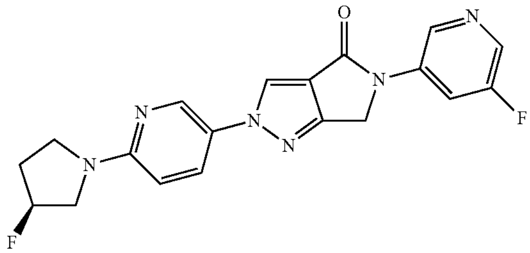
93
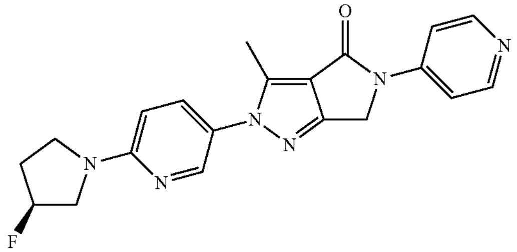

-continued
94
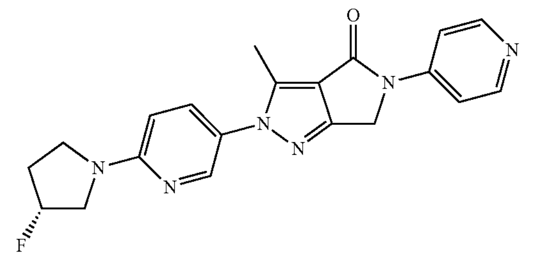
95
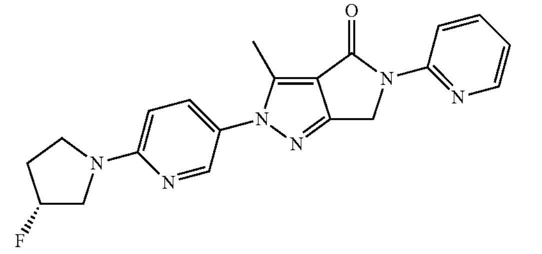
96
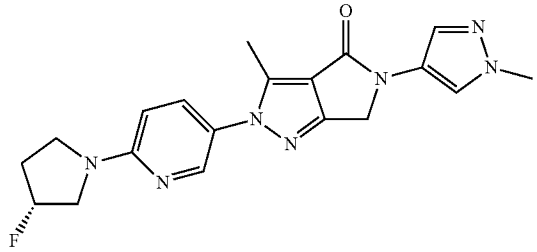
97
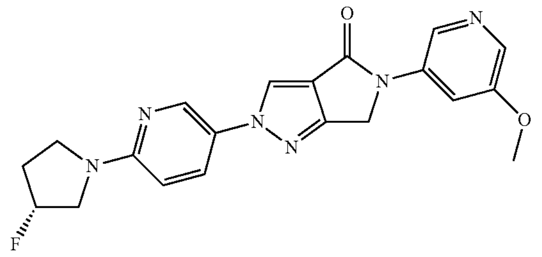
98
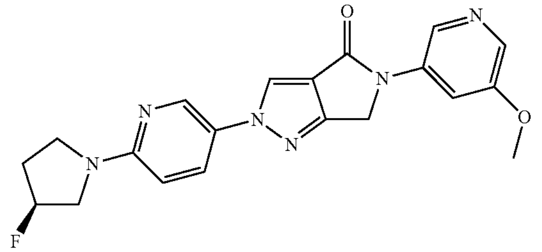
99
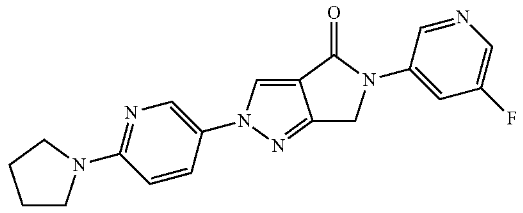
-continued
100
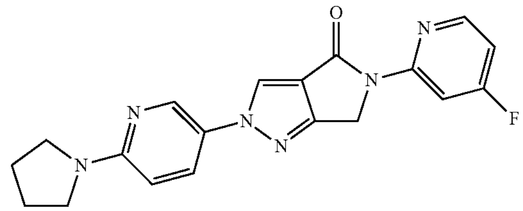
101
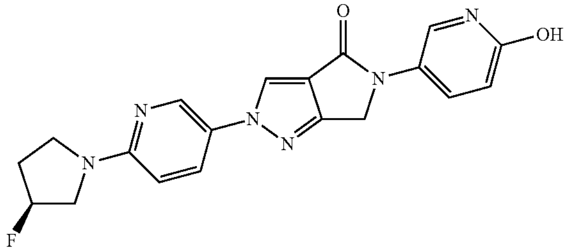
102
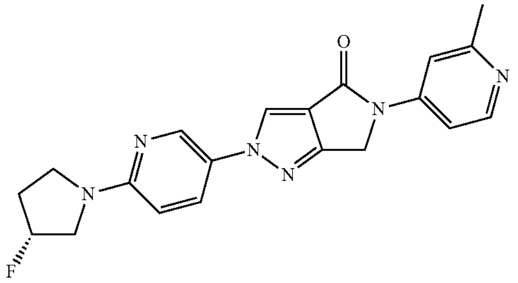
103
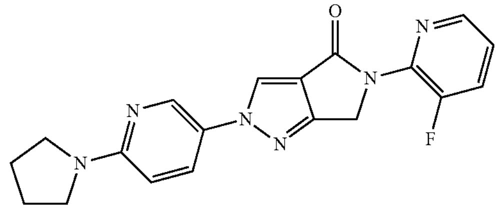
104
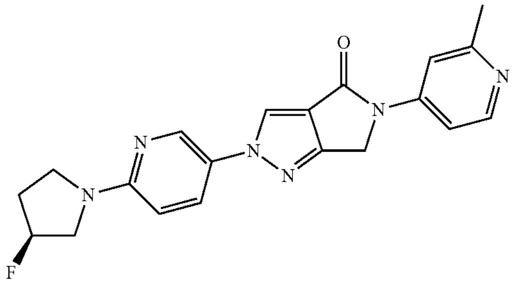
105
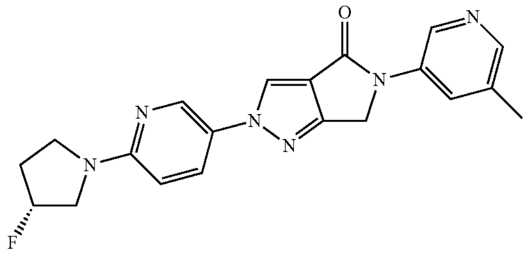

-continued
106
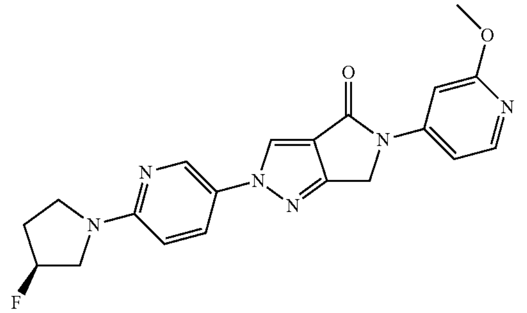
107
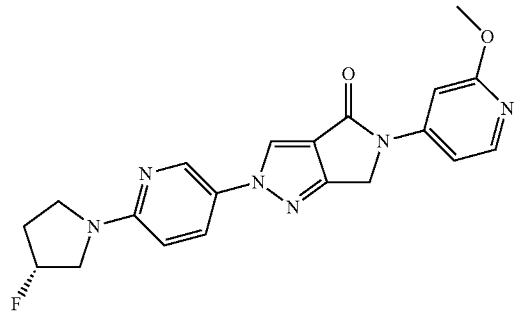
108
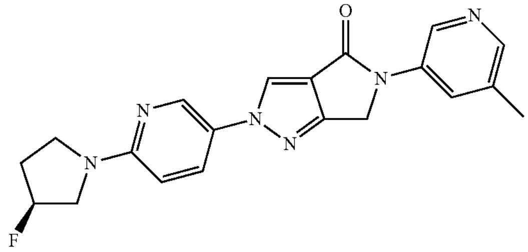
109
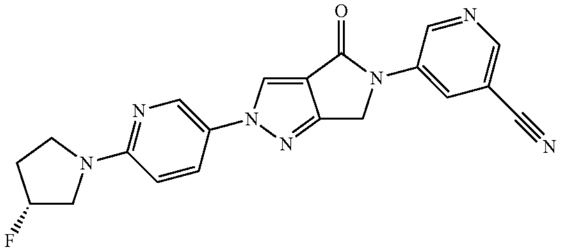
110
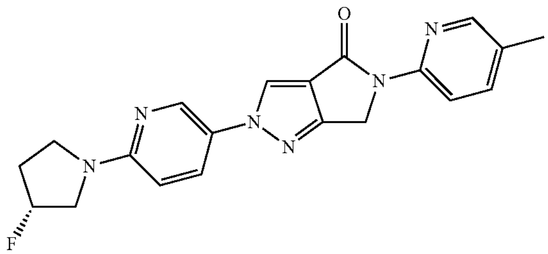
-continued
111
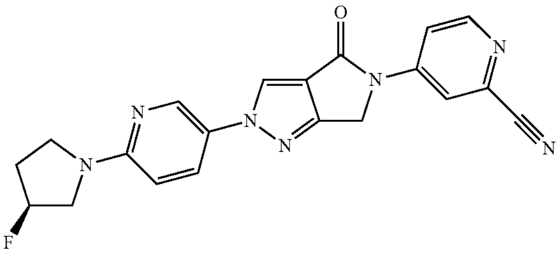
112
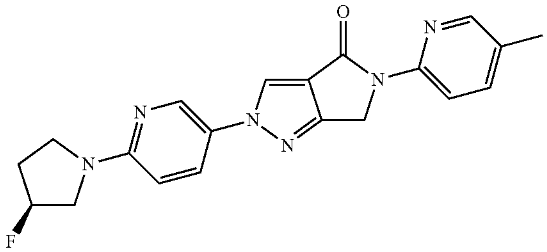
113
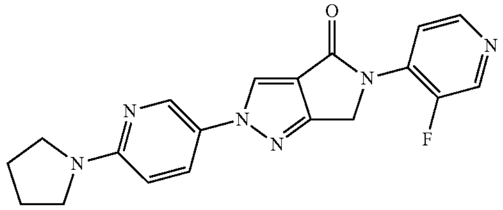
114
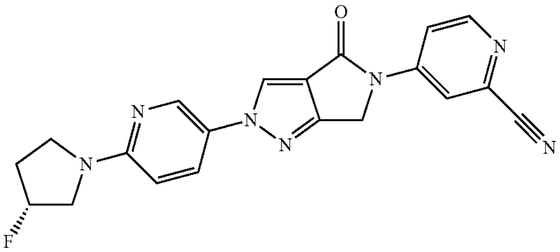
115
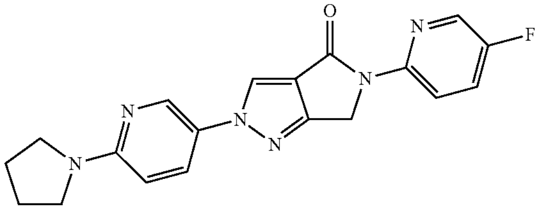
116
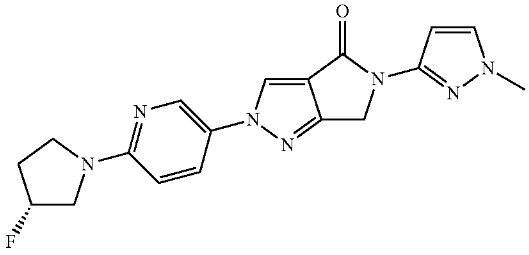

-continued
117
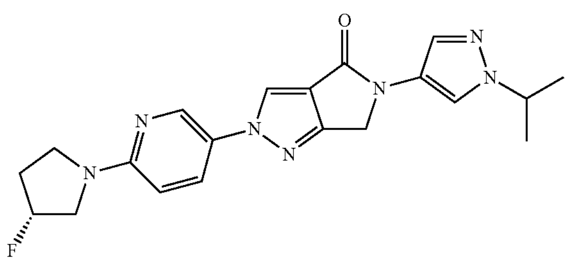
118
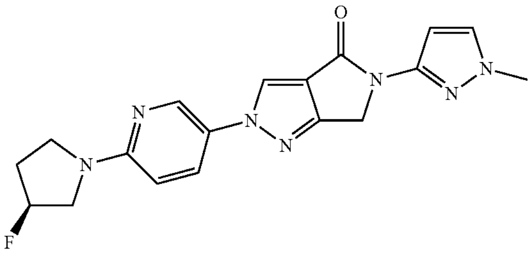
119
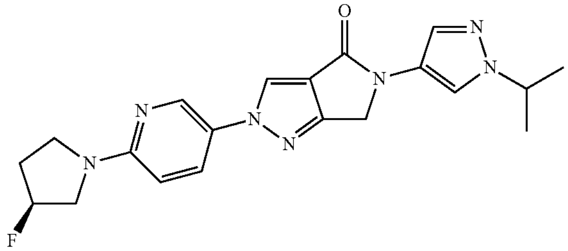
120
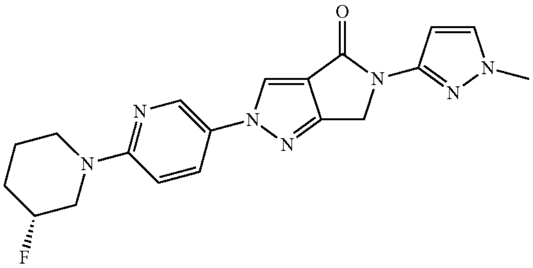
121
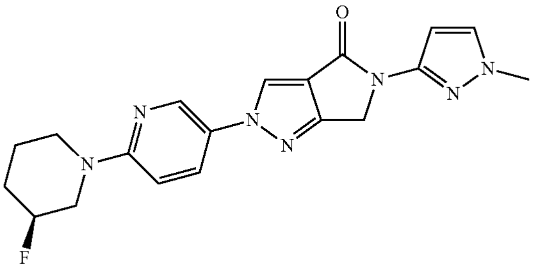
-continued
122
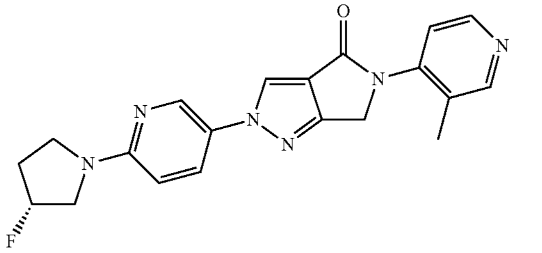
123
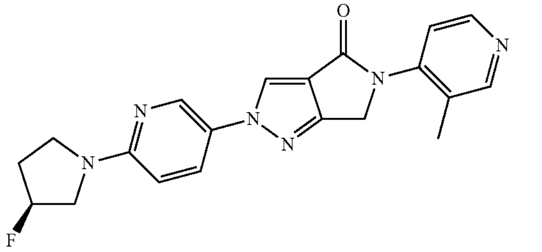
124
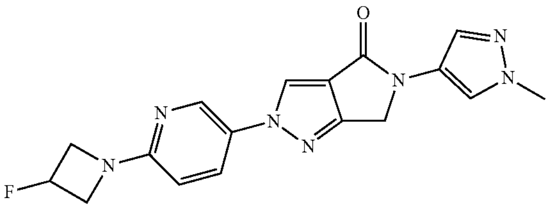
125
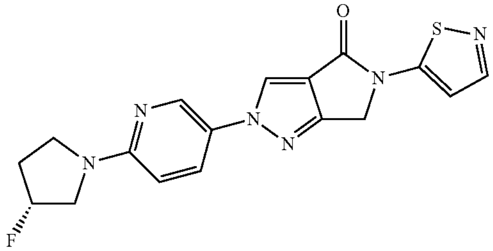
126
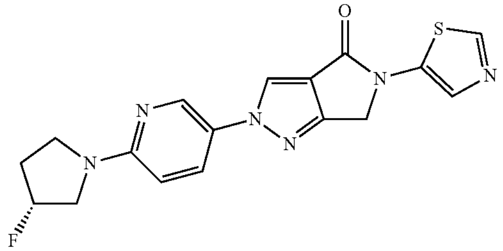
127
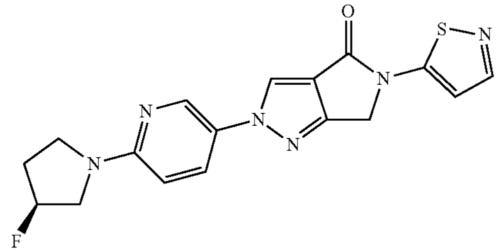

-continued
128
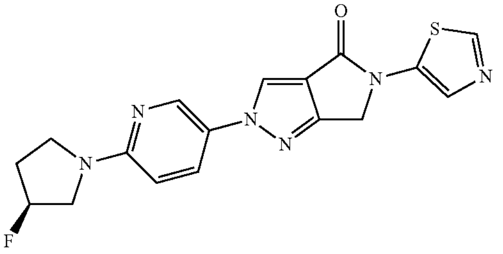
129
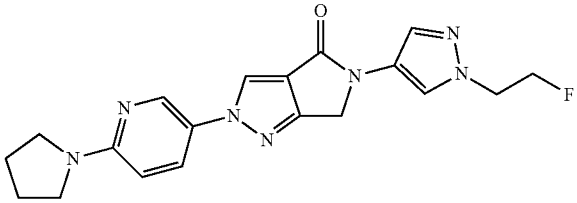
130
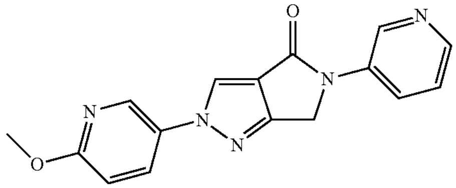
131
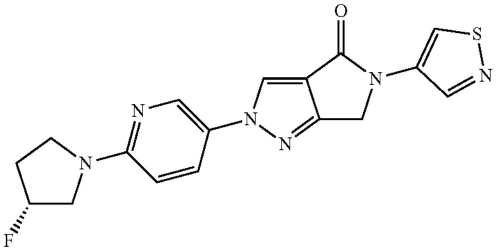
132
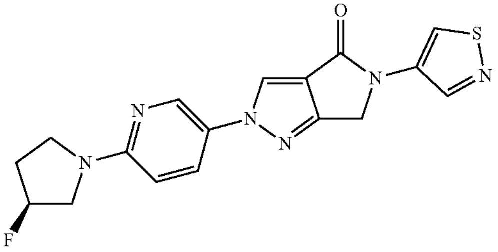
133
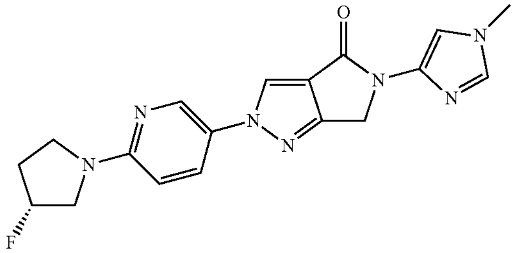
-continued
134
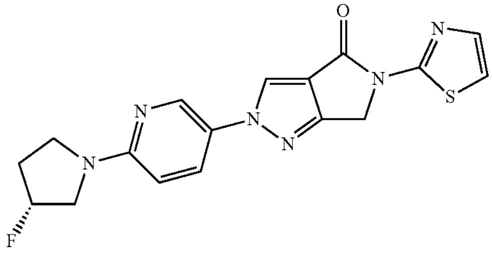
135
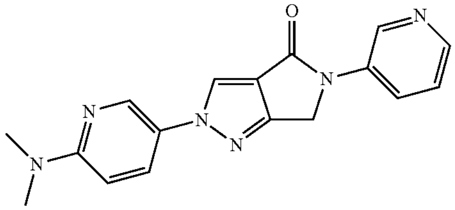
136
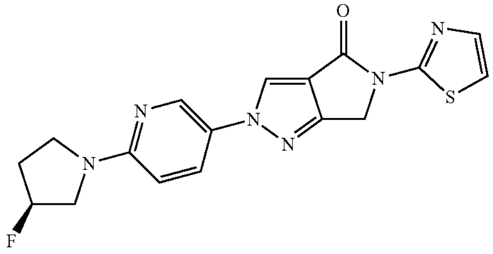
137
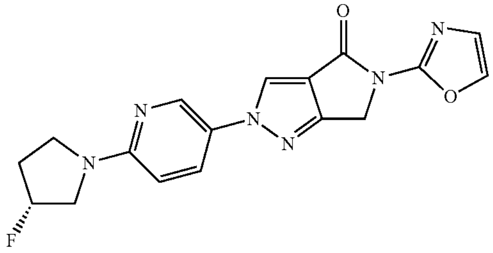
138
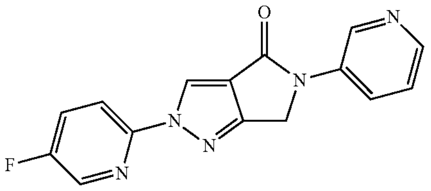
139
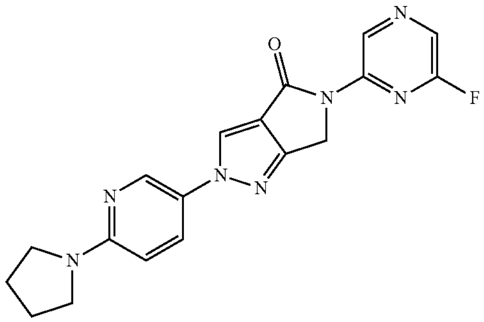

-continued
140
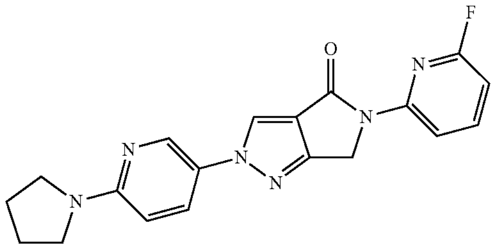
141
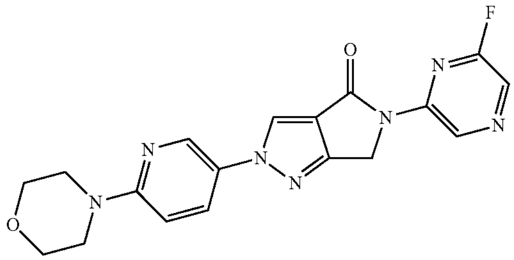
142
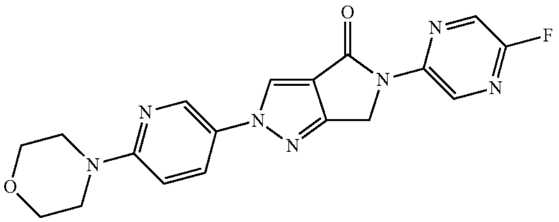
143
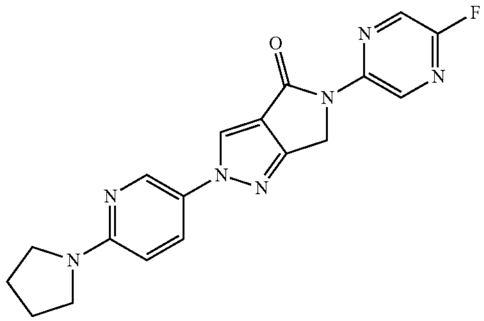
144
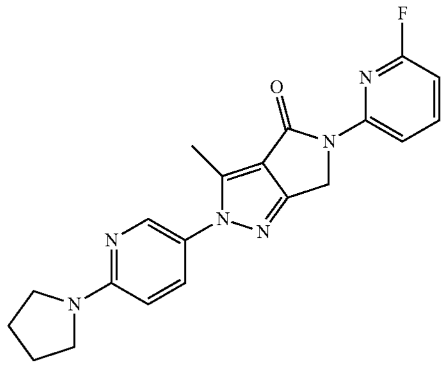
-continued
145
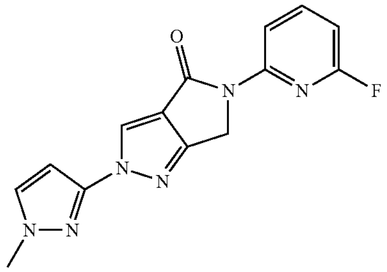
146
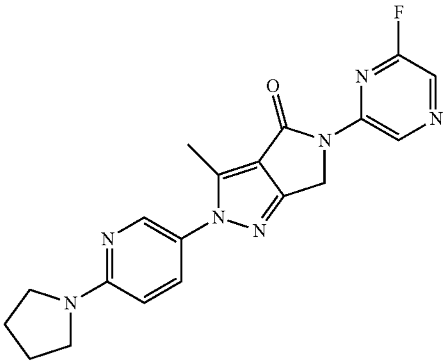
147
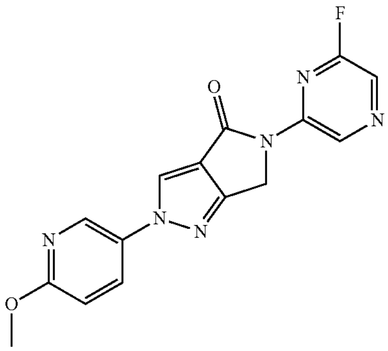
148
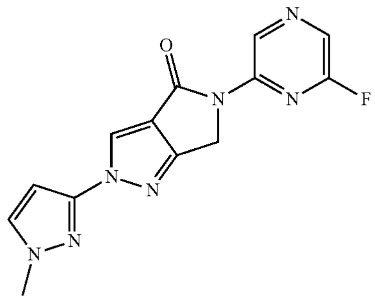
149
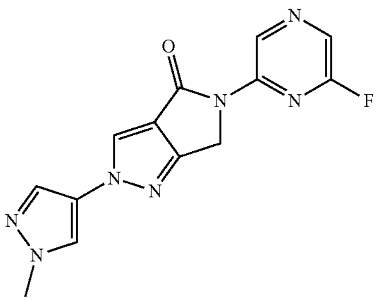

-continued
150
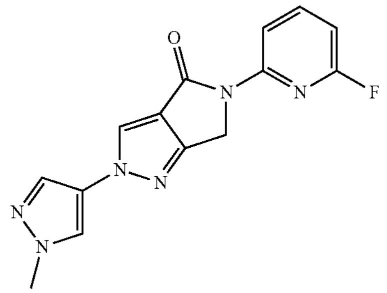
151
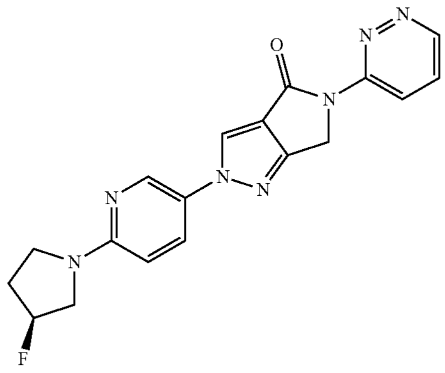
152
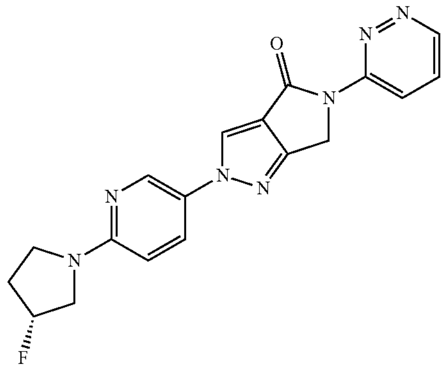
153
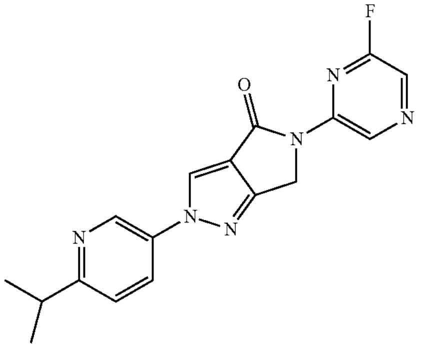
-continued
154
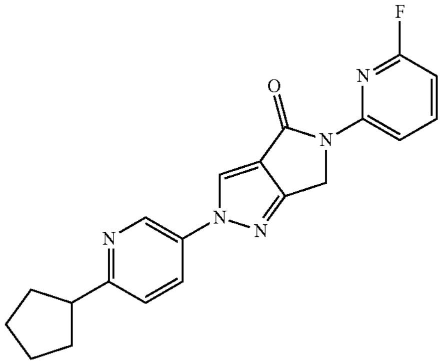
155
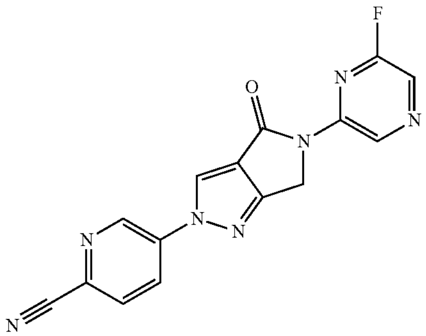
156
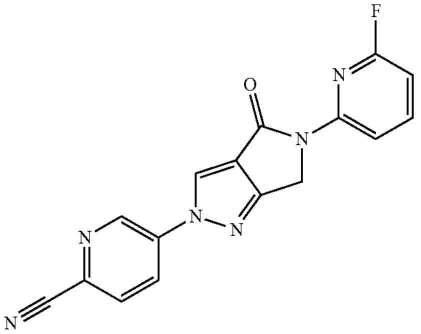
157
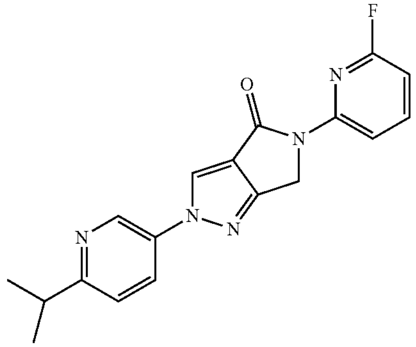

-continued
158
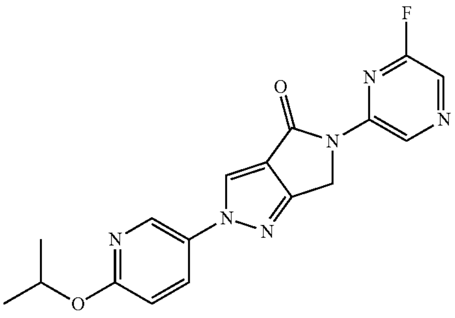
159
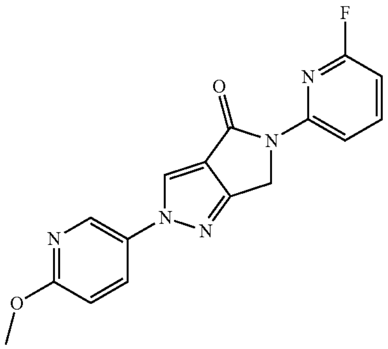
160
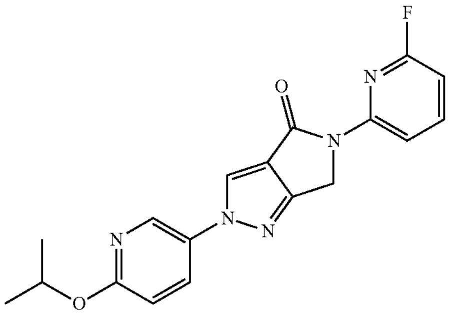
161
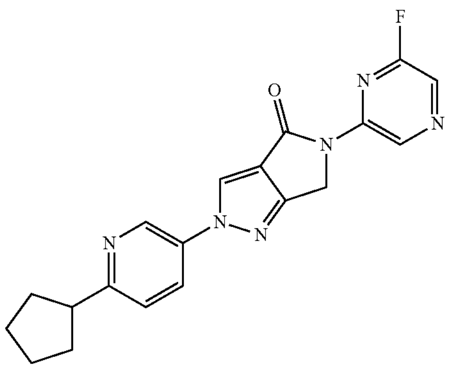
-continued
162
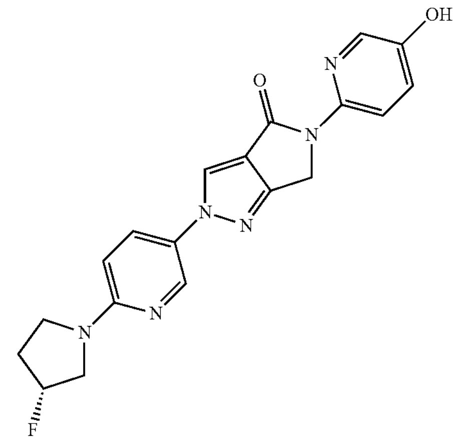
163
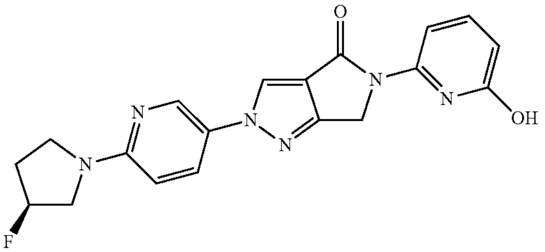
164
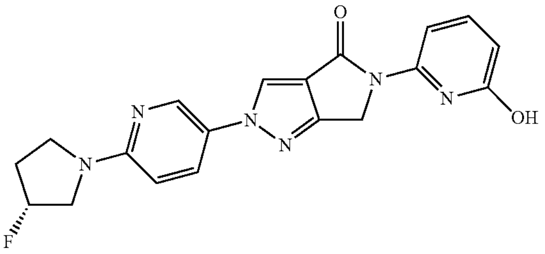
165
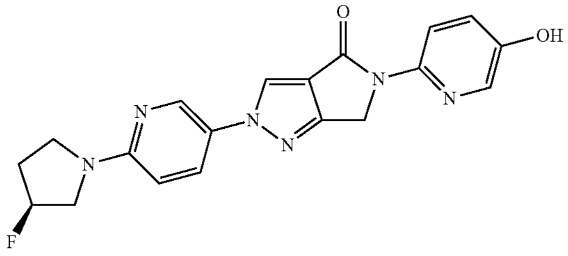
166
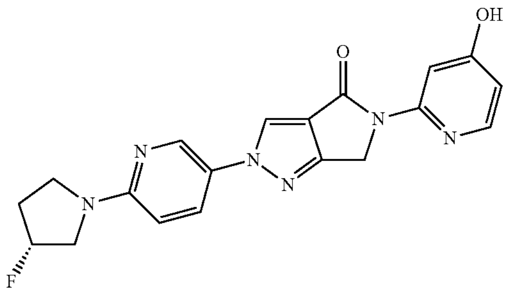

167
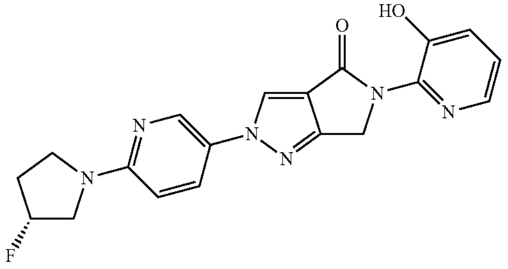
168
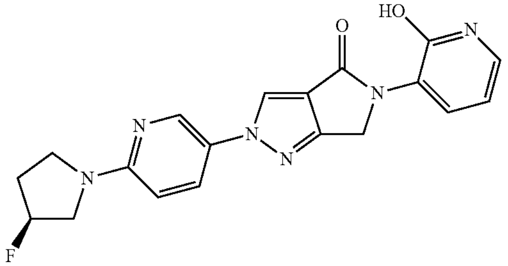
169
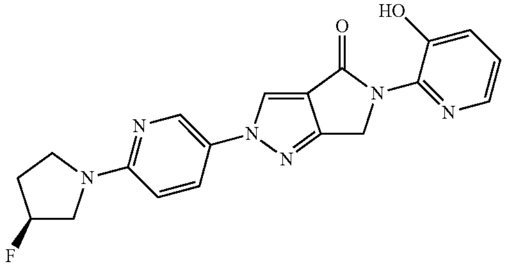
170
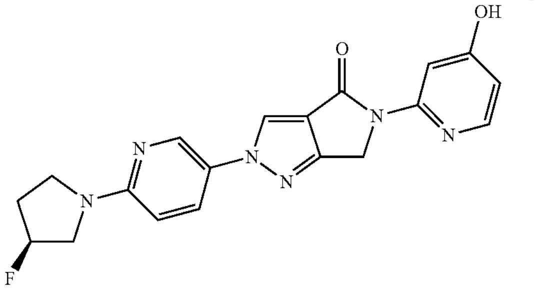
171
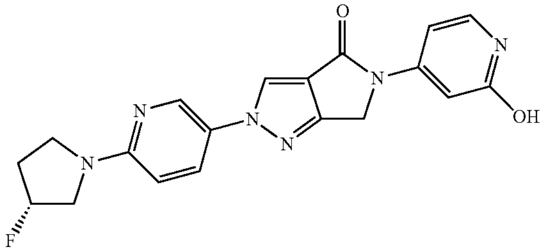
172
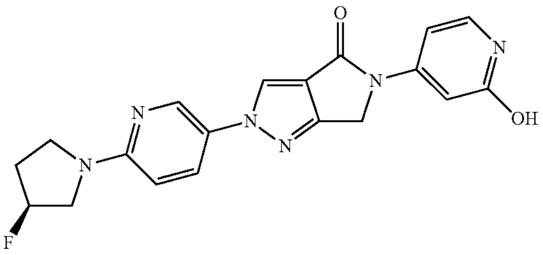
173
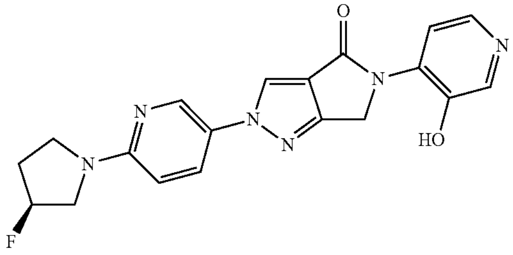
174
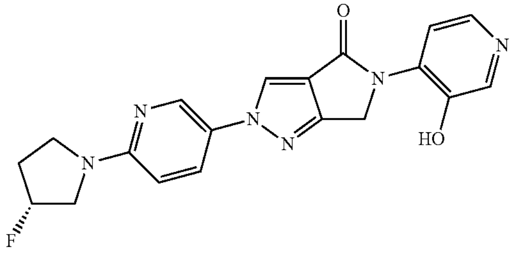
175
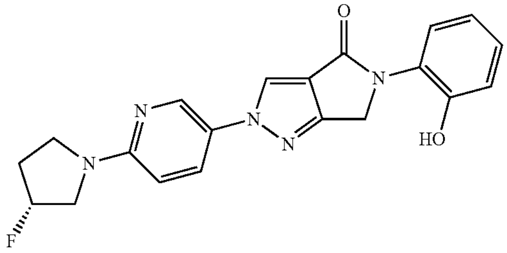
176
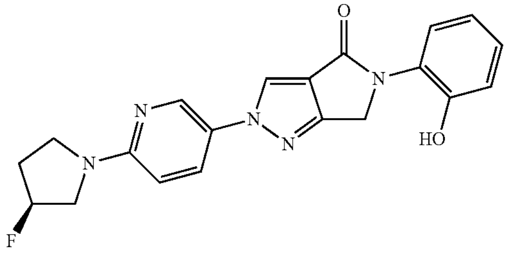
177
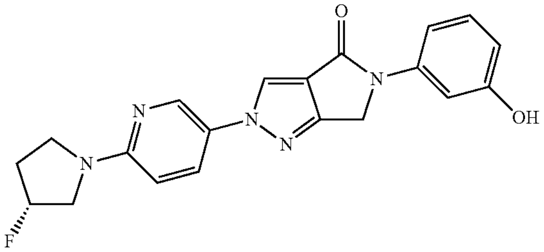

-continued

178

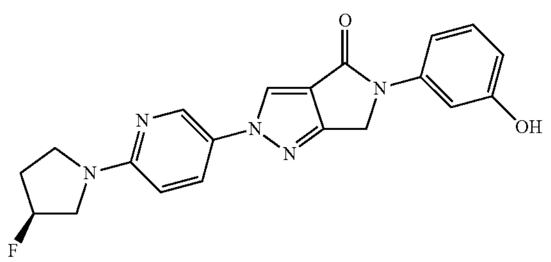

179

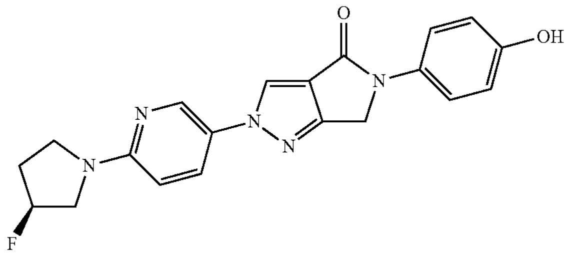

180

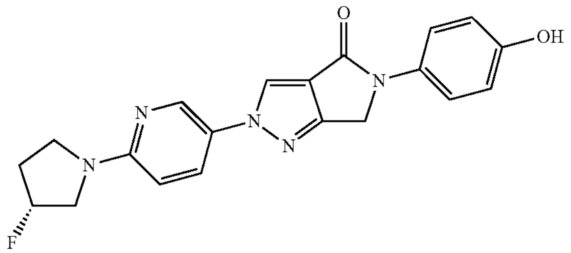

181

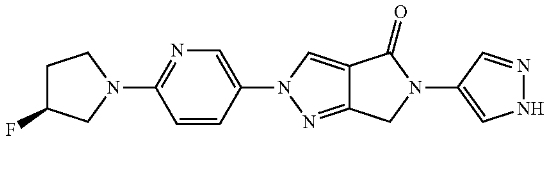

or a detectably labelled compound, stereoisomer, racemic mixture, pharmaceutically acceptable salt, hydrate, or solvate thereof.

5. A detectably labelled compound of formula (I)

(I)

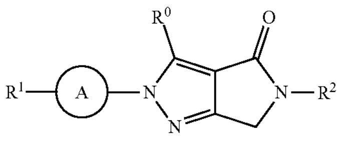

stereoisomer, racemic mixture, pharmaceutically acceptable salt, hydrate, or solvate thereof, wherein

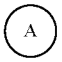

is an aryl or a heteroaryl which is directionally selected from the group consisting of:

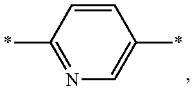
,
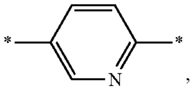
,
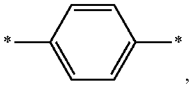
,
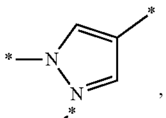
, and
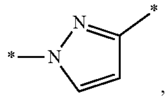
, $R^0$ is H or $C_1$-$C_4$alkyl;

$R^1$ is —CN; or halo; or $C_1$-$C_4$alkyl; or $C_1$-$C_4$alkoxy: or —N($C_1$-$C_4$alkyl)$_2$; or —NH($C_1$-$C_4$alkyl); or H;

or $R^1$ is —NH—$C_3$-$C_6$cycloalkyl, $C_3$-$C_6$cycloalkyl, or heterocyclyl, which is a 4- to 6-membered non-aromatic monocyclic ring radical containing 1 or 2 heteroatoms, each of which is optionally substituted with at least one halo;

$R^2$ is selected from the group consisting of:

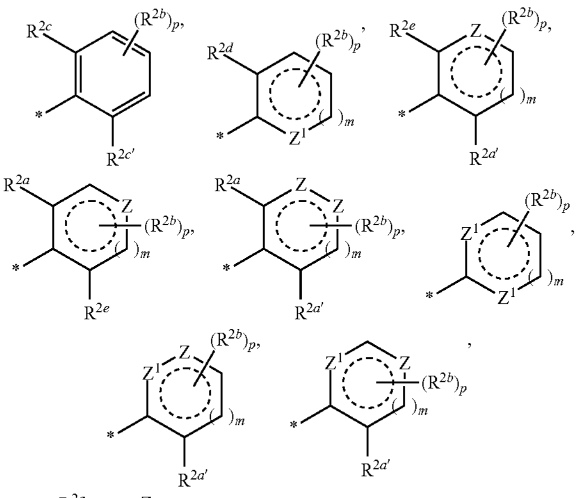

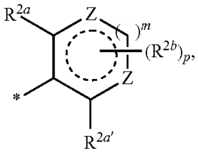

and

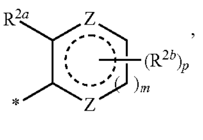

wherein $R^{2a}$, $R^{2a'}$ are independently H, or F;

$R^{2b}$ is independently F, OH, $C_1$-$C_4$alkyl, halo$C_1$-$C_4$alkyl, $NH_2$, CN, or $C_1$-$C_4$alkoxy;

$R^{2c}$, $R^{2c'}$ are independently H, F, OH, $OCH_3$, or $CH_3$;

$R^{2d}$ is H, F, or OH;

$R^{2e}$ is H, OH, $CH_3$, or F;

Z is independently N, NH, N($C_1$-$C_4$alkyl), N(halo$C_1$-$C_4$alkyl), O, or S;

$Z^1$ is independently N, NH, O, or S;

p is 0, 1 or 2;

m is 0 or 1;

as valency permits,  is a combination of single and double bonds; and

* is the position of bonding, wherein the compound is a detectably labelled compound.

6. The detectably labelled compound of formula (I) according to claim 5, wherein $R^1$ is

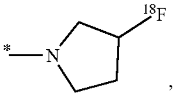,
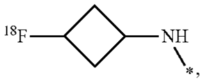,
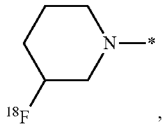, or
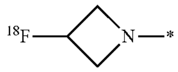;

or $R^1$ is

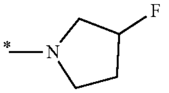,
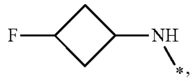,
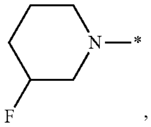, or
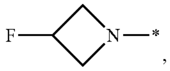, wherein

F means $^{19}F$; and the compound of formula (I) is detectably labelled at least at one available position by $^3H$ (Tritium);

or wherein the detectably labelled compound is

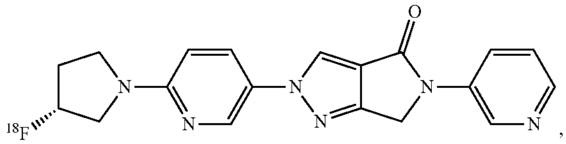,
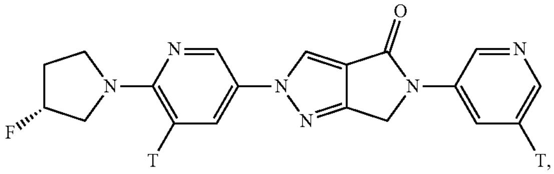, or
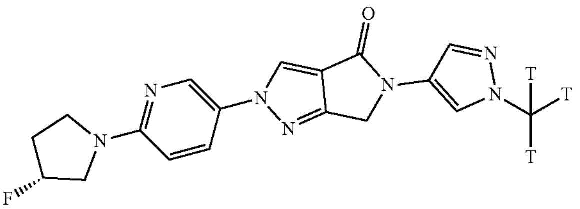

wherein

T means $^3H$ (Tritium) and

F means $^{19}F$;

or a pharmaceutically acceptable salt, hydrate, or solvate thereof.

7. A method of imaging of alpha-synuclein aggregates, comprising performing said imaging with the aid of the detectably labelled compound according to claim 5, or a stereoisomer, racemic mixture, pharmaceutically acceptable salt, hydrate, or solvate thereof.

8. A diagnostic composition comprising the detectably labelled compound according to claim 5, or a stereoisomer, racemic mixture, pharmaceutically acceptable salt, hydrate, or solvate thereof, and at least one pharmaceutically acceptable excipient, carrier, diluent or adjuvant.

9. A method selected from the group consisting of (A) a method of imaging a disease, disorder or abnormality associated with alpha-synuclein aggregates in a subject, the method comprising the steps:
  (a) administering the detectably labelled compound according to claim 6, or a stereoisomer, racemic mixture, pharmaceutically acceptable salt, hydrate, or solvate thereof, to the subject;
  (b) allowing the compound to bind to the alpha-synuclein aggregates; and
  (c) detecting the compound bound to the alpha-synuclein aggregates;

(B) a method of imaging a disease, disorder or abnormality associated with alpha-synuclein aggregates in a subject, the method comprising the steps:
  (a) administering the detectably labelled compound according to claim 6, or a stereoisomer, racemic mixture, pharmaceutically acceptable salt, hydrate, or solvate thereof, to the subject; and
  (b) imaging the brain of the subject;

(C) a method of imaging a disease, disorder or abnormality associated with alpha-synuclein aggregates in a subject according to above method (A) or (B), the method comprising the steps:
  (a) administering the detectably labelled compound according to claim 6, or a stereoisomer, racemic mixture, pharmaceutically acceptable salt, hydrate, or solvate thereof;
  (b) allowing the compound to bind to the alpha-synuclein aggregates;
  (c) detecting the compound bound to the alpha-synuclein aggregates; and
  (d) generating an image representative of the location and/or amount of the compound bound to the alpha-synuclein aggregates;

(D) a method of positron emission tomography (PET) imaging of alpha-synuclein aggregates in a tissue of a subject, the method comprising the steps:
  (a) administering the detectably labelled compound according to claim 6, or a stereoisomer, racemic mixture, pharmaceutically acceptable salt, hydrate, or solvate thereof, to the subject;
  (b) allowing the compound to penetrate into the tissue of the subject; and
  (c) collecting a positron emission tomography (PET) image of the tissue of the subject;
  wherein the tissue is tissue of the central nervous system (CNS), tissue of the eye or brain tissue;

(E) a method of detecting a neurological disease, disorder or abnormality associated with alpha-synuclein aggregates, in a subject, the method comprising the steps:
  (a) administering the detectably labelled compound according to claim 6, or a stereoisomer, racemic mixture, pharmaceutically acceptable salt, hydrate, or solvate thereof, to the subject;
  (b) allowing the compound to bind to the alpha-synuclein aggregates; and
  (c) measuring the radioactive signal of the compound, which is bound to the alpha-synuclein aggregates;

(F) a method for the detection and/or quantification of alpha-synuclein aggregates in a tissue of a subject, the method comprising the steps:

(a) contacting the tissue with the detectably labelled compound according to claim 6, or a stereoisomer, racemic mixture, pharmaceutically acceptable salt, hydrate, or solvate thereof, to the subject;

(b) allowing the compound to bind to the alpha-synuclein aggregates; and (c) detecting and/or quantifying the compound bound to the alpha-synuclein aggregates by positron emission tomography, (G) a method of the diagnostic imaging of the brain of a subject, the method comprising the steps:

(a) administering the detectably labelled compound according to claim 6, or a stereoisomer, racemic mixture, pharmaceutically acceptable salt, hydrate, or solvate thereof, to the subject; and (b) obtaining an image of the brain of the subject using positron emission tomography;

(H) a method of collecting data for the diagnosis of a disease, disorder or abnormality associated with alpha-synuclein aggregates, the method comprising the steps:

(a) bringing a sample or a specific body part or body area suspected to contain alpha-synuclein aggregates into contact with the detectably labelled compound according to claim 6, or a stereoisomer, racemic mixture, pharmaceutically acceptable salt, hydrate, or solvate thereof;

(b) allowing the compound to bind to the alpha-synuclein aggregates including;

(c) detecting the compound bound to the alpha-synuclein aggregates; and (d) optionally correlating the presence or absence of the compound bound to the alpha-synuclein aggregates with the presence or absence of the alpha-synuclein aggregates in the sample or specific body part or body area, (I) a method of collecting data for determining a predisposition to a disease, disorder or abnormality associated with alpha-synuclein aggregates, the method comprising the steps:

(a) bringing a sample or a specific body part or body area suspected to contain alpha-synuclein aggregates into contact with the detectably labelled compound according to claim 6, or a stereoisomer, racemic mixture, pharmaceutically acceptable salt, hydrate, or solvate thereof;

(b) allowing the compound to bind to the alpha-synuclein aggregates;

(c) detecting the compound bound to the alpha-synuclein aggregates; and (d) optionally correlating the presence or absence of the compound bound to the alpha-synuclein aggregates with the presence or absence of the alpha-synuclein aggregates in the sample or specific body part or body area;

(J) a method of prognosing a disease, disorder or abnormality associated with alpha-synuclein aggregates, wherein the method comprises the steps:

(a) bringing a sample, a specific body part or body area suspected to contain alpha-synuclein aggregates into contact with the detectably labelled compound according to claim 6, or a stereoisomer, racemic mixture, pharmaceutically acceptable salt, hydrate, or solvate thereof;

(b) allowing the compound to bind to the alpha-synuclein aggregates;

(c) detecting the compound bound to the alpha-synuclein aggregates;

(d) optionally correlating the presence or absence of the compound bound to the alpha-synuclein aggregates with the presence or absence of the alpha-synuclein aggregates in the sample or specific body part or body area; and (e) optionally repeating steps (a) to (c) and, if present, optional step (d) at least one time;

(K) a method of monitoring the progression of a disease, disorder or abnormality associated with alpha-synuclein aggregates in a patient, the method comprising the steps:

(a) bringing a sample, a specific body part or body area suspected to contain alpha-synuclein aggregates into contact with the detectably labelled compound according to claim 6, or a stereoisomer, racemic mixture, pharmaceutically acceptable salt, hydrate, or solvate thereof;

(b) allowing the compound to bind to the alpha-synuclein aggregates including;

(c) detecting the compound bound to the alpha-synuclein aggregates;

(d) optionally correlating the presence or absence of the compound bound to the alpha-synuclein aggregates with the presence or absence of the alpha-synuclein aggregates in the sample or specific body part or body area; and (e) optionally repeating steps (a) to (c) and, if present, optional step (d) at least one time;

(L) a method of predicting responsiveness of a patient suffering from a disease, disorder or abnormality associated with alpha-synuclein aggregates to a treatment of the disease, disorder or abnormality associated with alpha-synuclein, the method comprising the steps:

(a) bringing a sample, a specific body part or body area suspected to contain alpha-synuclein aggregates into contact with the detectably labelled compound according to claim 6, or a stereoisomer, racemic mixture, pharmaceutically acceptable salt, hydrate, or solvate thereof;

(b) allowing the compound to bind to the alpha-synuclein aggregates;

(c) detecting the compound bound to the alpha-synuclein aggregates;

(d) optionally correlating the presence or absence of the compound bound to the alpha-synuclein aggregates with the presence or absence of the alpha-synuclein aggregates in the sample or specific body part or body area; and (e) optionally repeating steps (a) to (c) and, if present, optional step (d) at least one time;

and (M) one of the above methods (H) to (L), wherein the step of optionally correlating the presence or absence of the compound bound to the alpha-synuclein aggregates with the presence or absence of the alpha-synuclein aggregates in the sample or specific body part or body area; comprises determining the amount of the compound bound to the alpha-synuclein aggregates;

correlating the amount of the compound bound to the alpha-synuclein aggregates with the amount of the alpha-synuclein aggregates in the sample or specific body part or body area; and optionally comparing the amount of the alpha-synuclein aggregates in the sample or specific body part or body area to a normal control value in a healthy control subject.

10. A compound selected from the group consisting of (A) a compound of formula (IV-F)

(IV-F)

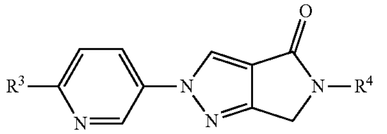

or a stereoisomer, racemic mixture, pharmaceutically acceptable salt, hydrate, or solvate thereof, wherein $R^3$ is

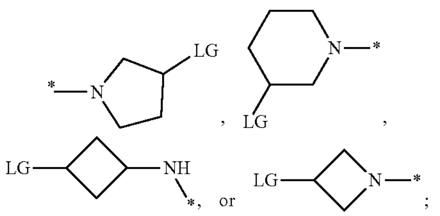

$R^4$ is selected from the group consisting of:

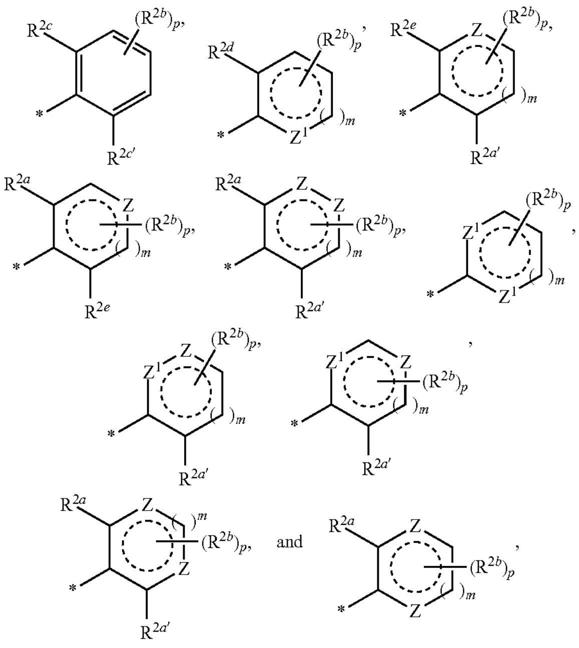

$R^{2a}$, $R^{2a'}$ are independently H, or F;

$R^{2b}$ is independently F, —OH, $C_1$-$C_4$alkyl, halo$C_1$-$C_4$alkyl, —$NH_2$, —CN, or $C_1$-$C_4$alkoxy;

$R^{2c}$, $R^{2c'}$ are independently H, F, OH, $OCH_3$, or $CH_3$;

$R^{2d}$ is H, F, or —OH;

$R^{2e}$ is H, OH, $CH_3$, or F;

Z is independently N, NH, N($C_1$-$C_4$alkyl), N(halo$C_1$-$C_4$alkyl), O, or S;

$Z^1$ is independently N, NH, O, or S;

p is 0, 1 or 2;

m is 0 or 1;

as valency permits,  is a combination of single and double bonds; and

* is the position of bonding;

(B) a compound of formula (IV-H)

(IV-H)

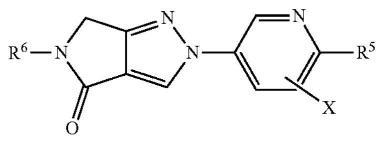

or a stereoisomer, racemic mixture, pharmaceutically acceptable salt, hydrate, or solvate thereof, wherein $R^5$ is

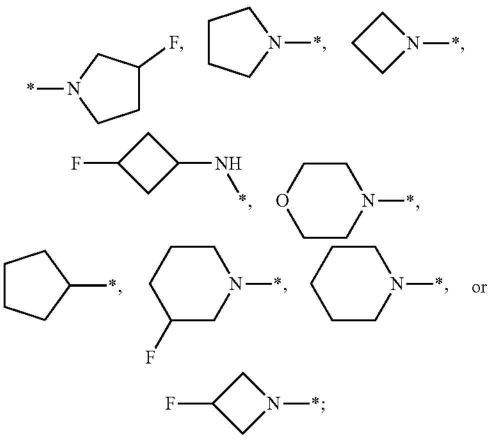

$R^6$ is selected from the group consisting of:

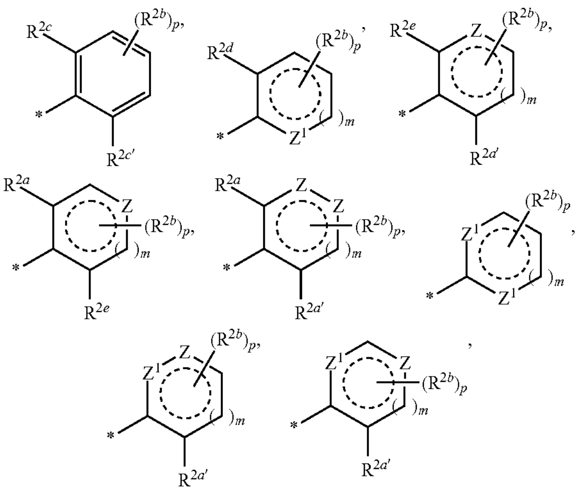

-continued

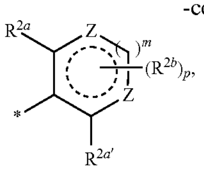

and

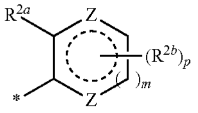

wherein $R^{2a}$, $R^{2a'}$ are independently H, X or F;

$R^{2b}$ is independently X, F, —OH, $C_1$-$C_4$alkyl, halo$C_1$-$C_4$alkyl, —$NH_2$, —CN, or $C_1$-$C_4$alkoxy, and wherein $C_1$-$C_4$alkyl, halo$C_1$-$C_4$alkyl, or $C_1$-$C_4$alkoxy optionally comprise one or more X;

$R^{2c}$, $R^{2c'}$ are independently X, H, F, OH, $OCH_3$, or $CH_3$;

$R^{2d}$ is X, H, F, or —OH;

$R^{2e}$ is X, H, OH, $CH_3$, or F;

Z is independently N, NH, N($C_1$-$C_4$alkyl), N(halo$C_1$-$C_4$alkyl), O, or S;

$Z^1$ is independently N, NH, O, or S;

p is 0, 1 or 2;

m is 0 or 1;

as valency permits, ⸨ is a combination of single and double bonds;

* is the position of bonding;

Fluoro is $^{19}F$;

X is Bromo, Chloro, or Iodo; and wherein $R^6$ comprises at least one X;

(C) a compound of formula (IV-J)

(IV-J)

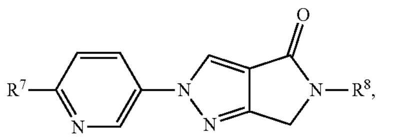

or a stereoisomer, racemic mixture, pharmaceutically acceptable salt, hydrate, or solvate thereof, wherein $R^7$ is

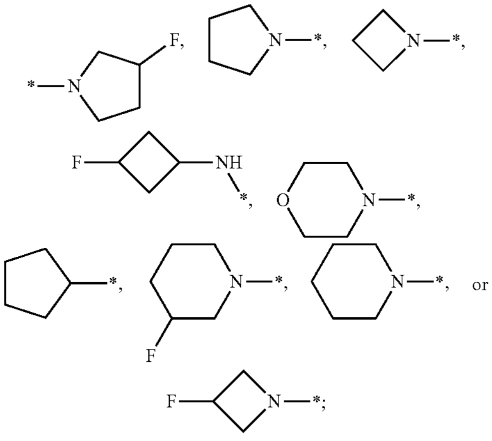

$R^8$ is selected from the group consisting of:

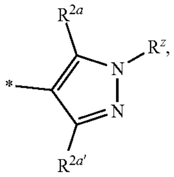

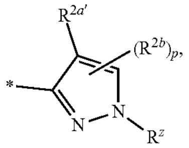

and

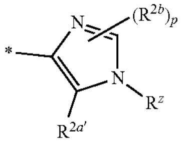

wherein $R^{2a}$, $R^{2a'}$ are independently H, or F;

$R^{2b}$ is independently F, —OH, $C_1$-$C_4$alkyl, halo$C_1$-$C_4$alkyl, —$NH_2$, —CN, or $C_1$-$C_4$alkoxy;

p is 0, 1 or 2;

$R^z$ is H, $C_1$-$C_4$alkyl or halo$C_1$-$C_4$alkyl;

as valency permits, ⸨ is a combination of single and double bonds;

Fluoro is $^{19}F$; and

* is the position of bonding.

11. The compound according to claim 10 which is of formula (IV-F), wherein LG is Bromo, Chloro, Iodo, $C_{1-4}$ alkyl sulfonate or $C_{6-10}$ aryl sulfonate, wherein the $C_{6-10}$ aryl is optionally substituted by —$CH_3$ or —$NO_2$.

12. The compound according to claim 10, which is of formula (IV-F), and which is of the following formula

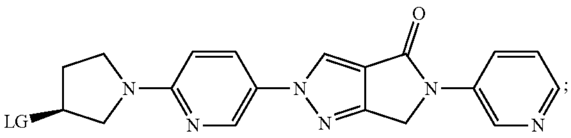

or a pharmaceutically acceptable salt, hydrate, or solvate thereof, wherein

LG is mesylate or nosylate;

or which is of formula (IV-H), and which is of the following formula

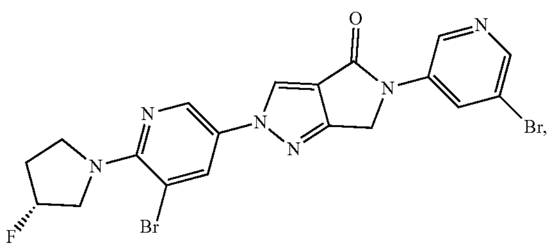 [SMILES: O=C1c2cn(-c3cnc(N4CC[C@@H](F)C4)c(Br)c3)nc2CN1c1cncc(Br)c1]

or a pharmaceutically acceptable salt, hydrate, or solvate thereof;

or which is of formula (IV-J), and which is of the following formula

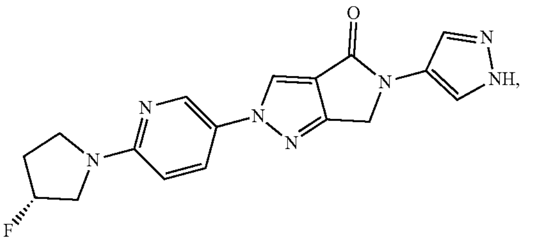 [SMILES: O=C1c2cn(-c3ccc(N4CC[C@@H](F)C4)nc3)nc2CN1c1cn[nH]c1]

or a pharmaceutically acceptable salt, hydrate, or solvate thereof.

13. A method of preparing the compound according to claim 5, comprising a method selected from the group consisting of (A) reacting a compound of formula (IV-F)

(IV-F)

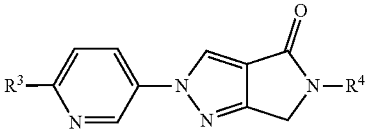

or a stereoisomer, racemic mixture, pharmaceutically acceptable salt, hydrate, or solvate thereof, wherein $R^3$ is

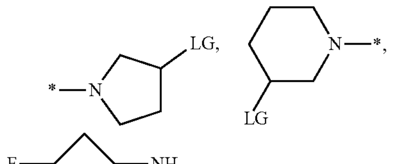

or

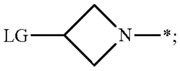

$R^4$ is selected from the group consisting of:

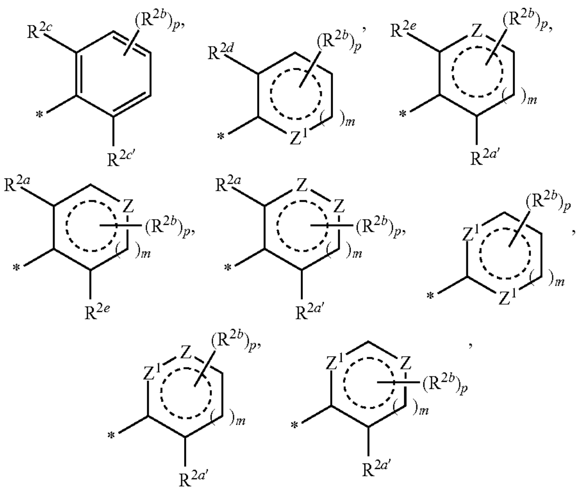

-continued

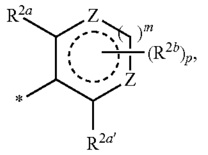

and

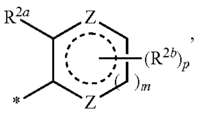

wherein $R^{2a}$, $R^{2a'}$ are independently H, or F;

$R^{2b}$ is independently F, —OH, $C_1$-$C_4$alkyl, halo$C_1$-$C_4$alkyl, —$NH_2$, —CN, or $C_1$-$C_4$alkoxy;

$R^{2c}$, $R^{2c'}$ are independently H, F, OH, $OCH_3$, or $CH_3$;

$R^{2d}$ is H, F, or —OH;

$R^{2e}$ is H, OH, $CH_3$, or F;

Z is independently N, NH, N($C_1$-$C_4$alkyl), N(halo$C_1$-$C_4$alkyl), O, or S;

$Z^1$ is independently N, NH, O, or S;

p is 0, 1 or 2;

m is 0 or 1;

as valency permits, ⸌ is a combination of single and double bonds; and

* is the position of bonding with a $^{18}$F-fluorinating agent, so that LG is replaced by $^{18}$F;

(B) reacting a compound of formula (IV-H)

(IV-H)

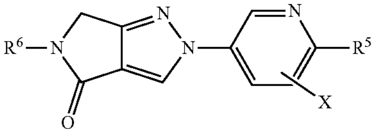

or a stereoisomer, racemic mixture, pharmaceutically acceptable salt, hydrate, or solvate thereof, wherein $R^5$ is

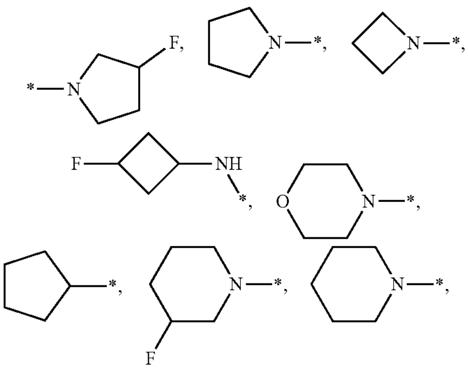

or

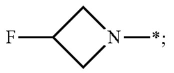

$R^6$ is selected from the group consisting of:

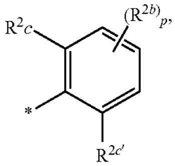, 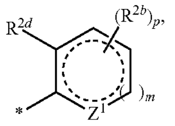,

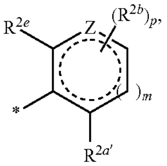, 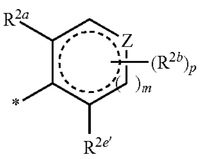,

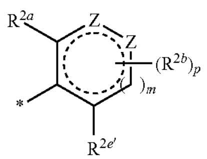, 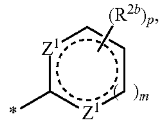,

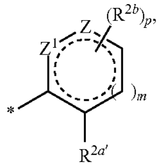, 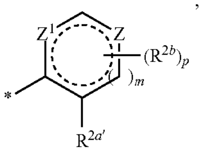,

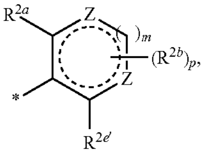 and 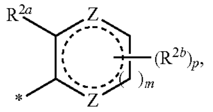

wherein $R^{2a}$, $R^{2a'}$ are independently H, X or F;

$R^{2b}$ is independently X, F, —OH, $C_1$-$C_4$alkyl, halo$C_1$-$C_4$alkyl, —$NH_2$, —CN, or $C_1$-$C_4$alkoxy, and wherein $C_1$-$C_4$alkyl, halo$C_1$-$C_4$alkyl, or $C_1$-$C_4$alkoxy optionally comprise one or more X;

$R^{2c}$, $R^{2c'}$ are independently X, H, F, OH, $OCH_3$, or $CH_3$;

$R^{2d}$ is X, H, F, or —OH;

$R^{2e}$ is X, H, OH, $CH_3$, or F;

Z is independently N, NH, N($C_1$-$C_4$alkyl), N(halo$C_1$-$C_4$alkyl), O, or S;

$Z^1$ is independently N, NH, O, or S;

p is 0, 1 or 2;

m is 0 or 1;

as valency permits, ⸰ is a combination of single and double bonds;

* is the position of bonding;

Fluoro is $^{19}F$;

X is Bromo, Chloro, or Iodo; and wherein $R^6$ comprises at least one X, with a $^3H$ radiolabeling agent;

and (C) reacting a compound of formula (IV-J)

(IV-J)

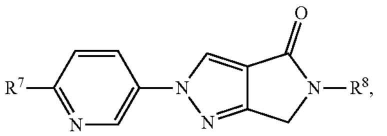

or a stereoisomer, racemic mixture, pharmaceutically acceptable salt, hydrate, or solvate thereof, wherein $R^7$ is

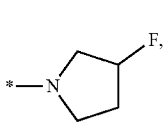, 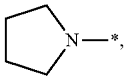, 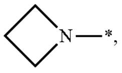,

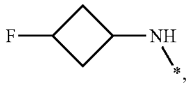, 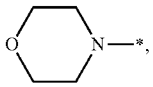,

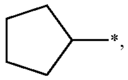, 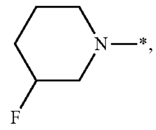, 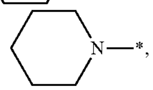, or

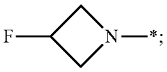;

$R^8$ is selected from the group consisting of:

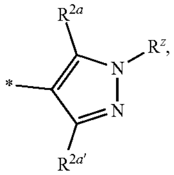, 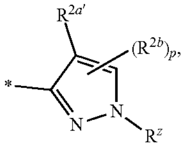, and

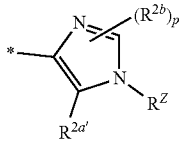

wherein $R^{2a}$, $R^{2a'}$ are independently H, or F;

$R^{2b}$ is independently F, —OH, $C_1$-$C_4$alkyl, halo$C_1$-$C_4$alkyl, —$NH_2$, —CN, or $C_1$-$C_4$alkoxy;

p is 0, 1 or 2;

$R^z$ is H, $C_1$-$C_4$alkyl or halo$C_1$-$C_4$alkyl;

as valency permits, ⸰ is a combination of single and double bonds;

Fluoro is $^{19}F$; and

* is the position of bonding, with a $CT_3$ radiolabeling agent, wherein T is $^3H$.

14. The method according to claim 13, wherein the $^{18}F$-fluorinating agent is selected from the group consisting of $K^{18}F$, $Rb^{18}F$, $Cs^{18}F$, $Na^{18}F$, $Rb^{18}F$, Kryptofix[222]$K^{18}F$, tetra($C_{1-6}$ alkyl) ammonium salt of $^{18}F$, and tetrabutylammonium [$^{18}F$]fluoride.

15. A test kit for the detection and/or diagnosis of a disease, disorder or abnormality associated with alpha-synuclein aggregates, wherein the test kit comprises at least one compound of formula (I)

(I)

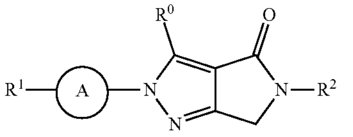

or a detectably labelled compound, stereoisomer, racemic mixture, pharmaceutically acceptable salt, hydrate, or solvate thereof wherein

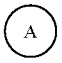

is an aryl or a heteroaryl which is directionally selected from the group consisting of:

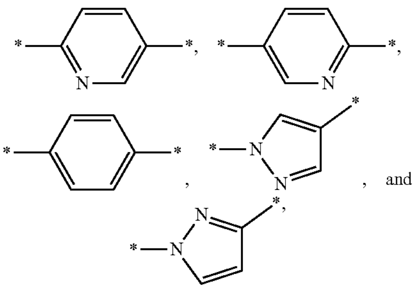

$R^0$ is H or $C_1$-$C_4$alkyl;

$R^1$ is —CN; or halo; or $C_1$-$C_4$alkyl; or $C_1$-$C_4$alkoxy; or —N($C_1$-$C_4$alkyl)$_2$; or —NH($C_1$-$C_4$alkyl); or H;

or $R^1$ is —NH—$C_3$-$C_6$cycloalkyl, $C_3$-$C_6$cycloalkyl, or heterocyclyl, which is a 4- to 6-membered non-aromatic monocyclic ring radical containing 1 or 2 heteroatoms, each of which is optionally substituted with at least one halo;

$R^2$ is selected from the group consisting of:

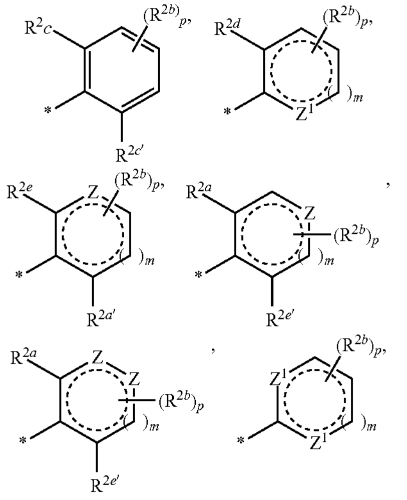

-continued

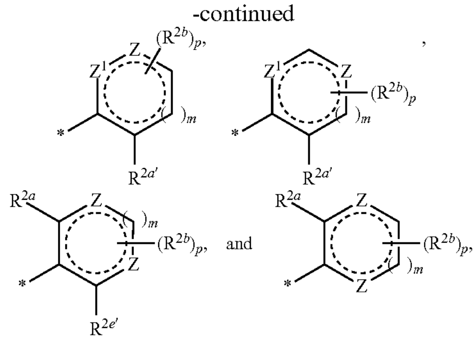

wherein $R^{2a}$, $R^{2a'}$ are independently H, or F;

$R^{2b}$ is independently F, OH, $C_1$-$C_4$alkyl, halo$C_1$-$C_4$alkyl, $NH_2$, CN, or $C_1$-$C_4$alkoxy;

$R^{2c}$, $R^{2c'}$ are independently H, F, OH, $OCH_3$, or $CH_3$;

$R^{2d}$ is H, F, or OH;

$R^{2e}$ is H, OH, $CH_3$, or F;

Z is independently N, NH, N($C_1$-$C_4$alkyl), N(halo$C_1$-$C_4$alkyl), O, or S;

$Z^1$ is independently N, NH, O, or S;

p is 0, 1 or 2;

m is 0 or 1;

as valency permits,  is a combination of single and double bonds; and

* is the position of bonding.

16. A kit for preparing a radiopharmaceutical preparation, wherein the kit comprises a sealed vial containing at least one compound as defined in claim 10.

17. The method according to claim 9, wherein the disease, disorder or abnormality is Parkinson's disease, SNCA duplication carrier, Lewy Body dementia (LBD), dementia with Lewy bodies (DLB), Parkinson's disease dementia (PDD), diffuse Lewy body disease (DLBD), Alzheimer's disease, sporadic Alzheimer's disease, familial Alzheimer's disease with APP mutations, familial Alzheimer's disease with PS-1, PS-2 or other mutations, familial British dementia, Lewy body variant of Alzheimer's disease, Down syndrome, multiple system atrophy (MSA), traumatic brain injury, chronic traumatic encephalopathy, dementia puglistica, tauopathies, Creutzfeldt-Jakob disease, Huntington's disease, motor neuron disease, amyotrophic lateral sclerosis, neuroaxonal dystrophy, neurodegeneration with brain iron accumulation type 1, a prion disease, ataxia telangiectatica, Meige's syndrome, subacute sclerosing panencephalitis, Gerstmann-Straussler-Scheinker disease, inclusion-body myositis, Gaucher disease, Krabbe disease, a lysosomal storage disorder or rapid eye movement (REM) sleep behavior disorder.

18. The compound according to claim 1, wherein $R^1$ is selected from the group consisting of

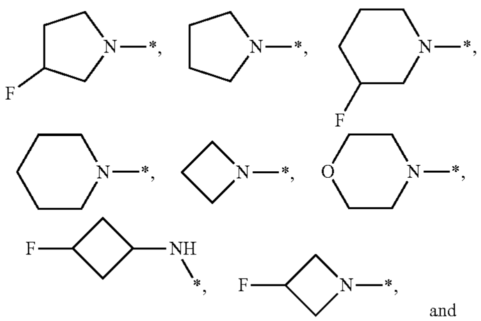

and

-continued

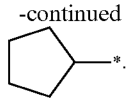

19. The detectably labelled compound of formula (I) according to claim 5, wherein the compound is a detectably labelled by $^2H$, $^3H$ or $^{18}F$.

20. The method according to claim 7, wherein the imaging is positron emission tomography imaging of alpha-synuclein aggregates.

21. The method according to claim 9, wherein the disease, disorder or abnormality is Parkinson's disease, multiple system atrophy, dementia with Lewy bodies, Parkinson's disease dementia, SNCA duplication carrier or Alzheimer's disease.

* * * * *